United States Patent
Chen et al.

(10) Patent No.: US 11,220,494 B2
(45) Date of Patent: Jan. 11, 2022

(54) CYCLIN DEPENDENT KINASE INHIBITORS

(71) Applicant: Pfizer Inc., New York, NY (US)

(72) Inventors: Ping Chen, San Diego, CA (US); Sujin Cho-Schultz, San Diego, CA (US); Judith Gail Deal, San Diego, CA (US); Gary Michael Gallego, San Diego, CA (US); Mehran Jalaie, San Diego, CA (US); Robert Steven Kania, San Diego, CA (US); Sajiv Krishnan Nair, San Diego, CA (US); Sacha Ninkovic, San Diego, CA (US); Suvi Tuula Marjukka Orr, San Diego, CA (US); Cynthia Louise Palmer, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/942,209

(22) Filed: Jul. 29, 2020

(65) Prior Publication Data
US 2020/0354350 A1  Nov. 12, 2020

Related U.S. Application Data

(63) Continuation of application No. 16/391,836, filed on Apr. 23, 2019, now Pat. No. 10,766,884.

(60) Provisional application No. 62/663,096, filed on Apr. 26, 2018, provisional application No. 62/750,454, filed on Oct. 25, 2018, provisional application No. 62/826,609, filed on Mar. 29, 2019.

(51) Int. Cl.
| | | |
|---|---|---|
| C07D 407/14 | (2006.01) | |
| C07D 401/14 | (2006.01) | |
| C07D 487/04 | (2006.01) | |
| C07D 498/04 | (2006.01) | |

(52) U.S. Cl.
CPC ......... *C07D 407/14* (2013.01); *C07D 401/14* (2013.01); *C07D 487/04* (2013.01); *C07D 498/04* (2013.01)

(58) Field of Classification Search
CPC .. C07D 407/14; C07D 401/14; C07D 487/04; C07D 498/04
See application file for complete search history.

(56) References Cited

U.S. PATENT DOCUMENTS

| | | | |
|---|---|---|---|
| 7,615,562 B2 | 11/2009 | Bollbuck et al. | |
| 7,855,211 B2 | 12/2010 | Coates et al. | |
| 8,227,478 B2 | 7/2012 | Gong et al. | |
| 8,618,103 B2 | 12/2013 | de Vicente Fidalgo et al. | |
| 9,376,450 B2 | 6/2016 | Allen et al. | |
| 10,059,690 B2 | 8/2018 | Ciblat et al. | |
| 10,154,995 B2 | 12/2018 | Blake et al. | |
| 10,239,864 B2 | 3/2019 | Greco et al. | |
| 10,766,884 B2 | 9/2020 | Chen et al. | |
| 2004/0171630 A1 | 9/2004 | Kim et al. | |
| 2016/0214978 A1 | 7/2016 | Du et al. | |
| 2016/0264552 A1 | 9/2016 | Ciblat et al. | |

FOREIGN PATENT DOCUMENTS

| | | |
|---|---|---|
| CN | 105111191 | 12/2015 |
| EA | 026269 | 3/2017 |
| RU | 2006105338 | 9/2007 |
| RU | 2009110254 | 9/2010 |
| WO | 200119798 | 3/2001 |
| WO | 200164642 | 9/2001 |
| WO | 2005/012256 | 2/2005 |
| WO | 2006/038001 | 4/2006 |
| WO | 2008/024390 | 2/2008 |
| WO | 2009158571 | 12/2009 |
| WO | 2011090760 | 7/2011 |
| WO | 2012129562 | 9/2012 |
| WO | 2013/184757 | 12/2013 |
| WO | 2014160017 | 10/2014 |

(Continued)

OTHER PUBLICATIONS

Parkard et al., Discovery and optimization of thieno[2,3-d]pyrimidines as B-Raf inhibitors; Bioorganic & Medicinal Chemistry; (2012), 22 (1), 747-752.*

(Continued)

*Primary Examiner* — Tracy Vivlemore
*Assistant Examiner* — Ebenezer O Sackey
(74) *Attorney, Agent, or Firm* — Leslie A. Robinson; Carmen K. Robinson

(57) ABSTRACT

This invention relates to compounds of Formula (I)

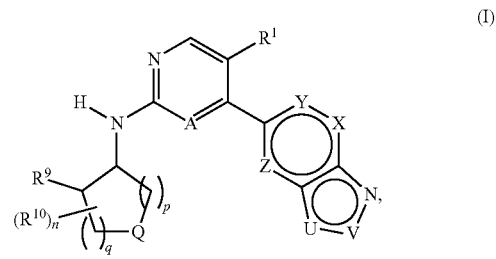

or a pharmaceutically acceptable salt thereof, in which R-groups $R^1$ to $R^{23}$, A, Q, U, V, W, X, Y, Z, n, p and q are as defined herein, to pharmaceutical compositions comprising such compounds and salts, and to methods of using such compounds, salts and compositions for the treatment of abnormal cell growth, including cancer, in a subject.

21 Claims, No Drawings
Specification includes a Sequence Listing.

(56) References Cited

FOREIGN PATENT DOCUMENTS

| WO | 2015030847 | 3/2015 |
|---|---|---|
| WO | 2016/015604 | 2/2016 |
| WO | 2016105118 | 6/2016 |
| WO | 2016/192630 | 12/2016 |
| WO | 2017/114510 | 7/2017 |
| WO | 2017/133701 | 8/2017 |
| WO | 2018/013867 | 1/2018 |
| WO | 2018161033 | 9/2018 |
| WO | 2019057123 | 3/2019 |

OTHER PUBLICATIONS

Cooper, A. B., et al., "A unique function for cyclin D3 in early B cell development", Nat. Immunol., (2006), 5(7):489-497.

Cordon-Cardo, C., "Mutations of cell cycle regulators: biological and clinical implications for human neoplasia", Am. J. Pathol., (1995), 147:545-560.

Hall, M., Peters, G., "Genetic alterations of cyclins, cyclin-dependent kinases, and Cdk inhibitors in human cancer", Adv. Cancer Res., (1996), 68:67-108.

Johnson, D. G., Walker, C.L., "Cyclins and Cell Cycle Checkpoints", Annu. Rev. Pharmacol. Toxicol., (1999), 39:295-312.

Karp, J. E., Broder, S., "Molecular foundations of cancer: new targets for intervention", Nat. Med., (1995), 1:309-320.

Malumbres, M., et al., "Mammalian Cells Cycle without the D-type Cyclin-Dependent Kinases Cdk4 and Cdk6", Cell,(2004), 118(4):493-504.

Morgan, D. O., "Cyclin-dependent kinases: engines, clocks, and microprocessors", Annu. Rev. Cell. Dev. Biol., (1997), 13:261-291.

Ortega, S., et al., "Cyclin D dependent kinases, INK4 inhibitors and cancer", Biochim. Biophys. Acta, (2002),1602:73-87.

Sánchez-Martinez, C., et al., "Cyclin dependent kinase (CDK) inhibitors as anticancer drugs", Bioorg. Med. Chem. Lett. (2015), 25:3420-3435.

Sicinska, E., et al., "Essential Role for Cyclin D3 in Granulocyte Colony-Stimulating Factor-Driven Expansion of Neutrophil Granulocytes", Mol. Cell Biol., (2006), 26(21):8052-8060.

Smalley, K. S. M., et al., "Identification of a novel subgroup of melanomas with KIT/cyclin-dependent kinase-4 overexpression", Cancer Res., (2008), 68:5743-52.

Zuo, L., et al., "Germline mutations in the p16INK4a binding domain of CDK4 in familial melanoma", Nature Genet., (1996), 12:97-99.

International Search Report for PCT/IB2019/053314, dated Jul. 29, 2019.

Written Opinion of the International Searching Authority for PCT/IB2019/053314, dated Jul. 29, 2019.

Federal Institute of Industrial Property (FIPS) Search Report for Russian Application No. 2020134811, based on PCT/IB2019/053314, dated Mar. 29, 2021 and English translation.

National Centre of the Intellectual Property of Georgia, Search Report for Georgian Application No. AP 2019 15475, based on PCT/IB2019/053314, dated May 28, 2021 and English translation.

* cited by examiner 100,494 B2

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 5-FAM Arginine
        <

<400> SEQUENCE: 1

Arg Arg Arg Phe Arg Pro Ala Ser Pro Leu Arg Gly Pro Pro Lys
1               5                   10                  15

CYCLIN DEPENDENT KINASE INHIBITORS

CROSS-REFERENCE TO RELATED APPLICATIONS

The present application is a Continuation of U.S. patent application Ser. No. 16/391,836, filed Apr. 23, 2019, now allowed, which claims the benefit of priority to U.S. Provisional Application No. 62/663,096, filed on Apr. 26, 2018, to U.S. Provisional Application No. 62/750,454, filed on Oct. 25, 2018, and to U.S. Provisional Application No. 62/826,609, filed on Mar. 29, 2019, each of which is incorporated by reference herein in its entirety.

REFERENCE TO SEQUENCE LISTING

This application is being filed electronically via EFS-Web and includes an electronically submitted sequence listing in .txt format. The .txt file contains a sequence listing entitled "PC72436BSEQLISTING ST25.txt" created on Jul. 29, 2020 and having a size of 1 KB. The sequence listing contained in this .txt file is part of the specification and is herein incorporated by reference in its entirety.

BACKGROUND OF THE INVENTION

Field of the Invention

The present invention relates to compounds of Formulae (I)-(XII), and pharmaceutically acceptable salts thereof, to pharmaceutical compositions comprising such compounds and salts, and to the uses thereof. The compounds, salts and compositions of the present invention may be useful for the treatment of abnormal cell growth, such as cancer, in a subject.

Description of the Related Art

Cyclin-dependent kinases (CDKs) and related serine/threonine protein kinases are important cellular enzymes that perform essential functions in regulating cell division and proliferation. The CDK catalytic units are activated by regulatory subunits known as cyclins. At least sixteen mammalian cyclins have been identified (Johnson D G, Walker C L. Cyclins and Cell Cycle Checkpoints. *Annu. Rev. Pharmacol. Toxicol.* (1999) 39:295-312). Additional functions of Cyclin/CDK heterodynes include regulation of transcription, DNA repair, differentiation and apoptosis (Morgan D O. Cyclin-dependent kinases: engines, clocks, and microprocessors. *Annu. Rev. Cell. Dev. Biol.* (1997) 13:261-291).

CDK inhibitors have been demonstrated to be useful in treating cancer. Increased activity or temporally abnormal activation of CDKs has been shown to result in the development of human tumors, and human tumor development is commonly associated with alterations in either the CDK proteins themselves or their regulators (Cordon-Cardo C. Mutations of cell cycle regulators: biological and clinical implications for human neoplasia. *Am. J. Pathol.* (1995) 147:545-560; Karp J E, Broder S. Molecular foundations of cancer: new targets for intervention. *Nat. Med.* (1995) 1:309-320; Hall M, Peters G. Genetic alterations of cyclins, cyclin-dependent kinases, and Cdk inhibitors in human cancer. *Adv. Cancer Res.* (1996) 68:67-108).

CDK4 and CDK6 are important regulators of cell cycle progression at the G1-S checkpoint, which are controlled by D-type cyclins and INK4 endogenous CDK inhibitors, such as p16$^{INK4a}$ (CDKN2A). Dysregulation of the cyclin D-CDK4/6-INK4-retinoblastoma (Rb) pathway has been reported to be associated with development of endocrine therapy resistance.

Mutations of CDK4 and CDK6 have been described in subgroups of melanoma and other tumors (Zuo L, et al., Germline mutations in the p16INK4a binding domain of CDK4 in familial melanoma. *Nature Genet.* (1996) 12, 97-99; Ortega S, et al. Cyclin D-dependent kinases, INK4 inhibitors and cancer. *Biochim. Biophys. Acta* (2002) 1602: 73-87; Smalley K S M et al. Identification of a novel subgroup of melanomas with KIT/cyclin-dependent kinase-4 overexpression. *Cancer Res* (2008) 68: 5743-52). Amplifications of the regulatory subunits of CDKs and cyclins, and mutation, gene deletion, or transcriptional silencing of endogenous INK4 CDK inhibitors have also been reported as mechanism by which the pathway can be activated (Smalley KSM (2008)).

The development of CDK inhibitors has been reviewed in the literature. For example, see Sánchez-Martinez et al. Cyclin dependent kinase (CDK) inhibitors as anticancer drugs, Bioorg. Med. Chem. Lett. (2015) 25: 3420-3435 (and references cited therein). The use of CDK4/6 inhibitors in combination with endocrine therapy has demonstrated significant efficacy in the treatment of hormone receptor (HR)-positive, human epidermal growth factor 2 (HER2)-negative advanced or metastatic breast cancers, and CDK4/6 inhibitors, including palbociclib, ribociclib and abemaciclib, have been approved in combination with endocrine therapy in a first- or second-line setting.

However, treatment with CDK4/6 inhibitors may result in adverse effects, such as gastrointestinal and/or hematologic toxicities, and acquired resistance may develop over time. Emerging data suggest that cyclin D3-CDK6 may be linked to the observed hematologic toxicity. (Malumbres et al., Mammalian Cells Cycle without the D-type Cyclin-Dependent Kinases Cdk4 and Cdk6, (2004) Cell 118(4):493-504; Sicinska et al. Essential Role for Cyclin D3 in Granulocyte Colony-Stimulating Factor-Driven Expansion of Neutrophil Granulocytes (2006), Mol. Cell Biol 26(21): 8052-8060; Cooper et al. A unique function for cyclin D3 in early B cell development, (2006), Nat. Immunol. 5(7):489-497). CDK4 has been identified as the singular oncogenic driver in many breast cancers. Accordingly, a CDK4 selective inhibitor may provide an improved safety profile or enhanced overall efficacy due to the potential of higher and/or continuous dosing compared to dual CDK4/6 inhibitors.

Accordingly, there remains a need for improved therapies for the treatment of cancers. The compounds, compositions and methods of the present invention are believed to have one or more advantages, such as greater efficacy; potential to reduce side effects; potential to reduce drug-drug interactions; potential to enable an improved dosing schedule; or potential to overcome resistance mechanisms, and the like.

BRIEF SUMMARY OF THE INVENTION

The present invention provides, in part, compounds of Formula (I)-(XII) and pharmaceutically acceptable salts thereof. Such compounds can inhibit the activity of CDKs, including CDK4 and/or CDK6, thereby effecting biological functions. In some embodiments, the invention provides compounds that are selective for CDK4. Also provided are pharmaceutical compositions and medicaments comprising the compounds or salts of the invention, alone or in combination with additional anticancer therapeutic agents.

The present invention also provides, in part, methods for preparing the compounds, pharmaceutically acceptable salts and compositions of the invention, and methods of using the foregoing alone or in combination with additional anticancer therapeutic agents.

In one aspect, the invention provides a compound of Formula (I):

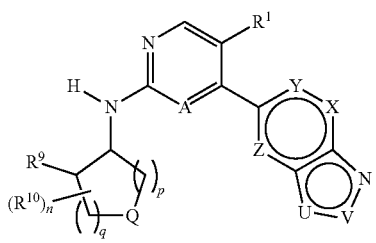

or a pharmaceutically acceptable salt thereof, wherein:
A is N or CH;
$R^1$ is H, F, Cl, CN, $C_1$-$C_2$ alkyl, $C_1$-$C_2$ fluoroalkyl or $C_1$-$C_2$ alkoxy, where each said $C_1$-$C_2$ alkyl and $C_1$-$C_2$ fluoroalkyl is optionally substituted by $R^{20}$;
U is $NR^2$ or $CR^3$;
V is N or $CR^4$ when U is $NR^2$; and
V is $NR^5$ when U is $CR^3$;
X is $CR^6$ or N;
Y is $CR^7$ or N;
Z is $CR^8$ or N;
$R^2$ and $R^3$ are H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$;
$R^4$ is H, $C_1$-$C_4$ alkyl, $C_1$-$C_4$ fluoroalkyl, $C_1$-$C_4$ alkoxy, $C_1$-$C_4$ fluoroalkoxy, $C(O)R^a$, $C(O)NR^b_2$, $C_3$-$C_8$ cycloalkyl or 3-6 membered heterocyclyl, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$, each said $C_3$-$C_8$ cycloalkyl and 3-6 membered heterocyclyl is optionally substituted by $R^{21}$, $R^a$ is $C_1$-$C_2$ alkyl, and each $R^b$ is independently H or $C_1$-$C_2$ alkyl; and
$R^5$ is H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$; or
$R^2$ can be taken together with $R^4$, or $R^3$ can be taken together with $R^5$, to form a 5-7 membered heterocyclic ring, optionally containing an additional heteroatom selected from $NR^{24}$, O and $S(O)_m$ as a ring member, which ring is optionally substituted by $R^{21}$;
$R^6$ is H, F, Cl, CN, $CH_3$, $CH_2F$, $CHF_2$ or $CF_3$;
$R^7$ and $R^8$ are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy, where each said $C_1$-$C_2$ alkyl, $C_1$-$C_2$ fluoroalkyl, $C_1$-$C_2$ alkoxy and $C_1$-$C_2$ fluoroalkoxy is optionally substituted by $R^{20}$;
$R^9$ is H, OH, $NH_2$, $NHCH_3$ or $N(CH_3)_2$;
each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;
Q is $NR^{11}$ or O; or
Q is $CR^{12}R^{13}$, where $R^{12}$ and $R^{13}$ are taken together with the C atom to which they are attached to form a 4-6 membered heterocyclic ring containing $NR^{11}$ or O as a ring member, which ring is optionally further substituted by $R^{10}$;
$R^{11}$ is H, $C_1$-$C_4$ alkyl, $C_1$-$C_4$ fluoroalkyl, $SO_2R^{14}$, $SO_2NR^{15}R^{16}$, $COR^{17}$, $COOR^{17}$ or $CONR^{18}R^{19}$, where each said $C_1$-$C_4$ alkyl and $C_1$-$C_4$ fluoroalkyl is optionally substituted by $R^{20}$, $SO_2R^{14}$, $SO_2NR^{15}R^{16}$, $COR^{17}$, $COOR^{17}$ or $CONR^{18}R^{19}$;
$R^{14}$ is $C_1$-$C_4$ alkyl or $C_1$-$C_4$ fluoroalkyl;
each $R^{15}$ and $R^{16}$ is independently H or $CH_3$;
$R^{17}$ is $C_1$-$C_4$ alkyl, $C_1$-$C_4$ fluoroalkyl, $C_3$-$C_8$ cycloalkyl or 3-6 membered heterocyclyl, where each said $C_1$-$C_4$ alkyl and $C_1$-$C_4$ fluoroalkyl is optionally substituted by $R^{20}$ and each said $C_3$-$C_8$ cycloalkyl and 3-6 membered heterocyclyl is optionally substituted by $R^{21}$;
each $R^{18}$ and $R^{19}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$;
each $R^{20}$ is independently OH, $C_1$-$C_2$ alkoxy, $C_1$-$C_2$ fluoroalkoxy, CN, $NR^{22}R^{23}$, $C_3$-$C_8$ cycloalkyl or 3-6 membered heterocyclyl, where each said $C_3$-$C_8$ cycloalkyl and 3-6 membered heterocyclyl is optionally substituted by $R^{21}$;
each $R^{21}$ is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$;
each $R^{22}$ and $R^{23}$ is independently H, $C_1$-$C_3$ alkyl, $C_1$-$C_3$ fluoroalkyl, $C_3$-$C_8$ cycloalkyl or 3-6 membered heterocyclyl, where each said $C_1$-$C_3$ alkyl and $C_1$-$C_3$ fluoroalkyl is optionally further substituted by OH, $C_1$-$C_2$ alkoxy or $C_1$-$C_2$ fluoroalkoxy and each said $C_3$-$C_8$ cycloalkyl and 3-6 membered heterocyclyl is optionally further substituted by F, OH, $C_1$-$C_2$ alkyl, $C_1$-$C_2$ fluoroalkyl, $C_1$-$C_2$ alkoxy or $C_1$-$C_2$ fluoroalkoxy; or
$R^{22}$ and $R^{23}$ may be taken together with the nitrogen atom to which they are attached to form an azetidinyl ring, where said ring is optionally substituted by F, OH, $C_1$-$C_2$ alkyl, $C_1$-$C_2$ fluoroalkyl, $C_1$-$C_2$ alkoxy or $C_1$-$C_2$ fluoroalkoxy;
$R^{24}$ is H, $C_1$-$C_4$ alkyl, $C_1$-$C_4$ fluoroalkyl, $SO_2R^{25}$, $SO_2NR^{26}R^{27}$, $COR^{28}$, $COOR^{28}$ or $CONR^{29}R^{30}$;
$R^{25}$ is $C_1$-$C_4$ alkyl or $C_1$-$C_4$ fluoroalkyl;
each $R^{26}$ and $R^{27}$ is independently H or $CH_3$;
$R^{28}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$;
each $R^{29}$ and $R^{30}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$;
m is 0, 1 or 2;
n is 0, 1, 2, 3 or 4;
p is 1, 2 or 3; and
q is 0, 1, 2 or 3;
wherein the sum of p and q is an integer from 1 to 4.

In another aspect, the invention provides a compound of Formula (II):

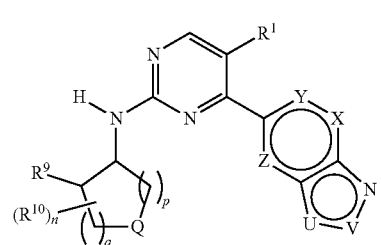

or a pharmaceutically acceptable salt thereof, wherein:

$R^1$ is H, F, Cl, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;

U is $NR^2$ or $CR^3$;

V is N or $CR^4$ when U is $NR^2$; and

V is $NR^5$ when U is $CR^3$;

X is $CR^6$ or N;

Y is $CR^7$ or N;

Z is $CR^8$ or N;

$R^2$ and $R^3$ are H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$;

$R^4$ is H, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$;

$R^5$ is H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$;

$R^6$ is H, F, Cl, CN, $CH_3$, $CH_2F$, $CHF_2$ or $CF_3$;

$R^7$ and $R^8$ are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy, where each said $C_1$-$C_2$ alkyl, $C_1$-$C_2$ fluoroalkyl, $C_1$-$C_2$ alkoxy and $C_1$-$C_2$ fluoroalkoxy is optionally substituted by $R^{20}$;

$R^9$ is H, OH, $NH_2$, $NHCH_3$ or $N(CH_3)_2$;

each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;

Q is $NR^{11}$ or O; or

Q is $CR^{12}R^{13}$, where $R^{12}$ and $R^{13}$ are taken together with the C atom to which they are attached to form a 4-6 membered heterocyclic ring containing $NR^{11}$ or O as a ring member, which ring is optionally further substituted by $R^{10}$;

$R^{11}$ is H, $C_1$-$C_4$ alkyl, $C_1$-$C_4$ fluoroalkyl, $SO_2R^{14}$, $SO_2NR^{15}R^{16}$, $COR^{17}$, $COOR^{17}$ or $CONR^{18}R^{19}$;

$R^{14}$ is $C_1$-$C_4$ alkyl or $C_1$-$C_4$ fluoroalkyl;

each $R^{15}$ and $R^{16}$ is independently H or $CH_3$;

$R^{17}$ is $C_1$-$C_4$ alkyl, $C_1$-$C_4$ fluoroalkyl, where each said $C_1$-$C_4$ alkyl and $C_1$-$C_4$ fluoroalkyl is optionally substituted by $R^{20}$;

each $R^{18}$ and $R^{19}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$;

each $R^{20}$ is independently OH, $C_1$-$C_2$ alkoxy, $C_1$-$C_2$ fluoroalkoxy, CN or $NR^{22}R^{23}$;

each $R^{21}$ is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$;

each $R^{22}$ and $R^{23}$ is independently H, $C_1$-$C_2$ alkyl or $C_1$-$C_2$ fluoroalkyl; or $R^{22}$ and $R^{23}$ may be taken together with the nitrogen atom to which they are attached to form an azetidinyl ring, which is optionally substituted by F or OH;

n is 0, 1, 2, 3 or 4;

p is 1, 2 or 3; and q is 0, 1, 2 or 3;

wherein the sum of p and q is an integer from 1 to 4.

In another aspect, the invention provides a pharmaceutical composition comprising a compound of the invention, according to any of the formulae described herein, or a pharmaceutically acceptable salt thereof, and a pharmaceutically acceptable carrier or excipient.

In some embodiments, the pharmaceutical composition comprises two or more pharmaceutically acceptable carriers and/or excipients.

The invention also provides therapeutic methods and uses comprising administering a compound of the invention, or a pharmaceutically acceptable salt thereof.

In one aspect, the invention provides a method for the treatment of abnormal cell growth, in particular cancer, in a subject in need thereof, comprising administering to the subject a therapeutically effective amount of a compound of the invention, or a pharmaceutically acceptable salt thereof. Compounds of the invention may be administered as single agents or may be administered in combination with other anti-cancer therapeutic agents, including standard of care agents appropriate for the particular form of cancer.

In a further aspect, the invention provides a method for the treatment of abnormal cell growth, in particular cancer, in a subject in need thereof, comprising administering to the subject an amount of a compound of the invention, or a pharmaceutically acceptable salt thereof, in combination with an amount of an additional anti-cancer therapeutic agent, which amounts are together effective in treating said abnormal cell growth.

In another aspect, the invention provides a compound of the invention, or a pharmaceutically acceptable salt thereof, for use in the treatment of abnormal cell growth, in particular, cancer, in a subject.

In a further aspect, the invention provides the use of a compound of the invention, or a pharmaceutically acceptable salt thereof, for the treatment of abnormal cell growth, in particular, cancer, in a subject.

In another aspect, the invention provides a pharmaceutical composition for use in the treatment of abnormal cell growth, in particular cancer, in a subject in need thereof, which pharmaceutical composition comprises a compound of the invention, or a pharmaceutically acceptable salt thereof, and a pharmaceutically acceptable carrier or excipient.

In another aspect, the invention provides a compound of the invention, or a pharmaceutically acceptable salt thereof, for use as a medicament, in particular a medicament for the treatment of abnormal cell growth, such as cancer.

In yet another aspect, the invention provides the use of a compound of the invention, or a pharmaceutically acceptable salt thereof, for the manufacture of a medicament for the treatment of abnormal cell growth, such as cancer, in a subject.

In another aspect, the invention provides a method for the treatment of a disorder mediated by CDK4 in a subject, comprising administering to the subject a compound of the invention, or a pharmaceutically acceptable salt thereof, in an amount that is effective for treating said disorder, in particular, cancer.

In another aspect, the invention provides a pharmaceutical composition comprising a compound of the invention, according to any of the formulae described herein, and a second pharmaceutically active agent.

In another aspect, the invention provides a compound of the invention, according to any of the formulae described herein, for use in the treatment of cancer, wherein said treatment comprises the administration of a second pharmaceutically active agent.

Each of the aspects and embodiments of the compounds of the present invention described below can be combined with one or more other embodiments of the compounds of the present invention described herein not inconsistent with the embodiment(s) with which it is combined.

In addition, each of the embodiments below describing the invention envisions within its scope the pharmaceutically acceptable salts of the compounds of the invention. Accordingly, the phrase "or a pharmaceutically acceptable salt thereof" is implicit in the description of all compounds described herein unless explicitly indicated to the contrary.

DETAILED DESCRIPTION OF THE INVENTION

The present invention may be understood more readily by reference to the following detailed description of the preferred embodiments of the invention and the Examples included herein. It is to be understood that the terminology used herein is provided for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents. The term "about" means having a value falling within an accepted standard of error of the mean, when considered by one of ordinary skill in the art.

The invention described herein suitably may be practiced in the absence of any element(s) not specifically disclosed herein. Thus, for example, in each instance herein any of the terms "comprising", "consisting essentially of", and "consisting of" may be replaced with either of the other two terms.

"Alkyl" refers to a saturated, monovalent aliphatic hydrocarbon radical including straight chain and branched chain groups having the specified number of carbon atoms. Alkyl substituents typically contain 1 to 12 carbon atoms ("$C_1$-$C_{12}$ alkyl"), frequently 1 to 8 carbon atoms ("$C_1$-$C_8$ alkyl"), or more frequently 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$ alkyl") or 1 to 2 carbon atoms ("$C_1$-$C_2$ alkyl"). Examples of alkyl groups include methyl, ethyl, n-propyl, isopropyl, n-butyl, iso-butyl, tert-butyl, n-pentyl, isopentyl, neopentyl, n-hexyl, n-heptyl, n-octyl and the like.

Alkyl groups described herein as optionally substituted may be substituted by one or more substituent groups, as further defined by the claims, which substituent groups are selected independently unless otherwise indicated. The total number of substituent groups may equal the total number of hydrogen atoms on the alkyl moiety, to the extent such substitution makes chemical sense. Optionally substituted alkyl groups typically contain from 1 to 6 optional substituents, sometimes 1 to 5 optional substituents, 1 to 4 optional substituents, or preferably 1 to 3 optional substituents.

Optional substituent that are suitable for alkyl include, but are not limited to, $C_3$-$C_8$ cycloalkyl, 3-12 membered heterocyclyl, $C_6$-$C_{12}$ aryl and 5-12 membered heteroaryl, halo, =O (oxo), =S (thiono), =N—CN, =N—$OR^x$, =$NR^x$, —CN, —C(O)$R^x$, —$CO_2R^x$, —C(O)$NR^xR^y$, —$SR^x$, —$SOR^x$, —$SO_2R^x$, —$SO_2NR^xR^y$, —$NO_2$, —$NR^xR^y$, —$NR^xC(O)R^y$, —$NR^xC(O)NR^xR^y$, —$NR^xC(O)OR^x$, —$NR^xSO_2R^y$, —$NR^xSO_2NR^xR^y$, —$OR^x$, —OC(O)$R^x$ and —OC(O)$NR^xR^y$; wherein each $R^x$ and $R^y$ is independently H, $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl, or $R^x$ and $R^y$ may be taken together with the N atom to which they are attached to form a 3-12 membered heterocyclyl or 5-12 membered heteroaryl, each optionally containing 1, 2 or 3 additional heteroatoms selected from O, N and S(O)$_q$ where q is 0-2; each $R^x$ and $R^y$ is optionally substituted with 1 to 3 substituents independently selected from the group consisting of halo, =O, =S, =N—CN, =N—OR', =NR', —CN, —C(O)R', —$CO_2$R', —C(O)$NR'_2$, —SOR', —$SO_2$R', —$SO_2NR'_2$, —$NO_2$, —$NR'_2$, —NR'C(O)R', —NR'C(O)$NR'_2$, —NR'C(O)OR', —NR'$SO_2$R', —NR'$SO_2NR'_2$, —OR', —OC(O)R' and —OC(O)$NR'_2$, wherein each R' is independently H, $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or $C_5$-$C_{12}$ heteroaryl; and wherein each said $C_3$-$C_8$ cycloalkyl, 3-12 membered heterocyclyl, $C_6$-$C_{12}$ aryl and 5-12 membered heteroaryl is optionally substituted as further defined herein.

Typical substituent groups on alkyl include halo, —OH, $C_1$-$C_4$ alkoxy, —O—$C_6$-$C_{12}$ aryl, —CN, =O, —$COOR^x$, —OC(O)$R^x$, —C(O)$NR^xR^y$, —$NR^xC(O)R^y$, —$NR^xR^y$, $C_3$-$C_0$ cycloalkyl, $C_6$-$C_{12}$ aryl, 5-12 membered heteroaryl and 3-12 membered heterocyclyl; where each $R^x$ and $R^y$ is independently H or $C_1$-$C_4$ alkyl, or $R^x$ and $R^y$ may be taken together with the N to which they are attached form a 3-12 membered heterocyclyl or 5-12 membered heteroaryl ring, each optionally containing 1, 2 or 3 additional heteroatoms selected from O, N and S(O)$_q$ where q is 0-2; wherein each said $C_3$-$C_8$ cycloalkyl, $C_6$-$C_{12}$ aryl, 5-12 membered heteroaryl and 3-12 membered heterocyclyl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —$NH_2$, —NH($C_1$-$C_4$ alkyl) and —N($C_1$-$C_4$ alkyl)$_2$.

In some instances, substituted alkyl groups are specifically named by reference to the substituent group. For example, "haloalkyl" refers to an alkyl group having the specified number of carbon atoms that is substituted by one or more halo substituents, up to the available valence number. Typically, haloalkyl groups contain 1-6 carbon atoms, 1-5 carbon atoms, 1-4 carbon atoms or 1-2 carbon atoms and 1, 2, 3, 4 or 5 halo atoms (i.e., "$C_1$-$C_5$ haloalkyl", "$C_1$-$C_4$ haloalkyl" or "$C_1$-$C_2$ haloalkyl").

More specifically, fluorinated alkyl groups may be specifically referred to as "fluoroalkyl" groups, (e.g., $C_1$-$C_5$, $C_1$-$C_4$ or $C_1$-$C_2$ fluoroalkyl groups), which are typically substituted by 1, 2, 3, 4 or 5 fluoro atoms. Thus, a $C_1$-$C_4$ fluoroalkyl includes trifluoromethyl (—$CF_3$), difluoromethyl (—$CF_2$H), fluoromethyl (—$CFH_2$), difluoroethyl (—$CH_2CF_2$H), and the like. Such groups may be further substituted by groups suitable for alkyl groups, as further described herein.

In some embodiments of the present invention, alkyl and fluoroalkyl groups are optionally substituted by one or more optional substituents, and preferably by 1 to 3 optional substituents, which are independently OH, $C_1$-$C_2$ alkoxy, $C_1$-$C_2$ fluoroalkoxy, CN or $NR'_2$, where each R' is independently H, $C_1$-$C_2$ alkyl or $C_1$-$C_2$ fluoroalkyl.

Similarly, "alkoxyalkyl" refers to an alkyl group having the specified number of carbon atoms that is substituted by one or more alkoxy substituents. Alkoxyalkyl groups typically contain 1-4 carbon atoms in the alkyl portion and are substituted by 1, 2 or 3 $C_1$-$C_4$ alkyoxy substituents. Such groups are sometimes described herein as $C_1$-$C_4$ alkyoxy-$C_1$-$C_4$ alkyl.

"Aminoalkyl" refers to alkyl group having the specified number of carbon atoms that is substituted by one or more substituted or unsubstituted amino groups, as such groups are further defined herein. Aminoalkyl groups typically contain 1-6 carbon atoms in the alkyl portion and are substituted by 1, 2 or 3 amino substituents. Thus, a $C_1$-$C_6$ aminoalkyl includes, for example, aminomethyl (—$CH_2NH_2$), N,N-dimethylaminoethyl (—$CH_2CH_2N(CH_3)_2$), 3-(N-cyclopropylamino)-propyl (—$CH_2CH_2CH_2NH$—$^cPr$) and N-pyrrolidinylethyl (—$CH_2CH_2$.N-pyrrolidinyl).

"Hydroxyalkyl" refers to an alkyl group having the specified number of carbon atoms that is substituted by one or more hydroxy substituents, and typically contain 1-6 carbon atoms, preferably 1-4 carbon atoms, and 1, 2 or 3 hydroxy (i.e., "$C_1$-$C_6$ hydroxyalkyl"). Thus, $C_1$-$C_6$ hydroxyalkyl includes hydroxymethyl (—$CH_2OH$) and 2-hydroxyethyl (—$CH_2CH_2OH$).

"Alkenyl" refers to an alkyl group, as defined herein, consisting of at least two carbon atoms and at least one carbon-carbon double bond. Typically, alkenyl groups have 2 to 20 carbon atoms ("$C_2$-$C_{20}$ alkenyl"), preferably 2 to 12 carbon atoms ("$C_2$-$C_{12}$ alkenyl"), more preferably 2 to 8 carbon atoms ("$C_2$-$C_8$ alkenyl"), or 2 to 6 carbon atoms ("$C_2$-$C_6$ alkenyl"), or 2 to 4 carbon atoms ("$C_2$-$C_4$ alkenyl"). Representative examples include, but are not limited to, ethenyl, 1-propenyl, 2-propenyl, 1-, 2-, or 3-butenyl, and the like. Alkenyl groups are unsubstituted or substituted by the same groups that are described herein as suitable for alkyl.

"Alkynyl" refers to an alkyl group, as defined herein, consisting of at least two carbon atoms and at least one carbon-carbon triple bond. Alkynyl groups have 2 to 20 carbon atoms ("$C_2$-$C_{20}$ alkynyl"), preferably 2 to 12 carbon atoms ("$C_2$-$C_{12}$ alkynyl"), more preferably 2 to 8 carbon atoms ("$C_2$-$C_8$ alkynyl"), or 2 to 6 carbon atoms ("$C_2$-$C_6$ alkynyl"), or 2 to 4 carbon atoms ("$C_2$-$C_4$ alkynyl"). Representative examples include, but are not limited to, ethynyl, 1-propynyl, 2-propynyl, 1-, 2-, or 3-butynyl, and the like. Alkynyl groups are unsubstituted or substituted by the same groups that are described herein as suitable for alkyl.

"Alkylene" as used herein refers to a divalent hydrocarbyl group having the specified number of carbon atoms which can link two other groups together. Sometimes it refers to a group —$(CH_2)_t$— where t is 1-8, and preferably t is 1-6, t is 1-4 or t is 1-2. Such groups may be referred to as a $C_1$-$C_8$ alkylene, $C_1$-$C_6$ alkylene, $C_1$-$C_4$ alkylene, etc. Where specified, an alkylene can also be substituted by other groups and may include one or more degrees of unsaturation (i.e., an alkenylene or alkynlene moiety) or rings. The open valences of an alkylene need not be at opposite ends of the chain. Thus branched alkylene groups such as —CH(Me)-, —$CH_2$CH(Me)- and —$C(Me)_2$- are also included within the scope of the term 'alkylenes', as are cyclic groups such as cyclopropan-1,1-diyl and unsaturated groups such as ethylene (—CH═CH—) or propylene (—$CH_2$—CH═CH—). Where an alkylene group is described as optionally substituted, the substituents include those typically present on alkyl groups as described herein.

"Heteroalkylene" refers to an alkylene group as described above, wherein one or more non-contiguous carbon atoms of the alkylene chain are replaced by —N(R)—, —O— or —$S(O)_x$, where R is H or a substituent group suitable for a secondary amino moiety and x is 0-2. For example, the group —O—$(CH_2)_{1-3}$— is a '$C_2$-$C_4$'-heteroalkylene group, where one of the carbon atoms of the corresponding alkylene is replaced by O.

"Alkoxy" refers to a monovalent —O-alkyl group, wherein the alkyl portion has the specified number of carbon atoms. Alkoxy groups typically contain 1 to 8 carbon atoms ("$C_1$-$C_8$ alkoxy"), or 1 to 6 carbon atoms ("$C_1$-$C_6$ alkoxy"), or 1 to 4 carbon atoms ("$C_1$-$C_4$ alkoxy"). For example, $C_1$-$C_4$ alkoxy includes methoxy, ethoxy, isopropoxy, tert-butyloxy (i.e., —$OCH_3$, —$OCH_2CH_3$, —$OCH(CH_3)_2$, —$OC(CH_3)_3$), and the like. Alkoxy groups are unsubstituted or substituted on the alkyl portion by the same groups that are described herein as suitable for alkyl. In particular, alkoxy groups may be optionally substituted by one or more halo atoms, and in particular one or more fluoro atoms, up to the total number of hydrogen atoms present on the alkyl portion. Such groups are referred to as "haloalkoxy" (or, where fluorinated, more specifically as "fluoroalkoxy") groups having the specified number of carbon atoms and substituted by one or more halo substituents, Typically such groups contain from 1-6 carbon atoms, preferably 1-4 carbon atoms, and sometimes 1-2 carbon atoms, and 1, 2 or 3 halo atoms (i.e., "$C_1$-$C_6$ haloalkoxy", "$C_1$-$C_4$ haloalkoxy" or "$C_1$-$C_2$ haloalkoxy"). More specifically, fluorinated alkoxy groups may be specifically referred to as "fluoroalkoxy" groups, e.g., $C_1$-$C_6$, $C_1$-$C_4$ or $C_1$-$C_2$ fluoroalkoxy groups, which are typically substituted by 1, 2 or 3 fluoro atoms. Thus, a $C_1$-$C_4$ fluoroalkoxy includes trifluoromethyloxy (—$OCF_3$), difluoromethyloxy (—$OCF_2H$), fluoromethyloxy (—$OCFH_2$), difluoroethyloxy (—$OCH_2CF_2H$), and the like.

Similarly, "thioalkoxy" refers to a monovalent —S-alkyl group, wherein the alkyl portion has the specified number of carbon atoms and is optionally substituted on the alkyl portion by the same groups that are described herein as suitable for alkyl. For example, a $C_1$-$C_4$ thioalkoxy includes —$SCH_3$ and —$SCH_2CH_3$.

"Cycloalkyl" refers to a non-aromatic, saturated carbocyclic ring system containing the specified number of carbon atoms, which may be a monocyclic, spirocyclic, bridged or fused bicyclic or polycyclic ring system that is connected to the base molecule through a carbon atom of the cycloalkyl ring. Typically, the cycloalkyl groups of the invention contain 3 to 12 carbon atoms ("$C_3$-$C_{12}$ cycloalkyl"), preferably 3 to 8 carbon atoms ("$C_3$-$C_8$ cycloalkyl"). Partially unsaturated carbocyclic rings may be referred to as "cycloalkenyl" rings. Representative examples of cycloalkyl and cycloalkenyl rings include, e.g., cyclopropane, cyclobutane, cyclopentane, cyclopentene, cyclohexane, cyclohexene, cyclohexadiene, cycloheptane, cycloheptatriene, adamantane, and the like. Cycloalkyl groups are unsubstituted or substituted by the same groups that are described herein as suitable for alkyl, except that cycloalkyl rings may also be substituted by alkyl groups having the specified number of carbon atoms, which may be further optionally substituted as described herein.

Illustrative examples of cycloalkyl and cycloalkenyl rings include, but are not limited to, the following:

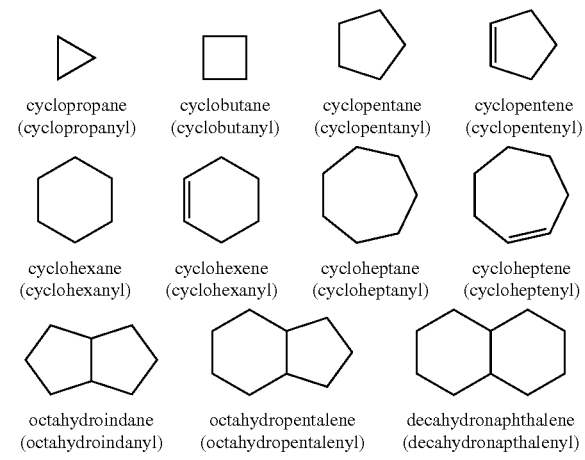

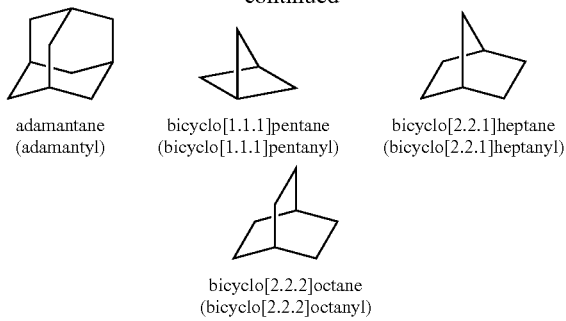

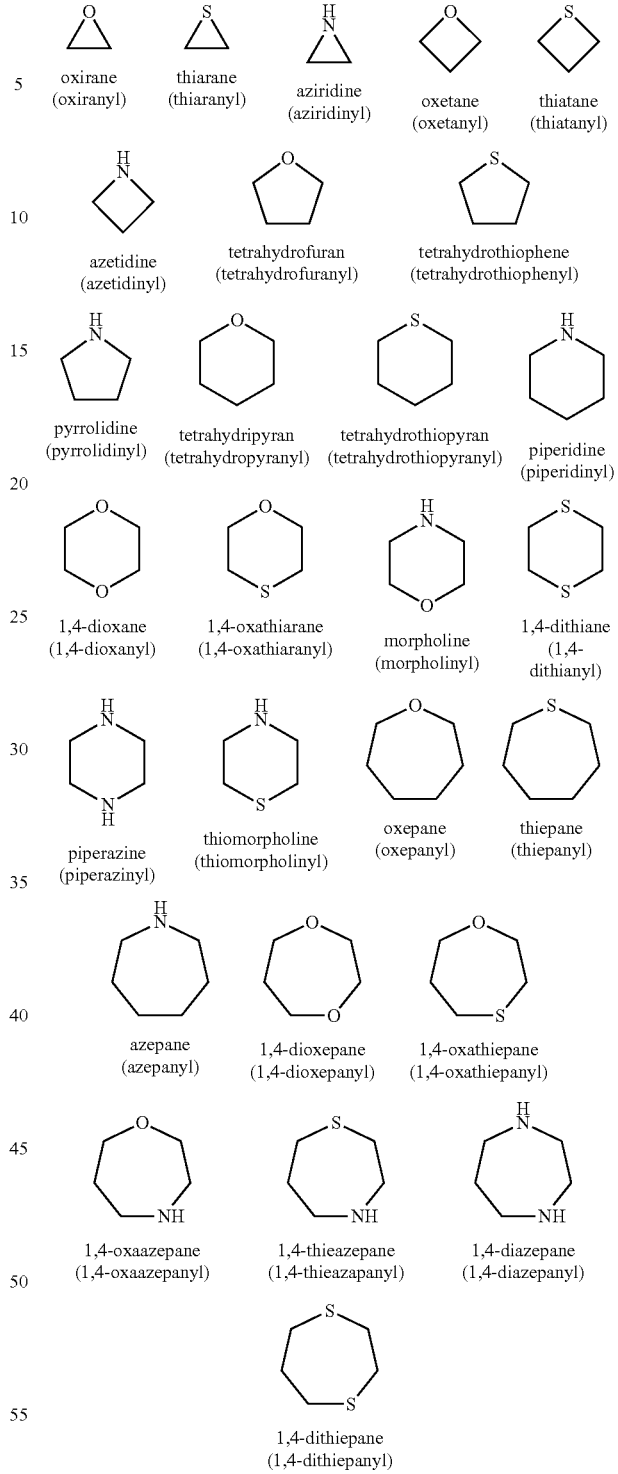

"Cycloalkylalkyl" is used to describe a cycloalkyl ring, typically a $C_3$-$C_8$ cycloalkyl, which is connected to the base molecule through an alkylene linker, typically a $C_1$-$C_4$ alkylene. Cycloalkylalkyl groups are sometimes described by the total number of carbon atoms in the carbocyclic ring and linker, and typically contain from 4-12 carbon atoms ("$C_4$-$C_{12}$ cycloalkylalkyl"). Thus a cyclopropylmethyl group is a $C_4$-cycloalkylalkyl group and a cyclohexylethyl is a $C_8$-cycloalkylalkyl. Cycloalkylalkyl groups are unsubstituted or substituted on the cycloalkyl and/or alkylene portions by the same groups that are described herein as suitable for alkyl groups.

The terms "heterocyclyl" or "heterocyclic" may be used interchangeably to refer to a non-aromatic, saturated ring system containing the specified number of ring atoms, including at least one heteroatom selected from N, O and S as a ring member, where ring S atoms are optionally substituted by one or two oxo groups (i.e., S(O), where x is 0, 1 or 2) and where the heterocyclic ring is connected to the base molecule via a ring atom, which may be C or N. Where specifically indicated, such heterocyclic rings may be partially unsaturated. Heterocyclic rings include rings which are spirocyclic, bridged, or fused to one or more other heterocyclic or carbocyclic rings, where such spirocyclic, bridged, or fused rings may themselves be saturated, partially unsaturated or aromatic to the extent unsaturation or aromaticity makes chemical sense, provided the point of attachment to the base molecule is an atom of the heterocyclic portion of the ring system. Preferably, heterocyclic rings contain 1 to 4 heteroatoms selected from N, O, and $S(O)_q$ as ring members, and more preferably 1 to 2 ring heteroatoms, provided that such heterocyclic rings do not contain two contiguous oxygen atoms.

Heterocyclyl groups are unsubstituted or substituted by suitable substituent groups, for example the same groups that are described herein as suitable for alkyl, except that heterocycyl rings may also be substituted by alkyl groups having the specified number of carbon atoms, which may be further optionally substituted as described herein. Such substituents may be present on the heterocycylic ring attached to the base molecule, or on a spirocyclic, bridged or fused ring attached thereto. In addition, ring N atoms are optionally substituted by groups suitable for an amine, e.g., alkyl, acyl, carbamoyl, sulfonyl, and the like.

Heterocycles typically include 3-12 membered heterocyclyl groups, 3-10 membered heterocyclyl groups, 3-8 membered heterocyclyl groups, and more preferably 3-6 membered heterocyclyl groups, in accordance with the definition herein.

Illustrative examples of saturated heterocycles include, but are not limited to:

Illustrative examples of partially unsaturated heterocycles include, but are not limited to:

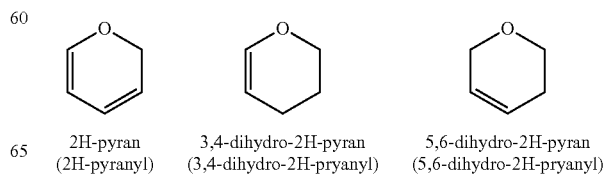

-continued

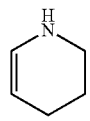
1,2,3,4-tetrahydropyridine
(1,2,3,4-tetrahydropyridinyl)

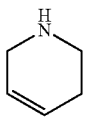
1,2,5,6-tetrahydropyridine
(1,2,5,6-tetrahyrodpyridinyl)

Illustrative examples of bridged, fused and spiro heterocycles include, but are not limited to:

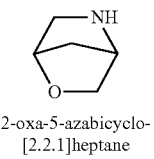
2-oxa-5-azabicyclo-[2.2.1]heptane

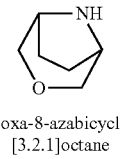
3-oxa-8-azabicyclo-[3.2.1]octane

3-azabicyclo-[3.1.0]hexane

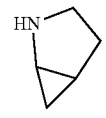
2-azabicyclo-[3.1.0]hexane

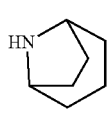
8-azabicyclo-[2.2.1]octane

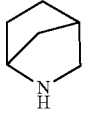
2-azabicyclo-[2.2.1]heptane

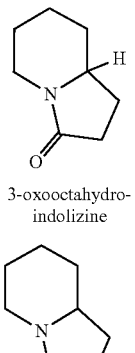
3-oxooctahydro-indolizine

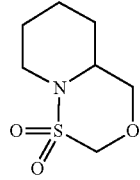
1,1-dioxidohexahydro-pyrido[1,2-d][1,3,4]-oxathiazine

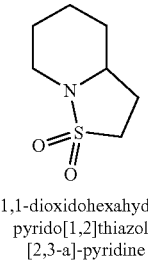
1,1-dioxidohexahydro-pyrido[1,2]thiazolo[2,3-a]-pyridine

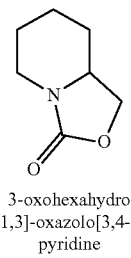
3-oxohexahydro[1,3]-oxazolo[3,4-a]pyridine

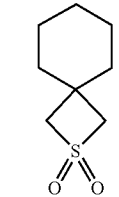
2,2-dioxido-2-thiaspiro-[3.5]nonane

In some embodiments, heterocyclic groups contain 3-12 ring members, including both carbon and non-carbon heteroatoms, and frequently 3-8 or 3-6 ring members. In certain preferred embodiments, substituent groups comprising 3-12 membered heterocycles are selected from azetidinyl, pyrrolidinyl, piperidinyl, piperazinyl, azepanyl, diazepanyl, oxetanyl, tetrahydrofuranyl, tetrahydropyranyl, tetrahydrothiopyranyl, morpholinyl and thiomorpholinyl rings, each of which are optionally substituted as described for the particular substituent group, to the extent such substitution makes chemical sense.

In some embodiments of the present invention, cycloalkyl and heterocyclyl groups are optionally substituted by one or more optional substituents, and preferably by 1 to 3 optional substituents, which are independently F, OH, CN, NR'$_2$ (where each R' is independently H, $C_1$-$C_2$ alkyl or $C_1$-$C_2$ fluoroalkyl), $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, NH$_2$, NHCH$_3$ or N(CH$_3$)$_2$.

It is understood that no more than two N, O or S atoms are ordinarily connected sequentially, except where an oxo group is attached to N or S to form a nitro or sulfonyl group, or in the case of certain heteroaromatic rings, such as triazine, triazole, tetrazole, oxadiazole, thiadiazole, and the like.

The term "heterocyclylalkyl" may be used to describe a heterocyclic group of the specified size that is connected to the base molecule through an alkylene linker of the specified length. Typically, such groups contain an optionally substituted 3-12 membered heterocycle attached to the base molecule through a $C_1$-$C_4$ alkylene linker. Where so indicated, such groups are optionally substituted on the alkylene portion by the same groups that are described herein as suitable for alkyl groups and on the heterocyclic portion by groups described as suitable for heterocyclic rings.

"Aryl" or "aromatic" refer to an optionally substituted monocyclic or fused bicyclic or polycyclic ring system having the well-known characteristics of aromaticity, wherein at least one ring contains a completely conjugated pi-electron system. Typically, aryl groups contain 6 to 20 carbon atoms ("$C_6$-$C_{20}$ aryl") as ring members, preferably 6 to 14 carbon atoms ("$C_6$-$C_{14}$ aryl") or more preferably, 6 to 12 carbon atoms ("$C_6$-$C_{12}$ aryl"). Fused aryl groups may include an aryl ring (e.g., a phenyl ring) fused to another aryl or heteroaryl ring or fused to a saturated or partially unsaturated carbocyclic or heterocyclic ring, provided the point of attachment to the base molecule on such fused ring systems is an atom of the aromatic portion of the ring system. Examples, without limitation, of aryl groups include phenyl, biphenyl, naphthyl, anthracenyl, phenanthrenyl, indanyl, indenyl, and tetrahydronaphthyl. The aryl group is unsubstituted or substituted as further described herein.

Similarly, "heteroaryl" or "heteroaromatic" refer to monocyclic or fused bicyclic or polycyclic ring systems having the well-known characteristics of aromaticity that contain the specified number of ring atoms and include at least one heteroatom selected from N, O and S as a ring member in an aromatic ring. The inclusion of a heteroatom permits aromaticity in 5-membered rings as well as 6-membered rings. Typically, heteroaryl groups contain 5 to 20 ring atoms ("5-20 membered heteroaryl"), preferably 5 to 14 ring atoms ("5-14 membered heteroaryl"), and more preferably 5 to 12 ring atoms ("5-12 membered heteroaryl"). Heteroaryl rings are attached to the base molecule via a ring atom of the heteroaromatic ring, such that aromaticity is maintained. Thus, 6-membered heteroaryl rings may be attached to the base molecule via a ring C atom, while 5-membered heteroaryl rings may be attached to the base molecule via a ring C or N atom. Heteroaryl groups may also be fused to another aryl or heteroaryl ring or fused to a saturated or partially unsaturated carbocyclic or heterocyclic ring, provided the point of attachment to the base molecule on such fused ring systems is an atom of the heteroaromatic portion of the ring system. Examples of unsubstituted heteroaryl groups often include, but are not limited to, pyrrole, furan, thiophene, pyrazole, imidazole, isoxazole, oxazole, isothiazole, thiazole, triazole, oxadiazole, thiadiazole, tetrazole, pyridine, pyridazine, pyrimidine, pyrazine, benzofuran, benzothiophene, indole, benzimidazole, indazole, quinoline, isoquinoline, purine, triazine, naphthryidine and carbazole. In frequent preferred embodiments, 5- or 6-membered heteroaryl groups are selected from the group consisting of pyrrolyl, furanyl, thiophenyl, pyrazolyl, imidazolyl, isoxazolyl, oxazolyl, isothiazolyl, thiazolyl, triazolyl, pyridinyl and pyrimidinyl, pyrazinyl or pyridazinyl rings. The heteroaryl group is unsubstituted or substituted as further described herein.

Aryl and heteroaryl moieties described herein as optionally substituted may be substituted by one or more substituent groups, which are selected independently unless otherwise indicated. The total number of substituent groups may equal the total number of hydrogen atoms on the aryl, heteroaryl or heterocyclyl moiety, to the extent such substitution makes chemical sense and aromaticity is maintained in the case of aryl and heteroaryl rings. Optionally substituted aryl or heteroaryl groups typically contain from 1 to 5 optional substituents, sometimes 1 to 4 optional substituents, preferably 1 to 3 optional substituents, or more preferably from 1-2 optional substituents.

Optional substituent groups suitable for use with aryl and heteroaryl rings include, but are not limited to: $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl and 5-12 membered heteroaryl; and halo, =O, —CN, —C(O)$R^x$, —CO$_2R^x$, —C(O)NR$^x$R$^y$, —SR$^x$, —SOR$^x$, —SO$_2$R$^x$, —SO$_2$NR$^x$R$^y$, —NO$_2$, —NR$^x$R$^y$, —N R$^x$C(O)R$^y$, —NR$^x$C(O)NR$^x$R$^y$, —NR$^x$C(O)OR$^x$, —NR$^x$SO$_2$R$^y$, —NR$^x$SO$_2$NR$^x$R$^y$, —OR$^x$, —OC(O)R$^x$ and —OC(O)NR$^x$R$^y$; where each R$^x$ and R$^y$ is independently H, $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl, or R$^x$ and R$^y$ may be taken together with the N atom to which they are attached to form a 3-12 membered heterocyclyl or 5-12 membered heteroaryl, each optionally containing 1, 2 or 3 additional heteroatoms selected from O, N and S(O)$_z$ where z is 0-2; each R and R$^y$ is optionally substituted with 1 to 3 substituents independently selected from the group consisting of halo, =O, =S, =N—CN, =N—OR', =NR', —CN, —C(O)R', —CO$_2$R', —C(O)NR'$_2$, SR', —SOR', —SO$_2$R', —SO$_2$NR'$_2$, —NO$_2$, —NR'$_2$, —NR'C(O)R', —NR'C(O)NR'$_2$, —NR'C(O)OR', —NR'SO$_2$ R', —NR'SO$_2$NR'$_2$, —OR', —OC(O)R' and —OC(O)NR'$_2$, wherein each R' is independently H, $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl; and each said $C_1$-$C_5$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl and 5-12 membered heteroaryl is optionally substituted as further defined herein.

In typical embodiments, optional substitution on aryl, heteroaryl and heterocyclyl rings includes one or more substituents, and preferably 1 to 3 substituents, independently selected from the group consisting of halo, $C_1$-$C_8$ alkyl, —OH, $C_1$-$C_8$ alkoxy, —CN, =O, —C(O)R$^x$, —COOR$^x$, —OC(O)R$^x$, —C(O)NR$^x$R$^y$, —NR$^x$C(O)R$^y$, —SR$^x$, —SOR$^x$, —SO$_2$R$^x$, —SO$_2$NR$^x$R$^y$, —NO$_2$, —NR$^x$R$^y$, —NR$^x$C(O)R$^y$, —NR$^x$C(O)NR$^x$R$^y$, —NR$^x$C(O)OR$^y$— NR$^x$SO$_2$R$^y$, —NR$^x$SO$_2$NR$^x$R$^y$, —OC(O)R$^x$, —OC(O)NR$^x$R$^y$, $C_3$-$C_8$ cycloalkyl, 3-12 membered heterocyclyl, $C_6$-$C_{12}$ aryl, 5-12 membered heteroaryl, —O—($C_3$-$C_8$ cycloalkyl), —O-(3-12 membered heterocyclyl), —O—($C_6$-$C_{12}$ aryl) and —O-(5-12 membered heteroaryl); where each R$^x$ and R$^y$ is independently H or $C_1$-$C_4$ alkyl, or R$^x$ and R$^y$ may be taken together with the N to which they are attached form a 3-12 membered heterocyclyl or 5-12 membered heteroaryl ring, each optionally containing 1, 2 or 3 additional heteroatoms selected from O, N and S(O)$_q$ where q is 0-2; and wherein each said $C_1$-$C_8$ alkyl, $C_1$-$C_8$ alkoxy, $C_3$-$C_8$ cycloalkyl, 3-12 membered heterocyclyl, $C_6$-$C_{12}$ aryl, 5-12 membered heteroaryl, —O—($C_3$-$C_8$ cycloalkyl), —O-(3-12 membered heterocyclyl), —O—($C_6$-$C_{12}$ aryl) and —O-(5-12 membered heteroaryl) that is described as an optional substituent or is part of R$^x$ or R$^y$ is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl), —N($C_1$-$C_4$ alkyl)$_2$ and N-pyrrolidinyl.

Examples of monocyclic heteroaryl groups include, but are not limited to:

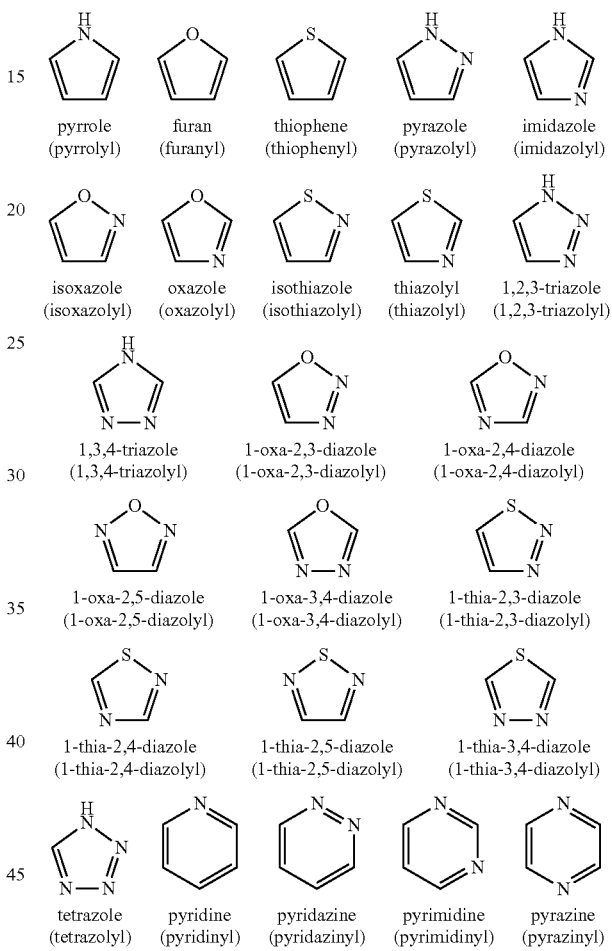

Illustrative examples of fused heteroaryl groups include, but are not limited to:

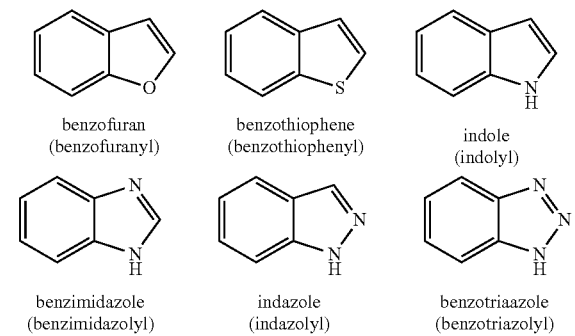

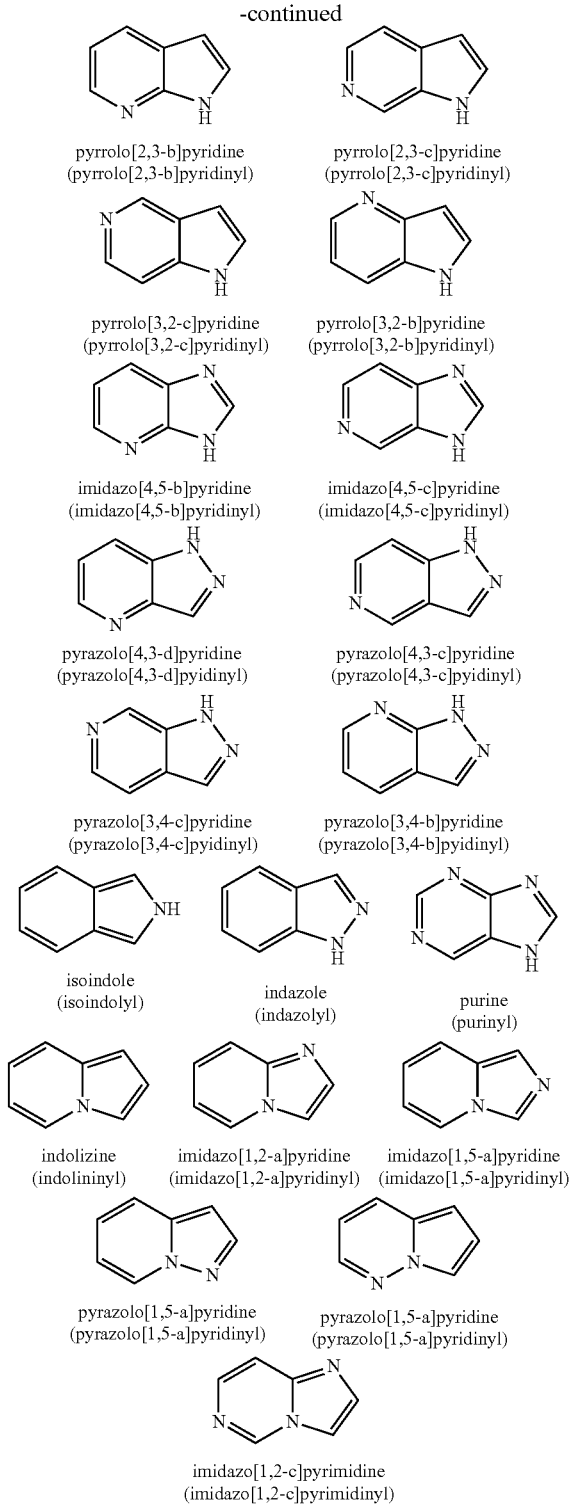

An "arylalkyl" group refers to an aryl group as described herein which is linked to the base molecule through an alkylene or similar linker. Arylalkyl groups are described by the total number of carbon atoms in the ring and linker. Thus, a benzyl group is a $C_7$-arylalkyl group and a phenylethyl is a $C_8$-arylalkyl. Typically, arylalkyl groups contain 7-16 carbon atoms ("$C_7$-$C_{16}$ arylalkyl"), wherein the aryl portion contains 6-12 carbon atoms and the alkylene portion contains 1-4 carbon atoms. Such groups may also be represented as —$C_1$-$C_4$ alkylene-$C_8$-$C_{12}$ aryl.

"Heteroarylalkyl" refers to a heteroaryl group as described above that is attached to the base molecule through an alkylene linker, and differs from "arylalkyl" in that at least one ring atom of the aromatic moiety is a heteroatom selected from N, O and S. Heteroarylalkyl groups are sometimes described herein according to the total number of non-hydrogen atoms (i.e., C, N, S and O atoms) in the ring and linker combined, excluding substituent groups. Thus, for example, pyridinylmethyl may be referred to as a "$C_7$"-heteroarylalkyl. Typically, unsubstituted heteroarylalkyl groups contain 6-20 non-hydrogen atoms (including C, N, S and O atoms), wherein the heteroaryl portion typically contains 5-12 atoms and the alkylene portion typically contains 1-4 carbon atoms. Such groups may also be represented as —$C_1$-$C_4$ alkylene-5-12 membered heteroaryl.

Similarly, "arylalkoxy" and "heteroarylalkoxy" refer to aryl and heteroaryl groups, attached to the base molecule through a heteroalkylene linker (i.e., —O-alkylene-), wherein the groups are described according to the total number of non-hydrogen atoms (i.e., C, N, S and O atoms) in the ring and linker combined. Thus, —O—$CH_2$-phenyl and —O—$CH_2$-pyridinyl groups would be referred to as C-arylalkoxy and C-heteroarylalkoxy groups, respectively.

Where an arylalkyl, arylalkoxy, heteroarylalkyl or heteroarylalkoxy group is described as optionally substituted, the substituents may be on either the divalent linker portion or on the aryl or heteroaryl portion of the group. The substituents optionally present on the alkylene or heteroalkylene portion are the same as those described above for alkyl or alkoxy groups generally, while the substituents optionally present on the aryl or heteroaryl portion are the same as those described above for aryl or heteroaryl groups generally.

"Hydroxy" refers to an OH group.

"Acyloxy" refers to a monovalent group —OC(O)alkyl, wherein the alkyl portion has the specified number of carbon atoms (typically $C_1$-$C_8$, preferably $C_1$-$C_6$ or $C_1$-$C_4$) that are optionally substituted by groups suitable for alkyl. Thus, $C_1$-$C_4$ acyloxy includes an —OC(O)$C_1$-$C_4$ alkyl substituent, e.g., —OC(O)$CH_3$.

"Acyl" refers to a monovalent group —C(O)alkyl, wherein the alkyl portion has the specified number of carbon atoms (typically $C_1$-$C_8$, preferably $C_1$-$C_6$ or $C_1$-$C_4$) and may be optionally substituted by groups suitable for alkyl, e.g., by F, OH or alkoxy. Thus, optionally substituted —C(O)$C_1$-$C_4$ alkyl includes unsubstituted acyl groups, such as —C(O)$CH_3$ (i.e., acetyl) and —C(O)$CH_2CH_3$ (i.e., propionyl), as well as substituted acyl groups such as —C(O)$CF_3$ (trifluoroacetyl), —C(O)$CH_2$OH (hydroxyacetyl), —C(O)$CH_2OCH_3$ (methoxyacetyl), —C(O)$CF_2$H (difluoroacetyl), and the like.

"Acylamino" refers to a monovalent group, —NHC(O)alkyl or —NRC(O)alkyl, wherein the alkyl portion has the specified number of carbon atoms (typically $C_1$-$C_8$, preferably $C_1$-$C_6$ or $C_1$-$C_4$) and is optionally substituted by groups suitable for alkyl. Thus, $C_1$-$C_4$ acylamino includes an —NHC(O)$C_1$-$C_4$ alkyl substituent, e.g., —NHC(O)$CH_3$.

"Aryloxy" or "heteroaryloxy" refer to optionally substituted O-aryl or O-heteroaryl, in each case where aryl and heteroaryl are as further defined herein.

"Arylamino" or "heteroarylamino" refer to an optionally substituted —NH-aryl, —NR-aryl, —NH-heteroaryl or —NR-heteroaryl, in each case where aryl and heteroaryl are as further defined herein and R represents a substituent suitable for an amine, e.g., an alkyl, acyl, carbamoyl or sulfonyl group, or the like.

"Cyano" refers to a —C≡N group.

"Unsubstituted amino" refers to a group —NH$_2$. Where the amino is described as substituted or optionally substituted, the term includes groups of the form —NR$^x$R$^y$, where each or R$^x$ and R$^y$ is independently H, alkyl, alkenyl, alkynyl, cycloalkyl, heterocyclyl, acyl, thioacyl, aryl, heteroaryl, cycloalkylalkyl, arylalkyl or heteroarylalkyl, in each case having the specified number of atoms and optionally substituted as described herein. For example, "alkylamino" refers to a group —NR$^x$R$^y$, wherein one of R$^x$ and R$^y$ is an alkyl moiety and the other is H, and "dialkylamino" refers to —NR$^x$R$^y$ wherein both of R$^x$ and R$^y$ are alkyl moieties, where the alkyl moieties having the specified number of carbon atoms (e.g., —NH—C$_1$-C$_4$ alkyl or —N(C$_1$-C$_4$ alkyl)$_2$). Typically, alkyl substituents on amines contain 1 to 8 carbon atoms, preferably 1 to 6 carbon atoms, or more preferably 1 to 4 carbon atoms. The term also includes forms wherein R$^x$ and R$^y$ are taken together with the N atom to which they are attached to form a 3-12 membered heterocyclyl or 5-12 membered heteroaryl ring, each of which may itself be optionally substituted as described herein for heterocyclyl or heteroaryl rings, and which may contain 1 to 3 additional heteroatoms selected from N, O and S(O)$_x$ where x is 0-2 as ring members, provided that such rings do not contain two contiguous oxygen atoms.

"Halogen" or "halo" refers to fluoro, chloro, bromo and iodo (F, Cl, Br, I). Preferably, halo refers to fluoro or chloro (F or Cl).

"Optional" or "optionally" means that the subsequently described event or circumstance may but need not occur, and the description includes instances where the event or circumstance occurs and instances in which it does not.

The terms "optionally substituted" and "substituted or unsubstituted" may be used interchangeably to indicate that the particular group being described may have no non-hydrogen substituents (i.e., unsubstituted), or the group may have one or more non-hydrogen substituents (i.e., substituted). If not otherwise specified, the total number of substituents that may be present is equal to the number of H atoms present on the unsubstituted form of the group being described. Where an optional substituent is attached via a double bond, such as an oxo (=O) substituent, the group occupies two available valences, so the total number of other substituents that are included is reduced by two.

Frequently, optionally substituted groups are substituted by 1 or more substituents independently selected from the list of optional substituents. In some embodiments, optionally substituted groups are substituted by 1, 2, 3, or more than 3 substituents independently selected from the list of optional substituents. For example, an alkyl group described as optionally substituted by R$^x$ means the alkyl group is optionally substituted by 1 or more R$^x$ substituents independently selected from the list of R$_x$ substituents provided for the alkyl group. Where deemed necessary, the description of an optionally substituted group herein may be revised to state that the group is optionally substituted by 1 or more of the indicated substituents. In the case where optional substituents are selected from a list of alternatives, the selected groups are independently selected and may be the same or different.

Throughout the disclosure, it will be understood that the number and nature of optional substituent groups will be limited to the extent that such substitutions make chemical sense.

In one aspect, the invention provides a compound of Formula (I):

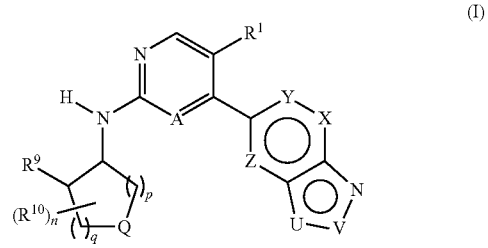

or a pharmaceutically acceptable salt thereof, wherein:
A is N or CH;
R$^1$ is H, F, Cl, CN, C$_1$-C$_2$ alkyl, C$_1$-C$_2$ fluoroalkyl or C$_1$-C$_2$ alkoxy, where each said C$_1$-C$_2$ alkyl and C$_1$-C$_2$ fluoroalkyl is optionally substituted by R$^{20}$;
U is NR$^2$ or CR$^3$;
V is N or CR$^4$ when U is NR$^2$; and
V is NR$^5$ when U is CR$^3$;
X is CR$^6$ or N;
Y is CR$^7$ or N;
Z is CR$^8$ or N;
R$^2$ and R$^3$ are H, C$_1$-C$_5$ alkyl, C$_1$-C$_5$ fluoroalkyl, C$_3$-C$_8$ cycloalkyl or 3-6 membered heterocyclyl, where each said C$_1$-C$_5$ alkyl and C$_1$-C$_5$ fluoroalkyl is optionally substituted by R$^{20}$ and each said C$_3$-C$_8$ cycloalkyl and 3-6 membered heterocyclyl is optionally substituted by R$^{21}$;
R$^4$ is H, C$_1$-C$_4$ alkyl, C$_1$-C$_4$ fluoroalkyl, C$_1$-C$_4$ alkoxy, C$_1$-C$_4$ fluoroalkoxy, C(O)R$^a$, C(O)NR$^b{}_2$, C$_3$-C$_8$ cycloalkyl or 3-6 membered heterocyclyl, where each said C$_1$-C$_4$ alkyl, C$_1$-C$_4$ fluoroalkyl, C$_1$-C$_4$ alkoxy and C$_1$-C$_4$ fluoroalkoxy is optionally substituted by R$^{20}$, each said C$_3$-C$_8$ cycloalkyl and 3-6 membered heterocyclyl is optionally substituted by R$^{21}$, R$^a$ is C$_1$-C$_2$ alkyl, and each R$^b$ is independently H or C$_1$-C$_2$ alkyl; and
R$^5$ is H, C$_1$-C$_4$ alkyl or C$_1$-C$_4$ fluoroalkyl, where each said C$_1$-C$_4$ alkyl and C$_1$-C$_4$ fluoroalkyl is optionally substituted by R$^{20}$; or
R$^2$ can be taken together with R$^4$, or R$^3$ can be taken together with R$^5$, to form a 5-7 membered heterocyclic ring, optionally containing an additional heteroatom selected from NR$^{24}$, O and S(O)$_m$ as a ring member, which ring is optionally substituted by R$^{21}$;
R$^6$ is H, F, Cl, CN, CH$_3$, CH$_2$F, CHF$_2$ or CF$_3$;
R$^7$ and R$^8$ are independently H, F, Cl, CN, C$_1$-C$_2$ alkyl, C$_1$-C$_2$ fluoroalkyl, C$_1$-C$_2$ alkoxy or C$_1$-C$_2$ fluoroalkoxy, where each said C$_1$-C$_2$ alkyl, C$_1$-C$_2$ fluoroalkyl, C$_1$-C$_2$ alkoxy and C$_1$-C$_2$ fluoroalkoxy is optionally substituted by R$^{20}$;
R$^9$ is H, OH, NH$_2$, NHCH$_3$ or N(CH$_3$)$_2$;
each R$^{10}$ is independently F, CN, C$_1$-C$_2$ alkyl or C$_1$-C$_2$ fluoroalkyl, where each said C$_1$-C$_2$ alkyl and C$_1$-C$_2$ fluoroalkyl is optionally substituted by R$^{20}$;
Q is NR$^{11}$ or O; or
Q is CR$^{12}$R$^{13}$, where R$^{12}$ and R$^{13}$ are taken together with the C atom to which they are attached to form a 4-6 membered heterocyclic ring containing NR$^{11}$ or O as a ring member, which ring is optionally further substituted by R$^{10}$;
R$^{11}$ is H, C$_1$-C$_4$ alkyl, C$_1$-C$_4$ fluoroalkyl, SO$_2$R$^{14}$, SO$_2$NR$^{15}$R$^{16}$, COR$^{17}$, COOR$^{17}$ or CONR$^{18}$R$^{19}$, where each said C$_1$-C$_4$ alkyl and C$_1$-C$_4$ fluoroalkyl is optionally substituted by R$^{20}$, SO$_2$R$^{14}$, SO$_2$NR$^{15}$R$^{16}$, COR$^{17}$, COOR$^{17}$ or CONR$^{18}$R$^{19}$;

$R^{14}$ is $C_1$-$C_4$ alkyl or $C_1$-$C_4$ fluoroalkyl;

each $R^{15}$ and $R^{16}$ is independently H or $CH_3$;

$R^{17}$ is $C_1$-$C_4$ alkyl, $C_1$-$C_4$ fluoroalkyl, $C_3$-$C_8$ cycloalkyl or 3-6 membered heterocyclyl, where each said $C_1$-$C_4$ alkyl and $C_1$-$C_4$ fluoroalkyl is optionally substituted by $R^{20}$ and each said $C_3$-$C_8$ cycloalkyl and 3-6 membered heterocyclyl is optionally substituted by $R^{21}$;

each $R^{18}$ and $R^{19}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$;

each $R^{20}$ is independently OH, $C_1$-$C_2$ alkoxy, $C_1$-$C_2$ fluoroalkoxy, CN, $NR^{22}R^{23}$, $C_3$-$C_8$ cycloalkyl or 3-6 membered heterocyclyl, where each said $C_3$-$C_8$ cycloalkyl and 3-6 membered heterocyclyl is optionally substituted by $R^{21}$;

each $R^{21}$ is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$;

each $R^{22}$ and $R^{23}$ is independently H, $C_1$-$C_3$ alkyl, $C_1$-$C_3$ fluoroalkyl, $C_3$-$C_8$ cycloalkyl or 3-6 membered heterocyclyl, where each said $C_1$-$C_3$ alkyl and $C_1$-$C_3$ fluoroalkyl is optionally further substituted by OH, $C_1$-$C_2$ alkoxy or $C_1$-$C_2$ fluoroalkoxy and each said $C_3$-$C_8$ cycloalkyl and 3-6 membered heterocyclyl is optionally further substituted by F, OH, $C_1$-$C_2$ alkyl, $C_1$-$C_2$ fluoroalkyl, $C_1$-$C_2$ alkoxy or $C_1$-$C_2$ fluoroalkoxy; or $R^{22}$ and $R^{23}$ may be taken together with the nitrogen atom to which they are attached to form an azetidinyl ring, where said ring is optionally substituted by F, OH, $C_1$-$C_2$ alkyl, $C_1$-$C_2$ fluoroalkyl, $C_1$-$C_2$ alkoxy or $C_1$-$C_2$ fluoroalkoxy;

$R^{24}$ is H, $C_1$-$C_4$ alkyl, $C_1$-$C_4$ fluoroalkyl, $SO_2R^{25}$, $SO_2NR^{26}R^{27}$, $COR^{28}$, $COOR^{28}$ or $CONR^{29}R^{30}$;

$R^{25}$ is $C_1$-$C_4$ alkyl or $C_1$-$C_4$ fluoroalkyl;

each $R^{26}$ and $R^{27}$ is independently H or $CH_3$;

$R^{28}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$;

each $R^{29}$ and $R^{30}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$;

m is 0, 1 or 2;

n is 0, 1, 2, 3 or 4;

p is 1, 2 or 3; and q is 0, 1, 2 or 3;

wherein the sum of p and q is an integer from 1 to 4.

In another aspect, the invention provides a compound of Formula (II):

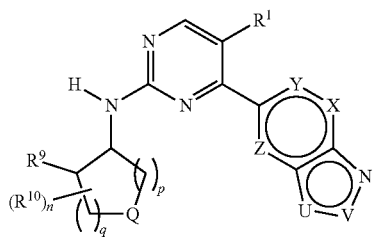

(II)

or a pharmaceutically acceptable salt thereof, wherein:

$R^1$ is H, F, Cl, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;

U is $NR^2$ or $CR^3$;

V is N or $CR^4$ when U is $NR^2$; and

V is $NR^5$ when U is $CR^3$;

X is $CR^6$ or N;

Y is $CR^7$ or N;

Z is $CR^8$ or N;

$R^2$ and $R^3$ are H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$;

$R^4$ is H, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$;

$R^5$ is H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$;

$R^6$ is H, F, Cl, CN, $CH_3$, $CH_2F$, $CHF_2$ or $CF_3$;

$R^7$ and $R^8$ are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy, where each said $C_1$-$C_2$ alkyl, $C_1$-$C_2$ fluoroalkyl, $C_1$-$C_2$ alkoxy and $C_1$-$C_2$ fluoroalkoxy is optionally substituted by $R^{20}$;

$R^9$ is H, OH, $NH_2$, $NHCH_3$ or $N(CH_3)_2$;

each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;

Q is $NR^{11}$ or O; or

Q is $CR^{12}R^{13}$, where $R^{12}$ and $R^{13}$ are taken together with the C atom to which they are attached to form a 4-6 membered heterocyclic ring containing $NR^{11}$ or O as a ring member, which ring is optionally further substituted by $R^{10}$;

$R^{11}$ is H, $C_1$-$C_4$ alkyl, $C_1$-$C_4$ fluoroalkyl, $SO_2R^{14}$, $SO_2NR^{15}R^{16}$, $COR^{17}$, $COOR^{17}$ or $CONR^{18}R^{19}$;

$R^{14}$ is $C_1$-$C_4$ alkyl or $C_1$-$C_4$ fluoroalkyl;

each $R^{15}$ and $R^{16}$ is independently H or $CH_3$;

$R^{17}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$;

each $R^{18}$ and $R^{19}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$;

each $R^{20}$ is independently OH, $C_1$-$C_2$ alkoxy, $C_1$-$C_2$ fluoroalkoxy, CN or $NR^{22}R^{23}$;

each $R^{21}$ is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$;

each $R^{22}$ and $R^{23}$ is independently H, $C_1$-$C_2$ alkyl or $C_1$-$C_2$ fluoroalkyl; or $R^{22}$ and $R^{23}$ may be taken together with the nitrogen atom to which they are attached to form an azetidinyl ring, which is optionally substituted by F or OH;

n is 0, 1, 2, 3 or 4;

p is 1, 2 or 3; and q is 0, 1, 2 or 3;

wherein the sum of p and q is an integer from 1 to 4.

In another aspect, the invention provides a compound of Formula (III):

(III)

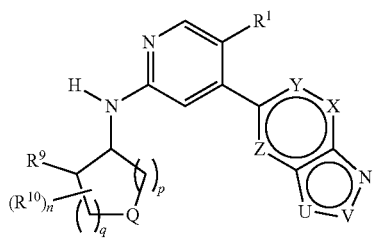

or a pharmaceutically acceptable salt thereof, wherein:

$R^1$ is H, F, Cl, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;

U is $NR^2$ or $CR^3$;

V is N or $CR^4$ when U is $NR^2$; and

V is $NR^5$ when U is $CR^3$;

X is $CR^6$ or N;

Y is $CR^7$ or N;

Z is $CR^8$ or N;

$R^2$ and $R^3$ are H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$;

$R^4$ is H, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$;

$R^5$ is H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$;

$R^6$ is H, F, Cl, CN, $CH_3$, $CH_2F$, $CHF_2$ or $CF_3$;

$R^7$ and $R^8$ are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy, where each said $C_1$-$C_2$ alkyl, $C_1$-$C_2$ fluoroalkyl, $C_1$-$C_2$ alkoxy and $C_1$-$C_2$ fluoroalkoxy is optionally substituted by $R^{20}$;

$R^9$ is H, OH, $NH_2$, $NHCH_3$ or $N(CH_3)_2$;

each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;

Q is $NR^{11}$ or O; or

Q is $CR^{12}R^{13}$, where $R^{12}$ and $R^{13}$ are taken together with the C atom to which they are attached to form a 4-6 membered heterocyclic ring containing $NR^{11}$ or O as a ring member, which ring is optionally further substituted by $R^{10}$;

$R^{11}$ is H, $C_1$-$C_4$ alkyl, $C_1$-$C_4$ fluoroalkyl, $SO_2R^{14}$, $SO_2NR^{15}R^{16}$, $COR^{17}$, $COOR^{17}$ or $CONR^{18}R^{19}$;

$R^{14}$ is $C_1$-$C_4$ alkyl or $C_1$-$C_4$ fluoroalkyl;

each $R^{15}$ and $R^{16}$ is independently H or $CH_3$;

$R^{17}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$;

each $R^{18}$ and $R^{19}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$;

each $R^{20}$ is independently OH, $C_1$-$C_2$ alkoxy, $C_1$-$C_2$ fluoroalkoxy, CN or $NR^{22}R^{23}$;

each $R^{21}$ is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$;

each $R^{22}$ and $R^{23}$ is independently H, $C_1$-$C_2$ alkyl or $C_1$-$C_2$ fluoroalkyl; or $R^{22}$ and $R^{23}$ may be taken together with the nitrogen atom to which they are attached to form an azetidinyl ring, which is optionally substituted by F or OH;

n is 0, 1, 2, 3 or 4;

p is 1, 2 or 3; and q is 0, 1, 2 or 3;

wherein the sum of p and q is an integer from 1 to 4.

In another aspect, the invention provides a compound of Formula (IV):

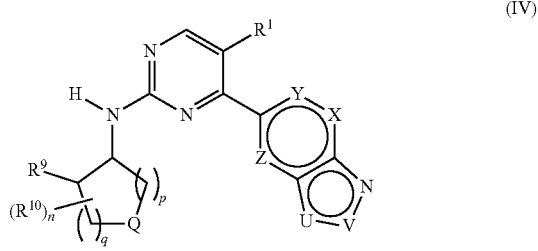

(IV)

or a pharmaceutically acceptable salt thereof, wherein:

$R^1$ is H, F, Cl, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;

U is $NR^2$ or $CR^3$;

V is N or $CR^4$ when U is $NR^2$; and

V is $NR^5$ when U is $CR^3$;

X is $CR^6$ or N;

Y is $CR^7$ or N;

Z is $CR^8$ or N;

$R^2$ and $R^3$ are H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$;

$R^4$ is H, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$; and $R^5$ is H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$; or $R^2$ can be taken together with $R^4$, or $R^3$ can be taken together with $R^5$, to form a 5-7 membered heterocyclic ring, optionally containing an additional heteroatom selected from $NR^{24}$, O and $S(O)_m$ as a ring member, which ring is optionally substituted by $R^{21}$;

$R^6$ is H, F, Cl, CN, $CH_3$, $CH_2F$, $CHF_2$ or $CF_3$;

$R^7$ and $R^8$ are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy, where each said $C_1$-$C_2$ alkyl, $C_1$-$C_2$ fluoroalkyl, $C_1$-$C_2$ alkoxy and $C_1$-$C_2$ fluoroalkoxy is optionally substituted by $R^{20}$;

$R^9$ is H, OH, $NH_2$, $NHCH_3$ or $N(CH_3)_2$;

each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;

Q is $NR^{11}$ or O; or

Q is $CR^{12}R^{13}$, where $R^{12}$ and $R^{13}$ are taken together with the C atom to which they are attached to form a 4-6 membered heterocyclic ring containing $NR^{11}$ or O as a ring member, which ring is optionally further substituted by $R^{10}$;

R[11] is H, $C_1$-$C_4$ alkyl, $C_1$-$C_4$ fluoroalkyl, $SO_2R^{14}$, $SO_2NR^{15}R^{16}$, $COR^{17}$, $COOR^{17}$ or $CONR^{18}R^{19}$;

R[14] is $C_1$-$C_4$ alkyl or $C_1$-$C_4$ fluoroalkyl;

each R[15] and R[16] is independently H or $CH_3$;

R[17] is $C_1$-$C_4$ alkyl or $C_1$-$C_4$ fluoroalkyl, where each said $C_1$-$C_4$ alkyl and $C_1$-$C_4$ fluoroalkyl is optionally substituted by R[20];

each R[18] and R[19] is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by R[20];

each R[20] is independently OH, $C_1$-$C_2$ alkoxy, $C_1$-$C_2$ fluoroalkoxy, CN or $NR^{22}R^{23}$;

each R[21] is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$;

each R[22] and R[23] is independently H, $C_1$-$C_2$ alkyl or $C_1$-$C_2$ fluoroalkyl; or R[22] and R[23] may be taken together with the nitrogen atom to which they are attached to form an azetidinyl ring, which is optionally substituted by F or OH;

R[24] is H, $C_1$-$C_4$ alkyl, $C_1$-$C_4$ fluoroalkyl, $SO_2R^{25}$, $SO_2NR^{26}R^{27}$, $COR^{28}$, $COOR^{28}$ or $CONR^{29}R^{30}$;

R[25] is $C_1$-$C_4$ alkyl or $C_1$-$C_4$ fluoroalkyl;

each R[26] and R[27] is independently H or $CH_3$;

R[28] is $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$;

each R[29] and R[30] is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$;

m is 0, 1 or 2;

n is 0, 1, 2, 3 or 4;

p is 1, 2 or 3; and q is 0, 1, 2 or 3;

wherein the sum of p and q is an integer from 1 to 4.

In another aspect, the invention provides a compound of Formula (V):

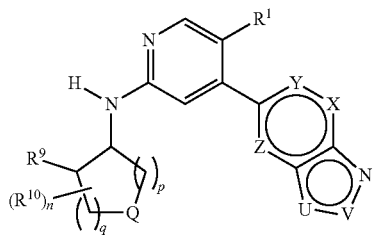

(V)

or a pharmaceutically acceptable salt thereof, wherein:

R[1] is H, F, Cl, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by R[20];

U is $NR^2$ or $CR^3$;

V is N or $CR^4$ when U is $NR^2$; and

V is $NR^5$ when U is $CR^3$;

X is $CR^6$ or N;

Y is $CR^7$ or N;

Z is $CR^8$ or N;

R[2] and R[3] are H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by R[20] and each said $C_3$-$C_8$ cycloalkyl and 3-6 membered heterocyclyl is optionally substituted by R[21];

R[4] is H, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally substituted by R[20]; and R[5] is H, $C_1$-$C_4$ alkyl or $C_1$-$C_4$ fluoroalkyl, where each said $C_1$-$C_4$ alkyl and $C_1$-$C_4$ fluoroalkyl is optionally substituted by R[20]; or R[2] can be taken together with R[4], or R[3] can be taken together with R[5], to form a 5-7 membered heterocyclic ring, optionally containing an additional heteroatom selected from $NR^{24}$, O and $S(O)_m$ as a ring member, which ring is optionally substituted by R[21];

R[6] is H, F, Cl, CN, $CH_3$, $CH_2F$, $CHF_2$ or $CF_3$;

R[7] and R[8] are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy, where each said $C_1$-$C_2$ alkyl, $C_1$-$C_2$ fluoroalkyl, $C_1$-$C_2$ alkoxy and $C_1$-$C_2$ fluoroalkoxy is optionally substituted by R[20];

R[9] is H, OH, $NH_2$, $NHCH_3$ or $N(CH_3)_2$;

each R[10] is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by R[20];

Q is $NR^{11}$ or O; or

Q is $CR^{12}R^{13}$, where R[12] and R[13] are taken together with the C atom to which they are attached to form a 4-6 membered heterocyclic ring containing $NR^{11}$ or O as a ring member, which ring is optionally further substituted by R[10];

R[11] is H, $C_1$-$C_4$ alkyl, $C_1$-$C_4$ fluoroalkyl, $SO_2R^{14}$, $SO_2NR^{15}R^{16}$, $COR^{17}$, $COOR^{17}$ or $CONR^{18}R^{19}$;

R[14] is $C_1$-$C_4$ alkyl or $C_1$-$C_4$ fluoroalkyl;

each R[15] and R[16] is independently H or $CH_3$;

R[17] is $C_1$-$C_4$ alkyl or $C_1$-$C_4$ fluoroalkyl, where each said $C_1$-$C_4$ alkyl and $C_1$-$C_4$ fluoroalkyl is optionally substituted by R[20];

each R[18] and R[19] is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by R[20];

each R[20] is independently OH, $C_1$-$C_2$ alkoxy, $C_1$-$C_2$ fluoroalkoxy, CN or $NR^{22}R^{23}$;

each R[21] is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$;

each R[22] and R[23] is independently H, $C_1$-$C_2$ alkyl or $C_1$-$C_2$ fluoroalkyl; or R[22] and R[23] may be taken together with the nitrogen atom to which they are attached to form an azetidinyl ring, which is optionally substituted by F or OH;

R[24] is H, $C_1$-$C_4$ alkyl, $C_1$-$C_4$ fluoroalkyl, $SO_2R^{25}$, $SO_2NR^{26}R^{27}$, $COR^{28}$, $COOR^{28}$ or $CONR^{29}R^{30}$;

R[25] is $C_1$-$C_4$ alkyl or $C_1$-$C_4$ fluoroalkyl;

each R[26] and R[27] is independently H or $CH_3$;

R[28] is $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$;

each R[29] and R[30] is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$;

m is 0, 1 or 2;

n is 0, 1, 2, 3 or 4;

p is 1, 2 or 3; and q is 0, 1, 2 or 3;

wherein the sum of p and q is an integer from 1 to 4.

In frequent embodiments of Formula (IV) and Formula (V), $R^2$ is taken together with $R^4$, or $R^3$ is taken together with $R^5$, to form a 5-7 membered heterocyclic ring, optionally containing an additional heteroatom selected from $NR^{24}$, O and $S(O)_m$ as a ring member, which ring is optionally substituted by $R^{21}$.

In some embodiments, the compounds of Formulae (I) to (V) have the absolute stereochemistry as shown in one of Formulae (I-A), (I-B), (I-C) or (I-D); (II-A), (II-B), (I-C) or (II-D); (III-A), (III-B), (III-C) or (III-D); (IV-A), (IV-B), (IV-C) or (IV-D); and (V-A), (V-B), (V-C) or (V-D):

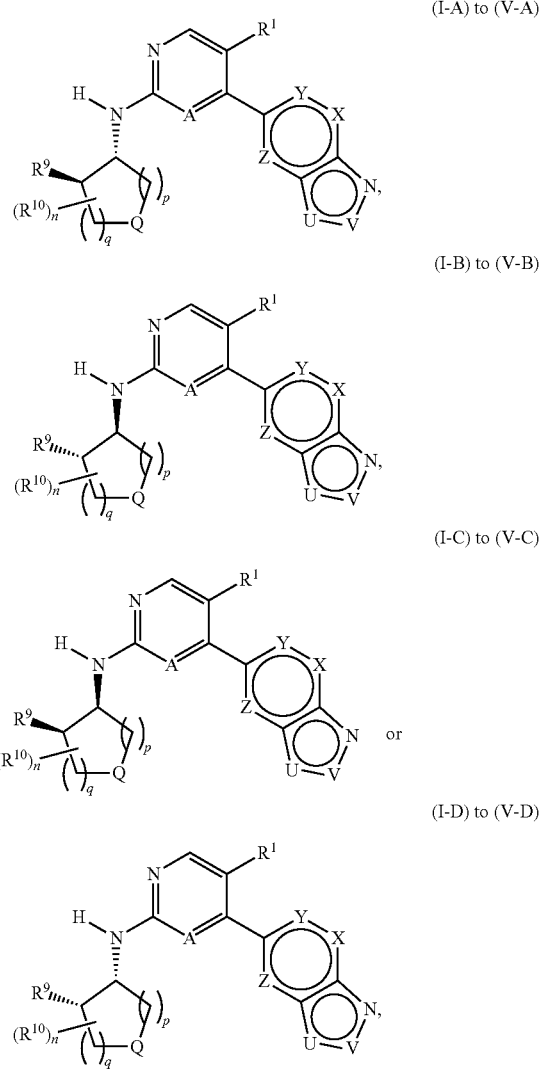

(I-A) to (V-A)

(I-B) to (V-B)

(I-C) to (V-C)

or (I-D) to (V-D)

wherein A in Formula (I-A) to (I-D) is N or CH; A in Formula (II-A) to (II-D) is replaced by N; A in Formula (III-A) to (III-D) is replaced by CH; A in Formula (IV-A) to (IV-D) is replaced by N; and A in Formula (V-A) to (V-D) is replaced by CH; or a pharmaceutically acceptable salt of one of the foregoing.

Each of the aspects and embodiments described herein with respect to Formula (I) is also applicable to compounds of Formulae (I-A), (I-B), (I-C) or (I-D).

Each of the aspects and embodiments described herein with respect to Formula (II) is also applicable to compounds of Formulae (II-A), (II-B), (I-C) or (II-D).

Each of the aspects and embodiments described herein with respect to Formula (III) is also applicable to compounds of Formulae (III-A), (III-B), (III-C) or (III-D).

Each of the aspects and embodiments described herein with respect to Formula (IV) is also applicable to compounds of Formulae (IV-A), (IV-B), (IV-C) or (IV-D).

Each of the aspects and embodiments described herein with respect to Formula (V) is also applicable to compounds of Formulae (V-A), (V-B), (V-C) or (V-D).

In compounds of Formula (I), A is N or CH. In some embodiments, A is N. In other embodiments, A is CH.

In compounds of Formula (I), $R^1$ is H, F, Cl, CN, $C_1$-$C_2$ alkyl, $C_1$-$C_2$ fluoroalkyl or $C_1$-$C_2$ alkoxy, where each said $C_1$-$C_2$ alkyl and $C_1$-$C_2$ fluoroalkyl is optionally substituted by $R^{20}$. In some embodiments, $R^1$ is F or Cl. In some such embodiments, $R^1$ is F. In some such embodiments, $R^1$ is Cl.

In compounds of Formula (I), U is $NR^2$ or $CR^3$; V is N or $CR^4$ when U is $NR^2$; and V is $NR^5$ when U is $CR^3$. In some embodiments, U is $NR^2$ and V is N or $CR^4$. In some such embodiments, U is $NR^2$ and V is $CR^4$. In some such embodiments, U is $NR^2$ and V is N. In some embodiments, U is $CR^3$ and V is $NR^5$.

In compounds of Formula (I), X is $CR^6$ or N. In some embodiments, X is $CR^6$. In some embodiments, X is N, In compounds of Formula (I), Y is $CR^7$ or N. In some embodiments, Y is $CR^7$. In some embodiments, Y is N.

In compounds of Formula (I), Z is $CR^8$ or N. In some embodiments, Z is $CR^8$. In some embodiments, Z is N.

In frequent embodiments of Formula (I), X is $CR^6$, Y is $CR^7$ and Z is $CR^8$. In other embodiments of Formula (I), at least one of X, Y and Z is N.

In some embodiments of Formula (I), $R^2$ and $R^3$ are H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$.

In some such embodiments, $R^2$ and $R^3$ are H, $C_1$-$C_5$ alkyl or $C_1$-$C_5$ fluoroalkyl, where each said $C_1$-$C_5$ alkyl and $C_1$-$C_5$ fluoroalkyl is optionally substituted by $R^{20}$. In other such embodiments, $R^2$ and $R^3$ are $C_3$-$C_8$ cycloalkyl or 3-6 membered heterocyclyl, where each said $C_3$-$C_8$ cycloalkyl and 3-6 membered heterocyclyl is optionally substituted by $R^{21}$.

In some embodiments of Formula (I), $R^2$ is $C_1$-$C_5$ alkyl or $C_1$-$C_5$ fluoroalkyl, where each said $C_1$-$C_5$ alkyl and $C_1$-$C_5$ fluoroalkyl is optionally substituted by $R^{20}$. In some embodiments of Formula (I), $R^3$ is $C_1$-$C_5$ alky or $C_1$-$C_5$ fluoroalkyl, where each said $C_1$-$C_5$ alkyl and $C_1$-$C_5$ fluoroalkyl is optionally substituted by $R^{20}$.

In some embodiments of Formula (I), $R^4$ is H, $C_1$-$C_4$ alkyl, $C_1$-$C_4$ fluoroalkyl, $C_1$-$C_4$ alkoxy, $C_1$-$C_4$ fluoroalkoxy, $C(O)R^a$, $C(O)NR^b_2$, $C_3$-$C_8$ cycloalkyl or 3-6 membered heterocyclyl; where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$, each said $C_3$-$C_8$ cycloalkyl and 3-6 membered heterocyclyl is optionally substituted by $R^{21}$, $R^a$ is $C_1$-$C_2$ alkyl, and each $R^b$ is independently H or $C_1$-$C_2$ alkyl.

In some such embodiments, $R^4$ is H, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$. In some such embodiments, $R^4$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some such embodiments, $R^{20}$ is OH. In other such embodiments, $R^{20}$ is $C_3$-$C_8$ cycloalkyl or 3-6 membered heterocyclyl, where each said $C_3$-$C_8$ cycloalkyl and 3-6 membered heterocyclyl is optionally substituted by $R^{21}$.

In other such embodiments, $R^4$ is $C(O)R^a$ or $C(O)NR^b_2$, where $R^a$ is $C_1$-$C_2$ alkyl, and each $R^b$ is independently H or $C_1$-$C_2$ alkyl. In still other such embodiments, $R^4$ is $C_3$-$C_8$ cycloalkyl or 3-6 membered heterocyclyl, where each said $C_3$-$C_8$ cycloalkyl and 3-6 membered heterocyclyl is optionally substituted by $R^{21}$.

In some embodiments of Formula (I), $R^5$ is H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$.

In other embodiments of Formula (I), $R^2$ can be taken together with $R^4$, or $R^3$ can be taken together with $R^5$, to form a 5-7 membered heterocyclic ring, optionally containing an additional heteroatom selected from $NR^{24}$, O and $S(O)_m$ as a ring member, which ring is optionally substituted by $R^{21}$.

In some embodiments of Formula (I), $R^2$ is taken together with $R^4$ to form a 5-7 membered heterocyclic ring, optionally containing an additional heteroatom selected from $NR^{24}$, O and $S(O)_m$ as a ring member, which ring is optionally substituted by $R^{21}$. In some such embodiments, the 5-7 membered heterocyclic ring contains O as an additional heteroatom. In some such embodiments, the 5-7 membered heterocyclic ring contains $NR^{24}$ as an additional heteroatom.

In some embodiments of Formula (I), $R^3$ is taken together with $R^5$ to form a 5-7 membered heterocyclic ring, optionally containing an additional heteroatom selected from $NR^{24}$, O and $S(O)_m$ as a ring member, which ring is optionally substituted by $R^{21}$. In some such embodiments, the 5-7 membered heterocyclic ring contains O as an additional heteroatom. In some such embodiments, the 5-7 membered heterocyclic ring contains $NR^{24}$ as an additional heteroatom.

In compounds of Formula (I), $R^6$ is H, F, Cl, CN, $CH_3$, $CH_2F$, $CHF_2$ or $CF_3$. In some embodiments, $R^6$ is F or Cl. In some such embodiments, $R^6$ is F. In some such embodiments, $R^6$ is Cl. In some embodiments, $R^6$ is H. In other embodiments, $R^6$ is CN, $CH_3$, $CH_2F$, $CHF_2$ or $CF_3$.

In compounds of Formula (I), $R^7$ and $R^8$ are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy, where each said $C_1$-$C_2$ alkyl, $C_1$-$C_2$ fluoroalkyl, $C_1$-$C_2$ alkoxy and $C_1$-$C_2$ fluoroalkoxy is optionally substituted by $R^{20}$. In some such embodiments, $R^7$ is H. In some such embodiments, $R^8$ is H. In some such embodiments, $R^7$ and $R^8$ are H.

In compounds of Formula (I), $R^9$ is H, OH, $NH_2$, $NHCH_3$ or $N(CH_3)_2$. In preferred embodiments of Formula (I), $R^9$ is OH.

In compounds of Formula (I), each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$. In some embodiments, n is 0 and $R^{10}$ is absent. In other embodiments, n is 1 or 2 and $R^{10}$ is independently F, CN, $C_1$-$C_2$ alkyl or $C_1$-$C_2$ fluoroalkyl. In some embodiments, n is 1 or 2 and $R^{10}$ is independently F or $CH_3$.

In some embodiments of Formula (I), Q is $NR^{11}$ or O. In some embodiments, Q is O. In some embodiments, Q is O, p is 2 and q is 1. In some such embodiments, n is 0 and $R^{10}$ is absent.

In other embodiments of Formula (I), Q is $NR^{11}$. In some embodiments, Q is $NR^{11}$, p is 2 and q is 1. In some such embodiments, $R^{11}$ is $SO_2R^{14}$. In other such embodiments, $R^{11}$ is $COR^{17}$. In some such embodiments, n is 0 and $R^{10}$ is absent.

In some embodiments of Formula (I), Q is $CR^{12}R^{13}$, where $R^{12}$ and $R^{13}$ are taken together with the C atom to which they are attached to form a 4-6 membered heterocyclic ring containing $NR^{11}$ or O as a ring member, which ring is optionally further substituted by $R^{10}$. In some such embodiments, n is 0 and $R^{10}$ is absent.

In compounds of Formula (I), $R^{11}$ is H, $C_1$-$C_4$ alkyl, $C_1$-$C_4$ fluoroalkyl, $SO_2R^{14}$, $SO_2NR^{15}R^{16}$, $COR^{17}$, $COOR^{17}$ or $CONR^{18}R^{19}$, where each said $C_1$-$C_4$ alkyl and $C_1$-$C_4$ fluoroalkyl is optionally substituted by $R^{20}$, $SO_2R^{14}$, $SO_2NR^{15}R^{16}$, $COR^{17}$, $COOR^{17}$ or $CONR^{18}R^{19}$.

In some embodiments, $R^{11}$ is $SO_2R^{14}$. In other embodiments, $R^{11}$ is $COR^{17}$. In still other embodiments, $R^{11}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$, $SO_2R^{14}$, $SO_2NR^{15}R^{16}$, $COR^{17}$, $COOR^{17}$ or $CONR^{18}R^{19}$. In some such embodiments, $R^{11}$ is $C_1$-$C_4$ alkyl substituted by $SO_2R^{14}$ or $COR^{17}$. In some such embodiments, $R^{11}$ is $C_1$-$C_4$ alkyl substituted by $R^{20}$.

In compounds of Formula (I), $R^{14}$ is $C_1$-$C_4$ alkyl or $C_1$-$C_4$ fluoroalkyl. In some embodiments, $R^{14}$ is $C_1$-$C_4$ alkyl. In some such embodiments, $R^{14}$ is $C_1$-$C_2$ alkyl. In some embodiments, $R^{14}$ is $C_1$-$C_4$ fluoroalkyl. In some such embodiments, $R^{14}$ is $C_1$-$C_2$ fluoroalkyl. In particular embodiments, $R^{14}$ is $CH_3$ or $C_2H_5$.

In compounds of Formula (I), each $R^{15}$ and $R^{16}$ is independently H or $CH_3$.

In compounds of Formula (I), $R^{17}$ is $C_1$-$C_4$ alkyl, $C_1$-$C_4$ fluoroalkyl, $C_3$-$C_8$ cycloalkyl or 3-6 membered heterocyclyl, where each said $C_1$-$C_4$ alkyl and $C_1$-$C_4$ fluoroalkyl is optionally substituted by $R^{20}$ and each said $C_3$-$C_8$ cycloalkyl and 3-6 membered heterocyclyl is optionally substituted by $R^{21}$. In some embodiments, $R^{17}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some embodiments, $R^{17}$ is $C_3$-$C_8$ cycloalkyl or 3-6 membered heterocyclyl, where each said $C_3$-$C_8$ cycloalkyl and 3-6 membered heterocyclyl is optionally substituted by $R^{21}$.

In compounds of Formula (I), each $R^{18}$ and $R^{19}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$.

In compounds of Formula (I), each $R^{20}$ is independently OH, $C_1$-$C_2$ alkoxy, $C_1$-$C_2$ fluoroalkoxy, CN, $NR^{22}R^{23}$, $C_3$-$C_8$ cycloalkyl or 3-6 membered heterocyclyl, where each said $C_3$-$C_8$ cycloalkyl and 3-6 membered heterocyclyl is optionally substituted by $R^{21}$.

In some embodiments, each $R^{20}$ is independently OH, $C_1$-$C_2$ alkoxy, $C_1$-$C_2$ fluoroalkoxy, CN or $NR^{22}R^{23}$. In some such embodiments, $R^{20}$ is OH. In some such embodiments, $R^{20}$ is OH, $C_1$-$C_2$ alkoxy or $NR^{22}R^{23}$. In some such embodiments, $R^{20}$ is OH. In some embodiments, $R^{20}$ is $C_3$-$C_8$ cycloalkyl or 3-6 membered heterocyclyl, where each said $C_3$-$C_8$ cycloalkyl and 3-6 membered heterocyclyl is optionally substituted by $R^{21}$.

In compounds of Formula (I), each $R^{21}$ is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$. In some embodiments, each $R^{21}$ is independently F, OH or $C_1$-$C_4$ alkyl.

In some embodiments of Formula (I), each $R^{22}$ and $R^{23}$ is independently H, $C_1$-$C_3$ alkyl, $C_1$-$C_3$ fluoroalkyl, $C_3$-$C_0$ cycloalkyl or 3-6 membered heterocyclyl, where each said $C_1$-$C_3$ alkyl and $C_1$-$C_3$ fluoroalkyl is optionally further substituted by OH, $C_1$-$C_2$ alkoxy or $C_1$-$C_2$ fluoroalkoxy and each said $C_3$-$C_8$ cycloalkyl and 3-6 membered heterocyclyl is optionally further substituted by F, OH, $C_1$-$C_2$ alkyl, $C_1$-$C_2$ fluoroalkyl, $C_1$-$C_2$ alkoxy or $C_1$-$C_2$ fluoroalkoxy.

In some such embodiments, each $R^{22}$ and $R^{23}$ is independently H, $C_1$-$C_2$ alkyl or $C_1$-$C_2$ fluoroalkyl. In some such embodiments, each $R^{22}$ and $R^{23}$ is independently H, $C_1$-$C_2$ alkyl or $C_1$-$C_2$ fluoroalkyl.

In some embodiments of Formula (I), $R^{22}$ and $R^{23}$ may be taken together with the nitrogen atom to which they are attached to form an azetidinyl ring, where said ring is optionally substituted by F, OH, $C_1$-$C_2$ alkyl, $C_1$-$C_2$ fluoroalkyl, $C_1$-$C_2$ alkoxy or $C_1$-$C_2$ fluoroalkoxy. In some such embodiments, $R^{22}$ and $R^{23}$ may be taken together with the nitrogen atom to which they are attached to form an azetidinyl ring, which is optionally substituted by F, OH or $C_1$-$C_2$ alkyl.

In compounds of Formula (I), $R^{24}$ is H, $C_1$-$C_4$ alkyl, $C_1$-$C_4$ fluoroalkyl, $SO_2R^{25}$, $SO_2NR^{26}R^{27}$, $COR^{28}$, $COOR^{28}$ or $CONR^{29}R^{30}$. In some embodiments, $R^{24}$ is H or $C_1$-$C_4$ alkyl. In some embodiments, $R^{24}$ is H or $C_1$-$C_2$ alkyl.

In compounds of Formula (I), $R^{25}$ is $C_1$-$C_4$ alkyl or $C_1$-$C_4$ fluoroalkyl. In some embodiments, $R^{25}$ is $C_1$-$C_2$ alkyl.

In compounds of Formula (I), each $R^{26}$ and $R^{27}$ is independently H or $CH_3$.

In compounds of Formula (I), $R^{28}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$. In some embodiments, $R^{28}$ is $C_1$-$C_4$ alkyl optionally substituted by OH or $C_1$-$C_2$ alkoxy. In some embodiments, $R^{28}$ is $C_1$-$C_2$ alkyl.

In compounds of Formula (I), each $R^{29}$ and $R^{30}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$. In some embodiments, each $R^{29}$ and $R^{30}$ is independently H or $C_1$-$C_4$ alkyl where each said $C_1$-$C_4$ alkyl is optionally substituted by OH or $C_1$-$C_2$ alkoxy. In some embodiments, each $R^{29}$ and $R^{30}$ is independently H or $C_1$-$C_2$ alkyl.

In compounds of Formula (I), m is 0, 1 or 2. In some embodiments, m is 2.

In compounds of Formula (I), n is 0, 1, 2, 3 or 4. In some embodiments, n is 0 and $R^{10}$ is absent. In some embodiments, n is 1 or 2.

In compounds of Formula (I), p is 1, 2 or 3; wherein the sum of p and q is an integer from 1 to 4. In some embodiments, p is 2. In other embodiments, p is 1. In some embodiments, the sum of p and q is an integer from 1 to 3.

In compounds of Formula (I), q is 0, 1, 2 or 3; wherein the sum of p and q is an integer from 1 to 4. In some embodiments, q is 1. In other embodiments, q is 0. In some embodiments, the sum of p and q is an integer from 1 to 3.

In some embodiments, p is 2 and q is 1. In other embodiments, p is 1 and q is 1. In other embodiments, p is 1 and q is 0. In further embodiments, the sum of p and q is an integer from 1 to 3.

In certain embodiments, the invention provides a compound of Formula (I), (I-A), (I-B), (I-C) or (I-D), or a pharmaceutically acceptable salt thereof, having a combination of two or more, preferably three or more, and more preferably four or more, of the following features: A is N; $R^1$ is Cl; U is $NR^2$ and V is $CR^4$; $R^2$ is $C_1$-$C_5$ alkyl; or $R^2$ is i-$C_3H_7$; $R^4$ is $C_1$-$C_4$ alkyl, where said $C_1$-$C_4$ alkyl is optionally substituted by $R^{20}$, where $R^{20}$ is OH; or $R^4$ is CH(OH)$CH_3$ or C(OH)$(CH_3)_2$; X is $CR^6$; $R^6$ is F; Y is $CR^7$; $R^7$ is H; Z is $CR^8$; $R^8$ is H; $R^9$ is OH; Q is O; or Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In certain embodiments, the invention provides a compound of Formula (I), (I-A), (I-B), (I-C) or (I-D), or a pharmaceutically acceptable salt thereof, having a combination of two or more, preferably three or more, and more preferably four or more, of the following features: A is N; $R^1$ is Cl; U is $CR^3$ and V is $NR^5$; $R^3$ is $C_1$-$C_5$ alkyl; or $R^3$ is i-$C_3H_7$; $R^5$ is $C_1$-$C_4$ alkyl, where said $C_1$-$C_4$ alkyl is optionally substituted by $R^{20}$, where $R^{20}$ is OH; X is $CR^6$; $R^6$ is F; Y is $CR^7$; $R^7$ is H; Z is $CR^8$; $R^8$ is H; $R^9$ is OH; Q is O; or Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In a preferred embodiment, the invention provides a compound of Formula (I), (I-A), (I-B), (I-C) or (I-D), or a pharmaceutically acceptable salt thereof, wherein: A is N; $R^1$ is C; U is $NR^2$; $R^2$ is $C_1$-$C_5$ alkyl; or $R^2$ is i-$C_3H_7$; V is $CR^4$; $R^4$ is $C_1$-$C_4$ alkyl optionally substituted by $R^{20}$, where $R^{20}$ is OH; or $R^4$ is CH(OH)$CH_3$ or C(OH)$(CH_3)_2$; X is $CR^6$; $R^6$ is F; Y is $CR^7$; $R^7$ is H; Z is $CR^8$; $R^8$ is H; $R^9$ is OH; Q is O; n is 0 and $R^{10}$ is absent; p is 2; and q is 1.

In another preferred embodiment, the invention provides a compound of Formula (I), (I-A), (I-B), (I-C) or (I-D), or a pharmaceutically acceptable salt thereof, wherein: A is N; $R^1$ is C; U is $NR^2$; $R^2$ is $C_1$-$C_5$ alkyl; or $R^2$ is i-$C_3H_7$; V is $CR^4$; $R^4$ is $C_1$-$C_4$ alkyl optionally substituted by $R^{20}$, where $R^{20}$ is OH; or $R^4$ is CH(OH)$CH_3$ or C(OH)$(CH_3)_2$; X is $CR^6$; $R^6$ is F; Y is $CR^7$; $R^7$ is H; Z is $CR^8$; $R^8$ is H; $R^9$ is OH; Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In another embodiment, the invention provides a compound of Formula (I), (I-A), (I-B), (I-C) or (I-D), or a pharmaceutically acceptable salt thereof, wherein: A is N; $R^1$ is C; U is $NR^2$; $R^2$ is $C_1$-$C_5$ alkyl; or $R^2$ is i-$C_3H_7$; V is $CR^4$; $R^4$ is $C_1$-$C_4$ alkyl optionally substituted by $R^{20}$, where $R^{20}$ is OH; or $R^4$ is CH(OH)$CH_3$ or C(OH)$(CH_3)_2$; X is $CR^6$; $R^6$ is F; Y is $CR^7$; $R^7$ is H; Z is $CR^8$; $R^8$ is H; $R^9$ is OH; Q is O; n is 0 and $R^{10}$ is absent; p is 2; and q is 1.

In another preferred embodiment, the invention provides a compound of Formula (I), (I-A), (I-B), (I-C) or (I-D), or a pharmaceutically acceptable salt thereof, wherein: A is CH; $R^1$ is Cl; U is $NR^2$; $R^2$ is $C_1$-$C_5$ alkyl; or $R^2$ is i-$C_3H_7$; V is $CR^4$; $R^4$ is $C_1$-$C_4$ alkyl optionally substituted by $R^{20}$, where $R^{20}$ is OH; or $R^4$ is CH(OH)$CH_3$ or C(OH)$(CH_3)_2$; X is $CR^6$; $R^6$ is F; Y is $CR^7$; $R^7$ is H; Z is $CR^8$; $R^8$ is H; $R^9$ is OH; Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In certain embodiments, the invention provides a compound of Formula (I), (I-A), (I-B), (I-C) or (I-D), or a pharmaceutically acceptable salt thereof, having a combination of two or more, preferably three or more, and more preferably four or more, of the following features: A is CH; $R^1$ is Cl; U is $CR^3$ and V is $NR^5$; $R^3$ is $C_1$-$C_5$ alkyl; or $R^3$ is i-$C_3H_7$; $R^5$ is $C_1$-$C_4$ alkyl, where said $C_1$-$C_4$ alkyl is optionally substituted by $R^{20}$, where $R^{20}$ is OH; X is $CR^6$; $R^6$ is F; Y is $CR^7$; $R^7$ is H; Z is $CR^8$; $R^8$ is H; $R^9$ is OH; Q is O; or Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

Each of the aspects and embodiments described herein with respect to Formula (I) is also applicable to compounds of Formulae (II)-(XII) that are not inconsistent with such aspect or embodiment.

In compounds of Formula (II), $R^1$ is H, F, Cl, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$. In some embodiments, $R^1$ is F or Cl. In some embodiments, $R^1$ is F. In some embodiments, $R^1$ is Cl.

In compounds of Formula (II), X is $CR^6$ or N. In some embodiments, X is $CR^6$. In some embodiments, X is N.

In compounds of Formula (II), Y is $CR^7$ or N. In some embodiments, Y is $CR^7$. In some embodiments, Y is N.

In compounds of Formula (II), Z is $CR^8$ or N. In some embodiments, Z is $CR^8$. In some embodiments, Z is N.

In frequent embodiments of Formula (II), X is $CR^6$, Y is $CR^7$ and Z is $CR^8$. In other embodiments of Formula (II), at least one of X, Y and Z is N.

In compounds of Formula (II), U is $NR^2$ or $CR^3$; V is N or $CR^4$ when U is $NR^2$; and V is $NR^5$ when U is $CR^3$. In some embodiments, U is $NR^2$ and V is N or $CR^4$. In some such embodiments, U is $NR^2$ and V is $CR^4$. In some such embodiments, U is $NR^2$ and V is N. In other embodiments, U is $CR^3$ and V is $NR^5$.

In some embodiments of Formula (II), U is $NR^2$ and $R^2$ is H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$.

In compounds of Formula (II), $R^2$ and $R^3$ are H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$.

In some such embodiments, $R^2$ is $C_1$-$C_5$ alkyl or $C_1$-$C_5$ fluoroalkyl, where each said $C_1$-$C_5$ alkyl and $C_1$-$C_5$ fluoroalkyl is optionally substituted by $R^{20}$. In some such embodiments, $R^2$ is $C_1$-$C_5$ alkyl optionally substituted by $R^{20}$. In some such embodiments, $R^{20}$ is OH. In particular embodiments, $R^2$ is $CH_3$, $C_2H_5$, n-$C_3H_7$, i-$C_3H_7$, n-$C_4H_9$, s-$C_4H_9$, i-$C_4H_9$, t-$C_4H_9$, $CHF_2$ or $CH_2CHF_2$ (i.e., methyl, ethyl, n-propyl, isopropyl, n-butyl, sec-butyl, isobutyl, tert-butyl, difluoromethyl or difluoroethyl), each optionally substituted by $R^{20}$. In specific embodiments, $R^2$ is isopropyl or tert-butyl. In specific embodiments, $R^2$ is isopropyl (i-$C_3H_7$) In some embodiments, $R^2$ is $C_1$-$C_5$ alkyl or $C_1$-$C_5$ fluoroalkyl optionally substituted by $R^{20}$ where $R^{20}$ is OH.

In other embodiments, $R^2$ is $C_3$-$C_8$ cycloalkyl or 3-6 membered heterocyclyl, where each said $C_3$-$C_8$ cycloalkyl and 3-6 membered heterocyclyl is optionally substituted by $R^{21}$. In some such embodiments, $R^2$ is 3-6 membered heterocyclyl optionally substituted by $R^{21}$. In particular embodiments, $R^2$ is oxetan-3-yl or azetidin-3-yl, each optionally substituted by $R^{21}$. In specific embodiments, $R^2$ is oxetan-3-yl. In other embodiments, $R^2$ is $C_3$-$C_8$ cycloalkyl, where said $C_3$-$C_8$ cycloalkyl is optionally substituted by $R^{21}$. In some such embodiments, $R^{21}$ is F, OH or $C_1$-$C_4$ alkyl.

In some embodiments of the foregoing where U is $NR^2$, V is N. In other embodiments of the foregoing where U is $NR^2$, V is $CR^4$.

In other embodiments of Formula (II), U is $CR^3$ and $R^3$ is H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$.

In some such embodiments, $R^3$ is $C_1$-$C_5$ alkyl or $C_1$-$C_5$ fluoroalkyl, where each said $C_1$-$C_5$ alkyl and $C_1$-$C_5$ fluoroalkyl is optionally substituted by $R^{20}$. In some such embodiments, $R^3$ is $C_1$-$C_5$ alkyl optionally substituted by $R^{20}$. In some such embodiments, $R^{20}$ is OH or $NR^{22}R^{23}$. In some such embodiments, $R^{20}$ is OH. In some such embodiments, $R^3$ is $CH_3$, $C_2H_5$, n-$C_3H_7$, i-$C_3H_7$, n-$C_4H_9$, s-$C_4H_9$, i-$C_4H_9$, t-$C_4H_9$, $CHF_2$ or $CH_2CHF_2$, each optionally substituted by $R^{20}$. In specific embodiments, $R^3$ is i-$C_3H_7$ or t-$C_4H$ (i.e., isopropyl or tert-butyl). In specific embodiments, $R^2$ is isopropyl.

In other embodiments, $R^3$ is $C_3$-$C_8$ cycloalkyl or 3-6 membered heterocyclyl, where each said $C_3$-$C_8$ cycloalkyl and 3-6 membered heterocyclyl is optionally substituted by $R^{21}$. In some such embodiments, $R^3$ is 3-6 membered heterocyclyl optionally substituted by $R^{21}$. In particular embodiments, $R^3$ is oxetan-3-yl or azetidin3-yl optionally substituted by $R^{21}$. In some such embodiments, $R^{21}$ is F, OH or $C_1$-$C_4$ alkyl. In specific embodiments, $R^3$ is oxetan-3-yl. In other embodiments, $R^3$ is $C_3$-$C_8$ cycloalkyl, where said $C_3$-$C_8$ cycloalkyl is optionally substituted by $R^{21}$.

In some such embodiments, $R^{21}$ is F, OH or $C_1$-$C_4$ alkyl.

In the foregoing embodiments where U is $CR^3$, V is $NR^5$.

In some embodiments of Formula (II), V is $CR^4$ when U is $NR^2$.

In compounds of Formula (II), $R^4$ is H, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$. In some embodiments, $R^4$ is H. In other embodiments, $R^4$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some such embodiments, $R^4$ is $C_1$-$C_4$ alkyl optionally substituted by $R^{20}$. In some such embodiments, $R^{20}$ is OH, $OCH_3$, $NH_2$, $NHCH_3$ or $NH(CH_3)_2$. In some such embodiments, $R^{20}$ is OH or $NH_2$. In some such embodiments, $R^{20}$ is OH. In certain embodiments, $R^4$ is $C_1$-$C_2$ alkyl optionally substituted by $R^{20}$, where $R^{20}$ is OH or $NH_2$. In specific embodiments, $R^4$ optionally substituted by $R^{20}$ (i.e., $R^4$-$R^{20}$) is H, $CH_3$, $C_2H_5$, $CH_2OH$, $CH(OH)CH_3$, $CH_2CH_2OH$ or $CH_2NH_2$ (i.e., methyl, ethyl, hydroxymethyl, 1-hydroxyethyl, 2-hydroxyethyl or aminomethyl). In some embodiments, $R^4$ substituted by $R^{20}$ is $CH(OH)CH_3$ or $C(OH)(CH_3)_2$. In other such embodiments, $R^4$ is $C_1$-$C_4$ fluoroalkyl optionally substituted by $R^{20}$. In other embodiments, $R^4$ is $C_1$-$C_4$ alkoxy or $C_1$-$C_4$ fluoroalkoxy, where each said $C_1$-$C_4$ alkoxy and $C_1$-$C_4$ fluoroalkoxy is optionally substituted by $R^{20}$.

In some embodiments of Formula (II), V is $NR^5$ when U is $CR^3$.

In compounds of Formula (II), $R^5$ is H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some embodiments, $R^5$ is H. In other embodiments, $R^5$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some such embodiments, $R^5$ is $C_1$-$C_4$ alkyl optionally substituted by $R^{20}$. In other such embodiments, $R^5$ is $C_1$-$C_4$ fluoroalkyl optionally substituted by $R^{20}$. In specific embodiments, $R^5$ is $C_1$-$C_2$ alkyl or $C_1$-$C_2$ fluoroalkyl. In specific embodiments, $R^5$ is $CH_3$, $C_2H$, $CHF_2$ or $CH_2CHF_2$ (i.e., methyl, ethyl, difluoromethyl or difluoroethyl).

In compounds of Formula (II), $R^6$ is H, F, Cl, CN, $CH_3$, $CH_2F$, $CHF_2$ or $CF_3$. In some embodiments, $R^6$ is H. In other embodiments, $R^6$ is F. In other embodiments, $R^6$ is C. In further embodiments, $R^6$ is CN. In other embodiments, $R^6$ is $CH_3$, $CH_2F$, $CHF_2$ or $CF_3$.

In compounds of Formula (II), $R^7$ and $R^8$ are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy, where each said $C_1$-$C_2$ alkyl, $C_1$-$C_2$ fluoroalkyl, $C_1$-$C_2$ alkoxy and $C_1$-$C_2$ fluoroalkoxy is optionally substituted by $R^{20}$.

In some embodiments of Formula (II), $R^7$ is H. In other embodiments, $R^7$ is F or C. In further embodiments, $R^7$ is $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$. In some such embodiments, $R^7$ is $CH_3$, optionally substituted by $R^{20}$. In some embodiments, $R^7$ is $CH_3$.

In some embodiments of Formula (II), $R^8$ is H. In other embodiments, $R^8$ is F or Cl. In further embodiments, $R^8$ is $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$. In some such embodiments, $R^8$ is $CH_3$, optionally substituted by $R^{20}$. In some embodiments, $R^8$ is $CH_3$.

In some embodiments, $R^7$ and $R^8$ are H.

In compounds of Formula (II), $R^9$ is H, OH, $NH_2$, $NHCH_3$ or $N(CH_3)_2$. In some preferred embodiments, $R^9$ is OH. In other embodiments, $R^9$ is $NH_2$, $NHCH_3$ or $N(CH_3)_2$. In further embodiments, $R^9$ is H.

In compounds of Formula (II), each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$. In some embodiments, n is 0 and $R^{10}$ is absent. In other embodiments, n is 1, 2, 3 or 4 and each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$. In other embodiments, n is 1 or 2 and $R^{10}$ is independently F, CN, $C_1$-$C_2$ alkyl or $C_1$-$C_2$ fluoroalkyl. In some embodiments, n is 1 or 2 and $R^{10}$ is independently F or $CH_3$.

In compounds of Formula (II), Q is $NR^{11}$ or O; or Q is $CR^{12}R^{13}$, where $R^{12}$ and $R^{13}$ are taken together with the C atom to which they are attached to form a 4-6 membered heterocyclic ring containing $NR^{11}$ or O as a ring member, which ring is optionally further substituted by $R^{10}$.

In some embodiments of Formula (II), Q is $NR^{11}$. In some embodiments, Q is $NR^{11}$, p is 2 and q is 1. In some such embodiments, $R^{11}$ is $SO_2R^{14}$. In other such embodiments, $R^{11}$ is $COR^{17}$. In some embodiments, n is 0 and $R^{10}$ is absent.

In compounds of Formula (II), $R^{11}$ is H, $C_1$-$C_4$ alkyl, $C_1$-$C_4$ fluoroalkyl, $SO_2R^{14}$, $S_2NR^{15}R^{16}$, $COR^{17}$, $COOR^{17}$ or $CONR^{18}R^{19}$. In some embodiments, $R^{11}$ is H, $C_1$-$C_4$ alkyl or $C_1$-$C_4$ fluoroalkyl. In some embodiments, $R^{11}$ is H. In other embodiments, $R^{11}$ is $C_1$-$C_4$ alkyl or $C_1$-$C_4$ fluoroalkyl. In some embodiments, $R^{11}$ is $C_1$-$C_4$ alkyl. In other embodiments, $R^{11}$ is $C_1$-$C_4$ fluoroalkyl. In some embodiments, $R^{11}$ is $SO_2R^{14}$, $SO_2NR^{15}R^{16}$, $COR^{17}$, $COOR^{17}$ or $CONR^{18}R^{19}$. In some embodiments, $R^{11}$ is $SO_2R^{14}$ or $SO_2NR^{15}R^{16}$. In some embodiments, $R^{11}$ is $SO_2R^{14}$. In other embodiments, $R^{11}$ is $SO_2NR^{15}R^{16}$. In some embodiments, $R^{11}$ is $COR^{17}$, $COOR^{17}$ or $CONR^{18}R^{19}$. In some embodiments, $R^{11}$ is $COR^{17}$. In some embodiments, $R^{11}$ is $COOR^{17}$. In other embodiments, $R^{11}$ is $CONR^{18}R^{19}$.

In other embodiments of Formula (II), Q is O. In some embodiments, Q is O, p is 2 and q is 1. In some such embodiments, n is 0 and $R^{10}$ is absent.

In further embodiments of Formula (II), Q is $CR^{12}R^{13}$, where $R^{12}$ and $R^{13}$ are taken together with the C atom to which they are attached to form a 4-6 membered heterocyclic ring containing $NR^{11}$ or O as a ring member, which ring is optionally further substituted by $R^{10}$. In some such embodiments, $R^{12}$ and $R^{13}$ are taken together with the C atom to which they are attached to form a 4-6 membered heterocyclic ring containing $NR^{11}$ as a ring member, which ring is optionally further substituted by $R^{10}$. In other such embodiments, $R^{12}$ and $R^{13}$ are taken together with the C atom to which they are attached to form a 4-6 membered heterocyclic ring containing O as a ring member, which ring is optionally further substituted by $R^{10}$. In some such embodiments, $R^{12}$ and $R^{13}$ are taken together to form a 4-membered optionally substituted heterocyclic ring. In other such embodiments, $R^{12}$ and $R^{13}$ are taken together to form a 5-membered optionally substituted heterocyclic ring. In other such embodiments, $R^{12}$ and $R^{13}$ are taken together to form a 6-membered optionally substituted heterocyclic ring. In each case, said 4-6 membered heterocyclic ring contains $NR^{11}$ or O as a ring member and is optionally further substituted by $R^{10}$, where each of $R^{10}$ and $R^{11}$ is as further defined herein. In some such embodiments, n is 0 and $R^{10}$ is absent.

In the foregoing embodiments, each $R^{10}$ is independently selected from the group as defined herein.

In compounds of Formula (II), $R^{14}$ is $C_1$-$C_4$ alkyl or $C_1$-$C_4$ fluoroalkyl. In some embodiments, $R^{14}$ is $C_1$-$C_4$ alkyl. In some embodiments, $R^{14}$ is $C_1$-$C_4$ fluoroalkyl. In specific embodiments, $R^{14}$ is $CH_3$ or $C_2H_5$ (i.e., methyl or ethyl).

In compounds of Formula (II), each $R^{15}$ and $R^{11}$ is independently H or $CH_3$.

In compounds of Formula (II), $R^{17}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some embodiments, $R^{17}$ is $C_1$-$C_4$ alkyl or $C_1$-$C_4$ fluoroalkyl. In some embodiments, $R^{17}$ is $C_1$-$C_4$ alkyl optionally substituted by $R^{20}$. In some embodiments, $R^{17}$ is $C_1$-$C_4$ fluoroalkyl optionally substituted by $R^{20}$. In specific embodiments, $R^{17}$ is $CH_3$ or $C_2H_5$.

In compounds of Formula (II), each $R^{18}$ and $R^{19}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some embodiments, each $R^{18}$ and $R^{19}$ is independently H, $C_1$-$C_4$ alkyl or $C_1$-$C_4$ fluoroalkyl. In some embodiments, each $R^{18}$ and $R^{19}$ is independently H or $C_1$-$C_4$ alkyl optionally substituted by $R^{20}$. In some embodiments, each $R^{18}$ and $R^{19}$ is independently H or $C_1$-$C_4$ fluoroalkyl optionally substituted by $R^{20}$. In specific embodiments, each $R^{18}$ and $R^{19}$ is independently H, $CH_3$ or $C_2H_5$.

In compounds of Formula (II), each $R^{20}$ is independently OH, $C_1$-$C_2$ alkoxy, $C_1$-$C_2$ fluoroalkoxy, CN or $NR^{22}R^{23}$. In some embodiments, $R^{20}$ is OH. In some such embodiments, $R^{20}$ is OH, $C_1$-$C_2$ alkoxy or $NR^{22}R^{23}$. In other embodiments, $R^{20}$ is $C_1$-$C_2$ alkoxy or $C_1$-$C_2$ fluoroalkoxy. In further embodiments, $R^{20}$ is CN. In still other embodiments, $R^{20}$ is $NR^{22}R^{23}$.

In compounds of Formula (II), each $R^{21}$ is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$. In some embodiments, $R^{21}$ is F. In some embodiments, $R^{21}$ is OH. In some embodiments, each $R^{21}$ is independently F, OH or $C_1$-$C_4$ alkyl. In other embodiments, $R^{21}$ is CN. In other embodiments, $R^{21}$ is $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$.

In compounds of Formula (II), each $R^{22}$ and $R^{23}$ is independently H, $C_1$-$C_2$ alkyl or $C_1$-$C_2$ fluoroalkyl; or $R^{22}$ and $R^{23}$ may be taken together with the nitrogen atom to which they are attached to form an azetidinyl ring, which is optionally substituted by F or OH.

In some embodiments, each $R^{22}$ and $R^{23}$ is independently H, $C_1$-$C_2$ alkyl or $C_1$-$C_2$ fluoroalkyl. In specific embodiments, each $R^{22}$ and $R^{23}$ is independently H or $CH_3$. In other embodiments, $R^{22}$ and $R^{23}$ are taken together with the nitrogen atom to which they are attached to form an azetidinyl ring, which is optionally substituted by F or OH.

In compounds of Formula (II), n is 0, 1, 2, 3 or 4. In some embodiments, n is 0 and $R^{10}$ is absent. In other embodiments, n is 1, 2, 3 or 4 and $R^{10}$ is as defined herein. In some embodiments, n is 1 or 2.

In compounds of Formula (II), p is 1, 2 or 3; and q is 0, 1, 2 or 3; wherein the sum of p and q is an integer from 1 to 4. In some embodiments, the sum of p and q is an integer from 1 to 3.

In some embodiments, p is 2 and q is 1. In other embodiments, p is 2 and q is 2. In some embodiments, p is 1 and q is 0. In other embodiments, p is 1 and q is 1. In still other embodiments, p is 1 and q is 2. In further embodiments, p is 1 and q is 3. In some embodiments, p is 2. In other embodiments, p is 1. In some embodiments, q is 1. In other embodiments, q is 0.

In certain embodiments, the invention provides a compound of Formula (II), (II-A), (I-B), (II-C) or (II-D), or a pharmaceutically acceptable salt thereof, having a combination of two or more, preferably three or more, and more preferably four or more, of the following features: $R^1$ is C; U is $NR^2$ and V is $CR^4$; $R^2$ is $C_1$-$C_5$ alkyl; or $R^2$ is i-$C_3H_7$; $R^4$ is $C_1$-$C_4$ alkyl, where said $C_1$-$C_4$ alkyl is optionally substituted by $R^{20}$, where $R^{20}$ is OH; or $R^4$ is CH(OH)CH$_3$ or C(OH)(CH$_3$)$_2$; X is $CR^6$; $R^6$ is F; Y is $CR^7$; Z is $CR^8$; $R^7$ and $R^8$ are H; $R^9$ is OH; Q is O; or Q is $NR^{11}$, where $R^{11}$ is SO$_2$R$^{14}$; $R^{14}$ is $C_1$-$C_4$ alkyl; n is 0 and $R^{10}$ is absent; p is 2; and q is 1.

In certain embodiments, the invention provides a compound of Formula (II), (II-A), (I-B), (I-C) or (II-D), or a pharmaceutically acceptable salt thereof, having a combination of two or more, preferably three or more, and more preferably four or more, of the following features: $R^1$ is C; U is $CR^3$ and V is $NR^5$; $R^3$ is $C_1$-$C_5$ alkyl; or $R^3$ is i-$C_3H_7$; $R^5$ is $C_1$-$C_4$ alkyl, where said $C_1$-$C_4$ alkyl is optionally substituted by $R^{20}$; $R^{20}$ is OH; X is $CR^6$; $R^6$ is F; Y is $CR^7$; Z is $CR^8$; $R^7$ and $R^8$ are H; $R^9$ is OH; Q is O; or Q is $NR^{11}$, where $R^{11}$ is SO$_2$R$^{14}$; $R^{14}$ is $C_1$-$C_4$ alkyl; n is 0 and $R^{10}$ is absent; p is 2; and q is 1.

In a preferred embodiment, the invention provides a compound of Formula (II), (II-A), (II-B), (I-C) or (II-D), or a pharmaceutically acceptable salt thereof, wherein: $R^1$ is Cl; U is $NR^2$; $R^2$ is $C_1$-$C_5$ alkyl; or $R^2$ is i-$C_3H_7$; V is $CR^4$; $R^4$ is $C_1$-$C_4$ alkyl optionally substituted by $R^{20}$, where $R^{20}$ is OH; or $R^4$ is CH(OH)CH$_3$ or C(OH)(CH$_3$)$_2$; X is $CR^6$; $R^6$ is F; Y is $CR^7$; $R^7$ is H; Z is $CR^8$; $R^8$ is H; $R^9$ is OH; Q is O; n is 0 and $R^{10}$ is absent; p is 2; and q is 1.

In another preferred embodiment, the invention provides a compound of Formula (II), (II-A), (I-B), (I-C) or (II-D), or a pharmaceutically acceptable salt thereof, wherein: $R^1$ is Cl; U is $NR^2$; $R^2$ is $C_1$-$C_5$ alkyl; or $R^2$ is i-$C_3H_7$; V is $CR^4$; $R^4$ is $C_1$-$C_4$ alkyl optionally substituted by $R^{20}$, where $R^{20}$ is OH; or $R^4$ is CH(OH)CH$_3$ or C(OH)(CH$_3$)$_2$; X is $CR^6$; $R^6$ is F; Y is $CR^7$; $R^7$ is H; Z is $CR^8$; $R^8$ is H; $R^9$ is OH; Q is $NR^{11}$, where $R^{11}$ is SO$_2$R$^{14}$; $R^{14}$ is $C_1$-$C_4$ alkyl; n is 0 and $R^{10}$ is absent; p is 2; and q is 1.

In compounds of Formula (III), $R^1$ is H, F, Cl, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$. In some embodiments, $R^1$ is F or Cl. In some embodiments, $R^1$ is F. In some embodiments, $R^1$ is Cl.

In compounds of Formula (III), X is $CR^6$ or N. In some embodiments, X is $CR^6$. In some embodiments, X is N.

In compounds of Formula (III), Y is $CR^7$ or N. In some embodiments, Y is $CR^7$. In some embodiments, Y is N.

In compounds of Formula (III), Z is $CR^8$ or N. In some embodiments, Z is $CR^8$. In some embodiments, Z is N.

In frequent embodiments of Formula (III), X is $CR^6$, Y is $CR^7$ and Z is $CR^8$. In other embodiments of Formula (III), at least one of X, Y and Z is N.

In compounds of Formula (III), U is $NR^2$ or $CR^3$; V is N or $CR^4$ when U is $NR^2$; and V is $NR^5$ when U is $CR^3$. In some embodiments, U is $NR^2$ and V is N or $CR^4$. In some such embodiments, U is $NR^2$ and V is $CR^4$. In some such embodiments, U is $NR^2$ and V is N. In other embodiments, U is $CR^3$ and V is $NR^5$.

In some embodiments of Formula (III), U is $NR^2$ and $R^2$ is H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$.

In compounds of Formula (III), $R^2$ and $R^3$ are H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$.

In some such embodiments, $R^2$ is $C_1$-$C_5$ alkyl or $C_1$-$C_5$ fluoroalkyl, where each said $C_1$-$C_5$ alkyl and $C_1$-$C_5$ fluoroalkyl is optionally substituted by $R^{20}$. In some such embodiments, $R^2$ is $C_1$-$C_5$ alkyl optionally substituted by $R^{20}$. In some such embodiments, $R^{20}$ is OH. In particular embodiments, $R^2$ is CH$_3$, $C_2$H$_5$, n-$C_3H_7$, i-$C_3H_7$, n-$C_4H_9$, s-$C_4H_9$, i-$C_4H_9$, t-$C_4H_9$, CHF$_2$ or CH$_2$CHF$_2$ (i.e., methyl, ethyl, n-propyl, isopropyl, n-butyl, sec-butyl, isobutyl, tert-butyl, difluoromethyl or difluoroethyl), each optionally substituted by $R^{20}$. In specific embodiments, $R^2$ is isopropyl or tert-butyl. In specific embodiments, $R^2$ is isopropyl. In some embodiments, $R^2$ is $C_1$-$C_5$ alkyl or $C_1$-$C_5$ fluoroalkyl optionally substituted by $R^{20}$ where $R^{20}$ is OH.

In other embodiments, $R^2$ is $C_3$-$C_8$ cycloalkyl or 3-6 membered heterocyclyl, where each said $C_3$-$C_8$ cycloalkyl and 3-6 membered heterocyclyl is optionally substituted by $R^{21}$. In some such embodiments, $R^2$ is 3-6 membered heterocyclyl optionally substituted by $R^{21}$. In particular embodiments, $R^2$ is oxetan-3-yl or azetidin-3-yl, each optionally substituted by $R^{21}$. In specific embodiments, $R^2$ is oxetan-3-yl. In other embodiments, $R^2$ is $C_3$-$C_8$ cycloalkyl, where said $C_3$-$C_8$ cycloalkyl is optionally substituted by $R^{21}$. In some such embodiments, $R^{21}$ is F, OH or $C_1$-$C_4$ alkyl.

In some such embodiments, $R^3$ is $C_1$-$C_5$ alkyl or $C_1$-$C_5$ fluoroalkyl, where each said $C_1$-$C_5$ alkyl and $C_1$-$C_5$ fluoroalkyl is optionally substituted by $R^{20}$. In some such embodiments, $R^3$ is $C_1$-$C_5$ alkyl optionally substituted by $R^{20}$. In some such embodiments, $R^{20}$ is OH or $NR^{22}R^{23}$. In some such embodiments, $R^{20}$ is OH. In some such embodiments, $R^3$ is CH$_3$, $C_2$H$_5$, n-$C_3H_7$, i-$C_3H_7$, n-$C_4H_9$, s-$C_4H_9$, i-$C_4H_9$, t-$C_4H_9$, CHF$_2$ or CH$_2$CHF$_2$, each optionally substituted by $R^{20}$. In specific embodiments, $R^3$ is i-$C_3H_7$ or t-$C_4H_9$ (i.e., isopropyl or tert-butyl). In specific embodiments, $R^2$ is isopropyl.

In other embodiments, $R^3$ is $C_3$-$C_8$ cycloalkyl or 3-6 membered heterocyclyl, where each said $C_3$-$C_8$ cycloalkyl and 3-6 membered heterocyclyl is optionally substituted by $R^{21}$. In some such embodiments, $R^3$ is 3-6 membered heterocyclyl optionally substituted by $R^{21}$. In particular embodiments, $R^3$ is oxetan-3-yl or azetidin3-yl optionally substituted by $R^{21}$. In some such embodiments, $R^{21}$ is F, OH or $C_1$-$C_4$ alkyl. In specific embodiments, $R^3$ is oxetan-3-yl. In other embodiments, $R^3$ is $C_3$-$C_8$ cycloalkyl, where said $C_3$-$C_8$ cycloalkyl is optionally substituted by $R^{21}$. In some such embodiments, $R^{21}$ is F, OH or $C_1$-$C_4$ alkyl.

In the foregoing embodiments where U is $CR^3$, V is $NR^5$.

In some embodiments of Formula (III), V is $CR^4$ when U is $NR^2$.

In compounds of Formula (III), $R^4$ is H, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$. In some embodiments, $R^4$ is H. In other embodiments, $R^4$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some such embodiments, $R^4$ is $C_1$-$C_4$ alkyl optionally substituted by $R^{20}$. In some such embodiments, $R^{20}$ is OH, $OCH_3$, $NH_2$, $NHCH_3$ or $NH(CH_3)_2$. In some such embodiments, $R^{20}$ is OH or $NH_2$. In some such embodiments, $R^{20}$ is OH. In certain embodiments, $R^4$ is $C_1$-$C_2$ alkyl optionally substituted by $R^{20}$, where $R^{20}$ is OH or $NH_2$. In specific embodiments, $R^4$-$R^{20}$ is H, $CH_3$, $C_2H_5$, $CH_2OH$, $CH(OH)CH_3$, $CH_2CH_2OH$ or $CH_2NH_2$ (i.e., methyl, ethyl, hydroxymethyl, 1-hydroxyethyl, 2-hydroxyethyl or aminomethyl). In some embodiments, $R^4$ substituted by $R^{20}$ is $CH(OH)CH_3$ or $C(OH)(CH_3)_2$. In other such embodiments, $R^4$ is $C_1$-$C_4$ fluoroalkyl optionally substituted by $R^{20}$. In other embodiments, $R^4$ is $C_1$-$C_4$ alkoxy or $C_1$-$C_4$ fluoroalkoxy, where each said $C_1$-$C_4$ alkoxy and $C_1$-$C_4$ fluoroalkoxy is optionally substituted by $R^{20}$.

In some embodiments of Formula (III), V is $NR^5$ when U is $CR^3$.

In compounds of Formula (III), $R^5$ is H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some embodiments, $R^5$ is H. In other embodiments, $R^5$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some such embodiments, $R^5$ is $C_1$-$C_4$ alkyl optionally substituted by $R^{20}$. In other such embodiments, $R^5$ is $C_1$-$C_4$ fluoroalkyl optionally substituted by $R^{20}$. In specific embodiments, $R^5$ is $C_1$-$C_2$ alkyl or $C_1$-$C_2$ fluoroalkyl. In specific embodiments, $R^5$ is $CH_3$, $C_2H_5$, $CHF_2$ or $CH_2CHF_2$ (i.e., methyl, ethyl, difluoromethyl or difluoroethyl).

In compounds of Formula (III), $R^6$ is H, F, Cl, CN, $CH_3$, $CH_2F$, $CHF_2$ or $CF_3$. In some embodiments, $R^6$ is H. In other embodiments, $R^6$ is F. In other embodiments, $R^6$ is C. In further embodiments, $R^6$ is CN. In other embodiments, $R^6$ is $CH_3$, $CH_2F$, $CHF_2$ or $CF_3$.

In compounds of Formula (III), $R^7$ and $R^8$ are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy, where each said $C_1$-$C_2$ alkyl, $C_1$-$C_2$ fluoroalkyl, $C_1$-$C_2$ alkoxy and $C_1$-$C_2$ fluoroalkoxy is optionally substituted by $R^{20}$.

In some embodiments of Formula (III), $R^7$ is H. In other embodiments, $R^7$ is F or Cl. In further embodiments, $R^7$ is $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$. In some such embodiments, $R^7$ is $CH_3$, optionally substituted by $R^{20}$. In some embodiments, $R^7$ is $CH_3$.

In some embodiments of Formula (III), $R^8$ is H. In other embodiments, $R^8$ is F or Cl. In further embodiments, $R^8$ is $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$. In some such embodiments, $R^8$ is $CH_3$, optionally substituted by $R^{20}$. In some embodiments, $R^8$ is $CH_3$.

In some embodiments, $R^7$ and $R^8$ are H.

In compounds of Formula (III), $R^9$ is H, OH, $NH_2$, $NHCH_3$ or $N(CH_3)_2$. In some preferred embodiments, $R^9$ is OH. In other embodiments, $R^9$ is $NH_2$, $NHCH_3$ or $N(CH_3)_2$. In further embodiments, $R^9$ is H.

In compounds of Formula (III), each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$. In some embodiments, n is 0 and $R^{10}$ is absent. In other embodiments, n is 1, 2, 3 or 4 and each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$. In other embodiments, n is 1 or 2 and $R^{10}$ is independently F, CN, $C_1$-$C_2$ alkyl or $C_1$-$C_2$ fluoroalkyl. In some embodiments, n is 1 or 2 and $R^{10}$ is independently F or $CH_3$.

In compounds of Formula (III), Q is $NR^{11}$ or O; or Q is $CR^{12}R^{13}$, where $R^{12}$ and $R^{13}$ are taken together with the C atom to which they are attached to form a 4-6 membered heterocyclic ring containing $NR^{11}$ or O as a ring member, which ring is optionally further substituted by $R^{10}$.

In some embodiments of Formula (III), Q is $NR^{11}$. In some embodiments, Q is $NR^{11}$, p is 2 and q is 1. In some such embodiments, $R^{11}$ is $SO_2R^{14}$. In other such embodiments, $R^{11}$ is $COR^{17}$. In some such embodiments, n is 0 and $R^{10}$ is absent.

In compounds of Formula (III), $R^{11}$ is H, $C_1$-$C_4$ alkyl, $C_1$-$C_4$ fluoroalkyl, $SO_2R^{14}$, $SO_2NR^{15}R^{16}$, $COR^{17}$, $COOR^{17}$ or $CONR^{18}R^{19}$. In some embodiments, $R^{11}$ is H, $C_1$-$C_4$ alkyl or $C_1$-$C_4$ fluoroalkyl. In some embodiments, $R^{11}$ is H. In other embodiments, $R^{11}$ is $C_1$-$C_4$ alkyl or $C_1$-$C_4$ fluoroalkyl. In some embodiments, $R^{11}$ is $C_1$-$C_4$ alkyl. In other embodiments, $R^{11}$ is $C_1$-$C_4$ fluoroalkyl. In some embodiments, $R^{11}$ is $SO_2R^{14}$, $SO_2NR^{15}R^{16}$, $COR^{17}$, $COOR^{17}$ or $CONR^{18}R^{19}$. In some embodiments, $R^{11}$ is $SO_2R^{14}$ or $SO_2NR^{15}R^{16}$. In some embodiments, $R^{11}$ is $SO_2R^{14}$. In other embodiments, $R^{11}$ is $SO_2NR^{15}R^{16}$. In some embodiments, $R^{11}$ is $COR^{17}$, $COOR^{17}$ or $CONR^{18}R^{19}$. In some embodiments, $R^{11}$ is $COR^{17}$. In some embodiments, $R^{11}$ is $COOR^{17}$. In other embodiments, $R^{11}$ is $CONR^{18}R^{19}$.

In other embodiments of Formula (III), Q is O. In some embodiments, Q is O, p is 2 and q is 1. In some such embodiments, n is 0 and $R^{10}$ is absent.

In further embodiments of Formula (III), Q is $CR^{12}R^{13}$, where $R^{12}$ and $R^{13}$ are taken together with the C atom to which they are attached to form a 4-6 membered heterocyclic ring containing $NR^{11}$ or O as a ring member, which ring is optionally further substituted by $R^{10}$. In some such embodiments, n is 0 and $R^{10}$ is absent. In some such embodiments, $R^{12}$ and $R^{13}$ are taken together with the C atom to which they are attached to form a 4-6 membered heterocyclic ring containing $NR^{11}$ as a ring member, which ring is optionally further substituted by $R^{10}$. In other such embodiments, $R^{12}$ and $R^{13}$ are taken together with the C atom to which they are attached to form a 4-6 membered heterocyclic ring containing O as a ring member, which ring is optionally further substituted by $R^{10}$. In some such embodiments, $R^{12}$ and $R^{13}$ are taken together to form a 4-membered optionally substituted heterocyclic ring. In other such embodiments, $R^{12}$ and $R^{13}$ are taken together to form a 5-membered optionally substituted heterocyclic ring. In other such embodiments, $R^{12}$ and $R^{13}$ are taken together to form a 6-membered optionally substituted heterocyclic ring. In each case, said 4-6 membered heterocyclic ring contains $NR^{11}$ or O as a ring member and is optionally further substituted by $R^{10}$, where each of $R^{10}$ and $R^{11}$ is as further defined herein. In some such embodiments, n is 0 and $R^{10}$ is absent.

In the foregoing embodiments, each $R^{10}$ is independently selected from the group as defined herein.

In compounds of Formula (III), $R^{14}$ is $C_1$-$C_4$ alkyl or $C_1$-$C_4$ fluoroalkyl. In some embodiments, $R^{14}$ is $C_1$-$C_4$ alkyl. In some embodiments, $R^{14}$ is $C_1$-$C_4$ fluoroalkyl. In specific embodiments, $R^{14}$ is $CH_3$ or $C_2H_5$ (i.e., methyl or ethyl).

In compounds of Formula (III), each $R^{15}$ and $R^{16}$ is independently H or $CH_3$.

In compounds of Formula (III), $R^{17}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some embodiments, $R^{17}$ is $C_1$-$C_4$ alkyl or $C_1$-$C_4$ fluoroalkyl. In some embodiments, $R^{17}$ is $C_1$-$C_4$ alkyl optionally substituted by $R^{20}$. In some embodiments, $R^{17}$ is $C_1$-$C_4$ fluoroalkyl optionally substituted by $R^{20}$. In specific embodiments, $R^{17}$ is $CH_3$ or $C_2H_5$.

In compounds of Formula (III), each $R^{18}$ and $R^{19}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some embodiments, each $R^{18}$ and $R^{19}$ is independently H, $C_1$-$C_4$ alkyl or $C_1$-$C_4$ fluoroalkyl. In some embodiments, each $R^{18}$ and $R^{19}$ is independently H or $C_1$-$C_4$ alkyl optionally substituted by $R^{20}$. In some embodiments, each $R^{18}$ and $R^{19}$ is independently H or $C_1$-$C_4$ fluoroalkyl optionally substituted by $R^{20}$. In specific embodiments, each $R^{18}$ and $R^{19}$ is independently H, $CH_3$ or $C_2H_5$.

In compounds of Formula (III), each $R^{20}$ is independently OH, $C_1$-$C_2$ alkoxy, $C_1$-$C_2$ fluoroalkoxy, CN or $NR^{22}R^{23}$. In some embodiments, $R^{20}$ is OH. In some such embodiments, $R^{20}$ is OH, $C_1$-$C_2$ alkoxy or $NR^{22}R^{23}$. In other embodiments, $R^{20}$ is $C_1$-$C_2$ alkoxy or $C_1$-$C_2$ fluoroalkoxy. In further embodiments, $R^{20}$ is CN. In still other embodiments, $R^{20}$ is $NR^{22}R^{23}$.

In compounds of Formula (III), each $R^{21}$ is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$. In some embodiments, $R^{21}$ is F. In some embodiments, $R^{21}$ is OH. In some embodiments, each $R^{21}$ is independently F, OH or $C_1$-$C_4$ alkyl. In other embodiments, $R^{21}$ is CN. In other embodiments, $R^{21}$ is $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$.

In compounds of Formula (III), each $R^{22}$ and $R^{23}$ is independently H, $C_1$-$C_2$ alkyl or $C_1$-$C_2$ fluoroalkyl; or $R^{22}$ and $R^{23}$ may be taken together with the nitrogen atom to which they are attached to form an azetidinyl ring, which is optionally substituted by F or OH.

In some embodiments, each $R^{22}$ and $R^{23}$ is independently H, $C_1$-$C_2$ alkyl or $C_1$-$C_2$ fluoroalkyl. In specific embodiments, each $R^{22}$ and $R^{23}$ is independently H or $CH_3$. In other embodiments, $R^{22}$ and $R^{23}$ are taken together with the nitrogen atom to which they are attached to form an azetidinyl ring, which is optionally substituted by F or OH.

In compounds of Formula (III), n is 0, 1, 2, 3 or 4. In some embodiments, n is 0 and $R^{10}$ is absent. In other embodiments, n is 1, 2, 3 or 4 and $R^{10}$ is as defined herein. In some embodiments, n is 1 or 2.

In compounds of Formula (III), p is 1, 2 or 3; and q is 0, 1, 2 or 3; wherein the sum of p and q is an integer from 1 to 4. In some embodiments, the sum of p and q is an integer from 1 to 3.

In some embodiments, p is 2 and q is 1. In other embodiments, p is 2 and q is 2. In some embodiments, p is 1 and q is 0. In other embodiments, p is 1 and q is 1. In still other embodiments, p is 1 and q is 2. In further embodiments, p is 1 and q is 3. In some embodiments, p is 2. In other embodiments, p is 1. In some embodiments, q is 1. In other embodiments, q is 0.

In certain embodiments, the invention provides a compound of Formula (III), (III-A), (III-B), (III-C) or (III-D), or a pharmaceutically acceptable salt thereof, having a combination of two or more, preferably three or more, and more preferably four or more, of the following features: $R^1$ is Cl; U is $NR^2$ and V is $CR^4$; $R^2$ is $C_1$-$C_5$ alkyl; or $R^2$ is i-$C_3H_7$; $R^4$ is $C_1$-$C_4$ alkyl, where said $C_1$-$C_4$ alkyl is optionally substituted by $R^{20}$, where $R^{20}$ is OH; or $R^4$ is $CH(OH)CH_3$ or $C(OH)(CH_3)_2$; X is $CR^6$; $R^6$ is F; Y is $CR^7$; Z is $CR^8$; $R^7$ and $R^8$ are H; $R^9$ is OH; Q is O; or Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In certain embodiments, the invention provides a compound of Formula (III), (III-A), (III-B), (III-C) or (III-D), or a pharmaceutically acceptable salt thereof, having a combination of two or more, preferably three or more, and more preferably four or more, of the following features: $R^1$ is Cl; U is $CR^3$ and V is $NR^5$; $R^3$ is $C_1$-$C_5$ alkyl; or $R^3$ is i-$C_3H_7$; $R^5$ is $C_1$-$C_4$ alkyl, where said $C_1$-$C_4$ alkyl is optionally substituted by $R^{20}$; $R^{20}$ is OH; X is $CR^6$; $R^6$ is F; Y is $CR^7$; Z is $CR^8$; $R^7$ and $R^8$ are H; $R^9$ is OH; Q is O; or Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In a preferred embodiment, the invention provides a compound of Formula (III), (III-A), (III-B), (III-C) or (III-D), or a pharmaceutically acceptable salt thereof, wherein: $R^1$ is C; U is $NR^2$; $R^2$ is $C_1$-$C_5$ alkyl; or $R^2$ is i-$C_3H_7$; V is $CR^4$; $R^4$ is $C_1$-$C_4$ alkyl optionally substituted by $R^{20}$, where $R^{20}$ is OH; or $R^4$ is $CH(OH)CH_3$ or $C(OH)(CH_3)_2$; X is $CR^6$; $R^6$ is F; Y is $CR^7$; $R^7$ is H; Z is $CR^8$; $R^8$ is H; $R^9$ is OH; Q is O; n is 0 and $R^{10}$ is absent; p is 2; and q is 1.

In another preferred embodiment, the invention provides a compound of Formula (III), (III-A), (III-B), (III-C) or (III-D), or a pharmaceutically acceptable salt thereof, wherein: $R^1$ is Cl; U is $NR^2$; $R^2$ is $C_1$-$C_5$ alkyl; or $R^2$ is i-$C_3H_7$; V is $CR^4$; $R^4$ is $C_1$-$C_4$ alkyl optionally substituted by $R^{20}$, where $R^{20}$ is OH; or $R^4$ is $CH(OH)CH_3$ or $C(OH)(CH_3)_2$; X is $CR^6$; $R^6$ is F; Y is $CR^7$; $R^7$ is H; Z is $CR^8$; $R^8$ is H; $R^9$ is OH; Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In certain embodiments, the invention provides a compound of Formula (II), (II-A), (I-B), (I-C) or (II-D), or a pharmaceutically acceptable salt thereof, or a compound of Formula (III), (III-A), (III-B), (III-C) or (III-D), or a pharmaceutically acceptable salt thereof, having a combination of two or more, preferably three or more, and more preferably four or more, of the following features: $R^1$ is F or Cl; U is $NR^2$ and V is $CR^4$; $R^2$ is $C_1$-$C_5$ alkyl, $C_1$-$C_5$ fluoroalkyl or 3-6 membered heterocyclyl; or $R^2$ is $CH_3$, i-$C_3H_7$, i-$C_4H_9$, s-$C_4H_9$, t-$C_4H_9$, $CH_2F$, $CHF_2$, $CH_2CHF_2$ or oxetan-3-yl; $R^4$ is H or $C_1$-$C_4$ alkyl, where said $C_1$-$C_4$ alkyl is optionally substituted by OH, $NH_2$, $NHCH_3$ or $N(CH_3)_2$; or $R^4$ is H, $CH_3$, $C_2H_5$, $CH_2OH$, $CH(OH)CH_3$, $CH_2CH_2OH$ or $CH_2NH_2$; X is $CR^6$; $R^6$ is H or F; Y is $CR^7$; Z is $CR^8$; $R^7$ and $R^8$ are H; $R^9$ is OH; n is 0 and $R^{10}$ is absent; Q is $NR^{11}$; $R^{11}$ is $SO_2R^{14}$; and $R^{14}$ is $C_1$-$C_4$ alkyl; p is 2; and q is 1.

In certain embodiments, the invention provides a compound of Formula (II), (II-A), (I-B), (I-C) or (II-D), or a pharmaceutically acceptable salt thereof, or a compound of Formula (III), (III-A), (III-B), (III-C) or (III-D), or a pharmaceutically acceptable salt thereof, having a combination of two or more, preferably three or more, and more preferably four or more, of the following features: $R^1$ is F or Cl;

U is $CR^3$ and V is $NR^5$; $R^3$ is $C_1$-$C_5$ alkyl, $C_1$-$C_5$ fluoroalkyl or 3-6 membered heterocyclyl; or $R^3$ is $CH_3$, i-$C_3H_7$, i-$C_4H_9$, s-$C_4H_9$, t-$C_4H_9$, $CH_2F$, $CHF_2$, $CH_2CHF_2$ or oxetan-3-yl; $R^5$ is H or $C_1$-$C_4$ alkyl; or $R^5$ is H or $CH_3$; X is $CR^6$; $R^6$ is H or F; Y is $CR^7$; Z is $CR^8$; $R^7$ and $R^8$ are H; $R^9$ is OH; n is 0 and $R^{10}$ is absent; Q is $NR^{11}$; $R^{11}$ is $SO_2R^{14}$; and $R^{14}$ is $C_1$-$C_4$ alkyl; p is 2; and q is 1.

In certain embodiments, the invention provides a compound of Formula (II), (II-A), (I-B), (I-C) or (II-D), or a pharmaceutically acceptable salt thereof, or a compound of Formula (III), (III-A), (III-B), (III-C) or (III-D), or a pharmaceutically acceptable salt thereof, having a combination of two or more, preferably three or more, and more preferably four or more, of the following features: $R^1$ is F or Cl; U is $NR^2$ and V is N; $R^2$ is $C_1$-$C_5$ alkyl, $C_1$-$C_5$ fluoroalkyl or 3-6 membered heterocyclyl; or $R^2$ is $CH_3$, i-$C_3H_7$, i-$C_4H_9$, s-$C_4H_9$, t-$C_4H_9$, $CH_2F$, $CHF_2$, $CH_2CHF_2$ or oxetan-3-yl; X is $CR^6$; $R^6$ is H or F; Y is $CR^7$; Z is $CR^8$; $R^7$ and $R^8$ are H; $R^9$ is OH; n is 0 and $R^{10}$ is absent; Q is $NR^{11}$; $R^{11}$ is $SO_2R^{14}$; and $R^{14}$ is $C_1$-$C_4$ alkyl; p is 2; and q is 1.

In compounds of Formula (IV), $R^1$ is H, F, Cl, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$. In some embodiments, $R^1$ is F or Cl. In some embodiments, $R^1$ is F. In some embodiments, $R^1$ is Cl.

In compounds of Formula (IV), U is $NR^2$ or $CR^3$; V is N or $CR^4$ when U is $NR^2$; and V is $NR^5$ when U is $CR^3$. In some embodiments, U is $NR^2$ and V is N or $CR^4$. In some such embodiments, U is $NR^2$ and V is N. In some such embodiments, U is $NR^2$ and V is $CR^4$. In some embodiments, U is $CR^3$ and V is $NR^5$.

In compounds of Formula (IV), X is $CR^6$ or N. In some embodiments, X is $CR^6$. In some embodiments, X is N, In compounds of Formula (IV), Y is $CR^7$ or N. In some embodiments, Y is $CR^7$. In some embodiments, Y is N.

In compounds of Formula (IV), Z is $CR^8$ or N. In some embodiments, Z is $CR^8$. In some embodiments, Z is N.

In frequent embodiments of Formula (IV), X is $CR^6$, Y is $CR^7$ and Z is $CR^8$. In other embodiments of Formula (IV), at least one of X, Y and Z is N.

In some embodiments of Formula (IV), $R^2$ and $R^3$ are H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$.

In some such embodiments, $R^2$ and $R^3$ are H, $C_1$-$C_5$ alkyl or $C_1$-$C_5$ fluoroalkyl, where each said $C_1$-$C_5$ alkyl and $C_1$-$C_5$ fluoroalkyl is optionally substituted by $R^{20}$. In other such embodiments, $R^2$ and $R^3$ are $C_3$-$C_8$ cycloalkyl or 3-6 membered heterocyclyl, where each said $C_3$-$C_8$ cycloalkyl and 3-6 membered heterocyclyl is optionally substituted by $R^{21}$. In some embodiments, $R^2$ is $C_1$-$C_4$ alkyl optionally substituted by $R^{20}$ where $R^{20}$ is OH. In some embodiments, $R^3$ is $C_1$-$C_4$ alkyl optionally substituted by $R^{20}$ where $R^{20}$ is OH.

In some embodiments of Formula (IV), $R^4$ is H, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$. In some embodiments, $R^4$ is $C_1$-$C_4$ alkyl optionally substituted by $R^{20}$ where $R^{20}$ is OH.

In some embodiments of Formula (IV), $R^5$ is H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some embodiments, $R^5$ is $C_1$-$C_4$ alkyl optionally substituted by $R^{20}$. In some such embodiments, $R^{20}$ is OH.

In some embodiments of Formula (IV), $R^2$ can be taken together with $R^4$, or $R^3$ can be taken together with $R^5$, to form a 5-7 membered heterocyclic ring, optionally containing an additional heteroatom selected from $NR^{24}$, O and $S(O)_m$ as a ring member, which ring is optionally substituted by $R^{21}$. It will be understood that $R^2$ is taken together with $R^4$, or $R^3$ is taken together with $R^5$ in combination with the atoms to which they are attached through a $C_3$-$C_5$ alkylene or $C_3$-$C_5$ heteroalkylene linker, which linker is optionally substituted as further defined herein.

In some embodiments of Formula (IV), $R^2$ is taken together with $R^4$ to form a 5-7 membered heterocyclic ring, optionally containing an additional heteroatom selected from $NR^{24}$, O and $S(O)_m$ as a ring member, which ring is optionally substituted by $R^{21}$. In some such embodiments, the 5-7 membered heterocyclic ring contains O as an additional heteroatom. In some such embodiments, the 5-7 membered heterocyclic ring contains $NR^{24}$ as an additional heteroatom.

In some embodiments, $R^2$ is taken together with $R^4$ to form a 5-membered ring containing no additional heteroatoms (i.e., pyrrolidine), which is optionally substituted by $R^{21}$. In other embodiments, $R^2$ is taken together with $R^4$ to form a 6-membered ring containing no additional heteroatoms (i.e., piperidine), which is optionally substituted by $R^{21}$. In other embodiments, $R^2$ is taken together with $R^4$ to form a 6-membered ring containing $NR^{24}$ (i.e., piperazine), which is optionally substituted by $R^{21}$. In further embodiments, $R^2$ is taken together with $R^4$ to form a 6-membered ring containing O or S (i.e., morpholine or thiomorpholine), which is optionally substituted by $R^{21}$. In further embodiments, $R^2$ is taken together with $R^4$ to form a 7-membered ring which may contain no additional heteroatoms (i.e., homopiperidine) or may contain $NR^{24}$ (i.e., homopiperazine), in each case optionally substituted by $R^{21}$.

In other embodiments of Formula (IV), $R^3$ is taken together with $R^5$ to form a 5-7 membered heterocyclic ring, optionally containing an additional heteroatom selected from $NR^{24}$, O and $S(O)_m$ as a ring member, which ring is optionally substituted by $R^{21}$. In some such embodiments, the 5-7 membered heterocyclic ring contains O as an additional heteroatom. In some such embodiments, the 5-7 membered heterocyclic ring contains $NR^{24}$ as an additional heteroatom.

In some embodiments, $R^3$ is taken together with $R^5$ to form a 5-membered ring containing no additional heteroatoms (i.e., pyrrolidine), which is optionally substituted by $R^{21}$. In other embodiments, $R^3$ is taken together with $R^5$ to form a 6-membered ring containing no additional heteroatoms (i.e., piperidine), which is optionally substituted by $R^{21}$. In other embodiments, $R^3$ is taken together with $R^5$ to form a 6-membered ring containing $NR^{24}$ (i.e., piperazine), which is optionally substituted by $R^{21}$. In further embodiments, $R^3$ is taken together with $R^5$ to form a 6-membered ring containing O or $S(O)_m$ (i.e., morpholine or thiomorpholine), which is optionally substituted by $R^{21}$. In further embodiments, $R^3$ is taken together with $R^5$ to form a 7-membered ring which may contain no additional heteroatoms (i.e., homopiperidine) or may contain $NR^{24}$ (i.e., homopiperazine), in each case optionally substituted by $R^{21}$.

In compounds of Formula (IV), $R^6$ is H, F, Cl, CN, $CH_3$, $CH_2F$, $CHF_2$ or $CF_3$. In some embodiments, $R^6$ is F or Cl. In some such embodiments, $R^6$ is F. In some such embodiments, $R^6$ is Cl. In some embodiments, $R^6$ is H. In other embodiments, $R^6$ is CN, $CH_3$, $CH_2F$, $CHF_2$ or $CF_3$.

In compounds of Formula (IV), $R^7$ and $R^8$ are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy, where each said $C_1$-$C_2$ alkyl, $C_1$-$C_2$ fluoroalkyl, $C_1$-$C_2$ alkoxy and $C_1$-$C_2$ fluoroalkoxy is optionally substituted by $R^{20}$. In some such embodiments, $R^7$ is H. In some such embodiments, $R^8$ is H. In some such embodiments, $R^7$ and $R^8$ are H.

In compounds of Formula (IV), $R^9$ is H, OH, $NH_2$, $NHCH_3$ or $N(CH_3)_2$. In preferred embodiments of Formula (IV), $R^9$ is OH.

In compounds of Formula (IV), each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$. In some embodiments, n is 0 and $R^{10}$ is absent. In other embodiments, n is 1 or 2 and $R^{10}$ is independently F, CN, $C_1$-$C_2$ alkyl or $C_1$-$C_2$ fluoroalkyl. In some embodiments, n is 1 or 2 and $R^{10}$ is independently F or $CH_3$.

In some embodiments of Formula (IV), Q is $NR^{11}$ or O. In some embodiments, Q is O. In some embodiments, Q is O, p is 2 and q is 1. In some such embodiments, n is 0 and $R^{10}$ is absent.

In other embodiments of Formula (IV), Q is $NR^{11}$. In some embodiments, Q is $NR^{11}$, p is 2 and q is 1. In some such embodiments, $R^{11}$ is $SO_2R^{14}$. In other such embodiments, $R^{11}$ is $COR^{17}$. In some such embodiments, n is 0 and $R^{10}$ is absent.

In some embodiments of Formula (VI), Q is $CR^{12}R^{13}$, where $R^{12}$ and $R^{13}$ are taken together with the C atom to which they are attached to form a 4-6 membered heterocyclic ring containing $NR^{11}$ or O as a ring member, which ring is optionally further substituted by $R^{10}$. In some such embodiments, n is 0 and $R^{10}$ is absent.

In compounds of Formula (IV), $R^{11}$ is H, $C_1$-$C_4$ alkyl, $C_1$-$C_4$ fluoroalkyl, $SO_2R^{14}$, $SO_2NR^{15}R^{16}$, $COR^{17}$, $COOR^{17}$ or $CONR^{18}R^{19}$. In some embodiments, $R^{11}$ is $SO_2R^{14}$. In other embodiments, $R^{11}$ is $COR^{17}$.

In compounds of Formula (IV), $R^{14}$ is $C_1$-$C_4$ alkyl or $C_1$-$C_4$ fluoroalkyl. In some embodiments, $R^{14}$ is $C_1$-$C_4$ alkyl. In some such embodiments, $R^{14}$ is $C_1$-$C_2$ alkyl. In some embodiments, $R^{14}$ is $C_1$-$C_4$ fluoroalkyl. In some such embodiments, $R^{14}$ is $C_1$-$C_2$ fluoroalkyl. In particular embodiments, $R^{14}$ is $CH_3$ or $C_2H_5$.

In compounds of Formula (IV), each $R^{15}$ and $R^{16}$ is independently H or $CH_3$.

In compounds of Formula (IV), $R^{17}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some embodiments, $R^{17}$ is $C_1$-$C_4$ alkyl, where each said $C_1$-$C_4$ alkyl is optionally substituted by $R^{20}$.

In compounds of Formula (IV), each $R^{18}$ and $R^{19}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$.

In compounds of Formula (IV), each $R^{20}$ is independently OH, $C_1$-$C_2$ alkoxy, $C_1$-$C_2$ fluoroalkoxy, CN, or $NR^{22}R^{23}$.

In compounds of Formula (IV), each $R^{21}$ is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$. In some embodiments, each $R^{21}$ is independently F, OH or $C_1$-$C_4$ alkyl.

In compounds of Formula (IV), each $R^{22}$ and $R^{23}$ is independently H, $C_1$-$C_2$ alkyl, $C_1$-$C_2$ fluoroalkyl. In other embodiments of Formula (IV), $R^{22}$ and $R^{23}$ may be taken together with the nitrogen atom to which they are attached to form an azetidinyl ring, where said ring is optionally substituted by F or OH.

In compounds of Formula (IV), $R^{24}$ is H, $C_1$-$C_4$ alkyl, $C_1$-$C_4$ fluoroalkyl, $SO_2R^{25}$, $SO_2NR^{26}R^{27}$, $COR^{28}$, $COOR^{28}$ or $CONR^{29}R^{30}$. In some embodiments, $R^{24}$ is H or $C_1$-$C_4$ alkyl. In some embodiments, $R^{24}$ is H or $C_1$-$C_2$ alkyl.

In compounds of Formula (IV), $R^{25}$ is $C_1$-$C_4$ alkyl or $C_1$-$C_4$ fluoroalkyl. In some embodiments, $R^{25}$ is $C_1$-$C_2$ alkyl.

In compounds of Formula (IV), each $R^{26}$ and $R^{27}$ is independently H or $CH_3$.

In compounds of Formula (IV), $R^{28}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$. In some embodiments, $R^{28}$ is $C_1$-$C_4$ alkyl optionally substituted by OH or $C_1$-$C_2$ alkoxy. In some embodiments, $R^{28}$ is $C_1$-$C_2$ alkyl.

In compounds of Formula (IV), each $R^{29}$ and $R^{30}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$. In some embodiments, each $R^{29}$ and $R^{30}$ is independently H or $C_1$-$C_4$ alkyl where each said $C_1$-$C_4$ alkyl is optionally substituted by OH or $C_1$-$C_2$ alkoxy. In some embodiments, each $R^{29}$ and $R^{30}$ is independently H or $C_1$-$C_2$ alkyl.

In compounds of Formula (IV), m is 0, 1 or 2. In some embodiments, m is 2.

In compounds of Formula (IV), n is 0, 1, 2, 3 or 4. In some embodiments, n is 0 and $R^{10}$ is absent. In some embodiments, n is 1 or 2.

In compounds of Formula (IV), p is 1, 2 or 3; wherein the sum of p and q is an integer from 1 to 4. In some embodiments, p is 2. In other embodiments, p is 1. In some embodiments, the sum of p and q is an integer from 1 to 3.

In compounds of Formula (IV), q is 0, 1, 2 or 3; wherein the sum of p and q is an integer from 1 to 4. In some embodiments, q is 1. In other embodiments, q is 0. In some embodiments, the sum of p and q is an integer from 1 to 3.

In some embodiments, p is 2 and q is 1. In other embodiments, p is 1 and q is 1. In other embodiments, p is 1 and q is 0. In further embodiments, the sum of p and q is an integer from 1 to 3.

In certain embodiments, the invention provides a compound of Formula (IV), (IV-A), (IV-B), (IV-C) or (IV-D), or a pharmaceutically acceptable salt thereof, having a combination of two or more, preferably three or more, and more preferably four or more, of the following features: $R^1$ is Cl; U is $NR^2$ and V is $CR^4$; $R^2$ is $C_1$-$C_5$ alkyl; or $R^2$ is i-$C_3H_7$; $R^4$ is $C_1$-$C_4$ alkyl, where said $C_1$-$C_4$ alkyl is optionally substituted by $R^{20}$, where $R^{20}$ is OH; or $R^4$ is $CH(OH)CH_3$ or $C(OH)(CH_3)_2$; X is $CR^6$; $R^6$ is F; Y is $CR^7$; $R^7$ is H; Z is $CR^8$; $R^8$ is H; $R^9$ is OH; Q is O; or Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In certain embodiments, the invention provides a compound of Formula (IV), (IV-A), (IV-B), (IV-C) or (IV-D), or a pharmaceutically acceptable salt thereof, having a combination of two or more, preferably three or more, and more preferably four or more, of the following features: $R^1$ is Cl; U is $CR^3$ and V is $NR^5$; $R^3$ is $C_1$-$C_5$ alkyl; or $R^3$ is i-$C_3H_7$; $R^5$ is $C_1$-$C_4$ alkyl, where said $C_1$-$C_4$ alkyl is optionally substituted by $R^{20}$; $R^{20}$ is OH; X is $CR^6$; $R^6$ is F; Y is $CR^7$; $R^7$ is H; Z is $CR^8$; $R^8$ is H; $R^9$ is OH; Q is O; or Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In a preferred embodiment, the invention provides a compound of Formula (IV), (IV-A), (IV-B), (IV-C) or (IV-D), or a pharmaceutically acceptable salt thereof, wherein:

$R^1$ is C; U is $NR^2$; $R^2$ is $C_1$-$C_5$ alkyl; V is $CR^4$; $R^4$ is $C_1$-$C_4$ alkyl optionally substituted by $R^{20}$, where $R^{20}$ is OH; X is $CR^6$; $R^6$ is F; Y is $CR^7$; $R^7$ is H; Z is $CR^8$; $R^8$ is H; $R^9$ is OH; Q is O; n is 0 and $R^{10}$ is absent; p is 2; and q is 1.

In another preferred embodiment, the invention provides a compound of Formula (IV), (IV-A), (IV-B), (IV-C) or (IV-D), or a pharmaceutically acceptable salt thereof, wherein: $R^1$ is Cl; U is $NR^2$; $R^2$ is $C_1$-$C_5$ alkyl; V is $CR^4$; $R^4$ is $C_1$-$C_4$ alkyl optionally substituted by $R^{20}$, where $R^{20}$ is OH; X is $CR^6$; $R^6$ is F; Y is $CR^7$; $R^7$ is H; Z is $CR^8$; $R^8$ is H; $R^9$ is OH; Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In certain embodiments, the invention provides a compound of Formula (IV), (IV-A), (IV-B), (IV-C) or (IV-D), or a pharmaceutically acceptable salt thereof, wherein: $R^1$ is Cl; U is $NR^2$; V is $CR^4$; $R^2$ is taken together with $R^4$ to form a 5-7 membered heterocyclic ring, optionally containing an additional heteroatom selected from $NR^{24}$, O and $S(O)_m$ as a ring member, which ring is optionally substituted by $R^{21}$; each $R^{21}$ is independently F, OH or $C_1$-$C_4$ alkyl; X is $CR^6$; $R^6$ is F; Y is $CR^7$; $R^7$ is H; Z is $CR^8$; $R^8$ is H; $R^9$ is OH; Q is O; or Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In certain embodiments, the invention provides a compound of Formula (IV), (IV-A), (IV-B), (IV-C) or (IV-D), or a pharmaceutically acceptable salt thereof, having a combination of two or more, preferably three or more, and more preferably four or more, of the following features: $R^1$ is Cl; U is $CR^3$; V is $NR^5$; $R^3$ is taken together with $R^5$ to form a 5-7 membered heterocyclic ring, optionally containing an additional heteroatom selected from $NR^{24}$, O and $S(O)_m$ as a ring member, which ring is optionally substituted by $R^{21}$; each $R^{21}$ is independently F, OH or $C_1$-$C_4$ alkyl; X is $CR^6$; $R^6$ is F; Y is $CR^7$; $R^7$ is H; Z is $CR^8$; $R^8$ is H; $R^9$ is OH; Q is O; or Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In compounds of Formula (V), $R^1$ is H, F, Cl, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$. In some embodiments, $R^1$ is F or Cl. In some embodiments, $R^1$ is F. In some embodiments, $R^1$ is Cl.

In compounds of Formula (V), U is $NR^2$ or $CR^3$; V is N or $CR^4$ when U is $NR^2$; and V is $NR^5$ when U is $CR^3$. In some embodiments, U is $NR^2$ and V is N or $CR^4$. In some such embodiments, U is $NR^2$ and V is N. In some such embodiments, U is $NR^2$ and V is $CR^4$. In some embodiments, U is $CR^3$ and V is $NR^5$.

In compounds of Formula (V), X is $CR^6$ or N. In some embodiments, X is $CR^6$. In some embodiments, X is N, In compounds of Formula (V), Y is $CR^7$ or N. In some embodiments, Y is $CR^7$. In some embodiments, Y is N.

In compounds of Formula (V), Z is $CR^8$ or N. In some embodiments, Z is $CR^8$. In some embodiments, Z is N.

In frequent embodiments of Formula (V), X is $CR^6$, Y is $CR^7$ and Z is $CR^8$. In other embodiments of Formula (V), at least one of X, Y and Z is N.

In some embodiments of Formula (V), $R^2$ and $R^3$ are H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$.

In some such embodiments, $R^2$ and $R^3$ are H, $C_1$-$C_5$ alkyl or $C_1$-$C_5$ fluoroalkyl, where each said $C_1$-$C_5$ alkyl and $C_1$-$C_5$ fluoroalkyl is optionally substituted by $R^{20}$. In other such embodiments, $R^2$ and $R^3$ are $C_3$-$C_8$ cycloalkyl or 3-6 membered heterocyclyl, where each said $C_3$-$C_8$ cycloalkyl and 3-6 membered heterocyclyl is optionally substituted by $R^{21}$. In some embodiments, $R^2$ is $C_1$-$C_4$ alkyl optionally substituted by $R^{20}$ where $R^{20}$ is OH. In some embodiments, $R^3$ is $C_1$-$C_4$ alkyl optionally substituted by $R^{20}$ where $R^{20}$ is OH.

In some embodiments of Formula (V), $R^4$ is H, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$. In some embodiments, $R^4$ is $C_1$-$C_4$ alkyl optionally substituted by $R^{20}$ where $R^{20}$ is OH.

In some embodiments of Formula (V), $R^5$ is H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some embodiments, $R^5$ is $C_1$-$C_4$ alkyl optionally substituted by $R^{20}$. In some such embodiments, $R^{20}$ is OH.

In some embodiments of Formula (V), $R^2$ can be taken together with $R^4$, or $R^3$ can be taken together with $R^5$, to form a 5-7 membered heterocyclic ring, optionally containing an additional heteroatom selected from $NR^{24}$, O and $S(O)_m$ as a ring member, which ring is optionally substituted by $R^{21}$. It will be understood that $R^2$ is taken together with $R^4$, or $R^3$ is taken together with $R^5$ in combination with the atoms to which they are attached through a $C_3$-$C_5$ alkylene or $C_3$-$C_5$ heteroalkylene linker, which linker is optionally substituted as further defined herein.

In some embodiments of Formula (V), $R^2$ is taken together with $R^4$ to form a 5-7 membered heterocyclic ring, optionally containing an additional heteroatom selected from $NR^{24}$, O and $S(O)_m$ as a ring member, which ring is optionally substituted by $R^{21}$. In some such embodiments, the 5-7 membered heterocyclic ring contains O as an additional heteroatom. In some such embodiments, the 5-7 membered heterocyclic ring contains $NR^{24}$ as an additional heteroatom.

In some embodiments, $R^2$ is taken together with $R^4$ to form a 5-membered ring containing no additional heteroatoms (i.e., pyrrolidine), which is optionally substituted by $R^{21}$. In other embodiments, $R^2$ is taken together with $R^4$ to form a 6-membered ring containing no additional heteroatoms (i.e., piperidine), which is optionally substituted by $R^{21}$. In other embodiments, $R^2$ is taken together with $R^4$ to form a 6-membered ring containing $NR^{24}$ (i.e., piperazine), which is optionally substituted by $R^{21}$. In further embodiments, $R^2$ is taken together with $R^4$ to form a 6-membered ring containing O or S (i.e., morpholine or thiomorpholine), which is optionally substituted by $R^{21}$. In further embodiments, $R^2$ is taken together with $R^4$ to form a 7-membered ring which may contain no additional heteroatoms (i.e., homopiperidine) or may contain $NR^{24}$ (i.e., homopiperazine), in each case optionally substituted by $R^{21}$.

In other embodiments of Formula (V), $R^3$ is taken together with $R^5$ to form a 5-7 membered heterocyclic ring, optionally containing an additional heteroatom selected from $NR^{24}$, O and $S(O)_m$ as a ring member, which ring is optionally substituted by $R^{21}$. In some such embodiments, the 5-7 membered heterocyclic ring contains O as an additional heteroatom. In some such embodiments, the 5-7 membered heterocyclic ring contains $NR^{24}$ as an additional heteroatom.

In some embodiments, $R^3$ is taken together with $R^5$ to form a 5-membered ring containing no additional heteroatoms (i.e., pyrrolidine), which is optionally substituted by $R^{21}$. In other embodiments, $R^3$ is taken together with $R^5$ to form a 6-membered ring containing no additional heteroatoms (i.e., piperidine), which is optionally substituted by $R^{21}$. In other embodiments, $R^3$ is taken together with $R^5$ to form a 6-membered ring containing $NR^{24}$ (i.e., piperazine), which is optionally substituted by $R^{21}$. In further embodiments, $R^3$ is taken together with $R^5$ to form a 6-membered ring containing O or $S(O)_m$ (i.e., morpholine or thiomorpholine), which is optionally substituted by $R^{21}$. In further embodiments, $R^3$ is taken together with $R^5$ to form a 7-membered ring which may contain no additional heteroatoms (i.e., homopiperidine) or may contain $NR^{24}$ (i.e., homopiperazine), in each case optionally substituted by $R^{21}$.

In compounds of Formula (V), $R^6$ is H, F, Cl, CN, $CH_3$, $CH_2F$, $CHF_2$ or $CF_3$. In some embodiments, $R^6$ is F or Cl. In some such embodiments, $R^6$ is F. In some such embodiments, $R^6$ is Cl. In some embodiments, $R^6$ is H. In other embodiments, $R^6$ is CN, $CH_3$, $CH_2F$, $CHF_2$ or $CF_3$.

In compounds of Formula (V), $R^7$ and $R^8$ are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy, where each said $C_1$-$C_2$ alkyl, $C_1$-$C_2$ fluoroalkyl, $C_1$-$C_2$ alkoxy and $C_1$-$C_2$ fluoroalkoxy is optionally substituted by $R^{20}$. In some such embodiments, $R^7$ is H. In some such embodiments, $R^8$ is H. In some such embodiments, $R^7$ and $R^8$ are H.

In compounds of Formula (V), $R^9$ is H, OH, $NH_2$, $NHCH_3$ or $N(CH_3)_2$. In preferred embodiments of Formula (V), $R^9$ is OH.

In compounds of Formula (V), each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$. In some embodiments, n is 0 and $R^{10}$ is absent. In other embodiments, n is 1 or 2 and $R^{10}$ is independently F, CN, $C_1$-$C_2$ alkyl or $C_1$-$C_2$ fluoroalkyl. In some embodiments, n is 1 or 2 and $R^{10}$ is independently F or $CH_3$.

In some embodiments of Formula (V), Q is $NR^{11}$ or O. In some embodiments, Q is O. In some embodiments, Q is O, p is 2 and q is 1. In some such embodiments, n is 0 and $R^{10}$ is absent.

In other embodiments of Formula (V), Q is $NR^{11}$. In some embodiments, Q is $NR^{11}$, p is 2 and q is 1. In some such embodiments, $R^{11}$ is $SO_2R^{14}$. In other such embodiments, $R^{11}$ is $COR^{17}$. In some embodiments, n is 0 and $R^{10}$ is absent.

In some embodiments of Formula (V), Q is $CR^{12}R^{13}$, where $R^{12}$ and $R^{13}$ are taken together with the C atom to which they are attached to form a 4-6 membered heterocyclic ring containing $NR^{11}$ or O as a ring member, which ring is optionally further substituted by $R^{10}$. In some such embodiments, n is 0 and $R^{10}$ is absent.

In compounds of Formula (V), $R^{11}$ is H, $C_1$-$C_4$ alkyl, $C_1$-$C_4$ fluoroalkyl, $SO_2R^{14}$, $SO_2NR^{15}R^{16}$, $COR^{17}$, $COOR^{17}$ or $CONR^{18}R^{19}$. In some embodiments, $R^{11}$ is $SO_2R^{14}$. In other embodiments, $R^{11}$ is $COR^{17}$.

In compounds of Formula (V), $R^{14}$ is $C_1$-$C_4$ alkyl or $C_1$-$C_4$ fluoroalkyl. In some embodiments, $R^{14}$ is $C_1$-$C_4$ alkyl. In some such embodiments, $R^{14}$ is $C_1$-$C_2$ alkyl. In some embodiments, $R^{14}$ is $C_1$-$C_4$ fluoroalkyl. In some such embodiments, $R^{14}$ is $C_1$-$C_2$ fluoroalkyl. In particular embodiments, $R^{14}$ is $CH_3$ or $C_2H_5$.

In compounds of Formula (V), each $R^{15}$ and $R^{16}$ is independently H or $CH_3$.

In compounds of Formula (V), $R^{17}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some embodiments, $R^{17}$ is $C_1$-$C_4$ alkyl, where each said $C_1$-$C_4$ alkyl is optionally substituted by $R^{20}$.

In compounds of Formula (V), each $R^{18}$ and $R^{19}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$.

In compounds of Formula (V), each $R^{20}$ is independently OH, $C_1$-$C_2$ alkoxy, $C_1$-$C_2$ fluoroalkoxy, CN, or $NR^{22}R^{23}$.

In compounds of Formula (V), each $R^{21}$ is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$. In some embodiments, each $R^{21}$ is independently F, OH or $C_1$-$C_4$ alkyl.

In some embodiments of Formula (V), each $R^{22}$ and $R^{23}$ is independently H, $C_1$-$C_2$ alkyl, $C_1$-$C_2$ fluoroalkyl. In other embodiments of Formula (V), $R^{22}$ and $R^{23}$ may be taken together with the nitrogen atom to which they are attached to form an azetidinyl ring, where said ring is optionally substituted by F or OH.

In compounds of Formula (V), $R^{24}$ is H, $C_1$-$C_4$ alkyl, $C_1$-$C_4$ fluoroalkyl, $SO_2R^{25}$, $SO_2NR^{26}R^{27}$, $COR^{28}$, $COOR^{28}$ or $CONR^{29}R^{30}$. In some embodiments, $R^{24}$ is H or $C_1$-$C_4$ alkyl. In some embodiments, $R^{24}$ is H or $C_1$-$C_2$ alkyl.

In compounds of Formula (V), $R^{25}$ is $C_1$-$C_4$ alkyl or $C_1$-$C_4$ fluoroalkyl. In some embodiments, $R^{25}$ is $C_1$-$C_2$ alkyl.

In compounds of Formula (V), each $R^{26}$ and $R^{27}$ is independently H or $CH_3$.

In compounds of Formula (V), $R^{28}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$. In some embodiments, $R^{28}$ is $C_1$-$C_4$ alkyl optionally substituted by OH or $C_1$-$C_2$ alkoxy. In some embodiments, $R^{28}$ is $C_1$-$C_2$ alkyl.

In compounds of Formula (V), each $R^{29}$ and $R^{30}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$. In some embodiments, each $R^{29}$ and $R^{30}$ is independently H or $C_1$-$C_4$ alkyl where each said $C_1$-$C_4$ alkyl is optionally substituted by OH or $C_1$-$C_2$ alkoxy. In some embodiments, each $R^{29}$ and $R^{30}$ is independently H or $C_1$-$C_2$ alkyl.

In compounds of Formula (V), m is 0, 1 or 2. In some embodiments, m is 2.

In compounds of Formula (V), n is 0, 1, 2, 3 or 4. In some embodiments, n is 0 and $R^{10}$ is absent. In some embodiments, n is 1 or 2.

In compounds of Formula (V), p is 1, 2 or 3; wherein the sum of p and q is an integer from 1 to 4. In some embodiments, p is 2. In other embodiments, p is 1. In some embodiments, the sum of p and q is an integer from 1 to 3.

In compounds of Formula (V), q is 0, 1, 2 or 3; wherein the sum of p and q is an integer from 1 to 4. In some embodiments, q is 1. In other embodiments, q is 0. In some embodiments, the sum of p and q is an integer from 1 to 3.

In some embodiments, p is 2 and q is 1. In other embodiments, p is 1 and q is 1. In other embodiments, p is 1 and q is 0. In further embodiments, the sum of p and q is an integer from 1 to 3.

In certain embodiments, the invention provides a compound of Formula (V), (V-A), (V-B), (V-C) or (V-D), or a pharmaceutically acceptable salt thereof, having a combination of two or more, preferably three or more, and more preferably four or more, of the following features: $R^1$ is Cl; U is $NR^2$ and V is $CR^4$; $R^2$ is $C_1$-$C_5$ alkyl; or $R^2$ is i-$C_3H_7$; $R^4$ is $C_1$-$C_4$ alkyl, where said $C_1$-$C_4$ alkyl is optionally substituted by $R^{20}$, where $R^{20}$ is OH; or $R^4$ is $CH(OH)CH_3$ or $C(OH)(CH_3)_2$; X is $CR^6$; $R^6$ is F; Y is $CR^7$; $R^7$ is H; Z is $CR^8$; $R^8$ is H; $R^9$ is OH; Q is O; or Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In certain embodiments, the invention provides a compound of Formula (V), (V-A), (V-B), (V-C) or (V-D), or a pharmaceutically acceptable salt thereof, having a combination of two or more, preferably three or more, and more preferably four or more, of the following features: $R^1$ is Cl; U is $CR^3$ and V is $NR^5$; $R^3$ is $C_1$-$C_5$ alkyl; or $R^3$ is i-$C_3H_7$; $R^5$ is $C_1$-$C_4$ alkyl, where said $C_1$-$C_4$ alkyl is optionally substituted by $R^{20}$; $R^{20}$ is OH; X is $CR^6$; $R^6$ is F; Y is $CR^7$; $R^7$ is H; Z is $CR^8$; $R^8$ is H; $R^9$ is OH; Q is O; or Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In a preferred embodiment, the invention provides a compound of Formula (V), (V-A), (V-B), (V-C) or (V-D), or a pharmaceutically acceptable salt thereof, wherein: $R^1$ is C; U is $NR^2$; $R^2$ is $C_1$-$C_5$ alkyl; V is $CR^4$; $R^4$ is $C_1$-$C_4$ alkyl optionally substituted by $R^{20}$, where $R^{20}$ is OH; X is $CR^6$; $R^6$ is F; Y is $CR^7$; $R^7$ is H; Z is $CR^8$; $R^8$ is H; $R^9$ is OH; Q is O; n is 0 and $R^{10}$ is absent; p is 2; and q is 1.

In another preferred embodiment, the invention provides a compound of Formula (V), (V-A), (V-B), (V-C) or (V-D), or a pharmaceutically acceptable salt thereof, wherein: $R^1$ is Cl; U is $NR^2$; $R^2$ is $C_1$-$C_5$ alkyl; V is $CR^4$; $R^4$ is $C_1$-$C_4$ alkyl optionally substituted by $R^{20}$, where $R^{20}$ is OH; X is $CR^6$; $R^6$ is F; Y is $CR^7$; $R^7$ is H; Z is $CR^8$; $R^8$ is H; $R^9$ is OH; Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In certain embodiments, the invention provides a compound of Formula (V), (V-A), (V-B), (V-C) or (V-D), or a pharmaceutically acceptable salt thereof, wherein: $R^1$ is C; U is $NR^2$; V is $CR^4$; $R^2$ is taken together with $R^4$ to form a 5-7 membered heterocyclic ring, optionally containing an additional heteroatom selected from $NR^{24}$, O and $S(O)_m$ as a ring member, which ring is optionally substituted by $R^{21}$; each $R^{21}$ is independently F, OH or $C_1$-$C_4$ alkyl; X is $CR^6$; $R^6$ is F; Y is $CR^7$; $R^7$ is H; Z is $CR^8$; $R^8$ is H; $R^9$ is OH; Q is O; or Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In certain embodiments, the invention provides a compound of Formula (V), (V-A), (V-B), (V-C) or (V-D), or a pharmaceutically acceptable salt thereof, having a combination of two or more, preferably three or more, and more preferably four or more, of the following features: $R^1$ is Cl; U is $CR^3$; V is $NR^5$; $R^3$ is taken together with $R^5$ to form a 5-7 membered heterocyclic ring, optionally containing an additional heteroatom selected from $NR^{24}$, O and $S(O)_m$ as a ring member, which ring is optionally substituted by $R^{21}$; each $R^{21}$ is independently F, OH or $C_1$-$C_4$ alkyl; X is $CR^6$; $R^6$ is F; Y is $CR^7$; $R^7$ is H; Z is $CR^8$; $R^8$ is H; $R^9$ is OH; Q is O; or Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In certain embodiments, the invention provides a compound of Formula (IV), (IV-A), (IV-B), (IV-C) or (IV-D), or a pharmaceutically acceptable salt thereof, or a compound of Formula (V), (V-A), (V-B), (V-C) or (V-D), or a pharmaceutically acceptable salt thereof, having a combination of two or more, preferably three or more, and more preferably four or more, of the following features: $R^1$ is F or Cl; U is $NR^2$ and V is $CR^4$; $R^2$ is $C_1$-$C_5$ alkyl, $C_1$-$C_5$ fluoroalkyl or 3-6 membered heterocyclyl; or $R^2$ is $CH_3$, i-$C_3H_7$, i-$C_4H_9$, s-$C_4H_9$, t-$C_4H_9$, $CH_2F$, $CHF_2$, $CH_2CHF_2$ or oxetan-3-yl; $R^4$ is H or $C_1$-$C_4$ alkyl, where said $C_1$-$C_4$ alkyl is optionally substituted by OH, $NH_2$, $NHCH_3$ or $N(CH_3)_2$; or $R^4$ is H, $CH_3$, $C_2H_5$, $CH_2OH$, $CH(OH)CH_3$, $CH_2CH_2OH$ or $CH_2NH_2$; or $R^2$ is taken together with $R^4$ to form a 5-7 membered heterocyclic ring, optionally containing an additional heteroatom selected from $NR^{24}$, O and $S(O)_m$ as a ring member, which ring is optionally substituted by $R^{21}$; or $R^4$ is $CH(OH)CH_3$ or $C(OH)(CH_3)_2$; X is $CR^6$; $R^6$ is H or F; Y is $CR^7$; Z is $CR^8$; $R^7$ and $R^8$ are H; $R^9$ is OH; Q is $NR^{11}$; $R^{11}$ is $SO_2R^{14}$; $R^{14}$ is $C_1$-$C_4$ alkyl; n is 0 and $R^{10}$ is absent; p is 2; and q is 1.

In certain embodiments, the invention provides a compound of Formula (IV), (IV-A), (IV-B), (IV-C) or (IV-D), or a pharmaceutically acceptable salt thereof, or a compound of Formula (V), (V-A), (V-B), (V-C) or (V-D), or a pharmaceutically acceptable salt thereof, having a combination of two or more, preferably three or more, and more preferably four or more, of the following features: $R^1$ is F or Cl; U is $CR^3$ and V is $NR^5$; $R^3$ is $C_1$-$C_5$ alkyl, $C_1$-$C_5$ fluoroalkyl or 3-6 membered heterocyclyl; or $R^3$ is $CH_3$, i-$C_3H_7$, i-$C_4H_9$, s-$C_4H_9$, t-$C_4H_9$, $CH_2F$, $CHF_2$, $CH_2CHF_2$ or oxetan-3-yl; $R^5$ is H or $C_1$-$C_4$ alkyl; or $R^5$ is H or $CH_3$; or $R^3$ is taken together with $R^5$ to form a 5-7 membered heterocyclic ring, optionally containing an additional heteroatom selected from $NR^{24}$, O and $S(O)_m$ as a ring member, which ring is optionally substituted by $R^{21}$; X is $CR^6$; $R^6$ is H or F; Y is $CR^7$; Z is $CR^8$; $R^7$ and $R^8$ are H; $R^9$ is OH; n is 0 and $R^{10}$ is absent; Q is $NR^{11}$; $R^{11}$ is $SO_2R^{14}$; and $R^{14}$ is $C_1$-$C_4$ alkyl; p is 2; and q is 1.

In compounds of Formula (II) and (IV), $R^1$ is H, F, Cl, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$.

In some embodiments of Formula (II) and (IV), $R^1$ is H. In other embodiments, $R^1$ is F or Cl. In other embodiments, $R^1$ is C. In further embodiments, $R^1$ is $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$. In some such embodiments, $R^1$ is $CH_3$, optionally substituted by $R^{20}$. In particular embodiments, $R^1$ is $CH_3$.

In compounds of Formula (II) and (IV), the ring system comprising U, V, X, Y and Z is a fused biaryl ring system.

In compounds of Formula (II) and (IV), U is $NR^2$ or $CR^3$. In some embodiments, U is $NR^2$. In other embodiments, U is $CR^3$.

In compounds of Formula (II) and (IV), V is N or $CR^4$ when U is $NR^2$; and V is $NR^5$ when U is $CR^3$. In some such embodiments, V is $CR^4$. In other such embodiments, V is N. In further such embodiments, V is $NR^5$.

In compounds of Formula (II) and (IV), X is $CR^6$ or N. In some embodiments, X is $CR^6$. In other embodiments, X is N.

In compounds of Formula (II) and (IV), Y is $CR^7$ or N. In some embodiments, Y is $CR^7$. In other embodiments, Y is N.

In compounds of Formula (II) and (IV), Z is $CR^8$ or N. In some embodiments, Z is $CR^8$. In other embodiments, Z is N.

In some embodiments of Formula (II) and (IV), X is $CR^6$, Y is CR and Z is $CR^8$. In some such embodiments, U is $NR^2$ and V is $CR^4$. In other such embodiments, U is $NR^2$ and V is N. In still other such embodiments, U is $CR^3$ and V is $NR^5$.

In some embodiments of Formula (II) and (IV), X is N, Y is $CR^7$, and Z is $CR^8$.

In some embodiments of Formula (II) and (IV), X is $CR^6$, Y is N, and Z is $CR^8$.

In some embodiments of Formula (II) and (IV), X is $CR^6$, Y is $CR^7$, and Z is N.

In some embodiments of Formula (II) and (IV), X is N, Y is N, and Z is $CR^8$.

In some embodiments of Formula (II) and (IV), X is $CR^6$, Y is N, and Z is N.

In some embodiments of Formula (II) and (IV), X is N, Y is CR$^7$, and Z is N.

In other embodiments of Formula (II) and (IV), at least one of X, Y and Z is N. In some such embodiments, U is NR$^2$ and V is CR$^4$. In other such embodiments, U is NR$^2$ and V is N. In still other such embodiments, U is CR$^3$ and V is NR$^5$.

In further embodiments of Formula (II) and (IV), two of X, Y and Z are N. In some such embodiments, U is NR$^2$ and V is CR$^4$. In other such embodiments, U is NR$^2$ and V is N. In still other such embodiments, U is CR$^3$ and V is NR$^5$.

In compounds of Formula (III) and (V), R$^1$ is H, F, Cl, CN, C$_1$-C$_2$ alkyl or C$_1$-C$_2$ fluoroalkyl, where each said C$_1$-C$_2$ alkyl and C$_1$-C$_2$ fluoroalkyl is optionally substituted by R$^{20}$.

In some embodiments of Formula (III) and (V), R$^1$ is H. In other embodiments, R$^1$ is F or Cl. In other embodiments, R$^1$ is C. In further embodiments, R$^1$ is C$_1$-C$_2$ alkyl or C$_1$-C$_2$ fluoroalkyl, where each said C$_1$-C$_2$ alkyl and C$_1$-C$_2$ fluoroalkyl is optionally substituted by R$^{20}$. In some such embodiments, R$^1$ is CH$_3$, optionally substituted by R$^{20}$. In particular embodiments, R$^1$ is CH$_3$.

In compounds of Formula (III) and (V), the ring system comprising U, V, X, Y and Z is a fused biaryl ring system.

In compounds of Formula (III) and (V), U is NR$^2$ or CR$^3$. In some embodiments, U is NR$^2$. In other embodiments, U is CR$^3$.

In compounds of Formula (III) and (V), V is N or CR$^4$ when U is NR$^2$; and V is NR$^5$ when U is CR$^3$. In some such embodiments, V is CR$^4$. In other such embodiments, V is N. In further such embodiments, V is NR$^5$.

In compounds of Formula (III) and (V), X is CR$^6$ or N. In some embodiments, X is CR$^6$. In other embodiments, X is N.

In compounds of Formula (III) and (V), Y is CR$^7$ or N. In some embodiments, Y is CR$^7$. In other embodiments, Y is N.

In compounds of Formula (III) and (V), Z is CR$^8$ or N. In some embodiments, Z is CR$^8$. In other embodiments, Z is N.

In some embodiments of Formula (III) and (V), X is CR$^6$, Y is CR$^7$ and Z is CR$^8$. In some such embodiments, U is NR$^2$ and V is CR$^4$. In other such embodiments, U is NR$^2$ and V is N. In still other such embodiments, U is CR$^3$ and V is NR$^5$.

In some embodiments of Formula (III) and (V), X is N, Y is CR$^7$, and Z is CR$^8$.

In some embodiments of Formula (III) and (V), X is CR$^6$, Y is N, and Z is CR$^8$.

In some embodiments of Formula (III) and (V), X is CR$^6$, Y is CR$^7$, and Z is N.

In some embodiments of Formula (III) and (V), X is N, Y is N, and Z is CR$^8$.

In some embodiments of Formula (III) and (V), X is CR$^6$, Y is N, and Z is N.

In some embodiments of Formula (III) and (V), X is N, Y is CR$^7$, and Z is N.

In other embodiments of Formula (III) and (V), at least one of X, Y and Z is N. In some such embodiments, U is NR$^2$ and V is CR$^4$. In other such embodiments, U is NR$^2$ and V is N. In still other such embodiments, U is CR$^3$ and V is NR$^5$.

In further embodiments of Formula (III) and (V), two of X, Y and Z are N. In some such embodiments, U is NR$^2$ and V is CR$^4$. In other such embodiments, U is NR$^2$ and V is N. In still other such embodiments, U is CR$^3$ and V is NR$^5$.

In particular embodiments of each of Formulae (I), (II), (III), (IV) and (V), the fused biaryl ring system comprising U, V, X, Y and Z is selected from the group consisting of:

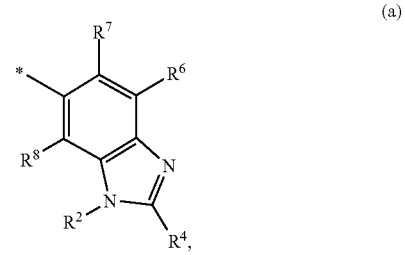
(a)

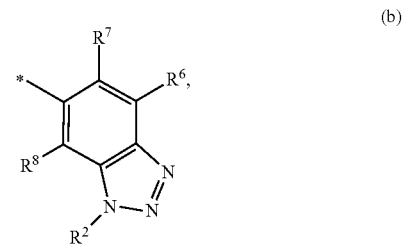
(b)

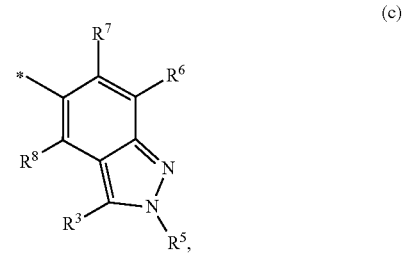
(c)

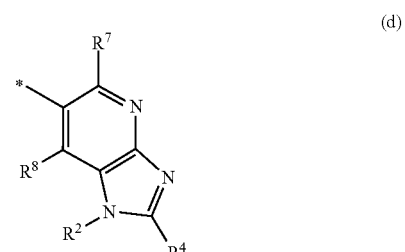
(d)

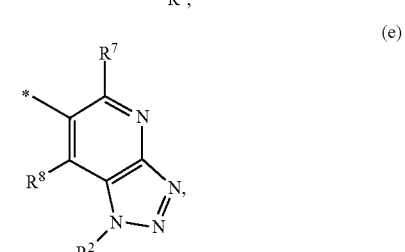
(e)

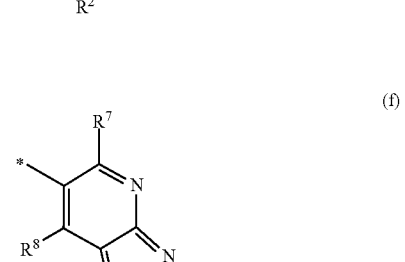
(f)

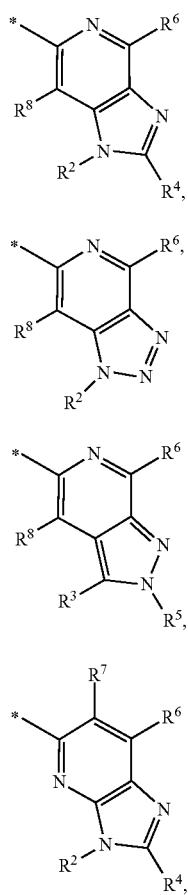

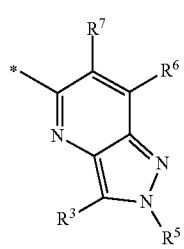

where the * represents the point of attachment to the pyrimidine ring or pyridine ring, and $R^2$, $R^3$, $R^4$, $R^5$, $R^6$, $R^7$ and $R^8$ are as further defined herein.

In another aspect, the invention provides a compound of Formula (VI):

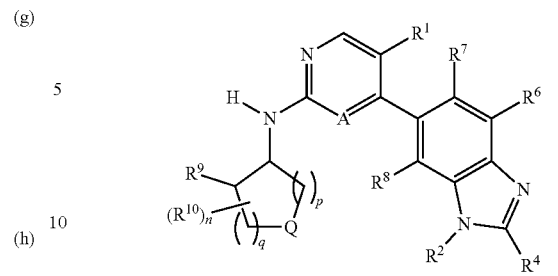

or a pharmaceutically acceptable salt thereof, wherein:

$R^1$, $R^2$, $R^4$, $R^6$ to $R^{23}$, Q, n, p and q are as defined for Formula (II); or $R^1$, $R^2$, $R^4$, $R^6$ to $R^{30}$, Q, m, n, p and q are as defined for Formula (IV).

In particular embodiments, the invention provides a compound of Formula (VI), (VI-A), (VI-B), (VI-C) or (VI-D), or a pharmaceutically acceptable salt thereof, wherein:

$R^1$, $R^2$, $R^4$, $R^6$ to $R^{23}$ and n are as defined for Formula (II).

In other embodiments, the invention provides a compound of Formula (VI), (VI-A), (VI-B), (VI-C) or (VI-D), or a pharmaceutically acceptable salt thereof, wherein:

$R^1$, $R^2$, $R^4$, $R^6$ to $R^{30}$, m and n are as defined for Formula (IV).

In some embodiments, the compound of Formula (VI) has the absolute stereochemistry as shown in one of Formulae (VI-A), (VI-B), (VI-C) or (VI-D):

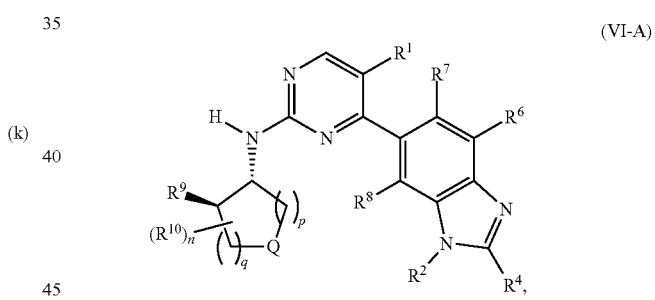

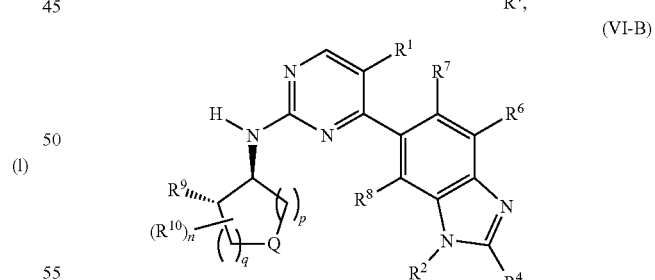

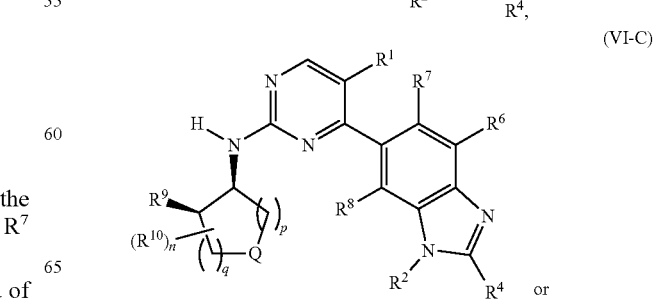

-continued (VI-D)

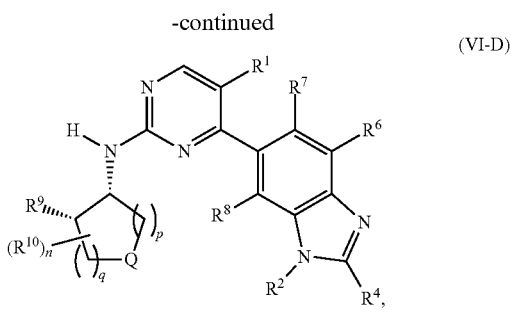

or a pharmaceutically acceptable salt thereof.

Each of the aspects and embodiments described herein with respect to Formula (II) is also applicable to compounds of Formula (VI) that are not inconsistent with such aspect or embodiment.

Each of the aspects and embodiments described herein with respect to Formula (IV) is also applicable to compounds of Formula (VI) that are not inconsistent with such aspect or embodiment.

In certain embodiments, the invention provides a compound of Formula (VI), (VI-A), (VI-B), (VI-C) or (VI-D), or a pharmaceutically acceptable salt thereof, having a combination of two or more, preferably three or more, and more preferably four or more, of the following features: $R^1$ is Cl; $R^2$ is $C_1$-$C_5$ alkyl; or $R^2$ is i-$C_3H_7$; $R^4$ is $C_1$-$C_4$ alkyl, where said $C_1$-$C_4$ alkyl is optionally substituted by $R^{20}$, where $R^{20}$ is OH; or $R^4$ is CH(OH)CH$_3$ or C(OH)(CH$_3$)$_2$; $R^6$ is F; $R^7$ is H; $R^8$ is H; $R^9$ is OH; Q is O; or Q is NR$^{11}$, where $R^{11}$ is SO$_2$R$^{14}$; $R^{14}$ is $C_1$-$C_4$ alkyl; n is 0 and $R^{10}$ is absent; p is 2; and q is 1.

In certain embodiments, the invention provides a compound of Formula (VI), (VI-A), (VI-B), (VI-C) or (VI-D), or a pharmaceutically acceptable salt thereof, having a combination of two or more, preferably three or more, and more preferably four or more, of the following features: $R^1$ is Cl; $R^3$ is $C_1$-$C_5$ alkyl; or $R^3$ is i-$C_3H_7$; $R^5$ is $C_1$-$C_4$ alkyl, where said $C_1$-$C_4$ alkyl is optionally substituted by $R^{20}$; $R^{20}$ is OH; $R^6$ is F; $R^7$ is H; $R^8$ is H; $R^9$ is OH; Q is O; or Q is NR$^{11}$, where $R^{11}$ is SO$_2$R$^{14}$; $R^{14}$ is $C_1$-$C_4$ alkyl; n is 0 and $R^{10}$ is absent; p is 2; and q is 1.

In a preferred embodiment, the invention provides a compound of Formula (VI), (VI-A), (VI-B), (VI-C) or (VI-D), or a pharmaceutically acceptable salt thereof, wherein: $R^1$ is Cl; $R^2$ is $C_1$-$C_5$ alkyl; $R^4$ is $C_1$-$C_4$ alkyl optionally substituted by $R^{20}$, where $R^{20}$ is OH; $R^6$ is F; $R^7$ is H; $R^8$ is H; $R^9$ is OH; Q is O; n is 0 and $R^{10}$ is absent; p is 2; and q is 1.

In another preferred embodiment, the invention provides a compound of Formula (VI), (VI-A), (VI-B), (VI-C) or (VI-D), or a pharmaceutically acceptable salt thereof, wherein: $R^1$ is Cl; $R^2$ is $C_1$-$C_5$ alkyl; $R^4$ is $C_1$-$C_4$ alkyl optionally substituted by $R^{20}$, where $R^{20}$ is OH; $R^6$ is F; $R^7$ is H; $R^8$ is H; $R^9$ is OH; Q is NR$^{11}$, where $R^{11}$ is SO$_2$R$^{14}$; $R^{14}$ is $C_1$-$C_4$ alkyl; n is 0 and $R^{10}$ is absent; p is 2; and q is 1.

In certain embodiments, the invention provides a compound of Formula (VI), (VI-A), (VI-B), (VI-C) or (VI-D), or a pharmaceutically acceptable salt thereof, having a combination of two or more, preferably three or more, and more preferably four or more, of the following features: $R^1$ is F or Cl; $R^2$ is $C_1$-$C_5$ alkyl, $C_1$-$C_5$ fluoroalkyl or 3-6 membered heterocyclyl; or $R^2$ is CH$_3$, i-$C_3H_7$, i-$C_4H_9$, s-$C_4H_9$, t-$C_4H_9$, CH$_2$F, CHF$_2$, CH$_2$CHF$_2$ or oxetan-3-yl; $R^4$ is H or $C_1$-$C_4$ alkyl, where said $C_1$-$C_4$ alkyl is optionally substituted by OH, NH$_2$, NHCH$_3$ or N(CH$_3$)$_2$; or $R^4$ is H, CH$_3$, C$_2$H$_5$, CH$_2$OH, CH(OH)CH$_3$, CH$_2$CH$_2$OH or CH$_2$NH$_2$; $R^6$ is H or F; $R^7$ and $R^8$ are H; $R^9$ is OH; Q is NR$^{11}$; $R^{11}$ is SO$_2$R$^{14}$; $R^{14}$ is $C_1$-$C_4$ alkyl; n is 0 and $R^{10}$ is absent; p is 2; and q is 1.

In certain embodiments, the invention provides a compound of Formula (VI), (VI-A), (VI-B), (VI-C) or (VI-D), or a pharmaceutically acceptable salt thereof, having a combination of two or more, preferably three or more, and more preferably four or more, of the following features: $R^1$ is F or Cl; $R^2$ is $C_1$-$C_5$ alkyl, $C_1$-$C_5$ fluoroalkyl or 3-6 membered heterocyclyl; or $R^2$ is CH$_3$, i-$C_3H_7$, i-$C_4H_9$, s-$C_4H_9$, t-$C_4H_9$, CH$_2$F, CHF$_2$, CH$_2$CHF$_2$ or oxetan-3-yl; $R^4$ is H or $C_1$-$C_4$ alkyl, where said $C_1$-$C_4$ alkyl is optionally substituted by OH, NH$_2$, NHCH$_3$ or N(CH$_3$)$_2$; or $R^4$ is H, CH$_3$, C$_2$H$_5$, CH$_2$OH, CH(OH)CH$_3$, CH$_2$CH$_2$OH or C H$_2$NH$_2$; or $R^2$ is taken together with $R^4$ to form a 5-7 membered heterocyclic ring, optionally containing an additional heteroatom selected from NR$^{24}$, O and S(O)$_m$ as a ring member, which ring is optionally substituted by $R^{21}$; $R^6$ is H or F; $R^7$ and $R^8$ are H; $R^9$ is OH; Q is NR$^{11}$; $R^{11}$ is SO$_2$R$^{14}$; $R^{14}$ is $C_1$-$C_4$ alkyl; n is 0 and $R^{10}$ is absent; p is 2; and q is 1.

In another aspect, the invention provides a compound of Formula (VII):

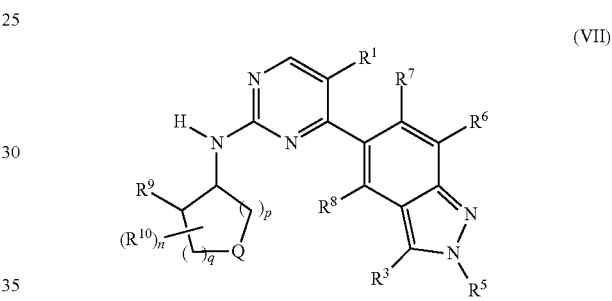

(VII)

or a pharmaceutically acceptable salt thereof, wherein:
$R^1$, $R^3$, $R^5$ to $R^{23}$, Q, n, p and q are as defined for Formula (II); or
$R^1$, $R^3$, $R^5$ to $R^{30}$, Q, m, n, p and q are as defined for Formula (IV).

In particular embodiments, the invention provides a compound of Formula (VII), (VII-A), (VII-B), (VII-C) or (VII-D), or a pharmaceutically acceptable salt thereof, wherein: $R^1$, $R^2$, $R^4$, $R^6$ to $R^{23}$ and n are as defined for Formula (II).

In other embodiments, the invention provides a compound of Formula (VII), (VII-A), (VII-B), (VII-C) or (VII-D), or a pharmaceutically acceptable salt thereof, wherein: $R^1$, $R^2$, $R^4$, $R^6$ to $R^{30}$, m and n are as defined for Formula (IV).

In some embodiments, the compound of Formula (VII) has the absolute stereochemistry as shown in one of Formulae (VII-A), (VII-B), (VII-C) or (VII-D):

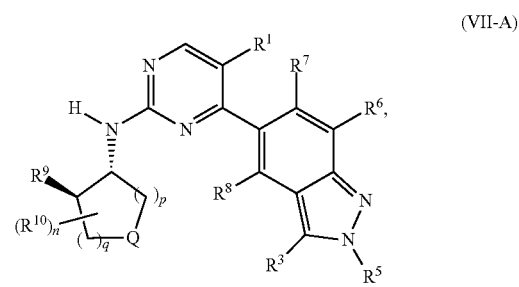

(VII-A)

(VII-B)

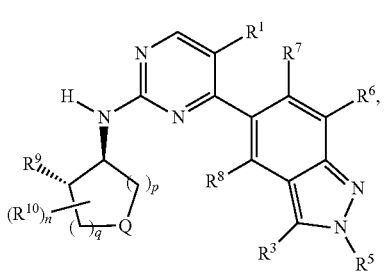

(VII-C)

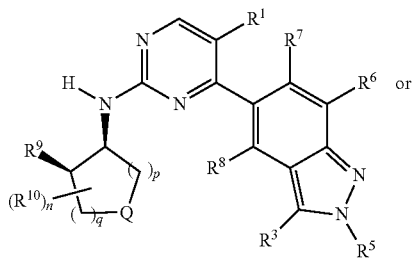

(VII-D)

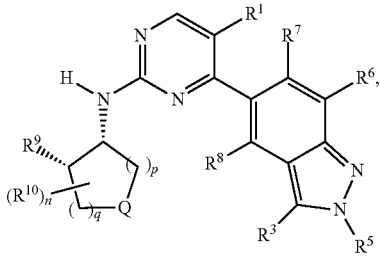

or a pharmaceutically acceptable salt thereof.

Each of the aspects and embodiments described herein with respect to Formula (II) is also applicable to compounds of Formula (VII) that are not inconsistent with such aspect or embodiment.

Each of the aspects and embodiments described herein with respect to Formula (IV) is also applicable to compounds of Formula (VII), that are not inconsistent with such aspect or embodiment.

In certain embodiments, the invention provides a compound of Formula (VII), (VII-A), (VII-B), (VII-C) or (VII-D), or a pharmaceutically acceptable salt thereof, having a combination of two or more, preferably three or more, and more preferably four or more, of the following features: $R^1$ is Cl; $R^3$ is $C_1$-$C_5$ alkyl; or $R^3$ is i-$C_3H_7$; $R^7$ is $C_1$-$C_4$ alkyl, where said $C_1$-$C_4$ alkyl is optionally substituted by $R^{20}$; $R^{20}$ is OH; $R^6$ is F; $R^7$ is H; $R^8$ is H; $R^9$ is OH; Q is O; or Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In a preferred embodiment, the invention provides a compound of Formula (VII), (VII-A), (VII-B), (VII-C) or (VII-D), or a pharmaceutically acceptable salt thereof, wherein: $R^1$ is Cl; $R^3$ is $C_1$-$C_5$ alkyl; $R^5$ is $C_1$-$C_4$ alkyl optionally substituted by $R^{20}$, where $R^{20}$ is OH; $R^6$ is F; $R^7$ is H; $R^8$ is H; $R^9$ is OH; Q is O; n is 0 and $R^{10}$ is absent; p is 2; and q is 1.

In another preferred embodiment, the invention provides a compound of Formula (VII), (VII-A), (VII-B), (VII-C) or (VII-D), or a pharmaceutically acceptable salt thereof, wherein: $R^1$ is C;

$R^3$ is $C_1$-$C_5$ alkyl; $R^5$ is $C_1$-$C_4$ alkyl optionally substituted by $R^{20}$, where $R^{20}$ is OH; $R^6$ is F; $R^7$ is H; $R^8$ is H; $R^9$ is OH;

Q is $NR^{11}$, where $R^{11}$ is $SO_2R^{14}$; $R^{14}$ is $C_1$-$C_4$ alkyl; n is 0 and $R^{10}$ is absent; p is 2; and q is 1.

In certain embodiments, the invention provides a compound of Formula (VII), (VII-A), (VII-B), (VII-C) or (VII-D), or a pharmaceutically acceptable salt thereof, having a combination of two or more, preferably three or more, and more preferably four or more, of the following features: $R^1$ is F or Cl; $R^3$ is $C_1$-$C_5$ alkyl, $C_1$-$C_5$ fluoroalkyl or 3-6 membered heterocyclyl; or $R^3$ is $CH_3$, i-$C_3H_7$, i-$C_4H_9$, s-$C_4H_9$, t-$C_4H_9$, $CH_2F$, $CHF_2$, $CH_2CHF_2$ or oxetan-3-yl; $R^5$ is H or $C_1$-$C_4$ alkyl; or $R^5$ is H or $CH_3$; $R^6$ is H or F; $R^7$ and $R^8$ are H; $R^9$ is OH; Q is $NR^{11}$; $R^{11}$ is $SO_2R^{14}$; $R^{14}$ is $C_1$-$C_4$ alkyl; n is 0 and $R^{10}$ is absent; p is 2; and q is 1.

In certain embodiments, the invention provides a compound of Formula (VII), (VII-A), (VII-B), (VII-C) or (VII-D), or a pharmaceutically acceptable salt thereof, having a combination of two or more, preferably three or more, and more preferably four or more, of the following features: $R^1$ is F or Cl; $R^3$ is $C_1$-$C_5$ alkyl, $C_1$-$C_5$ fluoroalkyl or 3-6 membered heterocyclyl; or $R^3$ is $CH_3$, i-$C_3H_7$, i-$C_4H_9$, s-$C_4H_9$, t-$C_4H_9$, $CH_2F$, $CHF_2$, $CH_2CHF_2$ or oxetan-3-yl; $R^5$ is H or $C_1$-$C_4$ alkyl; or $R^5$ is H or $CH_3$; or $R^3$ is taken together with $R^5$ to form a 5-7 membered heterocyclic ring, optionally containing an additional heteroatom selected from $NR^{24}$, O and $S(O)_m$ as a ring member, which ring is optionally substituted by $R^{21}$; $R^6$ is H or F; $R^7$ and $R^8$ are H; $R^9$ is OH; Q is $NR^{11}$; $R^{11}$ is $SO_2R^{14}$; $R^{14}$ is $C_1$-$C_4$ alkyl; n is 0 and $R^{10}$ is absent; p is 2; and q is 1.

In another aspect, the invention provides a compound of Formula (VIII):

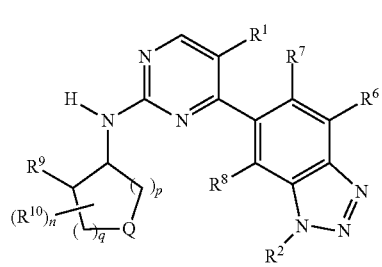

(VIII)

or a pharmaceutically acceptable salt thereof, wherein:

$R^1$, $R^2$, $R^6$ to $R^{23}$, Q, n, p and q are as defined for Formula (II); or $R^1$, $R^2$, $R^6$ to $R^{30}$, Q, m, n, p and q are as defined for Formula (IV).

In particular embodiments, the invention provides a compound of Formula (VIII), or a pharmaceutically acceptable salt thereof, wherein:

$R^1$, $R^2$, $R^4$, $R^6$ to $R^{23}$ and n are as defined for Formula (II).

In other embodiments, the invention provides a compound of Formula (VIII), or a pharmaceutically acceptable salt thereof, wherein:

$R^1$, $R^2$, $R^4$, $R^6$ to $R^{30}$, m and n are as defined for Formula (IV).

In some embodiments, the compound of Formula (VIII) has the absolute stereochemistry as shown in one of Formulae (VIII-A), (VIII-B), (VIII-C) or (VIII-D):

(VIII-A)

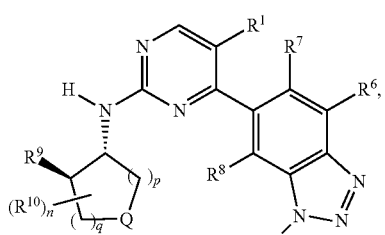

(VIII-B)

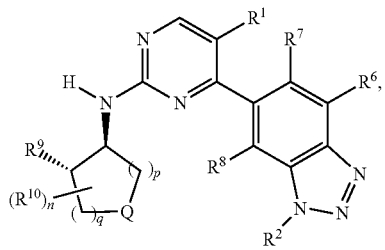

(VIII-C)

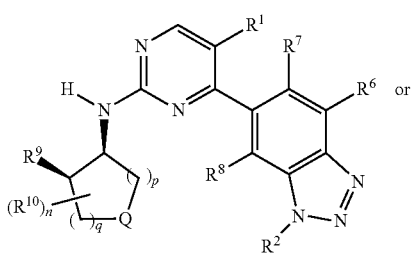

(VIII-D)

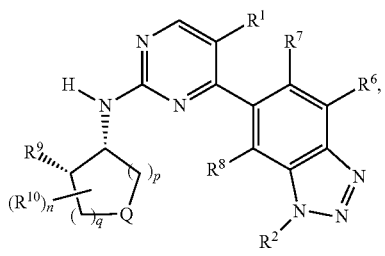

or a pharmaceutically acceptable salt thereof.

Each of the aspects and embodiments described herein with respect to Formula (II) is also applicable to compounds of Formula (VIII) that are not inconsistent with such aspect or embodiment.

Each of the aspects and embodiments described herein with respect to Formula (IV) is also applicable to compounds of Formula (VIII) that are not inconsistent with such aspect or embodiment.

In an embodiment, the invention provides a compound of Formula (VIII), (VIII-A), (VIII-B), (VIII-C) or (VIII-D), or a pharmaceutically acceptable salt thereof, wherein: $R^1$ is Cl; $R^2$ is $C_1$-$C_5$ alkyl optionally substituted by $R^{20}$, where $R^{20}$ is OH; $R^6$ is F; $R^7$ is H; $R^8$ is H; $R^9$ is OH; Q is O; or Q is $NR^{11}$; $R^{11}$ is $SO_2R^{14}$; $R^{14}$ is $C_1$-$C_4$ alkyl; n is 0 and $R^{10}$ is absent; p is 2; and q is 1.

In certain embodiments, the invention provides a compound of Formula (VIII), (VIII-A), (VIII-B), (VIII-C) or (VIII-D), or a pharmaceutically acceptable salt thereof, having a combination of two or more, preferably three or more, and more preferably four or more, of the following features: $R^1$ is F or Cl; $R^2$ is $C_1$-$C_5$ alkyl, $C_1$-$C_5$ fluoroalkyl or 3-6 membered heterocyclyl; or $R^2$ is $CH_3$, i-$C_3H_7$, i-$C_4H_9$, s-$C_4H_9$, t-$C_4H_9$, $CH_2F$, $CHF_2$, $CH_2CHF_2$ or oxetan-3-yl; $R^6$ is H or F; $R^7$ and $R^8$ are H; $R^9$ is OH; Q is O; or Q is $NR^{11}$; $R^{11}$ is $SO_2R^{14}$; $R^{14}$ is $C_1$-$C_4$ alkyl; n is 0 and $R^{10}$ is absent; p is 2; and q is 1.

In particular embodiments of Formulae (I) to (VIII), the ring comprising Q is selected from the group consisting of:

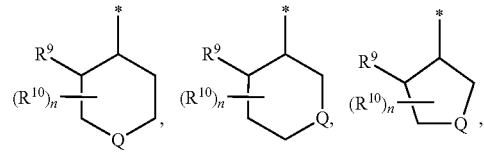

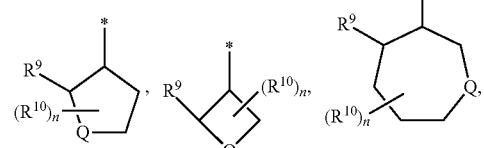

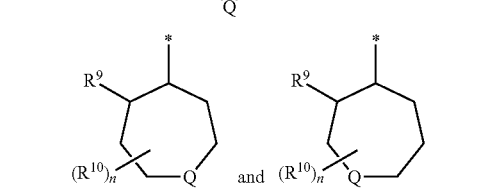

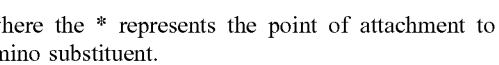

where the * represents the point of attachment to the 2-amino substituent.

In particular embodiments of Formulae (I) to (VIII), the ring comprising Q is selected from the group consisting of:

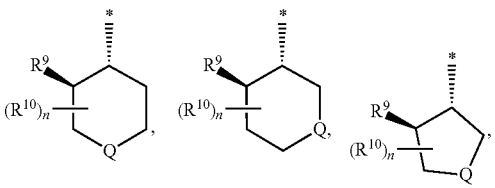

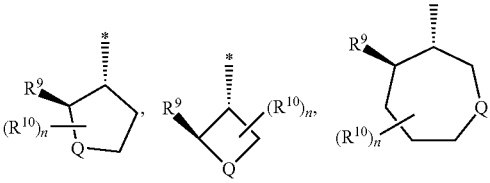

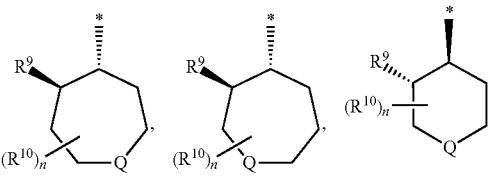

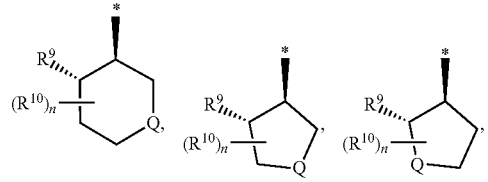

-continued

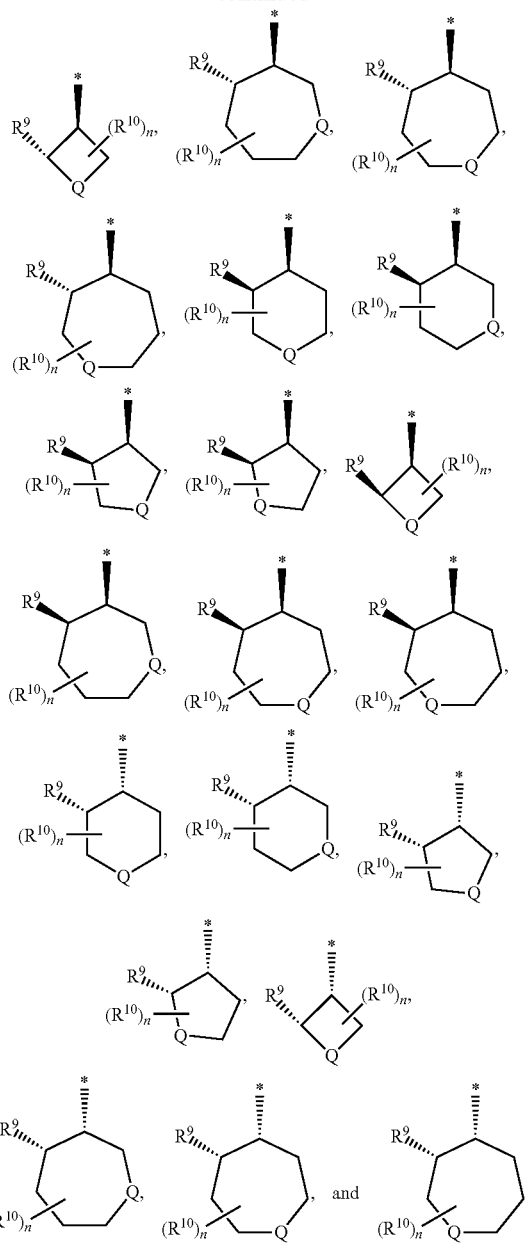

where the * represents the point of attachment to the 2-amino substituent.

In particular embodiments of Formulae (I) to (VIII), the ring comprising Q is selected from the group consisting of:

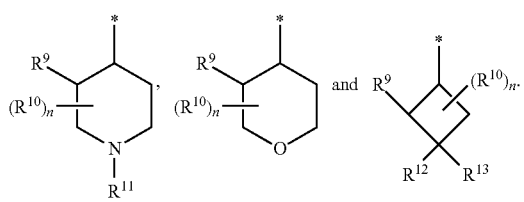

where the * represents the point of attachment to the 2-amino substituent.

In specific embodiments of Formulae (I) to (VIII), the ring comprising Q is selected from the group consisting of:

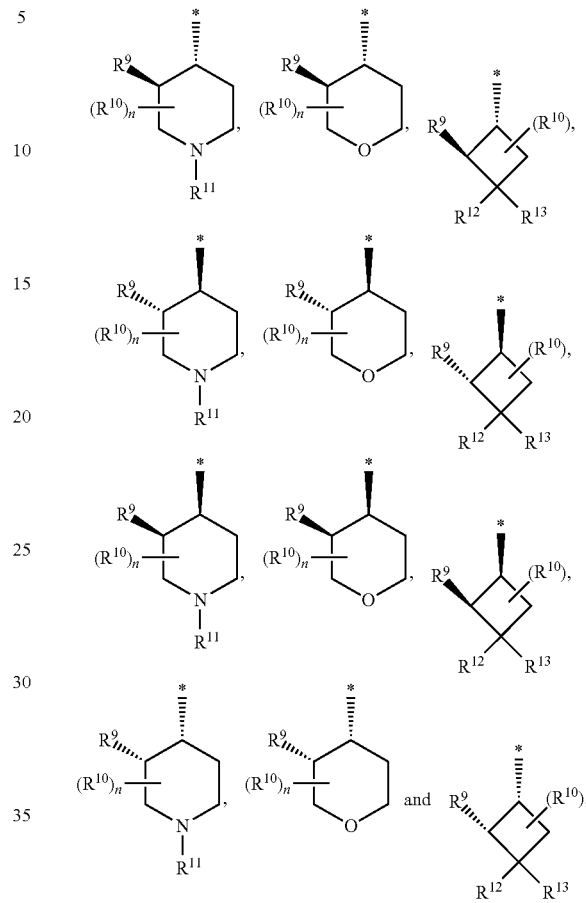

where the * represents the point of attachment to the 2-amino substituent.

In another aspect, the invention provides a compound of Formula (IX):

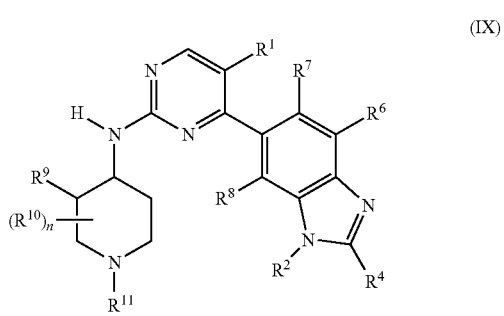

or a pharmaceutically acceptable salt thereof, wherein:
$R^1$, $R^2$, $R^4$, $R^6$ to $R^{11}$, $R^{14}$ to $R^{23}$ and n are as defined for Formula (II); or
$R^1$, $R^2$, $R^4$, $R^6$ to $R^{11}$, $R^{14}$ to $R^{30}$, m and n are as defined for Formula (IV).

In some embodiments, the invention provides a compound of Formula (IX), or a pharmaceutically acceptable salt thereof, wherein $R^1$, $R^2$, $R^4$, $R^6$ to $R^{11}$, $R^{14}$ to $R^{23}$ and n are as defined for Formula (II).

In embodiments of Formula (IX) wherein the substituent groups are as defined for Formula (II), the invention provides a compound of Formula (IX):

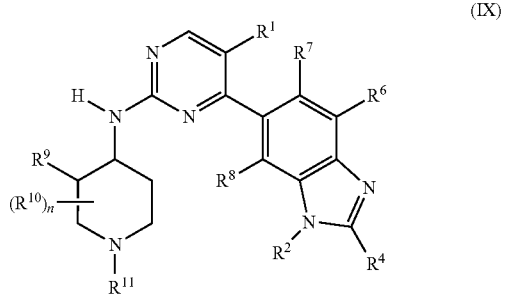

(IX)

or a pharmaceutically acceptable salt thereof, wherein:

$R^1$ is H, F, Cl, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;

$R^2$ is H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$;

$R^4$ is H, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$;

$R^6$ is H, F, Cl, CN, $CH_3$, $CH_2F$, $CHF_2$ or $CF_3$;

$R^7$ and $R^8$ are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy, where each said $C_1$-$C_2$ alkyl, $C_1$-$C_2$ fluoroalkyl, $C_1$-$C_2$ alkoxy and $C_1$-$C_2$ fluoroalkoxy is optionally substituted by $R^{20}$;

$R^9$ is H, OH, $NH_2$, $NHCH_3$ or $N(CH_3)_2$;

each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;

$R^{11}$ is H, $C_1$-$C_4$ alkyl, $C_1$-$C_4$ fluoroalkyl, $SO_2R^{14}$, $SO_2NR^{15}R^{16}$, $COR^{17}$, $COOR^{17}$ or $CONR^{18}R^{19}$;

$R^{14}$ is $C_1$-$C_4$ alkyl or $C_1$-$C_4$ fluoroalkyl;

each $R^{15}$ and $R^{16}$ is independently H or $CH_3$;

$R^{17}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$;

each $R^{18}$ and $R^{19}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$;

each $R^{20}$ is independently OH, $C_1$-$C_2$ alkoxy, $C_1$-$C_2$ fluoroalkoxy, CN or $NR^{22}R^{23}$;

each $R^{21}$ is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$;

each $R^{22}$ and $R^{23}$ is independently H, $C_1$-$C_2$ alkyl or $C_1$-$C_2$ fluoroalkyl; or $R^{22}$ and $R^{23}$ may be taken together with the nitrogen atom to which they are attached to form an azetidinyl ring, which is optionally substituted by F or OH; and n is 0, 1, 2, 3 or 4.

In other embodiments, the invention provides a compound of Formula (IX'), or a pharmaceutically acceptable salt thereof, wherein $R^1$, $R^2$, $R^4$, $R^6$ to $R^{11}$, $R^{14}$ to $R^{23}$ and n are as defined for Formula (IV).

In embodiments of Formula (IX) wherein the substituent groups are as defined for Formula (IV), the invention provides a compound of Formula (IX'):

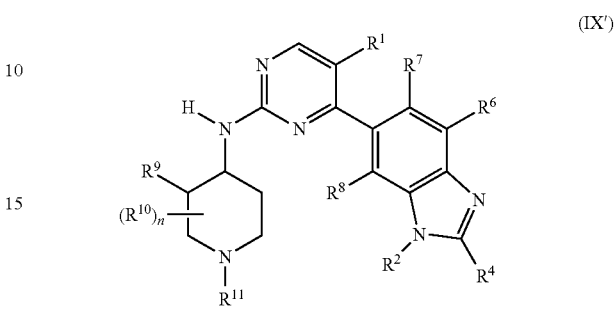

(IX')

or a pharmaceutically acceptable salt thereof, wherein:

$R^1$ is H, F, Cl, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;

$R^2$ is H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$; and $R^4$ is H, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$; or $R^2$ can be taken together with $R^4$ to form a 5-7 membered heterocyclic ring, optionally containing an additional heteroatom selected from $NR^{24}$, O and $S(O)_m$ as a ring member, which ring is optionally substituted by $R^{21}$;

$R^6$ is H, F, Cl, CN, $CH_3$, $CH_2F$, $CHF_2$ or $CF_3$;

$R^7$ and $R^8$ are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy, where each said $C_1$-$C_2$ alkyl, $C_1$-$C_2$ fluoroalkyl, $C_1$-$C_2$ alkoxy and $C_1$-$C_2$ fluoroalkoxy is optionally substituted by $R^{20}$;

$R^9$ is H, OH, $NH_2$, $NHCH_3$ or $N(CH_3)_2$;

each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;

$R^{11}$ is H, $C_1$-$C_4$ alkyl, $C_1$-$C_4$ fluoroalkyl, $SO_2R^{14}$, $SO_2NR^{15}R^{16}$, $COR^{17}$, $COOR^{17}$ or $CONR^{18}R^{19}$;

$R^{14}$ is $C_1$-$C_4$ alkyl or $C_1$-$C_4$ fluoroalkyl;

each $R^{15}$ and $R^{16}$ is independently H or $CH_3$;

$R^{17}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$;

each $R^{18}$ and $R^{19}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$;

each $R^{20}$ is independently OH, $C_1$-$C_2$ alkoxy, $C_1$-$C_2$ fluoroalkoxy, CN or $NR^{22}R^{23}$;

each $R^{21}$ is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$;

each $R^{22}$ and $R^{23}$ is independently H, $C_1$-$C_2$ alkyl or $C_1$-$C_2$ fluoroalkyl; or $R^{22}$ and $R^{23}$ may be taken together with the nitrogen atom to which they are attached to form an azetidinyl ring, which is optionally substituted by F or OH;

$R^{24}$ is H, $C_1$-$C_4$ alkyl, $C_1$-$C_4$ fluoroalkyl, $SO_2R^2$, $SO_2NR^{26}R^{27}$, $COR^{28}$, $COOR^{28}$ or $CONR^{29}R^{30}$;

$R^{25}$ is $C_1$-$C_4$ alkyl or $C_1$-$C_4$ fluoroalkyl;

each $R^{26}$ and $R^{27}$ is independently H or $CH_3$;

$R^{28}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$;

each $R^{29}$ and $R^{30}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$;

m is 0, 1 or 2; and n is 0, 1, 2, 3 or 4.

In some embodiments, the compound of Formula (IX) or (IX') has the absolute stereochemistry as shown in one of Formulae (IX-A), (IX-B), (IX-C) or (IX-D), or Formulae (IX'-A), (IX'-B), (IX'-C) or (IX'-D)

(IX-A)

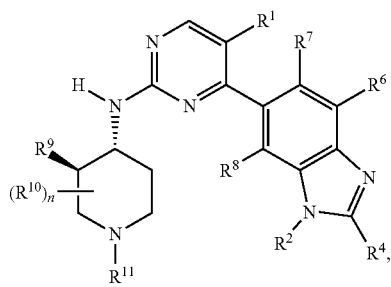

(IX-A')

(IX-B)

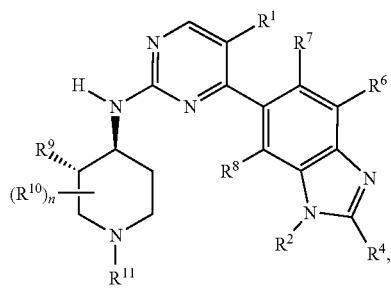

(IX-B')

(IX-C)

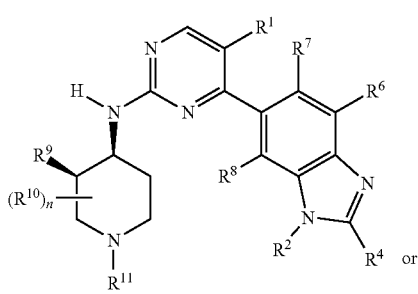

(IX-C')

(IX-D)

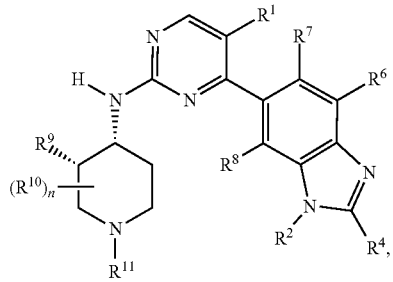

(IX-D')

or a pharmaceutically acceptable salt thereof.

Each of the aspects and embodiments described herein with respect to Formula (II) is also applicable to compounds of Formulae (IX), (IX-A), (IX-B), (IX-C) or (IX-D) that are not inconsistent with such aspect or embodiment.

Each of the aspects and embodiments described herein with respect to Formula (IX) is also applicable to compounds of Formulae (IX-A), (IX-B), (IX-C) or (IX-D).

In certain embodiments, the invention provides a compound of Formula (IX), (IX-A), (IX-B), (IX-C) or (IX-D), or a pharmaceutically acceptable salt thereof, having a combination of two or more, preferably three or more, and more preferably four or more, of the following features: $R^1$ is Cl; $R^2$ is $C_1$-$C_5$ alkyl; or $R^2$ is i-$C_3H_7$; $R^4$ is $C_1$-$C_4$ alkyl, where said $C_1$-$C_4$ alkyl is optionally substituted by $R^{20}$, where $R^{20}$ is OH; or $R^4$ is $CH(OH)CH_3$ or $C(OH)(CH_3)_2$; $R^6$ is F; $R^7$ is H; $R^8$ is H; $R^9$ is OH; $R^{11}$ is $SO_2R^{14}$; $R^{14}$ is $C_1$-$C_4$ alkyl; n is 0 and $R^{10}$ is absent.

In a preferred embodiment, the invention provides a compound of Formula (IX), (IX-A), (IX-B), (IX-C) or (IX-D), or a pharmaceutically acceptable salt thereof, wherein: $R^1$ is Cl; $R^2$ is $C_1$-$C_5$ alkyl; or $R^2$ is i-$C_3H_7$; $R^4$ is $C_1$-$C_4$ alkyl optionally substituted by $R^{20}$, where $R^{20}$ is OH; or $R^4$ is $CH(OH)CH_3$ or $C(OH)(CH_3)_2$; $R^6$ is F; $R^7$ is H; $R^8$ is H; $R^9$ is OH; $R^{11}$ is $SO_2R^{14}$; $R^{14}$ is $C_1$-$C_4$ alkyl; n is 0 and $R^{10}$ is absent.

In certain embodiments, the invention provides a compound of Formulae (IX), (IX-A), (IX-B), (IX-C) or (IX-D), or a pharmaceutically acceptable salt thereof, having a combination of two or more, preferably three or more, and more preferably four or more, of the following features: $R^1$ is F or Cl; $R^2$ is $C_1$-$C_5$ alkyl, $C_1$-$C_5$ fluoroalkyl or 3-6 membered heterocyclyl; or $R^2$ is $CH_3$, i-$C_3H_7$, i-$C_4H_8$, s-$C_4H_8$, t-$C_4H_8$, $CH_2F$, $CHF_2$, $CH_2CHF_2$ or oxetan-3-yl; $R^4$ is H or $C_1$-$C_4$ alkyl, where said $C_1$-$C_4$ alkyl is optionally substituted by OH, $NH_2$, $NHCH_3$ or $N(CH_3)_2$; or $R^4$ is H, $CH_3$, $C_2H_5$, $CH_2OH$, $CH(OH)CH_3$, $CH_2CH_2OH$ or $CH_2NH_2$; $R^6$ is H or F; $R^7$ and $R^8$ are H; $R^9$ is OH; n is 0 and $R^{10}$ is absent; $R^{11}$ is $SO_2R^{14}$; and $R^{14}$ is $C_1$-$C_4$ alkyl.

In specific embodiments, the invention provides a compound of Formulae (IX), (IX-A), (IX-B), (IX-C) or (IX-D), or a pharmaceutically acceptable salt thereof, having a combination of two or more, preferably three or more, and more preferably four or more, of the following features: $R^1$ is Cl; $R^2$ is $C_1$-$C_5$ alkyl; $R^4$ is H or $C_1$-$C_4$ alkyl, where said $C_1$-$C_4$ alkyl is optionally substituted by $R^{20}$; $R^6$ is F; $R^7$ and $R^8$ are H; $R^9$ is OH; $R^{11}$ is $SO_2R^{14}$; $R^{14}$ is $C_1$-$C_4$ alkyl; and $R^{20}$ is OH.

Each of the aspects and embodiments described herein with respect to Formula (IV) is also applicable to compounds of Formulae (IX'), (IX'-A), (IX'-B), (IX'-C) or (IX'-D) that are not inconsistent with such aspect or embodiment.

Each of the aspects and embodiments described herein with respect to Formula (IX') is also applicable to compounds of Formulae (IX'-A), (IX'-B), (IX'-C) or (IX'-D).

In certain embodiments, the invention provides a compound of Formulae (IX'), (IX'-A), (IX'-B), (IX'-C) or (IX'-D), or a pharmaceutically acceptable salt thereof, having a combination of two or more, preferably three or more, and more preferably four or more, of the following features: $R^1$ is F or Cl; $R^2$ is $C_1$-$C_5$ alkyl, $C_1$-$C_5$ fluoroalkyl or 3-6 membered heterocyclyl; or $R^2$ is $CH_3$, i-$C_3H_7$, i-$C_4H_9$, s-$C_4H_9$, t-$C_4H_9$, $CH_2F$, $CHF_2$, $CH_2CHF_2$ or oxetan-3-yl; $R^4$ is H or $C_1$-$C_4$ alkyl, where said $C_1$-$C_4$ alkyl is optionally substituted by OH, $NH_2$, $NHCH_3$ or $N(CH_3)_2$; or $R^4$ is H, $CH_3$, $C_2H_5$, $CH_2OH$, $CH(OH)CH_3$, $CH_2CH_2OH$ or $CH_2NH_2$; or $R^2$ is taken together with $R^4$ to form a 5-7 membered heterocyclic ring, optionally containing an additional heteroatom selected from $NR^{24}$, O and $S(O)_m$ as a ring member, which ring is optionally substituted by $R^{21}$; $R^6$ is H or F; $R^7$ and $R^8$ are H; $R^9$ is OH; n is 0 and $R^{10}$ is absent; $R^{11}$ is $SO_2R^{14}$; and $R^{14}$ is $C_1$-$C_4$ alkyl.

In specific embodiments, the invention provides a compound of Formulae (IX'), (IX'-A), (IX'-B), (IX'-C) or (IX'-D), or a pharmaceutically acceptable salt thereof, having a combination of two or more, preferably three or more, and more preferably four or more, of the following features: $R^1$ is F or Cl; $R^2$ is $CH_3$, i-$C_3H_7$, i-$C_4H_9$, s-$C_4H_9$, t-$C_4H_9$, $CH_2F$, $CHF_2$, $CH_2CHF_2$ or oxetan-3-yl; $R^4$ is H, $CH_3$, $C_2H_5$, $CH_2OH$, $CH(OH)CH_3$, $CH_2CH_2OH$ or $CH_2NH_2$; or $R^2$ is taken together with $R^4$ to form a 5-membered heterocyclic ring optionally substituted by $R^{21}$; each $R^{21}$ is independently F, OH, $NH_2$, $C_1$-$C_2$ alkyl or $C_1$-$C_2$ fluoroalkyl; $R^6$ is F; $R^7$ and $R^8$ are H; $R^9$ is OH; n is 0 and $R^{10}$ is absent; $R^{11}$ is $SO_2R^{14}$; and $R^{14}$ is $CH_3$.

In specific embodiments, the invention provides a compound of Formulae (IX'), (IX'-A), (IX'-B), (IX'-C) or (IX'-D), or a pharmaceutically acceptable salt thereof, having a combination of two or more, preferably three or more, and more preferably four or more, of the following features: $R^1$ is Cl; $R^2$ is $C_1$-$C_5$ alkyl; $R^4$ is H or $C_1$-$C_4$ alkyl, where said $C_1$-$C_4$ alkyl is optionally substituted by $R^{20}$; $R^6$ is F; $R^7$ and $R^8$ are H; $R^9$ is OH; $R^{11}$ is $SO_2R^{14}$; $R^{14}$ is $C_1$-$C_4$ alkyl; and $R^{20}$ is OH.

In another aspect, the invention provides a compound of Formula (X):

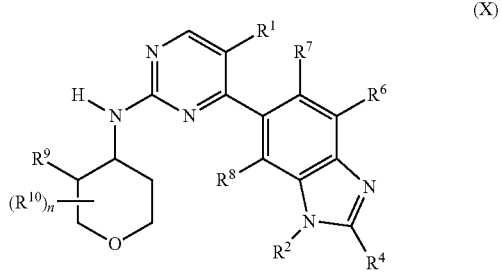

(X)

or a pharmaceutically acceptable salt thereof, wherein:
$R^1$ is H, F, Cl, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;
$R^2$ is H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$;

$R^4$ is H, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$;
$R^6$ is H, F, Cl, CN, $CH_3$, $CH_2F$, $CHF_2$ or $CF_3$;
$R^7$ and $R^8$ are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy, where each said $C_1$-$C_2$ alkyl, $C_1$-$C_2$ fluoroalkyl, $C_1$-$C_2$ alkoxy and $C_1$-$C_2$ fluoroalkoxy is optionally substituted by $R^{20}$;
$R^9$ is H, OH, $NH_2$, $NHCH_3$ or $N(CH_3)_2$;
each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;
each $R^{20}$ is independently OH, $C_1$-$C_2$ alkoxy, $C_1$-$C_2$ fluoroalkoxy, CN or $NR^{22}R^{23}$;
each $R^{21}$ is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$;
each $R^{22}$ and $R^{23}$ is independently H, $C_1$-$C_2$ alkyl or $C_1$-$C_2$ fluoroalkyl; or
$R^{22}$ and $R^{23}$ may be taken together with the nitrogen atom to which they are attached to form an azetidinyl ring, which is optionally substituted by F or OH; and
n is 0, 1, 2, 3 or 4.

In another aspect, the invention provides a compound of Formula (XI):

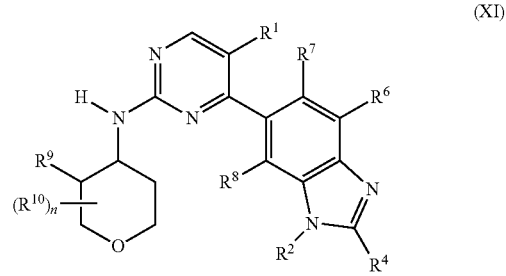

(XI)

or a pharmaceutically acceptable salt thereof, wherein:
$R^1$ is H, F, Cl, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;
$R^2$ is H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$;
$R^4$ is H, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$; or
$R^2$ can be taken together with $R^4$ to form a 5-7 membered heterocyclic ring, optionally containing an additional heteroatom selected from $NR^{24}$, O and $S(O)_m$ as a ring member, which ring is optionally substituted by $R^{21}$;
$R^6$ is H, F, Cl, CN, $CH_3$, $CH_2F$, $CHF_2$ or $CF_3$;
$R^7$ and $R^8$ are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy, where each said $C_1$-$C_2$ alkyl, $C_1$-$C_2$ fluoroalkyl, $C_1$-$C_2$ alkoxy and $C_1$-$C_2$ fluoroalkoxy is optionally substituted by $R^{20}$;

$R^9$ is H, OH, $NH_2$, $NHCH_3$ or $N(CH_3)_2$;

each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;

each $R^{20}$ is independently OH, $C_1$-$C_2$ alkoxy, $C_1$-$C_2$ fluoroalkoxy, CN or $NR^{22}R^{23}$;

each $R^{21}$ is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$;

each $R^{22}$ and $R^{23}$ is independently H, $C_1$-$C_2$ alkyl or $C_1$-$C_2$ fluoroalkyl; or $R^{22}$ and $R^{23}$ may be taken together with the nitrogen atom to which they are attached to form an azetidinyl ring, which is optionally substituted by F or OH;

$R^{24}$ is H, $C_1$-$C_4$ alkyl, $C_1$-$C_4$ fluoroalkyl, $SO_2R^{25}$, $SO_2NR^{26}R^{27}$, $COR^{28}$, $COOR^{28}$ or $CONR^{29}R^{30}$;

$R^{25}$ is $C_1$-$C_4$ alkyl or $C_1$-$C_4$ fluoroalkyl;

each $R^{26}$ and $R^{27}$ is independently H or $CH_3$;

$R^{28}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$;

each $R^{29}$ and $R^{30}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by OH, $C_1$-$C_2$ alkoxy, $C_1$-$C_2$ fluoroalkoxy, CN, $NH_2$, $NHCH_3$ or $N(CH_3)_2$;

m is 0, 1 or 2; and n is 0, 1, 2, 3 or 4.

In some embodiments, the compound of Formula (X) or (XI) has the absolute stereochemistry as shown in one of Formulae (X-A), (X-B), (X-C) or (X-D) or (XI-A), (XI-B), (XI-C) or (XI-D):

(XI-A)

(X-A)

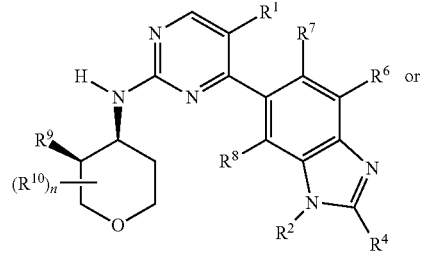

(XI-B)

(X-B)

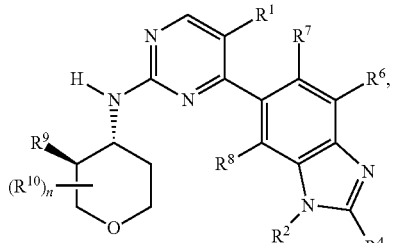

(XI-C)

(X-C)

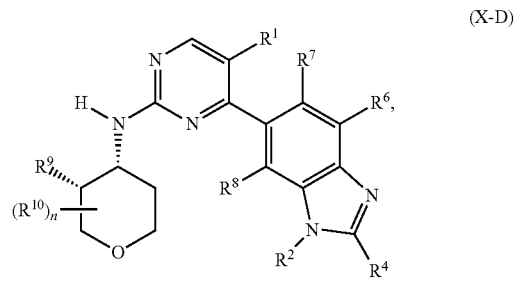

(XI-D)

(X-D)

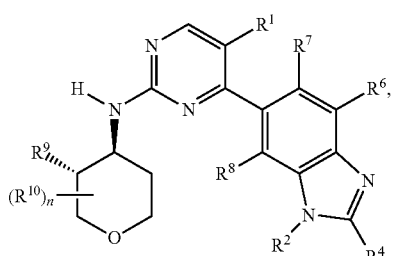

or a pharmaceutically acceptable salt thereof.

Each of the aspects and embodiments described herein with respect to Formula (II) is also applicable to compounds of Formulae (X), (X-A), (X-B), (X-C) or (X-D) that are not inconsistent with such aspect or embodiment.

Each of the aspects and embodiments described herein with respect to Formula (X) is also applicable to compounds of Formulae (X-A), (X-B), (X-C) or (X-D).

In certain embodiments, the invention provides a compound of Formula (X), (X-A), (X-B), (X-C) or (X-D), or a pharmaceutically acceptable salt thereof, having a combination of two or more, preferably three or more, and more preferably four or more, of the following features: $R^1$ is Cl; $R^2$ is $C_1$-$C_5$ alkyl; or $R^2$ is i-$C_3H_7$; $R^4$ is $C_1$-$C_4$ alkyl, where said $C_1$-$C_4$ alkyl is optionally substituted by $R^{20}$, where $R^{20}$ is OH; or $R^4$ is $CH(OH)CH_3$ or $C(OH)(CH_3)_2$; $R^6$ is F; $R^7$ is H; $R^8$ is H; $R^9$ is OH; n is 0 and $R^{10}$ is absent.

In a preferred embodiment, the invention provides a compound of Formula (X), (X-A), (X-B), (X-C) or (X-D), or a pharmaceutically acceptable salt thereof, wherein: $R^1$ is Cl; $R^2$ is $C_1$-$C_5$ alkyl; or $R^2$ is i-$C_3H_7$; $R^4$ is $C_1$-$C_4$ alkyl optionally substituted by $R^{20}$, where $R^{20}$ is OH; or $R^4$ is $CH(OH)CH_3$ or $C(OH)(CH_3)_2$; $R^6$ is F; $R^7$ is H; $R^8$ is H; $R^9$ is OH; n is 0 and $R^{10}$ is absent.

In certain embodiments, the invention provides a compound of Formulae (X), (X-A), (X-B), (X-C) or (X-D), or a pharmaceutically acceptable salt thereof, having a combination of two or more, preferably three or more, and more preferably four or more, of the following features: $R^1$ is F or Cl; $R^2$ is $C_1$-$C_5$ alkyl, $C_1$-$C_5$ fluoroalkyl or 3-6 membered heterocyclyl; or $R^2$ is $CH_3$, i-$C_3H_7$, i-$C_4H_9$, s-$C_4H_9$, t-$C_4H_9$, $CH_2F$, $CHF_2$, $CH_2CHF_2$ or oxetan-3-yl; $R^4$ is H or $C_1$-$C_4$ alkyl, where said $C_1$-$C_4$ alkyl is optionally substituted by OH, $NH_2$, $NHCH_3$ or $N(CH_3)_2$; or $R^4$ is H, $CH_3$, $C_2H_5$, $CH_2OH$, $CH(OH)CH_3$, $C(OH)(CH_3)_2$ or $CH_2CH_2OH$; $R^6$ is H or F; $R^7$ is H; $R^8$ is H; $R^9$ is OH; n is 0 and $R^{10}$ is absent.

Each of the aspects and embodiments described herein with respect to Formula (IV) is also applicable to compounds of Formulae (XI), (XI-A), (XI-B), (XI-C) or (XI-D) that are not inconsistent with such aspect or embodiment.

Each of the aspects and embodiments described herein with respect to Formula (XI) is also applicable to compounds of Formulae (XI-A), (XI-B), (XI-C) or (XI-D).

In certain embodiments, the invention provides a compound of Formula (XI), (XI-A), (XI-B), (XI-C) or (XI-D), or a pharmaceutically acceptable salt thereof, having a combination of two or more, preferably three or more, and more preferably four or more, of the following features: $R^1$ is Cl; $R^2$ is $C_1$-$C_5$ alkyl; or $R^2$ is i-$C_3H_7$; $R^4$ is $C_1$-$C_4$ alkyl, where said $C_1$-$C_4$ alkyl is optionally substituted by $R^{20}$, where $R^{20}$ is OH; or $R^4$ is CH(OH)CH$_3$ or C(OH)(CH$_3$)$_2$; $R^6$ is F; $R^7$ is H; $R^8$ is H; $R^9$ is OH; n is 0 and $R^{10}$ is absent.

In a preferred embodiment, the invention provides a compound of Formula (XI), (XI-A), (XI-B), (XI-C) or (XI-D), or a pharmaceutically acceptable salt thereof, wherein: $R^1$ is C; $R^2$ is $C_1$-$C_5$ alkyl; or $R^2$ is i-$C_3H_7$; $R^4$ is $C_1$-$C_4$ alkyl optionally substituted by $R^{20}$, where $R^{20}$ is OH; or $R^4$ is CH(OH)CH$_3$ or C(OH)(CH$_3$)$_2$; $R^6$ is F; $R^7$ is H; $R^8$ is H; $R^9$ is OH; n is 0 and $R^{10}$ is absent.

In certain embodiments, the invention provides a compound of Formulae (XI), (XI-A), (XI-B), (XI-C) or (XI-D), or a pharmaceutically acceptable salt thereof, having a combination of two or more, preferably three or more, and more preferably four or more, of the following features: $R^1$ is F or Cl; $R^2$ is $C_1$-$C_5$ alkyl, $C_1$-$C_5$ fluoroalkyl or 3-6 membered heterocyclyl; or $R^2$ is CH$_3$, i-$C_3H_7$, i-$C_4H_9$, s-$C_4H_9$, t-$C_4H_9$, CH$_2$F, CHF$_2$, CH$_2$CHF$_2$ or oxetan-3-yl; $R^4$ is H or $C_1$-$C_4$ alkyl, where said $C_1$-$C_4$ alkyl is optionally substituted by OH, NH$_2$, NHCH$_3$ or N(CH$_3$)$_2$; or $R^4$ is H, CH$_3$, C$_2$H$_5$, CH$_2$OH, CH(OH)CH$_3$, C(OH)(CH$_3$)$_2$ or CH$_2$CH$_2$OH; $R^6$ is H or F; $R^7$ is H; $R^8$ is H; $R^9$ is OH; n is 0 and $R^{10}$ is absent.

In another aspect, the invention provides a compound of Formula (XII):

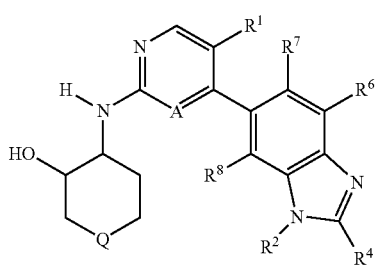

(XII)

or a pharmaceutically acceptable salt thereof, wherein:
A is N or CH;
$R^1$ is H, F or Cl;
$R^2$ is H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$;
$R^4$ is H, $C_1$-$C_4$ alkyl, $C_1$-$C_4$ fluoroalkyl, $C_1$-$C_4$ alkoxy, $C_1$-$C_4$ fluoroalkoxy, C(O)R$^a$, C(O)NR$^b_2$, $C_3$-$C_8$ cycloalkyl or 3-6 membered heterocyclyl, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$, each said $C_3$-$C_8$ cycloalkyl and 3-6 membered heterocyclyl is optionally substituted by $R^{21}$, $R^a$ is $C_1$-$C_2$ alkyl, and each R$^b$ is independently H or $C_1$-$C_2$ alkyl;
$R^6$ is H or F;
$R^7$ and $R^8$ are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy;
Q is O; or
Q is NR$^{11}$;

$R^{11}$ is SO$_2$R$^{14}$ or COR$^{17}$;
$R^{14}$ is $C_1$-$C_4$ alkyl or $C_1$-$C_4$ fluoroalkyl;
$R^{17}$ is $C_1$-$C_4$ alkyl, $C_1$-$C_4$ fluoroalkyl, $C_3$-$C_8$ cycloalkyl or 3-6 membered heterocyclyl, where each said $C_1$-$C_4$ alkyl and $C_1$-$C_4$ fluoroalkyl is optionally substituted by $R^{20}$ and each said $C_3$-$C_8$ cycloalkyl and 3-6 membered heterocyclyl is optionally substituted by $R^{21}$;

each $R^{20}$ is independently OH, $C_1$-$C_2$ alkoxy, $C_1$-$C_2$ fluoroalkoxy, CN, NR$^{22}$R$^{23}$, $C_3$-$C_8$ cycloalkyl or 3-6 membered heterocyclyl, where each said $C_3$-$C_8$ cycloalkyl and 3-6 membered heterocyclyl is optionally substituted by $R^{21}$;

each $R^{21}$ is independently F, OH, CN, NR$^{22}$R$^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, NH$_2$, NHCH$_3$ or N(CH$_3$)$_2$;

each $R^{22}$ and $R^{23}$ is independently H, $C_1$-$C_3$ alkyl, $C_1$-$C_3$ fluoroalkyl, $C_3$-$C_8$ cycloalkyl or 3-6 membered heterocyclyl, where each said $C_1$-$C_3$ alkyl and $C_1$-$C_3$ fluoroalkyl is optionally further substituted by OH, $C_1$-$C_2$ alkoxy or $C_1$-$C_2$ fluoroalkoxy and each said $C_3$-$C_8$ cycloalkyl and 3-6 membered heterocyclyl is optionally further substituted by F, OH, $C_1$-$C_2$ alkyl, $C_1$-$C_2$ fluoroalkyl, $C_1$-$C_2$ alkoxy or $C_1$-$C_2$ fluoroalkoxy; or $R^{22}$ and $R^{23}$ may be taken together with the nitrogen atom to which they are attached to form an azetidinyl ring, where said ring is optionally substituted by F, OH, $C_1$-$C_2$ alkyl, $C_1$-$C_2$ fluoroalkyl, $C_1$-$C_2$ alkoxy or $C_1$-$C_2$ fluoroalkoxy.

In some embodiments, the compound of Formula (XII) has the absolute stereochemistry as shown in one of Formulae (XII-A), (XII-B), (XII-C) or (XII-D):

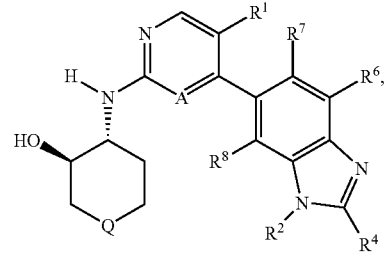

(XII-A)

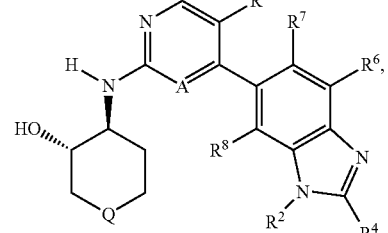

(XII-B)

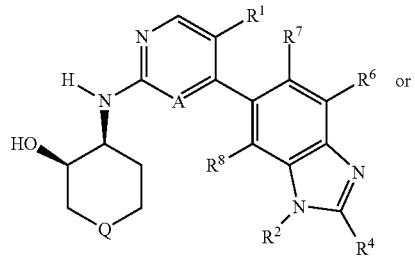

(XII-C) or (XII-D)

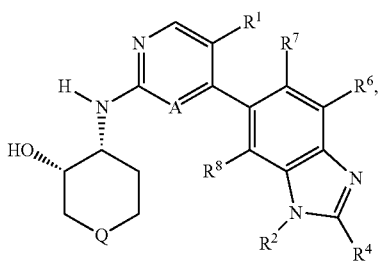

or a pharmaceutically acceptable salt thereof.

Each of the aspects and embodiments described herein with respect to Formula (I)-(XI) is also applicable to compounds of Formulae (XII), (XII-A), (XII-B), (XII-C) or (XII-D) that are not inconsistent with such aspect or embodiment.

Each of the aspects and embodiments described herein with respect to Formula (XII) is also applicable to compounds of Formulae (XII-A), (XII-B), (XII-C) or (XII-D).

In some embodiments of Formulae (XII), (XII-A), (XII-B), (XII-C) or (XII-D), A is N. In some embodiments of Formulae (XII), (XII-A), (XII-B), (XII-C) or (XII-D), A is CH.

In some embodiments of Formulae (XII), (XII-A), (XII-B), (XII-C) or (XII-D), $R^1$ is Cl.

In some embodiments of Formulae (XII), (XII-A), (XII-B), (XII-C) or (XII-D), $R^2$ is $C_1$-$C_5$ alkyl or $C_1$-$C_5$ fluoroalkyl, where each said $C_1$-$C_5$ alkyl and $C_1$-$C_5$ fluoroalkyl is optionally substituted by $R^{20}$. In some embodiments, $R^2$ is $C_1$-$C_5$ alkyl. In specific embodiments, $R^2$ is isopropyl.

In some embodiments of Formulae (XII), (XII-A), (XII-B), (XII-C) or (XII-D), $R^2$ is $C_3$-$C_8$ cycloalkyl or 3-6 membered heterocyclyl, where each said $C_3$-$C_8$ cycloalkyl and 3-6 membered heterocyclyl is optionally substituted by $R^{21}$.

In some embodiments of Formulae (XII), (XII-A), (XII-B), (XII-C) or (XII-D), $R^4$ is H, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$.

In some such embodiments, $R^{20}$ is OH. In some embodiments, $R^4$ is $C_1$-$C_4$ alkyl optionally substituted by $R^{20}$ where $R^{20}$ is OH. In specific embodiments, $R^4$ is CH(OH)CH$_3$ or C(OH)(CH$_3$)$_2$.

In other such embodiments, $R^{20}$ is $C_3$-$C_8$ cycloalkyl or 3-6 membered heterocyclyl, where each said $C_3$-$C_8$ cycloalkyl and 3-6 membered heterocyclyl is optionally substituted by $R^{21}$. In some such embodiments, $R^4$ is $C_1$-$C_4$ alkyl optionally substituted by $R^{20}$ where $R^{20}$ is $C_3$-$C_8$ cycloalkyl or 3-6 membered heterocyclyl, where each said $C_3$-$C_8$ cycloalkyl and 3-6 membered heterocyclyl is optionally substituted by $R^{21}$.

In some embodiments of Formulae (XII), (XII-A), (XII-B), (XII-C) or (XII-D), $R^4$ is C(O)R$^a$, C(O)NR$_2$, R$^a$ is $C_1$-$C_2$ alkyl, and each R$^b$ is independently H or $C_1$-$C_2$ alkyl.

In some embodiments of Formulae (XII), (XII-A), (XII-B), (XII-C) or (XII-D), $R^4$ is $C_3$-$C_8$ cycloalkyl or 3-6 membered heterocyclyl, where each said $C_3$-$C_8$ cycloalkyl and 3-6 membered heterocyclyl is optionally substituted by $R^{21}$.

In some embodiments of Formulae (XII), (XII-A), (XII-B), (XII-C) or (XII-D), $R^6$ is F.

In some embodiments of Formulae (XII), (XII-A), (XII-B), (XII-C) or (XII-D), $R^7$ and $R^8$ are independently H or F. In some such embodiments, $R^7$ and $R^8$ are H.

In some embodiments of Formulae (XII), (XII-A), (XII-B), (XII-C) or (XII-D), Q is O.

In some embodiments of Formulae (XII), (XII-A), (XII-B), (XII-C) or (XII-D), Q is NR$^{11}$. In some such embodiments, $R^{11}$ is SO$_2$R$^{14}$. In some such embodiments, $R^{14}$ is $C_1$-$C_4$ alkyl. In some such embodiments, $R^{11}$ is COR$^{17}$. In some such embodiments, $R^{17}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$. In some such embodiments, $R^{17}$ is $C_3$-$C_8$ cycloalkyl or 3-6 membered heterocyclyl, where each said $C_3$-$C_8$ cycloalkyl and 3-6 membered heterocyclyl is optionally substituted by $R^{21}$.

In certain embodiments, the invention provides a compound of Formula (XII), (XII-A), (XII-B), (XII-C) or (XII-D), or a pharmaceutically acceptable salt thereof, having a combination of two or more, preferably three or more, and more preferably four or more, of the following features: A is N; $R^1$ is Cl; $R^2$ is $C_1$-$C_5$ alkyl; or $R^2$ is i-$C_3$H$_7$; $R^4$ is $C_1$-$C_4$ alkyl, where said $C_1$-$C_4$ alkyl is optionally substituted by $R^{20}$, where $R^{20}$ is OH; or $R^4$ is CH(OH)CH$_3$ or C(OH)(CH$_3$)$_2$; $R^6$ is F; $R^7$ is H; $R^8$ is H; and Q is O.

In certain embodiments, the invention provides a compound of Formula (XII), (XII-A), (XII-B), (XII-C) or (XII-D), or a pharmaceutically acceptable salt thereof, having a combination of two or more, preferably three or more, and more preferably four or more, of the following features: A is N; $R^1$ is Cl; $R^2$ is $C_1$-$C_5$ alkyl; or $R^2$ is i-$C_3$H$_7$; $R^4$ is $C_1$-$C_4$ alkyl, where said $C_1$-$C_4$ alkyl is optionally substituted by $R^{20}$, where $R^{20}$ is OH; or $R^4$ is CH(OH)CH$_3$ or C(OH)(CH$_3$)$_2$; $R^6$ is F; $R^7$ is H; $R^8$ is H; Q is NR$^{11}$; $R^{11}$ is SO$_2$R$^{14}$; and $R^{14}$ is $C_1$-$C_4$ alkyl.

In certain embodiments, the invention provides a compound of Formula (XII), (XII-A), (XII-B), (XII-C) or (XII-D), or a pharmaceutically acceptable salt thereof, having a combination of two or more, preferably three or more, and more preferably four or more, of the following features: A is CH; $R^1$ is Cl; $R^2$ is $C_1$-$C_5$ alkyl; or $R^2$ is i-$C_3$H$_7$; $R^4$ is $C_1$-$C_4$ alkyl, where said $C_1$-$C_4$ alkyl is optionally substituted by $R^{20}$, where $R^{20}$ is OH; or $R^4$ is CH(OH)CH$_3$ or C(OH)(CH$_3$)$_2$; $R^6$ is F; $R^7$ is H; $R^8$ is H; and Q is O.

In certain embodiments, the invention provides a compound of Formula (XII), (XII-A), (XII-B), (XII-C) or (XII-D), or a pharmaceutically acceptable salt thereof, having a combination of two or more, preferably three or more, and more preferably four or more, of the following features: A is CH; $R^1$ is Cl; $R^2$ is $C_1$-$C_5$ alkyl; or $R^2$ is i-$C_3$H$_7$; $R^4$ is $C_1$-$C_4$ alkyl, where said $C_1$-$C_4$ alkyl is optionally substituted by $R^{20}$, where $R^{20}$ is OH; or $R^4$ is CH(OH)CH$_3$ or C(OH)(CH$_3$)$_2$; $R^6$ is F; $R^7$ is H; $R^8$ is H; Q is NR$^{11}$; $R^{11}$ is SO$_2$R$^{14}$; and $R^{14}$ is $C_1$-$C_4$ alkyl.

In another aspect, the invention provides a compound selected from the group consisting of:

(3R,4R)-4-({5-chloro-4-[4-fluoro-2-methyl-1-(propan-2-yl)-1H-benzimidazol-6-yl]pyrimidin-2-yl}amino)-1-(methanesulfonyl)piperidin-3-ol;

(3R,4R)-4-({4-[4-fluoro-2-methyl-1-(propan-2-yl)-1H-benzimidazol-6-yl]pyrimidin-2-yl}amino)-1-(methanesulfonyl)piperidin-3-ol;

4-(1-tert-butyl-4-fluoro-1H-benzimidazol-6-yl)-5-fluoro-N-(1-methylpiperidin-4-yl)pyrimidin-2-amine;

(3R,4R)-4-({5-fluoro-4-[4-fluoro-2-methyl-1-(propan-2-yl)-1H-benzimidazol-6-yl]pyrimidin-2-yl}amino)-1-(methanesulfonyl)piperidin-3-ol;

(3R,4R)-4-({5-ethyl-4-[4-fluoro-2-methyl-1-(propan-2-yl)-1H-benzimidazol-6-yl]pyrimidin-2-yl}amino)-1-(methanesulfonyl)piperidin-3-ol;

(3R,4R)-4-({5-chloro-4-[1-(propan-2-yl)-1H-benzotriazol-6-yl]pyrimidin-2-yl}amino)-1-(methanesulfonyl)piperidin-3-ol;

(3R,4R)-4-({4-[4-fluoro-2-methyl-1-(propan-2-yl)-1H-benzimidazol-6-yl]-5-methylpyrimidin-2-yl}amino)-1-(methanesulfonyl)piperidin-3-ol;

(3R,4R)-4-({4-[4-fluoro-2-methyl-1-(propan-2-yl)-1H-benzimidazol-6-yl]-5-methoxypyrimidin-2-yl}amino)-1-(methanesulfonyl)piperidin-3-ol;

(3R,4R)-4-({4-[4-fluoro-2-methyl-1-(propan-2-yl)-1H-benzimidazol-6-yl]-5-(propan-2-yl)pyrimidin-2-yl}amino)-1-(methanesulfonyl)piperidin-3-ol;

(3R,4R)-4-({5-chloro-4-[4-fluoro-2-methyl-1-(oxetan-3-yl)-1H-benzimidazol-6-yl]pyrimidin-2-yl}amino)-1-(methanesulfonyl)piperidin-3-ol;

(3R,4R)-4-({5-chloro-4-[4-fluoro-2-(hydroxymethyl)-1-(propan-2-yl)-1H-benzimidazol-6-yl]pyrimidin-2-yl}amino)-1-(methanesulfonyl)piperidin-3-ol;

(3R,4R)-4-({4-[1-(azetidin-3-yl)-4-fluoro-2-methyl-1H-benzimidazol-6-yl]-5-fluoropyrimidin-2-yl}amino)-1-(methanesulfonyl)piperidin-3-ol;

(3R,4R)-4-{[4-(1-tert-butyl-1H-benzimidazol-6-yl)-5-fluoropyrimidin-2-yl]amino}-1-(methanesulfonyl)piperidin-3-ol;

(3R,4R)-4-({5-fluoro-4-[2-methyl-1-(propan-2-yl)-1H-benzimidazol-6-yl]pyrimidin-2-yl}amino)-1-(methanesulfonyl)piperidin-3-ol;

(3R,4R)-4-({5-fluoro-4-[4-fluoro-2-methyl-1-(propan-2-yl)-1H-benzimidazol-6-yl]pyrimidin-2-yl}amino)piperidin-3-ol;

1-[(3R,4R)-4-({5-fluoro-4-[4-fluoro-2-methyl-1-(propan-2-yl)-1H-benzimidazol-6-yl]pyrimidin-2-yl}amino)-3-hydroxypiperidin-1-yl]ethanone;

(3R,4R)-4-{[4-(1-tert-butyl-4-fluoro-1H-benzimidazol-6-yl)-5-fluoropyrimidin-2-yl]amino}-1-(methanesulfonyl)piperidin-3-ol;

(3S,4S)-4-({5-fluoro-4-[4-fluoro-2-methyl-1-(propan-2-yl)-1H-benzimidazol-6-yl]pyrimidin-2-yl}amino)-1-methylpiperidin-3-ol;

(3S,4S)-4-({5-fluoro-4-[4-fluoro-2-methyl-1-(propan-2-yl)-1H-benzimidazol-6-yl]pyrimidin-2-yl}amino)-1-(methanesulfonyl)piperidin-3-ol;

1,5-anhydro-3-[(5-chloro-4-{4-fluoro-2-[(1R)-1-hydroxyethyl]-1-(propan-2-yl)-1H-benzimidazol-6-yl}pyrimidin-2-yl)amino]-2,3-dideoxy-D-threo-pentitol;

1,5-anhydro-3-[(5-chloro-4-{4-fluoro-2-[(1S)-1-hydroxyethyl]-1-(propan-2-yl)-1H-benzimidazol-6-yl}pyrimidin-2-yl)amino]-2,3-dideoxy-D-threo-pentitol;

(2S)-1-[(3R,4R)-4-{[4-(1-tert-butyl-4-fluoro-1H-benzimidazol-6-yl)-5-chloropyrimidin-2-yl]amino}-3-hydroxypiperidin-1-yl]-2-hydroxypropan-1-one;

(3R,4R)-4-({5-chloro-4-[4-fluoro-2-(2-hydroxypropan-2-yl)-1-(propan-2-yl)-1H-benzimidazol-6-yl]pyrimidin-2-yl}amino)-1-(methanesulfonyl)piperidin-3-ol;

(3R,4R)-4-[(5-chloro-4-{4-fluoro-2-[(1R)-1-hydroxyethyl]-1-(propan-2-yl)-1H-benzimidazol-6-yl}pyrimidin-2-yl)amino]-1-(methanesulfonyl)piperidin-3-ol; and 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol;

or a pharmaceutically acceptable salt thereof.

In another aspect, the invention provides a compound selected from the group consisting of the compounds exemplified in the Examples provided herein, including A1-A94, B1-B2, C1-C2, D1-D6, E1, F1-F33, G1 and H1-H11, inclusive, or a pharmaceutically acceptable salt thereof.

In another aspect, the invention provides (3R,4R)-4-[(5-chloro-4-{4-fluoro-2-[(1R)-1-hydroxyethyl]-1-(propan-2-yl)-1H-benzimidazol-6-yl}pyrimidin-2-yl)amino]-1-(methanesulfonyl)piperidin-3-ol, or a pharmaceutically acceptable salt thereof.

In another aspect, the invention provides (3R,4R)-4-[(5-chloro-4-{4-fluoro-2-[(1R)-1-hydroxyethyl]-1-(propan-2-yl)-1H-benzimidazol-6-yl}pyrimidin-2-yl)amino]-1-(methanesulfonyl)piperidin-3-ol.

In another aspect, the invention provides a pharmaceutically acceptable salt of (3R,4R)-4-[(5-chloro-4-{4-fluoro-2-[(1R)-1-hydroxyethyl]-1-(propan-2-yl)-1H-benzimidazol-6-yl}pyrimidin-2-yl)amino]-1-(methanesulfonyl)piperidin-3-ol.

In another aspect, the invention provides 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol, or a pharmaceutically acceptable salt thereof.

In another aspect, the invention provides 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol.

In another aspect, the invention provides a pharmaceutically acceptable salt of 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol.

A "pharmaceutical composition" refers to a mixture of one or more of the compounds of the invention, or a pharmaceutically acceptable salt, solvate, hydrate or prodrug thereof as an active ingredient, and at least one pharmaceutically acceptable carrier or excipient. In some embodiments, the pharmaceutical composition comprises two or more pharmaceutically acceptable carriers and/or excipients. In other embodiments, the pharmaceutical composition further comprises at least one additional anticancer therapeutic agent.

In one aspect, the invention provides a pharmaceutical composition comprising a compound of the invention, or a pharmaceutically acceptable salt thereof, and a pharmaceutically acceptable carrier or excipient. In some embodiments, the pharmaceutical composition comprises two or more pharmaceutically acceptable carriers and/or excipients.

In some embodiments, the pharmaceutical composition further comprises at least one additional anti-cancer therapeutic agent. In some such embodiments, the combination provides an additive, greater than additive, or synergistic anti-cancer effect.

The term "additive" is used to mean that the result of the combination of two compounds, components or targeted agents is no greater than the sum of each compound, component or targeted agent individually.

The term "synergy" or "synergistic" are used to mean that the result of the combination of two compounds, components or targeted agents is greater than the sum of each compound, component or targeted agent individually. This improvement in the disease, condition or disorder being treated is a "synergistic" effect. A "synergistic amount" is an amount of the combination of the two compounds, components or targeted agents that results in a synergistic effect, as "synergistic" is defined herein.

Determining a synergistic interaction between one or two components, the optimum range for the effect and absolute dose ranges of each component for the effect may be definitively measured by administration of the components over different dose ranges, and/or dose ratios to patients in need of treatment. However, the observation of synergy in in vitro models or in vivo models can be predictive of the effect in humans and other species and in vitro models or in vivo models exist, as described herein, to measure a synergistic effect. The results of such studies can also be used to predict effective dose and plasma concentration ratio ranges and the absolute doses and plasma concentrations required in humans and other species such as by the application of pharmacokinetic and/or pharmacodynamics methods.

Unless indicated otherwise, all references herein to the inventive compounds include references to salts, solvates, hydrates and complexes thereof, and to solvates, hydrates and complexes of salts thereof, including polymorphs, stereoisomers, and isotopically labelled versions thereof.

Compounds of the invention may exist in the form of pharmaceutically acceptable salts such as, e.g., acid addition salts and base addition salts of the compounds of one of the formulae provided herein. As used herein, the term "pharmaceutically acceptable salt" refers to those salts which retain the biological effectiveness and properties of the parent compound. The phrase "pharmaceutically acceptable salt(s)", as used herein, unless otherwise indicated, includes salts of acidic or basic groups which may be present in the compounds of the formulae disclosed herein.

For example, the compounds of the invention that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

The acids that may be used to prepare pharmaceutically acceptable acid addition salts of such basic compounds of those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate salts.

Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phosphate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate and valerate salts.

Illustrative examples of suitable salts include organic salts derived from amino acids, such as glycine and arginine, ammonia, primary, secondary, and tertiary amines and cyclic amines, such as piperidine, morpholine and piperazine, and inorganic salts derived from sodium, calcium, potassium, magnesium, manganese, iron, copper, zinc, aluminum and lithium.

The compounds of the invention that include a basic moiety, such as an amino group, may form pharmaceutically acceptable salts with various amino acids, in addition to the acids mentioned above.

Alternatively, the compounds useful that are acidic in nature may be capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds herein. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The chemical bases that may be used as reagents to prepare pharmaceutically acceptable base salts of the compounds of the invention that are acidic in nature are those that form non-toxic base salts with such compounds. Such non-toxic base salts include, but are not limited to, those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds of the invention, and of interconverting salt and free base forms, are known to one of skill in the art.

Salts of the present invention can be prepared according to methods known to those of skill in the art. A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

It will be understood by those of skill in the art that the compounds of the invention in free base form having a basic functionality may be converted to the acid addition salts by treating with a stoichiometric excess of the appropriate acid. The acid addition salts of the compounds of the invention may be reconverted to the corresponding free base by treating with a stoichiometric excess of a suitable base, such as potassium carbonate or sodium hydroxide, typically in the presence of aqueous solvent, and at a temperature of between about 0° C. and 100° C. The free base form may be isolated by conventional means, such as extraction with an organic solvent. In addition, acid addition salts of the compounds of the invention may be interchanged by taking advantage of differential solubilities of the salts, volatilities or acidities of the acids, or by treating with the appropriately loaded ion exchange resin. For example, the interchange may be affected by the reaction of a salt of the compounds of the invention with a slight stoichiometric excess of an acid of a lower pK than the acid component of the starting salt. This conversion is typically carried out at a temperature between about 0° C. and the boiling point of the solvent being used as the medium for the procedure. Similar exchanges are possible with base addition salts, typically via the intermediacy of the free base form.

The compounds of the invention may exist in both unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. The term 'solvate' is used herein to describe a molecular complex comprising a compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

The invention also relates to prodrugs of the compounds of the formulae provided herein. Thus, certain derivatives of compounds of the invention which may have little or no pharmacological activity themselves can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some non-limiting examples of prodrugs in accordance with the invention include:

(i) where the compound contains a carboxylic acid functionality (—COOH), an ester thereof, for example, replacement of the hydrogen with $(C_1-C_8)$alkyl;

(ii) where the compound contains an alcohol functionality (—OH), an ether thereof, for example, replacement of the hydrogen with $(C_1-C_6)$alkanoyloxymethyl, or with a phosphate ether group; and (iii) where the compound contains a primary or secondary amino functionality (—$NH_2$ or —NHR where R≠H), an amide thereof, for example, replacement of one or both hydrogens with a suitably metabolically labile group, such as an amide, carbamate, urea, phosphonate, sulfonate, etc.

Further examples of replacement groups in accordance with the foregoing examples and examples of other prodrug types may be found in the aforementioned references.

Finally, certain inventive compounds may themselves act as prodrugs of other of the inventive compounds.

Also included within the scope of the invention are metabolites of compounds of the formulae described herein, i.e., compounds formed in vivo upon administration of the drug.

The compounds of the formulae provided herein may have asymmetric carbon atoms. The carbon-carbon bonds of the compounds of the invention may be depicted herein using a solid line ( ———— ), a solid wedge ( ◢◣ ), or a dotted wedge ( ·······‖‖‖ ). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included and the attached stereocenter. For example, unless stated otherwise, it is intended that the compounds of the invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Compounds of the invention that have chiral centers may exist as stereoisomers, such as racemates, enantiomers, or diastereomers.

Stereoisomers of the compounds of the formulae herein can include cis and trans isomers, optical isomers such as (R) and (S) enantiomers, diastereomers, geometric isomers, rotational isomers, atropisomers, conformational isomers, and tautomers of the compounds of the invention, including compounds exhibiting more than one type of isomerism; and mixtures thereof (such as racemates and diastereomeric pairs).

Also included are acid addition salts or base addition salts, wherein the counterion is optically active, for example, d-lactate or l-lysine, or racemic, for example, dl-tartrate or dl-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention may exhibit the phenomena of tautomerism and structural isomerism. For example, the compounds may exist in several tautomeric forms, including the enol and imine form, and the keto and enamine form and geometric isomers and mixtures thereof. All such tautomeric forms are included within the scope of compounds of the invention. Tautomers exist as mixtures of a tautomeric set in solution. In solid form, usually one tautomer predominates. Even though one tautomer may be described, the present invention includes all tautomers of the compounds of the formulae provided.

In addition, some of the compounds of the invention may form atropisomers (e.g., substituted biaryls). Atropisomers are conformational stereoisomers which occur when rotation about a single bond in the molecule is prevented, or greatly slowed, as a result of steric interactions with other parts of the molecule and the substituents at both ends of the single bond are unsymmetrical. The interconversion of atropisomers is slow enough to allow separation and isolation under predetermined conditions. The energy barrier to thermal racemization may be determined by the steric hindrance to free rotation of one or more bonds forming a chiral axis.

Where a compound of the invention contains an alkenyl or alkenylene group, geometric cis/trans (or Z/E) isomers are possible. Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC) or superfluid critical chromatography (SFC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The enantiomeric purity of compounds described herein may be described in terms of enantiomeric excess (ee), which indicates the degree to which a sample contains one enantiomer in greater amounts than the other. A racemic mixture has an ee of 0%, while a single completely pure enantiomer has an ee of 100%. Similarly, diastereomeric purity may be described in terms of diasteriomeric excess (de).

The present invention also includes isotopically-labeled compounds, which are identical to those recited in one of the formulae provided, but for the fact that one or more atoms are replaced by an atom having an atomic mass or mass number different from the atomic mass or mass number usually found in nature.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Examples of isotopes that may be incorporated into compounds of the invention include isotopes of hydrogen, carbon, nitrogen, oxygen, phosphorus, sulfur, fluorine and chlorine, such as, but not limited to, $^2$H, $^3$H, $^{13}$C, $^{14}$C, $^{15}$N, $^{18}$O, $^{17}$O $^{32}$P, $^{35}$S, $^{18}$F and $^{36}$Cl. Certain isotopically-labeled compounds of the invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labeled compounds of the invention may generally be prepared by carrying out the procedures disclosed in the Schemes and/or in the Examples and Preparations below, by substituting an isotopically-labeled reagent for a non-isotopically-labeled reagent.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used.

Therapeutic Methods and Uses

The invention further provides therapeutic methods and uses comprising administering the compounds of the invention, or pharmaceutically acceptable salts thereof, alone or in combination with other therapeutic agents or palliative agents.

In one aspect, the invention provides a method for the treatment of abnormal cell growth in a subject in need thereof, comprising administering to the subject a therapeutically effective amount of a compound of the invention, or a pharmaceutically acceptable salt thereof.

In one aspect, the invention provides a method for the treatment of cancer in a subject in need thereof, comprising administering to the subject a therapeutically effective amount of a compound of the invention, or a pharmaceutically acceptable salt thereof.

In another aspect, the invention provides a method for the treatment of abnormal cell growth in a subject in need thereof, comprising administering to the subject an amount of a compound of the invention, or a pharmaceutically acceptable salt thereof, in combination with an amount of an additional therapeutic agent (e.g., an anticancer therapeutic agent), which amounts are together effective in treating said abnormal cell growth.

In another aspect, the invention provides a method for the treatment of cancer in a subject in need thereof, comprising administering to the subject an amount of a compound of the invention, or a pharmaceutically acceptable salt thereof, in combination with an amount of an additional therapeutic agent (e.g., an anticancer therapeutic agent), which amounts are together effective in treating said abnormal cell growth.

In another aspect, the invention provides a compound of the invention, or a pharmaceutically acceptable salt thereof, for use in the treatment of abnormal cell growth in a subject.

In another aspect, the invention provides a compound of the invention, or a pharmaceutically acceptable salt thereof, for use in the treatment of cancer in a subject.

In a further aspect, the invention provides the use of a compound of the invention, or a pharmaceutically acceptable salt thereof, for the treatment of abnormal cell growth in a subject.

In a further aspect, the invention provides the use of a compound of the invention, or a pharmaceutically acceptable salt thereof, for the treatment of cancer in a subject.

In another aspect, the invention provides a pharmaceutical composition for use in the treatment of abnormal cell growth in a subject in need thereof, which pharmaceutical composition comprises a compound of the invention, or a pharmaceutically acceptable salt thereof, and a pharmaceutically acceptable carrier or excipient.

In another aspect, the invention provides a pharmaceutical composition for use in the treatment of cancer in a subject in need thereof, which pharmaceutical composition comprises a compound of the invention, or a pharmaceutically acceptable salt thereof, and a pharmaceutically acceptable carrier or excipient.

In another aspect, the invention provides a compound of the invention, or a pharmaceutically acceptable salt thereof, for use as a medicament, in particular a medicament for the treatment of abnormal cell growth such as cancer.

In another aspect, the invention provides a compound of the invention, or a pharmaceutically acceptable salt thereof, for use as a medicament for the treatment of cancer.

In yet another aspect, the invention provides the use of a compound of the invention, or a pharmaceutically acceptable salt thereof, for the manufacture of a medicament for the treatment of abnormal cell growth, such as cancer, in a subject.

In frequent embodiments of the methods provided herein, the abnormal cell growth is cancer. Compounds of the invention may be administered as single agents or may be administered in combination with other anti-cancer therapeutic agents, in particular with standard of care agents appropriate for the particular cancer.

In some embodiments, the methods provided result in one or more of the following effects: (1) inhibiting cancer cell proliferation; (2) inhibiting cancer cell invasiveness; (3) inducing apoptosis of cancer cells; (4) inhibiting cancer cell metastasis; or (5) inhibiting angiogenesis.

In another aspect, the invention provides a method for the treatment of a disorder mediated by CDK4 in a subject, comprising administering to the subject a compound of the invention, or a pharmaceutically acceptable salt thereof, in an amount that is effective for treating said disorder, in particular cancer.

In preferred aspects and embodiments of the compounds, compositions, methods and uses described herein, the compounds of the invention are selective for CDK4 over CDK6. In frequent embodiments, the binding affinity for CDK6 is at least 10-fold, 15-fold, 20-fold, 25-fold, 30-fold, 40-fold, 50-fold, 60-fold, 75-fold, 100-fold, or greater than 100-fold larger than the binding affinity for CDK4.

In view of the potential role of CDK6 in hematologic toxicities, such as neutropenia or leukopenia, a CDK4 selective inhibitor may provide an improved safety profile, improved dosing schedule (e.g., by decreasing the need for dose reduction or dosing holidays), and/or enhanced overall efficacy, due to the potential of higher dosing, use of a continuous dosing regimen, and/or extended time of overall treatment as compared to current dual CDK4/6 inhibitors. Animal models to assess neutropenia are described in the art. For example, see Fine et al. A Specific Stimulator of Granulocyte Colony-Stimulating Factor Accelerates Recover from Cyclophophamide-Induced Neutropenia in the Mouse (1997) Blood, 90(2):795-802; Hu et al., Mechanistic Investigation of Bone Marrow Suppression Associated with Palbociclib and its Differentiation from Cytotoxic Chemotherapies (2016), Clin. Cancer Res. 22(8):2000-2008.

It may also be preferable to obtain selectivity for CDK4 over other CDKs, such as CDK1, CDK2 and/or CDK9.

Compounds of the invention include compounds of any of the formulae described herein, or pharmaceutically acceptable salts thereof.

In another aspect, the invention provides a method of inhibiting cancer cell proliferation in a subject, comprising administering to the subject a compound of the invention, or a pharmaceutically acceptable salt thereof, in an amount effective to inhibit cell proliferation.

In another aspect, the invention provides a method of inhibiting cancer cell invasiveness in a subject, comprising administering to the subject a compound of the invention, or a pharmaceutically acceptable salt thereof, in an amount effective to inhibit cell invasiveness.

In another aspect, the invention provides a method of inducing apoptosis in cancer cells in a subject, comprising administering to the subject a compound of the invention, or a pharmaceutically acceptable salt thereof, in an amount effective to induce apoptosis.

In another aspect, the invention provides a method of inhibiting cancer cell metastasis in a subject, comprising administering to the subject a compound of the invention, or a pharmaceutically acceptable salt thereof, in an amount effective to inhibit cell metastasis.

In another aspect, the invention provides a method of inhibiting angiogenesis in a subject, comprising administering to the subject a compound of the invention, or a pharmaceutically acceptable salt thereof, in an amount effective to inhibit angiogenesis.

In frequent embodiments of the methods provided herein, the abnormal cell growth is cancer. In some such embodiments, the cancer is selected from the group consisting of breast cancer, ovarian cancer, bladder cancer, uterine cancer, prostate cancer, lung cancer (including NSCLC, SCLC, squamous cell carcinoma or adenocarcinoma), esophageal cancer, head and neck cancer, colorectal cancer, kidney cancer (including RCC), liver cancer (including HCC), pancreatic cancer, stomach (i.e., gastric) cancer and thyroid cancer. In further embodiments of the methods provided herein, the cancer is selected from the group consisting of breast cancer, ovarian cancer, bladder cancer, uterine cancer, prostate cancer, lung cancer, esophageal cancer, liver cancer, pancreatic cancer and stomach cancer.

In other embodiments, the cancer is breast cancer, including, e.g., ER-positive/HR-positive, HER2-negative breast cancer; ER-positive/HR-positive, HER2-positive breast cancer; triple negative breast cancer (TNBC); or inflammatory breast cancer. In some embodiments, the breast cancer is endocrine resistant breast cancer, trastuzumab or pertuzumab resistant breast cancer, or breast cancer demonstrating primary or acquired resistance to CDK4/CDK6 inhibition. In some embodiments, the breast cancer is advanced or metastatic breast cancer.

In some embodiments, the compound of the invention is administered as first line therapy. In other embodiments, the compound of the invention is administered as second (or later) line therapy. In some embodiments, the compound of the invention is administered as second (or later) line therapy following treatment with an endocrine therapeutic agent and/or a CDK4/CDK6 inhibitor. In some embodiments, the compound of the invention is administered as second (or later) line therapy following treatment with an endocrine therapeutic agent, e.g., an aromatase inhibitor, a SERM or a SERD. In some embodiments, the compound of the invention is administered as second (or later) line therapy following treatment with a CDK4/CDK6 inhibitor. In some embodiments, the compound of the invention is administered as second (or later) line therapy following treatment with one or more chemotherapy regimens, e.g., including taxanes or platinum agents. In some embodiments, the compound of the invention is administered as second (or later) line therapy following treatment with HER2 targeted agents, e.g., trastuzumab.

As used herein, an "effective dosage" or "effective amount" of drug, compound or pharmaceutical composition is an amount sufficient to affect any one or more beneficial or desired, including biochemical, histological and/or behavioral symptoms, of the disease, its complications and intermediate pathological phenotypes presenting during development of the disease. For therapeutic use, a "therapeutically effective amount" refers to that amount of a compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, (4) relieving to some extent (or, preferably, eliminating) one or more signs or symptoms associated with the cancer, (5) decreasing the dose of other medications required to treat the disease, and/or (6) enhancing the effect of another medication, and/or (7) delaying the progression of the disease in a patient.

An effective dosage can be administered in one or more administrations. For the purposes of this invention, an effective dosage of drug, compound, or pharmaceutical composition is an amount sufficient to accomplish prophylactic or therapeutic treatment either directly or indirectly. As is understood in the clinical context, an effective dosage of drug, compound or pharmaceutical composition may or may not be achieved in conjunction with another drug, compound or pharmaceutical composition.

"Tumor" as it applies to a subject diagnosed with, or suspected of having, a cancer refers to a malignant or potentially malignant neoplasm or tissue mass of any size and includes primary tumors and secondary neoplasms. A solid tumor is an abnormal growth or mass of tissue that usually does not contain cysts or liquid areas. Examples of solid tumors are sarcomas, carcinomas, and lymphomas. Leukaemia's (cancers of the blood) generally do not form solid tumors (National Cancer Institute, Dictionary of Cancer Terms).

"Tumor burden" or "tumor load', refers to the total amount of tumorous material distributed throughout the body. Tumor burden refers to the total number of cancer cells or the total size of tumor(s), throughout the body, including lymph nodes and bone marrow. Tumor burden can be determined by a variety of methods known in the art, such as, e.g., using callipers, or while in the body using imaging techniques, e.g., ultrasound, bone scan, computed tomography (CT), or magnetic resonance imaging (MRI) scans.

The term "tumor size" refers to the total size of the tumor which can be measured as the length and width of a tumor. Tumor size may be determined by a variety of methods known in the art, such as, e.g., by measuring the dimensions of tumor(s) upon removal from the subject, e.g., using callipers, or while in the body using imaging techniques, e.g., bone scan, ultrasound, CR or MRI scans.

As used herein, "subject" refers to a human or animal subject. In certain preferred embodiments, the subject is a human.

The term "treat" or "treating" a cancer as used herein means to administer a compound of the present invention to a subject having cancer, or diagnosed with cancer, to achieve at least one positive therapeutic effect, such as, for example, reduced number of cancer cells, reduced tumor size, reduced rate of cancer cell infiltration into peripheral organs, or reduced rate of tumor metastases or tumor growth, reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

For the purposes of this invention, beneficial or desired clinical results include, but are not limited to, one or more of the following: reducing the proliferation of (or destroying) neoplastic or cancerous cell; inhibiting metastasis or neoplastic cells; shrinking or decreasing the size of a tumor; remission of the cancer; decreasing symptoms resulting from the cancer; increasing the quality of life of those suffering from the cancer; decreasing the dose of other medications required to treat the cancer; delaying the progression of the cancer; curing the cancer; overcoming one or more resistance mechanisms of the cancer; and/or prolonging survival of patients the cancer. Positive therapeutic effects in cancer can be measured in several ways (see, for example, W. A. Weber, Assessing tumor response to therapy, J. Nucl. Med. 50 Suppl. 1:1S-10S (2009). For example, with respect to tumor growth inhibition (T/C), according to the National Cancer Institute (NCI) standards, a T/C less than or equal to 42% is the minimum level of anti-tumor activity. A T/C<10% is considered a high anti-tumor activity level, with T/C (%)=median tumor volume of the treated/median tumor volume of the control x 100.

In some embodiments, the treatment achieved by a compound of the invention is defined by reference to any of the following: partial response (PR), complete response (CR), overall response (OR), progression free survival (PFS), disease free survival (DFS) and overall survival (OS). PFS, also referred to as "Time to Tumor Progression" indicates the length of time during and after treatment that the cancer does not grow and includes the amount of time patients have experienced a CR or PR, as well as the amount of time patients have experienced stable disease (SD). DFS refers to the length of time during and after treatment that the patient remains free of disease. OS refers to a prolongation in life expectancy as compared to naïve or untreated subjects or patients. In some embodiments, response to a combination of the invention is any of PR, CR, PFS, DFS, OR or OS that is assessed using Response Evaluation Criteria in Solid Tumors (RECIST) 1.1 response criteria.

The treatment regimen for a compound of the invention that is effective to treat a cancer patient may vary according to factors such as the disease state, age, and weight of the patient, and the ability of the therapy to elicit an anti-cancer response in the subject. While an embodiment of any of the aspects of the invention may not be effective in achieving a positive therapeutic effect in every subject, it should do so in a statistically significant number of subjects as determined by any statistical test known in the art such as the Student's t-test, the chi2-test the U-test according to Mann and Whitney, the Kruskal-Wallis test (H-test), Jonckheere-Terpstrattesty and the Wilcon on-test.

The terms "treatment regimen", "dosing protocol" and "dosing regimen" are used interchangeably to refer to the dose and timing of administration of each compound of the invention, alone or in combination with another therapeutic agent.

"Ameliorating" means a lessening or improvement of one or more symptoms upon treatment with a combination described herein, as compared to not administering the combination. "Ameliorating" also includes shortening or reduction in duration of a symptom.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous).

Abnormal cell growth includes the abnormal growth of: (1) tumor cells (tumors) that show increased expression of CDK4 and/or CDK6; (2) tumors that proliferate by aberrant CDK4 and/or CDK6 activation; and (3) tumors that are resistant to endocrine therapy, CDK4/6 inhibition, or HER2 antagonists.

The term "additional anticancer therapeutic agent" as used herein means any one or more therapeutic agent, other than a compound of the invention, that is or can be used in the treatment of cancer. In some embodiments, such additional anticancer therapeutic agents include compounds derived from the following classes: mitotic inhibitors, alkylating agents, antimetabolites, antitumor antibiotics, anti-angiogenesis agents, topoisomerase I and II inhibitors, plant alkaloids, hormonal agents and antagonists, growth factor inhibitors, radiation, signal transduction inhibitors, such as inhibitors of protein tyrosine kinases and/or serine/threonine kinases, cell cycle inhibitors, biological response modifiers, enzyme inhibitors, antisense oligonucleotides or oligonucleotide derivatives, cytotoxics, immuno-oncology agents, and the like.

In some embodiments, the additional anticancer agent is an endocrine agent, such as an aromatase inhibitor, a SERD or a SERM. In some such embodiments, a compound of the invention may be administered in combination with a standard of care agent, such as tamoxifen, exemestane, letrozole, fulvestrant, or anastrozole.

In other embodiments, a compound of the invention may be administered in combination with a chemotherapeutic agent, such as docetaxel, paclitaxel, paclitaxel protein-bound particles, cisplatin, carboplatin, oxaliplatin, capecitabine, gemcitabine or vinorelbine, In some embodiments, the additional anticancer agent is an anti-angiogenesis agent, including for example VEGF inhibitors, VEGFR inhibitors, TIE-2 inhibitors, PDGFR inhibitors, angiopoetin inhibitors, PKCβ inhibitors, COX-2 (cyclooxygenase II) inhibitors, integrins (alpha-v/beta-3), MMP-2 (matrix-metalloproteinase 2) inhibitors, and MMP-9 (matrix-metalloproteinase 9) inhibitors. Preferred anti-angiogenesis agents include sunitinib (Sutent™), bevacizumab (Avastin™), axitinib (AG 13736), SU 14813 (Pfizer), and AG 13958 (Pfizer). Additional anti-angiogenesis agents include vatalanib (CGP 79787), Sorafenib (Nexavar™), pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™ (AE 941), tetrathiomolybdata (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer). Other anti-angiogenesis agents include enzastaurin (LY 317615), midostaurin (CGP 41251), perifosine (KRX 0401), teprenone (Selbex™) and UCN 01 (Kyowa Hakko). Other examples of anti-angiogenesis agents include celecoxib (Celebrex™), parecoxib (Dynastat™), deracoxib (SC 59046), lumiracoxib (Preige™) valdecoxib (Bextra™), rofecoxib (Vioxx™), iguratimod (Careram™), IP 751 (Invedus), SC-58125 (Pharmacia) and etoricoxib (Arcoxia™). Yet further anti-angiogenesis agents include exisulind (Aptosyn™), salsalate (Amigesic™), diflunisal (Dolobid™), ibuprofen (Motrin™), ketoprofen (Orudis™), nabumetone (Relafen™), piroxicam (Feldene™), naproxen (Aleve™, Naprosyn™) diclofenac (Voltaren™), indomethacin (Indocin™), sulindac (Clinoril™), tolmetin (Tolectin™) etodolac (Lodine™), ketorolac (Toradol™), and oxaprozin (Daypro™). Yet further anti-angiogenesis agents include ABT 510 (Abbott), apratastat (TMI 005), AZD 8955 (AstraZeneca), incyclinide (Metastat™), and PCK 3145 (Procyon). Yet further anti-angiogenesis agents include acitretin (Neotigason™), plitidepsin (Aplidine™), cilengtide (EMD 121974), combretastatin A4 (CA4P), fenretinide (4 HPR), halofuginone (Tempostatin™), Panzem™ (2-methoxyestradiol), PF-03446962 (Pfizer), rebimastat (BMS 275291), catumaxomab (Removab™), lenalidomide (Revlimid™), squalamine (EVIZON™), thalidomide (Thalomid™), Ukrain™ (NSC 631570), Vitaxin™ (MEDI 522), and zoledronic acid (Zometa™).

In other embodiments, the additional anti-cancer agent is a signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EGF inhibitor, ErbB-1 (EGFR), ErbB-2, pan erb, IGF1R inhibitors, MEK, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway and multi-targeted kinase inhibitors.

Additional examples of anti-cancer agents which may be used in conjunction with a compound of the invention and pharmaceutical compositions described herein include palbociclib (Ibrance®), ribociclib (Kisqali®), abemaciclib (Verzenio®), BMS 214662 (Bristol-Myers Squibb), lonafarnib (Sarasar™), pelitrexol (AG 2037), matuzumab (EMD 7200), nimotuzumab (TheraCIM h-R3™), panitumumab (Vectibix™), Vandetanib (Zactima™), pazopanib (SB 786034), ALT 110 (Alteris Therapeutics), BIBW 2992 (Boehringer Ingelheim), and Cervene™ (TP 38). Other examples include gefitinib (Iressa®), cetuximab (Erbitux®), erlotinib (Tarceva®), trastuzumab (Herceptin®), ado-trastuzumab emtansine (Kadcyla®), pertuzumab (Perjeta®), osimertinib (Tagrisso®), atezolizumab (Tecentriq™), sunitinib (Sutent®), ibrutinib (Imbruvica®), imatinib (Gleevec®), crizotinib (Xalkor®), lorlatinib (Lorbrena®), dacomitinib (Vizimpro®), bosutinib (Bosulif®), glasdegib (Daurismo™), canertinib (CI 1033), lapatinib (Tycerb™), pelitinib (EKB 569), miltefosine (Miltefosin™), BMS 599626 (Bristol-Myers Squibb), Lapuleucel-T (Neuvenge™) NeuVax™ (E75 cancer vaccine), Osidem™ (IDM 1), mubritinib (TAK-165), CP-724,714 (Pfizer), panitumumab (Vectibix™), ARRY 142886 (Array Biopharm), everolimus (Certican™) zotarolimus (Endeavor™), temsirolimus (Torisel™), AP 23573 (ARIAD), and VX680 (Vertex), XL 647 (Exelixis), sorafenib (Nexavar™), LE-AON (Georgetown University), and GI-4000 (Globelmmune). Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (Onc Bio), BMS 387032 (Bristol-Myers Squibb), and AG 024322 (Pfizer), or PD-1 or PD-L1 antagonists, e.g., pembrolizumab (Keytruda®), nivolumab (Opdivo™), or avelumab (Bavencio®).

In other embodiments, the additional anti-cancer agent is a so-called classical antineoplastic agent. Classical antineoplastic agents include but are not limited to hormonal modulators such as hormonal, anti-hormonal, androgen agonist, androgen antagonist and anti-estrogen therapeutic agents, histone deacetylase (HDAC) inhibitors, DNA methyltransferase inhibitors, silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitor (such as, e.g., talazoparib (Talzenna®), olaparib, rucaparib, niraparib, iniparib, veliparib), microtubulin inhibitors, antibiotics, plant derived spindle inhibitors, platinum-coordinated compounds, gene therapeutic agents, antisense oligonucleotides, vascular targeting agents (VTAs), and statins. Examples of classical antineoplastic agents used in combination therapy with a compound of the invention, optionally with one or more other agents include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, trilostane and CHF 4227 (Cheisi), Selective Estrogen-Receptor Downregulators (SERD's; such as fulvestrant), exemestane (Aromasin), anastrozole (Arimidex), atamestane, fadrozole, letrozole (Femara), formestane; gonadotropin-releasing hormone (GnRH; also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), cyproterone, flutamide (Eulexin), megestrol, nilutamide (Nilandron), and osaterone, dutasteride, epristeride, finasteride, Serenoa repens, PHL 00801, abarelix, goserelin, leuprorelin, triptorelin, bicalutamide; antiandrogen agents, such as enzalutamide (Xtandi®), abiraterone acetate, bicalutamide (Casodex); and combinations thereof. Other examples of classical antineoplastic agents used in combination with a compound of the invention include but are not limited to PARP inhibitors, such as talazoparib, olapariv, rucaparib, niraparib, iniparib, veliparib; suberolanilide hydroxamic acid (SAHA, Merck Inc./Aton Pharmaceuticals), depsipeptide (FR901228 or FK228), G2M-777, MS-275, pivaloyloxymethyl butyrate and PXD-101; Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, camptothecin, 10-hydroxycamptothecin, 9-aminocamptothecin, irinotecan, SN-38, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, carboplatin, eptaplatin, lobaplatin, nedaplatin, oxaliplatin, streptozocin, satrplatin, and combinations thereof.

In still other embodiments, the additional anti-cancer agent is a so called dihydrofolate reductase inhibitors (such as methotrexate and NeuTrexin (trimetresate glucuronate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda™) cytosine arabinoside, Gemzar™ (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]-2-thenoyl)-L-glutamic acid, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paclitaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcyta™), DMXAA (Antisoma), ibandronic acid, L-asparaginase, pegaspargase (Oncaspar™), Efaproxiral (Efaproxyn™—radiation therapy), bexarotene (Targretin™), Tesmilifene (DPPE—enhances efficacy of cytotoxics), Theratope™ (Biomira), Tretinoin (Vesanoid™), tirapazamine (Trizaone™), motexafin gadolinium (Xcytrin™) Cotara™ (mAb), and NBI-3001 (Protox Therapeutics), polyglutamate-paclitaxel (Xyotax™) and combinations thereof. Further examples of classical antineoplastic agents include, but are not limited to, as Advexin (ING 201), TNFerade (GeneVec, a compound which express TNFalpha in response to radiotherapy), RB94 (Baylor College of Medicine), Genasense (Oblimersen, Genta), Combretastatin A4P (CA4P), Oxi-4503, AVE-8062, ZD-6126, TZT-1027, Atorvastatin (Lipitor, Pfizer Inc.), Provastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovostatin, Niacin (Advicor, Kos Pharmaceuticals), Caduet, Lipitor, torcetrapib, and combinations thereof.

In some embodiments, the additional anti-cancer agent is an epigenetic modulator, for example an inhibitor or EZH2, SMARCA4, PBRM1, ARID1A, ARID2, ARID1B, DNMT3A, TET2, MLL1/2/3, NSD1/2, SETD2, BRD4, DOT1L, HKMTsanti, PRMT1-9, LSD1, UTX, IDH1/2 orBCL6.

In further embodiments, the additional anti-cancer agent is an immunomodulatory agent, such as an inhibitor of CTLA-4, PD-1 or PD-L1 (e.g., pembrolizumab, nivolumab or avelumab), LAG-3, TIM-3, TIGIT, 4-1BB, OX40, GITR, CD40, or a CAR-T-cell therapy.

As used herein "cancer" refers to any malignant and/or invasive growth or tumor caused by abnormal cell growth. Cancer includes solid tumors named for the type of cells that form them, cancer of blood, bone marrow, or the lymphatic system. Examples of solid tumors include sarcomas and carcinomas. Cancers of the blood include, but are not limited to, leukemia, lymphoma and myeloma. Cancer also includes primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of a different type from the latter one.

In some embodiments of the methods provided herein, the cancer is selected from the group consisting of breast cancer, ovarian cancer, bladder cancer, uterine cancer, prostate cancer, lung cancer (including NSCLC), esophageal cancer, head and neck cancer, liver cancer, pancreatic cancer and stomach cancer.

Dosage Forms and Regimens

Administration of the compounds of the invention may be affected by any method that enables delivery of the compounds to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The amount of the compound of the invention administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Formulations and Routes of Administration

As used herein, a "pharmaceutically acceptable carrier" refers to a carrier or diluent that does not cause significant irritation to an organism and does not abrogate the biological activity and properties of the administered compound.

The pharmaceutical acceptable carrier may comprise any conventional pharmaceutical carrier or excipient. The choice of carrier and/or excipient will to a large extent depend on factors such as the particular mode of administration, the effect of the carrier or excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11(6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus, compounds of the invention may be formulated as a solid, semi-solid, or thixotropic liquid for administration as an implanted depot providing modified release of the active compound. Examples of such formulations include drug-coated stents and PGLA microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 μg to 20 mg of the compound of the invention per actuation and the actuation volume may vary from 1 μL to 100 μL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, and frequently about 0.01 to about 35 mg/kg/day, in single or divided doses. For a 70 kg human, this would amount to about 0.07 mg/day to about 7000 mg/day, more commonly, from about 10 mg/day to about 1000 mg/day. Sometimes, the dosage is about 10, 20, 30, 40, 50, 60, 75, 100, 125, 150, 175, 200, 225, 250, 275, 300, 325, 350, 375, 400, 425, 450, 475, 500, 525, 550, 575, 600, 625, 650, 675, 700, 750, 800, 900 or 1000 mg/day. Sometimes, the dosage is from about 10 mg/day to about 1000 mg/day, from about 10 mg/day to about 750 mg/day, from about 10 mg/day to about 600 mg/day, from about 10 mg/day to about 300 mg/day, from about 10 mg/day to about 150 mg/day, from about 20 mg/day to about 750 mg/day, from about 20 mg/day to about to 600 mg/day, from about 20 mg/day to about to 300 mg/day, from about 20 mg/day to about to 150 mg/day, from about 50 mg/day to about 750 mg/day, from about 50 mg/day to about 600 mg/day, from about 50 mg/day to about 300 mg/day, from about 50 mg/day to about 150 mg/day, from about 75 mg/day to about 750 mg/day, from about 75 mg/day to about 600 mg/day, from about 75 mg/day to about 300 mg/day, or from about 75 mg/day to about 150 mg/day.

In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus, the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

Combination Therapy

As used herein, the term "combination therapy" refers to the administration of a compound of the invention together with an at least one additional pharmaceutical or medicinal agent (e.g., an anti-cancer agent), either sequentially or simultaneously.

As noted above, the compounds of the invention may be used in combination with one or more additional anti-cancer agents. The efficacy of the compounds of the invention in certain tumors may be enhanced by combination with other approved or experimental cancer therapies, e.g., radiation, surgery, chemotherapeutic agents, targeted therapies, agents that inhibit other signaling pathways that are dysregulated in tumors, and other immune enhancing agents, such as PD-1 or PD-L1 antagonists and the like.

When a combination therapy is used, the one or more additional anti-cancer agents may be administered sequentially or simultaneously with the compound of the invention. In one embodiment, the additional anti-cancer agent is administered to a mammal (e.g., a human) prior to administration of the compound of the invention. In another embodiment, the additional anti-cancer agent is administered to the mammal after administration of the compound of the invention. In another embodiment, the additional anti-cancer agent is administered to the mammal (e.g., a human) simultaneously with the administration of the compound of the invention.

The invention also relates to a pharmaceutical composition for the treatment of abnormal cell growth in a mammal, including a human, which comprises an amount of a compound of the invention, as defined above (including hydrates, solvates and polymorphs of said compound or pharmaceutically acceptable salts thereof), in combination with one or more (preferably one to three) additional anti-cancer therapeutic agents.

Synthetic Methods

Compounds of the invention are prepared according to the exemplary procedures and Schemes provided herein, and modifications thereof known to those of skill in the art. Scheme 1 shows a general route for making pyrimidine compounds 6 having varying saturated heterocyclyl or cycloalkyl moieties (comprising Q) and a heteroaromatic ring (comprising U, V, X, Y and Z). It will be understood that the order of the steps could be reversed.

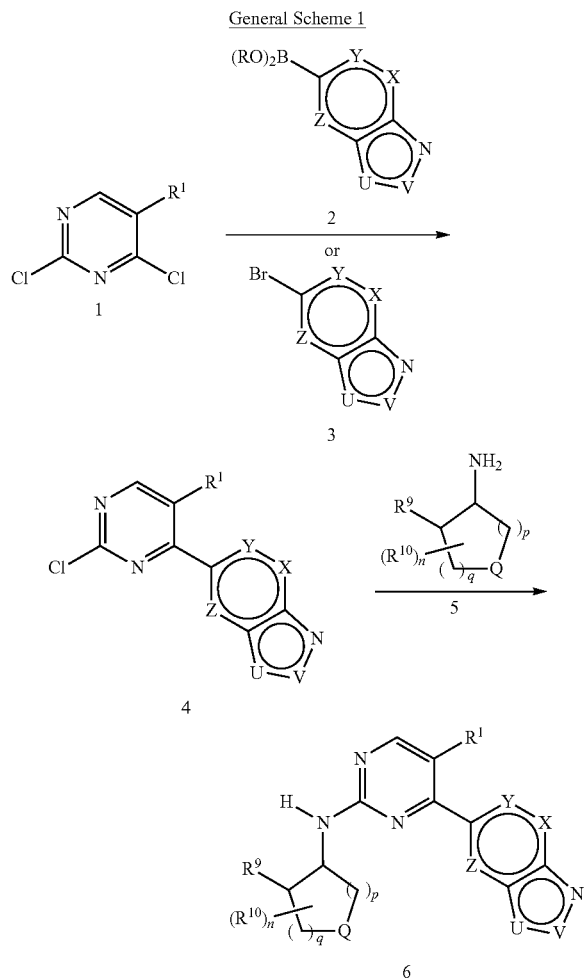

General Scheme 1

As exemplified in Scheme 1, substituted dichloropyrimidines 1 are subjected to Suzuki coupling conditions with aryl or heteroaryl boronates 2 in the presence of a suitable catalyst (such as Pd(PPh$_3$)$_4$ or Pd(PPh$_3$)$_2$C$_2$) and a suitable base (such as Na$_2$CO$_3$ or K$_2$CO$_3$) in a suitable solvent system (such as dioxane:water or DME:water) to afford an aryl- or heteroaryl-substituted chloropyrimidines 4. Alternatively, aryl or heteroaryl bromides 3 can be utilized in the Suzuki cross-coupling following treatment of the bromo compound with bis(pinacolato)diboron, a suitable catalyst (such as Pd(OAc)$_2$ or Pd(dppf)Cl$_2$), ligand (such as PCy$_3$) and base (such as KOAc or NaOAc) in a suitable solvent (such as DMSO or dioxane). The resulting heterobiaryl intermediates 4 are treated under nucleophilic chloride displacement conditions with a primary heterocyclylamine or cycloalkylamine 5 in the presence of a suitable base (such as DIPEA) in a suitable solvent (e.g., DMSO), to afford amino-substituted pyrimidine compounds 6. When intermediate 4 is reacted with a primary heterocyclylamine, Q in 5 and 6 represents an appropriately substituted amino group (e.g., NR$^{11}$), an appropriately protected amino group (e.g., a carbamoyl, tetrahyrdopyranyl or trialkylsilyl protected amine) or oxygen. When intermediate 4 is reacted with a primary cycloalkylamine, Q in 5 and 6 represents an optionally substituted carbon.

Alternatively, the heterobiaryl intermediates 4 can be subjected to Buchwald-Hartwig coupling conditions in the presence of a suitable amine 5, a suitable catalyst (e.g., Pd$_2$(dba)$_3$, chloro-2-(dimethylaminomethyl)-ferrocen-1-yl-(dinorbornylphosphine)-palladium or Pd(OAc)$_2$, BINAP and a suitable base (e.g., Cs$_2$CO$_3$) in a suitable solvent (such as THF, dioxane or 2-methyl-2-butanol) to afford the compounds 6.

It will be understood that reactive functional groups present at any position in intermediates 1 to 5 and penultimate compounds 6 may be masked using suitable protecting groups known to those of skill in the art. For examples, such compounds may contain amine or hydroxyl moieties masked with protecting groups (such as tert-butylcarbamate or tetrahydropyran) that can be removed via conditions known in art (such as TFA or HCl) in a suitable solvent. In some embodiments, Q in compound 6 may represent a protected amino group, which is removed under standard conditions to provide a free secondary amine that is further we reacted with a suitably reactive reagent (e.g., a sulfonyl halide, acyl halide, alkyl halide or the like) to install the R$^{11}$ substituent.

Analogous reactions could be used to prepare the corresponding pyridine derivatives, as exemplified in the examples herein.

General Synthetic Methods:

Abbreviations:

The following abbreviations are used throughout the Examples: "Ac" means acetyl, "AcO" or "OAc" means acetoxy, "ACN" means acetonitrile, "aq" means aqueous, "atm" means atmosphere(s), "BOC", "Boc" or "boc" means N-tert-butoxycarbonyl, "Bn" means benzyl, "Bu" means butyl, "nBu" means normal-butyl, "tBu" means tert-butyl, "DBU" means 1,8-diazabicyclo[5.4.0]undec-7-ene, "Cbz" means benzyloxycarbonyl, "DCM" (CH$_2$Cl$_2$) means methylene chloride, "de" means diastereomeric excess, "DEA" means diethylamine, "DIPEA" means diisopropyl ethyl amine, "DMA" means N,N-dimethylacetamide, "DME" means 1,2-dimethoxyethane, "DMF" means N,N-dimethyl formamide, "DMSO" means dimethylsulfoxide, "EDTA" means ethylenediaminetetraacetic acid, "ee" means enantiomeric excess, "Et" means ethyl, "EtOAc" means ethyl acetate, "EtOH" means ethanol, "HOAc" or "AcOH" means acetic acid, "i-Pr" or "$^i$Pr" means isopropyl, "IPA" means isopropyl alcohol, "LAH" means lithium aluminum hydride, "LHMDS" means lithium hexamethyldisilazide (lithium bis (trimethylsilyl)amide), "mCPBA" means meta-chloroperoxy-benzoic acid, "Me" means methyl, "MeOH" means methanol, "MS" means mass spectrometry, "MTBE" means methyl tert-butyl ether, "NCS" means N-chlorosuccinimide, "Ph" means phenyl, "TBHP" means tert-butyl hydroperoxide, "TFA" means trifluoroacetic acid, "THF" means tetrahydrofuran, "SFC" means supercritical fluid chromatography, "TLC" means thin layer chromatography, "Rf" means retention fraction, "~" means approximately, "rt" means retention time, "h" means hours, "min" means minutes, "equiv" means equivalents, "sat." means saturated.

Scheme I

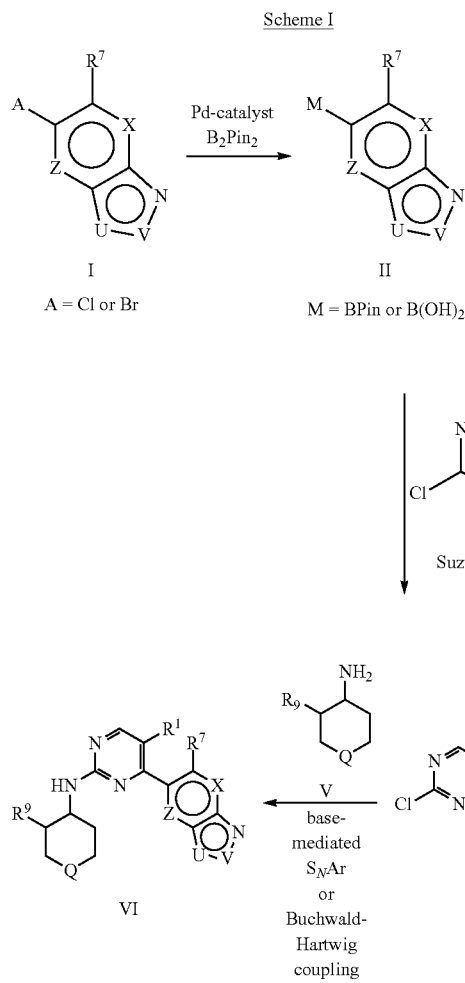

As exemplified in Scheme I, a compound such as I (purchased or synthesized) can be borylated with $B_2Pin_2$ in the presence of a suitable catalyst system (such as $PdCl_2$(dppf) or $Pd(OAc)_2+PCy_3$) with a suitable base (such as KOAc) in an appropriate solvent (such as 1,4-dioxane or DMSO) to provide a compound such as II. A compound such as II can be generated and reacted in-situ. Alternatively, a compound such as II can be isolated prior to subsequent reactions to provide the corresponding boronic acid or BPin ester. A compound such as II can undergo arylation with an aryl chloride such as III under standard Suzuki cross-coupling conditions in the presence of a suitable catalyst (such as $Pd(PPh_3)_4$ or $PdCl_2(PPh_3)_2$) with a suitable base (such as $K_2CO_3$ or $Na_2CO_3$) in an appropriate solvent (such as DMSO or 1,4-dioxane) to provide a compound such as IV. A compound such as IV can be coupled with an amine such as V to provide a compound such as VI under standard nucleophilic aromatic substitution conditions ($S_NAr$) in the presence of a suitable base (such as DIPEA) in an appropriate solvent (such as DMSO). Alternatively, a compound such as IV can be coupled with an amine such as V to provide a compound such as VI under standard Buchwald-Hartwig coupling conditions in the presence of a suitable catalyst system (such as $Pd(OAc)_2+rac$-BINAP or chloro-2-(dimethylaminomethyl)-ferrocen-1-yl-(dinorbornylphosphine)palladium complex) with a suitable base (such as $Cs_2CO_3$) in an appropriate solvent (such as THF or 1,4-dioxane). In some cases a compound such as VI may contain protecting groups, which can be removed by an additional step in the synthetic sequence using conditions known in the art (*Protective Groups in Organic Synthesis*, A. Wiley-Interscience Publication, 1981 or Protecting groups, 10 Georg Thieme Verlag, 1994). Compounds at every step may be purified by standard techniques, such as column chromatography, crystallization, or reverse phase SFC or HPLC. If necessary, separation of the enantiomers of VI may be carried out under standard methods known in the art such as chiral SFC or HPLC to afford single enantiomers. Variables Q, U, V, X, Z, $R^1$, and $R^7$, and $R^9$ are as defined as in the embodiments, schemes, examples, and claims herein.

Scheme II

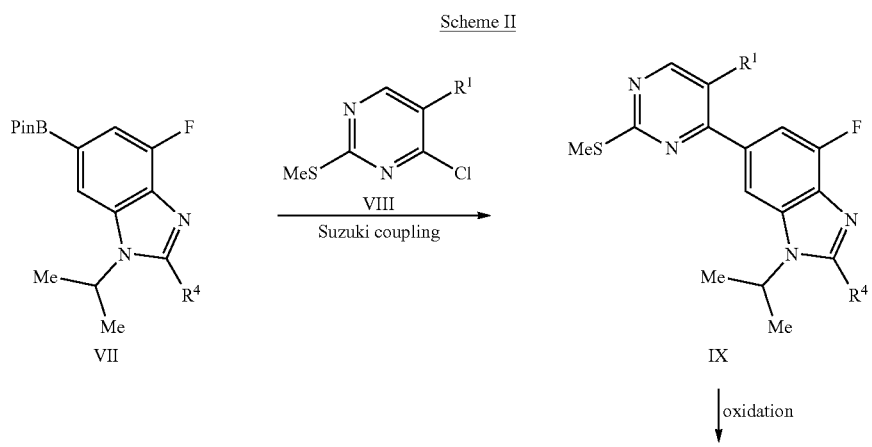

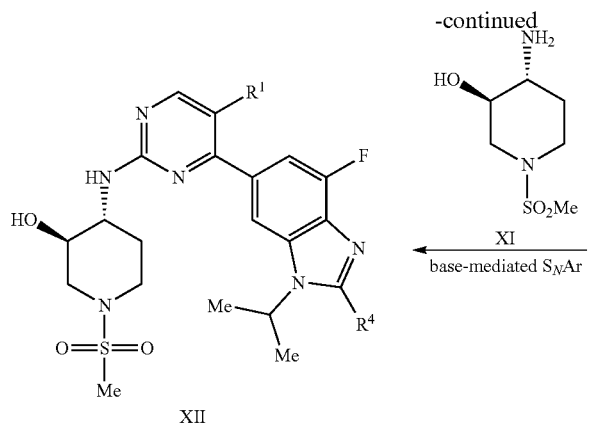

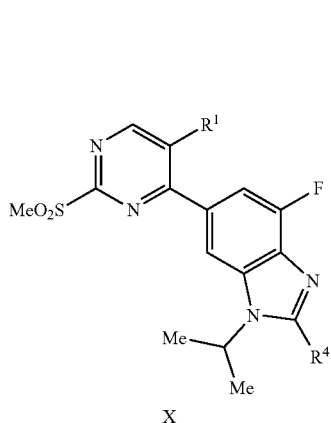

As shown in Scheme II, a compound such a VII (prepared as in Scheme I) can be coupled to an aryl chloride such as VIII under standard Suzuki cross-coupling conditions with a suitable catalyst system (such as Pd(t-Bu$_3$P)$_2$) with a suitable base (such as K$_2$CO$_3$) in an appropriate solvent (such as 1,4-dioxane) to provide a compound such as IX. A compound such as IX can be oxidized with a suitable oxidant (such as oxone) to provide a compound such as X. A compound such as X can be coupled to an amine such as XI under standard S$_N$Ar conditions in the presence of a suitable base (such as Na$_2$CO$_3$) in an appropriate solvent (such as THF) to provide a compound such as XII. Compounds at every step may be purified by standard techniques, such as column chromatography, crystallization, or reverse phase SFC or HPLC. Variables R$^1$, and R$^4$ are as defined as in the embodiments, schemes, examples, and claims herein.

Scheme III

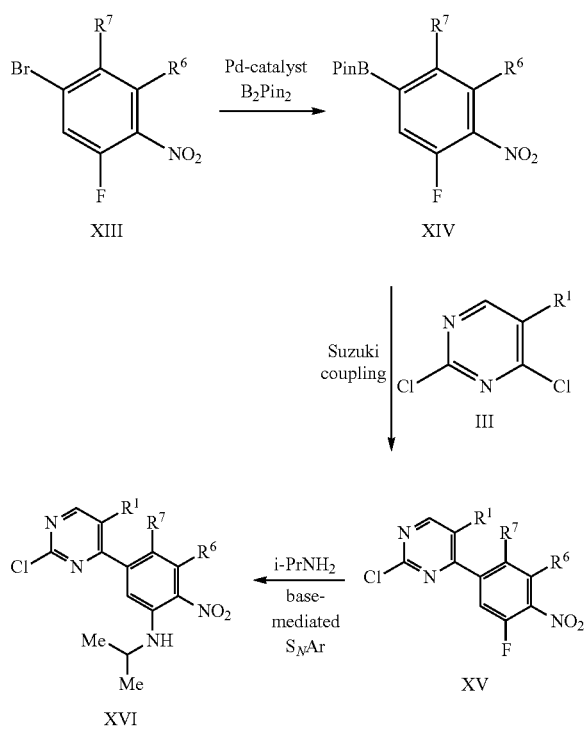

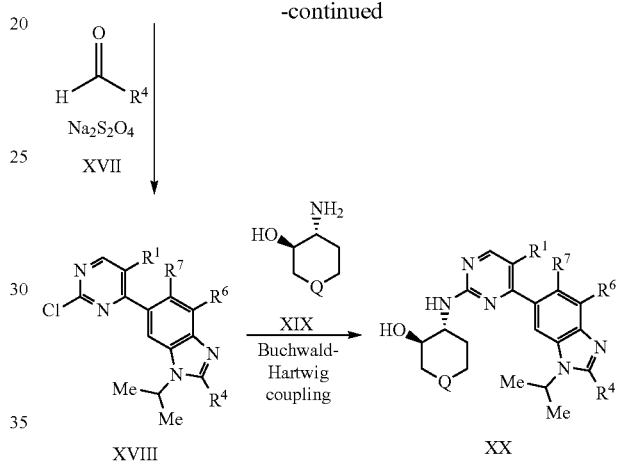

As shown in Scheme III, an aryl bromide such as compound XIII can be converted to a boronate ester such as compound XIV with B$_2$Pin$_2$ in the presence of a suitable catalyst (such as Pd$_2$Cl$_2$(dppf)) with a suitable base (such as KOAc) in an appropriate solvent (such as 1,4-dioxane). A compound such as XIV can be generated and used in-situ or isolated to provide the corresponding boronate ester. A compound such as XIV can be coupled with an aryl chloride such as compound III under standard Suzuki cross-coupling conditions with a suitable catalyst (such as PdCl$_2$(PPh$_3$)$_2$) and suitable base (such as Na$_2$CO$_3$) in an appropriate solvent (such as 1,4-dioxane) to provide a compound such as XV. A compound such as XV can be converted to a compound such as XVI in the presence of excess i-PrNH$_2$ in an appropriate solvent (such as DMSO). A compound such as XVI can be cyclized with an aldehyde such as XVII in the presence of a suitable reductant (such as Na$_2$S$_2$O$_4$) in an appropriate solvent (such as EtOH) to provide a compound such as XVIII. A compound such as XVIII can be coupled with an amine such as XIX under standard Buchwald-Hartwig conditions in the presence of a suitable catalyst system (such as Pd(OAc)$_2$+rac-BINAP) and a suitable base (such as Cs$_2$CO$_3$) in an appropriate solvent system (such as 1,4-dioxane or THF) to provide a compound such as XX. Compounds at every step may be purified by standard techniques, such as column chromatography, crystallization, or reverse phase SFC or HPLC. Variables Q, R$^1$, R$^4$, R$^6$, and R$^7$ are as defined as in the embodiments, schemes, examples, and claims herein.

Scheme IV

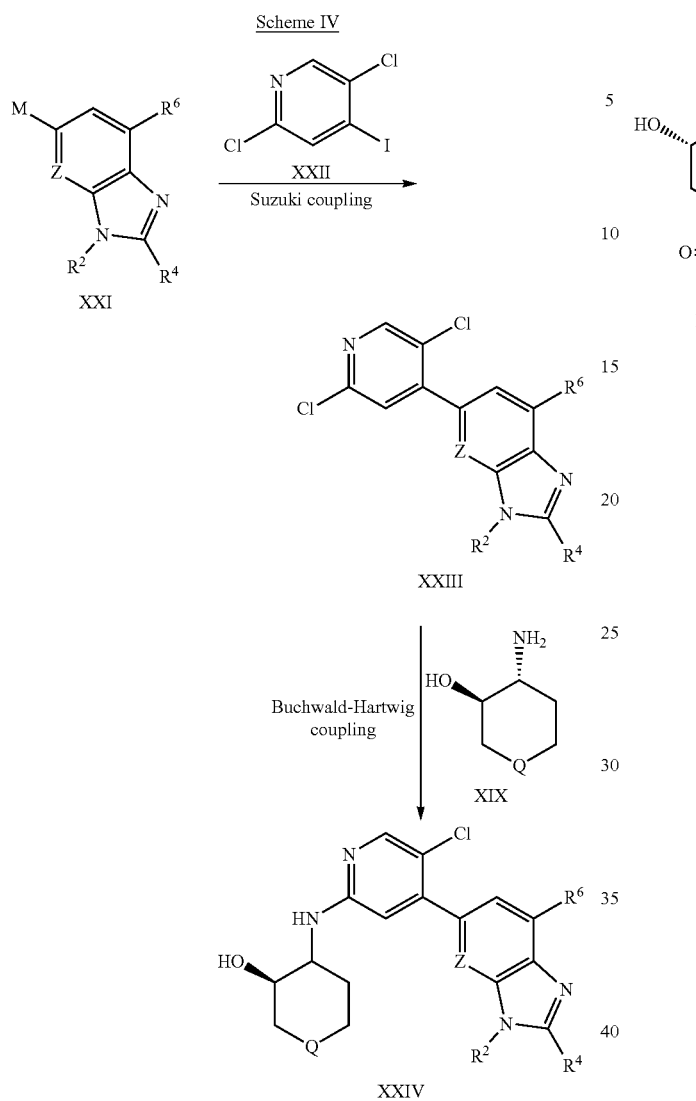

Scheme V

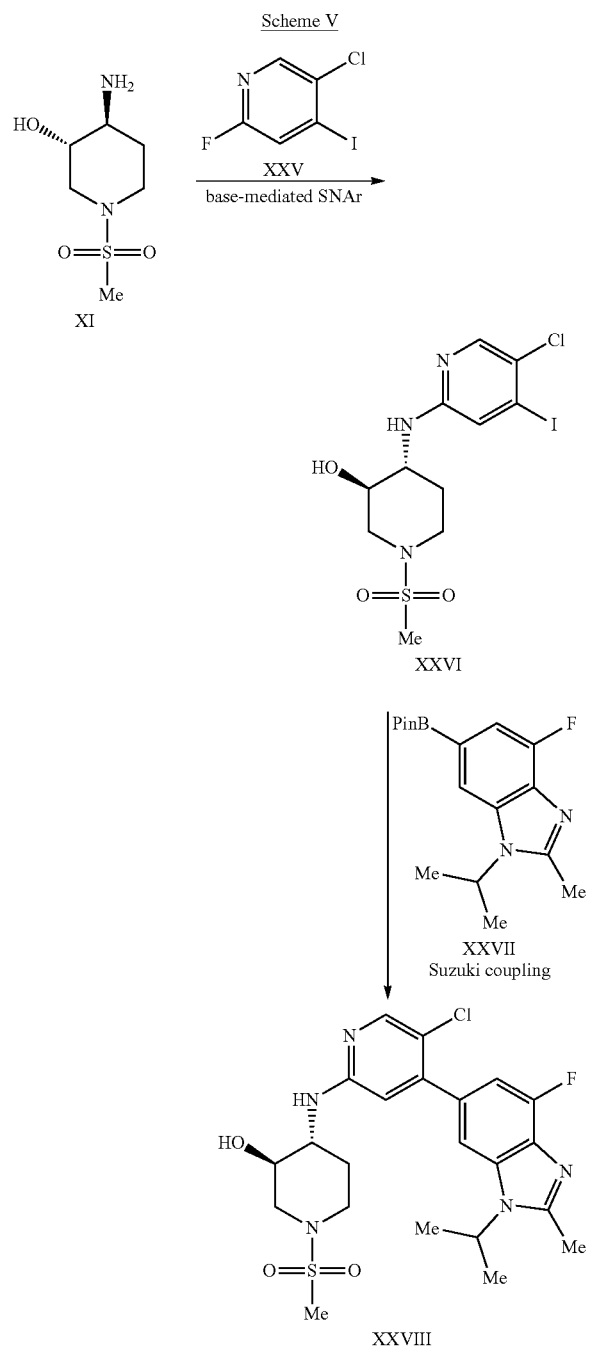

As shown in Scheme IV, a compound such as XXI (prepared as in Scheme I) can be coupled with an aryl chloride such as compound XXII under standard Suzuki cross-coupling conditions with a suitable catalyst (such as $PdCl_2(PPh_3)_2$) and a suitable base (such as $Na_2CO_3$) in an appropriate solvent (such as 1,4-dioxane) to provide a compound such as XXIII. A compound such as XXIII can be coupled with an amine such as XIX under standard Buchwald-Hartwig coupling conditions with a suitable palladium catalyst system (such as Bretphos-Pd-G3 or $Pd_2(dba)_3$+rac-BINAP) with a suitable base (such as t-BuONa, $Cs_2CO_3$, or phosphazene $P_2$-Et) in an appropriate solvent (such as 1,4-dioxane or PhMe) to provide a compound such as XXIV. In some cases a compound such as XXIV may contain protecting groups, which can be removed by an additional step in the synthetic sequence using conditions known in the art (*Protective Groups in Organic Synthesis*, A. Wiley-Interscience Publication, 1981 or Protecting groups, Georg Thieme Verlag, 1994). Compounds at every step may be purified by standard techniques, such as column chromatography, crystallization, or reverse phase SFC or HPLC. Variables Q, Z, $R^2$, $R^4$, and $R^6$, are as defined as in the embodiments, schemes, examples, and claims herein.

As shown in Scheme V, an amine such as XI can be coupled with an aryl fluoride such as XXV to provide a compound such as XXVI under standard $S_NAr$ conditions with a suitable base (such as DIPEA) in an appropriate solvent (such as DMSO). A compound such as XXVI can coupled with a compound such as XXVII (prepared as in Scheme I) under standard Suzuki cross-coupling conditions with a suitable catalyst (such as $PdCl_2(PPh_3)_2$) with a suitable base (such as $Na_2CO_3$) in an appropriate solvent (such as 1,4-dioxane) to provide a compound such as XXVIII. Compounds at every step may be purified by standard techniques, such as column chromatography, crystallization, or reverse phase SFC or HPLC.

Scheme VI

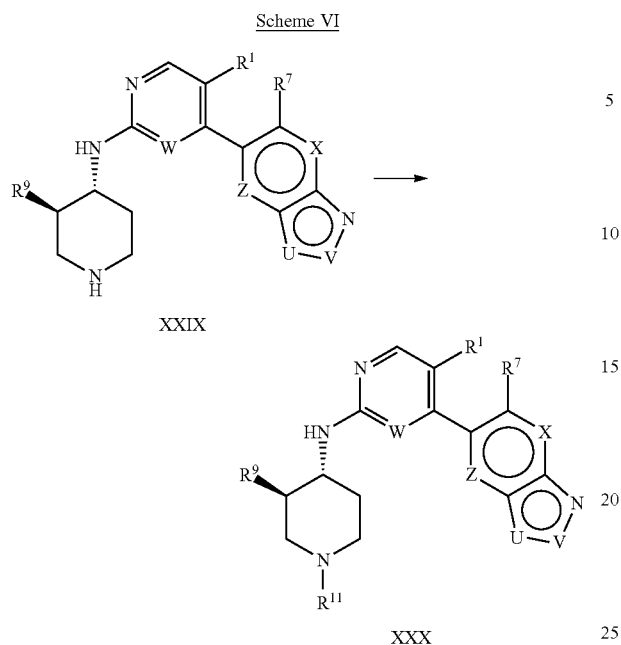

As shown in Scheme VI, a compound such as XXIX (Prepared as in Scheme I or Scheme IV) can be converted to a compound such as XXX under various conditions well known in the art including:
  i. Carbamate formation with a chloroformate in the presence of a suitable base (such as $NEt_3$) in an appropriate solvent (such as DCM) to provide a compound such as XXX wherein $R^{11}=CO_2R^{17}$.
  ii. Tertiary amine formation in the presence of a aldehyde under standard reductive amination conditions with a suitable reducing agent (such as $NaBH_3CN$) in a suitable solvent (such as MeOH) or alkylation with an alkyl halide with a suitable base (such as $NaHCO_3$) in an appropriate solvent (such as EtOAc) to provide a compound such as XXX where in $R^{11}=C_1$-$C_2$ alkyl.
  iii. Sulfonamide formation with a sulfonyl chloride in the presence of a suitable base (such as $NaHCO_3$) in an appropriate solvent (such as EtOAc) to provide a compound such as XXX where in $R^{11}=SO_2R^{14}$
  iv. Amide formation via acylation with an anhydride in the presence of a suitable base (such as TEA) in an appropriate solvent (such as DCM) or a carboxylic acid in the presence of a suitable coupling agent (such as HATU or EDCI) and a suitable base (such as DIPEA) in an appropriate solvent (such as DCM or DMF) to provide a compound such as XXX where in $R^{11}=COR^{17}$ In some cases, a compound such as XXX may contain protecting groups, which can be removed by an additional step in the synthetic sequence using conditions known in the art (*Protective Groups in Organic Synthesis*, A. Wiley-Interscience Publication, 1981 or Protecting groups, 10 Georg Thieme Verlag, 1994). Compounds at every step may be purified by standard techniques, such as column chromatography, crystallization, or reverse phase SFC or HPLC. If necessary, separation of the enantiomers of XXX may be carried out under standard methods known in the art such as chiral SFC or HPLC to afford single enantiomers.

Variables U, V, W, X, Z, $R^1$, $R^7$, $R^{11}$, $R^{14}$, and $R^{17}$ are as defined as in the embodiments, schemes, examples, and claims herein.

Scheme VII

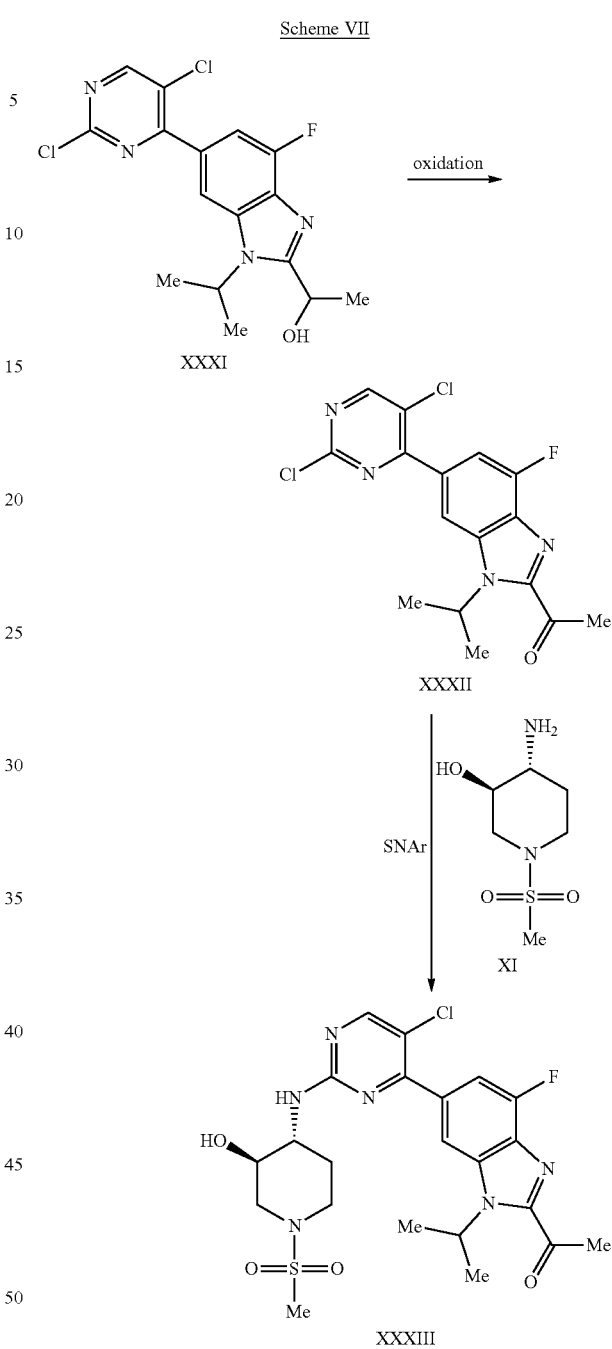

As shown in Scheme VII, a compound such as XXXI (prepared as in Scheme I) can be oxidized with a suitable oxidant (such as $MnO_2$, $SO_3$.pyr, or TEMPO/NaClO) in an appropriate solvent (such as $CHCl_3$ or DCM) to provide a compound such as XXXII. A compound such as XXXII can be coupled with an amine such as XI under standard $S_NAr$ conditions in the presence of a suitable base (such as DIPEA) in an appropriate solvent (such as DMSO) to provide a compound such as XXXIII. Compounds at every step may be purified by standard techniques, such as column chromatography, crystallization, or reverse phase SFC or HPLC.

Scheme VIII

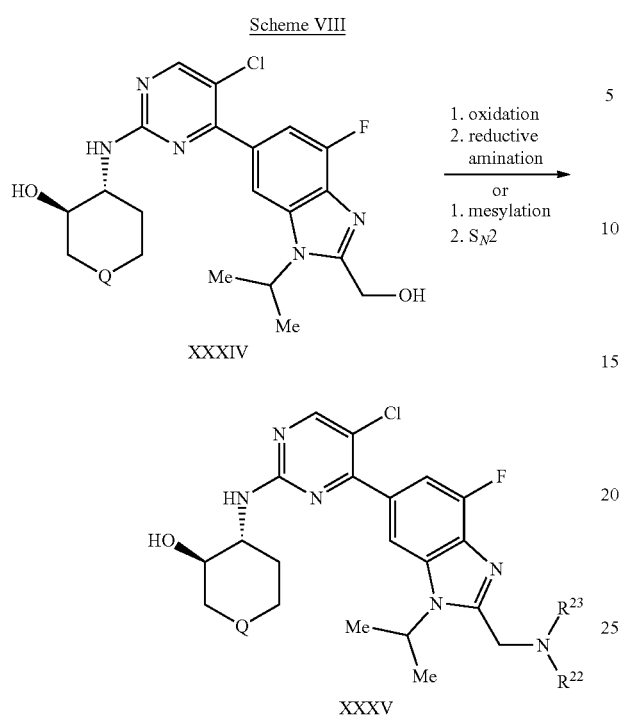

A shown in Scheme VIII, a compound such as XXXIV (prepared as in Scheme I) can be converted to a compound such as XXXV by oxidation with a suitable oxidant (such as $MnO_2$) in an appropriate solvent (such as MeOH) followed by reductive amination in the presence of an amine with a suitable reductant (such as $NaBH_3CN$) in an appropriate solvent (such as MeCN). Alternatively, a compound such as XXXIV can be activated by treatment with methanesulfonyl chloride in the presence of a suitable base (such as TEA) in an appropriate solvent (such as DCM). Subsequent displacement of the mesylate with an amine in the presence of NaI and a suitable base (such as DIPEA) in an appropriate solvent (such as MeCN) can provide a compound such as XXXV. Compounds at every step may be purified by standard techniques, such as column chromatography, crystallization, or reverse phase SFC or HPLC. Variables Q, $R^{22}$, and $R^{23}$ are as defined as in the embodiments, schemes, examples, and claims herein.

Scheme IX

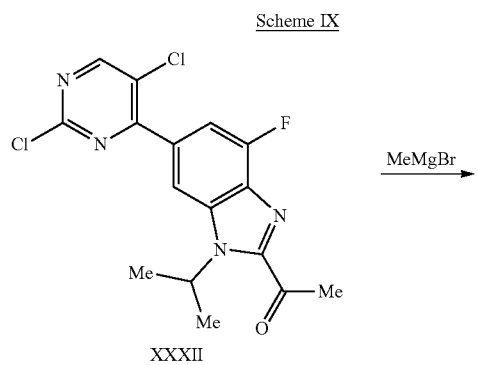

As shown in Scheme IX, a ketone such as XXXII (prepared as in Scheme VII) can be treated with a Grignard reagent (such as MeMgBr) in an appropriate solvent (such as THF) to provide a compound such as XXXVI. A compound such as XXXVI can be coupled with an amine such as XI under standard SNAr conditions in the presence of a suitable base (such as DIPEA) in an appropriate solvent (such as DMSO) to provide a compound such as XXXVII. Compounds at every step may be purified by standard techniques, such as column chromatography, crystallization or reverse phase SFC or HPLC.

Preparation of Intermediates

Preparation of (1S)-1-(6-bromo-1-tert-butyl-4-fluoro-1H-benzimidazol-2-yl)ethan-1-ol (Int-01)
According to Scheme 1

Scheme 1

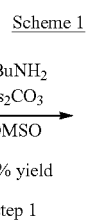

113

-continued

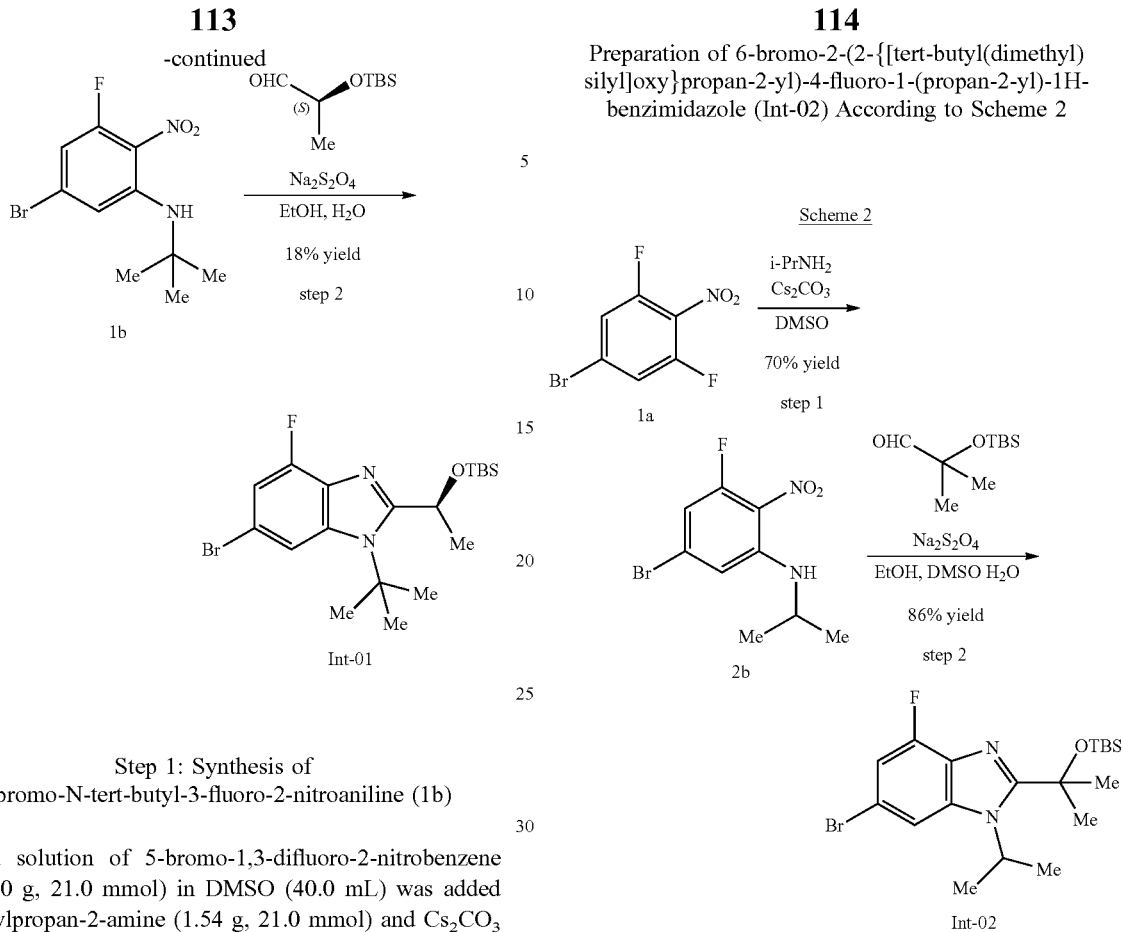

Step 1: Synthesis of
5-bromo-N-tert-butyl-3-fluoro-2-nitroaniline (1b)

To a solution of 5-bromo-1,3-difluoro-2-nitrobenzene (1a) (5.0 g, 21.0 mmol) in DMSO (40.0 mL) was added 2-methylpropan-2-amine (1.54 g, 21.0 mmol) and Cs₂CO₃ (13.7 g, 42 mmol). The reaction was stirred at 40° C. for 3 h. TLC analysis (petroleum ether) showed consumption of the starting material. The reaction was diluted with H₂O (20 mL) and extracted with EtOAc (3×20 mL). The combined organic phases were washed with brine, dried over Na₂SO₄, filtered, and concentrated. The residue was purified by flash chromatography (ISCO, SiO₂, 0-10% EtOAc/petroleum ether) to provide 5-bromo-N-tert-butyl-3-fluoro-2-nitroaniline (1b) (5.5 g, 90% yield) as a red oil. ¹H NMR (400 MHz, DMSO-d₆) δ 7.13-7.01 (m, 2H), 6.94 (dd, J=1.9, 11.1 Hz, 1H), 1.40 (s, 9H).

Step 2: Synthesis of (1S)-1-(6-bromo-1-tert-butyl-4-fluoro-1H-benzimidazol-2-yl)ethan-1-ol (Int-01)

To a solution of 5-bromo-N-tert-butyl-3-fluoro-2-nitroaniline (1b) (1.5 g, 5.2 mmol) and (2S)-2-{[tert-butyl(dimethyl)silyl]oxy}propanal (1.94 g, 10.3 mmol) in EtOH (30.0 mL) and DMSO (7.5 mL) was added Na₂S₂O₄ (4.5 g, 25.8 mmol). The reaction was stirred at 80° C. for 16 h. TLC analysis (EtOAc) showed consumption of the starting material. EtOAc (10 mL) and H₂O (5 mL) were added and the layers were separated. The aqueous layer was extracted with EtOAc (3×10 mL). The combined organic phases were washed with brine, dried over Na₂SO₄, filtered, and concentrated. The residue was purified by flash chromatography (ISCO, 12 g SiO₂, 0-20% EtOAc/petroleum ether) to provide (1S)-1-(6-bromo-1-tert-butyl-4-fluoro-1H-benzimidazol-2-yl)ethan-1-ol (Int-01) (400 mg, 18% yield) as a yellow oil. m/z (ESI) for ($C_{19}H_{30}BrFN_2OSi$), 431.1 (M+H)⁺.

114

Preparation of 6-bromo-2-(2-{[tert-butyl(dimethyl)silyl]oxy}propan-2-yl)-4-fluoro-1-(propan-2-yl)-1H-benzimidazole (Int-02) According to Scheme 2

Scheme 2

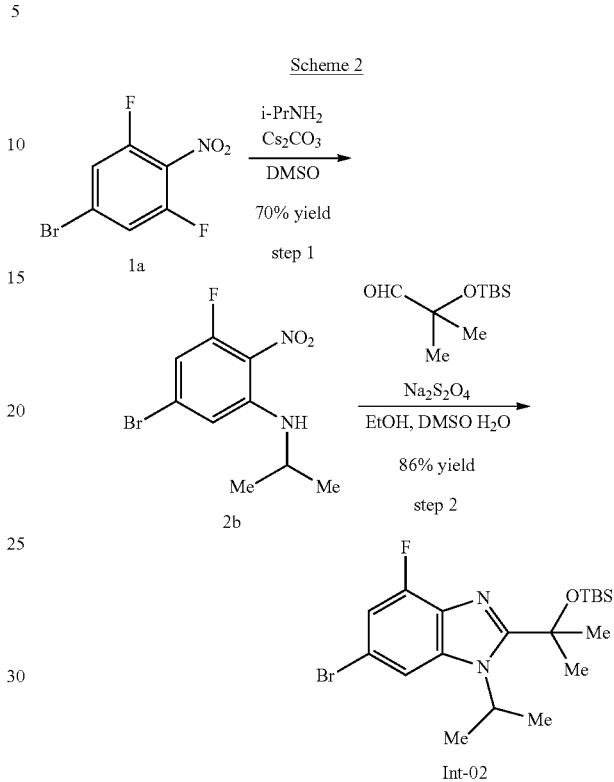

Step 1: Synthesis of 5-bromo-3-fluoro-2-nitro-N-(propan-2-yl)aniline (2b)

A solution of 5-bromo-1,3-difluoro-2-nitrobenzene (1a) (25.0 g, 105 mmol) and isopropylamine (8.95 mL, 105 mmol) in DMSO (525 mL) was stirred at ambient temperature for 4 d, after which the mixture was concentrated. The crude residue was purified by flash chromatography (SiO₂, 0-30% EtOAc/heptanes) to provide 5-bromo-3-fluoro-2-nitro-N-(propan-2-yl)aniline (2b) (20.3 g, 70% yield) as a red/orange solid. ¹H NMR (400 MHz, DMSO-d₆) δ 7.07-6.98 (m, 2H), 6.89 (dd, J=2.0, 11.1 Hz, 1H), 3.88 (dd, J=6.4, 13.9 Hz, 1H), 1.26-1.13 (m, 6H). m/z (ESI+) for ($C_9H_{10}BrFN_2O_2$), 278.1 (M+H)⁺.

Step 2: Synthesis of 6-bromo-2-(2-{[tert-butyl(dimethyl)silyl]oxy}propan-2-yl)-4-fluoro-1-(propan-2-yl)-1H-benzimidazole (Int-02)

To a solution of 5-bromo-3-fluoro-2-nitro-N-(propan-2-yl)aniline (2b) (1.0 g, 3.2 mmol) and 2-{[tert-butyl(dimethyl)silyl]oxy}-2-methylpropanal (655 mg, 3.2 mmol) in EtOH (8.0 mL) and DMSO (2.0 mL) was added Na₂S₂O₄ (2.82 g, 16.2 mmol). The suspension was stirred at 90° C. for 16 h. LCMS analysis showed consumption of the starting material with formation of the desired product mass. The reaction mixture was diluted with H₂O (200 mL) and extracted with EtOAc (2×200 mL). The combined organic phases were washed with brine (150 mL), dried over Na₂SO₄, filtered, and concentrated. The residue was purified by flash chromatography (Biotage, 40 g SiO₂, 1/10 EtOAc/ petroleum ether) to provide 6-bromo-2-(2-{[tert-butyl(dimethyl)silyl]oxy}propan-2-yl)-4-fluoro-1-(propan-2-yl)-1H-benzimidazole (Int-02) (1.2 g, 86% yield) as a white solid. $^1$H NMR (400 MHz, CDCl$_3$) δ 7.51 (d, J=1.5 Hz, 1H), 7.09 (dd, J=1.5, 9.7 Hz, 1H), 5.62 (td, J=7.0, 14.0 Hz, 1H), 1.85 (s, 6H), 1.71-1.60 (m, 6H), 0.92 (s, 9H), 0.21-0.17 (m, 6H).

Preparation of 6-bromo-4-fluoro-2-methyl-1-(oxetan-3-yl)-1H-benzimidazole (Int-03) According to Scheme 3

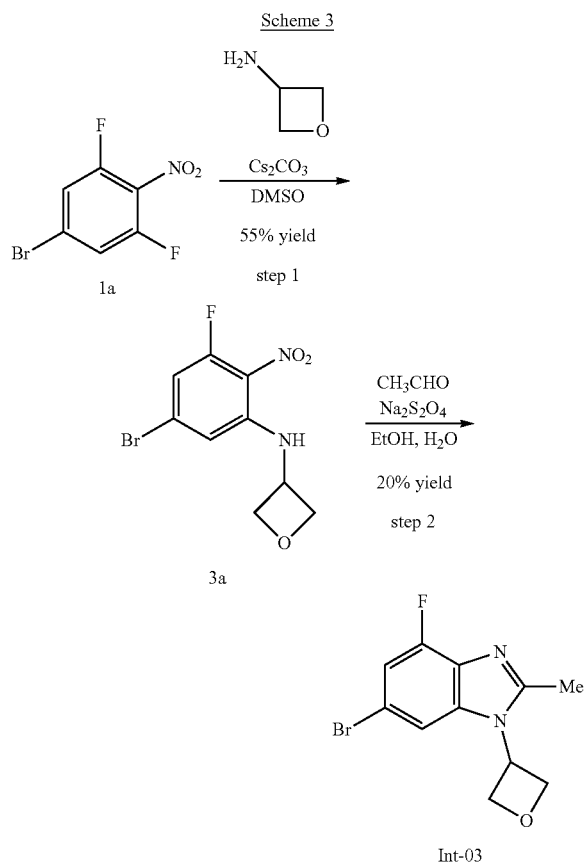

Step 1: Synthesis of N-(5-bromo-3-fluoro-2-nitrophenyl)oxetan-3-amine (3a)

To a solution of 5-bromo-1,3-difluoro-2-nitrobenzene (1.5 g, 6.3 mmol) (1a) in DMSO (15.0 mL) was added oxetan-3-amine (507 mg, 6.93 mmol) and Cs$_2$CO$_3$ (2.46 g, 7.56 mmol). The reaction was stirred at 25° C. for 2 h. TLC analysis (1/4 EtOAc/petroleum ether) showed consumption of the starting material. The reaction was diluted with brine (10 mL) and extracted with EtOAc (2×10 mL). The combined organic phases were washed with brine, dried over Na$_2$SO$_4$, filtered, and concentrated. The residue was purified by flash chromatography (ISCO, SiO$_2$, 0-30% EtOAc/petroleum ether) to provide N-(5-bromo-3-fluoro-2-nitrophenyl)oxetan-3-amine (3a) (1.0 g, 55% yield) as a yellow solid. $^1$H NMR (400 MHz, DMSO-d$_6$) δ 7.59 (br d, J=5.3 Hz, 1H), 7.04 (dd, J=1.8, 10.8 Hz, 1H), 6.69 (s, 1H), 4.87-4.81 (m, 2H), 4.80-4.71 (m, 1H), 4.60-4.47 (m, 2H).

Step 2: Synthesis of 6-bromo-4-fluoro-2-methyl-1-(oxetan-3-yl)-1H-benzimidazole (Int-03)

To a solution of N-(5-bromo-3-fluoro-2-nitrophenyl)oxetan-3-amine (3a) (500 mg, 1.72 mmol) in EtOH (16.0 mL) and H$_2$O (4.0 mL) was added acetaldehyde (2.0 mL, 8.6 mmol) and Na$_2$S$_2$O$_4$ (1.5 g, 8.6 mmol). The reaction was sealed and stirred at 80° C. with microwave irradiation for 10 h. LCMS analysis showed consumption of the starting material. The solution was cooled and partitioned between EtOAc (40 mL) and H$_2$O (20 mL). The combined layers were dried over Na$_2$SO$_4$, filtered, and concentrated. The crude residue was purified by flash chromatography (SiO$_2$, 0-100% EtOAc/petroleum ether) to provide 6-bromo-4-fluoro-2-methyl-1-(oxetan-3-yl)-1H-benzimidazole (Int-03) (100 mg, 20% yield) as a yellow solid. $^1$H NMR (400 MHz, DMSO-d$_6$) δ 7.95 (s, 1H), 7.34 (br d, J=10.0 Hz, 1H), 5.66 (br t, J=5.5 Hz, 1H), 5.11 (br t, J=7.7 Hz, 2H), 5.03-4.88 (m, 2H), 2.55 (s, 3H). m/z (ESI+) for (C$_{11}$H$_{10}$BrFN$_2$O), 284.9 (M+H).

The intermediates in the below table were synthesized according to the methods used for the synthesis of (1S)-1-(6-bromo-1-tert-butyl-4-fluoro-1H-benzimidazol-2-yl)ethan-1-ol (Int-01), 6-bromo-2-(2-{[tert-butyl(dimethyl)silyl]oxy}propan-2-yl)-4-fluoro-1-(propan-2-yl)-1H-benzimidazole (Int-02) and 6-bromo-4-fluoro-2-methyl-1-(oxetan-3-yl)-1H-benzimidazole (Int-03). The following intermediates were synthesized with non-critical changes or substitutions to the exemplified procedures that someone who is skilled in the art would be able to realize.

| Compound number | Structure/IUPAC Name | Analytical data |
|---|---|---|
| Int-04 | 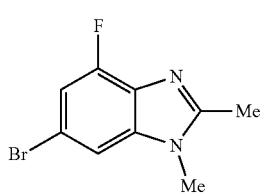<br>6-bromo-4-fluoro-1,2-dimethyl-1H-benzimidazole | m/z (ESI+) for (C$_9$H$_8$BrFN$_2$), 242.6 (M + H)$^+$ |

| Compound number | Structure/IUPAC Name | Analytical data |
|---|---|---|
| Int-05 | 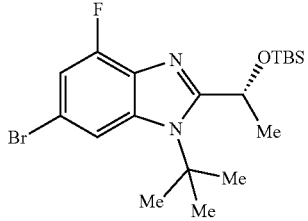<br>6-bromo-1-tert-butyl-2-[(1R)-1-{[tert-butyl(dimethyl)silyl]oxy}ethyl]-4-fluoro-1H-benzimidazole | m/z (ESI+) for ($C_{19}H_{30}BrFN_2OSi$), 430.9 (M + H)$^+$ |
| Int-06 | 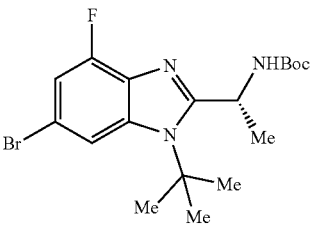<br>tert-butyl [(1R)-1-(6-bromo-1-tert-butyl-4-fluoro-1H-benzimidazol-2-yl)ethyl]carbamate | m/z (ESI+) for ($C_{18}H_{25}BrFN_3O_2$), 415.9 (M + H)$^+$ |
| Int-07 | 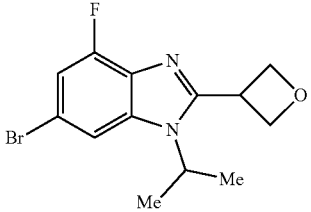<br>6-bromo-4-fluoro-2-(oxetan-3-yl)-1-(propan-2-yl)-1H-benzimidazole | $^1$H NMR (400 MHz, DMSO-$d_6$) δ 7.79 (d, J = 1.5 Hz, 1H), 7.30 (dd, J = 1.5, 10.1 Hz, 1H), 5.01-4.91 (m, 4H), 4.80-4.66 (m, 1H), 4.55-4.42 (m, 1H), 1.49 (d, J = 7.0 Hz, 6H); m/z (ESI+) for ($C_{13}H_{14}BrFN_2O$), 324.2 (M + H)$^+$ |
| Int-08 | 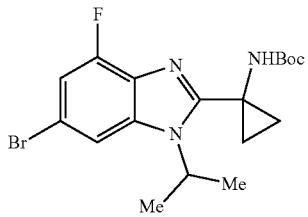<br>tert-butyl {1-[6-bromo-4-fluoro-1-(propan-2-yl)-1H-benzimidazol-2-yl]cyclopropyl}carbamate | $^1$H NMR (400 MHz, CDCl$_3$) δ 9.16 (br s, 1H), 7.49 (d, J = 1.0 Hz, 1H), 7.09 (dd, J = 1.5, 9.5 Hz, 1H), 5.84 (br s, 1H), 5.39 (br s, 1H), 1.63 (s, 9H), 1.57 (s, 3H), 1.46 (s, 6H), 1.39 (s, 9H); m/z (ESI+) for ($C_{18}H_{23}BrFN_3O_2$), 357.9 (M − tBu + H)$^+$ |
| Int-09 | 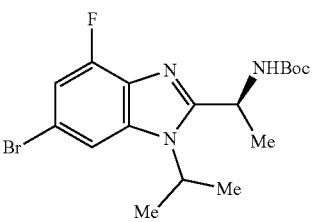<br>tert-butyl {(1S)-1-[6-bromo-4-fluoro-1-(propan-2-yl)-1H-benzimidazol-2-yl]ethyl}carbamate | $^1$H NMR (400 MHz, CDCl$_3$) δ 9.58 (s, 1H), 7.49 (d, J = 1.5 Hz, 1H), 7.12 (dd, J = 9.7, 1.5 Hz, 1H), 5.24-5.03 (m, 1H), 4.86 (p, J = 6.9 Hz, 1H), 1.66-1.57 (m, 6H), 1.47 (s, 9H), 1.35 (d, J = 7.4 Hz, 3H) |

| Compound number | Structure/IUPAC Name | Analytical data |
|---|---|---|
| Int-10 | 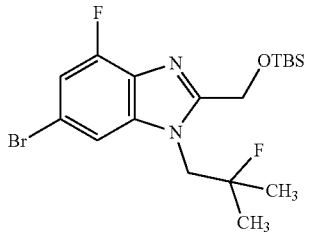<br>6-bromo-2-({[tert-butyl(dimethyl)silyl]oxy}methyl)-4-fluoro-1-(2-fluoro-2-methylpropyl)-1H-benzimidazole | m/z (ESI+) for ($C_{18}H_{27}BrF_2N_2OSi$), 433.1 (M + H)$^+$ |
| Int-11 | 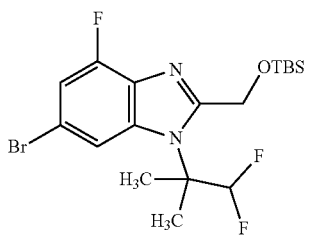<br>6-bromo-2-({[tert-butyl(dimethyl)silyl]oxy}methyl)-1-(1,1-difluoro-2-methylpropan-2-yl)-4-fluoro-1H-benzimidazole | m/z (ESI+) for ($C_{18}H_{26}BrF_3N_2OSi$), 451.2 (M + H)$^+$ |
| Int-12 | 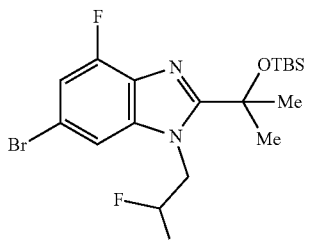<br>6-bromo-2-(2-{[tert-butyl(dimethyl)silyl]oxy}propan-2-yl)-1-(2,2-difluoroethyl)-4-fluoro-1H-benzimidazole | m/z (ESI+) for ($C_{18}H_{26}BrF_3N_2OSi$), 450.8 (M + H)$^+$ |
| Int-13 | 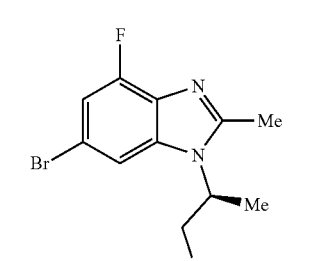<br>tert-butyl [(2S)-2-(6-bromo-4-fluoro-2-methyl-1H-benzimidazol-1-yl)propyl]carbamate | $^1$H NMR (400 MHz, CDCl$_3$) δ 7.32 (d, J = 1.5 Hz, 1H), 7.04 (dd, J = 9.6, 1.5 Hz, 1H), 5.13 (s, 1H), 4.73 (s, 1H), 3.70 (dt, J = 11.5, 6.2 Hz, 1H), 3.47-3.38 (m, 1H), 2.56 (s, 3H), 1.61 (d, J = 7.0 Hz, 3H), 1.41 (s, 9H); m/z (ESI+) for ($C_{18}H_{21}BrFN_3O_2$), 387.9 (M + H)$^+$ |

-continued

| Compound number | Structure/IUPAC Name | Analytical data |
|---|---|---|
| Int-14 | 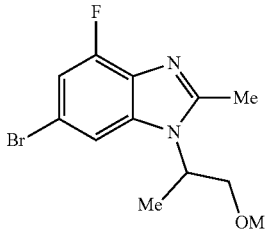<br>6-bromo-4-fluoro-1-(1-methoxypropan-2-yl)-2-methyl-1H-benzimidazole | $^1$H NMR (400 MHz, DMSO-d$_6$) δ 7.75 (d, J = 1.6 Hz, 1H), 7.23 (dd, J = 1.5, 10.1 Hz, 1H), 4.78 (ddd, J = 4.6, 7.1, 8.9 Hz, 1H), 3.86 (dd, J = 9.2, 10.4 Hz, 1H), 3.62 (dd, J = 4.5, 10.5 Hz, 1H), 3.18 (s, 3H), 2.55 (s, 3H), 1.52 (d, J = 7.1 Hz, 3H); m/z (APCI+) for (C$_{12}$H$_{14}$BrFN$_2$O), 301.0, 303.0 (M + H)$^+$ |
| Int-15 | 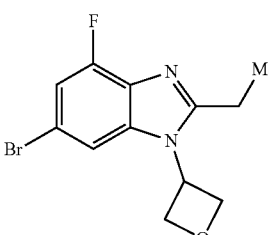<br>6-bromo-2-ethyl-4-fluoro-1-(oxetan-3-yl)-1H-benzimidazole | $^1$H NMR (400 MHz, DMSO-d$_6$) δ 7.97 (d, J = 1.6 Hz, 1H), 7.34 (dd, J = 10.2, 1.6 Hz, 1H), 5.77-5.53 (m, 1H), 5.12 (t, J = 7.7 Hz, 2H), 4.98 (dd, J = 7.8, 5.3 Hz, 2H), 2.88 (q, J = 7.5 Hz, 2H), 1.29 (t, J = 7.4 Hz, 3H); m/z (APCI+) for (C$_{12}$H$_{12}$BrFN$_2$O), 298.9 (M + H)$^+$ |
| Int-16 | 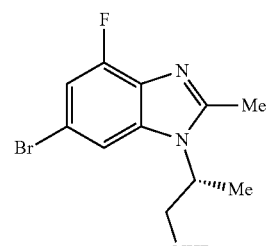<br>tert-butyl [(2R)-2-(6-bromo-4-fluoro-2-methyl-1H-benzimidazol-1-yl)propyl] carbamate | $^1$H NMR (400 MHz, DMSO-d$_6$) δ 7.77-7.53 (m, 1H), 7.21 (br d, J = 10.0 Hz, 1H), 7.09-6.92 (m, 1H), 6.65 (dd, J = 2.0, 7.0 Hz, 1H), 4.71-4.60 (m, 1H), 4.45-4.33 (m, 1H), 3.83-3.60 (m, 2H), 1.61-1.46 (m, 5H), 1.32-1.20 (m, 8H); m/z (ESI+) for (C$_{16}$H$_{21}$BrFN$_3$O$_2$), 387.9 (M + H)$^+$ |
| Int-17 | 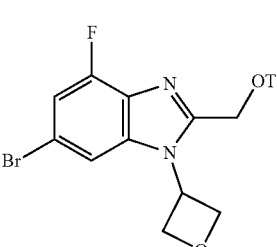<br>(6-bromo-1-cyclobutyl-4-fluoro-1H-benzimidazol-2-yl)methanol | $^1$H NMR (400 MHz, CDCl$_3$) δ 7.63 (d, J = 1.5 Hz, 1H), 7.13 (dd, J = 1.5, 9.6 Hz, 1H), 5.31-5.12 (m, 1H), 4.94 (s, 2H), 2.98-2.81 (m, 2H), 2.65-2.49 (m, 2H), 2.06-1.87 (m, 2H), 0.92-0.90 (m, 9H), 0.10-0.07 (m, 6H); m/z (ESI+) for (C$_{18}$H$_{26}$BrFN$_2$OSi), 414.8 (M + H)$^+$ |

| Compound number | Structure/IUPAC Name | Analytical data |
|---|---|---|
| Int-18 | 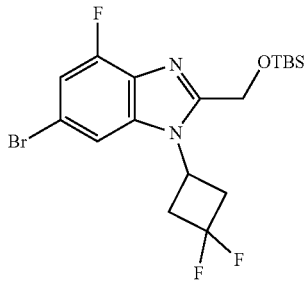<br>6-bromo-2-({[tert-butyl(dimethyl)silyl]oxy}methyl)-1-(3,3-difluorocyclobutyl)-4-fluoro-1H-benzimidazole | $^1$H NMR (400 MHz, CDCl$_3$) δ 7.51 (d, J = 1.3 Hz, 1H), 7.19 (dd, J = 1.5, 9.5 Hz, 1H), 5.27 (dquin, J = 3.7, 8.7 Hz, 1H), 4.97 (s, 2H), 3.60-3.41 (m, 2H), 3.32-3.17 (m, 2H), 0.92-0.90 (m, 9H), 0.12-0.10 (m, 6H); m/z (ESI+) for (C$_{18}$H$_{24}$BrF$_3$N$_2$OSi), (M + H)$^+$ |

Preparation of [6-bromo-4-fluoro-1-(propan-2-yl)-1H-benzimidazol-2-yl]methanol (Int-19) According to Scheme 4

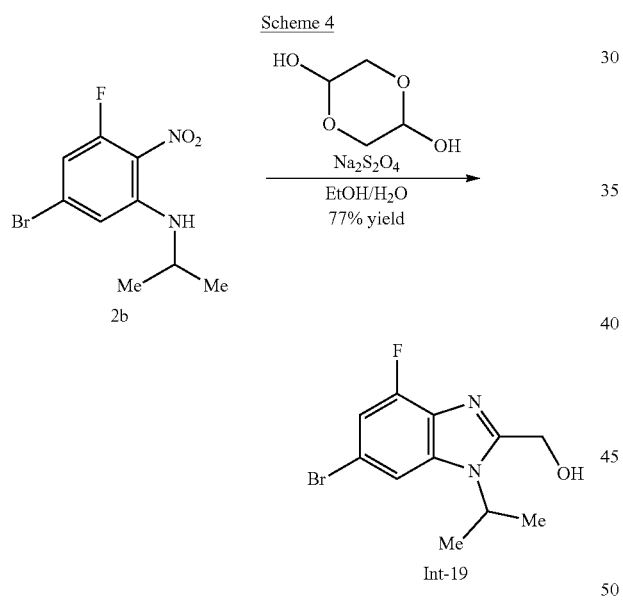

A mixture of 5-bromo-3-fluoro-2-nitro-N-(propan-2-yl)aniline (2b) (994 mg g, 3.59 mmol), Na$_2$S$_2$O$_4$ (3.12 g, 17.9 mmol), and glycolaldehyde dimer (517 mg, 4.30 mmol) in EtOH/H$_2$O (4:1, 50 mL) was stirred at 80° C. for 21 h. The mixture was concentrated and partitioned between H$_2$O (100 mL) and EtOAc (100 mL). The layers were separated and the aqueous phase extracted with EtOAc (3×100 mL). The combined organic phases were washed with water (50 mL) and brine (50 mL), dried over Na$_2$SO$_4$, filtered, and concentrated. The crude product was purified by flash chromatography (SiO$_2$, 40-100% EtOAc/heptanes) to provide [6-bromo-4-fluoro-1-(propan-2-yl)-1H-benzimidazol-2-yl]methanol (Int-19) (790 mg, 77% yield) as a white waxy solid. $^1$H NMR (400 MHz, DMSO-d$_6$) δ 7.81 (d, J=1.5 Hz, 1H), 7.28 (dd, J=10.1, 1.6 Hz, 1H), 5.71 (t, J=5.8 Hz, 1H), 4.95 (hept, J=6.8 Hz, 1H), 4.72 (d, J=5.7 Hz, 2H), 1.56 (d, J=6.9 Hz, 6H); m/z (APCl+) for (C$_{11}$H$_{12}$BrFN$_2$O), 286.8 (M+H)$^+$.

Preparation of 6-bromo-4-fluoro-2-{[(oxan-2-yl)oxy]methyl}-1-(propan-2-yl)-1H-benzimidazole (Int-20) According to Scheme 5

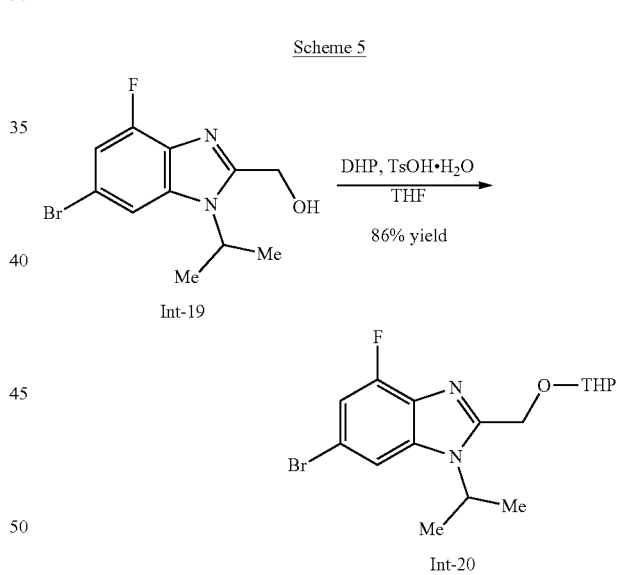

A solution of [6-bromo-4-fluoro-1-(propan-2-yl)-1H-benzimidazol-2-yl]methanol (Int-19) (590 mg, 2.05 mmol), 3,4-dihydro-2H-pyran (1.21 g, 1.3 mL, 14.4 mmol) and p-TSA acid monohydrate (35.4 mg, 0.205 mmol) in THF (21 mL) was stirred at reflux temperature for 4 h. The mixture was concentrated and purified by flash chromatography (SiO$_2$, 20-50% EtOAc/heptanes) to provide 6-bromo-4-fluoro-2-{[(oxan-2-yl)oxy]methyl}-1-(propan-2-yl)-1H-benzimidazole (Int-20) (710 mg, 93% yield) as a viscous yellow oil. $^1$H NMR (400 MHz, DMSO-d$_6$) δ 7.85 (d, J=1.5 Hz, 1H), 7.31 (dd, J=10.1, 1.5 Hz, 1H), 4.95-4.85 (m, 2H), 4.77-4.72 (m, 2H), 3.81-3.73 (m, 1H), 3.56-3.49 (m, 1H), 1.74-1.61 (m, 2H), 1.58 (d, J=6.9 Hz, 6H), 1.55-1.45 (m, 4H); m/z (APCl+) for (C$_{16}$H$_{20}$BrFN$_2$O$_2$), 370.9 (M+H)$^+$.

Preparation of 6-bromo-4-fluoro-2-(methoxymethyl)-1-(propan-2-yl)-1H-benzimidazole (Int-21) According to Scheme 6

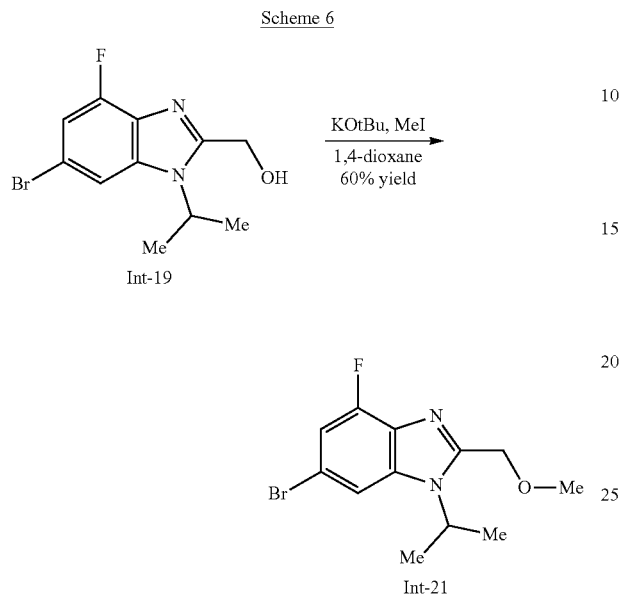

To a solution of [6-bromo-4-fluoro-1-(propan-2-yl)-1H-benzimidazol-2-yl]methanol (Int-19) (134 mg, 0.467 mmol) in 1,4-dioxane (4.67 mL) was added KOtPn (25% in toluene, 0.265 mL, 0.560 mmol). To the resultant dark reaction mixture at 0° C. was added MeI (66.2 mg, 0.029 mL, 0.467 mmol). After 15 min LCMS analysis showed consumption of the starting material with formation of the desired product mass. H$_2$O (5 mL) was added and the mixture was extracted with DCM (3×10 mL). The combined organic phases were dried over Na$_2$SO$_4$, filtered, and concentrated. The residue was purified by flash chromatography (12 g SiO$_2$, 0-100% EtOAc/heptanes) to provide (Int-21) (85 mg, 60% yield). $^1$H NMR (400 MHz, CDCl$_3$) δ 7.50 (d, J=1.47 Hz, 1H) 7.12 (dd, J=9.54, 1.47 Hz, 1H) 4.91 (dt, J=13.94, 6.97 Hz, 1H) 4.75 (s, 2H) 3.38 (s, 3H) 1.63 (d, J=6.97 Hz, 6H).

Preparation of 6-bromo-4-fluoro-1-(propan-2-yl)-1H-benzimidazole (Int-22) According to Scheme 7

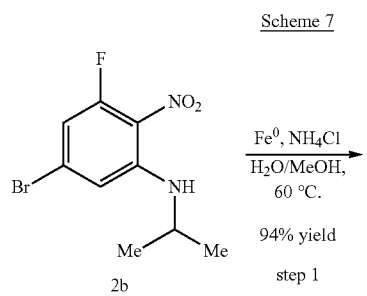

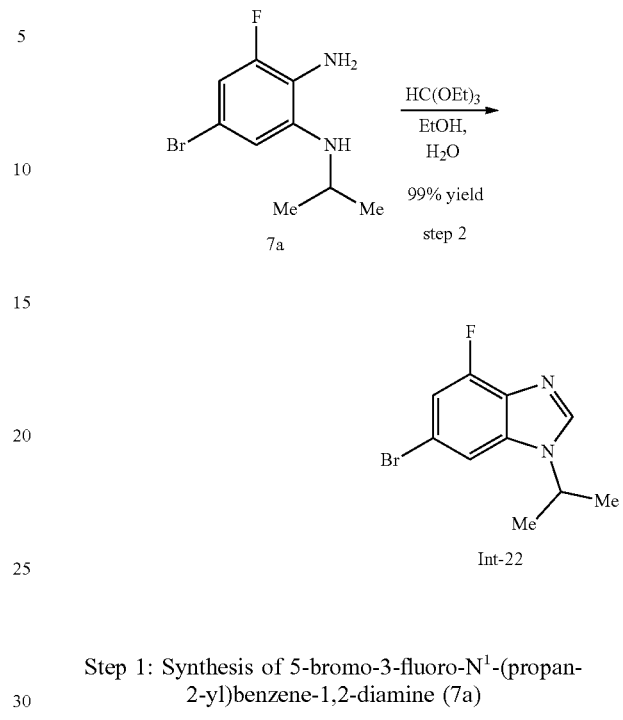

Step 1: Synthesis of 5-bromo-3-fluoro-N$^1$-(propan-2-yl)benzene-1,2-diamine (7a)

To a solution of 5-bromo-3-fluoro-2-nitro-N-(propan-2-yl)aniline (2b) (25.0 g, 90.2 mmol) in MeOH (300 mL) was added saturated aqueous NH$_4$Cl (150 mL) and Fe (25.2 g, 451 mmol). The reaction suspension was heated to 60° C. and stirred at this temperature for 3 h. LCMS analysis showed consumption of the starting material. The reaction suspension was filtered and the filter cake was washed with EtOAc. The filtrate was concentrated. The residue was taken up in EtOAc (200 mL) and filtered. The filtrate was washed with H$_2$O (200 mL). The combined aqueous washes were extracted with EtOAc (2×200 mL). The combined organic phases were dried over Na$_2$SO$_4$, filtered, and concentrated to provide 5-bromo-3-fluoro-N$^1$-(propan-2-yl)benzene-1,2-diamine (7a) (21.0 g, 94% yield). m/z (ESI+) for (C$_9$H$_{12}$BrFN$_2$), 246.7 (M+H)$^+$.

Step 2: Synthesis of 6-bromo-4-fluoro-1-(propan-2-yl)-1H-benzimidazole (Int-22)

A solution of 5-bromo-3-fluoro-N$^1$-(propan-2-yl)benzene-1,2-diamine (7a) (3.86 g, 15.6 mmol) in HC(OEt)$_3$ (100 mL) was stirred at 150° C. for 15 h. LCMS analysis showed consumption of the starting material with formation of the desired product mass. The solution was cooled to room temperature and concentrated to provide 6-bromo-4-fluoro-1-(propan-2-yl)-1H-benzimidazole (Int-22) (4.02 g, >99% yield) as a black oil, which was taken on without further purification. H NMR (400 MHz, DMSO-d$_6$) δ 8.04 (d, J=3.3 Hz, 1H), 6.66 (dd, J=2.0, 10.0 Hz, 1H), 6.54 (s, 1H), 3.69-3.56 (m, 1H), 1.15 (d, J=6.2 Hz, 6H); m/z (ESI+) for (C$_{10}$H$_{10}$BrFN$_2$), 258.7 (M+H)$^+$.

Preparation of 6-bromo-1-tert-butyl-2-methyl-1H-benzimidazole (Int-23) According to Scheme 8

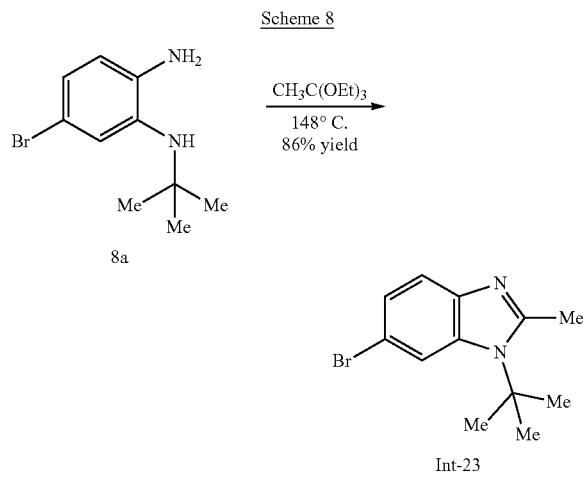

Synthesis of 6-bromo-1-tert-butyl-2-methyl-1H-benzimidazole (Int-23)

A mixture of 4-bromo-$N^2$-tert-butylbenzene-1,2-diamine (8a) (1.3 g, 5.35 mmol) and triethyl orthoacetate (8.7 g, 53.5 mmol) was stirred at 148° C. for 1 h. LCMS analysis showed consumption of the starting material with formation of the desired product mass. The solution was cooled to room temperature and concentrated. The residue was purified by flash chromatography (20 g SiO$_2$, 20% EtOAc/petroleum ether) to provide 6-bromo-1-tert-butyl-2-methyl-1H-benzimidazole (Int-23) (1.23 g, 95% yield) as a yellow oil. m/z (ESI+) for ($C_{12}H_{15}BrN_2$), 268.7 (M+H)$^+$.

Preparation of 6-bromo-5-fluoro-2-methyl-1-(propan-2-yl)-1H-benzimidazole (Int-24) According to Scheme 9

Step 1: Synthesis of 5-bromo-4-fluoro-2-nitro-N-(propan-2-yl)aniline (9b)

To a suspension of 1-bromo-2,5-difluoro-4-nitrobenzene (9a) (1.0 g, 4.2 mmol) in THF (10 mL) was added K$_2$CO$_3$ (581, 4.2 mmol) and i-PrNH$_2$ (248 mg, 4.2 mmol). The mixture was stirred at ambient temperature for 16 h. LCMS analysis showed consumption of the starting material with formation of the desired product mass. The reaction solution was diluted with H$_2$O (30 mL) and extracted with EtOAc (3×20 mL). The combined organic phases were washed with brine (20 mL), dried over Na$_2$SO$_4$, filtered, and concentrated. The residue was purified by flash chromatography (ISCO, 20 g SiO$_2$, 10% EtOAc/petroleum ether) to provide 5-bromo-4-fluoro-2-nitro-N-(propan-2-yl)aniline (9b) (900 mg, 77% yield) as a yellow solid. m/z (ESI+) for ($C_9H_{10}BrFN_2O_2$), 276.7 (M+H)$^+$.

Step 2: Synthesis of 5-bromo-4-fluoro-$N^1$-(propan-2-yl)benzene-1,2-diamine (9c)

To a solution of 5-bromo-4-fluoro-2-nitro-N-(propan-2-yl)aniline (9b) (1.9 g, 6.9 mmol) in MeOH (30 mL) was added saturated aqueous NH$_4$Cl (15 mL) and Fe$^0$ (1.9 g, 34.3 mmol). The reaction suspension was stirred at 60° C. for 16 h overnight. LCMS analysis showed consumption of the starting material with formation of the desired product mass. The reaction suspension was filtered and the filter cake was washed with EtOH (50 mL). The combined filtrate was diluted with H$_2$O (100 mL) and extracted with EtOAc (2×80 mL). The combined organic phases were dried over Na$_2$SO$_4$, filtered, and concentrated. The crude residue was purified by flash chromatography (40 g SiO$_2$, 1:2 EtOAc/petroleum ether) to provide 5-bromo-4-fluoro-N-(propan-2-yl)benzene-1,2-diamine (9c) (900 mg, 53% yield) as a brown gum. m/z (ESI+) for ($C_9H_{12}BrFN_2$), 246.7 (M+H)$^+$.

Step 3: Synthesis of 6-bromo-5-fluoro-2-methyl-1-(propan-2-yl)-1H-benzimidazole (Int-24)

A mixture of 5-bromo-4-fluoro-$N^1$-(propan-2-yl)benzene-1,2-diamine (9c) (800 mg, 3.24 mmol) and triethyl orthoacetate (5.3 g, 32.4 mmol) was stirred at 148° C. for 1

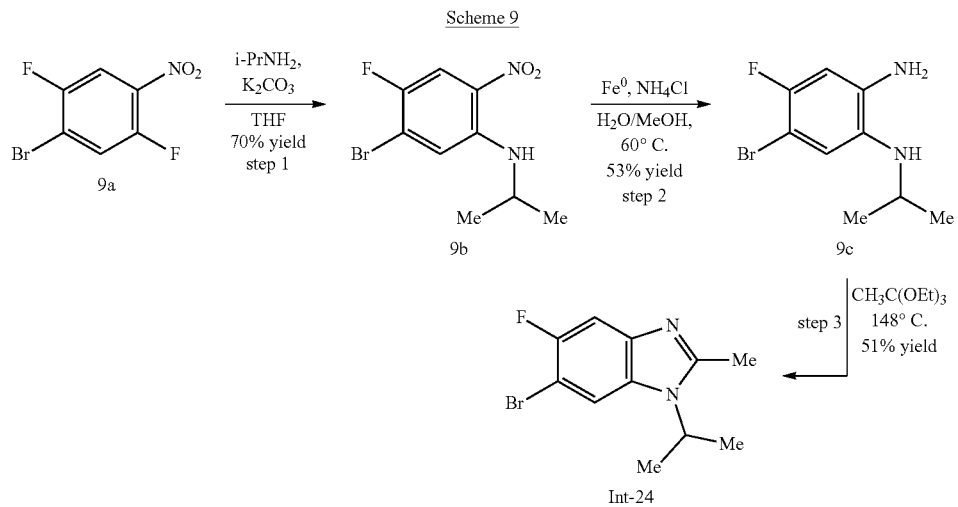 [SMILES: O=[N+]([O-])c1cc(F)c(Br)cc1F ; CC(C)Nc1cc(Br)c(F)cc1[N+](=O)[O-] ; CC(C)Nc1cc(Br)c(F)cc1N ; Cc1nc2cc(F)c(Br)cc2n1C(C)C]

h. LCMS analysis showed consumption of the starting material with formation of the desired product. The solution was cooled to room temperature and concentrated. The residue was combined with a parallel reaction run on 100 mg scale and purified by flash chromatography (20 g SiO$_2$, 100% EtOAc) to provide 6-bromo-5-fluoro-2-methyl-1-(propan-2-yl)-1H-benzimidazole (Int-24) (500 mg, 51% yield). $^1$H NMR (400 MHz, DMSO-d$_6$) δ 7.99 (d, J=6.2 Hz, 1H), 7.51 (d, J=9.5 Hz, 1H), 4.74 (spt, J=6.9 Hz, 1H), 2.55 (s, 3H), 1.53 (d, J=7.0 Hz, 6H); m/z (ESI+) for (CH$_{12}$BrFN$_2$), 270.9 (M+H)$^+$.

The intermediates in the below table were synthesized according to the methods used for the synthesis of 6-bromo-4-fluoro-1-(propan-2-yl)-1H-benzimidazole (Int-22), 6-bromo-4-fluoro-1-(propan-2-yl)-1H-benzimidazole (Int-23), and 6-bromo-5-fluoro-2-methyl-1-(propan-2-yl)-1H-benzimidazole (Int-24). The following intermediates were synthesized with non-critical changes or substitutions to the exemplified procedures that someone who is skilled in the art would be able to realize.

| Compound number | Structure/IUPAC Name | Analytical data |
|---|---|---|
| Int-25 | 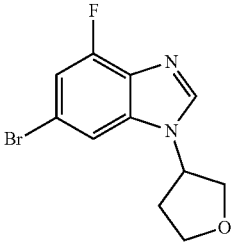<br>6-bromo-4-fluoro-1-(oxolan-3-yl)-1H-benzimidazole | $^1$H NMR (400 MHz, DMSO-d$_6$) δ 8.34 (s, 1H), 7.85 (d, J = 1.6 Hz, 1H), 7.34 (dd, J = 10.3, 1.6 Hz, 1H), 5.30 (ddt, J = 8.4, 5.8, 3.1 Hz, 1H), 4.13 (td, J = 8.4, 6.0 Hz, 1H), 4.01 (dd, J = 10.0, 2.6 Hz, 1H), 3.93 (dd, J = 10.0, 5.6 Hz, 1H), 3.87-3.78 (m, 1H), 2.59-2.53 (m, 1H), 2.26-2.13 (m, 1H).; m/z (ESI+) for (C$_{11}$H$_{10}$BrFN$_2$O), 258.7 (M + H)$^+$ |
| Int-26 | 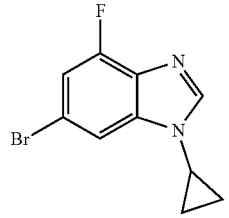<br>6-bromo-1-cyclopropyl-4-fluoro-1H-benzimidazole | $^1$H NMR (400 MHz, CDCl$_3$) δ 7.90 (s, 1H), 7.53 (d, J = 1.5 Hz, 1H), 7.15 (dd, J = 1.5, 9.8 Hz, 1H), 3.36 (td, J = 3.5, 7.0 Hz, 1H), 1.24-1.17 (m, 2H), 1.10-1.03 (m, 2H); m/z (ESI+) for (C$_{10}$H$_8$BrFN$_2$), 256.7 (M + H)$^+$ |
| Int-27 | 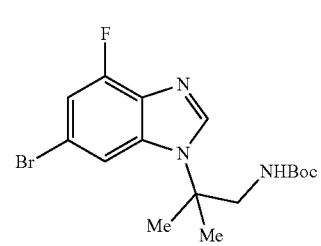<br>tert-butyl [2-(6-bromo-4-fluoro-1H-benzimidazol-1-yl)-2-methylpropyl]carbamate | m/z (ESI+) for (C$_{16}$H$_{21}$BrFN$_3$O$_2$), 387.6 (M + H)$^+$ |
| Int-28 | 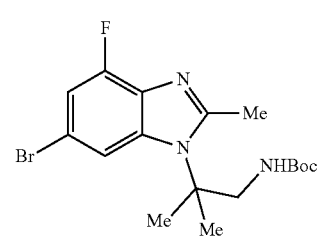<br>tert-butyl [2-(6-bromo-4-fluoro-2-methyl-1H-benzimidazol-1-yl)-2-methylpropyl]carbamate | m/z (ESI+) for (C$_{17}$H$_{23}$BrFN$_3$O$_2$), 400.0 (M + H)$^+$ |

Preparation of tert-butyl {[6-bromo-4-fluoro-1-(propan-2-yl)-1H-benzimidazol-2-yl]methyl}methycarbamate (Int-29) According to Scheme 10

Scheme 10

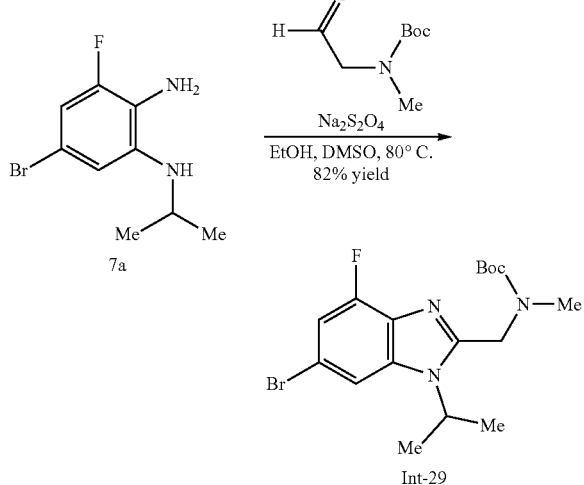

To a solution of 5-bromo-3-fluoro-N$^1$-(propan-2-yl)benzene-1,2-diamine (7a) (300 mg, 1.2 mmol) and tert-butyl methyl (2-oxoethyl) carbamate (421 mg, 2.43 mmol) in EtOH (4.0 mL) and DMSO (1.0 mL) was added Na$_2$S$_2$O$_4$ (1.1 g, 6.1 mmol). The suspension was stirred at 80° C. for 16 h. LCMS analysis showed consumption of the starting material with formation of the desired product mass. The mixture was concentrated to dryness. The residue was purified by flash chromatography (Biotage, 20 g SiO$_2$, 25% EtOAc/petroleum ether) to provide tert-butyl {[6-bromo-4-fluoro-1-(propan-2-yl)-1H-benzimidazol-2-yl]methyl}methylcarbamate (Int-29) (400 mg, 82% yield) as a yellow oil. m/z (ESI+) for (C$_{17}$H$_{23}$BrFN$_3$O$_2$), 401.6 (M+H)$^+$.

The intermediates in the below table were synthesized according to the methods used for the synthesis of tert-butyl {[6-bromo-4-fluoro-1-(propan-2-yl)-1H-benzimidazol-2-yl]methyl}methylcarbamate (Int-29). The following intermediates were synthesized with non-critical changes or substitutions to the exemplified procedures that someone who is skilled in the art would be able to realize.

| Compound number | Structure/IUPAC Name | Analytical data |
|---|---|---|
| Int-30 | tert-butyl {2-[6-bromo-4-fluoro-1-(propan-2-yl)-1H-benzimidazol-2-yl]propan-2-yl}carbamate | m/z (ESI+) for (C$_{18}$H$_{25}$BrFN$_3$O$_2$), 415.7 (M + H)$^+$ |
| Int-31 | 6-bromo-2-({[tert-butyl(dimethyl)silyl]oxy}methyl)-4-fluoro-1-(1-methylcyclopropyl)-1H-benzimidazole | $^1$H NMR (400 MHz, CDC$_3$) δ 7.50 (d, J = 1.6 Hz, 1H), 7.10 (dd, J = 9.6, 1.6 Hz, 1H), 4.97 (s, 2H), 1.60 (s, 7H), 0.92 (s, 9H), 0.15 (s, 6H); m/z (ESI+) for (C$_{18}$H$_{26}$BrFN$_2$OSi), 414.9 (M + H)$^+$ |

Preparation of 6-bromo-4-fluoro-N-methyl-1-(propan-2-yl)-1H-benzimidazole-2-carboxamide (Int-32) According to Scheme 11

Scheme 11

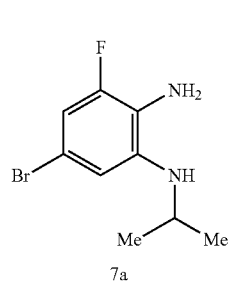

7a

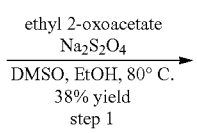

ethyl 2-oxoacetate
Na$_2$S$_2$O$_4$
———————→
DMSO, EtOH, 80° C.
38% yield
step 1

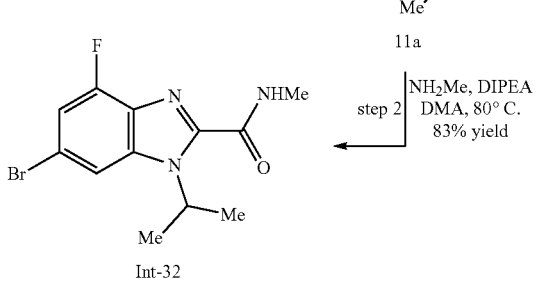

11a

NH$_2$Me, DIPEA
step 2  DMA, 80° C.
83% yield

Int-32

Step 1: Synthesis of ethyl 6-bromo-4-fluoro-1-(propan-2-yl)-1H-benzimidazole-2-carboxylate (11a)

To a solution of 5-bromo-3-fluoro-N$^1$-(propan-2-yl)benzene-1,2-diamine (7a) (1.0 g, 4.05 mmol) and ethyl 2-oxoacetate (1.65 g, 8.09 mmol) in EtOH (20.0 mL) and DMSO (5.0 mL) was added Na$_2$S204 (3.5 g, 20.2 mmol). The suspension was stirred at 80° C. for 16 h. LCMS analysis showed consumption of the starting material with formation of the desired product mass. The mixture was diluted with H$_2$O (15 mL) and extracted with EtOAc (15 mL). The combined organic phases were dried over Na$_2$SO$_4$, filtered, and concentrated. The residue was purified by flash chromatography (ISCO, 20 g SiO$_2$, 25% EtOAc/heptanes) to provide ethyl 6-bromo-4-fluoro-1-(propan-2-yl)-1H-benzimidazole-2-carboxylate (11a) (500 mg, 38% yield) as a solid. m/z (ESI+) for (C$_{13}$H$_{14}$BrFN$_2$O$_2$), 328.7 (M+H)$^+$.

Step 2: Synthesis of 6-bromo-4-fluoro-N-methyl-1-(propan-2-yl)-1H-benzimidazole-2-carboxamide (Int-32)

A mixture of ethyl 6-bromo-4-fluoro-1-(propan-2-yl)-1H-benzimidazole-2-carboxylate (11a) (200 mg, 0.608 mmol), DIPEA (236 mg, 1.82 mmol), and MeNH$_2$ (22.6 mg, 0.729 mmol) in DMA (8.0 mL) was stirred at 80° C. for 16 h. LCMS analysis showed consumption of the starting material with formation of the desired product mass. The mixture was diluted with EtOAc (15 mL) and washed with H$_2$O (15 mL). The combined organic phases were dried over Na$_2$SO$_4$, filtered, and concentrated. The material obtained was combined the product of a parallel reaction run with 48 mg of ethyl 6-bromo-4-fluoro-1-(propan-2-yl)-1H-benzimidazole-2-carboxylate to provide 6-bromo-4-fluoro-N-methyl-1-(propan-2-yl)-1H-benzimidazole-2-carboxamide (Int-32) (200 mg, 83% yield). m/z (ESI+) for (C$_{12}$H$_{13}$BrFN$_3$O), 313.7 (M+H)$^+$.

Preparation of 6-bromo-4-fluoro-1-(propan-2-yl)-1H-benzimidazole-2-carboxamide (Int-33) According to Scheme 12

Scheme 12

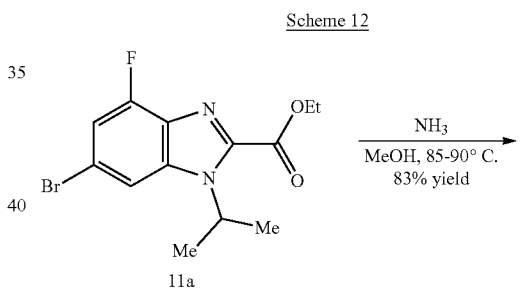

11a

NH$_3$
————————→
MeOH, 85-90° C.
83% yield

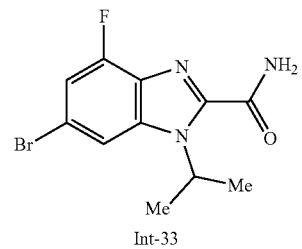

Int-33

Ethyl 6-bromo-4-fluoro-1-(propan-2-yl)-1H-benzimidazole-2-carboxylate (11a) (200 mg, 0.608 mmol) was dissolved in a solution of ammonia in MeOH (7.0 N, 15 mL) and stirred at 85-90° C. for 16 h. LCMS analysis showed consumption of the starting material with formation of the desired product mass. The reaction mixture was cooled to room temperature and concentrated to provide (Int-33) (190 mg, >99% yield) as a solid. m/z (ESI+) for (C$_{11}$H$_{11}$BrFN$_3$O), 299.7 (M+H)$^+$.

Preparation of tert-butyl {1-[6-bromo-4-fluoro-1-(propan-2-yl)-1H-benzimidazol-2-yl]-2-methylpropan-2-yl}carbamate (Int-34) According to Scheme 13

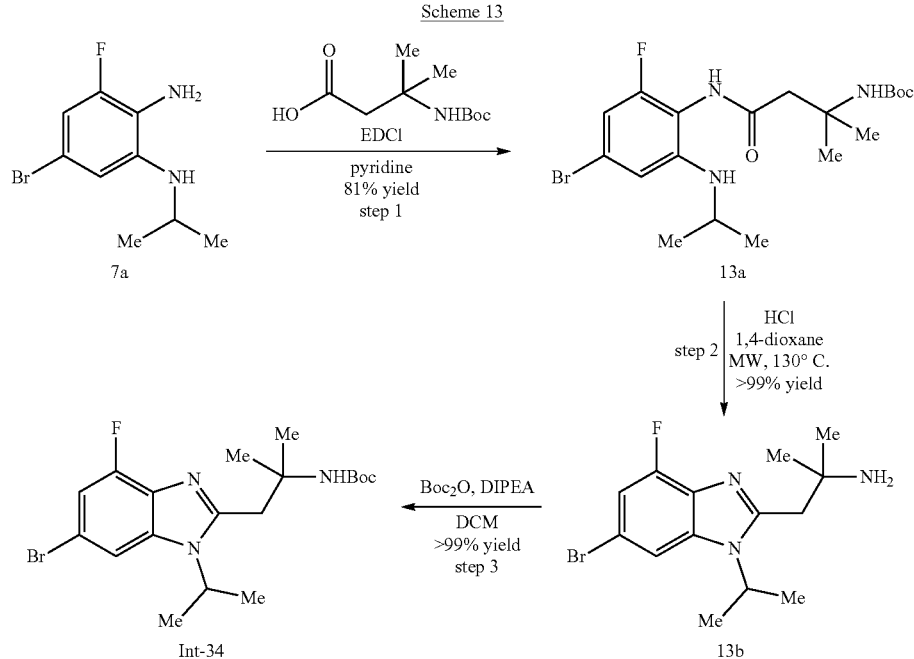

Scheme 13

Step 1: Synthesis of tert-butyl (4-{4-bromo-2-fluoro-6-[(propan-2-yl)amino]anilino}-2-methyl-4-oxobutan-2-yl)carbamate (13a)

To a stirring solution of 5-bromo-3-fluoro-N¹-(propan-2-yl)benzene-1,2-diamine (7a) (1.1 g, 4.5 mmol) in pyridine (10.0 mL) was added 3-[(tert-butoxycarbonyl)amino]-3-methylbutanoic acid (967 mg, 4.5 mmol) and EDCI (1.7 g, 8.9 mmol) at 0° C. under an atmosphere of N$_2$. The mixture was stirred at 25° C. for 4 h. LCMS analysis showed consumption of starting material with formation of the desired product mass. The solution was diluted with H$_2$O (20 mL) and extracted with EtOAc (3×20 mL). The combined organic phases were washed with brine, dried over Na$_2$SO$_4$, filtered, and concentrated. The residue was purified by flash chromatography (ISCO, 20 g SiO$_2$, 0-50% EtOAc/petroleum ether) to provide 1-[6-bromo-4-fluoro-1-(propan-2-yl)-1H-benzimidazol-2-yl]-2-methylpropan-2-amine (13a) (1.6 g, 81% yield) as a white solid. m/z (ESI+) for (C$_{19}$H$_{29}$BrFN$_3$O$_3$), 446.1 (M+H)$^+$.

Step 2: Synthesis of 1-[6-bromo-4-fluoro-1-(propan-2-yl)-1H-benzimidazol-2-yl]-2-methylpropan-2-amine (13b)

This reaction was run in three parallel batches. To the solid 1-[6-bromo-4-fluoro-1-(propan-2-yl)-1H-benzimidazol-2-yl]-2-methylpropan-2-amine (13a) (600 mg, 1.8 mmol) was added a solution of HCl (4.0 M in 1,4-dioxane, 10.0 mL). The mixture was stirred at 130° C. for 15 min under microwave irradiation. LCMS analysis showed consumption of the starting material with formation of the desired product mass. The three reaction batches were combined and concentrated to dryness. The residue was taken up in H$_2$O (10 mL) and the mixture was basified with NH$_4$OH to pH~9. The mixture was extracted with EtOAc (3×15 mL). The combined organic phases were washed with brine, dried over Na$_2$SO$_4$, filtered, and concentrated to provide 1-[6-bromo-4-fluoro-1-(propan-2-yl)-1H-benzimidazol-2-yl]-2-methylpropan-2-amine (13b) (1.2 g, >99% yield). m/z (ESI+) for (C$_{14}$H$_{19}$BrFN$_3$), 329.9 (M+H)$^+$.

Step 3: Synthesis of tert-butyl {1-[6-bromo-4-fluoro-1-(propan-2-yl)-1H-benzimidazol-2-yl]-2-methylpropan-2-yl}carbamate (Int-34)

To a solution of 1-[6-bromo-4-fluoro-1-(propan-2-yl)-1H-benzimidazol-2-yl]-2-methylpropan-2-amine (13b) (1.2 g, 3.7 mmol) in DCM (20 mL) was added DIPEA (473 mg, 3.7 mmol) and Boc$_2$O (958 mg, 4.4 mmol) at 0° C. The solution was stirred at 25° C. for 18 h. LCMS analysis showed consumption of the starting material with formation of the desired product mass. The reaction was diluted with H$_2$O (15 mL) and the layers were separated. The aqueous layer was extracted with DCM (3×15 mL). The combined organic phases were washed with brine, dried over Na$_2$SO$_4$, filtered, and concentrated. The residue was purified by flash chromatography (ISCO, 20 g SiO$_2$, 0-51% EtOAc/petroleum ether) to provide tert-butyl {1-[6-bromo-4-fluoro-1-(propan-2-yl)-1H-benzimidazol-2-yl]-2-methylpropan-2-yl}carbamate (Int-34) (1.6 g, >99% yield) as a brown solid. m/z (ESI+) for (C$_{19}$H$_{27}$BrFN$_3$O$_2$), 430.0 (M+H)$^+$.

The intermediate in the below table was synthesized according to the methods used for the synthesis of tert-butyl {1-[6-bromo-4-fluoro-1-(propan-2-yl)-1H-benzimidazol-2-yl]-2-methylpropan-2-yl}carbamate (Int-34). The following intermediate was synthesized with non-critical changes or substitutions to the exemplified procedures that someone who is skilled in the art would be able to realize.

| Compound number | Structure/IUPAC Name | Analytical data |
|---|---|---|
| Int-35 | 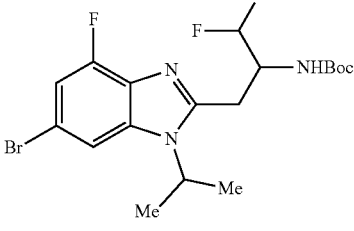<br>tert-butyl {3-[6-bromo-4-fluoro-1-(propan-2-yl)-1H-benzimidazol-2-yl]-1,1-difluoropropan-2-yl}carbamate | $^1$H NMR (400 MHz, CDCl$_3$) δ 7.47 (s, 1H), 7.11 (dd, J = 1.1, 9.6 Hz, 1H), 6.30-5.97 (m, 1H), 5.72 (br d, J = 9.1 Hz, 1H), 4.72-4.57 (m, 1H), 4.52-4.30 (m, 1H), 3.34-3.13 (m, 2H), 1.70-1.60 (m, 6H), 1.36 (s, 9H); m/z (ESI+) for (C$_{18}$H$_{23}$BrF$_3$N$_3$O$_2$), 396.0 (M − tBu + H)$^+$ |
Preparation of 6-bromo-4-fluoro-2-(oxetan-2-yl)-1-(propan-2-yl)-1H-benzimidazole (Int-36) According to Scheme 14
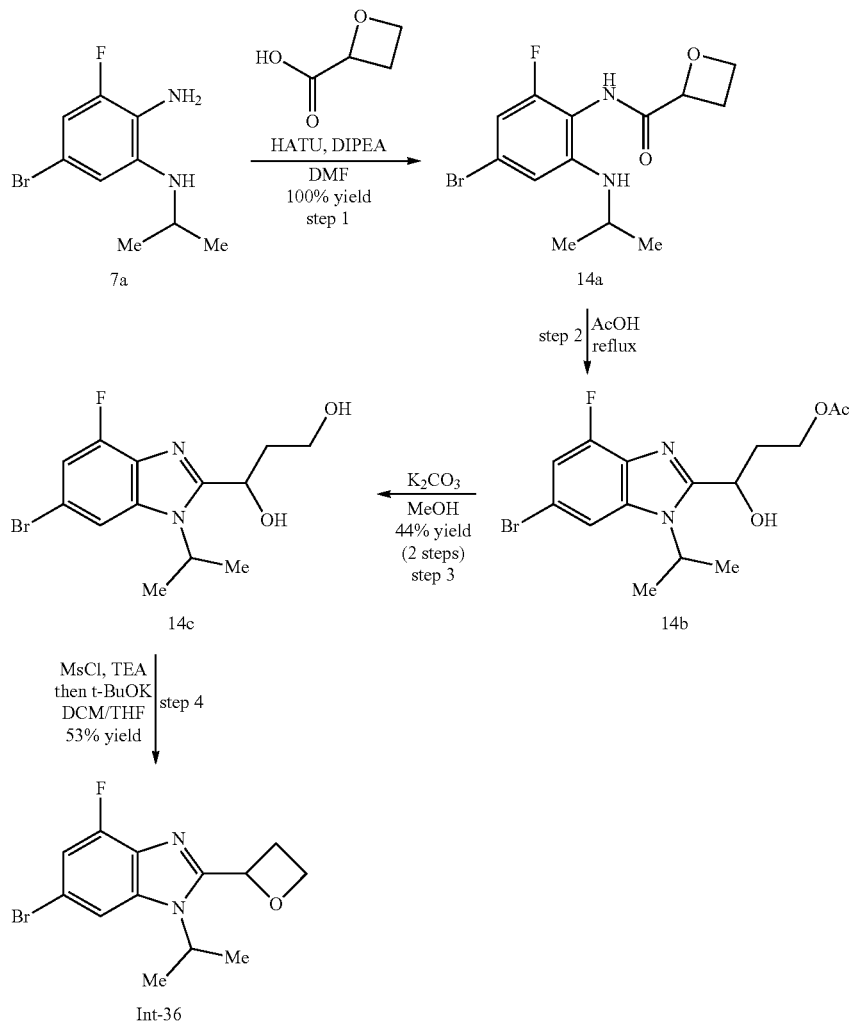
Scheme 14

Step 1: Synthesis of N-{4-bromo-2-fluoro-6-[(propan-2-yl)amino]phenyl}oxetane-2-carboxamide (14a)

To a solution of 5-bromo-3-fluoro-$N^1$-(propan-2-yl)benzene-1,2-diamine (7a) (1.0 g, 4.05 mmol) in DMF (10.0 mL) was added oxetane-2-carboxylic acid (413 mg, 4.05 mmol). Then DIPEA (1.6 g, 12.1 mmol) and HATU (2.3 g, 6.1 mmol) were added and the mixture was stirred for 16 h. TLC analysis (25% EtOAc/petroleum ether) showed consumption of the starting material. The solvent was removed in vacuum. The residue was diluted with saturated aqueous $Na_2CO_3$ (100 mL). The solution was extracted with EtOAc (2×100 mL). The combined organic phases were dried over $Na_2SO_4$, filtered, and concentrated to provide N-{4-bromo-2-fluoro-6-[(propan-2-yl)amino]phenyl}oxetane-2-carboxamide (14a) (1.5 g, 100% yield), which was taken on directly to the next step.

Step 2: Synthesis of 3-[6-bromo-4-fluoro-1-(propan-2-yl)-1H-benzimidazol-2-yl]-3-hydroxypropyl acetate (14b)

A brown solution of N-{4-bromo-2-fluoro-6-[(propan-2-yl)amino]phenyl}oxetane-2-carboxamide (14a) (1.5 g, 4.5 mmol) in AcOH (20 mL) was stirred at 110° C. for 1.5 h. LCMS analysis showed consumption of the starting material with formation of the product mass. The mixture was concentrated to dryness to provide 3-[6-bromo-4-fluoro-1-(propan-2-yl)-1H-benzimidazol-2-yl]-3-hydroxypropyl acetate (14b) (1.5 g, 62% yield), which was taken directly into the next step without further purification. m/z (ESI+) for ($C_{15}H_{18}BrFN_2O$), 374.9 $(M+H)^+$.

Step 3: Synthesis of 1-[6-bromo-4-fluoro-1-(propan-2-yl)-1H-benzimidazol-2-yl]propane-1,3-diol (14c)

To a brown solution of 3-[6-bromo-4-fluoro-1-(propan-2-yl)-1H-benzimidazol-2-yl]-3-hydroxypropyl acetate (14b) (1.5 g, 2.8 mmol) in MeOH (30 mL) was added $K_2CO_3$. The mixture was stirred at room temperature for 2 h. LCMS analysis showed consumption of the starting material with formation of the product mass. The reaction mixture was filtered and the filtrate was concentrated to dryness. The residue was purified by flash chromatography (Biotage, 40 g $SiO_2$, 0-30% MeOH/EtOAc) to provide 1-[6-bromo-4-fluoro-1-(propan-2-yl)-1H-benzimidazol-2-yl]propane-1,3-diol (14c) (660 mg, 44% yield, 2 steps) as a pale brown solid. m/z (ESI+) for ($C_{13}H_{16}BrFN_2O_2$), 332.9 $(M+H)^+$.

Step 4: Synthesis of 6-bromo-4-fluoro-2-(oxetan-2-yl)-1-(propan-2-yl)-1H-benzimidazole (Int-36)

To a solution of 1-[6-bromo-4-fluoro-1-(propan-2-yl)-1H-benzimidazol-2-yl]propane-1,3-diol (14c) (600 mg, 1.81 mmol) and TEA (275 mg, 2.72 mmol) in DCM (5.0 mL) and THF (5.0 mL) at 0° C. was added a solution of MsCl (208 mg, 7.25 mmol) in DCM drop-wise. After 2 h, solid t-BuOK (813 mg, 7.25 mmol) was added in one portion. The resulting solution was stirred at room temperature for 2 h. TLC analysis (EtOAc) showed consumption of the starting material. The reaction was concentrated to dryness. The residue was purified by flash chromatography (Biotage, EtOAc, Rf~0.5) to provide 6-bromo-4-fluoro-2-(oxetan-2-yl)-1-(propan-2-yl)-1H-benzimidazole (Int-36) (300 mg, 53% yield) as a brown gum.

Preparation of 6-bromo-4-fluoro-2-(oxetan-2-yl)-1-(propan-2-yl)-1H-benzimidazole (Int-37) According to Scheme 15

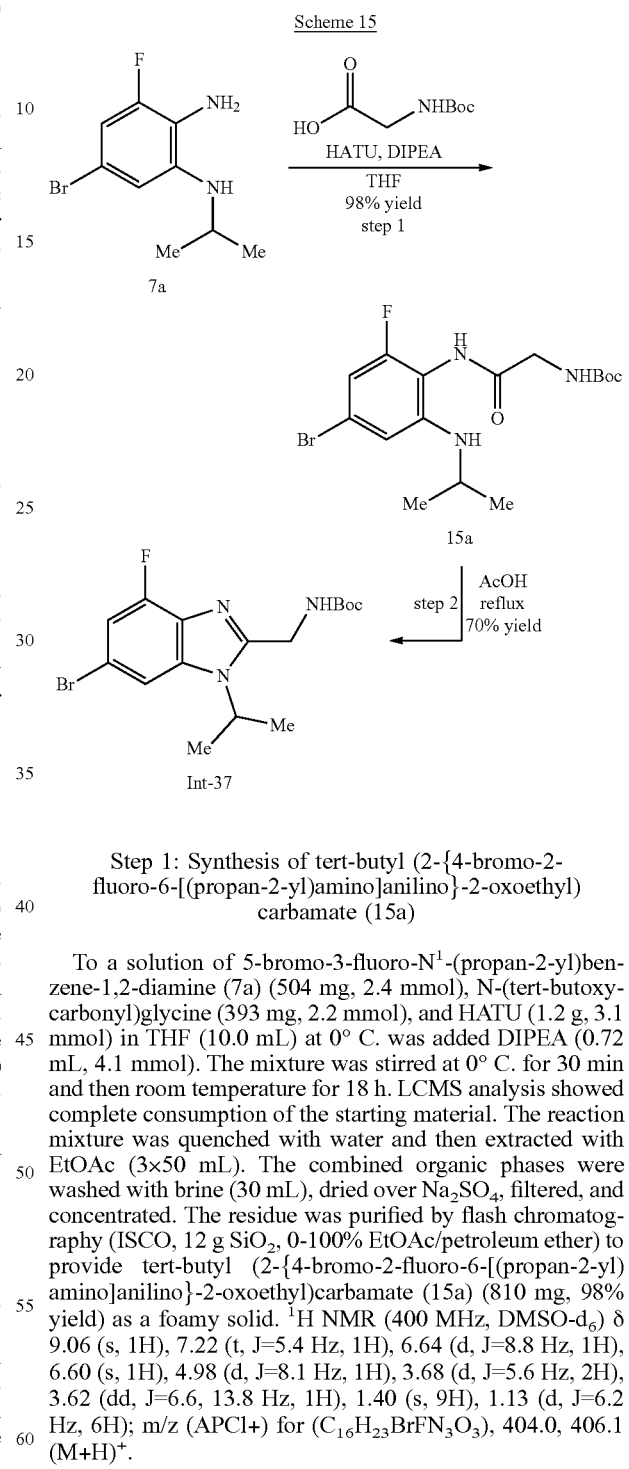

Scheme 15

Step 1: Synthesis of tert-butyl (2-{4-bromo-2-fluoro-6-[(propan-2-yl)amino]anilino}-2-oxoethyl)carbamate (15a)

To a solution of 5-bromo-3-fluoro-$N^1$-(propan-2-yl)benzene-1,2-diamine (7a) (504 mg, 2.4 mmol), N-(tert-butoxycarbonyl)glycine (393 mg, 2.2 mmol), and HATU (1.2 g, 3.1 mmol) in THF (10.0 mL) at 0° C. was added DIPEA (0.72 mL, 4.1 mmol). The mixture was stirred at 0° C. for 30 min and then room temperature for 18 h. LCMS analysis showed complete consumption of the starting material. The reaction mixture was quenched with water and then extracted with EtOAc (3×50 mL). The combined organic phases were washed with brine (30 mL), dried over $Na_2SO_4$, filtered, and concentrated. The residue was purified by flash chromatography (ISCO, 12 g $SiO_2$, 0-100% EtOAc/petroleum ether) to provide tert-butyl (2-{4-bromo-2-fluoro-6-[(propan-2-yl)amino]anilino}-2-oxoethyl)carbamate (15a) (810 mg, 98% yield) as a foamy solid. $^1$H NMR (400 MHz, DMSO-$d_6$) δ 9.06 (s, 1H), 7.22 (t, J=5.4 Hz, 1H), 6.64 (d, J=8.8 Hz, 1H), 6.60 (s, 1H), 4.98 (d, J=8.1 Hz, 1H), 3.68 (d, J=5.6 Hz, 2H), 3.62 (dd, J=6.6, 13.8 Hz, 1H), 1.40 (s, 9H), 1.13 (d, J=6.2 Hz, 6H); m/z (APCI+) for ($C_{16}H_{23}BrFN_3O_3$), 404.0, 406.1 $(M+H)^+$.

Step 2: Synthesis of tert-butyl {[6-bromo-4-fluoro-1-(propan-2-yl)-1H-benzimidazol-2-yl]methyl}carbamate (Int-37)

A solution of tert-butyl (2-{4-bromo-2-fluoro-6-[(propan-2-yl)amino]anilino}-2-oxoethyl)carbamate (15a) (809 mg, 2.0 mmol) in AcOH (4.0 mL) was stirred at 90° C. for 3.5 h. LCMS analysis showed some remaining starting material. The reaction was stirred for an additional 2.5 h at 100° C. The reaction mixture was concentrated. The residue was purified by flash chromatography (ISCO, 12 g SiO$_2$, 0-100% EtOAc/heptanes) to provide tert-butyl{[6-bromo-4-fluoro-1-(propan-2-yl)-1H-benzimidazol-2-yl]methyl}carbamate (Int-37) (547 mg, 70% yield) as a white solid. $^1$H NMR (400 MHz, DMSO-d$_6$) δ 7.79 (d, J=1.3 Hz, 1H), 7.51 (br. s., 1H), 7.28 (dd, J=1.3, 10.1 Hz, 1H), 4.97-4.78 (m, 1H), 4.45 (d, J=5.7 Hz, 2H), 1.53 (d, J=6.8 Hz, 6H), 1.39 (s, 9H); m/z (APCl+) for (C$_{16}$H$_{21}$BrFN$_3$O$_2$), 388.0 (M+H)$^+$.

Preparation of tert-butyl {1-[6-bromo-4-fluoro-1-(propan-2-yl)-1H-benzimidazol-2-yl]ethyl}carbamate (Int-38) According to Scheme 16

Step 2: Synthesis of tert-butyl {1-[6-bromo-4-fluoro-1-(propan-2-yl)-1H-benzimidazol-2-yl]ethyl}carbamate (Int-38)

A mixture of tert-butyl (1-{4-bromo-2-fluoro-6-[(propan-2-yl)amino]anilino}-1-oxopropan-2-yl)carbamate (16a) (4.4 g, 10.5 mmol) in AcOH (20 mL) was stirred at 120° C. for 2 h. The solution was diluted with EtOAc (50 mL) and extracted with H$_2$O (50 mL). To the aqueous solution was added THF (100 mL) and Boc$_2$O (1.09 g, 5.0 mmol). The mixture was stirred at room temperature for 16 h. TLC analysis showed consumption of the intermediate. The solution was diluted with H$_2$O (30 mL) and extracted with EtOAc (30 mL). The organic phase was dried over Na$_2$SO$_4$,

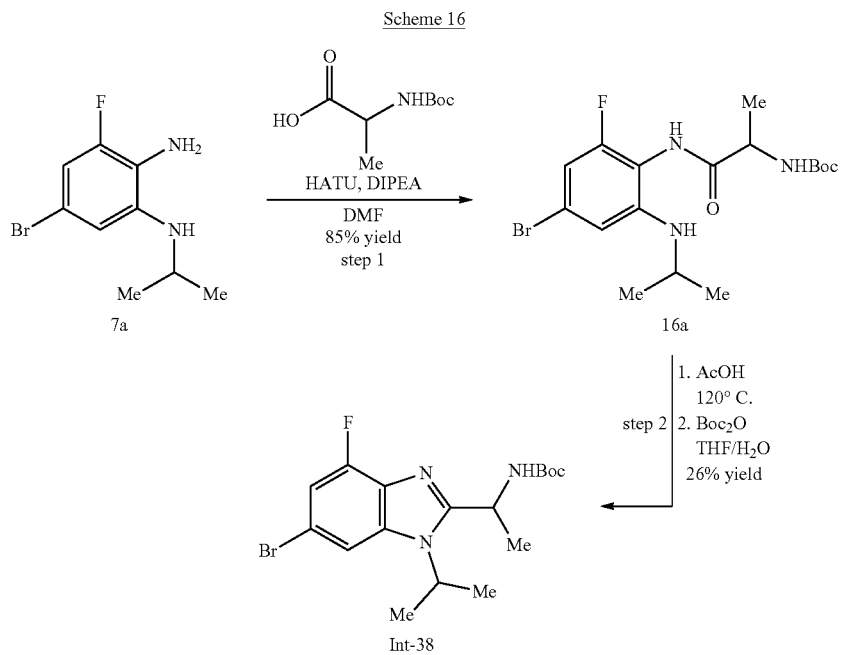 [SMILES: CC(C)Nc1cc(Br)cc(F)c1N ; CC(NC(=O)OC(C)(C)C)C(=O)O ; CC(C)Nc1cc(Br)cc(F)c1NC(=O)C(C)NC(=O)OC(C)(C)C ; CC(NC(=O)OC(C)(C)C)c1nc2c(F)cc(Br)cc2n1C(C)C]

Scheme 16

Step 1: Synthesis of tert-butyl (1-{4-bromo-2-fluoro-6-[(propan-2-yl)amino]anilino}-1-oxopropan-2-yl)carbamate (16a)

To a solution of 5-bromo-3-fluoro-N$^1$-(propan-2-yl)benzene-1,2-diamine (7a) (900 mg, 3.2 mmol) in DMF (8.0 mL) were added N-(tert-butoxycarbonyl)alanine, DIPEA (1.26 g, 9.7 mmol), and HATU (1.85 g, 4.9 mmol). The mixture was stirred at ambient temperature for 16 h. LCMS analysis showed consumption of the starting material with formation of the desired product mass. The reaction mixture was concentrated to dryness. The residue was purified by flash chromatography (ISCO, 20 g SiO$_2$, 30-50% EtOAc/petroleum ether) to provide tert-butyl (1-{4-bromo-2-fluoro-6-[(propan-2-yl)amino]anilino}-1-oxopropan-2-yl)carbamate (16a) (1.14 g, 84% yield) as a white solid.

filtered, and concentrated. The residue was purified by flash chromatography (ISCO, 20 g SiO$_2$, 25% EtOAc/petroleum ether) to provide tert-butyl {1-[6-bromo-4-fluoro-1-(propan-2-yl)-1H-benzimidazol-2-yl]ethyl}carbamate (Int-38) (1.1 g, 26% yield) as a gummy solid. m/z (ESI+) for (C$_{17}$H$_{23}$BrFN$_3$O$_2$), 401.7 (M+H)$^+$.

The intermediate in the below table was synthesized according to the methods used for the synthesis of tert-butyl {1-[6-bromo-4-fluoro-1-(propan-2-yl)-1H-benzimidazol-2-yl]ethyl}carbamate (Int-38). The following intermediate was synthesized with non-critical changes or substitutions to the exemplified procedures that someone who is skilled in the art would be able to realize.

| Compound number | Structure/IUPAC Name | Analytical data |
|---|---|---|
| Int-39 | 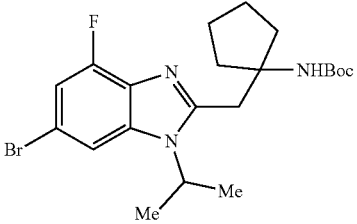<br>tert-butyl (1-{[6-bromo-4-fluoro-1-(propan-2-yl)-1H-benzimidazol-2-yl]methyl}cyclopentyl)carbamate | $^1$H NMR (400 MHz, CDCl$_3$) δ 7.41 (s, 1H), 7.02 (d, J = 9.7 Hz, 1H), 4.78 (p, J = 7.0 Hz, 1H), 4.66 (s, 1H), 3.35 (s, 2H), 1.89-1.59 (m, 8H), 1.54 (d, J = 7.0 Hz, 6H), 1.34 (br d, J = 6.7 Hz, 9H); m/z (ESI+) for (C$_{18}$H$_{26}$BrFN$_2$OSi), 454.1 (M + H)$^+$ |

Preparation of (1R)-1-[6-bromo-4-fluoro-1-(propan-2-yl)-1H-benzimidazol-2-yl]ethan-1-ol (Int-40) According to Scheme 17

Scheme 17

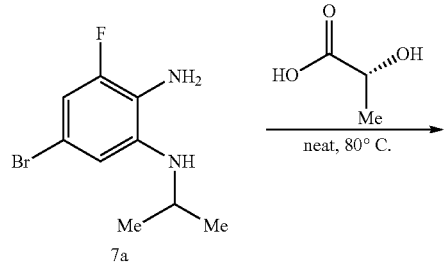

A mixture of the 5-bromo-3-fluoro-N$^1$-(propan-2-yl)benzene-1,2-diamine (7a) (5.74 g, 23.2 mmol) and (2R)-2-hydroxypropanoic acid (17.4 g, 193 mmol) was stirred at 82° C. for 44 h. The dark, viscous mixture was carefully added into a stirring mixture of DCM (100 mL) and saturated NaHCO$_3$ (250 mL) (gas evolution). The biphasic mixture was stirred at ambient temperature until gas evolution ceased. The layers were separated and the aqueous phase extracted was with DCM (2×100 mL). The combined organic phases were dried over MgSO$_4$, filtered, and concentrated. The crude residue was purified by flash chromatography (SiO$_2$, 20-80% MTBE/heptanes). The fractions containing product were further purified by first concentrating to a minimum volume. The resulting residue was dissolved in a small volume of MTBE then diluted with an equal volume of heptanes. The solution was sonicated, causing precipitation. The resulting suspension was concentrated until only a small amount of solvent remained. The supernatant was decanted off. The solids were rinsed with 10% MTBE/heptanes followed by heptanes and then dried under vacuum to provide (1R)-1-[6-bromo-4-fluoro-1-(propan-2-yl)-1H-benzimidazol-2-yl]ethan-1-ol (Int-40) (4.97 g, 71% yield) as a tan solid. $^1$H NMR (400 MHz, DMSO-d$_6$) δ 7.79 (d, J=1.6 Hz, 1H), 7.26 (dd, J=1.5, 10.1 Hz, 1H), 5.71 (d, J=6.5 Hz, 1H), 5.17-5.00 (m, 2H), 1.62-1.51 (m, 9H); m/z (APCI+) for (C$_{12}$H$_{14}$BrFN$_2$O) 300.8 (M+H)$^+$.

The intermediates in the below table were synthesized according to the methods used for the synthesis of (1R)-1-[6-bromo-4-fluoro-1-(propan-2-yl)-1H-benzimidazol-2-yl]ethan-1-ol (Int-40). The following intermediates were synthesized with non-critical changes or substitutions to the exemplified procedures that someone who is skilled in the art would be able to realize.

| Compound number | Structure/IUPAC Name | Analytical data |
|---|---|---|
| Int-41 | 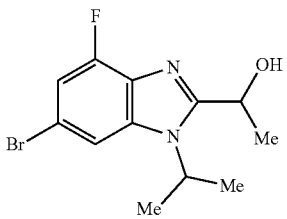<br>1-[6-bromo-4-fluoro-1-(propan-2-yl)-1H-benzimidazol-2-yl]ethan-1-ol | m/z (APCI+) for (C$_{12}$H$_{14}$BrFN$_2$O), 302.7 (M + H)$^+$ |
| Int-42 | 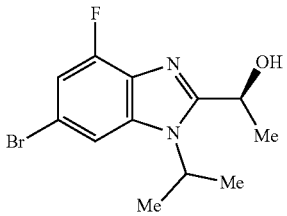<br>(1S)-1-[6-bromo-4-fluoro-1-(propan-2-yl)-1H-benzimidazol-2-yl]ethan-1-ol | m/z (APCI+) for (C$_{12}$H$_{14}$BrFN$_2$O), 302.9 (M + H)$^+$ |

Preparation of 1-[6-bromo-1-(1,1-difluoropropan-2-yl)-4-fluoro-1H-benzimidazol-2-yl]ethan-1-ol (Int-43) According to Scheme 18

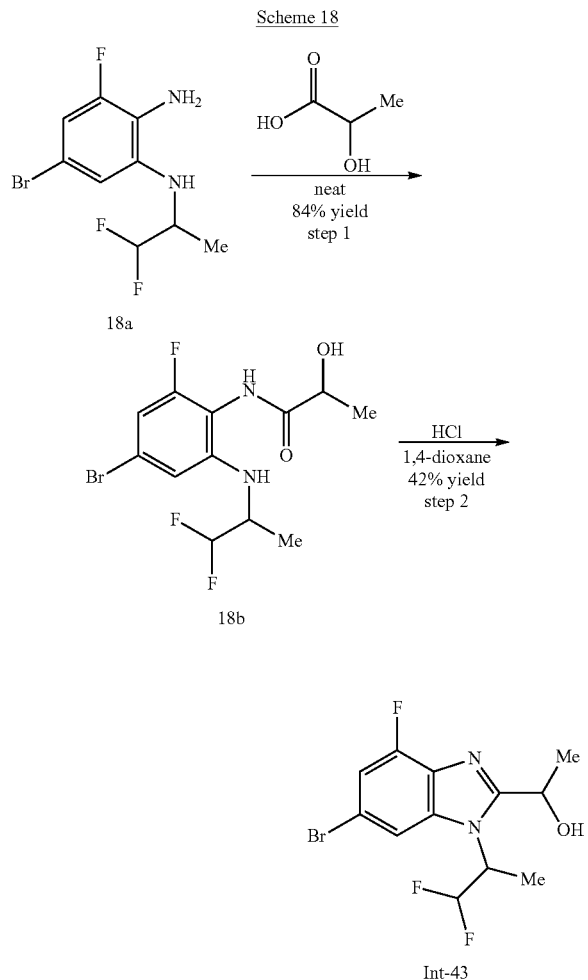

Step 1: Synthesis of N-{4-bromo-2-[(1,1-difluoropropan-2-yl)amino]-6-fluorophenyl}-2-hydroxypropanamide (18b)

A mixture of 5-bromo-N$^1$-(1,1-difluoropropan-2-yl)-3-fluorobenzene-1,2-diamine (18a) (Prepared as in Scheme 7, 1.0 g, 3.5 mmol) and 2-hydroxypropanoic acid (10.0 mL) was stirred at 85° C. for 16 h. LCMS indicated consumption of the starting material with formation of the desired product mass. H$_2$O (15 mL) and EtOAc (15 mL) were added and the mixture was cooled to 0° C. The mixture was adjusted to pH~7 with 50% aqueous NaOH. The layers were separated. The aqueous layer was extracted with EtOAc (2×20 mL). The combined organic layers were dried over Na$_2$SO$_4$, filtered, and concentrated. The residue was purified by flash chromatography (20 g SiO$_2$, 0-50% EtOAc/petroleum ether) to provide N-{4-bromo-2-[(1,1-difluoropropan-2-yl)amino]-6-fluorophenyl}-2-hydroxypropanamide (18b) (1.0 g, 84% yield) as a dark oil. m/z (ESI) for (C$_{12}$H$_{14}$BrF$_3$N$_2$O$_2$), 356.6 (M+H)$^+$.

Step 2: Synthesis of 1-[6-bromo-1-(1,1-difluoropropan-2-yl)-4-fluoro-1H-benzimidazol-2-yl]ethan-1- (Int-43)

A solution of N-{4-bromo-2-[(1,1-difluoropropan-2-yl)amino]-6-fluorophenyl}-2-hydroxypropanamide (18b) (1.0 g, 3.0 mmol) in 1,4-dioxane (10 mL) was stirred at 130° C. for 15 min with microwave irradiation. LCMS analysis showed consumption of the starting material with formation of the desired product mass. The solution was concentrated to dryness. The residue was taken up in H$_2$O (3 mL) and then basified with aqueous NH$_4$OH (1 mL) to pH~8 m. The solution was extracted with EtOAc (3×5 mL). The combined organic layers were washed with brine, dried over Na$_2$SO$_4$, filtered, and concentrated. The residue was purified by flash chromatography (ISCO, 20 g SiO$_2$, 1:1 EtOAc/petroleum ether) to provide (Int-43) (400 mg, 42% yield) as a dark oil. $^1$H NMR (400 MHz, CDCl$_3$) δ 7.47 (d, J=8.5 Hz, 1H), 7.16 (dd, J=1.5, 9.5 Hz, 1H), 6.31-5.98 (m, 1H), 5.14 (br dd, J=6.8, 10.3 Hz, 2H), 3.69-3.58 (m, 1H), 1.83-1.70 (m, 6H); m/z (ESI) for (C$_{12}$H$_{12}$BrF$_3$N$_2$O), 338.7 (M+H)$^+$.

Preparation of 6-bromo-2-(difluoromethyl)-4-fluoro-1-(propan-2-yl)-1H-benzimidazole (Int-44) According to Scheme 19

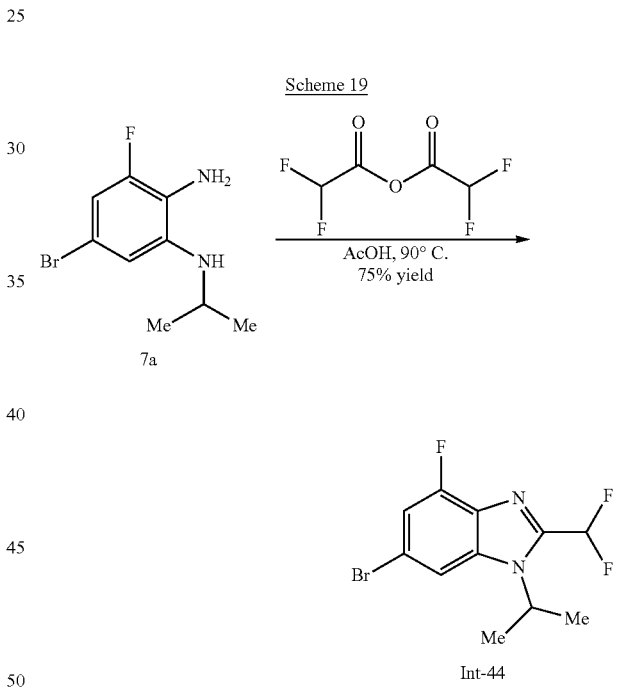

A mixture of 5-bromo-3-fluoro-N$^1$-(propan-2-yl)benzene-1,2-diamine (7a) and difluoroacetic anhydride (1.47 mL, 11.8 mmol) in AcOH (4.6 mL) was stirred at 90° C. for 3 h. The solvent was removed by vacuum. The residue was taken up into DCM (30 mL). The mixture was adjusted to pH~8-9 with 1.0 N aqueous NaOH and the layers were separated. The organic layer was washed with brine (10 mL), dried over Na$_2$SO$_4$, filtered, and concentrated. The residue was purified by flash chromatography (ISCO, 12 g SiO$_2$, 0-50% EtOAc/petroleum ether) to provide 6-bromo-2-(difluoromethyl)-4-fluoro-1-(propan-2-yl)-1H-benzimidazole (Int-44) (523 mg, 72% yield) as a white solid. $^1$H NMR (400 MHz, DMSO-d$_6$) δ 8.02 (d, J=1.5 Hz, 1H), 7.63-7.28 (m, 2H), 5.04-4.84 (m, 1H), 1.60 (d, J=6.8 Hz, 6H); m/z (APCl+) for (C$_{11}$H$_{10}$BrF$_3$N$_2$), 309.1 (M+H)$^+$.

Preparation of 6-bromo-1-tert-butyl-4-fluoro-1H-benzimidazole (Int-45) According to Scheme 20

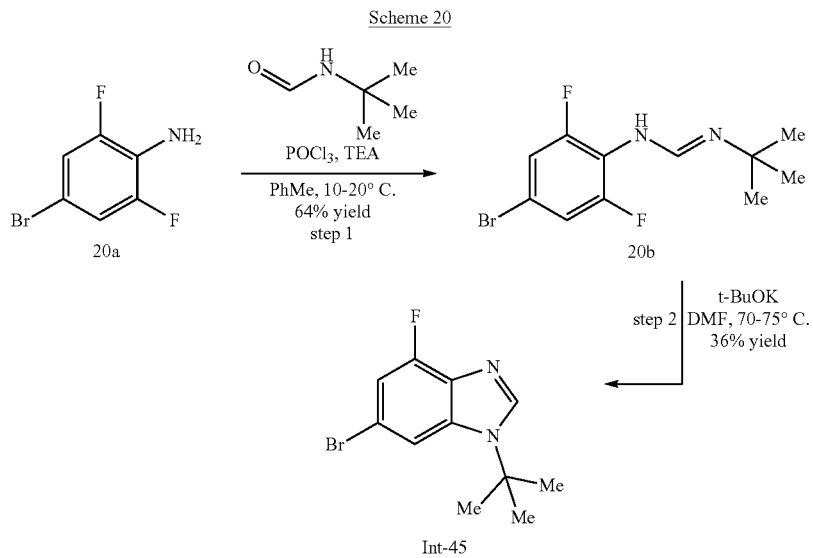 [SMILES: Nc1c(F)cc(Br)cc1F ; CC(C)(C)NC=O ; CC(C)(C)/N=C/Nc1c(F)cc(Br)cc1F ; CC(C)(C)n1cnc2c(F)cc(Br)cc21]

Step 1: Synthesis of N-(4-bromo-2,6-difluorophenyl)-N-tert-butylmethanimidamide (20b)

A solution of 4-bromo-2,6-difluoroaniline (20a) (5.00 g, 24.0 mmol), triethylamine (4.86 g, 6.7 mL, 48.1 mmol) and N-tert-butylformamide (2.92 g, 3.2 mL, 28.8 mmol) in PhMe (50 mL) was treated with $POCl_3$ (5.53 g, 3.36 mL, 36.1 mmol) at 0° C. (maintaining an internal temperature below 20° C.). The mixture was stirred at ambient temperature for 15 h and then quenched with aqueous $Na_2CO_3$ (80 mL). The organic layer was collected. The aqueous layer was extracted with EtOAc (3×30 mL). The combined organic phases were washed with brine (50 mL), dried over $Na_2SO_4$, filtered, and concentrated. The crude residue was suspended in EtOAc (5 mL) and petroleum ether (40 mL), slurried for 10 min, and collected by filtration to provide N-(4-bromo-2,6-difluorophenyl)-$N^1$-tert-butylmethanimidamide (20b) (4.50 g, 64% yield) as a yellow solid. m/z (ESI+) for ($C_{11}H_{13}BrF_2N_2$), 292.6 (M+H)$^+$.

Step 2: Synthesis of 6-bromo-1-tert-butyl-4-fluoro-1H-benzimidazole (Int-45)

To a solution of N-(4-bromo-2,6-difluorophenyl)-$N^1$-tert-butylmethanimidamide (20b) (4.50 g, 15.5 mmol) in DMF (40 mL) was added KOtBu (2.60 g, 23.2 mmol) and the mixture was stirred at 80° C. for 14 h. $H_2O$ (100 mL) was added and the mixture was extracted with EtOAc (3×50 mL). The combined organic phases were washed with brine (50 mL), dried over $Na_2SO_4$, filtered, and concentrated. The crude residue was purified in two stages, first by flash chromatography ($SiO_2$, 20% EtOAc/petroleum ether) then by preparative HPLC on a Phenomenex Synergi Max-RP column (250×80 mm, 10 µm particle size, column temperature of 25° C.), which was eluted with 35-65% $MeCN/H_2O$ (+0.225% formic acid) with flow rate of 80 mL/min to provide 6-bromo-1-tert-butyl-4-fluoro-1H-benzimidazole (Int-45) (1.5 g, 36% yield) as a grey solid. m/z (ESI+) for ($C_{11}H_{12}BrFN_2$), 270.9 (M+H)$^+$.

The intermediate in the below table was synthesized according to the methods used for the synthesis of 6-bromo-1-tert-butyl-4-fluoro-1H-benzimidazole (Int-45). The following intermediate was synthesized with non-critical changes or substitutions to the exemplified procedures that someone who is skilled in the art would be able to realize.

| Compound number | Structure/IUPAC Name | Analytical data |
|---|---|---|
| Int-46 | ![structure] 6-bromo-4-fluoro-2-methyl-1-(propan-2-yl)-1H-benzimidazole | m/z (ESI+) for ($C_{11}H_{12}BrFN_2$), 270.6 (M + H)$^+$ |

Preparation of tert-butyl 3-(6-bromo-4-fluoro-2-methyl-1H-benzimidazol-1-yl)azetidine-1-carboxylate (Int-47) According to Scheme 21

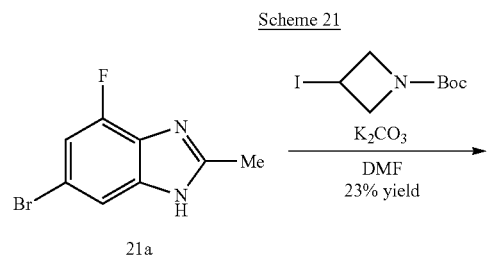

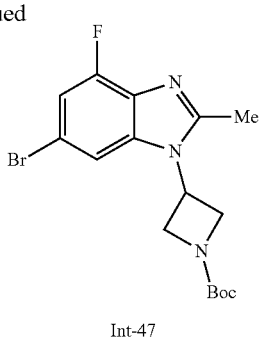

Int-47

To a solution of 6-bromo-4-fluoro-2-methyl-1H-benzimidazole (21a) (271 mg, 1.18 mmol) and tert-butyl 3-iodoazetidine-1-carboxylate (670 mg, 2.37 mmol) in DMF (5.9 mL) was added K$_2$CO$_3$ (491 mg, 3.55 mmol). The reaction mixture was stirred at 100° C. for 16 h. The reaction mixture was cooled to room temperature and loaded onto SiO$_2$. The crude material was purified via flash chromatography (SiO$_2$, 0-100% EtOAc/heptane) to provide a mixture of regioisomers. These compounds were subsequently separated by preparative SFC on a Waters SFC 200 Glacier/Two Zymor-SPHER HADP column (150×21.1 mm I.D., 5 µm particle size), which was eluted with 10-35% MeOH/CO$_2$ (100 bar, 35° C.) with a flow rate of 80 mL/min to provide tert-butyl 3-(6-bromo-4-fluoro-2-methyl-1H-benzimidazol-1-yl)azetidine-1-carboxylate (Int-47) (106 mg, 23% yield) as a solid. $^1$H NMR (400 MHz, DMSO-d$_6$) δ 7.55 (d, J=1.5 Hz, 1H), 7.34 (dd, J=1.5, 10.1 Hz, 1H), 5.41 (s, 1H), 4.48-4.37 (m, 2H), 4.28 (dd, J=5.1, 10.0 Hz, 2H), 2.56 (s, 3H), 1.46 (s, 9H); m/z (APCl+) for (C$_{16}$H$_{19}$BrFN$_3$O$_2$), 384.0 (M+H)$^+$.

Preparation of 6-bromo-2,4-dimethyl-1-(propan-2-yl)-1H-benzimidazole (Int-48) according to Scheme 22

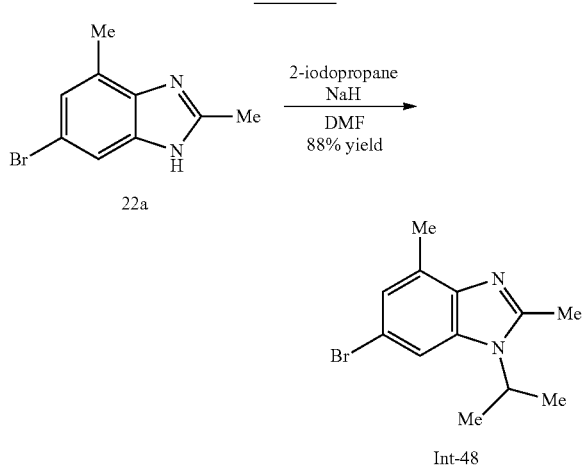

To a solution of 6-bromo-2,4-dimethyl-1H-benzimidazole (22a) (250 mg, 1.11 mmol) in anhydrous DMF (8.0 mL) was added 2-iodopropane (189 mg, 1.11 mmol) and NaH (60% dispersion in mineral oil, 222 mg, 5.55 mmol). The reaction mixture was stirred at ambient temperature 16 h. LCMS analysis showed consumption of the starting material with formation of the desired product mass. The reaction was quenched with H$_2$O (3 mL) and then concentrated under vacuum. The crude residue was purified by flash chromatography (ISCO, 20 g SiO$_2$, 70% EtOAc/petroleum ether) to provide 6-bromo-2,4-dimethyl-1-(propan-2-yl)-1H-benzimidazole (Int-48) (260 mg, 88% yield). m/z (ESI+) for (C$_{12}$H$_{15}$BrN$_2$), 268.8 (M+H)$^+$.

The intermediate in the below table was synthesized according to the methods used for the synthesis of 6-bromo-2,4-dimethyl-1-(propan-2-yl)-1H-benzimidazole (Int-48). The following intermediate was synthesized with non-critical changes or substitutions to the exemplified procedures that someone who is skilled in the art would be able to realize.

| Compound number | Structure/IUPAC Name | Analytical data |
| --- | --- | --- |
| Int-49 | Cl, Br, Me, Me on benzimidazole<br>6-bromo-4-chloro-1-(propan-2-yl)-1H-benzimidazole | $^1$H NMR (400 MHz, CDCl$_3$) δ 8.05 (s, 1H), 7.84 (d, J = 1.5 Hz, 1H), 7.39 (d, J = 1.3 Hz, 1H), 5.40 (quin.d, J = 6.6, 13.3 Hz, 1H), 1.62 (d, J = 6.5 Hz, 6H); m/z (ESI+) for (C$_{10}$H$_{10}$BrClN$_2$), 274.8 (M + H)$^+$ |

Preparation of tert-butyl [1-(6-bromo-4-fluoro-2-methyl-1H-benzimidazol-1-yl)propan-2-yl]carbamate (Int-50) According to Scheme 23

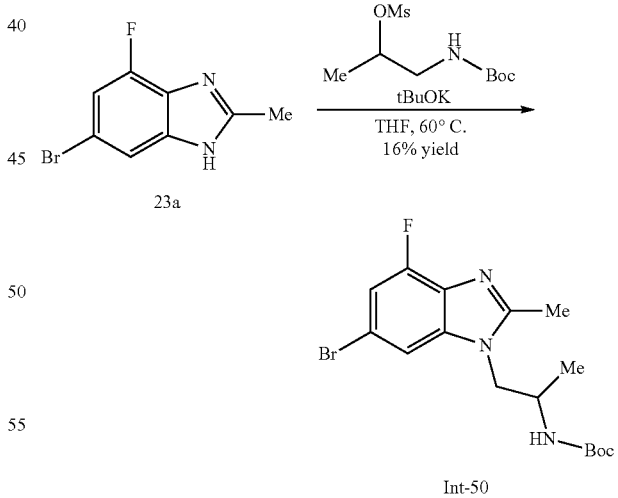

To a solution of 6-bromo-4-fluoro-2-methyl-1H-benzimidazole (23a) (500 mg, 2.18 mmol) in anhydrous THF (15.0 mL) was added solid t-BuOK (294 mg, 2.62 mmol). The mixture was stirred at ambient temperature for 10 min followed by addition of 1-[(tert-butoxycarbonyl)amino]propan-2-yl methanesulfonate (888 mg, 3.51 mmol). The mixture was stirred at 60° C. under an atmosphere of Ar for 17 h. LCMS analysis showed ~50% consumption of the starting material. The reaction was cooled to room temperature and additional t-BuOK (122 mg, 1.09 mmol) was added followed by additional 1-[(tert-butoxycarbonyl)amino]propan-2-yl methanesulfonate (730 mg, 1.46 mmol). The mixture was stirred at 60° C. for 18 h. LCMS analysis showed ~65% conversion. The mixture was diluted with H$_2$O (30 mL) and extracted with DCM (3×15 mL). The combined organic phases were dried over Na$_2$SO$_4$, filtered, and concentrated. The crude mixture was purified by flash chromatography (20 g SiO$_2$, 10-65% EtOAc/petroleum ether). The fractions containing the desired product were collected and re-purified by preparative HPLC on a YMC-Actus Triart C18 column (150×40 mm, 5 μm particle size), which was eluted with 33-73% MeCN/H$_2$O (0.05% NH$_4$OH) with a flow rate of 25 mL/min to provide tert-butyl [1-(6-bromo-4-fluoro-2-methyl-1H-benzimidazol-1-yl)propan-2-yl]carbamate (Int-50) (112 mg, 16% yield). $^1$H NMR (400 MHz, CDCl$_3$) δ 7.58 (d, J=1.6 Hz, 1H), 7.08 (dd, J=11.1, 1.6 Hz, 1H), 4.48 (s, 1H), 4.21 (td, J=16.1, 14.5, 6.9 Hz, 2H), 4.06 (p, J=7.0 Hz, 1H), 2.63 (s, 3H), 1.28-1.20 (m, 12H); m/z (ESI+) for (C$_{16}$H$_{21}$BrFN$_3$O$_2$), 387.8 (M+H)$^+$.

Preparation of tert-butyl [1-(6-bromo-4-fluoro-2-methyl-1H-benzimidazol-1-yl)propan-2-yl]carbamate (Int-49) According to Scheme 24

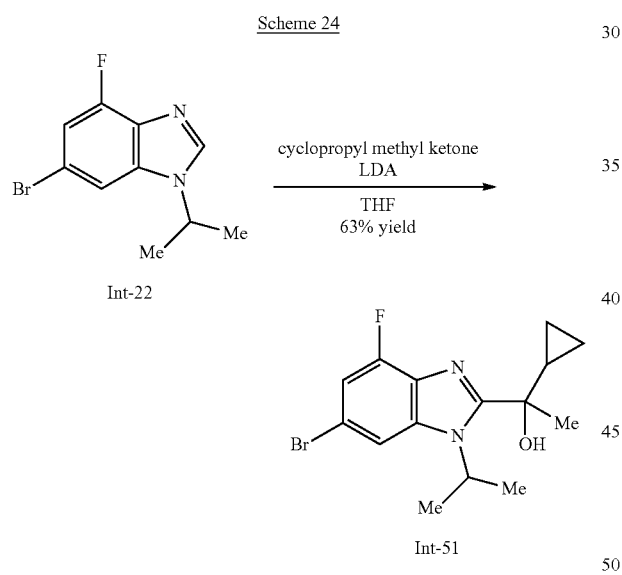

A solution of 6-bromo-4-fluoro-1-(propan-2-yl)-1H-benzimidazole (Int-22) (500 mg, 1.94 mmol) in THF (20.0 mL) under a N$_2$ atmosphere was cooled to −65° C. with a dry ice/acetone bath. A solution of LDA (2.0 M in THF, 1.94 mL, 3.89 mmol) was added drop-wise. The reaction mixture was stirred at the same temperature for 1 h followed by the addition of cyclopropyl methyl ketone (327 mg, 3.89 mmol). After 1 h at −65° C. LCMS analysis showed consumption of the starting material with conversion to the desired product mass. The reaction mixture was quenched with saturated aqueous NH$_4$Cl (10 mL). The phases were separated. The aqueous phase was extracted with EtOAc (3×15 mL). The combined organic phases were dried over Na$_2$SO$_4$, filtered, and concentrated. The crude residue was purified by flash chromatography (ISCO, 1:3 EtOAc/petroleum ether) to provide [1-(6-bromo-4-fluoro-2-methyl-1H-benzimidazol-1-yl)propan-2-yl]carbamate (Int-51) (420 mg, 63% yield) as a white solid. $^1$H NMR (400 MHz, CDCl$_3$) δ 7.52 (d, J=1.5 Hz, 1H), 7.12 (dd, J=1.5, 9.7 Hz, 1H), 5.46-5.22 (m, 1H), 3.71 (s, 1H), 1.72 (s, 3H), 1.67 (dd, J=6.1, 6.8 Hz, 6H), 1.41-1.30 (m, 1H), 0.77-0.67 (m, 1H), 0.64-0.53 (m, 2H), 0.52-0.44 (m, 1H); m/z (ESI+) for (C$_{15}$H$_{18}$BrFN$_2$O), 340.7 (M+H)$^+$.

Preparation of (4R)-7-bromo-9-fluoro-4-methyl-3,4-dihydro-1H-[1,4]oxazino[4,3-a]benzimidazole (Int-50) According to Scheme 24

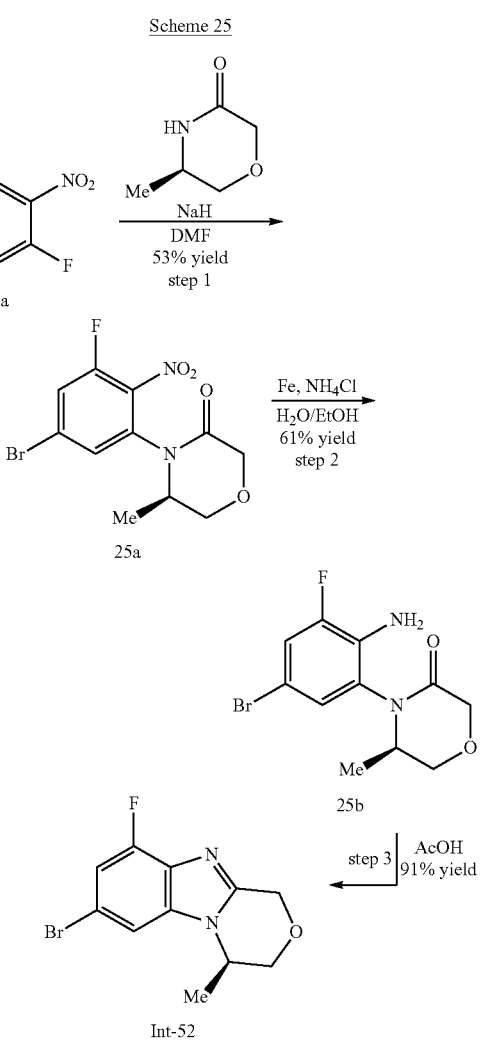

Step 1: Synthesis of (5R)-4-(5-bromo-3-fluoro-2-nitrophenyl)-5-methylmorpholin-3-one (25a)

To a solution of (5R)-5-methylmorpholin-3-one (500 mg, 4.34 mmol) in DMF (10.0 mL) was added NaH (60% dispersion in mineral oil, 208 mg, 5.21 mmol). The reaction suspension was stirred at ambient temperature for 30 min and then 5-bromo-1,3-difluoro-2-nitrobenzene (1a) (1.03 mg, 4.34 mmol) was added. The reaction suspension was stirred for 1 h. LCMS analysis showed consumption of the starting material. H$_2$O (2 mL) was added and the reaction suspension was concentrated to dryness. The residue was taken up into EtOAc (80 mL) and was washed with H$_2$O (60 mL). The organic layer was dried over Na$_2$SO$_4$, filtered, and concentrated to dryness. The residue was purified by flash chromatography (ISCO, 20 g SiO$_2$, 1:3 EtOAc/petroleum ether) to provide (5R)-4-(5-bromo-3-fluoro-2-nitrophenyl)-5-methylmorpholin-3-one (25a) (760 mg, 53% yield) as a light yellow solid. m/z (ESI+) for (C$_{11}$H$_{10}$BrFN$_2$O$_4$), 334.3 (M+H)$^+$.

Step 2: Synthesis of (5R)-4-(2-amino-5-bromo-3-fluorophenyl)-5-methylmorpholin-3-one (25b)

To a solution of (5R)-4-(5-bromo-3-fluoro-2-nitrophenyl)-5-methylmorpholin-3-one (25a) (760 mg, 2.28 mmol) in EtOH (16.0 mL) and H$_2$O (4.0 mL) were added Fe$^0$ (637 mg, 11.4 mmol) and NH$_4$Cl (610 mg, 11.4 mmol). The reaction suspension was stirred at 80° C. for 4 h under an atmosphere of N$_2$. LCMS analysis indicated complete consumption of the starting material with formation of the desired product mass. The reaction mixture was filtered and concentrated to dryness. The residue was purified by flash chromatography (SiO$_2$, 1:3 EtOAc/petroleum ether to provide (5R)-4-(2-amino-5-bromo-3-fluorophenyl)-5-methylmorpholin-3-one (25b) (420 mg, 61% yield) as a light brown gum. m/z (ESI+) for (C$_{11}$H$_{12}$BrFN$_2$O$_2$), 303.1 (M+H)$^+$.

Step 3: Synthesis of (4R)-7-bromo-9-fluoro-4-methyl-3,4-dihydro-1H-[1,4]oxazino[4,3-a]benzimidazole (Int-52)

A solution of (5R)-4-(2-amino-5-bromo-3-fluorophenyl)-5-methylmorpholin-3-one (25b) (420 mg, 1.39 mmol) in AcOH (6.0 mL) was stirred at 110° C. for 2 h. LCMS analysis showed consumption of the starting material with formation of the desired product mass. The reaction mixture was concentrated to dryness. The residue was taken up in EtOAc (50 mL) and washed with aqueous saturated NaHCO$_3$ (30 mL). The organic phase was dried over Na$_2$SO filtered, and concentrated to provide (4R)-7-bromo-9-fluoro-4-methyl-3,4-dihydro-1H-[1,4]oxazino[4,3-a]benzimidazole (Int-52) (360 mg, 91% yield) as a light-yellow solid. m/z (ESI+) for (C$_{11}$H$_{10}$BrFN$_2$O), 286.6 (M+H)$^+$.

The intermediates in the below table were synthesized according to the methods used for the synthesis of (4R)-7-bromo-9-fluoro-4-methyl-3,4-dihydro-1H-[1,4]oxazino[4,3-a]benzimidazole (Int-52). The following intermediates were synthesized with non-critical changes or substitutions to the exemplified procedures that someone who is skilled in the art would be able to realize.

| Compound number | Structure/IUPAC Name | Analytical data |
| --- | --- | --- |
| Int-53 | 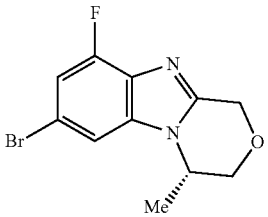<br>(4S)-7-bromo-9-fluoro-4-methyl-3,4-dihydro-1H-[1,4]oxazino[4,3-a]benzimidazole | m/z (ESI+) for (C$_{11}$H$_{10}$BrFN$_2$O), 286.6 (M + H)$^+$ |
| Int-54 | 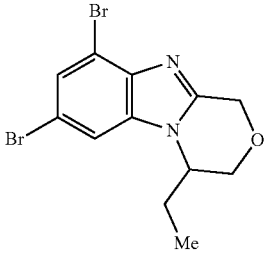<br>7-bromo-4-ethyl-9-fluoro-3,4-dihydro-1H-[1,4]oxazino[4,3-a]benzimidazole | m/z (ESI+) for (C$_{12}$H$_{12}$BrFN$_2$O), 300.9 (M + H)$^+$ |

-continued

| Compound number | Structure/IUPAC Name | Analytical data |
|---|---|---|
| Int-55 | 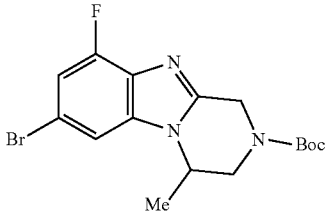<br>tert-butyl 7-bromo-9-fluoro-4-methyl-3,4-dihydropyrazino[1,2-a]benzimidazole-2(1H)-carboxylate | $^1$H NMR (400 MHz, DMSO-$d_6$) δ 7.79 (d, J = 1.5 Hz, 1H), 7.33 (dd, J = 1.5, 10.3 Hz, 1H), 5.21-4.96 (m, 1H), 4.75 (br s, 1H), 4.26-4.09 (m, 1H), 3.67-3.57 (m, 2H), 1.46 (s, 9H), 1.35 (br d, J = 6.3 Hz, 3H); m/z (ESI+) for ($C_{16}H_{19}BrFN_3O_2$), 385.9 (M + H)$^+$ |
| Int-56 | 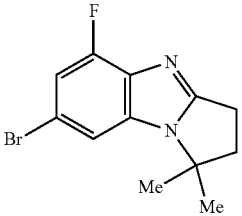<br>7-bromo-5-fluoro-1,1-dimethyl-2,3-dihydro-1H-pyrrolo[1,2-a]benzimidazole | m/z (ESI+) for ($C_{12}H_{12}BrFN_2$), 284.9 (M + H)$^+$ |

Preparation of 7-bromo-9-fluoro-4,4-dimethyl-3,4-dihydro-1H-[1,4]oxazino[4,3-a]benzimidazole (Int-57) According to Scheme 26

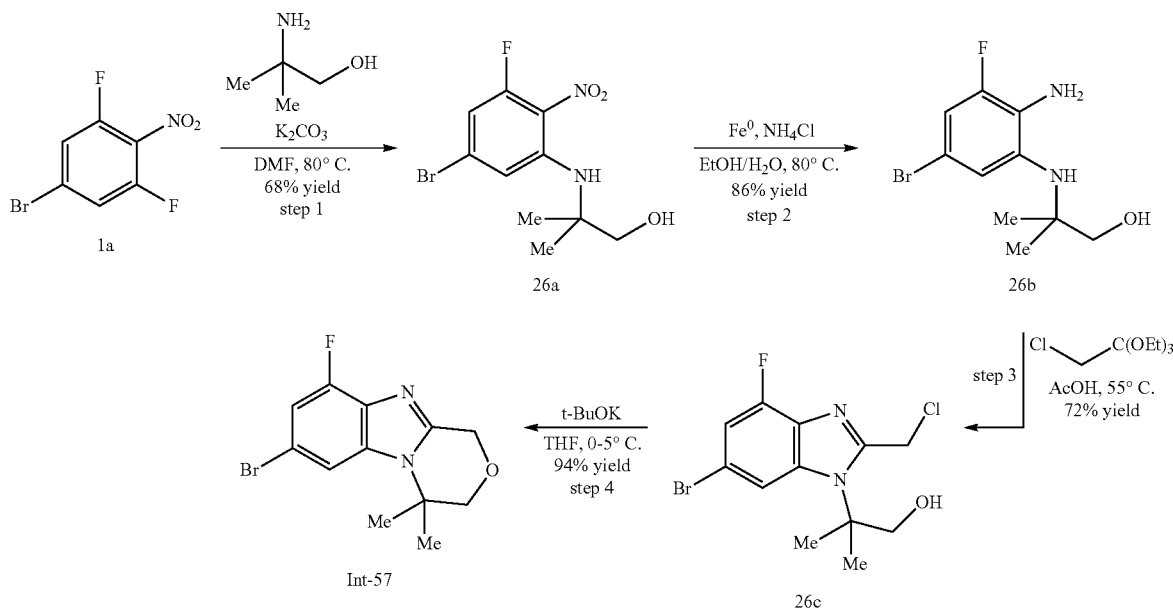

Step 1: Synthesis of 2-(5-bromo-3-fluoro-2-nitroanilino)-2-methylpropan-1-ol (26a)

To a yellow solution of 5-bromo-1,3-difluoro-2-nitrobenzene (1a) (8.0 g, 33.6 mmol) in DMF (30 mL) were added $K_2CO_3$ (9.3 g, 67.2 mmol) and 2-amino-2-methylpropan-1-ol (3.0 g, 33.6 mmol). The mixture was stirred at 80° C. for 1 h. LCMS analysis showed consumption of the starting material with formation of the desired product mass. The reaction was cooled to room temperature, filtered, and concentrated. The residue was purified by flash chromatography (ISCO, 80 g $SiO_2$, 15% EtOAc/petroleum ether) to provide 2-(5-bromo-3-fluoro-2-nitroanilino)-2-methylpropan-1-ol (26a) (7.0 g, 68% yield) as a yellow solid. m/z (ESI+) for ($C_{10}H_{12}BrFN_2O_3$), 307.0 (M+H)$^+$.

Step 2: Synthesis of 2-(2-amino-5-bromo-3-fluoroanilino)-2-methylpropan-1-ol (26b)

To a solution of 2-(5-bromo-3-fluoro-2-nitroanilino)-2-methylpropan-1-ol (26a) (7.0 g, 22.8 mmol) in EtOH (50 mL) was added saturated aqueous $NH_4Cl$ (10 mL) and $Fe^0$ (6.36 mg, 114 mmol) and the mixture was stirred at 80° C. for 1 h. TLC analysis showed consumption of the starting material. The mixture was filtered and concentrated to dryness. The residue was purified by flash chromatography (ISCO, 80 g $SiO_2$, 30% EtOAc/petroleum ether) to provide 2-(2-amino-5-bromo-3-fluoroanilino)-2-methylpropan-1-ol (26b) (5.4 g, 86% yield) as a black oil. m/z (ESI+) for ($C_{10}H_{14}BrFN_2$), 277.0, 279.0 (M+H)$^+$.

Step 3: Synthesis of 2-[6-bromo-2-(chloromethyl)-4-fluoro-1H-benzimidazol-1-yl]-2-methylpropan-1-ol (26c)

A yellow solution 2-(2-amino-5-bromo-3-fluoroanilino)-2-methylpropan-1-ol (26b) (1.8 g, 6.5 mmol) and 2-chloro-1,1,1-triethoxyethane (1.5 g, 9.7 mmol) in AcOH (10.0 mL) was stirred at 55° C. for 8 min. LCMS analysis showed consumption of the starting material with formation of the product mass. After cooling to room temperature the reaction mixture was combined with parallel reactions run on smaller sale (5×100 mg). The combined reaction mixtures were basified with saturated aqueous $NaHCO_3$ to adjust to pH~7-8 and extracted with EtOAc (3×20 mL). The combined organic phases were washed with brine (20 mL), dried over $Na_2SO_4$, filtered, and concentrated. The residue was purified by flash chromatography (ISCO, 40 g $SiO_2$, 30% EtOAc/petroleum ether) to provide 2-[6-bromo-2-(chloromethyl)-4-fluoro-1H-benzimidazol-1-yl]-2-methylpropan-1-ol (26c) (2.0 g, 72% yield) as a light yellow solid. $^1$H NMR (400 MHz, DMSO-$d_6$) δ 7.90 (d, J=1.5 Hz, 1H), 7.36 (dd, J=1.3, 9.8 Hz, 1H), 5.41 (t, J=5.6 Hz, 1H), 5.18 (s, 2H), 3.87 (d, J=5.3 Hz, 2H), 1.78 (s, 6H). m/z (ESI+) for ($C_{12}H_{13}BrClFN_2O$), 336.9 (M+H)$^+$.

Step 4: Synthesis of 7-bromo-9-fluoro-4,4-dimethyl-3,4-dihydro-1H-[1,4]oxazino[4,3-a]benzimidazole (Int-57)

To a solution of 2-[6-bromo-2-(chloromethyl)-4-fluoro-1H-benzimidazol-1-yl]-2-methylpropan-1-ol (26c) in THF (5.0 mL) was added t-BuOK (251 mg, 2.23 mmol) at 0° C. The solution was stirred at 0° C. for 30 min. LCMS analysis showed consumption of the starting material with formation of the desired product mass. The reaction mixture was diluted with $H_2O$ (10 mL) and extracted with EtOAc (3×10 mL). The combined organic phases were washed with brine (15 mL), dried over $Na_2SO_4$, filtered, and concentrated. The residue was purified by flash chromatography (ISCO, 20 g $SiO_2$, 30% EtOAc/petroleum ether) to provide 7-bromo-9-fluoro-4,4-dimethyl-3,4-dihydro-1H-[1,4]oxazino[4,3-a]benzimidazole (Int-57) (420 mg, 94% yield) as a yellow solid. $^1$H NMR (400 MHz, CDCl$_3$) δ 7.47 (d, J=1.5 Hz, 1H), 7.14 (dd, J=1.5, 9.5 Hz, 1H), 4.98 (s, 2H), 3.84 (s, 2H), 1.67 (s, 6H); m/z (ESI+) for ($C_{12}H_{12}BrFN_2O$), 298.7 (M+H)$^+$.

Preparation of 7-bromo-9-fluoro-2,4,4-trimethyl-1,2,3,4-tetrahydropyrazino[1,2-a]benzimidazole (Int-58) According to Scheme 27

Scheme 27

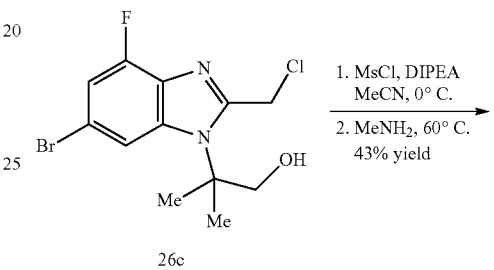

To a solution of 2-[6-bromo-2-(chloromethyl)-4-fluoro-1H-benzimidazol-1-yl]-2-methylpropan-1-ol (26c) (500 mg, 1.49 mmol) and DIPEA (578 mg, 4.47 mmol) in MeCN (5.0 mL) was added MsCl (256 mg, 2.23 mmol) drop-wise. After addition, the resulting solution was allowed to warm to room temperature and stirred for 1 h. LCMS analysis showed consumption of the starting material with formation of the desired product mass. To the solution was added DIPEA (963 mg, 7.45 mmol) and methylamine hydrochloride (201 mg, 2.98 mmol). The resulting solution was stirred at 60° C. for 14 h. LCMS analysis showed consumption of the mesylate intermediate with formation of the desired product mass. The reaction mixture was concentrated to dryness. The residue was purified by flash chromatography (ISCO, 20 g $SiO_2$, 30% EtOAc/petroleum ether) to provide 7-bromo-9-fluoro-2,4,4-trimethyl-1,2,3,4-tetrahydropyrazino[1,2-a]benzimidazole (Int-58) (200 mg, 43% yield) as a yellow gum. $^1$H NMR (400 MHz, CDCl$_3$) δ 7.46 (d, J=1.3 Hz, 1H), 7.11 (dd, J=1.4, 9.6 Hz, 1H), 3.77 (s, 2H), 2.68 (s, 2H), 2.50 (s, 3H), 1.67 (s, 6H); m/z (ESI+) for ($C_{13}H_{15}BrFN_3$), 314.0 (M+H)$^+$.

Preparation of 7-bromo-9-fluoro-1,4-dimethyl-3,4-dihydro-1H-[1,4]oxazino[4,3-a]benzimidazole (Int-59) According to Scheme 28

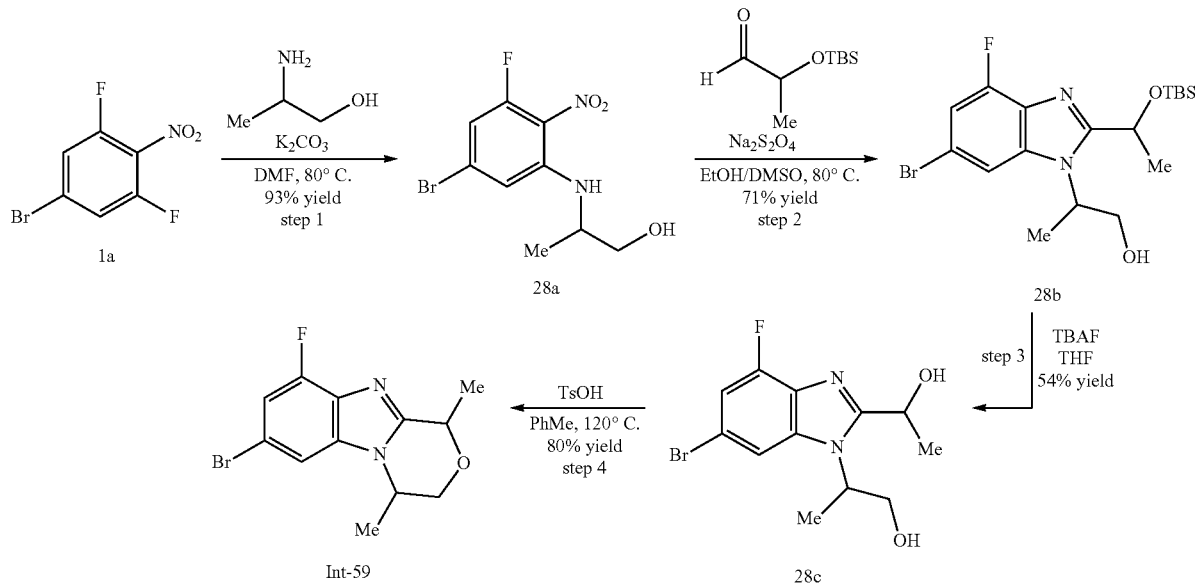

Scheme 28

Step 1: Synthesis of 2-(5-bromo-3-fluoro-2-nitroanilino)propan-1-ol (28a)

To a solution of 5-bromo-1,3-difluoro-2-nitrobenzene (1a) (4.0 g, 16.8 mmol) in DMF (40.0 mL) was added $K_2CO_3$ (4.65 g, 33.6 mmol) and 2-aminopropan-1-ol (1.26 g, 16.9 mmol). The mixture was stirred at 80° C. for 1 h. TLC analysis (3:1 petroleum ether/EtOAc) showed consumption of the starting material. After cooling to room temperature, the reaction mixture was diluted with $H_2O$ (150 mL) and extracted with EtOAc (2×150 mL). The combined organic phases were dried over $Na_2SO_4$, filtered, and concentrated to provide 2-(5-bromo-3-fluoro-2-nitroanilino)propan-1-ol (28a) (4.7 g, 93% yield) as a yellow oil. m/z (ESI+) for ($C_9H_{10}BrFN_2O$), 294.6 $(M+H)^+$.

Step 2: Synthesis of 2-[6-bromo-2-(1-{[tert-butyl(dimethyl)silyl]oxy}ethyl)-4-fluoro-1H-benzimidazol-1-yl]propan-1-ol (28b)

To a yellow solution of 2-(5-bromo-3-fluoro-2-nitroanilino)propan-1-ol (28a) (1.3 g, 3.3 mmol) and 2-{[tert-butyl(dimethyl)silyl]oxy}propanal (1.0 g, 5.3 mmol) in EtOH (10.0 mL) and DMSO (3.0 mL) was added $Na_2S_2O_4$ (2.9 g, 16.4 mmol). The suspension was stirred at 80° C. for 16 h. LCMS analysis showed consumption of the starting material with formation of the desired product mass. The mixture was concentrated to remove the EtOH. The solution was diluted with EtOAc (100 mL) and washed with $H_2O$ (50 mL). The organic phase was dried over $Na_2SO_4$, filtered, and concentrated. The residue was purified by flash chromatography (ISCO, 20 g $SiO_2$, 25% EtOAc/petroleum ether) to provide 2-[6-bromo-2-(1-{[tert-butyl(dimethyl)silyl]oxy}ethyl)-4-fluoro-1H-benzimidazol-1-yl]propan-1-ol (28b) (1.0 g, 71% yield) as a white solid. m/z (ESI+) for ($C_{18}H_{28}BrFN_2O_2Si$), 432.8 $(M+H)^+$.

Step 3: Synthesis of 2-[6-bromo-4-fluoro-2-(1-hydroxyethyl)-1H-benzimidazol-1-yl]propan-1-ol (28c)

To a solution of 2-[6-bromo-2-(1-{[tert-butyl(dimethyl)silyl]oxy}ethyl)-4-fluoro-1H-benzimidazol-1-yl]propan-1-ol (28b) (1.0 g, 2.32 mmol) in THF (5.0 mL) was added TBAF (1.2 g, 4.64 mmol) at ambient temperature. After 1 h, TLC analysis (100% EtOAc) showed consumption of the starting material. The reaction solution was diluted with EtOAc (100 mL) and washed with $H_2O$ (2×50 mL). The organic phase was dried over $Na_2SO_4$, filtered, and concentrated. The residue was purified by flash chromatography (ISCO, 20 g $SiO_2$, 80% EtOAc/petroleum ether) to provide 2-[6-bromo-4-fluoro-2-(1-hydroxyethyl)-1H-benzimidazol-1-yl]propan-1-ol (28c) (400 mg, 54% yield) as a white solid. m/z (ESI+) for ($C_{12}H_{14}BrFN_2O_2$), 316.7 $(M+H)^+$.

Step 4: Synthesis of 7-bromo-9-fluoro-1,4-dimethyl-3,4-dihydro-1H-[1,4]oxazino[4,3-a]benzimidazole (Int-59)

A solution of 2-[6-bromo-4-fluoro-2-(1-hydroxyethyl)-1H-benzimidazol-1-yl]propan-1-ol (28c) (400 mg, 1.26 mmol) and TsOH (434 mg, 2.52 mmol) in PhMe (5.0 mL) was stirred at 120° C. for 16 h. To the solution was added saturated aqueous $NaHCO_3$ (20 mL). The mixture was extracted with EtOAc (2×100 mL). The combined organic phases were dried over $Na_2SO_4$, filtered, and concentrated. The residue was purified by flash chromatography (ISCO, 20 g $SiO_2$, 80-90% EtOAc/petroleum ether) to provide 7-bromo-9-fluoro-1,4-dimethyl-3,4-dihydro-1H-[1,4]oxazino[4,3-a]benzimidazole (Int-59) (300 mg, 80% yield, diastereoisomeric mixture) as a yellow oil. m/z (ESI+) for (C$_{12}$H$_{12}$BrFN$_2$O), 298.7 (M+H)$^+$.

Preparation of 6-bromo-1-(propan-2-yl)-1H-benzotriazole (Int-60) According to Scheme 29

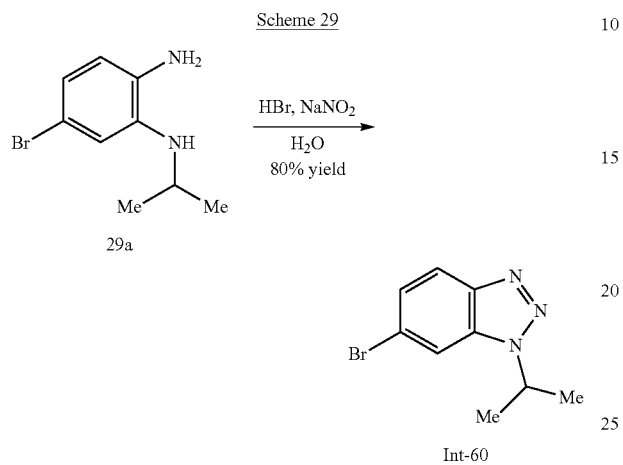

Int-60

To a solution of 4-bromo-N$^2$-(propan-2-yl)benzene-1,2-diamine (29a) (3.00 g, 13.1 mmol) in hydrobromic acid (2.0 M in H$_2$O, 30 mL) was added a solution of sodium nitrite (1.36 g, 19.6 mmol) in H$_2$O (15 mL) at 0° C. The reaction mixture was stirred at this temperature for 30 min then allowed to warm to ambient temperature over a period of 2 h. The reaction mixture was poured into saturated aqueous Na$_2$CO$_3$ (150 mL) and extracted with EtOAc (2×150 mL). The combined organic phases were washed with brine, dried over Na$_2$SO$_4$, filtered, and concentrated. The crude residue was purified by flash chromatography (SiO$_2$, 0-30% EtOAc/petroleum ether) to provide 6-bromo-1-(propan-2-yl)-1H-benzotriazole (Int-60) (2.50 g, 80% yield) as a brown oil. m/z (ESI+) for (C$_9$H$_{10}$BrN$_3$), 239.6 (M+H)$^+$.

Preparation of 2-(5-bromo-2-methyl-2H-indazol-3-yl)propan-2-ol (Int-61) According to Scheme 30

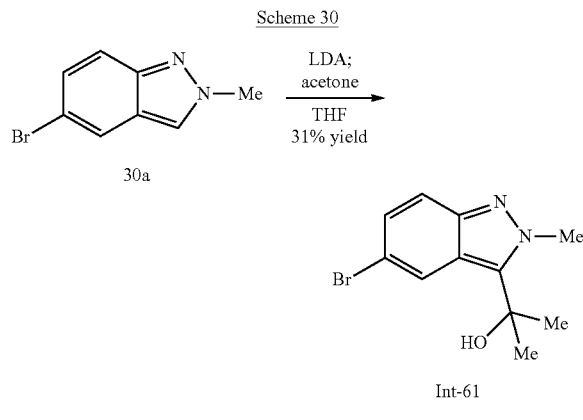

To a stirred solution of 5-bromo-2-methyl-2H-indazole (30a) (300 mg, 1.42 mmol) in THF (10.0 mL) was added LDA (2.0 M in THF, 2.13 mL, 4.26 mmol) at −78° C. The reaction mixture was stirred at 0° C. for 10 min and then cooled to −78° C. Acetone (124 mg, 2.14 mmol) was added to the reaction mixture at −78° C. The reaction was then allowed to warm to ambient temperature and stirred for 18 h. LCMS analysis showed consumption of the starting material with formation of the desired product mass. The reaction was quenched with saturated aqueous NaHCO$_3$ (10 mL) and the layers were separated. The aqueous layer was extracted with EtOAc (3×10 mL). The combined organic phases were washed with brine, dried over Na$_2$SO$_4$, filtered, and concentrated. The residue was purified by flash chromatography (ISCO, 20 g SiO$_2$, 0-100% EtOAc/petroleum ether) to provide 2-(5-bromo-2-methyl-2H-indazol-3-yl)propan-2-ol (Int-61) (120 mg, 31% yield) as a colorless oil. m/z (ESI+) for (CH$_{13}$BrN$_2$O (270.9 (M+H)$^+$.

Preparation of 5-bromo-2-methyl-3-(propan-2-yl)-2H-indazole (Int-62) According to Scheme 31

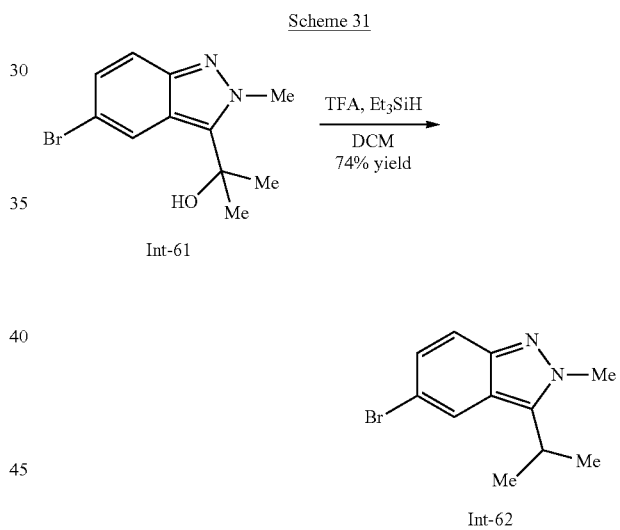

To a stirring solution of 2-(5-bromo-2-methyl-2H-indazol-3-yl)propan-2-ol (Int-61) in DCM (10 mL) were added TFA (847 mg, 7.43 mmol) and Et$_3$SiH (846 mg, 7.43 mmol) at 0° C. The mixture was stirred at 25° C. for 36 h. LCMS analysis showed consumption of the starting material. The reaction was quenched with H$_2$O, adjusted to pH~8 with saturated aqueous NaHCO$_3$, and extracted with DCM (3×10 mL). The combined organic phases were washed with brine, dried over Na$_2$SO$_4$, filtered, and concentrated. The residue was purified by flash chromatography (ISCO, 4 g SiO$_2$, 0-100% EtOAc/petroleum ether) to provide 5-bromo-2-methyl-3-(propan-2-yl)-2H-indazole (Int-62) (140 mg, 74% yield) as a yellow oil. $^1$H NMR (400 MHz, CDCl$_3$) δ 7.91-7.88 (m, 1H), 7.50 (d, J=9.0 Hz, 1H), 7.29 (d, J=1.8 Hz, 1H), 4.12 (s, 3H), 3.40 (td, J=7.2, 14.2 Hz, 1H), 1.49 (d, J=7.0 Hz, 6H); m/z (ESI+) for (C$_{11}$H$_{13}$BrN$_2$), 252.8 (M+H)$^+$.

Preparation of 9-bromo-7-fluoro-1,1-dimethyl-3,4-dihydro-1H-[1,4]oxazino[4,3-b]indazole (Int-61)
According to Scheme 32

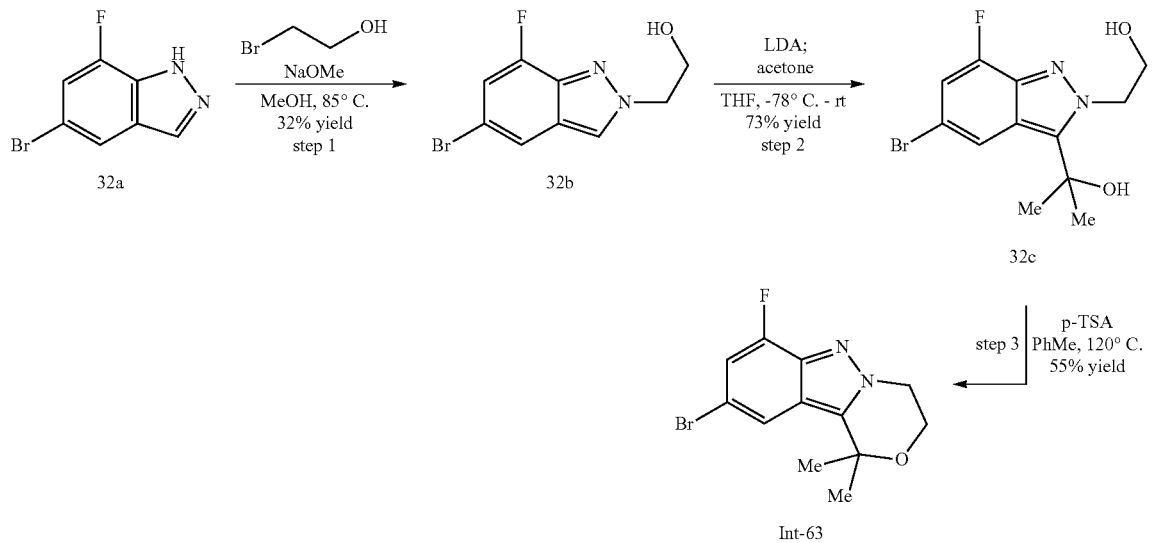

Step 1: Synthesis of 2-(5-bromo-7-fluoro-2H-indazol-2-yl)ethan-1-ol (32b)

To a solution of 5-bromo-7-fluoro-1H-indazole (32a) (2.5 g, 11.6 mmol) in MeOH (10.0 mL) was added NaOMe (1.26 g, 23.3 mmol) and 2-bromoethan-1-ol (2.0 g, 11.6 mmol) under an atmosphere of $N_2$. The resultant solution stirred at 85° C. for 16 h. The reaction mixture was cooled to room temperature. TLC analysis (1:1 EtOAc/petroleum ether) showed partial consumption of the starting material. The reaction mixture was concentrated to dryness and purified by flash chromatography (ISCO, 80 g $SiO_2$, 0-100% EtOAc/petroleum ether) to provide 2-(5-bromo-7-fluoro-2H-indazol-2-yl)ethan-1-ol (32b) (950 mg, 32% yield) as a white solid. m/z (ESI+) for ($C_9H_8BrFN_2$), 260.8 (M+H)$^+$.

Step 2: Synthesis of 2-[5-bromo-7-fluoro-2-(2-hydroxyethyl)-2H-indazol-3-yl]propan-2-ol (32c)

A solution of 2-(5-bromo-7-fluoro-2H-indazol-2-yl)ethan-1-ol (32b) (550 mg, 2.12 mmol) in THF (10.0 mL) was purged with $N_2$ and then a solution of LDA (2.0 M in THF, 2.34 mL, 4.67 mmol) was added at −78° C. The solution was stirred at −10° C. for 30 min and then cooled back to −78° C. To the solution was added acetone (247 mg, 4.25 mmol). The resulting solution was stirred for 16 h at room temperature. LCMS analysis showed complete consumption of the starting material with formation of the desired product mass. The reaction was quenched with $H_2O$ (30 mL) and extracted with EtOAc (50 mL). The organic layer was dried over $Na_2SO_4$, filtered, and concentrated. The crude residue was purified by flash chromatography (ISCO, 20 g $SiO_2$, 50-70% EtOAc/petroleum ether) to provide 2-[5-bromo-7-fluoro-2-(2-hydroxyethyl)-2H-indazol-3-yl]propan-2-ol (32c) (490 mg, 73% yield) as a colorless oil.

Step 3: Synthesis of 9-bromo-7-fluoro-1,1-dimethyl-3,4-dihydro-1H-[1,4]oxazino[4,3-b]indazole (Int-63)

To a solution of 2-[5-bromo-7-fluoro-2-(2-hydroxyethyl)-2H-indazol-3-yl]propan-2-ol (32c) (490 mg, 0.61 mmol) in PhMe (10.0 mL) was added p-TSA (210 mg, 1.22 mmol) at 0° C. The mixture was stirred at 120° C. for 16 h. LCMS analysis indicated consumption of the starting material with formation of the desired product mass. The reaction mixture was concentrated to dryness and the residue was purified by flash chromatography (ISCO, 20 g $SiO_2$, 50% EtOAc/petroleum ether) to provide 9-bromo-7-fluoro-1,1-dimethyl-3,4-dihydro-1H-[1,4]oxazino[4,3-b]indazole (Int-63) (100 mg, 55% yield) as a yellow oil. m/z (ESI+) for ($C_{12}H_{12}BrFN_2$), 298.6 (M+H)$^+$.

Preparation of tert-butyl [2-(5-bromo-7-fluoro-2-methyl-2H-indazol-3-yl)propan-2-yl]carbamate (Int-64) According to Scheme 33

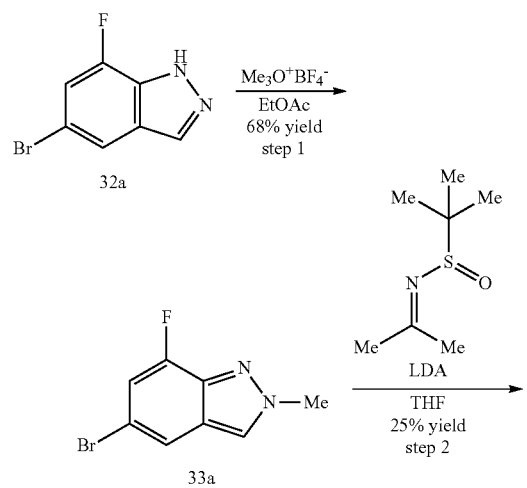

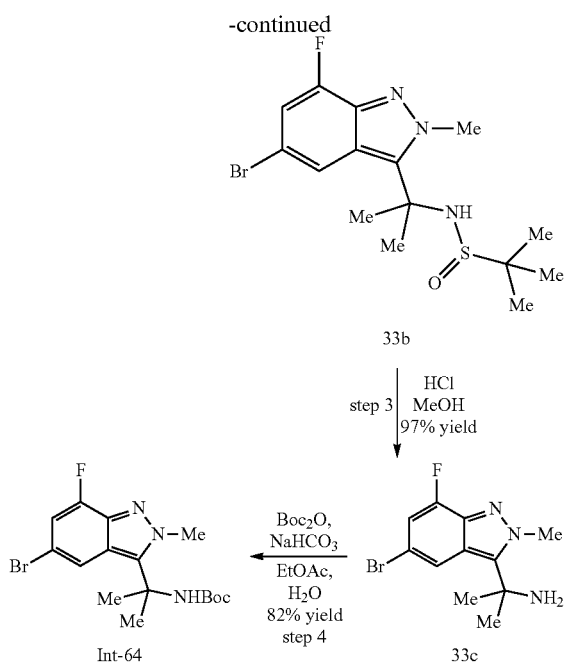

Step 1: Synthesis of 5-bromo-7-fluoro-2-methyl-2H-indazole (33a)

To a solution of 5-bromo-7-fluoro-1H-indazole (32a) (550 mg, 2.12 mmol) in EtOAc (30.0 mL) was added trimethyloxonium tertrafluoroborate (1.97 g, 13.3 mmol). The resulting solution was stirred at ambient temperature for 5 h. LCMS analysis showed consumption of starting material with formation of the desired product mass. The reaction solution was diluted with H$_2$O (20 mL) and extracted with EtOAc (100 mL). The organic phase was dried over Na$_2$SO$_4$, filtered, and concentrated. The crude residue was purified by flash chromatography (ISCO, 40 g SiO$_2$, 20-25% EtOAc/petroleum ether) to provide 5-bromo-7-fluoro-2-methyl-2H-indazole (33a) (1.6 g, 68% yield) as a pale yellow solid. $^1$H NMR (400 MHz, DMSO-d$_6$) δ 8.45 (d, J=2.7 Hz, 1H), 7.79 (d, J=1.3 Hz, 1H), 7.22 (dd, J=1.3, 11.0 Hz, 1H), 4.20 (s, 3H); m/z (ESI+) for (C$_8$H$_6$BrFN$_2$), 230.9 (M+H)$^+$.

Step 2: Synthesis of N-[2-(5-bromo-7-fluoro-2-methyl-2H-indazol-3-yl)propan-2-yl]-2-methylpropane-2-sulfinamide (33b)

To a solution of 5-bromo-7-fluoro-2-methyl-2H-indazole (33a) (1.0 g, 4.4 mmol) in PhMe (10 mL) was added a solution of LDA (2.0 M in THF, 2.6 mL, 5.24 mmol) at −78° C. The reaction mixture was stirred at −78° C. for 1 h. 2-Methyl-N-(propan-2-ylidene)propane-2-sulfinamide (704 mg, 4.4 mmol) was then added to the reaction mixture at −78° C. The reaction mixture was allowed to warm to room temperature and stirred for 24 h. LCMS analysis showed complete consumption of the starting material with formation of the desired product mass. The reaction was quenched by addition of saturated aqueous NH$_4$Cl (10 mL) and extracted with EtOAc (2×30 mL). The combined organic phases were dried over Na$_2$SO$_4$, filtered, and concentrated. The crude residue was purified by flash chromatography (ISCO, 20 g Si$_2$, 30-40% MeOH/EtOAc) to provide N-[2-(5-bromo-7-fluoro-2-methyl-2H-indazol-3-yl)propan-2-yl]-2-methylpropane-2-sulfinamide (33b) (420 mg, 25% yield) as a yellow gum. m/z (ESI+) for (C$_{15}$H$_{21}$BrFN$_3$OS), 392.0 (M+H)$^+$.

Step 3: Synthesis of 2-(5-bromo-7-fluoro-2-methyl-2H-indazol-3-yl)propan-2-amine (33c)

To a yellow solution of N-[2-(5-bromo-7-fluoro-2-methyl-2H-indazol-3-yl)propan-2-yl]-2-methylpropane-2-sulfinamide (33b) (420 mg, 1.08 mmol) in MeOH (5.0 mL) was added concentrated HCl (1.0 mL) at room temperature. The reaction mixture was stirred for 2 h. LCMS analysis showed consumption of the starting material with formation of the desired product mass. The reaction mixture was concentrated under reduced pressure. The residue was dissolved in DCM (10 mL) and TEA (2 mL) was added. The mixture was stirred for 20 min. The reaction solution was extracted with DCM (2×20 mL). The combined organic phases were dried over Na$_2$SO$_4$, filtered, and concentrated to provide 2-(5-bromo-7-fluoro-2-methyl-2H-indazol-3-yl)propan-2-amine (33c) (300 mg, 97% yield) as a yellow solid. m/z (ESI+) for (CH$_{13}$BrFN$_3$), 268.9 (M+H)$^+$.

Step 4: Synthesis of tert-butyl [2-(5-bromo-7-fluoro-2-methyl-2H-indazol-3-yl)propan-2-yl]carbamate (Int-64)

To a yellow solution of 2-(5-bromo-7-fluoro-2-methyl-2H-indazol-3-yl)propan-2-amine (33c) (300 mg, 0.75 mmol) in THF (3.0 mL) was added saturated aqueous NaHCO$_3$ (3.0 mL) and Boc$_2$O (659 mg, 3.0 mmol). The mixture was stirred at room temperature for 16 h. The reaction solution was diluted with H$_2$O (10 mL) and extracted with EtOAc (2×30 mL). The combined organic phases were dried over Na$_2$SO$_4$, filtered, and concentrated. The crude residue was purified by flash chromatography (ISCO, 20 g SiO$_2$, EtOAc/petroleum ether) to provide (Int-64) (240 mg, 82% yield) as a yellow oil. m/z (ESI+) for (C$_{16}$H$_{21}$BrFN$_3$O$_2$), 387.6 (M+H)$^+$.

Preparation of 5-bromo-7-fluoro-2-methyl-3-(propan-2-yl)-2H-indazole (Int-65) according to Scheme 34

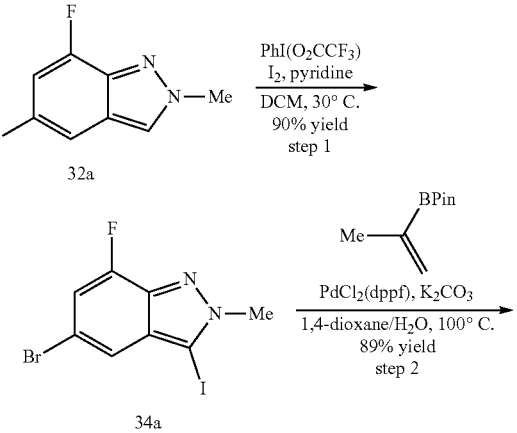

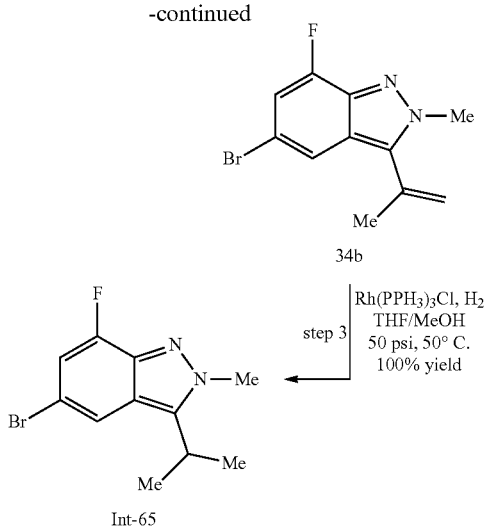

Step 1: Synthesis of 5-bromo-7-fluoro-3-iodo-2-methyl-2H-indazole (34a)

To a solution of 5-bromo-7-fluoro-2-methyl-2H-indazole (33a) (500 mg, 2.18 mmol) in DCM (10.0 mL) was added bis(trifluoroacetoxy)iodobenzene (1.13 g, 2.62 mmol) and pyridine (259 mg, 3.27 mmol). The mixture was stirred at 30° C. for 30 minutes and then I2 (556 mg, 2.62 mmol) was added. The mixture was stirred at 30° C. for 16 h. LCMS analysis showed consumption of the starting material with formation of the desired product mass. The reaction mixture was diluted with EtOAc (50 mL) and then filtered. The filtrate was concentrated to dryness. The residue was purified by flash chromatography (ISCO, 40 g SiO$_2$, 30-40% EtOAc/petroleum ether) to provide 5-bromo-7-fluoro-3-iodo-2-methyl-2H-indazole (34a) (700 mg, 90% yield) as a pale yellow solid. m/z (ESI+) for (C$_8$H$_5$BrFIN$_2$), 354.8 (M+H)$^+$.

Step 2: Synthesis of 5-bromo-7-fluoro-2-methyl-3-(prop-1-en-2-yl)-2H-indazole (34b)

A mixture of 5-bromo-7-fluoro-3-iodo-2-methyl-2H-indazole (34a) (400 mg, 1.13 mmol), isopropenylboronic acid pinacol ester (189 mg, 1.13 mmol), K$_2$CO$_3$ (467 mg, 3.38 mmol), and Pd(dppf)Cl$_2$ (82.5 mg, 0.113 mmol) in 1,4-dioxane (6.0 mL) and H$_2$O (1.0 mL) was stirred under an atmosphere of N$_2$ at 100° C. for 3 h. The reaction suspension became black. LCMS analysis showed complete consumption of the starting material with formation of the desired product mass. The suspension was diluted with EtOAc (50 mL) and filtered. The filtrate was concentrated under reduced pressure. The residue was purified by flash chromatography (ISCO, 20 g SiO$_2$, 30% EtOAc/petroleum ether) to provide 5-bromo-7-fluoro-2-methyl-3-(prop-1-en-2-yl)-2H-indazole (34b) (270 mg, 89% yield) as a yellow oil. m/z (ESI+) for (CH$_{10}$BrFN$_2$), 268.9 (M+H)$^+$.

Step 3: Synthesis of 5-bromo-7-fluoro-2-methyl-3-(propan-2-yl)-2H-indazole (Int-65)

A solution of 5-bromo-7-fluoro-2-methyl-3-(prop-1-en-2-yl)-2H-indazole (34b) (270 mg, 1.0 mmol) and Rh(PPh$_3$)$_3$Cl (92.8 mg, 0.1 mmol) in MeOH (10.0 mL) and THF (10.0 mL) was sparged with H$_2$ and then stirred at 50° C. for 16 h under H$_2$ at a pressure of 50 psi. LCMS analysis showed consumption of the starting material with formation of the desired product mass. The reaction mixture was concentrated to dryness and the residue was purified by flash chromatography (ISCO, 1:1 EtOAc/petroleum ether) to provide 5-bromo-7-fluoro-2-methyl-3-(propan-2-yl)-2H-indazole (Int-65) (300 mg, >99% yield) as a pale brown gum. m/z (ESI+) for (C$_{11}$H$_{10}$BrFN$_2$), 270.8 (M+H)$^+$.

Preparation of 6-bromo-1-(propan-2-yl)-1H-imidazo[4,5-b]pyridine (Int-66) According to Scheme 35

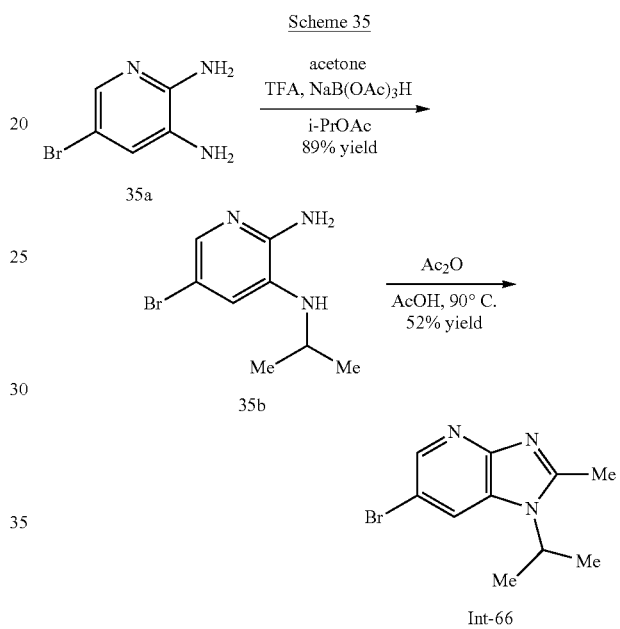

Step 1: Synthesis of 5-bromo-N$^3$-(propan-2-yl)pyridine-2,3-diamine (35b)

To a solution of 5-bromopyridine-2,3-diamine (35a) (2.51 g, 13.4 mmol) and acetone (1.2 mL, 16 mmol) in i-PrOAc (20 mL) were added TFA (2.25 mL, 29.3 mmol) and NaBH(OAc)$_3$ (4.25 g, 20 mmol) at 0° C. The mixture was stirred at room temperature for 2 h. EtOAc (50 mL) was added to quench the reaction. The mixture was washed with saturated aqueous NaHCO$_3$ (40 mL) and brine (30 mL), dried over Na$_2$SO$_4$, filtered, and concentrated. The residue was purified by flash chromatography (40 g SiO$_2$, 0-65% EtOAc/petroleum ether) to provide 5-bromo-N$^3$-(propan-2-yl)pyridine-2,3-diamine (35b) (2.7 g, 89% yield) as a brown gum. $^1$H NMR (400 MHz, DMSO-d$_6$) δ 7.28 (d, J=2.1 Hz, 1H), 6.66 (d, J=1.8 Hz, 1H), 4.97 (br. s., 1H), 3.55 (td, J=6.1, 12.3 Hz, 1H), 1.15 (d, J=6.2 Hz, 6H); m/z (APCI) for (CH$_{12}$BrN$_3$), 230.1, 232.2 (M+H)$^+$.

Step 2: Synthesis of 6-bromo-1-(propan-2-yl)-1H-imidazo[4,5-b]pyridine (Int-66)

A mixture of 5-bromo-N$^3$-(propan-2-yl)pyridine-2,3-diamine (35b) (1.5 g, 6.52 mmol) and Ac$_2$O (30.8 mL, 32.6 mmol) in AcOH (12.5 mL) was stirred at 90° C. overnight. The solvent was removed by evaporation. The residue was taken up in DCM (50 mL) and adjusted to pH~8-9 with aqueous NaOH (1.0 N). The organic layer was collected, washed with brine (50 mL), dried over Na$_2$SO$_4$, filtered, and concentrated. The residue was purified by column chromatography (24 g SiO$_2$, 10% MeOH/EtOAc) to provide 6-bromo-1-(propan-2-yl)-1H-imidazo[4,5-b]pyridine (Int-66) (866 mg, 52% yield) as a light brown solid. $^1$H NMR (400 MHz, DMSO-d$_6$) δ 8.42-8.32 (m, 2H), 4.76 (td, J=6.9, 13.8 Hz, 1H), 2.61 (s, 3H), 1.54 (d, J=7.0 Hz, 6H); m/z (APCl) for (C$_9$H$_{10}$BrN$_3$), 254.2, 256.1 (M+H)$^+$.

Preparation of 5-chloro-2-methyl-3-(propan-2-yl)-3H-imidazo[4,5-b]pyridine (Int-67) According to Scheme 36

Scheme 36

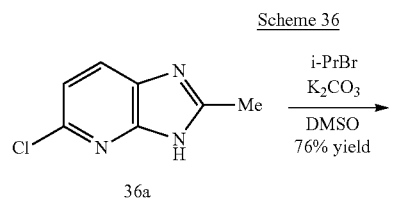

36a

-continued

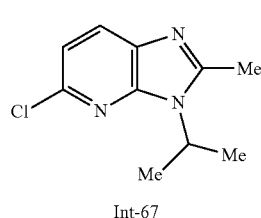

Int-67

To a slurry of K$_2$CO$_3$ (4.1 g, 29.8 mmol) in DMSO (6.0 mL) were added 5-chloro-2-methyl-3H-imidazo[4,5-b]pyridine (36a) (1.0 g, 5.7 mmol) and 2-bromopropane (2.8 mL, 29.8 mmol). The mixture was stirred for 20 h at room temperature and an additional 1 h at 60° C. LCMS analysis showed consumption of the starting material with formation of the desired product mass (~4:1 mixture of regioisomers). The mixture was partitioned between H$_2$O (25 mL) and EtOAc (25 mL). The aqueous layer was extracted with EtOAc (3×25 mL). The combined organic layers were washed with H$_2$O (2×25 mL) and brine (25 mL), dried over Na$_2$SO$_4$, filtered, and concentrated directly onto SiO$_2$. The crude material was purified by flash chromatography (SiO$_2$, 80-100% EtOAc/heptanes) to provide 5-chloro-2-methyl-3-(propan-2-yl)-3H-imidazo[4,5-b]pyridine (Int-67) (950 mg, 76% yield) as the first eluting regioisomer. $^1$H NMR (400 MHz, CDCl$_3$) δ 7.85 (d, J=8.3 Hz, 1H), 7.17 (d, J=8.3 Hz, 1H), 4.84 (p, J=7.0 Hz, 1H), 2.68 (s, 3H), 1.69 (d, J=7.0 Hz, 6H); m/z (APCl) for (C$_{10}$H$_{12}$ClN$_3$), 209.9 (M+H)$^+$.

Preparation of 6-bromo-1-(propan-2-yl)-1H-imidazo[4,5-b]pyridine (Int-68) According to Scheme 37

Scheme 37

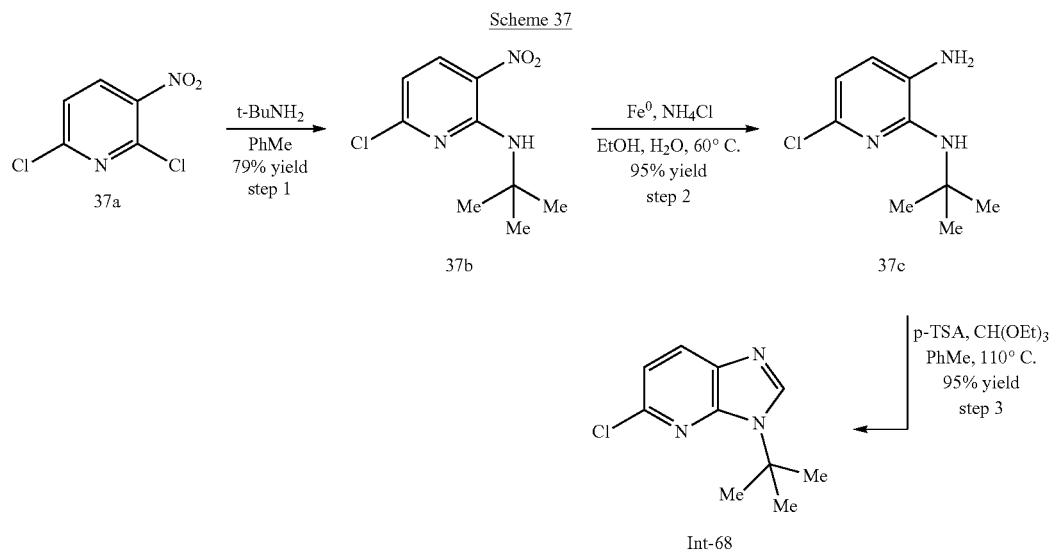 [SMILES: "t-BuNH2" ; O=[N+]([O-])c1ccc(Cl)nc1Cl ; CC(C)(C)Nc1nc(Cl)ccc1[N+](=O)[O-] ; CC(C)(C)Nc1nc(Cl)ccc1N ; CC(C)(C)n1cnc2ccc(Cl)nc21]

Step 1: Synthesis of N-tert-butyl-6-chloro-3-nitropyridin-2-amine (37b)

To a solution of 2,6-dichloro-3-nitropyridine (37a) in PhMe (30 mL) was added 2-methylpropan-2-amine (3.8 g, 51.8 mmol) at 0° C. The yellow solution was stirred at room temperature for 16 h. LCMS analysis showed consumption of the starting material with formation of the desired product mass. The reaction was concentrated to dryness. The residue was purified by flash chromatography (ISCO, 20 g SiO$_2$, 100% petroleum ether) to provide N-tert-butyl-6-chloro-3-nitropyridin-2-amine (37b) (4.7 g, 79% yield) as a yellow solid. m/z (ESI) for (C$_9$H$_{12}$ClN$_3$O$_2$), 229.9 (M+H)$^+$.

Step 2: Synthesis of N²-tert-butyl-6-chloropyridine-2,3-diamine (37c)

To a solution of N-tert-butyl-6-chloro-3-nitropyridin-2-amine (37b) (4.7 g, 20.5 mmol) in EtOH (200 mL) was added saturated aqueous NH$_4$Cl (60 mL) and Fe⁰ (5.7 g, 102 mmol). The mixture was stirred at 60° C. for 3 h. LCMS analysis indicated consumption of the starting material with formation of the desired product mass. The mixture was filtered and concentrated to remove EtOH. The mixture was diluted with H$_2$O (100 mL) and extracted with EtOAc (200 mL). The combined organic layers were dried over anhydrous Na$_2$SO$_4$, filtered, and concentrated to provide N²-tert-butyl-6-chloropyridine-2,3-diamine (37c) (3.9 g, 95% yield) as a black oil, which was taken on without further purification. m/z (ESI) for (C$_9$H$_{14}$ClN$_3$), 199.9 (M+H)⁺.

Step 3: Synthesis of 3-tert-butyl-5-chloro-3H-imidazo[4,5-b]pyridine (Int-68)

To a black mixture of N²-tert-butyl-6-chloropyridine-2,3-diamine (37c) (3.0 g, 15.0 mmol) and CH(OEt)$_3$ (4.5 g, 30.0 mmol) in PhMe (40.0 mL) was added p-TSA monohydrate (286 mg, 1.5 mmol). The mixture was stirred for 16 h at 110° C. LCMS analysis showed consumption of the starting material with formation of the desired product mass. The mixture was washed with saturated aqueous NaHCO$_3$ (60 mL). The aqueous layers were extracted with EtOAc (2×100 mL). The combined organic layers were dried over Na$_2$SO$_4$, filtered, and concentrated to provide 3-tert-butyl-5-chloro-3H-imidazo[4,5-b]pyridine (Int-68) as a black solid, which was taken on without further purification. m/z (ESI) for (C$_{10}$H$_{12}$ClN$_3$), 209.8 (M+H)⁺.

Preparation of (3R,4R)-4-Amino-1-(methanesulfonyl)piperidin-3-ol (Int-69) According to Scheme 38

(100 mL) and saturated Na$_2$CO$_3$ (100 mL) was added benzyl chloroformate (24.1 mL, 72.1 mmol, 50% in PhMe) drop-wise at 0° C. The mixture was stirred for 4 h then the organic phase was collected. The aqueous phase was extracted with DCM (2×100 mL). The combined organic phases were washed with H$_2$O (2×100 mL) and brine (100 mL), dried over Na$_2$SO$_4$, filtered, and concentrated. The crude residue was purified by flash chromatography (SiO$_2$, 0-60% EtOAc/hexanes) to provide tert-butyl (3R,4R)-4-{[(benzyloxy)carbonyl]amino}-3-hydroxypiperidine-1-carboxylate (38b) (18.0 g, 85% yield) as a light yellow oil. m/z (ESI+) for (C$_{18}$H$_{26}$N$_2$O$_5$), 251.3 (M+H-Boc)*.

Step 2: Synthesis of benzyl [(3R,4R)-3-hydroxy-1-(methanesulfonyl)piperidin-4-yl]carbamate (38c)

A solution of tert-butyl (3R,4R)-4-{[(benzyloxy)carbonyl]amino}-3-hydroxypiperidine-1-carboxylate (38b) (18.0 g, 51.4 mmol) and HCl in EtOH (1.25 M in EtOH, 123 mL, 154 mmol) was stirred at ambient temperature for 6 h and then concentrated. The residue was diluted with EtOAc (100 mL). Saturated aqueous NaHCO$_3$ (100 mL) was added and the mixture was cooled to 0° C. Methanesulfonyl chloride (6.5 mL, 83.9 mmol) was added drop-wise and the mixture was stirred at this temperature for 4 h. The layers were separated and the aqueous layer extracted with EtOAc (2×100 mL). The combined organic phases were washed with H$_2$O (2×100 mL) and brine (100 mL), dried over Na$_2$SO$_4$, filtered, and concentrated. The residue was triturated with pentane to provide benzyl [(3R,4R)-3-hydroxy-1-(methanesulfonyl)piperidin-4-yl]carbamate (38c) (12.0 g, 71% yield) as a white solid. m/z (ESI+) for (C$_{14}$H$_{20}$N$_2$O$_5$S), 329.4 (M+H)⁺.

Step 3: Synthesis of (3R,4R)-4-amino-1-(methanesulfonyl)piperidin-3-ol (Int-69)

A solution of benzyl [(3R,4R)-3-hydroxy-1-(methanesulfonyl)piperidin-4-yl]carbamate (38c) (12.0 g, 36.5 mmol)

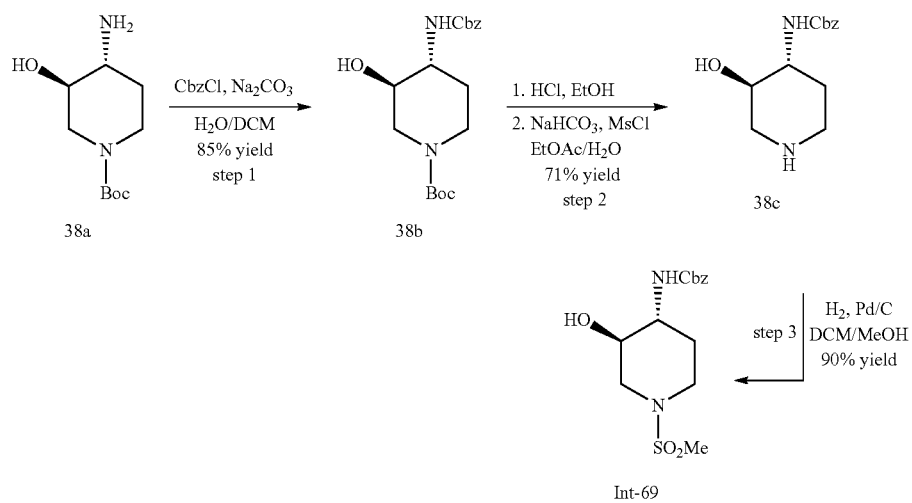

Scheme 38

Step 1: Synthesis of tert-butyl (3R,4R)-4-{[(benzyloxy)carbonyl]amino}-3-hydroxypiperidine-1-carboxylate (38b)

To a solution of tert-butyl (3R,4R)-4-amino-3-hydroxypiperidine-1-carboxylate (38a) (13.0 g, 60.1 mmol) in DCM in DCM:MeOH (5:4, 180 mL) was stirred in the presence of 15% Pd/C (0.583 g, 5.48 mmol) under a balloon of hydrogen at ambient temperature for 16 h. The reaction mixture was filtered through celite and washed with methanol (100 mL). The filtrate was concentrated under reduced pressure to provide (Int-69) (6.41 g, 90% yield) as white solid. ¹H NMR (400 MHz, CD$_3$OD) δ 3.83 (ddd, J=11.6, 5.0, 2.2 Hz, 1H), 3.73 (ddt, J=12.3, 4.8, 2.5 Hz, 1H), 3.46 (td, J=9.8, 5.0 Hz, 1H), 2.89-2.75 (m, 5H), 2.58 (dd, J=11.6, 10.1 Hz, 1H), (ddt, J=13.1, 5.0, 2.7 Hz, 1H) 1.66-1.54 (m, 1H); m/z (APCl+) for (C$_6$H$_{14}$N$_2$O$_3$S), 195.0 (M+H)$^+$; [α]D−19° (c 0.1, MeOH).

Preparation of (3R,4R)-4-amino-1-(methanesulfonyl)piperidin-3-ol (2S)-2-hydroxy-3-phenylpropanoic acid salt (Int-70) According to Scheme 39

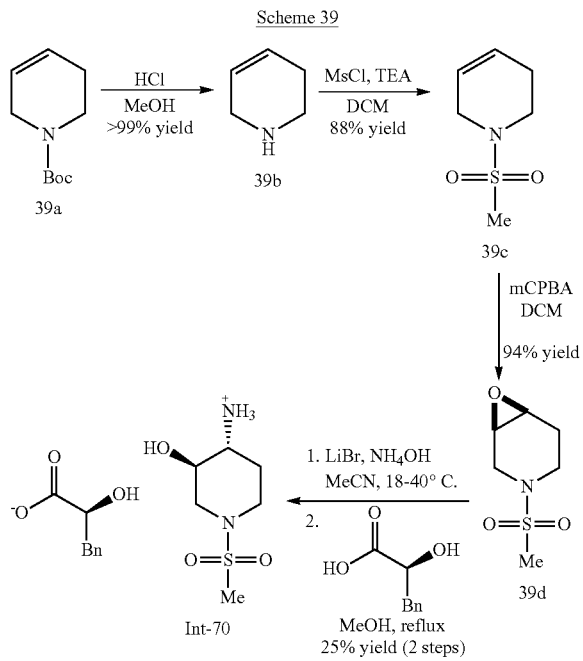

Scheme 39

Step 1: Synthesis of 1,2,3,6-tetrahydropyridine hydrochloride (39b)

To tert-butyl 3,6-dihydropyridine-1(2H)-carboxylate (39a) (150 g, 819 mmol) was added a solution of HCl (4.0 N in MeOH, 500 mL) and the mixture was stirred at room temperature for 16 h. LCMS analysis showed consumption of the starting material. The reaction was concentrated to dryness to provide 1,2,3,6-tetrahydropyridine hydrochloride (39b) (97.9 g, >99% yield), which was taken on without further purification. $^1$H NMR (400 MHz, D$_2$O) δ 5.96 (tdd, J=1.7, 3.9, 10.5 Hz, 1H), 5.80-5.61 (m, 1H), 3.65 (br s, 2H), 3.31 (t, J=6.1 Hz, 2H), 2.49-2.28 (m, 2H).

Step 2: Synthesis of 1-(methanesulfonyl)-1,2,3,6-tetrahydropyridine (39c)

To a slurry of 1,2,3,6-tetrahydropyridine hydrochloride (39b) (97.9 g, 818 mmol) in DCM (1.0 L) was added TEA (248 g, 2.5 mol). The mixture was cooled to 0-5° C. and then treated slowly dropwise with methane sulfonylchloride (112 g, 982 mmol), maintaining the reaction temperature <20° C. After addition the mixture was stirred a further 16 h at room temperature. The reaction was quenched by slow addition of H$_2$O (1 L). The phases were separated. The aqueous layer was extracted with DCM (1.5 L). The combined organics were washed successively with saturated aqueous NH$_4$Cl (500 mL), saturated aqueous NaHCO$_3$ (500 mL), saturated aqueous NH$_4$Cl (500 mL), and brine (500 mL), dried over Na$_2$SO$_4$, filtered, and concentrated. The resultant yellow solid was triturated with DCM/petroleum ether (1:15, 500 mL). The solids were collected by filtration and dried under vacuum to provide 1-(methanesulfonyl)-1,2,3,6-tetrahydropyridine (39c) (116 g, 88% yield) as a light yellow solid, which was taken on without further purification. $^1$H NMR (400 MHz, CDCl$_3$) δ 5.86 (dtd, J=1.7, 4.0, 8.1 Hz, 1H), 5.71 (dtd, J=1.2, 3.4, 8.5 Hz, 1H), 3.76 (quin, J=2.8 Hz, 2H), 3.37 (t, J=5.7 Hz, 2H), 2.81 (s, 3H), 2.26 (tt, J=2.9, 5.7 Hz, 2H)

Step 3: Synthesis of 3-(methanesulfonyl)-7-oxa-3-azabicyclo[4.1.0]heptane (39d)

To a solution of 1-(methanesulfonyl)-1,2,3,6-tetrahydropyridine (39c) (116 g, 720 mmol) in DCM (1.5 L) was added m-CPBA (175 g, 863 mmol) portion-wise. The mixture was stirred at ambient temperature for 48 h. TLC analysis indicated consumption of the starting material. The heterogeneous mixture was filtered to remove the solids. The filtrate was basified with saturated aqueous Na$_2$CO$_3$ (1.0 L) and washed with saturated aqueous Na$_2$SO$_3$ (1.5 L). The aqueous layer was extracted with DCM (2×1.5 L). The combined organics were washed with brine (1.5 L), dried over Na$_2$SO$_4$, filtered, and concentrated to provide 3-(methanesulfonyl)-7-oxa-3-azabicyclo[4.1.0]heptane (39d) (120 g, 94% yield) as a light yellow solid, which was taken on without further purification. $^1$H NMR (400 MHz, CDCl$_3$) δ 3.84 (ddd, J=1.0, 3.6, 14.3 Hz, 1H), 3.57 (d, J=14.3 Hz, 1H), 3.36 (dd, J=2.0, 3.7 Hz, 1H), 3.34-3.26 (m, 2H), 3.09 (ddd, J=4.7, 8.4, 12.9 Hz, 1H), 2.82 (s, 3H), 2.21-2.04 (m, 2H).

Step 4: Synthesis of (3R,4R)-4-amino-1-(methanesulfonyl)piperidin-3-ol (2S)-2-hydroxy-3-phenylpropanoic acid salt (Int-70)

To a solution of 3-(methanesulfonyl)-7-oxa-3-azabicyclo [4.1.0]heptane (39d) (10.0 g, 56 mmol) in MeCN (100 mL) was added LiBr (1.96 g, 22.6 mmol) and NH$_4$OH (14.1 g, 113 mmol). The mixture was stirred at ambient temperature for 48 h. TLC analysis (1:1 petroleum ether/EtOAc) indicated remaining starting material. The reaction mixture was warmed to 40° C. and stirred at this temperature for 36 h. TLC analysis (1:1 petroleum ether/EtOAc) indicated consumption of the starting material. The reaction was concentrated to dryness to provide rac-(3R,4R)-4-amino-1-(methanesulfonyl)piperidin-3-ol (11 g, crude). The crude mixture containing rac-(3R,4R)-4-amino-1-(methanesulfonyl)piperidin-3-ol (11 g) was taken up in MeOH (120 mL) and the mixture was warmed to reflux until the solution became clear. The mixture was cooled to room temperature and a solution of (2S)-2-hydroxy-3-phenylpropanoic acid (9.41 g, 56.6 mmol) in MeOH (30 mL) was added. The solution turned cloudy followed by extensive precipitation. The mixture was stirred at reflux for 10 min and then allowed to slowly cool to room temperature. The solution was stirred at room temperature for 16 h. The precipitate was collected by filtration. The solids were taken up in MeOH (30 mL) and stirred at reflux for 10 min. The solution was slowly cooled to room temperature. The resultant precipitate was collected by filtration to provide (3R,4R)-4-amino-1-(methanesulfonyl)piperidin-3-ol (2S)-2-hydroxy-3-phenylpropanoic acid salt (Int-70) (5.0 g, 25% yield) as a white solid. Enantiomeric excess (97% ee) was determined for the corresponding N-CBz protected derivative by chiral SFC with a Chiralpak AS-3 column (4.6×150 mm, 3 μm particle size, 35°

C.), which was eluted with 5-40% EtOH/CO$_2$ (+0.05% diethylamine) with a flow rate of 2.5 mL/min. $^1$H NMR (400 MHz, CD$_3$OD) δ 7.35-7.13 (m, 5H), 4.14 (dd, J=3.5, 8.2 Hz, 1H), 3.89 (ddd, J=2.1, 5.0, 11.7 Hz, 1H), 3.83-3.73 (m, 1H), 3.60 (dt, J=5.1, 10.0 Hz, 1H), 3.13 (dd, J=3.4, 13.8 Hz, 1H), 2.98 (ddd, J=4.5, 9.8, 12.1 Hz, 1H), 2.92-2.77 (m, 5H), 2.69-2.56 (m, 1H), 2.18-2.02 (m, 1H), 1.78-1.60 (m, 1H).

PREPARATION OF EXAMPLES

Example 1 (Scheme A-1): Preparation of (3R,4R)-4-({5-chloro-4-[4-fluoro-2-methyl-1-(propan-2-yl)-1H-benzimidazol-6-yl]pyrimidin-2-yl}amino)-1-(methanesulfonyl)piperidin-3-ol sparged with N$_2$ and then stirred at 100° C. for 16 h. TLC analysis (1:1 petroleum ether/EtOAc) showed complete consumption of the starting material. The black suspension was poured into H$_2$O (3.0 L) and extracted with EtOAc (2×3 L). The combined organic phases were washed with brine, dried over Na$_2$SO$_4$, filtered, and concentrated. The residue was purified by flash chromatography (Biotage, 1.0 kg, 0-40% EtOAc/petroleum ether) to provide 4-fluoro-2-methyl-1-(propan-2-yl)-6-(4,4,5,5-tetramethyl-1,3,2-dioxaborolan-2-yl)-1H-benzimidazole (A-1) (77 g, 73% yield) as a yellow solid. $^1$H NMR (400 MHz, CDCl$_3$) δ 7.69 (s, 1H), 7.33 (d, J=10.8 Hz, 1H), 4.77-4.61 (m, 1H), 2.65 (s, 3H), 1.65 (d, J=7.0 Hz, 6H), 1.36 (s, 12H); m/z (ESI+) for (C$_7$H$_{24}$BFN$_2$O$_2$), 319.2 (M+H)$^+$.

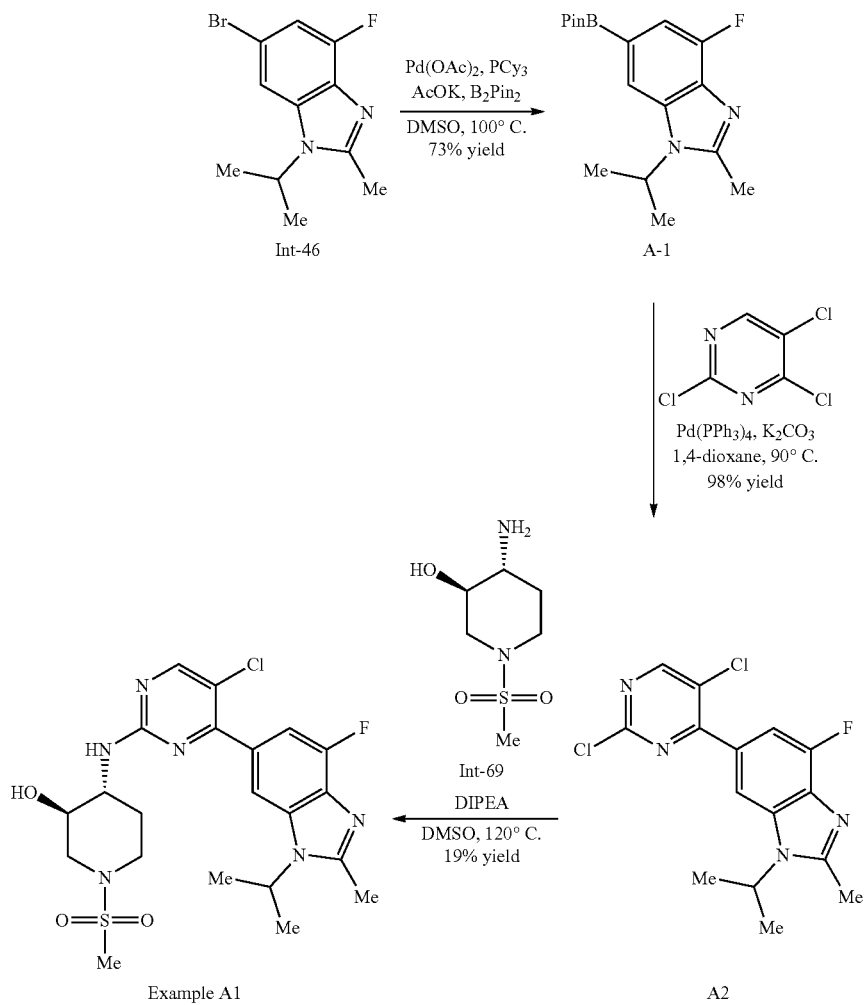

Step 1: Synthesis of 4-fluoro-2-methyl-1-(propan-2-yl)-6-(4,4,5,5-tetramethyl-1,3,2-dioxaborolan-2-yl)-1H-benzimidazole (A-1)

A suspension of 6-bromo-4-fluoro-2-methyl-1-(propan-2-yl)-1H-benzimidazole (Int-46) (90 g, 331.95 mmol), bis(pinacolato)diboron (126 g, 498 mmol), AcOK (80 g, 815.15 mmol), tricyclohexylphosphine (14 g, 49.8 mmol), and Pd(OAc)$_2$ (7.45 g, 33.2 mmol) in DMSO (1.0 L) was Step 2: Synthesis of 6-(2,5-dichloropyrimidin-4-yl)-4-fluoro-2-methyl-1-(propan-2-yl)-1H-benzimidazole (A-2)

A mixture of 4-fluoro-2-methyl-1-(propan-2-yl)-6-(4,4,5,5-tetramethyl-1,3,2-dioxaborolan-2-yl)-1H-benzimidazole (A-1) (300 mg, 0.943 mmol), 2,4,5-trichloropyrimidine (259 mg, 0.16 mL, 1.41 mmol) and K$_2$CO$_3$ (260 mg, 1.89 mmol) in 1,4-dioxane (9 mL) and H$_2$O (3 mL) was sparged with N$_2$ for 5 min. Pd(PPh$_3$)$_4$ (54.5 mg, 0.047 mmol) was added and the mixture was sparged with N$_2$ for an additional 10 min. The mixture was stirred at 90° C. for 16 h before being cooled to ambient temperature, diluted with H$_2$O (15 mL), and extracted with EtOAc (3×10 mL). The combined organic phases were washed with brine (10 mL), dried over Na$_2$SO$_4$, filtered, and concentrated. To this crude mixture was added a second crude mixture from a reaction run in analogous fashion on a 100 mg scale. The reside was purified by flash chromatography (SiO$_2$, 100% EtOAc) to provide 6-(2,5-dichloropyrimidin-4-yl)-4-fluoro-2-methyl-1-(propan-2-yl)-1H-benzimidazole (A-2) (420 mg, 98% yield). m/z (ESI+) for (C$_{15}$H$_{13}$N$_4$FCl$_2$), 338.9 (M+H)$^+$.

Step 3: Synthesis of (3R,4R)-4-({5-chloro-4-[4-fluoro-2-methyl-1-(propan-2-yl)-1H-benzimidazol-6-yl]pyrimidin-2-yl}amino)-1-(methanesulfonyl)piperidin-3-ol (Example A1)

To a yellow suspension of 6-(2,5-dichloropyrimidin-4-yl)-4-fluoro-2-methyl-1-(propan-2-yl)-1H-benzimidazole (A-2) (210 mg, 0.619 mmol) in DMSO (5 mL) was added DIPEA (240 mg, 0.331 mL, 1.86 mmol) and (3R,4R)-4-amino-1-(methanesulfonyl)piperidin-3-ol (Int-69) (241 mg, 1.24 mmol). The mixture was stirred at 120° C. for 16 h and then diluted with H$_2$O (20 mL) and extracted with EtOAc (3×20 mL). The combined organic phases were washed with brine (20 mL), dried over Na$_2$SO$_4$, filtered, and concentrated. The crude residue was purified by preparative HPLC with an Agela Durashell C18 column (150×25 mm, 5 µm particle size; column temperature 25° C.), which was eluted with 34-54% MeCN/H$_2$O (+0.05% NH$_4$OH) with a flow rate of 25 mL/min to provide (3R,4R)-4-({5-chloro-4-[4-fluoro-2-methyl-1-(propan-2-yl)-1H-benzimidazol-6-yl]pyrimidin-2-yl}amino)-1-(methanesulfonyl)piperidin-3-ol (Example A1) (54.7 mg, 19% yield) as a yellow solid. $^1$H NMR (400 MHz, DMSO-d$_6$) δ 8.41 (s, 1H), 8.02-7.79 (m, 1H), 7.54-7.27 (m, 2H), 5.24 (d, J=4.5 Hz, 1H), 4.86-4.71 (m, 1H), 3.86-3.74 (m, 1H), 3.60 (br d, J=9.5 Hz, 2H), 3.53-3.45 (m, 1H), 2.94-2.79 (m, 4H), 2.69-2.59 (m, 4H), 2.07 (s, 1H), 1.62-1.46 (m, 7H); m/z (ESI+) for (C$_{21}$H$_{26}$ClFN$_6$O$_3$S), 497.3 (M+H)$^+$.

The examples in the below table were synthesized according to the methods used for the synthesis of (3R,4R)-4-({5-chloro-4-[4-fluoro-2-methyl-1-(propan-2-yl)-1H-benzimidazol-6-yl]pyrimidin-2-yl}amino)-1-(methanesulfonyl)piperidin-3-ol (Example A1). The following examples were synthesized with non-critical changes or substitutions to the exemplified procedures that someone who is skilled in the art would be able to realize. If necessary, separation of enantiomers of was carried out under standard methods known in the art, such as chiral SFC or HPLC, to afford single enantiomers.

| Example number | Structure/Name | LCMS | NMR |
| --- | --- | --- | --- |
| A2 | (3R,4R)-4-({5-fluoro-4-[4-fluoro-2-methyl-1-(propan-2-yl)-1H-benzimidazol-6-yl]pyrimidin-2-yl}amino)-1-(methanesulfonyl)piperidin-3-ol | 481.2 [M + H]$^+$ (ESI) | $^1$H NMR (400 MHz, DMSO-d$_6$) δ 8.44 (d, J = 4.03 Hz, 1H), 8.16-8.03 (m, 1H), 7.71-7.50 (m, 1H), 7.32-7.17 (m, 1H), 5.28-5.19 (m, 1H), 4.90-4.74 (m, 1H), 3.87-3.72 (m, 1H), 3.70-3.57 (m, 2H), 3.54-3.45 (m, 1H), 2.92 (s, 3H), 2.89-2.83 (m, 1H), 2.73-2.66 (m, 1H), 2.64 (s, 3H), 2.36-2.30 (m, 1H), 1.60 (d, J = 6.85 Hz, 6H), 1.57-1.50 (m, 1H) |
| A3 | 4-(1-tert-butyl-4-fluoro-1H-benzimidazol-6-yl)-5-fluoro-N-(1-methylpiperidin-4-yl)pyrimidin-2-amine | 401.1 [M + H]$^+$ (ESI) | $^1$H NMR (400 MHz, CD$_3$OD) δ 8.51 (br s, 1H), 8.43-8.34 (m, 3H), 7.82 (d, J = 12.0 Hz, 1H), 4.19-4.06 (m, 1H), 3.50-3.40 (m, 2H), 3.29-3.13 (m, 2H), 2.83 (s, 3H), 2.35-2.25 (m, 2H), 1.95-1.82 (m, 11H) |

| Example number | Structure/Name | LCMS | NMR |
|---|---|---|---|
| A4 | 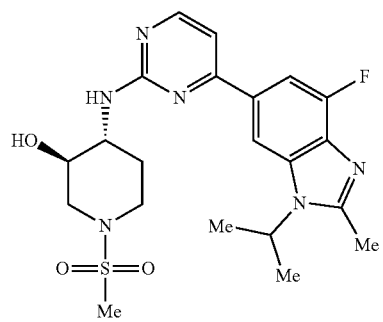<br>(3R,4R)-4-({4-[4-fluoro-2-methyl-1-(propan-2-yl)-1H-benzimidazol-6-yl]pyrimidin-2-yl}amino)-1-(methanesulfonyl)piperidin-3-ol | 463.3 $[M + H]^+$ (ESI) | $^1$H NMR (400 MHz, DMSO-d$_6$) δ 8.35 (d, J = 5.3 Hz, 1H), 8.22 (s, 1H), 7.76 (d, J = 12.3 Hz, 1H), 7.32 (d, J = 5.5 Hz, 1H), 7.14 (d, J = 7.8 Hz, 1H), 5.27 (br d, J = 4.0 Hz, 1H), 4.90-4.75 (m, 1H), 3.84 (br s, 1H), 3.73-3.44 (m, 3H), 3.05-2.87 (m, 4H), 2.69-2.65 (m, 1H), 2.62 (s, 3H), 2.19-2.00 (m, 1H), 1.61 (d, J = 6.3 Hz, 7H) |
| A5 | 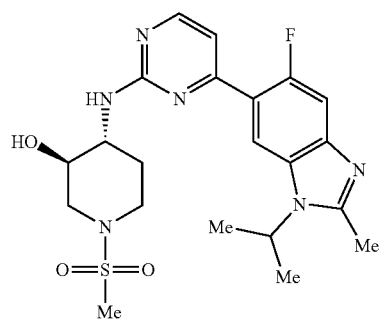<br>(3R,4R)-4-({4-[5-fluoro-2-methyl-1-(propan-2-yl)-1H-benzimidazol-6-yl]pyrimidin-2-yl}amino)-1-(methanesulfonyl)piperidin-3-ol | 463.1 $[M + H]^+$ (ESI) | $^1$H NMR (400 MHz, DMSO-d$_6$) δ 8.39-8.09 (m, 2H), 7.47-7.41 (m, 1H), 7.20 (d, J = 7.8 Hz, 1H), 7.03 (br s, 1H), 5.27 (br s, 1H), 4.85-4.70 (m, 1H), 3.82 (br s, 1H), 3.75-3.60 (m, 2H), 3.56-3.45 (m, 1H), 2.91 (s, 3H), 2.88-2.79 (m, 1H), 2.70-2.60 (m, 1H), 2.59 (s, 3H), 2.20-2.00 (m, 1H), 1.65-1.60 (m, 7H) |
| A6 | 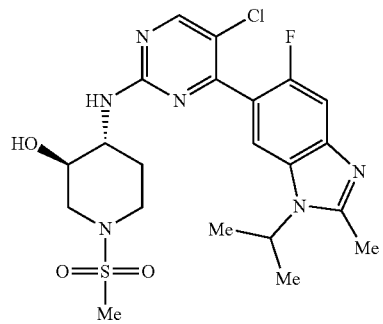<br>(3R,4R)-4-({5-chloro-4-[5-fluoro-2-methyl-1-(propan-2-yl)-1H-benzimidazol-6-yl]pyrimidin-2-yl}amino)-1-(methanesulfonyl)piperidin-3-ol | 497.3 $[M + H]^+$ (ESI) | $^1$H NMR (400 MHz, DMSO-d$_6$) δ 8.42 (s, 1H), 7.73 (d, J = 6.0 Hz, 1H), 7.66-7.48 (m, 1H), 7.44 (d, J = 10.5 Hz, 1H), 5.22 (d, J = 4.3 Hz, 1H), 4.85-4.70 (m, 1H), 3.79 (br s, 1H), 3.65-3.55 (m, 2H), 3.50-3.40 (m, 1H), 2.88 (br s, 4H), 2.70-2.60 (m, 1H), 2.58 (s, 3H), 2.08 (s, 1H), 1.60-1.45 (m, 7H) |

| Example number | Structure/Name | LCMS | NMR |
|---|---|---|---|
| A7 | 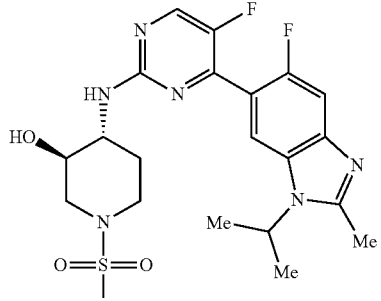<br>(3R,4R)-4-({5-fluoro-4-[5-fluoro-2-methyl-1-(propan-2-yl)-1H-benzimidazol-6-yl]pyrimidin-2-yl}amino)-1-(methanesulfonyl)piperidin-3-ol | 481.3 [M + H]⁺ (ESI) | ¹H NMR (400 MHz, DMSO-d₆) δ 8.42 (d, J = 2.0 Hz, 1H), 7.82 (d, J = 6.0 Hz, 1H), 7.46 (d, J = 10.8 Hz, 1H), 7.32 (br s, 1H), 5.21 (d, J = 4.5 Hz, 1H), 4.85-4.70 (m, 1H), 3.73 (br s, 1H), 3.67-3.56 (m, 2H), 3.50-3.40 (m, 1H), 2.88 (s, 3H), 2.86-2.78 (m, 1H), 2.70-2.60 (m, 1H), 2.59 (s, 3H), 2.07 (s, 1H), 1.60-1.45 (m, 7H) |
| A8 | 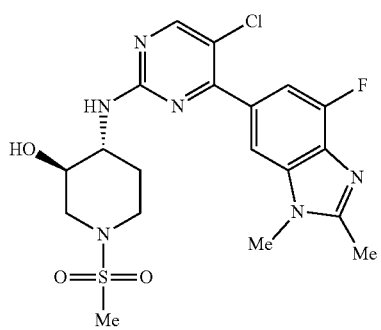<br>(3R,4R)-4-{[5-chloro-4-(4-fluoro-1,2-dimethyl-1H-benzimidazol-6-yl)pyrimidin-2-yl]amino}-1-(methanesulfonyl)piperidin-3-ol | 469.2 [M + H]⁺ (ESI) | ¹H NMR (400 MHz, DMSO-d₆) δ 8.42 (s, 1H), 7.77 (br s, 1H), 7.60-7.31 (m, 2H), 5.22 (d, J = 4.5 Hz, 1H), 3.81 (br s, 1H), 3.79 (s, 3H), 3.67-3.55 (m, 2H), 3.50-3.40 (m, 1H), 2.89 (s, 3H), 2.88-2.82 (m, 1H), 2.70-2.60 (m, 1H), 2.58 (s, 3H), 2.04 (br s, 1H), 1.59-1.42 (m, 1H) |
| A9 | 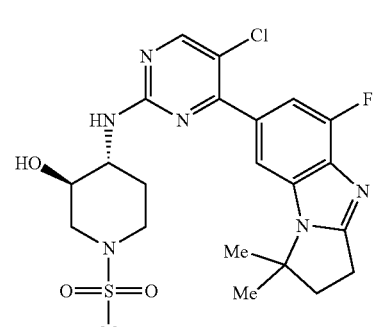<br>(3R,4R)-4-{[5-chloro-4-(5-fluoro-1,1-dimethyl-2,3-dihydro-1H-pyrrolo[1,2-a]benzimidazol-7-yl)pyrimidin-2-yl]amino}-1-(methanesulfonyl)piperidin-3-ol | 509.3 [M + H]⁺ (ESI) | ¹H NMR (400 MHz, DMSO-d₆) δ 8.42 (s, 1H), 7.84 (br s, 1H), 7.59-7.32 (m, 2H), 5.22 (br s, 1H), 3.78 (br s, 1H), 3.59 (br d, J = 10.0 Hz, 2H), 3.48 (br d, J = 11.7 Hz, 1H), 3.08 (t, J = 7.5 Hz, 2H), 2.89 (s, 3H), 2.86-2.79 (m, 1H), 2.69-2.61 (m, 1H), 2.58-2.53 (m, 2H), 2.05 (br s, 1H), 1.62 (s, 6H), 1.52 (br d, J = 11.7 Hz, 1H) |

| Example number | Structure/Name | LCMS | NMR |
|---|---|---|---|
| A10 | (3R,4R)-4-({5-chloro-4-[(4S)-9-fluoro-4-methyl-3,4-dihydro-1H-[1,4]oxazino[4,3-a]benzimidazol-7-yl]pyrimidin-2-yl}amino)-1-(methanesulfonyl)piperidine-3-ol | 511.2 [M + H]$^+$ (ESI) | $^1$H NMR (400 MHz, DMSO-d$_6$) δ 8.44 (s, 1H), 7.89 (br s, 1H), 7.58-7.39 (m, 2H), 5.22 (d, J = 4.5 Hz, 1H), 5.09-5.03 (m, 1H), 4.97-4.91 (m, 1H), 4.70 (br d, J = 5.5 Hz, 1H), 4.17-4.10 (m, 1H), 4.06-3.98 (m, 1H), 3.82 (br d, J = 5.8 Hz, 1H), 3.67-3.57 (m, 2H), 3.50-3.40 (m, 1H), 2.93-2.82 (m, 4H), 2.70-2.60 (m, 1H), 2.11-2.00 (m, 1H), 1.60-1.45 (m, 4H) |
| A11 | (3R,4R)-4-({5-chloro-4-[(4R)-9-fluoro-4-methyl-3,4-dihydro-1H-[1,4]oxazino[4,3-a]benzimidazol-7-yl]pyrimidin-2-yl}amino)-1-(methanesulfonyl)piperidin-3-ol | 511.2 [M + H]$^+$ (ESI) | $^1$H NMR (400 MHz, DMSO-d$_6$) δ 8.44 (s, 1H), 7.82 (s, 1H), 7.59-7.44 (m, 2H), 5.23 (d, J = 4.8 Hz, 1H), 5.13-5.07 (m, 1H), 5.02-4.96 (m, 1H), 4.42 (dd, J = 3.0, 12.0 Hz, 1H), 4.19 (ddd, J = 3.5, 6.3, 10.0 Hz, 1H), 3.90-3.76 (m, 2H), 3.68-3.56 (m, 2H), 3.50-3.40 (m, 1H), 2.90 (s, 3H), 2.88-2.81 (m, 1H), 2.73-2.61 (m, 1H), 2.11-2.00 (m, 1H), 1.62-1.46 (m, 1H), 1.38 (d, J = 6.3 Hz, 3H) |
| A12 | 1,5-anhydro-3-[(5-chloro-4-{4-fluoro-2-[(1S)-1-hydroxyethyl]-1-(propan-2-yl)-1H-benzimidazol-6-yl}pyrimidin-2-yl)amino]-2,3-dideoxy-D-threo-pentitol | 450.1 [M + H]$^+$ (ESI) | $^1$H NMR (400 MHz, CD$_3$OD) δ 8.37-8.31 (m, 1H), 8.05 (s, 1H), 7.50 (br d, J = 11.5 Hz, 1H), 5.39-5.29 (m, 1H), 5.23 (q, J = 6.6 Hz, 1H), 4.03-3.88 (m, 3H), 3.63 (dt, J = 4.8, 9.4 Hz, 1H), 3.48 (dt, J = 2.0, 11.6 Hz, 1H), 3.21 (dd, J = 9.8, 11.0 Hz, 1H), 2.19-2.09 (m, 1H), 1.75-1.53 (m, 10H) |

| Example number | Structure/Name | LCMS | NMR |
|---|---|---|---|
| A13 | 1,5-anhydro-3-[(5-chloro-4-{4-fluoro-2-[(1R)-1-hydroxyethyl]-1-(propan-2-yl)-1H-benzimidazol-6-yl}pyrimidin-2-yl)amino]-2,3-dideoxy-D-threo-pentitol | 450.3 [M + H]+ (ESI) | $^1$H NMR (400 MHz, DMSO-d$_6$) δ 8.43 (s, 1H), 8.09-7.83 (m, 1H), 7.59-7.32 (m, 2H), 5.79 (br d, J = 6.4 Hz, 1H), 5.20-5.15 (m, 1H), 5.14-5.06 (m, 1H), 4.96 (br d, J = 5.2 Hz, 1H), 3.88-3.78 (m, 3H), 3.51 (br s, 1H), 3.10-2.98 (m, 1H), 1.96 (br s, 1H), 1.65-1.55 (m, 10H). one signal obscured by residual water |
| A14 | *first eluting stereomisomer (3R,4R)-4-({5-chloro-4-[4-fluoro-1-(oxolan-3-yl)-1H-benzimidazol-6-yl]pyrimidin-2-yl}amino)-1-(methanesulfonyl)piperidin-3-ol | 511.1 [M + H]+ (ESI) | $^1$H NMR (400 MHz, DMSO-d$_6$) δ 8.44 (s, 2H), 7.98 (br s, 1H), 7.64-7.36 (m, 2H), 5.36 (br s, 1H), 5.22 (d, J = 4.5 Hz, 1H), 4.20-4.12 (m, 1H), 4.07 (br d, J = 9.0 Hz, 1H), 4.01-3.94 (m, 1H), 3.88-3.78 (m, 2H), 3.67-3.56 (m, 2H), 3.49 (s, 1H), 2.90 (s, 3H), 2.87-2.81 (m, 1H), 2.66 (br t, J = 10.8 Hz, 1H), 2.61-2.54 (m, 1H), 2.32-2.20 (m, 1H), 2.10-1.99 (m, 1H), 1.60-1.47 (m, 1H) |
| A15 | (3R,4R)-4-{[5-chloro-4-(1-cyclopropyl-4-fluoro-1H-benzimidazol-6-yl)pyrimidin-2-yl]amino}-1-(methanesulfonyl)piperidin-3-ol | 481.2 [M + H]+ (ESI) | $^1$H NMR (4500 MHz, CD$_3$OD) δ 8.38 (s, 1H), 8.35 (s, 1H), 8.06 (s, 1H), 7.56 (dd, J = 1.0, 11.7 Hz, 1H), 3.98-3.92 (m, 1H), 3.85 (ddd, J = 1.8, 4.7, 11.7 Hz, 1H), 3.76 (dt, J = 4.9, 9.0 Hz, 1H), 3.72-3.67 (m, 1H), 3.60 (m, 1H), 2.96 (dt, J = 2.7, 11.9 Hz, 1H), 2.90 (s, 3H), 2.77 (dd, J = 9.5, 11.6 Hz, 1H), 2.25 (br dd, J = 3.7, 13.4 Hz, 1H), 1.80-1.61 (m, 1H), 1.31-1.22 (m, 2H), 1.20-1.09 (m, 2H) |

| Example number | Structure/Name | LCMS | NMR |
|---|---|---|---|
| A16 | (3R,4R)-4-({5-chloro-4-[4-chloro-1-(propan-2-yl)-1H-benzimidazol-6-yl]pyrimidin-2-yl}amino)-1-(methanesulfonyl)piperidin-3-ol | 521.1 [M + Na]⁺ (ESI) | $^1$H NMR (400 MHz, DMSO-$d_6$) δ 8.58 (s, 1H), 8.44 (s, 1H), 8.04 (s, 1H), 7.67 (d, J = 1.1 Hz, 1H), 7.55 (br s, 1H), 5.23 (d, J = 4.5 Hz, 1H), 4.83 (td, J = 6.7, 13.4 Hz, 1H), 3.81 (br d, J = 5.6 Hz, 1H), 3.70-3.55 (m, 2H), 3.50-3.40 (m, 1H), 2.96-2.77 (m, 4H), 2.72-2.61 (m, 1H), 2.06 (br s, 1H), 1.64-1.46 (m, J = 6.7 Hz, 7H) |
| A17 | *first eluting stereoisomer (3R,4R)-4-{[4-(4-ethyl-9-fluoro-3,4-dihydro-1H-[1,4]oxazino[4,3-a]benzimidazol-7-yl)-5-fluoropyrimidin-2-yl]amino}-1-(methanesulfonyl)piperidin-3-ol | 509.0 [M + H]⁺ (ESI) | $^1$H NMR (400 MHz, DMSO-$d_6$) δ 8.45 (d, J = 4.0 Hz, 1H), 8.05 (s, 1H), 7.70 (d, J = 12.0 Hz, 1H), 7.24 (d, J = 7.8 Hz, 1H), 5.21 (d, J = 4.5 Hz, 1H), 5.13-5.02 (m, 1H), 4.99-4.89 (m, 1H), 4.54 (br s, 1H), 4.22 (d, J = 12.0 Hz, 1H), 4.04 (dd, J = 3.5, 12.3 Hz, 1H), 3.78 (br s, 1H), 3.67-3.55 (m, 2H), 3.55-3.45 (m, 1H), 2.99-2.83 (m, 4H), 2.75-2.61 (m, 1H), 2.21-2.05 (m, 1H), 2.00-1.84 (m, 2H), 1.65-1.45 (m, 1H), 0.99 (t, J = 7.5 Hz, 3H); $[\alpha]_D^{20}$ = −66 (c = 0.1, MeOH) |
| A18 | (3R,4R)-4-{[5-fluoro-4-(9-fluoro-4,4-dimethyl-3,4-dihydro-1H-[1,4]oxazino[4,3-a]benzimidazol-7-yl)pyrimidin-2-yl]amino}-1-(methanesulfonyl)piperidin-3-ol | 509.1 [M + H]⁺ (ESI) | $^1$H NMR (400 MHz, DMSO-$d_6$) δ 8.45 (d, J = 3.8 Hz, 1H), 8.18 (s, 1H), 7.68 (br d, J = 11.8 Hz, 1H), 7.26 (br d, J = 7.8 Hz, 1H), 5.23 (d, J = 4.5 Hz, 1H), 4.99 (s, 2H), 3.93 (s, 2H), 3.78 (br s, 1H), 3.69-3.57 (m, 2H), 3.55-3.45 (m, 1H), 2.93-2.83 (m, 4H), 2.71-2.65 (m, 1H), 2.11 (br s, 1H), 1.65 (s, 6H), 1.56-1.46 (m, 1H) |

| Example number | Structure/Name | LCMS | NMR |
|---|---|---|---|
| A19 | 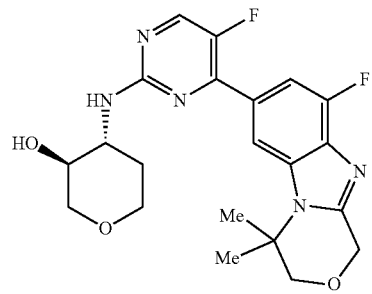<br>1,5-anhydro-2,3-dideoxy-3-{[5-fluoro-4-(9-fluoro-4,4-dimethyl-3,4-dihydro-1H-[1,4]oxazino[4,3-a]benzimidazol-7-yl)pyrimidin-2-yl]amino}-D-threo-pentitol | 432.1 [M + H]+ (ESI) | $^1$H NMR (400 MHz, DMSO-d$_6$) δ 8.44 (d, J = 4.0 Hz, 1H), 8.21 (br s, 1H), 7.67 (d, J = 12.0 Hz, 1H), 7.23 (d, J = 7.8 Hz, 1H), 5.02-4.93 (m, 3H), 3.93 (s, 2H), 3.87-3.76 (m, 3H), 3.55-3.45 (m, 1H), 3.32 (br s, 1H), 3.06 (t, J = 10.4 Hz, 1H), 2.00 (br s, 1H), 1.65 (d, J = 1.8 Hz, 6H), 1.56-1.44 (m, 1H) |
| A20 | 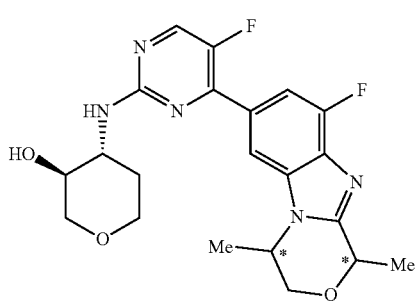<br>*second eluting stereoisomer<br>1,5-anhydro-3-{[5-chloro-4-(9-fluoro-1,4-dimethyl-3,4-dihydro-1H-[1,4]oxazino[4,3-a]benzimidazol-7-yl)pyrimidin-2-yl]amino}-2,3-dideoxy-D-threo-pentitol | 447.8 [M + H]+ (ESI) | $^1$H NMR (400 MHz, CDCl$_3$) δ 8.33 (s, 1H), 7.64 (d, J = 1.2 Hz, 1H), 7.47 (dd, J = 1.2, 11.2 Hz, 1H), 5.29 (br d, J = 5.9 Hz, 1H), 4.99 (q, J = 6.6 Hz, 1H), 4.48 (q, J = 6.8 Hz, 1H), 4.12 (d, J = 1.5 Hz, 2H), 4.06 (dd, J = 5.0, 11.4 Hz, 1H), 3.99 (br dd, J = 4.3, 11.3 Hz, 1H), 3.89-3.80 (m, 1H), 3.63 (dt, J = 5.0, 9.4 Hz, 1H), 3.46 (dt, J = 2.1, 11.8 Hz, 1H), 3.18 (t, J = 10.7 Hz, 1H), 2.10-2.01 (m, 1H), 1.80 (d, J = 6.6 Hz, 3H), 1.77-1.67 (m, 1H), 1.64 (d, J = 6.6 Hz, 3H) |
| A21 | 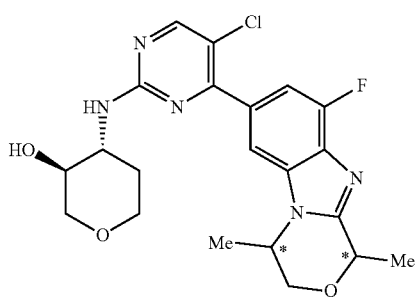<br>*first eluting stereoisomer<br>1,5-anhydro-3-{[5-chloro-4-(9-fluoro-1,4-dimethyl-3,4-dihydro-1H-[1,4]oxazino[4,3-a]benzimidazol-7-yl)pyrimidin-2-yl]amino}-2,3-dideoxy-D-threo-pentitol | 447.8 [M + H]+ (ESI) | $^1$H NMR (400 MHz, CDCl$_3$) δ 8.33 (s, 1H), 7.62 (s, 1H), 7.47 (dd, J = 1.1, 11.2 Hz, 1H), 5.28 (br d, J = 5.7 Hz, 1H), 5.06-4.72 (m, 2H), 4.48 (q, J = 6.6 Hz, 1H), 4.12 (d, J = 1.7 Hz, 2H), 4.06 (dd, J = 5.0, 11.4 Hz, 1H), 3.99 (br dd, J = 4.3, 11.7 Hz, 1H), 3.90-3.80 (m, 1H), 3.63 (dt, J = 4.8, 9.4 Hz, 1H), 3.51-3.42 (m, 1H), 3.18 (t, J = 10.6 Hz, 1H), 2.09-2.01 (m, 1H), 1.81 (d, J = 6.6 Hz, 3H), 1.77-1.69 (m, 1H), 1.64 (d, J = 6.6 Hz, 3H) |

| Example number | Structure/Name | LCMS | NMR |
|---|---|---|---|
| A22 | 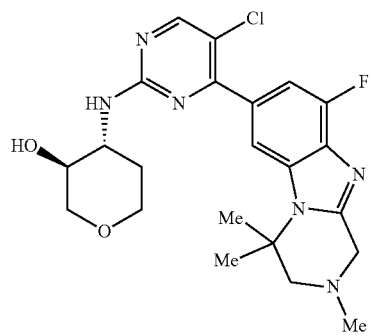<br>1,5-anhydro-3-{[5-chloro-4-(9-fluoro-2,4,4-trimethyl-1,2,3,4-tetrahydropyrazino[1,2-a]benzimidazol-7-yl)pyrimidin-2-yl]amino}-2,3-dideoxy-D-threo-pentitol | 461.1 [M + H]⁺ (ESI) | $^1$H NMR (400 MHz, DMSO-$d_6$) δ 8.41 (s, 1H), 8.09-7.88 (m, 1H), 7.47 (br s, 2H), 4.94 (br d, J = 5.4 Hz, 1H), 3.86-3.71 (m, 5H), 3.50 (br s, 1H), 3.29-3.25 (m, 1H), 3.03 (br t, J = 10.3 Hz, 1H), 2.75 (s, 2H), 2.44 (s, 3H), 1.95 (br s, 1H), 1.65 (s, 6H), 1.56-1.48 (m, 1H) |
| A23 | 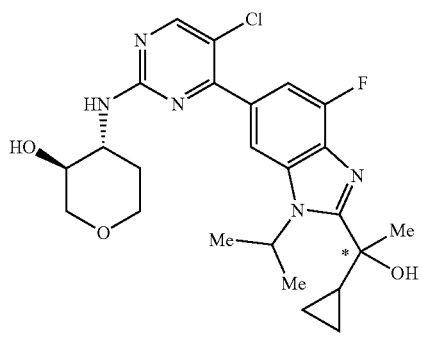<br>*first eluting stereoisomer<br>1,5-anhydro-3-({5-chloro-4-[2-(1-cyclopropyl-1-hydroxyethyl)-4-fluoro-1-(propan-2-yl)-1H-benzimidazol-6-yl]pyrimidin-2-yl}amino)-2,3-dideoxy-D-threo-pentitol | 490.0 [M + H]⁺ (ESI) | $^1$H NMR (400 MHz, DMSO-$d_6$) δ 8.42 (s, 1H), 8.12-7.87 (m, 1H), 7.63-7.26 (m, 2H), 5.90-5.75 (m, 1H), 5.64 (s, 1H), 4.98 (br d, J = 5.0 Hz, 1H), 3.94-3.76 (m, 3H), 3.58-3.48 (m, 1H), 3.32-3.27 (m, 1H), 3.03 (br t, J = 10.5 Hz, 1H), 2.05-1.87 (m, 1H), 1.70-1.56 (m, 9H), 1.51 (br d, J = 13.1 Hz, 1H), 1.42-1.31 (m, 1H), 0.74-0.61 (m, 1H), 0.55-0.34 (m, 3H); $[\alpha]_D^{22}$ = −6 (c = 0.1, MeOH) |
| A24 | 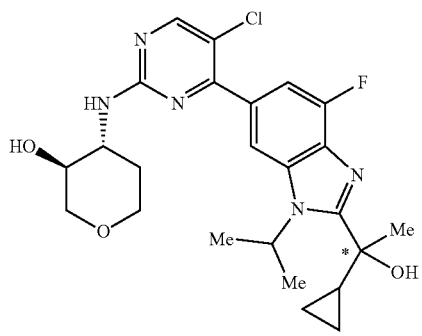<br>*second eluting stereoisomer<br>1,5-anhydro-3-({5-chloro-4-[2-(1-cyclopropyl-1-hydroxyethyl)-4-fluoro-1-(propan-2-yl)-1H-benzimidazol-6-yl]pyrimidin-2-yl}amino)-2,3-dideoxy-D-threo-pentitol | 490.1 [M + H]⁺ (ESI) | $^1$H NMR (400 MHz, DMSO-$d_6$) δ 8.42 (s, 1H), 8.13-7.81 (m, 1H), 7.62-7.15 (m, 2H), 5.90-5.75 (m, 1H), 5.64 (s, 1H), 4.97 (br d, J = 5.0 Hz, 1H), 3.94-3.70 (m, 3H), 3.59-3.47 (m, 1H), 3.32-3.25 (m, 1H), 3.03 (br t, J = 10.3 Hz, 1H), 2.04-1.84 (m, 1H), 1.70-1.57 (m, 9H), 1.55-1.45 (m, 1H), 1.42-1.31 (m, 1H), 0.74-0.63 (m, 1H), 0.59-0.30 (m, 3H); $[\alpha]_D^{22}$ = −22 (c = 0.1, MeOH) |

-continued

| Example number | Structure/Name | LCMS | NMR |
|---|---|---|---|
| A25 | 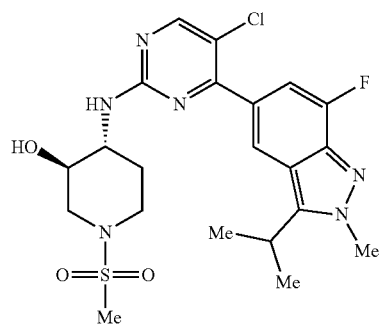<br>(3R,4R)-4-({5-chloro-4-[7-fluoro-2-methyl-3-(propan-2-yl)-2H-indazol-5-yl]pyrimidin-2-yl}amino)-1-(methanesulfonyl)piperidin-3-ol | 496.9 [M + H]$^+$ (ESI) | $^1$H NMR (400 MHz, DMSO-d$_6$) δ 8.40 (s, 1H), 8.18 (br s, 1H), 7.57-7.34 (m, 2H), 5.22 (br s, 1H), 4.17 (s, 3H), 3.79 (br s, 1H), 3.67-3.56 (m, 3H), 3.55-3.45 (m, 1H), 2.89 (s, 3H), 2.87-2.80 (m, 1H), 2.66 (br t, J = 10.5 Hz, 1H), 2.05 (br s, 1H), 1.60-1.40 (m, 1H), 1.46 (br d, J = 6.7 Hz, 6H) |
| A26 | 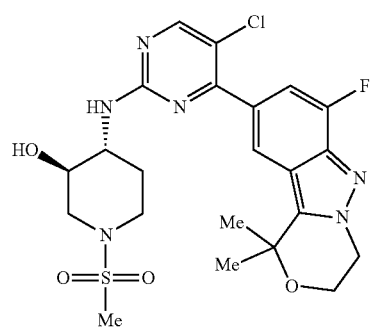<br>(3R,4R)-4-{[5-chloro-4-(7-fluoro-1,1-dimethyl-3,4-dihydro-1H-[1,4]oxazino[4,3-b]indazol-9-yl)pyrimidin-2-yl]amino}-1-(methanesulfonyl)piperidin-3-ol | 525.1 [M + H]$^+$ (ESI) | $^1$H NMR (400 MHz, DMSO-d$_6$) δ 8.42 (s, 1H), 8.04 (br s, 1H), 7.68-7.24 (m, 2H), 5.22 (d, J = 4.5 Hz, 1H), 4.46 (t, J = 4.8 Hz, 2H), 4.22 (br t, J = 4.6 Hz, 2H), 3.93-3.72 (m, 1H), 3.60 (br d, J = 8.8 Hz, 2H), 3.49 (br d, J = 11.3 Hz, 1H), 2.90 (s, 3H), 2.88-2.80 (m, 1H), 2.74-2.55 (m, 2H), 2.07 (br d, J = 10.8 Hz, 1H), 1.70 (s, 6H), 1.53 (br d, J = 10.0 Hz, 1H) |
| A27 | 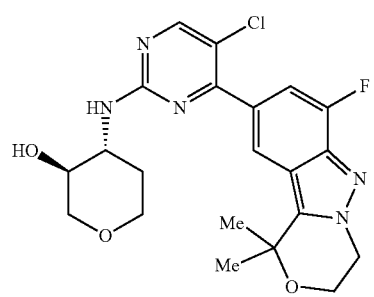<br>1,5-anhydro-3-{[5-chloro-4-(7-fluoro-1,1-dimethyl-3,4-dihydro-1H-[1,4]oxazino[4,3-b]indazol-9-yl)pyrimidin-2-yl]amino}-2,3-dideoxy-D-threo-pentitol | 448.0 [M + H]$^+$ (ESI) | $^1$H NMR (500 MHz, DMSO-d$_6$) δ 8.40 (s, 1H), 8.03 (br s, 1H), 7.57-7.34 (m, 2H), 4.94 (d, J = 5.3 Hz, 1H), 4.45 (t, J = 5.0 Hz, 2H), 4.21 (t, J = 4.9 Hz, 2H), 3.86-3.77 (m, 3H), 3.49 (br d, J = 4.1 Hz, 1H), 3.03 (t, J = 10.5 Hz, 1H), 1.94 (br s, 1H), 1.68 (s, 6H), 1.57-1.40 (m, 1H); one proton obscured by solvent peak |

-continued

| Example number | Structure/Name | LCMS | NMR |
|---|---|---|---|
| A28 | 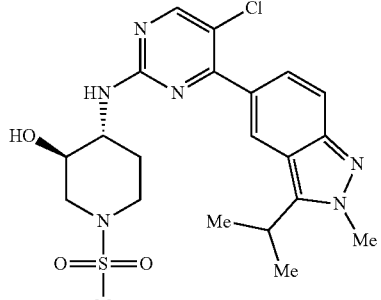<br>(3R,4R)-4-({5-chloro-4-[2-methyl-3-(propan-2-yl)-2H-indazol-5-yl]pyrimidin-2-yl}amino)-1-(methanesulfonyl)piperidin-3-ol | 479.3 [M + H]$^+$ (ESI) | $^1$H NMR (400 MHz, DMSO-d$_6$) δ 8.38 (s, 1H), 8.32-8.22 (m, 1H), 7.59 (br s, 2H), 7.51-7.35 (m, 1H), 5.22 (d, J = 4.3 Hz, 1H), 4.13 (s, 3H), 3.84-3.74 (m, 1H), 3.65-3.53 (m, 3H), 3.53-3.47 m, 1H), 2.89 (s, 3H), 2.87-2.78 (m, 1H), 2.69-2.60 (m, 1H), 2.13-1.97 (m, 1H), 1.57-1.50 (m, 1H), 1.46 (d, J = 6.8 Hz, 6H) |
| A29 | 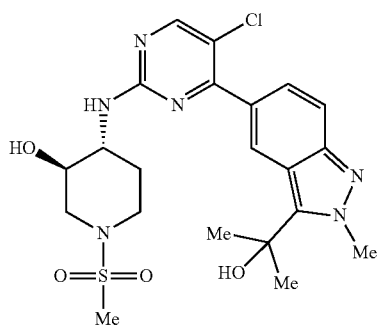<br>(3R,4R)-4-({5-chloro-4-[3-(2-hydroxypropan-2-yl)-2-methyl-2H-indazol-5-yl]pyrimidin-2-yl}amino)-1-(methanesulfonyl)piperidin-3-ol | 495.3 [M + H]$^+$ (ESI) | $^1$H NMR (400 MHz, DMSO-d$_6$) δ 8.39 (s, 1H), 8.37-8.24 (m, 1H), 7.60 (br d, J = 7.0 Hz, 2H), 7.53-7.38 (m, 1H), 5.76 (s, 1H), 5.22 (d, J = 4.5 Hz, 1H), 4.33 (s, 3H), 3.83-3.74 (m, 1H), 3.59 (m, 2H), 3.51-3.44 (m, 1H), 2.89 (s, 3H), 2.87-2.79 (m, 1H), 2.68-2.60 (m, 1H), 2.10-1.99 (m, 1H), 1.75 (s, 6H), 1.58-1.46 (m, 1H) |
| A30 | 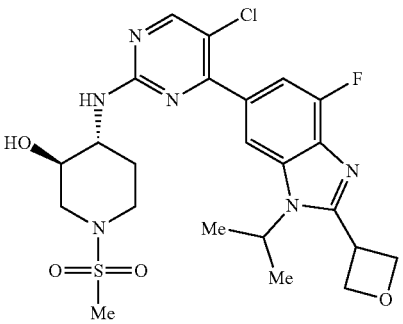<br>(3R,4R)-4-({5-chloro-4-[4-fluoro-2-(oxetan-3-yl)-1-(propan-2-yl)-1H-benzimidazol-6-yl]pyrimidin-2-yl}amino)-1-(methanesulfonyl)piperidin-3-ol | 539.2 [M + H]$^+$ (APCI) | $^1$H NMR (400 MHz, DMSO-d$_6$, VT 80° C.) δ 8.39 (s, 1H), 7.95 (d, J = 1.0 Hz, 1H), 7.44 (dd, J = 0.9, 11.9 Hz, 1H), 7.18 (d, J = 7.7 Hz, 1H), 5.05-4.93 (m, 5H), 4.83-4.71 (m, 1H), 4.64-4.50 (m, 1H), 3.88-3.75 (m, 1H), 3.72-3.60 (m, 1H), 3.59-3.46 (m, 1H), 3.20 (d, J = 4.6 Hz, 2H), 2.95-2.83 (m, 4H), 2.78-2.63 (m, 1H), 2.12 (dd, J = 3.4, 13.4 Hz, 1H), 1.56 (d, J = 6.8 Hz, 6H) |

-continued

| Example number | Structure/Name | LCMS | NMR |
|---|---|---|---|
| A31 | 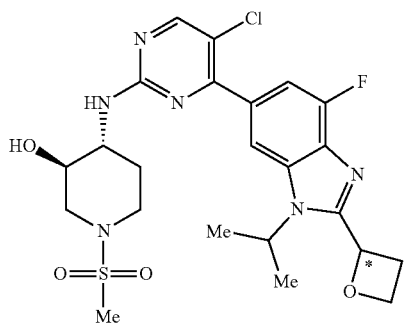<br>*first eluting stereoisomer<br>(3R,4R)-4-({5-chloro-4-[4-fluoro-2-(oxetan-2-yl)-1-(propan-2-yl)-1H-benzimidazol-6-yl]pyrimidin-2-yl}amino)-1-(methanesulfonyl)piperidin-3-ol | 538.9 [M + H]⁺ (ESI) | ¹H NMR (400 MHz, CD₃OD) δ 8.36 (s, 1H), 8.09-7.96 (m, 1H), 7.56-7.47 (m, 1H), 6.19 (dd, J = 7.1, 7.9 Hz, 1H), 4.91-4.88 (m, 1H), 4.86-4.82 (m, 1H), 4.78-4.69 (m, 1H), 4.00-3.88 (m, 1H), 3.86-3.78 (m, 1H), 3.76-3.71 (m, 1H), 3.70-3.64 (m, 1H), 3.51-3.40 (m, 1H), 3.21-3.08 (m, 1H), 2.98-2.89 (m, 1H), 2.88 (s, 3H), 2.79-2.68 (m, 1H), 2.27-2.17 (m, 1H), 1.74-1.62 (m, 7H) |
| A32 | 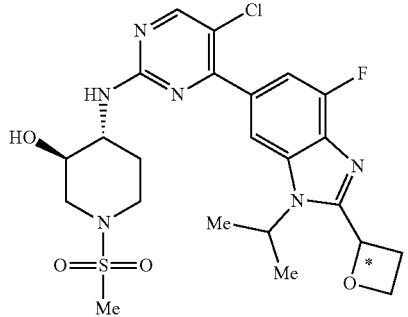<br>*second eluting stereoisomer<br>(3R,4R)-4-({5-chloro-4-[4-fluoro-2-(oxetan-2-yl)-1-(propan-2-yl)-1H-benzimidazol-6-yl]pyrimidin-2-yl}amino)-1-(methanesulfonyl)piperidin-3-ol | 539.1 [M + H]⁺ (ESI) | ¹H NMR (400 MHz, CD₃OD) δ 8.36 (s, 1H), 8.09-7.97 (m, 1H), 7.56-7.47 (m, 1H), 6.19 (dd, J = 7.0, 7.9 Hz, 1H), 4.91-4.88 (m, 1H), 4.86-4.82 (m, 1H), 4.78-4.69 (m, 1H), 4.00-3.89 (m, 1H), 3.86-3.78 (m, 1H), 3.77-3.62 (m, 2H), 3.52-3.38 (m, 1H), 3.20-3.08 (m, 1H), 2.98-2.90 (m, 1H), 2.88 (s, 3H), 2.79-2.67 (m, 1H), 2.31-2.16 (m, 1H), 1.71-1.63 (m, J = 1.0, 6.9 Hz, 7H) |
| A33 | 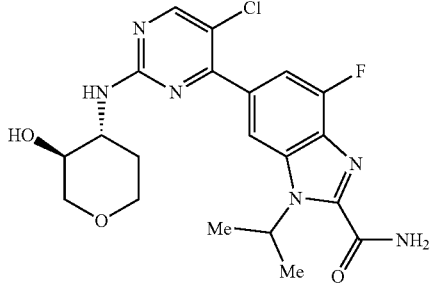<br>1,5-anhydro-3-({4-[2-carbamoyl-4-fluoro-1-(propan-2-yl)-1H-benzimidazol-6-yl]-5-chloropyrimidin-2-yl}amino)-2,3-dideoxy-D-threo-pentitol | 449.1 [M + H]⁺ (ESI) | ¹H NMR (500 MHz, DMSO-d₆) δ 8.51-8.38 (m, 2H), 8.18-7.99 (m, 2H), 7.65-7.42 (m, 2H), 6.04-5.80 (m, 1H), 4.98-4.91 (m, 1H), 3.90-3.73 (m, 3H), 3.57-3.44 (m, 1H), 3.10-2.96 (m, 1H), 2.05-1.85 (m, 1H), 1.65 (d, J = 7.0 Hz, 6H), 1.53-1.37 (m, 1H) |

-continued

| Example number | Structure/Name | LCMS | NMR |
|---|---|---|---|
| A34 | 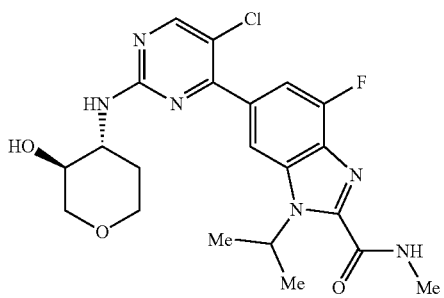<br>1,5-anhydro-3-({5-chloro-4-[4-fluoro-2-(methylcarbamoyl)-1-(propan-2-yl)-1H-benzimidazol-6-yl]pyrimidin-2-yl}amino)-2,3-dideoxy-D-threo-pentitol | 463.2 [M + H]⁺ (ESI) | $^1$H NMR (400 MHz, CD$_3$OD) δ 8.36 (s, 1H), 8.15-8.04 (m, 1H), 7.54 (d, J = 11.5 Hz, 1H), 6.04-5.83 (m, 1H), 4.04-3.84 (m, 3H), 3.70-3.55 (m, 1H), 3.52-3.42 (m, 1H), 3.25-3.15 (m, 1H), 2.97 (s, 3H), 2.17-2.06 (m, 1H), 1.70 (d, J = 6.8 Hz, 6H), 1.67-1.57 (m, 1H) |
| A35 | 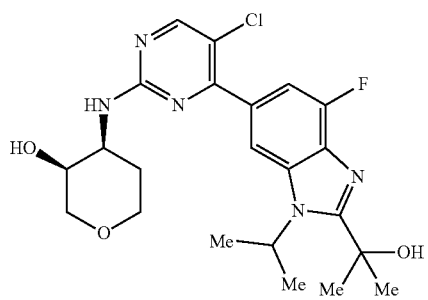<br>*first eluting stereoisomer<br>1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-erythro-pentitol | 464.1 [M + H]⁺ (ESI) | $^1$H NMR (400 MHz, DMSO-d$_6$) δ 8.44 (s, 1H), 8.05-7.87 (m, 1H), 7.53-7.27 (m, 1H), 7.06-6.90 (m, 1H), 5.98-5.66 (m, 2H), 5.06-4.75 (m, 1H), 4.06-3.94 (m, 1H), 3.87-3.68 (m, 3H), 3.48-3.38 (m, 2H), 2.01-1.83 (m, 1H), 1.66 (s, 6H), 1.63-1.55 (m, 7H); [α]$_D^{20}$ = −41.9 (c = 0.14, MeOH) |
| A36 | 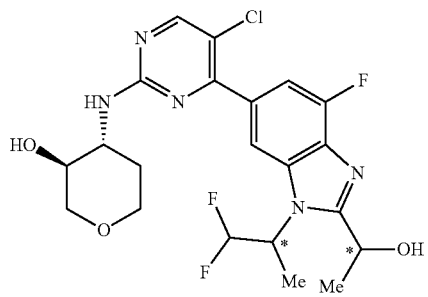<br>*second eluting stereoisomer<br>1,5-anhydro-3-({5-chloro-4-[1-(1,1-difluoropropan-2-yl)-4-fluoro-2-(1-hydroxyethyl)-1H-benzimidazol-6-yl]pyrimidin-2-yl}amino)-2,3-dideoxy-D-threo-pentitol | 485.9 [M + H]⁺ (ESI) | $^1$H NMR (700 MHz, DMSO-d$_6$) δ 8.42 (s, 1H), 8.13-7.73 (m, 1H), 7.60-7.27 (m, 2H), 6.63-6.40 (m, 1H), 6.00-5.82 (m, 1H), 5.55-5.41 (m, 1H), 5.22-5.13 (m, 1H), 5.01-4.85 (m, 1H), 3.91-3.74 (m, 3H), 3.53-3.45 (m, 1H), 3.07-2.97 (m, 1H), 2.04-1.85 (m, 1H), 1.68 (d, J = 7.1 Hz, 3H), 1.62 (d, J = 6.7 Hz, 3H), 1.55-1.42 (m, 1H); [α]$_D^{22}$ = −37.3 (c = 0.1, MeOH) |

Example A37 (Scheme A-2): Preparation of (3R, 4R)-4-({5-fluoro-4-[4-fluoro-2-methyl-1-(propan-2-yl)-1H-benzimidazol-6-yl]pyrimidin-2-yl}amino)piperidin-3-ol

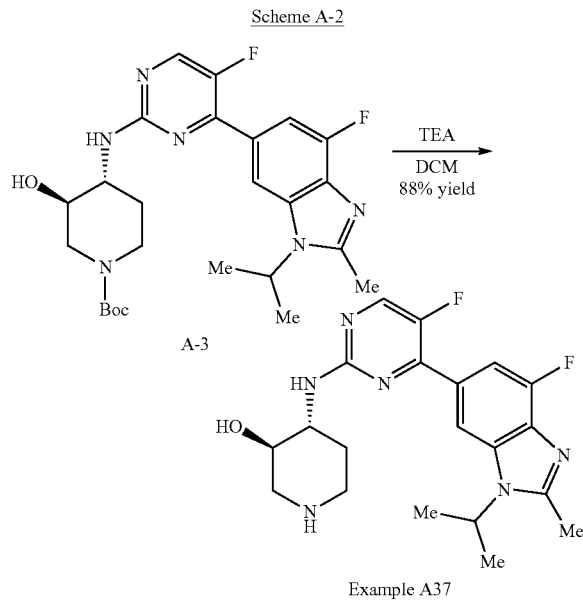

Example A37

A solution of tert-butyl (3R,4R)-4-({5-fluoro-4-[4-fluoro-2-methyl-1-(propan-2-yl)-1H-benzimidazol-6-yl]pyrimidin-2-yl}amino)-3-hydroxypiperidine-1-carboxylate (A-3) (prepared as in Example A1, 1.25 g, 2.49 mmol) in DCM (10 mL) was treated with TFA (10 mL) and then stirred at ambient temperature for 1 h. The mixture was concentrated and the crude residue was taken up into DCM (10 mL). The pH was adjusted to ~7-8 with NH$_4$OH. The product was extracted with water (20 mL). The aqueous phase was washed with DCM (3×15 mL). A white solid formed in the aqueous layer, which was collected by filtration to provide (3R,4R)-4-({5-fluoro-4-[4-fluoro-2-methyl-1-(propan-2-yl)-1H-benzimidazol-6-yl]pyrimidin-2-yl}amino)piperidin-3-ol (Example A37) (880 mg, 88% yield) as a white solid. $^1$H NMR (400 MHz, DMSO-d$_6$) δ 8.47 (d, J=3.8 Hz, 1H), 8.10 (s, 1H), 7.73-7.57 (m, 1H), 7.51-7.39 (m, 1H), 5.69-5.62 (m, 1H), 4.90-4.72 (m, 1H), 4.43-4.30 (m, 1H), 4.08-3.93 (m, 1H), 3.90-3.77 (m, 1H), 3.50-3.39 (m, 2H), 3.07-2.96 (m, 1H), 2.95-2.82 (m, 1H), 2.63 (s, 3H), 2.28-2.15 (m, 1H), 1.74-1.64 (m, 1H), 1.59 (d, J=6.8 Hz, 6H); m/z (ESI+) for (C$_{20}$H$_{24}$F$_2$N$_6$O), 403.1 (M+H)$^+$.

Example A38 (Scheme A-3): Preparation of (3R, 4R)-4-[(4-{1-[(2R)-1-aminopropan-2-yl]-4-fluoro-2-methyl-1H-benzimidazol-6-yl}-5-chloropyrimidin-2-yl)amino]-1-(methanesulfonyl)piperidin-3-ol

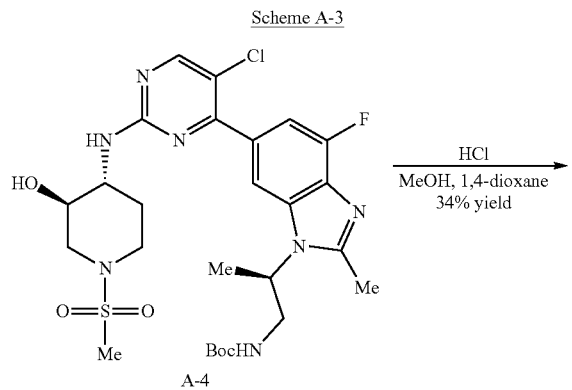

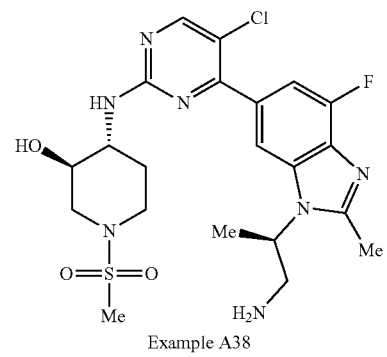

Example A38

To a solution of tert-butyl {(2R)-2-[6-(5-chloro-2-{[(3R,4R)-3-hydroxy-1-(methanesulfonyl)piperidin-4-yl]amino}pyrimidin-4-yl)-4-fluoro-2-methyl-1H-benzimidazol-1-yl]propyl}carbamate (A-4) (Prepared as in Example A1, 130 mg, 0.212 mmol) in MeOH (2.5 mL) was added a solution of HCl (4.0 M in 1,4-dioxane, 2.5 mL) dropwise at 0° C. After the addition the reaction solution was stirred at room temperature for 2 h. LCMS analysis showed consumption of the starting material with formation of the desired product mass. The reaction was concentrated to dryness. The residue was purified by preparative HPLC on a DuraShell column (150×25 mm, 5 μm particle size) which was eluted with 7-37% MeCN/H$_2$O (+0.05% HCl) with a flow rate of 30 mL/min to provide (3R,4R)-4-[(4-{1-[(2R)-1-aminopropan-2-yl]-4-fluoro-2-methyl-1H-benzimidazol-6-yl}-5-chloropyrimidin-2-yl)amino]-1-(methanesulfonyl)piperidin-3-ol (Example A38) (39.5 mg, 34% yield) as a yellow solid. $^1$H NMR (400 MHz, DMSO-d$_6$) δ 8.39 (s, 1H), 8.06-7.97 (m, 1H), 7.67-7.52 (m, 1H), 5.06-4.79 (m, 1H), 3.81-3.70 (m, 1H), 3.66-3.54 (m, 3H), 3.51-3.43 (m, 1H), 3.42-3.33 (m, 1H), 2.85 (s, 3H), 2.82-2.77 (m, 1H), 2.74 (s, 3H), 2.68-2.56 (m, 1H), 2.05-1.96 (m, 1H), 1.64 (d, J=6.8 Hz, 3H), 1.58-1.45 (m, 1H); m/z (ESI+) for (C$_{21}$H$_{27}$ClFN$_7$O$_3$S), 512.2 (M+H)$^+$.

The examples in the below table were synthesized according to the methods used for the synthesis of (3R,4R)-4-({5-fluoro-4-[4-fluoro-2-methyl-1-(propan-2-yl)-1H-benzimidazol-6-yl]pyrimidin-2-yl}amino)-1-(methanesulfonyl)piperidin-3-ol (Example A37) (Scheme A-2) and (3R,4R)-4-[(4-{1-[(2R)-1-aminopropan-2-yl]-4-fluoro-2-methyl-1H-benzimidazol-6-yl}-5-chloropyrimidin-2-yl)amino]-1-(methanesulfonyl)piperidin-3-ol (Example A38) (Scheme A-3). The following examples were synthesized with non-critical changes or substitutions to the exemplified procedures that someone who is skilled in the art would be able to realize. If necessary, separation of the enantiomers was carried out under standard methods known in the art, such as chiral SFC or HPLC, to afford single enantiomers.

| Example number | Structure/Name | LCMS | NMR |
|---|---|---|---|
| A39 | 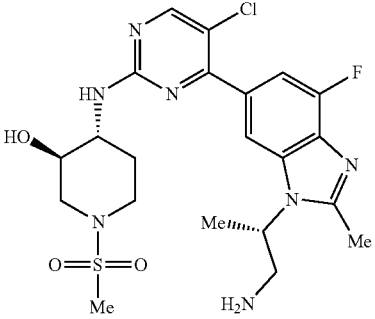<br>(3R,4R)-4-[(4-{1-[(2S)-1-aminopropan-2-yl]-4-fluoro-2-methyl-1H-benzimidazol-6-yl}-5-chloropyrimidin-2-yl)amino]-1-(methanesulfonyl)piperidin-3-ol | 534.2 [M + Na]$^+$ (ESI) | $^1$H NMR (400 MHz, DMSO-d$_6$) δ 8.45-8.27 (m, 1H), 8.03-7.87 (m, 1H), 7.65-7.49 (m, 1H), 5.08-4.85 (m, 1H), 3.83-3.68 (m, 1H), 3.67-3.56 (m, 2H), 3.54-3.35 (m, 2H), 2.91-2.79 (m, 4H), 2.75-2.61 (m, 4H), 2.12-1.95 (m, 1H), 1.71-1.50 (m, 4H) |
| A40 | 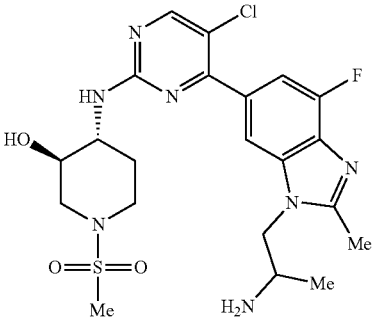<br>(3R,4R)-4-({4-[1-(2-aminopropyl)-4-fluoro-6-yl]-5-1H-benzimidazol-6-yl]-5-chloropyrimidin-2-yl}amino)-1-(methanesulfonyl)piperidin-3-ol | 512.2 [M + H]$^+$ (ESI) | $^1$H NMR (400 MHz, DMSO-d$_6$) δ 8.39 (s, 1H), 8.01-7.82 (m, 1H), 7.58-7.31 (m, 1H), 4.48-4.34 (m, 2H), 3.82-3.72 (m, 1H), 3.71-3.63 (m, 1H), 3.63-3.54 (m, 2H), 3.51-3.42 (m, 1H), 2.85 (s, 3H), 2.82-2.73 (m, 1H), 2.67-2.57 (m, 4H), 2.10-1.95 (m, 1H), 1.59-1.45 (m, 1H), 1.24 (d, J = 6.5 Hz, 3H) |
| A41 | 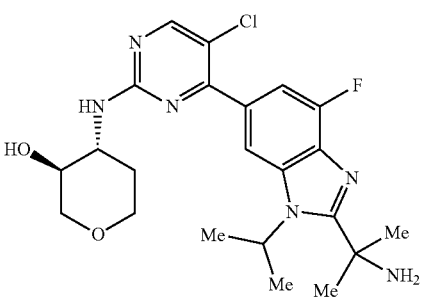<br>3-({4-[2-(2-aminopropan-2-yl)-4-fluoro-1-(propan-2-yl)-1H-benzimidazol-6-yl]-5-chloropyrimidin-2-yl}amino)-1,5-anhydro-2,3-dideoxy-D-threo-pentitol | 463.4 [M + H]$^+$ (ESI) | $^1$H NMR (500 MHz, DMSO-d$_6$) δ 8.41 (s, 1H), 8.05-7.81 (m, 1H), 7.57-7.22 (m, 2H), 6.24-6.06 (m, 1H), 4.99-4.89 (m, 1H), 3.90-3.73 (m, 3H), 3.54-3.46 (m, 1H), 3.32-3.30 (m, 1H), 3.07-2.95 (m, 1H), 2.33-2.22 (m, 1H), 2.04-1.88 (m, 1H), 1.60-1.56 (m, 12H), 1.53-1.40 (m, 1H) |

| Example number | Structure/Name | LCMS | NMR |
|---|---|---|---|
| A42 | 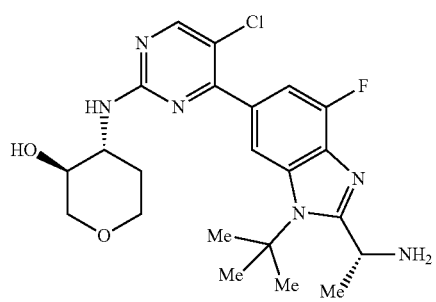<br>3-[(4-{2-[(1R)-1-aminoethyl]-1-tert-butyl-4-fluoro-1H-benzimidazol-6-yl}-5-chloropyrimidin-2-yl)amino]-1,5-anhydro-2,3-dideoxy-D-threo-pentitol | 463.4 [M + H]⁺ (ESI) | ¹H NMR (500 MHz, CD₃OD) δ 8.34 (s, 1H), 8.25-8.14 (m, 1H), 7.56-7.38 (m, 1H), 4.84-4.77 (m, 1H), 4.66-4.58 (m, 1H), 4.01-3.94 (m, 2H), 3.93-3.87 (m, 1H), 3.65-3.57 (m, 1H), 3.52-3.44 (m, 1H), 3.24-3.13 (m, 1H), 2.17-2.07 (m, 1H), 1.94 (s, 9H), 1.68-1.61 (m, 1H), 1.59 (d, J = 6.8 Hz, 3H) |
| A43 | 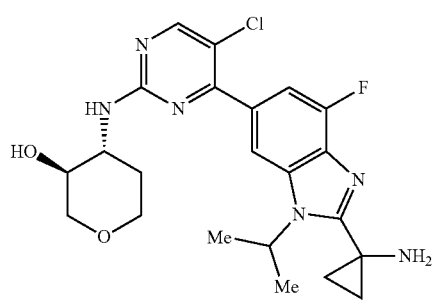<br>3-({4-[2-(1-aminocyclopropyl)-4-fluoro-1-(propan-2-yl)-1H-benzimidazol-6-yl]-5-chloropyrimidin-2-yl}amino)-1,5-anhydro-2,3-dideoxy-D-threo-pentitol | 461.3 [M + H]⁺ (ESI) | ¹H NMR (400 MHz, DMSO-d₆) δ 8.41 (s, 1H), 8.03-7.82 (m, 1H), 7.57-7.22 (m, 2H), 5.50-5.24 (m, 1H), 4.99-4.91 (m, 1H), 3.91-3.75 (m, 3H), 3.57-3.44 (m, 1H), 3.09-2.96 (m, 1H), 2.63-2.54 (m, 1H), 2.06-1.86 (m, 1H), 1.62 (d, J = 7.0 Hz, 6H), 1.56-1.41 (m, 1H), 1.21-1.13 (m, 2H), 1.03-0.94 (m, 2H) |
| A44 | 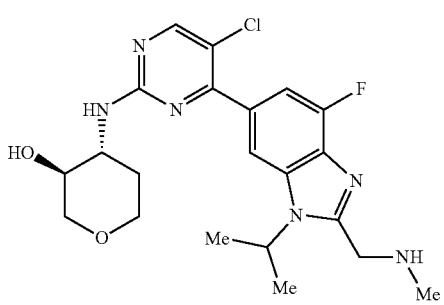<br>1,5-anhydro-3-[(5-chloro-4-{4-fluoro-2-[(methylamino)methyl]-1-(propan-2-yl)-1H-benzimidazol-6-yl}pyrimidin-2-yl)amino]-2,3-dideoxy-D-threo-pentitol | 448.9 [M + H]⁺ (ESI) | ¹H NMR (400 MHz, DMSO-d₆) δ 8.41 (s, 1H), 8.05-7.75 (m, 1H), 7.55-7.26 (m, 2H), 5.11-5.01 (m, 1H), 4.99-4.89 (m, 1H), 3.99 (s, 2H), 3.88-3.74 (m, 3H), 3.54-3.46 (m, 1H), 3.06-2.98 (m, 1H), 2.32 (s, 3H), 2.04-1.84 (m, 1H), 1.58 (d, J = 7.0 Hz, 6H), 1.53-1.40 (m, 1H) |

-continued

| Example number | Structure/Name | LCMS | NMR |
|---|---|---|---|
| A45 | 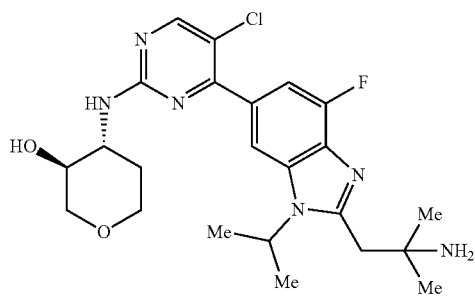<br>3-({4-[2-(2-amino-2-methylpropyl)-4-fluoro-1-(propan-2-yl)-1H-benzimidazol-6-yl]-5-chloropyrimidin-2-yl}amino)-1,5-anhydro-2,3-dideoxy-D-threo-pentitol | 477.1 [M + H]⁺ (ESI) | ¹H NMR (400 MHz, CD₃OD) δ 8.57 (s, 1H), 8.30 (s, 1H), 7.79-7.70 (m, 1H), 5.14-5.02 (m, 1H), 4.08-3.88 (m, 3H), 3.71-3.62 (m, 1H), 3.62-3.58 (m, 1H), 3.54 (s, 2H), 3.52-3.42 (m, 1H), 3.25-3.17 (m, 1H), 2.16-2.02 (m, 1H), 1.82-1.71 (m, 7H), 1.57 (s, 6H) |
| A46 | 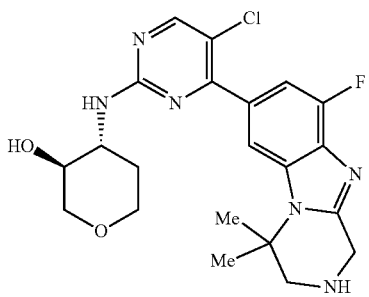<br>1,5-anhydro-3-{[5-chloro-4-(9-fluoro-4,4-dimethyl-1,2,3,4-tetrahydropyrazino[1,2-a]benzimidazol-7-yl)pyrimidin-2-yl]amino}-2,3-dideoxy-D-threo-pentitol | 447.1 [M + H]⁺ (ESI) | ¹H NMR (400 MHz, DMSO-d₆ + D₂O) δ 8.38 (s, 1H), 7.96 (br s, 1H), 7.39 (br d, J = 7.8 Hz, 2H), 4.95 (d, J = 5.3 Hz, 1H), 4.03 (s, 2H), 3.81 (br dd, J = 5.3, 10.8 Hz, 3H), 3.49 (br s, 1H), 3.30 (br t, J = 11.2 Hz, 1H), 3.07-2.94 (m, 3H), 1.94 (br s, 1H), 1.60 (s, 6H), 1.49 (br d, J = 9.5 Hz, 1H) |
| A47 | 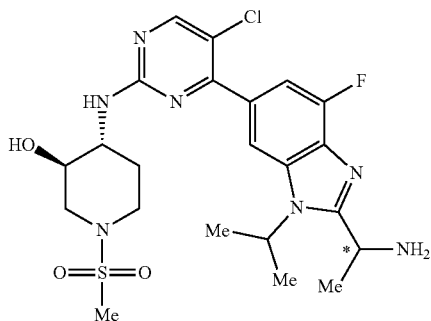<br>*single stereoisomer<br>(3R,4R)-4-({4-[2-(1-aminoethyl)-4-fluoro-1-(propan-2-yl)-1H-benzimidazol-6-yl]-5-chloropyrimidin-2-yl}amino)-1-(methanesulfonyl)piperidin-3-ol | 526.3 [M + H]⁺ (ESI) | ¹H NMR (400 MHz, DMSO-d₆) δ 8.43 (s, 1H), 7.92 (br s, 1H), 7.57-7.31 (m, 2H), 5.23 (d, J = 4.5 Hz, 1H), 5.15 (td, J = 6.9, 14.0 Hz, 1H), 4.35 (q, J = 6.5 Hz, 1H), 3.87-3.75 (m, 1H), 3.61 (br d, J = 8.5 Hz, 2H), 3.50 (br d, J = 12.3 Hz, 1H), 2.93-2.82 (m, 4H), 2.66 (br t, J = 11.0 Hz, 1H), 2.20-2.04 (m, 3H), 1.67-1.42 (m, 10H); [α]$_D^{20}$ = −13.3 (c = 0.1, MeOH) |

| Example number | Structure/Name | LCMS | NMR |
|---|---|---|---|
| A48 | 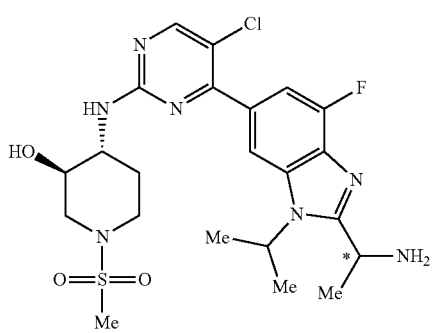<br>*single stereoisomer<br>(3R,4R)-4-({4-[2-(1-aminoethyl)-4-fluoro-1-(propan-2-yl)-1H-benzimidazol-6-yl]-5-chloropyrimidin-2-yl}amino)-1-(methanesulfonyl)piperidin-3-ol | 526.3 [M + H]+ (ESI) | $^1$H NMR (400 MHz, DMSO-d$_6$) δ 8.43 (s, 1H), 8.05-7.87 (m, 1H), 7.59-7.30 (m, 2H), 5.23 (d, J = 4.5 Hz, 1H), 5.15 (quin, J = 6.9 Hz, 1H), 4.35 (q, J = 6.5 Hz, 1H), 3.81 (br d, J = 5.8 Hz, 1H), 3.61 (br d, J = 9.3 Hz, 2H), 3.49 (br d, J = 12.3 Hz, 1H), 2.90 (s, 3H), 2.88-2.79 (m, 1H), 2.70-2.61 (m, 1H), 2.16 (br s, 3H), 1.63-1.47 (m, 10H); [α]$_D^{20}$ = −18.1 (c = 0.1, MeOH) |
| A49 | 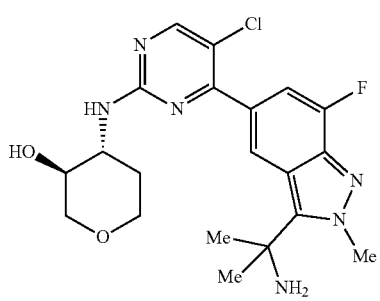<br>3-({4-[3-(2-aminopropan-2-yl)-7-fluoro-2-methyl-2H-indazol-5-yl]-5-chloropyrimidin-2-yl}amino)-1,5-anhydro-2,3-dideoxy-D-threo-pentitol | 435.0 [M + H]+ (ESI) | $^1$H NMR (500 MHz, DMSO-d$_6$) δ 8.53-8.26 (m, 2H), 7.61-7.28 (m, 2H), 4.99-4.88 (m, 1H), 4.49 (s, 3H), 3.86-3.75 (m, 3H), 3.53-3.43 (m, 1H), 3.07-2.99 (m, 1H), 2.03-1.89 (m, 1H), 1.72 (s, 6H), 1.57-1.41 (m, 1H) |
| A50 | 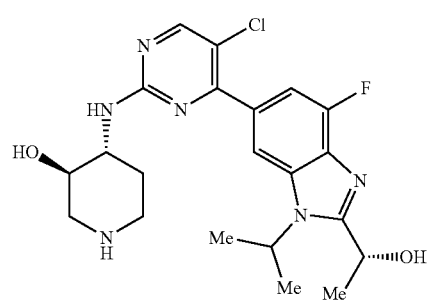<br>(3R,4R)-4-[(5-chloro-4-{4-fluoro-2-[(1R)-1-hydroxyethyl]-1-(propan-2-yl)-1H-benzimidazol-6-yl}pyrimidin-2-yl)amino]piperidin-3-ol | 448.9 [M + H]+ (ESI) | $^1$H NMR (400 MHz, DMSO-d$_6$, 80° C.) δ 8.87 (br. s, 1H), 8.64 (br. s, 1H), 8.43 (s, 1H), 7.99 (d, J = 1.3 Hz, 1H), 7.51-7.38 (m, 2H), 5.24 (hept, J = 7.6, 7.1 Hz, 1H), 5.13 (q, J = 6.5 Hz, 1H), 3.38-3.23 (m, 2H), 3.06-2.95 (m, 1H), 3.05-2.80 (m, 1H), 2.31-2.19 (m, 1H), 1.82-1.70 (m, 1H), 1.67-1.58 (m, 9H); two protons obscured by solvent peak |

-continued

| Example number | Structure/Name | LCMS | NMR |
|---|---|---|---|
| A51 | 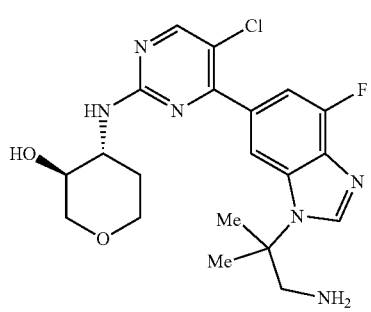<br>3-({4-[1-(1-amino-2-methylpropan-2-yl)-4-fluoro-1H-benzimidazol-6-yl]-5-chloropyrimidin-2-yl}amino)-1,5-anhydro-2,3-dideoxy-D-threo-pentitol | 435.0 [M + H]+ (ESI) | $^1$H NMR (500 MHz, DMSO-$d_6$) δ 8.35 (s, 1H), 8.31 (s, 1H), 8.07-7.92 (m, 1H), 7.52-7.30 (m, 1H), 3.88-3.69 (m, 3H), 3.56-3.43 (m, 1H), 3.38-3.21 (m, 1H), 3.11-2.96 (m, 3H), 2.00-1.86 (m, 1H), 1.64 (s, 6H), 1.54-1.40 (m, 1H) |
| A52 | 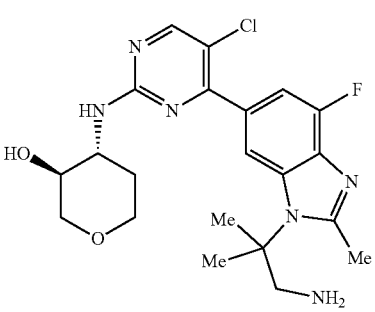<br>3-({4-[1-(1-amino-2-methylpropan-2-yl)-4-fluoro-2-methyl-1H-benzimidazol-6-yl]-5-chloropyrimidin-2-yl}amino)-1,5-anhydro-2,3-dideoxy-D-threo-pentitol | 448.9 [M + H]+ (ESI) | $^1$H NMR (400 MHz, $D_2O$) δ 8.50-8.33 (m, 1H), 8.24-8.13 (m, 1H), 7.78-7.64 (m, 1H), 4.03-3.89 (m, 3H), 3.87-3.80 (m, 2H), 3.74-3.62 (m, 1H), 3.59-3.44 (m, 1H), 3.30-3.20 (m, 1H), 3.15-2.97 (m, 3H), 2.12-1.97 (m, 7H), 1.77-1.55 (m, 1H) |
| A53 | 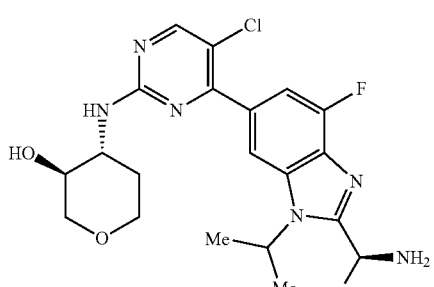<br>3-[(4-{2-[(1S)-1-aminoethyl]-4-fluoro-1-(propan-2-yl)-1H-benzimidazol-6-yl}-5-chloropyrimidin-2-yl)amino]-1,5-anhydro-2,3-dideoxy-D-threo-pentitol | 448.9 [M + H]+ (ESI) | $^1$H NMR (600 MHz, DMSO-$d_6$) δ 8.41 (s, 1H), 8.07-7.87 (m, 1H), 7.54-7.25 (m, 2H), 5.15-5.00 (m, 1H), 4.97-4.85 (m, 1H), 4.61-4.46 (m, 1H), 3.87-3.75 (m, 3H), 3.59-3.48 (m, 1H), 3.07-2.98 (m, 1H), 2.03-1.89 (m, 1H), 1.60 (d, J = 6.6 Hz, 6H), 1.55-1.45 (m, 4H) |

| Example number | Structure/Name | LCMS | NMR |
|---|---|---|---|
| A54 | 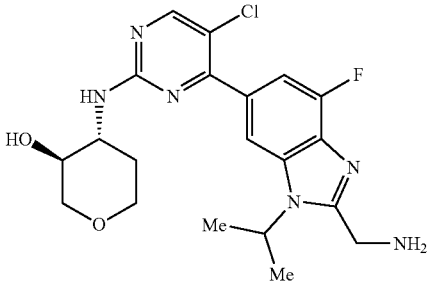<br>3-({4-[2-(aminomethyl)-4-fluoro-1-(propan-2-yl)-1H-benzimidazol-6-yl]-5-chloropyrimidin-2-yl}amino)-1,5-anhydro-2,3-dideoxy-D-threo-pentitol | 435.1 [M + H]⁺ (ESI) | ¹H NMR (400 MHz, DMSO-d₆) at 80° C. δ = 8.40 (s, 1H), 8.10-7.98 (m, 1H), 7.48 (br d, J = 11.0 Hz, 1H), 7.21-7.11 (m, 1H), 4.89 (m, 1H), 4.73 (m, 1H), 4.36 (m, 2H), 3.84 (m, 4H), 3.66-3.50 (m, 1H), 3.35 (m, 2H), 3.11 (m, 1H), 2.14-1.99 (m, 1H), 1.73-1.49 (m, 7H) |
| A55 | 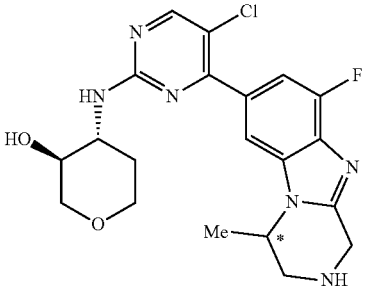<br>*first eluting stereoisomer<br>1,5-anhydro-3-{[5-chloro-4-(9-fluoro-4-methyl-1,2,3,4-tetrahydropyrazino[1,2-a]benzimidazol-7-yl)pyrimidin-2-yl]amino}-2,3-dideoxy-D-threo-pentitol | 433.1 [M + H]⁺ (ESI) | ¹H NMR (400 MHz, DMSO-d₆) δ 8.42 (s, 1H), 7.83 (br s, 1H), 7.58-7.31 (m, 2H), 4.95 (d, J = 5.3 Hz, 1H), 4.58 (br s, 1H), 4.20-4.02 (m, 2H), 3.90-3.76 (m, 3H), 3.51 (br d, J = 5.3 Hz, 2H), 3.30-3.24 (m, 1H), 3.12-2.99 (m, 2H), 1.95 (br d, J = 12.0 Hz, 1H), 1.50 (d, J = 6.5 Hz, 4H); [α]$_D^{20}$ = 27.7 (c = 0.13, MeOH) |
| A56 | 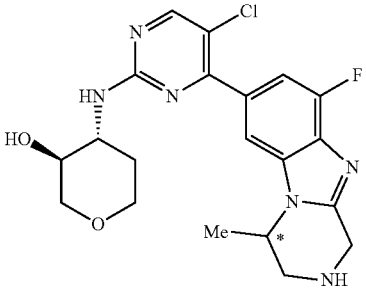<br>*second eluting stereoisomer<br>1,5-anhydro-3-{[5-chloro-4-(9-fluoro-4-methyl-1,2,3,4-tetrahydropyrazino[1,2-a]benzimidazol-7-yl)pyrimidin-2-yl]amino}-2,3-dideoxy-D-threo-pentitol | 433.2 [M + H]⁺ (ESI) | ¹H NMR (400 MHz, DMSO-d₆) δ 8.47-8.34 (m, 1H), 7.82 (br s, 1H), 7.62-7.32 (m, 2H), 4.94 (d, J = 5.3 Hz, 1H), 4.57 (br s, 1H), 4.17-4.00 (m, 2H), 3.82 (br dd, J = 4.9, 10.7 Hz, 3H), 3.50 (br s, 2H), 3.29-3.21 (m, 1H), 3.09-2.97 (m, 2H), 1.97 (br s, 1H), 1.58-1.41 (m, 4H); [α]$_D^{20}$ = 48.2 (c = 0.13, MeOH) |

| Example number | Structure/Name | LCMS | NMR |
|---|---|---|---|
| A57 | 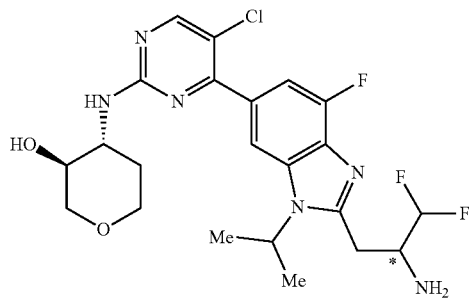<br>*second eluting stereoisomer<br>3-({4-[2-(2-amino-3,3-difluoropropyl)-4-fluoro-1-(propan-2-yl)-1H-benzimidazol-6-yl]-5-chloropyrimidin-2-yl}amino)-1,5-anhydro-2,3-dideoxy-D-threo-pentitol | 499.4 [M + H]+ (ESI) | $^1$H NMR (400 MHz, DMSO-d$_6$) δ 8.41 (s, 1H), 8.08-7.80 (m, 1H), 7.57-7.28 (m, 2H), 6.26-5.80 (m, 1H), 5.01-4.78 (m, 2H), 3.91-3.73 (m, 3H), 3.60-3.44 (m, 2H), 3.22-3.11 (m, 1H), 3.08-2.89 (m, 2H), 2.04-1.80 (m, 3H), 1.66-1.55 (m, 6H), 1.53-1.44 (m, 1H) |
| A58 | 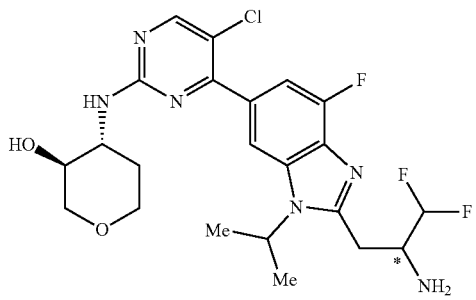<br>3-({4-[2-(2-amino-3,3-difluoropropyl)-4-fluoro-1-(propan-2-yl)-1H-benzimidazol-6-yl]-5-chloropyrimidin-2-yl}amino)-1,5-anhydro-2,3-dideoxy-D-threo-pentitol | 499.0 [M + H]+ (ESI) | $^1$H NMR (400 MHz, DMSO-d$_6$) δ 8.42 (s, 1H), 7.98 (br s, 1H), 7.56-7.17 (m, 2H), 6.21 (td, J = 55.6, 3.2 Hz, 1H), 4.91 (dq, J = 20.7, 6.9, 6.1 Hz, 2H), 3.98-3.69 (m, 4H), 3.51 (s, 1H), 3.30-3.26 (m, 1H), 3.21-2.89 (m, 2H), 1.97 (br s, 1H), 1.60 (dd, J = 6.9, 3.5 Hz, 6H), 1.57-1.45 (m, 1H) |
| A59 | 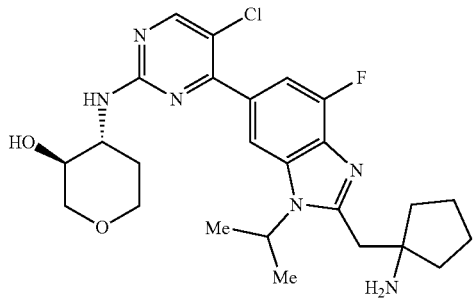<br>3-[(4-{2-[(1-aminocyclopentyl)methyl]-4-fluoro-1-(propan-2-yl)-1H-benzimidazol-6-yl}-5-chloropyrimidin-2-yl)amino]-1,5-anhydro-2,3-dideoxy-D-threo-pentitol | 503.1 [M + H]+ (ESI) | $^1$H NMR (400 MHz, CD$_3$OD) δ 8.34 (s, 1H), 8.05 (s, 1H), 7.49 (d, J = 11.5 Hz, 1H), 5.07-4.91 (m, 1H), 4.03-3.85 (m, 3H), 3.62 (s, 1H), 3.53-3.43 (m, 1H), 3.26-3.14 (m, 3H), 2.19-2.10 (m, 1H), 1.92-1.76 (m, 4H), 1.77-1.56 (m, 11H) |

217

Example A60 (Scheme A-4): Preparation of 1,5-anhydro-3-[(4-{1-tert-butyl-4-fluoro-2-[(1R)-1-hydroxyethyl]-1H-benzimidazo-6-yl}-5-chloropyrimidin-2-yl)amino]-2,3-dideoxy-D-threo-pentitol

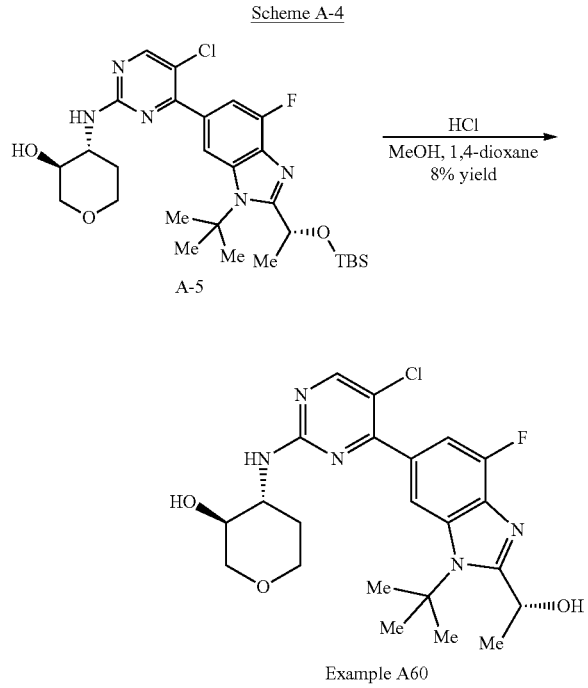

Scheme A-4

A-5

→ HCl, MeOH, 1,4-dioxane, 8% yield

Example A60

218

To a solution of 1,5-anhydro-3-[(4-{1-tert-butyl-2-[(1R)-1-{[ter-butyl(dimethyl)silyl]oxy}ethyl]-4-fluoro-1H-benzimnidazol-6-yl}-5-chloropyrimnidin-2-yl)amnino]-2,3-dideoxy-D-threo-pentitol (A-5)(Prepared as in Example A1, 70.0 mg, 0.121 mmol) in MeOH (1.0 mL) was added HCl (4.0 N in 1,4-dioxane, 3.0 mL) dropwise at 0° C. The solution was stirred at 30° C. for 4 h. TLC analysis showed consumption of the starting material. The solution was basified with NH$_4$OH to pH~9 and then concentrated to dryness. The residue was purified by preparative HPLC on a Boston Uni C-18 column (40×150 mm, 5 μm particle size), which was eluted with 13-53% MeCN/H$_2$O (+0.05% HCl) with a flow rate of 60 mL/min. The material was re-purified by preparative HPLC on a DuraShell column (150×25 mm, 5 μm particle size), which was eluted with 27-47% MeCN/H$_2$O (+0.05% NH$_4$OH) with a flow rate of 25 mL/min to provide 1,5-anhydro-3-[(4-{1-tert-butyl-4-fluoro-2-[(1R)-1-hydroxyethyl]-1H-benzimidazol-6-yl}-5-chloropyrimidin-2-yl)amino]-2,3-dideoxy-D-threo-pentitol (Example A60) (4.2 mg, 8% yield) as a white solid. $^1$H NMR (400 MHz, DMSO-d$_6$) δ 8.41 (s, 1H), 8.04 (br s, 1H), 7.54-7.32 (m, 1H), 5.53 (d, J=7.9 Hz, 1H), 5.28-5.20 (m, 1H), 4.95 (d, J=5.3 Hz, 1H), 3.86-3.76 (m, 3H), 3.50 (br d, J=1.2 Hz, 1H), 3.03 (br t, J=10.3 Hz, 1H), 2.07 (s, 1H), 2.01-1.91 (m, 1H), 1.88 (s, 9H), 1.67 (d, J=6.2 Hz, 3H), 1.56-1.44 (m, 1H); one proton obscured by solvent peak; m/z (ESI+) for (C$_{22}$H$_{27}$ClFN$_5$O$_3$), 464.1 (M+H)$^+$.

The examples in the below table were synthesized according to the methods used for the synthesis of 1,5-anhydro-3-[(4-{1-tert-butyl-4-fluoro-2-[(1R)-1-hydroxyethyl]-1H-benzimidazol-6-yl}-5-chloropyrimidin-2-yl)amino]-2,3-dideoxy-D-threo-pentitol (Example A60) (Scheme A-4). The following examples were synthesized with non-critical changes or substitutions to the exemplified procedures that someone who is skilled in the art would be able to realize.

| Example number | Structure/Name | LCMS | NMR |
|---|---|---|---|
| A61 | 1,5-anhydro-3-[(4-{1-tert-butyl-4-fluoro-2-[(1S)-1-hydroxyethyl]-1H-benzimidazol-6-yl}-5-chloropyrimidin-2-yl)amino]-2,3-dideoxy-D-threo-pentitol | 464.1 [M + H]$^+$ (ESI) | $^1$H NMR (400 MHz, CD$_3$OD) δ 8.34 (s, 1H), 8.19 (s, 1H), 7.48 (d, J = 11.3 Hz, 1H), 5.46 (q, J = 6.4 Hz, 1H), 4.02-3.87 (m, 3H), 3.66-3.57 (m, 1H), 3.48 (td, J = 11.7, 2.3 Hz, 1H), 3.24-3.16 (m, 1H), 2.18-2.09 (m, 1H), 1.97 (s, 9H), 1.76 (d, J = 6.4 Hz, 3H), 1.70-1.57 (m, 1H) |

| Example number | Structure/Name | LCMS | NMR |
|---|---|---|---|
| A62 | 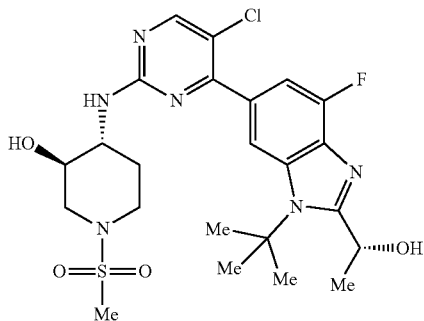<br>(3R,4R)-4-[(4-{1-tert-butyl-4-fluoro-2-[(1R)-1-hydroxyethyl]-1H-benzimidazol-6-yl}-5-chloropyrimidin-2-yl)amino]-1-(methanesulfonyl)piperidin-3-ol | 541.0 [M + H]+ (ESI) | $^1$H NMR (400 MHz, DMSO-$d_6$) δ 8.42 (s, 1H), 8.26-7.97 (m, 1H), 7.44 (d, J = 53.2 Hz, 2H), 5.53 (d, J = 7.8 Hz, 1H), 5.29-5.21 (m, 2H), 3.80 (s, 1H), 3.60 (d, 2H), 3.48 (d, J = 12.0 Hz, 1H), 2.93-2.78 (m, 4H), 2.71-2.60 (m, 1H), 2.07-1.96 (m, 1H), 1.88 (s, 9H), 1.67 (d, J = 6.2 Hz, 3H), 1.53 (d, J = 12.2 Hz, 1H) |
| A63 | 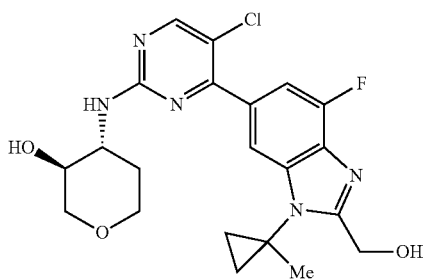<br>1,5-anhydro-3-({5-chloro-4-[4-fluoro-2-(hydroxymethyl)-1-(1-methylcyclopropyl)-1H-benzimidazol-6-yl]pyrimidin-2-yl}amino)-2,3-dideoxy-D-threo-pentitol | 447.9 [M + H]+ (ESI) | $^1$H NMR (400 MHz, CD$_3$OD) δ 8.58 (s, 1H), 8.35 (d, J = 1.1 Hz, 1H), 7.97 (d, J = 11.0 Hz, 1H), 5.29 (s, 2H), 4.07-3.92 (m, 3H), 3.67 (td, J = 9.6, 4.9 Hz, 1H), 3.54-3.44 (m, 1H), 3.28-3.19 (m, 1H), 2.16-2.08 (m, 1H), 1.82-1.70 (m, 4H), 1.49 (s, 2H), 1.36 (s, 2H) |
| A64 | 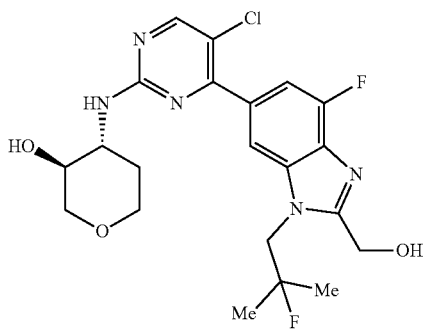<br>1,5-anhydro-3-({5-chloro-4-[4-fluoro-1-(2-fluoro-2-methylpropyl)-2-(hydroxymethyl)-1H-benzimidazol-6-yl]pyrimidin-2-yl}amino)-2,3-dideoxy-D-threo-pentitol | 468.2 [M + H]+ (ESI) | $^1$H NMR (600 MHz, DMSO-$d_6$) δ 8.42 (s, 1H), 7.91 (br s, 1H), 7.42 (br s, 2H), 5.72 (t, J = 6.0 Hz, 1H), 4.91 (dd, J = 5.4, 1.3 Hz, 1H), 4.79 (d, J = 6.0 Hz, 2H), 4.63 (d, J = 22.6 Hz, 2H), 3.82 (qt, J = 10.8, 6.4 Hz, 3H), 3.56-3.47 (m, 1H), 3.04 (t, J = 10.4 Hz, 1H), 1.98 (br s, 1H), 1.50 (qd, J = 12.0, 4.5 Hz, 2H), 1.39 (s, 3H), 1.35 (s, 3H) |

| Example number | Structure/Name | LCMS | NMR |
|---|---|---|---|
| A65 | 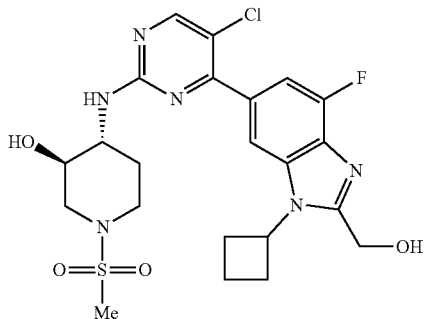<br>(3R,4R)-4-({5-chloro-4-[1-cyclobutyl-4-fluoro-2-(hydroxymethyl)-1H-benzimidazol-6-yl]pyrimidin-2-yl}amino)-1-(methanesulfonyl)piperidin-3-ol | 524.9 [M + H]$^+$ (ESI) | $^1$H NMR (400 MHz, DMSO-d$_6$) δ 8.47 (s, 1H), 8.18 (br s, 1H), 7.61 (br s, 2H), 5.25 (td, J = 8.9, 17.6 Hz, 1H), 4.87 (s, 2H), 3.81 (br s, 1H), 3.61 (br d, J = 10.3 Hz, 2H), 3.49 (br d, J = 12.1 Hz, 1H), 2.90 (s, 3H), 2.85 (br t, J = 9.8 Hz, 3H), 2.71-2.54 (m, 3H), 2.13-1.84 (m, 3H), 1.55 (br s, 1H) |
| A66 | 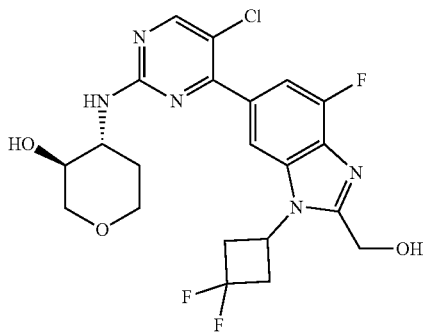<br>1,5-anhydro-3-({5-chloro-4-[1-(3,3-difluorocyclobutyl)-4-fluoro-2-(hydroxymethyl)-1H-benzimidazol-6-yl]pyrimidin-2-yl}amino)-2,3-dideoxy-D-threo-pentitol | 483.9 [M + H]$^+$ (ESI) | $^1$H NMR (400 MHz, DMSO-d$_6$) δ 8.46 (s, 1H), 7.99 (br s, 1H), 7.77-7.37 (m, 2H), 5.30 (br d, J = 3.7 Hz, 1H), 4.86 (s, 2H), 3.92-3.74 (m, 3H), 3.64-3.43 (m, 3H), 3.43-3.25 (m, 3H), 3.04 (t, J = 10.4 Hz, 1H), 2.16-1.86 (m, 1H), 1.61-1.39 (m, 1H) |

Example A67 (Scheme A-5): Preparation of 1,5-anhydro-3-({5-chloro-4-[1-(2,2-difluoroethyl)-4-fluoro-2-(2-hydroxypropan-2-yl)-1H-benzimidazol-6-yl]pyrimidin-2-yl}amino)-2,3-dideoxy-D-threo-pentitol Scheme A-5

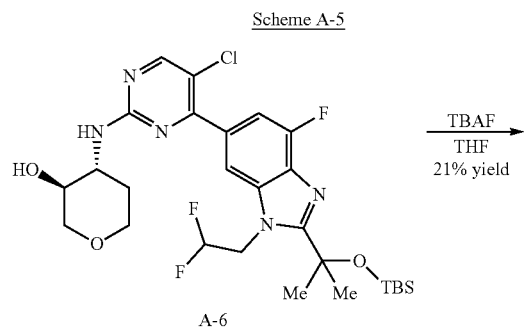

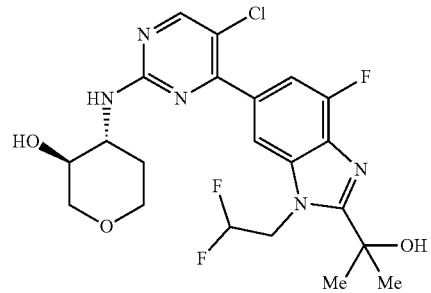

Example A67

To a yellow solution of 1,5-anhydro-3-({5-chloro-4-[1-(2,2-difluoroethyl)-4-fluoro-2-(2-hydroxypropan-2-yl)-1H-benzimnidazol-6-yl]pyrimidin-2-yl}amnino)-2,3-dideoxy-D-threo-pentitol (A-6) (Prepared as in Example A1, 200 mg, 0.33 mmol) in THF (10.0 mL) was added TBAF (174 mg, 0.67 mmol) at room temperature. The mixture was stirred for 2 h, at which time LCMS analysis indicated complete consumption of starting material with formation of the desired product mass. The reaction was concentrated. The residue was taken up in EtOAc (50 mL), washed with $H_2O$ (2×50 mL) and brine (50 mL), dried over $Na_2SO_4$, filtered, and concentrated. The residue was purified by preparative HPLC on a DuraShell column (150×25 mm, 5 μm particle size), which was eluted with 26-46% MeCN/$H_2O$ (+0.05% $NH_4OH$) with a flow rate of 25 mL/min to provide 1,5-anhydro-3-({5-chloro-4-[1-(2,2-difluoroethyl)-4-fluoro-2-(2-hydroxypropan-2-yl)-1H-benzimidazol-6-yl]pyrimidin-2-yl}amino)-2,3-dideoxy-D-threo-pentitol (Example A67) (34.2 mg, 21% yield) as a white solid. $^1$H NMR (500 MHz, DMSO-$d_6$) δ 8.42 (s, 1H), 7.88 (s, 1H), 7.56-7.34 (m, 2H), 6.41 (tt, J=55.9, 4.3 Hz, 1H), 5.98 (s, 1H), 5.04 (td, J=14.0, 4.2 Hz, 2H), 4.93 (d, J=5.4 Hz, 1H), 3.88-3.74 (m, 3H), 3.55-3.46 (m, 1H), 3.03 (t, J=10.4 Hz, 1H), 2.04-1.83 (m, 1H), 1.68 (d, J=1.8 Hz, 6H), 1.56-1.42 (m, 1H); one proton obscured by solvent peak; m/z (ESI+) for ($C_{21}H_{23}ClF_3N_5O_3$), 486.0 (M+H)$^+$.

The example in the below table was synthesized according to the methods used for the synthesis of 1,5-anhydro-3-({5-chloro-4-[1-(2,2-difluoroethyl)-4-fluoro-2-(2-hydroxypropan-2-yl)-1H-benzimidazol-6-yl]pyrimidin-2-yl}amino)-2,3-dideoxy-D-threo-pentitol (Example A67) (Scheme A-5). The following example was synthesized with non-critical changes or substitutions to the exemplified procedures that someone who is skilled in the art would be able to realize.

Example A69 (Scheme A-6): Preparation of (3R, 4R)-4-({5-chloro-4-[2-(difluoromethyl)-4-fluoro-1-(propan-2-yl)-1H-benzimidazol-6-yl]pyrimidin-2-yl}amino)-1-(methanesulfonyl)piperidin-3-ol Scheme A-6

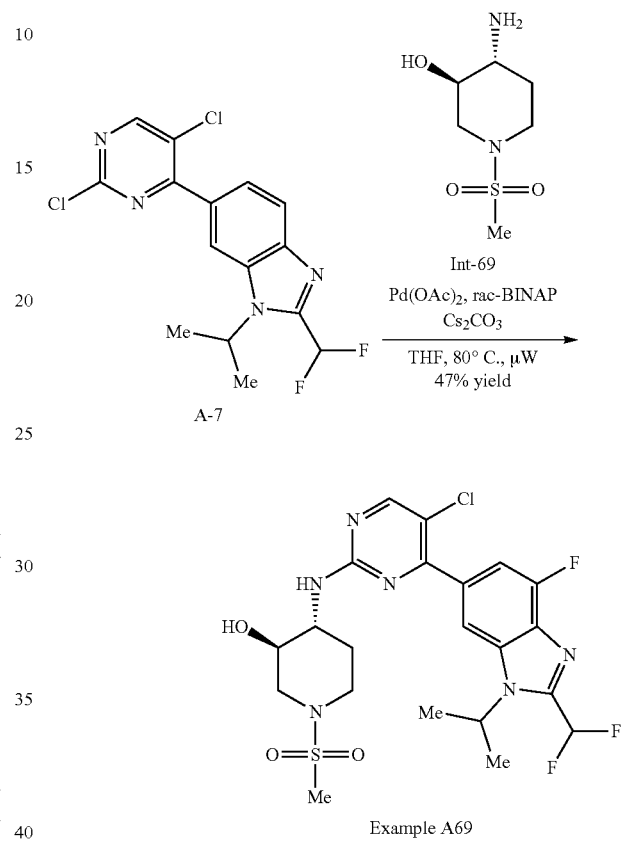

Example A69

| Example number | Structure/Name | LCMS | NMR |
|---|---|---|---|
| A68 | 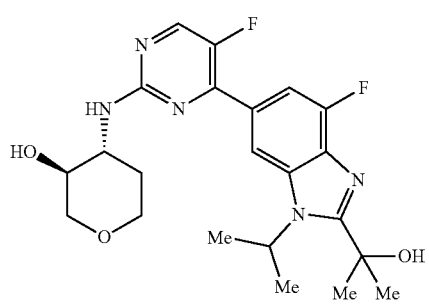<br>1,5-anhydro-2,3-dideoxy-3-({5-fluoro-4-[4-fluoro-2-(2-hydroxypropan-2-yl)-1-(propan-2-yl)-1H-benzimidazol-6-yl]pyrimidin-2-yl}amino)-D-threo-pentitol | 448.2 [M + H]$^+$ (ESI) | $^1$H NMR (400 MHz, DMSO-$d_6$) δ 8.43 (d, J = 4.0 Hz, 1H), 8.21 (s, 1H), 7.62 (d, J = 12.1 Hz, 1H), 7.19 (d, J = 7.6 Hz, 1H), 5.92-5.70 (m, 2H), 4.96 (s, 1H), 3.91-3.73 (m, 3H), 3.62-3.46 (m, 1H), 3.13-2.99 (m, 1H), 2.14-1.96 (m, 1H), 1.67 (s, 6H), 1.65-1.44 (m, 7H); one proton obscured by solvent peak |

To a solution of 6-(2,5-dichloropyrimidin-4-yl)-2-(difluoromethyl)-1-(propan-2-yl)-1H-benzimidazole (A-7) (prepared as in Example A1, 49.6 mg, 0.132 mmol) in THF (1.32 mL) were added (3R,4R)-4-amino-1-(methanesulfonyl)piperidin-3-ol (Int-69) (38.5 mg, 0.198 mmol), Cs$_2$CO$_3$ (129 mg, 0.397 mmol), Pd(OAc)$_2$ (6 mg, 0.0264 mmol), and rac-BINAP (17 mg, 0.0264 mmol). The mixture was sparged with N$_2$ for 10 min and then stirred for 105 min at 80° C. with microwave irradiation. LCMS analysis indicated complete consumption of the starting material with formation of the desired product mass. The reaction was diluted with MeOH and then filtered through a filter disc (0.2 m). The material was purified by preparative SFC on a Nacalai Cosmosil 3-hydroxyphenyl-bonded column (150×20 mm), which was eluted with 12-23% MeOH/CO$_2$ with a flow rate of 85 mL/min to provide (3R,4R)-4-({5-chloro-4-[2-(difluoromethyl)-4-fluoro-1-(propan-2-yl)-1H-benzimidazol-6-yl]pyrimidin-2-yl}amino)-1-(methanesulfonyl)piperidin-3-ol (Example A69) (33.1 mg, 47% yield) as a solid. $^1$H NMR (400 MHz, DMSO-d$_6$, 80° C.) δ=8.43 (s, 1H), 8.10 (d, J=1.0 Hz, 1H), 7.57-7.23 (m, 3H), 5.14-5.02 (m, 1H), 4.97 (br. s., 1H), 3.90-3.75 (m, 2H), 3.73-3.63 (m, 2H), 3.55 (d, J=13.1 Hz, 1H), 2.89-2.86 (s, 3H), 2.78-2.66 (m, 1H), 2.18-2.08 (m, 1H), 1.68 (d, J=6.8 Hz, 6H), 1.63-1.59 (m, 1H); m/z (APCl) for (C$_{21}$H$_{24}$ClF$_3$N$_6$O$_3$S), 533.0 (M+H)$^+$.

Example A70 (Scheme A-7): Preparation of (3R,4R)-4-({5-ethyl-4-[4-fluoro-2-methyl-1-(propan-2-yl)-1H-benzimidazol-6-yl]pyrimidin-2-yl}amino)-1-(methanesulfonyl)piperidin-3-ol Scheme A-7

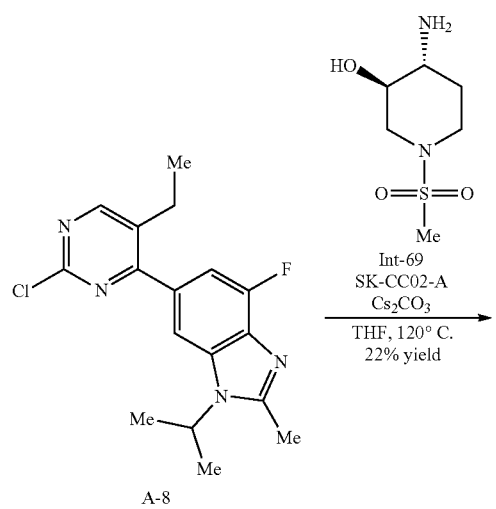

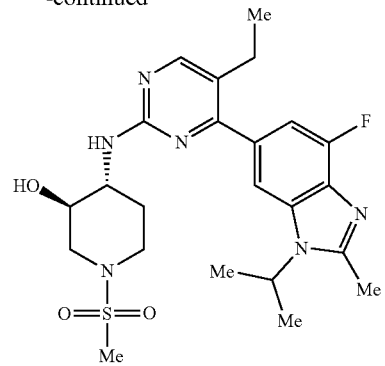

Example A70

A solution of 6-(2-chloro-5-ethylpyrimidin-4-yl)-4-fluoro-2-methyl-1-(propan-2-yl)-1H-benzimidazole (A-8) (prepared as in Example A1, 80.0 mg, 0.240 mmol) in 2-methyl-2-butanol (6 mL) was treated with Cs$_2$CO$_3$ (157 mg, 0.481 mmol) and (3R,4R)-4-amino-1-(methanesulfonyl)piperidin-3-ol (Int-69) (60.7 mg, 0.312 mmol) and sparged with N$_2$. Chloro-2-(dimethylaminomethyl)-ferrocen-1-yl-(dinorbornylphosphine)palladium (SK-0002-A) (14.6 mg, 0.024 mmol) was added and the mixture again sparged with N$_2$. The reaction mixture was stirred at 120° C. for 16 h. The crude mixture was combined with a second reaction run in analogous fashion on a 30 mg scale and concentrated. The residue was partitioned between water (30 mL) and EtOAc (30 mL). The aqueous phase was extracted with EtOAc (30 mL). The combined organic phases were washed with brine, dried over Na$_2$SO$_4$, filtered, and concentrated. The crude residue was purified in two stages, first by preparative TLC (SiO$_2$, 10:1 DCM/MeOH, R$_f$=0.5) and then by preparative HPLC with an Xbridge column (150×30 mm, 10 μm particle size, column temperature 25° C.), which was eluted with 15-55% MeCN/H$_2$O (+0.05% NH$_4$OH) with a flow rate of 25 mL/min to provide (3R,4R)-4-({5-ethyl-4-[4-fluoro-2-methyl-1-(propan-2-yl)-1H-benzimidazol-6-yl]pyrimidin-2-yl}amino)-1-(methanesulfonyl)piperidin-3-ol (Example A70) (25.4 mg, 22% yield) as a white solid. $^1$H NMR (400 MHz, DMSO-d$_6$) δ 8.27 (s, 1H), 7.60 (s, 1H), 7.12 (br d, J=11.5 Hz, 1H), 6.99 (br d, J=7.5 Hz, 1H), 5.24 (d, J=4.3 Hz, 1H), 4.84-4.75 (m, 1H), 3.81-3.74 (m, 1H), 3.65-3.55 (m, 2H), 3.49-3.44 (m, 1H), 2.89 (s, 3H), 2.87-2.81 (m, 1H), 2.71-2.64 (m, 1H), 2.61 (s, 3H), 2.59-2.54 (m, 2H), 2.12-2.04 (m, 1H), 1.57 (d, J=6.8 Hz, 6H), 1.54-1.45 (m, J=10.0 Hz, 1H), 1.04 (t, J=7.5 Hz, 3H); m/z (ESI+) for (C$_{23}$H$_{31}$FN$_6$O$_3$S), 491.1 (M+H)$^+$.

The examples in the below table were synthesized according to the methods used for the synthesis of (3R,4R)-4-({5-chloro-4-[2-(difluoromethyl)-4-fluoro-1-(propan-2-yl)-1H-benzimidazol-6-yl]pyrimidin-2-yl}amino)-1-(methanesulfonyl)piperidin-3-ol (Example A70) (Scheme A-6) and (3R,4R)-4-({5-ethyl-4-[4-fluoro-2-methyl-1-(propan-2-yl)-1H-benzimidazol-6-yl]pyrimidin-2-yl}amino)-1-(methanesulfonyl)piperidin-3-ol (Example A65) (Scheme A-7). The following examples were synthesized with non-critical changes or substitutions to the exemplified procedures that someone who is skilled in the art would be able to realize.

| Example number | Structure/Name | LCMS | NMR |
|---|---|---|---|
| A71 | (3R,4R)-4-({5-chloro-4-[2-ethyl-4-fluoro-1-(oxetan-3-yl)-1H-benzimidazol-6-yl]pyrimidin-2-yl}amino)-1-(methanesulfonyl)piperidin-3-ol | 525.1 [M + H]+ (ESI) | $^1$H NMR (700 MHz, DMSO-$d_6$) δ 8.73-8.18 (m, 2H), 7.83-6.97 (m, 2H), 5.75 (ddd, J = 13.2, 7.7, 5.4 Hz, 1H), 5.19-5.08 (m, 2H), 5.07-4.89 (m, 2H), 3.79 (s, 1H), 3.67-3.59 (m, 5H), 2.94-2.87 (m, 5H), 2.86-2.79 (m, 1H), 2.64 (t, J = 10.3 Hz, 1H), 1.57-1.44 (m, 1H), 1.30 (t, J = 7.5 Hz, 3H) |
| A72 | (3R,4R)-4-{[5-chloro-4-(1-cyclopropyl-4-fluoro-2-methyl-1H-benzimidazol-6-yl)pyrimidin-2-yl]amino}-1-(methanesulfonyl)piperidin-3-ol | 495.1 [M + H]+ (ESI) | $^1$H NMR (600 MHz, DMSO-$d_6$) δ 7.96 (s, 1H) 7.30-7.57 (m, 1H) 6.99-7.11 (m, 1H) 6.89-6.98 (m, 1H) 4.74 (d, J = 4.59 Hz, 1H) 3.30-3.38 (m, 1H) 3.15 (d, J = 10.64 Hz, 2H) 3.04 (d, J = 12.10 Hz, 2H) 2.44 (s, 3H) 2.41 (d, J = 2.38 Hz, 1H) 2.21 (s, 1H) 2.18 (s, 3H) 1.01-1.15 (m, 1H) 0.72-0.82 (m, 3H) 0.56-0.64 (m, 2H) |
| A73 | *first eluting stereoisomer (3R,4R)-4-({5-chloro-4-[4-fluoro-1-(1-methoxypropan-2-yl)-2-methyl-1H-benzimidazol-6-yl]pyrimidin-2-yl}amino)-1-(methanesulfonyl)piperidin-3-ol | 527.5 [M + H]+ (APCI) | $^1$H NMR (400 MHz, DMSO-$d_6$) δ 8.39 (s, 1H), 7.93 (d, J = 1.3 Hz, 1H), 7.40 (dd, J = 11.8, 1.3 Hz, 1H), 7.16 (d, J = 7.6 Hz, 1H), 4.98 (d, J = 4.6 Hz, 1H), 4.84 (ddd, J = 8.4, 7.0, 4.7 Hz, 1H), 3.90 (dd, J = 10.5, 8.5 Hz, 1H), 3.82 (ddd, J = 12.3, 6.1, 4.3 Hz, 1H), 3.73 (dd, J = 10.5, 4.8 Hz, 1H), 3.70-3.64 (m, 1H), 3.59-3.48 (m, 1H), 3.22 (s, 3H), 2.92 (dd, J = 10.4, 2.0 Hz, 1H), 2.89 (s, 3H), 2.77-2.68 (m, 1H), 2.62 (s, 3H), 2.18-2.08 (m, 1H), 1.68-1.50 (m, 5H); [α]$_D^{22}$ = +42.1° (c = 0.1, MeOH) |

-continued

| Example number | Structure/Name | LCMS | NMR |
|---|---|---|---|
| A74 | 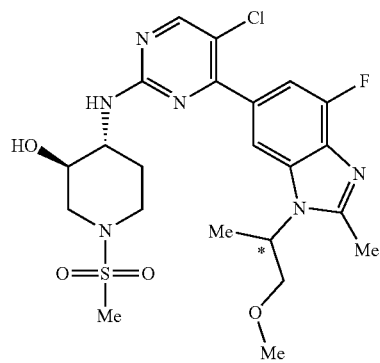<br>*second eluting stereoisomer<br>(3R,4R)-4-({5-chloro-4-[4-fluoro-1-(1-methoxypropan-2-yl)-2-methyl-1H-benzimidazol-6-yl]pyrimidin-2-yl}amino)-1-(methanesulfonyl)piperidin-3-ol | 527.5 [M + H]⁺ (APCI) | ¹H NMR (400 MHz, DMSO-d₆) δ 8.39 (s, 1H), 7.93 (d, J = 1.4 Hz, 1H), 7.39 (dd, J = 11.8, 1.3 Hz, 1H), 7.16 (d, J = 7.7 Hz, 1H), 4.97 (s, 1H), 4.91-4.73 (m, 1H), 3.89 (dd, J = 10.5, 8.5 Hz, 1H), 3.82 (ddd, J = 9.3, 7.9, 4.5 Hz, 1H), 3.72 (dd, J = 10.5, 4.8 Hz, 1H), 3.70-3.63 (m, 1H), 3.58-3.52 (m, 1H), 3.22 (s, 3H), 2.94-2.89 (m, 1H), 2.89 (s, 3H), 2.77-2.68 (m, 1H), 2.62 (s, 3H), 2.16-2.08 (m, 1H), 1.60 (d, J = 7.1 Hz, 5H) |
| A75 | 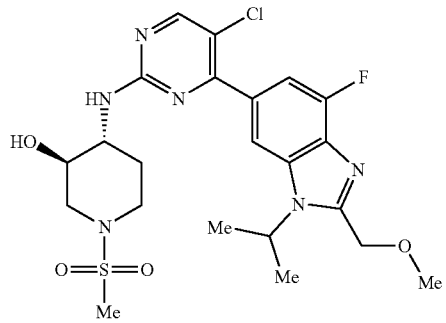<br>(3R,4R)-4-({5-chloro-4-[4-fluoro-2-(methoxymethyl)-1-(propan-2-yl)-1H-benzimidazol-6-yl]pyrimidin-2-yl}amino)-1-(methanesulfonyl)piperidin-3-ol | 527.1 [M + H]⁺ (APCI) | ¹H NMR (400 MHz, DMSO-d₆) δ 8.40 (s, 1H), 8.00 (d, J = 0.98 Hz, 1H), 7.38-7.51 (m, 1H), 7.12-7.23 (m, 1H), 4.96 (s, 2H), 4.76 (s, 2H), 3.75-3.89 (m, 1H), 3.67 (s, 2H), 3.47-3.58 (m, 1H), 3.37 (s, 3H), 2.89-2.94 (m, 1H), 2.88 (s, 3H), 2.65-2.77 (m, 1H), 2.07-2.17 (m, 1H), 1.63 (d, J = 6.97 Hz, 6H), 1.57-1.48 (m, 1H). |
| A76 | 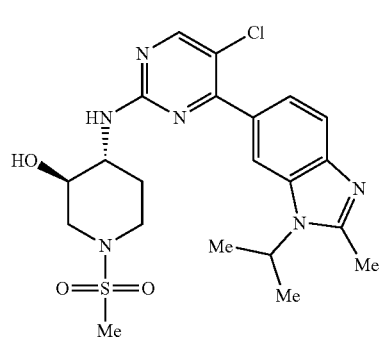<br>(3R,4R)-4-({5-fluoro-4-[2-methyl-1-(propan-2-yl)-1H-benzimidazol-6-yl]pyrimidin-2-yl}amino)-1-(methanesulfonyl)piperidin-3-ol | 463.4 [M + H]⁺ (ESI) | ¹H NMR (400 MHz, CD₃OD) δ 8.40 (s, 1H), 8.28 (d, J = 4.2 Hz, 1H), 7.99 (dt, J = 8.5, 1.4 Hz, 1H), 7.65 (d, J = 8.6 Hz, 1H), 3.95-3.66 (m, 4H), 2.98 (td, J = 11.8, 2.8 Hz, 1H), 2.91 (s, 3H), 2.78 (dd, J = 11.5, 9.1 Hz, 1H), 2.67 (s, 3H), 2.36-2.24 (m, 1H), 1.80-1.64 (m, 7H); one proton obscured by solvent peak |

| Example number | Structure/Name | LCMS | NMR |
|---|---|---|---|
| A77 | 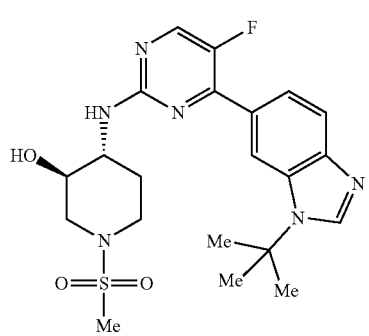<br>(3R,4R)-4-{[4-(1-tert-butyl-1H-benzimidazol-6-yl)-5-fluoropyrimidin-2-yl]amino}-1-(methanesulfonyl)piperidin-3-ol | 463.3 [M + H]+ (ESI) | $^1$H NMR (400 MHz, DMSO-d$_6$) δ 8.47-8.34 (M, 3H), 7.91-7.83 (m, 1H), 7.82-7.75 (m, 1H), 7.18 (br d, J = 7.7 Hz, 1H), 5.22 (d, J = 4.4 Hz, 1H), 3.82-3.46 (m, 4H), 2.95-2.80 (m, 4H), 2.69-2.65 (m, 1H), 2.18-2.02 (m, 1H), 1.75 (s, 9H), 1.63-1.44 (m, 1H) |
| A78 | 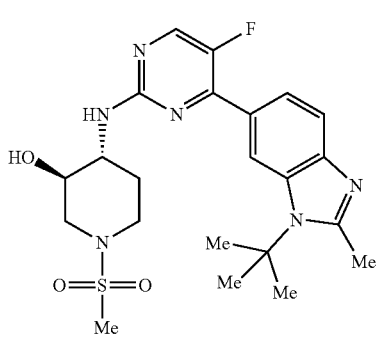<br>(3R,4R)-4-{[4-(1-tert-butyl-2-methyl-1H-benzimidazol-6-yl)-5-fluoropyrimidin-2-yl]amino}-1-(methanesulfonyl)piperidin-3-ol | 476.8 [M + H]+ (ESI) | $^1$H NMR (400 MHz, DMSO-d$_6$) δ 8.57-8.26 (m, 2H), 7.82 (d, J = 8.4 Hz, 1H), 7.62 (d, J = 8.5 Hz, 1H), 7.16 (d, J = 7.7 Hz, 1H), 5.24 (d, J = 4.5 Hz, 1H), 3.84-3.72 (m, 1H), 3.72-3.59 (m, 2H), 3.52 (d, J = 12.0 Hz, 1H), 2.92 (s, 3H), 2.90-2.81 (m, 1H), 2.78 (s, 3H), 2.71-2.60 (m, 1H), 2.19-2.05 (m, 1H), 1.84 (s, 9H), 1.55 (q, J = 11.5 Hz, 1H) |
| A79 | 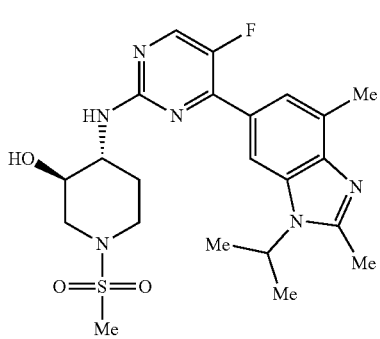<br>(3R,4R)-4-({4-[2,4-dimethyl-1-(propan-2-yl)-1H-benzimidazol-6-yl]-5-fluoropyrimidin-2-yl}amino)-1-(methanesulfonyl)piperidin-3-ol | 476.9 [M + H]+ (ESI) | $^1$H NMR (400 MHz, DMSO-d$_6$) δ 8.38 (d, J = 4.0 Hz, 1H), 8.08 (s, 1H), 7.64 (q, J = 1.2 Hz, 1H), 7.16 (d, J = 7.6 Hz, 1H), 5.23 (d, J = 4.5 Hz, 1H), 4.78 (hept, J = 6.8 Hz, 1H), 3.83-3.71 (m, 1H), 3.70-3.56 (m, 2H), 3.55-3.46 (m, 1H), 2.96-2.82 (m, 4H), 2.71-2.64 (m, 1H), 2.60 (s, 3H), 2.54 (s, 3H), 2.09 (d, J = 13.7 Hz, 1H), 1.64-1.48 (m, 7H) |

-continued

| Example number | Structure/Name | LCMS | NMR |
|---|---|---|---|
| A80 | 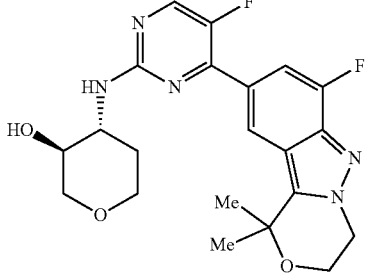<br>1,5-anhydro-2,3-dideoxy-3-{[5-fluoro-4-(7-fluoro-1,1-dimethyl-3,4-dihydro-1H-[1,4]oxazino[4,3-b]indazol-9-yl)pyrimidin-2-yl]amino}-D-threo-pentitol | 432.1 [M + H]+ (ESI) | $^1$H NMR (400 MHz, DMSO-$d_6$) δ 8.42 (d, J = 4.0 Hz, 1H), 8.22 (s, 1H), 7.67 (d, J = 13.1 Hz, 1H), 7.20 (br d, J = 7.8 Hz, 1H), 4.95 (d, J = 5.3 Hz, 1H), 4.45 (t, J = 5.0 Hz, 2H), 4.22 (t, J = 5.0 Hz, 2H), 3.87-3.75 (m, 3H), 3.56-3.45 (m, 1H), 3.06 (t, J = 10.4 Hz, 1H), 2.00 (br d, J = 9.6 Hz, 1H), 1.70 (s, 6H), 1.55-1.42 (m, 1H) |
| A81 | 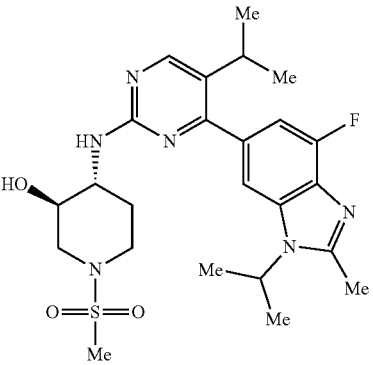<br>(3R,4R)-4-({4-[4-fluoro-2-methyl-1-(propan-2-yl)-1H-benzimidazol-6-yl]-5-(propan-2-yl)pyrimidin-2-yl}amino)-1-(methanesulfonyl)piperidin-3-ol | 504.9 [M + H]+ (ESI) | $^1$H NMR (400 MHz, DMSO-$d_6$) δ 8.41 (s, 1H), 7.50 (s, 1H), 7.10-6.95 (m, 2H), 5.23 (d, J = 4.3 Hz, 1H), 4.86-4.73 (m, 1H), 3.77 (br s, 1H), 3.67-3.54 (m, 2H), 3.50-3.39 (m, 2H), 2.99-2.81 (m, 5H), 2.71-2.60 (m, 4H), 2.14-2.03 (m, 1H), 1.56 (d, J = 6.8 Hz, 6H), 1.45-1.25 (m, 6H) |
| A82 | 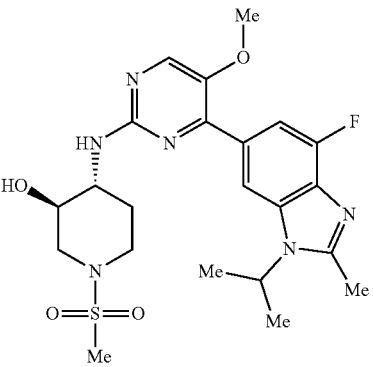<br>(3R,4R)-4-({4-[4-fluoro-2-methyl-1-(propan-2-yl)-1H-benzimidazol-6-yl]-5-methoxypyrimidin-2-yl}amino)-1-(methanesulfonyl)piperidin-3-ol | 493.1 [M + H]+ (ESI) | $^1$H NMR (400 MHz, DMSO-$d_6$) δ 8.30 (s, 1H), 8.25 (s, 1H), 7.70 (d, J = 12.6 Hz, 1H), 6.80 (d, J = 7.5 Hz, 1H), 5.24 (d, J = 4.5 Hz, 1H), 4.88-4.73 (m, 1H), 3.83 (s, 3H), 3.74 (m, 2H), 3.69-3.57 (m, 2H), 2.96-2.83 (m, 4H), 2.73-2.65 (m, 1H), 2.61 (s, 3H), 2.12 (d, J = 13.2 Hz, 1H), 1.66-1.46 (m, 7H) |

-continued

| Example number | Structure/Name | LCMS | NMR |
|---|---|---|---|
| A83 | 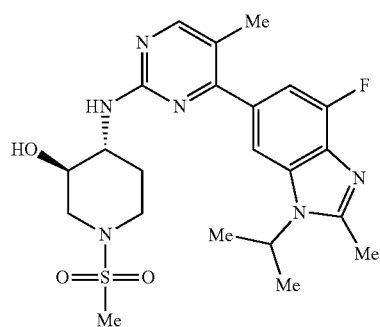<br>(3R,4R)-4-({4-[4-fluoro-2-methyl-1-(propan-2-yl)-1H-benzimidazol-6-yl]-5-methylpyrimidin-2-yl}amino)-1-(methanesulfonyl)piperidin-3-ol | 477.1 [M + H]+ (ESI) | $^1$H NMR (400 MHz, CD$_3$OD) δ 8.22 (s, 1H), 7.70 (d, J = 1.3 Hz, 1H), 7.24 (dd, J = 11.4, 1.2 Hz, 1H), 3.93-3.78 (m, 2H), 3.75-3.62 (m, 2H), 2.87 (s, 4H), 2.77-2.64 (m, 4H), 2.25 (m, 4H), 1.72-1.60 (m, 7H); one proton obscured by solvent peak |
| A84 | 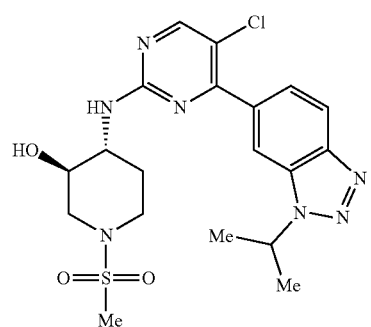<br>(3R,4R)-4-({5-chloro-4-[1-(propan-2-yl)-1H-benzotriazol-6-yl]pyrimidin-2-yl}amino)-1-(methanesulfonyl)piperidin-3-ol | 456.8 [M + H]+ (ESI) | $^1$H NMR (600 MHz, DMSO-d$_6$) δ 8.47 (s, 1H), 8.25 (b s, 1H), 8.15 (d, J = 8.6 Hz, 1H), 7.72-7.68 (m, 1H), 7.53 (br s, 1H), 5.29 (hept, J = 6.7 Hz, 1H), 5.21 (m, 1H), 3.80 (b s, 1H), 3.65-3.57 (m, 2H), 3.52-3.46 (m, 1H), 2.91-2.84 (m, 4H), 2.66 (t, J = 10.3 Hz, 1H), 2.10-2.01 (m, 1H), 1.66 (d, J = 6.7 Hz, 6H), 1.58-1.49 (m, 1H) |
| A85 | 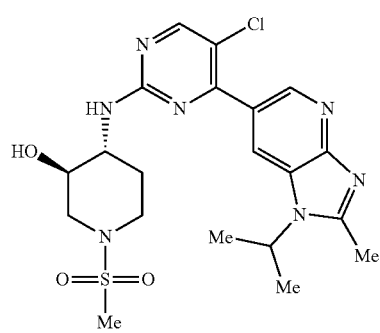<br>(3R,4R)-4-({5-chloro-4-[2-methyl-1-(propan-2-yl)-1H-imidazo[4,5-b]pyridin-6-yl]pyrimidin-2-yl}amino)-1-(methanesulfonyl)piperidin-3-ol | 480.1 [M + H]+ (ESI) | $^1$H NMR (400 MHz, DMSO-d$_6$) δ 8.75 (d, J = 2.0 Hz, 1H), 8.42-8.37 (m, 2H), 7.23 (d, J = 7.6 Hz, 1H), 4.84 (hept, J = 6.8 Hz, 1H), 3.63 (m, 2H), 2.95-2.85 (m, 4H), 2.77-2.64 (m, 4H), 2.19-2.08 (m, 1H), 1.80-1.74 (m, 3H), 1.61 (m, 7H) |

| Example number | Structure/Name | LCMS | NMR |
|---|---|---|---|
| A86 | 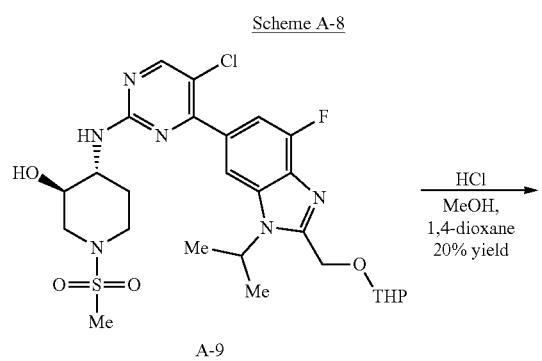<br>(3R,4R)-4-({5-chloro-4-[2-methyl-3-(propan-2-yl)-3H-imidazo[4,5-b]pyridin-5-yl]pyrimidin-2-yl}amino)-1-(methanesulfonyl)piperidin-3-ol | 480.1 [M + H]⁺ (ESI) | ¹H NMR (600 MHz, DMSO-d₆) δ 8.42 (s, 1H), 8.03 (d, J = 8.2, 1.3 Hz, 1H), 7.77 (s, 1H), 7.42 (s, 1H), 5.23 (s, 1H), 4.79 (h, J = 6.8 Hz, 1H), 3.87-3.78 (m, 1H), 3.68-3.56 (m, 3H), 2.92-2.82 (m, 4H), 2.71-2.63 (m, 4H), 2.10-2.01 (m, 1H), 1.67 (d, J = 6.8 Hz, 6H), 1.53 (m, 1H) |

Example A87 (Scheme A-8): Preparation of (3R, 4R)-4-({5-chloro-4-[4-fluoro-2-(hydroxymethyl)-1-(propan-2-yl)-1H-benzimidazol-6-yl]pyrimidin-2-yl}amino)-1-(methanesulfonyl)piperidin-3-ol Scheme A-8

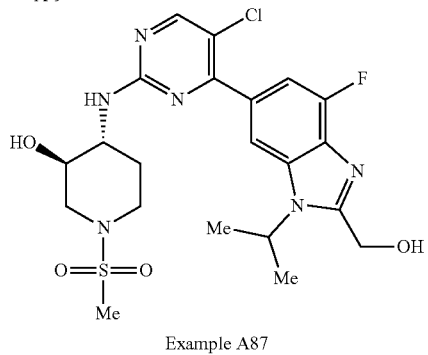

Example A87

A solution of (3R,4R)-4-({5-chloro-4-[4-fluoro-2-{[(oxan-2-yl)oxy]methyl}-1-(propan-2-yl)-1H-benzimidazol-6-yl]pyrimidin-2-yl}amino)-1-(methanesulfonyl)piperidin-3-ol (A-9) (Prepared as in Example A69, 88 mg, 0.15 mmol) in MeOH (3.0 mL) at 0° C. was added a solution of HCl (4.0 N in 1,4-dioxane, 0.55 mL, 2.2 mmol). After 2.5 h, LCMS analysis showed consumption of the starting material with formation of the desired product mass. The reaction mixture was concentrated to dryness. The residue was purified by preparative SFC on a Princeton Ha-Morpholine column (150×21.1 mm, 5 μm particle size, column temperature at 35° C.), which was eluted with 22-50% MeOH/CO₂ with a flow rate of 60 mL/min to provide (3R,4R)-4-({5-chloro-4-[4-fluoro-2-(hydroxymethyl)-1-(propan-2-yl)-1H-benzimidazol-6-yl]pyrimidin-2-yl}amino)-1-(methanesulfonyl)piperidin-3-ol (Example A87) (15 mg, 20% yield) as a white solid. ¹H NMR (600 MHz, DMSO-d₆) δ 8.42 (s, 1H), 7.97 (s, 1H), 7.52-7.31 (m, 2H), 5.73 (t, J=5.5 Hz, 1H), 5.20 (d, J=5.0 Hz, 1H), 5.02 (hept, J=7.0 Hz, 1H), 4.77 (d, J=5.7 Hz, 2H), 3.86-3.75 (m, 1H), 3.68-3.56 (m, 2H), 3.53-3.46 (m, 1H), 2.94-2.80 (m, 4H), 2.71-2.60 (m, 1H), 2.06 (s, 1H), 1.66-1.47 (m, 7H); m/z (ESI+) for (C₂₁H₂₆ClFN₆O₄S), 512.8 (M+H)⁺.

Example A88 (Scheme A-9): Preparation of (3R, 4R)-4-({4-[1-(azetidin-3-yl)-4-fluoro-2-methyl-1H-benzimidazol-6-yl]-5-fluoropyrimidin-2-yl}amino)-1-(methanesulfonyl)piperidin-3-ol Scheme A-9

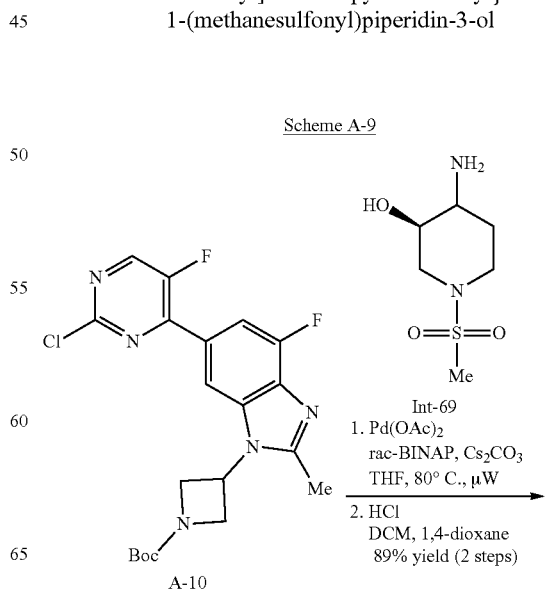

239

-continued

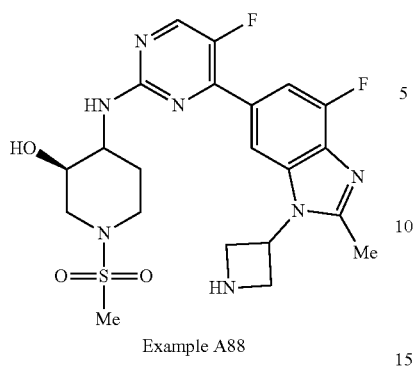

Example A88

A solution of tert-butyl 3-[6-(2-chloro-5-fluoropyrimidin-4-yl)-4-fluoro-2-methyl-1H-benzimidazol-1-yl]azetidine-1-carboxylate (A-10) (Prepared as in Example A1, 75.0 mg, 0.170 mmol), (3R,4R)-4-amino-1-(methanesulfonyl)piperidin-3-ol (Int-69) (50.1 mg, 0.258 mmol), Pd(OAc)$_2$ (7.73 mg, 0.034 mmol), rac-BINAP (21.4 mg, 0.034 mmol), and Cs$_2$CO$_3$ (168 mg, 0.516 mmol) in THF (1.7 mL) was stirred under microwave irradiation at 80° C. for 30 min. The mixture was purified via flash chromatography (SiO$_2$, 0-100% EtOAc/heptanes). The product-containing fractions were concentrated, taken up into DCM (5 mL), and treated with HCl (4.0 M in 1,4-dioxane, 1.0 mL). The mixture was stirred at ambient temperature for 4 h. The solution was concentrated and the crude residue was purified by preparative HPLC on a Phenomenex Gemini NX C18 column (150×21.2 mm, 5 µm particle size), which was eluted with 20-100% MeCN/H2O (+10 mM NH$_4$OAc) with a flow rate of 40 mL/min to provide (3R,4R)-4-({4-[1-(azetidin-3-yl)-4-fluoro-2-methyl-1H-benzimidazol-6-yl]-5-fluoropyrimidin-2-yl}amino)-1-(methanesulfonyl)piperidin-3-ol (Example A88) (76 mg, 89% yield) as a solid. $^1$H NMR (600 MHz, DMSO-d$_6$) δ 8.70 (s, 1H), 8.47-8.29 (m, 1H), 7.64 (d, J=12.0 Hz, 1H), 7.15 (d, J=7.7 Hz, 1H), 5.43 (s, 1H), 4.27-3.87 (m, 4H), 3.79 (s, 1H), 3.71-3.54 (m, 2H), 3.50 (s, 1H), 3.01-2.78 (m, 5H), 2.68 (t, J=10.3 Hz, 1H), 2.56 (d, J=1.4 Hz, 3H), 2.12 (s, 1H), 1.62-1.43 (m, 1H); m/z (APCl+) for (C$_{21}$H$_{25}$F$_2$N$_7$O$_3$S), 494.2 (M+H)$^+$.

Example A89 (Scheme A-10): Preparation of (3R,4R)-4-({5-chloro-4-[4-fluoro-2-methyl-1-(oxetan-3-yl)-1H-benzimidazol-6-yl]pyrimidin-2-yl}amino)-1-(methanesulfonyl)piperidin-3-ol Scheme A-10

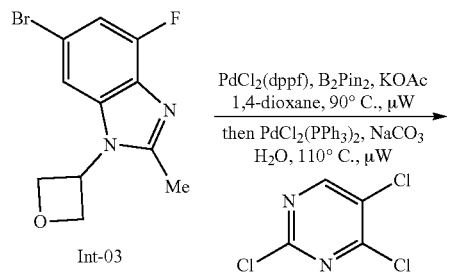

240

-continued

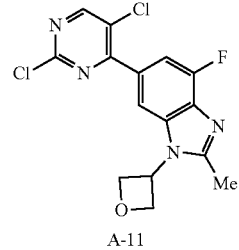

A-11

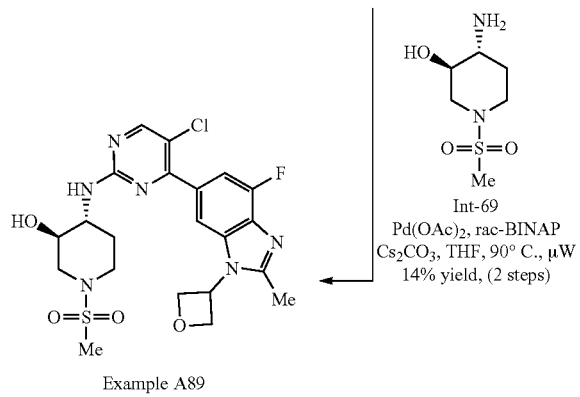

Example A89

Step 1: Synthesis of 6-(2,5-dichloropyrimidin-4-yl)-4-fluoro-2-methyl-1-(oxetan-3-yl)-1H-benzimidazole (A-11)

A mixture of 6-bromo-4-fluoro-2-methyl-1-(oxetan-3-yl)-1H-benzimidazole (Int-03) (63.0 mg, 0.220 mmol), B$_2$Pin$_2$ (84.2 mg, 0.331 mmol), KOAc (65.1 mg, 0.663 mmol), and PdCl$_2$(dppf) (18.0 mg, 0.022 mmol) in 1,4-dioxane (1.1 mL) was sparged with N$_2$ for 10 min and then heated in a microwave at 90° C. for 1 h. The mixture was cooled to ambient temperature and charged with PdCl$_2$(PPh$_3$)$_2$ (7.71 mg, 0.011 mmol), aqueous Na$_2$CO$_3$ (2.0 M, 0.33 mL, 0.659 mmol) and 2,4,5-trichloropyrimidine (60.5 mg, 37.8 uL, 0.330 mmol). The mixture was sparged with nitrogen for 10 min and then heated in the microwave at 110° C. for 70 min. The mixture was partitioned between water (2 mL) and EtOAc (2 mL). The aqueous phase was extracted with EtOAc (3×2 mL). The combined organic phases were concentrated to provide 6-(2,5-dichloropyrimidin-4-yl)-4-fluoro-2-methyl-1-(oxetan-3-yl)-1H-benzimidazole (A-11), which was taken on without further purification. m/z (APCl+) for (C$_{15}$H$_{11}$Cl$_2$FN$_4$O), 352.8 (M+H)$^+$.

Step 2: Synthesis of (3R,4R)-4-({5-chloro-4-[4-fluoro-2-methyl-1-(oxetan-3-yl)-1H-benzimidazol-6-yl]pyrimidin-2-yl}amino)-1-(methanesulfonyl)piperidin-3-ol (Example A89)

Crude 6-(2,5-dichloropyrimidin-4-yl)-4-fluoro-2-methyl-1-(oxetan-3-yl)-1H-benzimidazole (A-11) was dissolved in THF (1.8 mL). (3R,4R)-4-Amino-1-(methanesulfonyl)piperidin-3-ol (Int-69) (64.4 mg, 0.331 mmol), Pd(OAc)$_2$ (9.9 mg, 0.044 mmol), rac-BINAP (27.5 mg, 0.044 mmol), and Cs$_2$CO$_3$ (216 mg, 0.663 mmol) were added and the mixture was sparged with N$_2$ for 10 min. The mixture was stirred at 90° C. for 1.5 h with microwave irradiation. The mixture was cooled to ambient temperature, diluted with DMSO and filtered through a 0.2 micron filter disc. The crude material was purified by preparative SFC with a Princeton HA-morpholine column (150×21.1 mm, 5 μm column particle size, column temperature of 35° C.), which was eluted with 15-50% MeOH/CO₂ (+10 mM NH₃) with a flow rate of 80 g/min. The material was re-purified by preparative SFC with a Diacel DC pak SFC-B (150×21.1 mm, 5 μm particle size, column temperature of 35° C.), which was eluted with 18-45% MeOH/CO₂ with a flow rate of 80 g/min to provide (3R,4R)-4-({5-chloro-4-[4-fluoro-2-methyl-1-(oxetan-3-yl)-1H-benzimidazol-6-yl]pyrimidin-2-yl}amino)-1-(methanesulfonyl)piperidin-3-ol (Example A89) (15.9 mg, 14% yield over two steps) as a white solid. $^1$H NMR (600 MHz, DMSO-d₆, 75° C.) δ 8.40 (s, 1H), 8.35 (b s, 1H), 7.49 (d, J=11.7 Hz, 1H), 7.20 (d, J=7.4 Hz, 1H), 5.76-5.71 (m, 1H), 5.16 (td, J=7.6, 2.7 Hz, 2H), 5.09-5.04 (m, 2H), 5.01 (b s, 1H), 3.85-3.78 (m, 1H), 3.70-3.62 (m, 2H), 3.55-3.50 (m, 1H), 2.91-2.85 (m, 4H), 2.72-2.66 (m, 1H), 2.58 (s, 3H), 2.15-2.10 (m, 1H), 1.62-1.46 (m, 1H); m/z (APCI+) for ($C_{21}H_{24}ClFN_6O_4S$), 510.8 (M+H)⁺.

Example A90 (Scheme A-11): Preparation of (3R,4R)-4-({5-chloro-4-[4-fluoro-2-(hydroxymethyl)-1-(2,2,2-trifluoroethyl)-1H-benzimidazol-6-yl]pyrimidin-2-yl}amino)-1-(methanesulfonyl)piperidin-3-ol

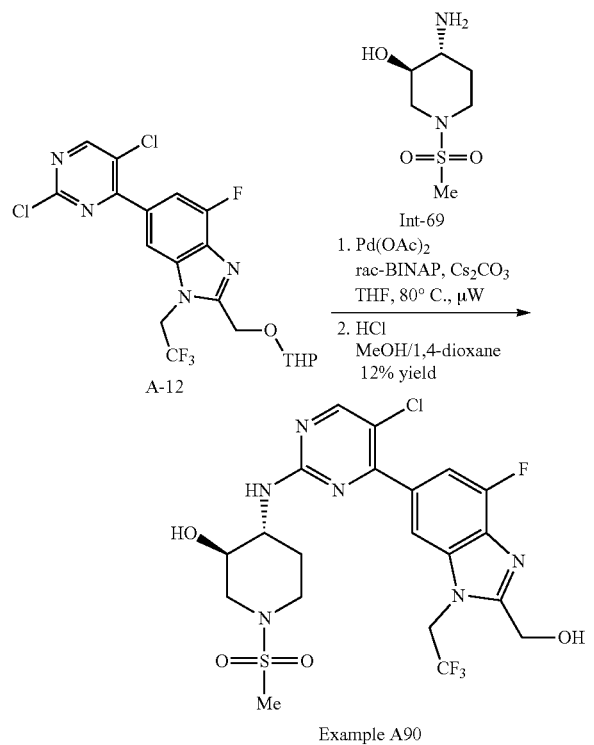

Example A90

To a vial was added 6-(2,5-dichloropyrimidin-4-yl)-4-fluoro-2-{[(oxan-2-yl)oxy]methyl}-1-(2,2,2-trifluoroethyl)-1H-benzimidazole (A-12) (Prepared according to Example A89, 121 mg, 0.25 mmol), (3R,4R)-4-amino-1-(methanesulfonyl)piperidin-3-ol (Int-69) (73.6 mg, 0.38 mmol), Pd(OAc)₂ (11.3 mg, 0.051 mmol), rac-BINAP (31.4 mg, 0.051 mmol), Cs₂CO₃ (247 mg, 0.76 mmol), and THF (2.5 mL). The mixture was stirred at 80° C. with microwave irradiation for 30 min. LCMS analysis showed consumption of the starting material with formation of the desired product mass. The mixture was concentrated on SiO₂ and purified by flash chromatography (ISCO, 12 g SiO₂, 0-100% EtOAc/heptanes). The product containing-fractions were concentrated. The residue was taken up in MeOH (5 mL) and treated with HCl (4.0 N in 1,4-dioxane, 1.0 mL) and the mixture was stirred at ambient temperature for 16 h overnight. LCMS analysis showed partial consumption of the starting material. An additional aliquot of HCl (4.0 N in 1,4-dioxane, 1.0 mL) was added. The mixture was stirred for 6 h, at which time LCMS analysis indicated consumption of the starting material. The mixture was concentrated and purified by preparative SFC with a Princeton HA-morpholine column (150×21.1 mm, 5 μm particle size, column temperature 35° C.), which was eluted with 14-50% MeOH/CO₂ at 80 g/min to provide (3R,4R)-4-({5-chloro-4-[4-fluoro-2-(hydroxymethyl)-1-(2,2,2-trifluoroethyl)-1H-benzimidazol-6-yl]pyrimidin-2-yl}amino)-1-(methanesulfonyl)piperidin-3-ol (Example A90) (17 mg, 12% yield) as a gum. $^1$H NMR (400 MHz, DMSO-d₆) δ 8.46 (s, 1H), 7.99 (s, 1H), 7.58-7.41 (m, 2H), 5.93 (t, J=6.0 Hz, 1H), 5.49 (q, J=9.1 Hz, 2H), 5.21 (d, J=4.5 Hz, 1H), 4.82 (d, J=5.8 Hz, 2H), 3.81 (s, 1H), 3.68-3.56 (m, 2H), 3.49 (d, J=12.1 Hz, 1H), 2.94-2.77 (m, 4H), 2.72-2.61 (m, 1H), 2.02 (s, 1H), 1.60-1.44 (m, 1H); m/z (ESI+) for ($C_{20}H_{21}ClF_4N_6O_4S$), 522.9 (M+H)⁺.

Example A91 (Scheme A-12): Preparation of (3R,4R)-4-({5-chloro-4-[4-fluoro-2-(2-hydroxypropan-2-yl)-1-(propan-2-yl)-1H-benzimidazol-6-yl]pyrimidin-2-yl}amino)-1-(methanesulfonyl)piperidin-3-ol

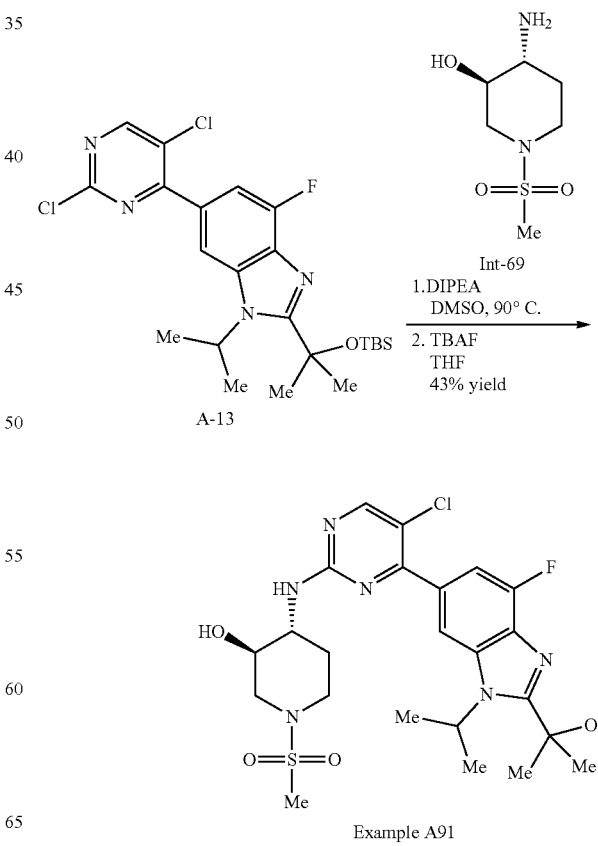

Example A91

A mixture of 2-(2-{[tert-butyl(dimethyl)silyl]oxy}propan-2-yl)-6-(2,5-dichloropyrimidin-4-yl)-4-fluoro-1-(propan-2-yl)-1H-benzimidazole (A-13) (Prepared as in Example A89, 294 mg, 0.590 mmol), (3R,4R)-4-amino-1-(methanesulfonyl)piperidin-3-ol (Int-69) (149 mg, 0.767 mmol), and DIPEA (0.55 mL, 2.95 mmol) in DMSO (2.8 mL) was stirred at 90° C. for 18 h. The resulting solution was cooled to ambient temperature and partitioned between water (30 mL) and EtOAc (30 mL). The layers were separated and the aqueous phase was extracted with EtOAc (5×30 mL). The combined organic phases were washed with water (3×20 mL), dried over $Na_2SO_4$, filtered, and concentrated. The resultant yellow foam was dissolved in THF, cooled to 0° C., and treated with TBAF (1.0 M in THF, 1.2 mL, 1.2 mmol). The resulting solution was allowed to warm to ambient temperature and stirred for 2.5 h before being concentrated. The residue was purified by preparative SFC with a ZymorSpher HADP column (150×21.2 mm, 5 μm particle size, 40° C. column temperature), which was eluted with 18% MeOH/$CO_2$ with a flow rate of 90 mL/min to provide (3R,4R)-4-({5-chloro-4-[4-fluoro-2-(2-hydroxypropan-2-yl)-1-(propan-2-yl)-1H-benzimidazol-6-yl]pyrimidin-2-yl}amino)-1-(methanesulfonyl)piperidin-3-ol (Example A91) (137 mg, 43% yield) as a solid. $^1$H NMR (400 MHz, DMSO-$d_6$, 80° C.) δ 8.39 (s, 1H), 7.98 (d, J=1.3 Hz, 1H), 7.40 (dd, J=11.8, 1.3 Hz, 1H), 7.17 (d, J=7.7 Hz, 1H), 5.80 (h, J=6.8 Hz, 1H), 5.56 (s, 1H), 4.97 (d, J=4.5 Hz, 1H), 3.87-3.78 (m, 1H), 3.71-3.63 (m, 2H), 3.57-3.51 (m, 1H), 2.93-2.85 (m, 4H), 2.75-2.67 (m, 1H), 2.16-2.09 (m, 1H), 1.70 (s, 6H), 1.63 (d, J=7.0 Hz, 7H); m/z (APCl+) for ($C_{23}H_{30}ClFN_6O_4S$), 540.8 (M+H)$^+$.

Example A92 (Scheme A-13): (3R,4R)-4-({5-chloro-4-[1-(1,1-difluoropropan-2-yl)-4-fluoro-2-(hydroxymethyl)-1H-benzimidazol-6-yl]pyrimidin-2-yl}amino)-1-(methanesulfonyl)piperidin-3-ol Scheme A-13

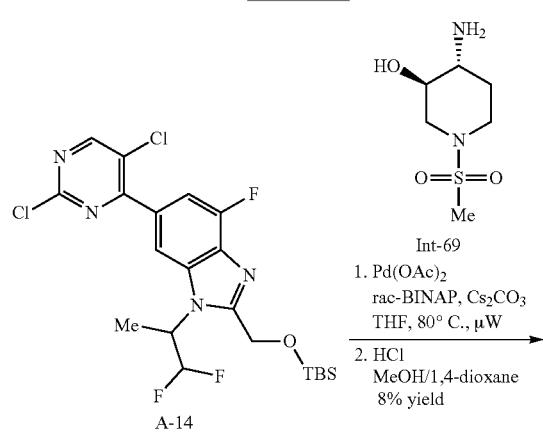

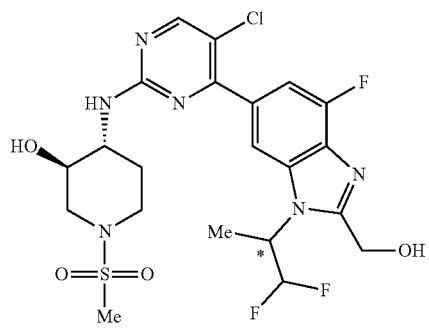

Example A92

To a vial was added 2-({[tert-butyl(dimethyl)silyl]oxy}methyl)-6-(2,5-dichloropyrimidin-4-yl)-1-(1,1-difluoropropan-2-yl)-4-fluoro-1H-benzimidazole (A-14) (Prepared according to Example A89, 81 mg, 0.16 mmol), (3R,4R)-4-Amino-1-(methanesulfonyl)piperidin-3-ol (Int-69) (46.7 mg, 0.24 mmol), Pd(OAc)$_2$ (7.2 mg, 0.032 mmol), rac-BINAP (20.0 mg, 0.032 mmol), $Cs_2CO_3$ (157 mg, 0.48 mmol), and THF (1.6 mL). The mixture was stirred at 80° C. in a microwave for 30 min. LCMS analysis showed consumption of the starting material with formation of the desired product mass. The mixture was concentrated onto $SiO_2$ and purified by flash chromatography (ISCO, 12 g $SiO_2$, 0-100% EtOAc/heptanes). The product-containing fractions were concentrated and taken up in MeOH (5.0 mL). The mixture was treated with HCl (4.0 N in 1,4-dioxane, 2.0 mL) and stirred at ambient temperature for 16 h. LCMS analysis showed consumption of the starting material with formation of the desired product mass. The mixture was concentrated to dryness and then purified by chiral SFC with a ChiralPak AS-H column (100×4.6 mm, 3 μm particle size), which was eluted with 5-60% MeOH/$CO_2$ with a flow rate of 4.0 mL/min to provide (3R,4R)-4-({5-chloro-4-[1-(1,1-difluoropropan-2-yl)-4-fluoro-2-(hydroxymethyl)-1H-benzimidazol-6-yl]pyrimidin-2-yl}amino)-1-(methanesulfonyl)piperidin-3-ol (Example A92) (7.4 mg, 8% yield) as the first eluting fraction. $^1$H NMR (400 MHz, DMSO-$d_6$, 80° C.) δ 8.41 (s, 1H), 8.00 (s, 1H), 7.47 (d, J=11.6 Hz, 1H), 7.19 (d, J=7.7 Hz, 1H), 6.52 (td, J=55.3, 3.7 Hz, 1H), 5.65 (t, J=5.7 Hz, 1H), 5.40-5.26 (m, 1H), 4.97 (d, J=4.6 Hz, 1H), 4.83 (d, J=5.6 Hz, 2H), 3.87-3.76 (m, 1H), 3.72-3.62 (m, 2H), 3.59-3.51 (m, 1H), 2.95-2.84 (m, 4H), 2.75-2.66 (m, 1H), 2.17-2.09 (m, 1H), 1.75 (d, J=7.1 Hz, 3H), 1.65-1.54 (m, 1H); m/z (ESI+) for ($C_{21}H_{24}ClF_3N_6O_4S$), 522.9 (M+H)$^+$; $[α]_D^{22}$=−26.5° (c=0.1 M, MeOH).

Example A93 (Scheme A-14): Preparation of (3R, 4R)-4-[(5-chloro-4-{4-fluoro-2-[(1R)-1-hydroxy-ethyl]-1-(propan-2-yl)-1H-benzimidazol-6-yl}pyrimidin-2-yl)amino]-1-(methanesulfonyl)piperidin-3-ol
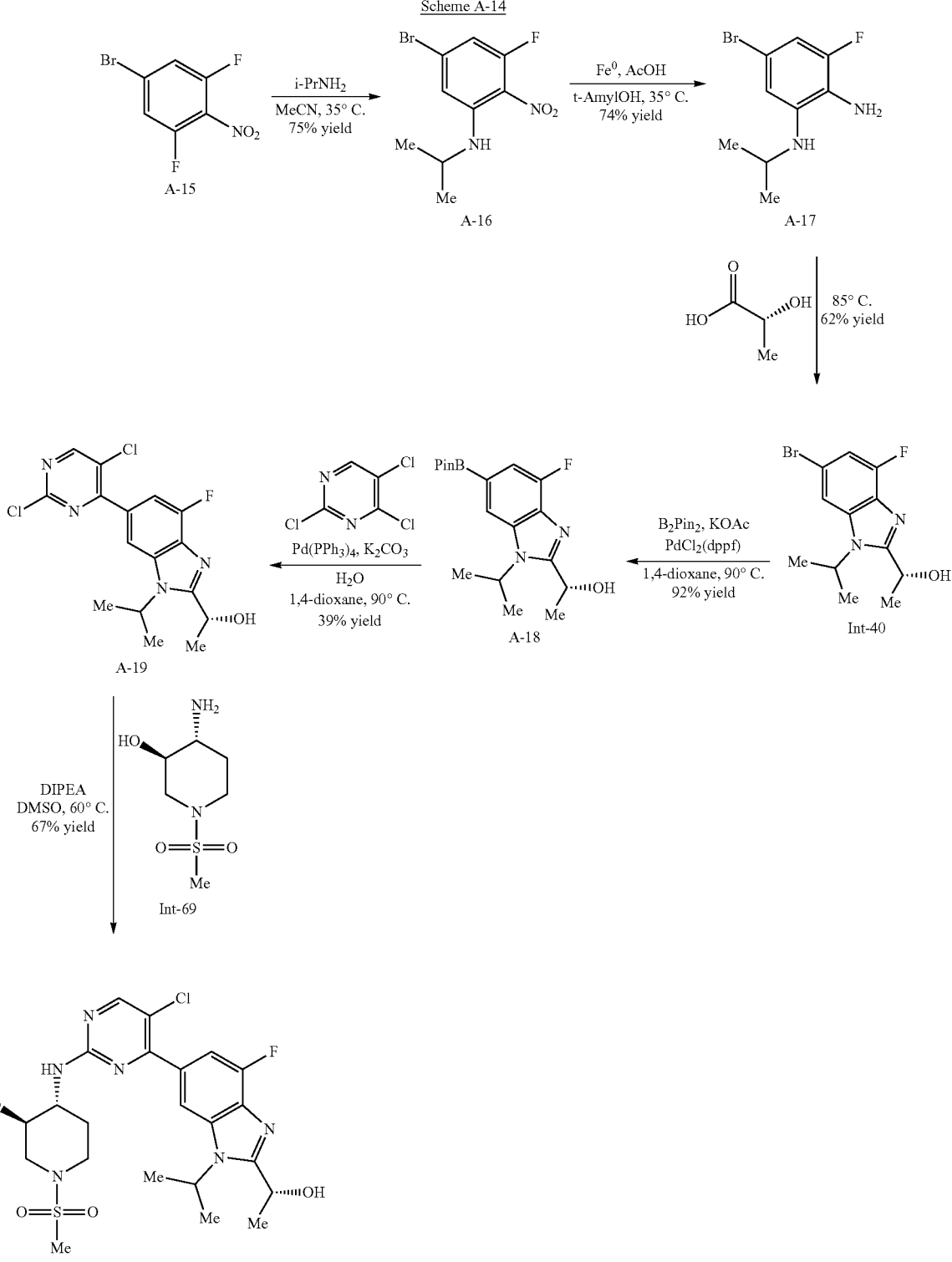

Step 1: Synthesis of 5-bromo-3-fluoro-2-nitro-N-(propan-2-yl)aniline (A-16)

This transformation was run in four parallel batches. To a solution 5-bromo-1,3-difluoro-2-nitrobenzene (A-15) (100 g, 420.2 mmol) in MeCN (2 L) was added i-PrNH$_2$ (27.5 g, 441.2 mmol) at 20-25° C. (ice-bath cooling) to provide a yellow reaction solution. The resulting mixture was stirred at 35° C. for 60 h. LCMS analysis showed consumption of the starting material with formation of the desired product mass. The mixture was concentrated to dryness. The crude residue from the four parallel reactions were combined and purified by flash chromatography (SiO$_2$, 0-2% EtOAc/petroleum ether) to provide 5-bromo-3-fluoro-2-nitro-N-(propan-2-yl) aniline (A-16) (350 g, 75% yield) as a yellow solid. $^1$H NMR (400 MHz, DMSO-d$_6$) δ 7.09-7.00 (m, 2H), 6.90 (dd, J=11.1, 2.0 Hz, 1H), 3.94-3.84 (m, 1H), 1.20 (d, J=6.3 Hz, 6H); m/z (ESI+) for (C$_9$H$_{10}$BrFN$_2$O$_2$), 247.0 (M+H)$^+$; $^{19}$F NMR (377 MHz, DMSO-d$_6$) 5-116.9.

Step 2: Synthesis of 5-bromo-3-fluoro-N$^1$-(propan-2-yl)benzene-1,2-diamine (A-17)

To a stirred mixture of AcOH (2 L) and t-AmylOH (2 L) was added 5-bromo-3-fluoro-2-nitro-N-(propan-2-yl)aniline (A-16) (200 g, 721 mmol) at 35° C. Fe$^0$ (282 g, 5.05 mol) was added in portions at 25-35° C. (ice-bath cooling). The resulting mixture was stirred at 35° C. for 16 h to provide an off-white slurry. TLC analysis (1:9 EtOAc/petroleum ether, R$_f$=0.8, UV254) showed consumption of the starting material. The mixture was diluted with EtOAc (2 L) and H$_2$O (2 L). The mixture was neutralized by slow addition of solid Na$_2$CO$_3$. The slurry was filtered and the mixture was separated. The aqueous layer was extracted with EtOAc (3×1 L). The combined organic layers were washed with saturated aqueous NaHCO$_3$ (2×1 L) and brine (2×1 L), dried over Na$_2$SO$_4$, filtered, and concentrated. The residue was combined with a parallel reaction in an identical fashion with 150 g of 5-bromo-3-fluoro-2-nitro-N-(propan-2-yl)aniline (A-16). The mixture was purified by flash chromatography (SiO$_2$, 0-25% EtOAc/petroleum ether) to provide 5-bromo-3-fluoro-N$^1$-(propan-2-yl)benzene-1,2-diamine (A-17) (230 g, 74% yield) as a brown oil. $^1$H NMR (400 MHz, DMSO-d$_6$) δ 6.55 (dd, J=10.0, 2.1 Hz, 1H), 6.38-6.34 (m, 1H), 4.93-4.41 (m, 3H), 3.55 (hept, J=6.2 Hz, 1H), 1.14 (d, J=6.3 Hz, 6H); $^{19}$F NMR (377 MHz, DMSO-d$_6$) 5-132.8; m/z (ESI+) for (C$_9$H$_{10}$BrFN$_2$O$_2$), 247.0 (M+H)$^+$.

Step 3: Synthesis of (1R)-1-[6-bromo-4-fluoro-1-(propan-2-yl)-1H-benzimidazol-2-yl]ethan-1-ol (Int-40)

To a mixture of 5-bromo-3-fluoro-N$^1$-(propan-2-yl)benzene-1,2-diamine (A-17) (200.0 g, 809.4 mmol) and (2R)-2-hydroxypropanoic acid (605.1 g, 6.72 mol) was heated from 25° C. to 85° C. and then stirred at 85° C. for 16 h. TLC analysis (1:1 EtOAc/petroleum ether), R$_f$=0.5, UV254) showed consumption of the starting material. The reaction mixture was cooled to 25° C. and diluted with EtOAc (1 L) and H$_2$O (1 L). The mixture was basified with aqueous NaOH (50%, ~300 mL) to pH~8-9, maintaining the internal temperature below 30° C. by cooling with an ice-bath. The mixture was separated and the aqueous layer was extracted with EtOAc (2×1 L). The combined organics layers were dried over Na$_2$SO$_4$, filtered, and concentrated. To the residue was added MTBE (400 mL) and petroleum ether (200 mL). A precipitate was formed. The resultant slurry was stirred at 25° C. for 1 h. The slurry was filtered and the filter cake was washed with petroleum ether (2×80 mL). The filter cake was dried in vacuum to provide (1R)-1-[6-bromo-4-fluoro-1-(propan-2-yl)-1H-benzimidazol-2-yl]ethan-1-ol (Int-40) (150 g, 62% yield) as a light-yellow solid. $^1$H NMR (400 MHz, DMSO-d$_6$) δ 7.80 (d, J=1.5 Hz, 1H), 7.27 (dd, J=10.1, 1.5 Hz, 1H), 5.74 (d, J=6.6 Hz, 1H), 5.17-5.00 (m, 2H), 1.63-1.49 (m, 9H).

Step 4: Synthesis of (1R)-1-[4-fluoro-1-(propan-2-yl)-6-(4,4,5,5-tetramethyl-1,3,2-dioxaborolan-2-yl)-1H-benzimidazol-2-yl]ethan-1-ol (A-18)

A stirred mixture of (1R)-1-[6-bromo-4-fluoro-1-(propan-2-yl)-1H-benzimidazol-2-yl]ethan-1-ol (Int-40) (150.0 g, 498.1 mmol), B$_2$Pin$_2$ (164.4 g, 647.5 mmol), PdCl$_2$(dppf) (18.2 g, 24.9 mmol) and KOAc (146.6 g, 1.49 mmol) in 1,4-dioxane (1.2 L) was heated from 25° C. to 90° C. The reaction mixture was stirred at 90° C. for 3 h under N$_2$. TLC analysis (1:1 EtOAc/petroleum ether, R$_f$=0.46, UV254) indicated consumption of the starting material. The reaction mixture was cooled to 25° C. and quenched with H$_2$O (800 mL). The mixture was concentrated in vacuum to remove the 1,4-dioxane. The residue was filtered and the filter cake was washed with EtOAc (2×100 mL). The filtrate was extracted with EtOAc (2×800 mL, 400 mL). The combined organic layers were dried over Na$_2$SO$_4$, filtered, and concentrated. The residue was purified by flash chromatography (SiO$_2$, 1:5 EtOAc/petroleum ether-100% EtOAc) to provide (1R)-1-[4-fluoro-1-(propan-2-yl)-6-(4,4,5,5-tetramethyl-1,3,2-dioxaborolan-2-yl)-1H-benzimidazo-2-yl]ethan-1-ol (A-18) (160 g, 92% yield) as a light-yellow solid. $^1$H NMR (400 MHz, CDCl$_3$) δ 7.73 (s, 1H), 7.35 (d, J=10.8 Hz, 1H), 5.17 (quin, J=6.4 Hz, 1H), 4.95 (sept, J=7.0 Hz, 1H), 4.10 (d, J=7.0 Hz, 1H), 1.70-1.63 (m, 9H), 1.36 (s, 12H); m/z (ESI+) for (C$_{18}$H$_{26}$BFN$_2$O$_3$), 348.9 (M+H)$^+$.

Step 5: Synthesis of (1R)-1-[6-(2,5-dichloropyrimidin-4-yl)-4-fluoro-1-(propan-2-yl)-1H-benzimidazol-2-yl]ethan-1-ol (A-19)

This transformation was carried out in two parallel batches. A stirred mixture of (1R)-1-[4-fluoro-1-(propan-2-yl)-6-(4,4,5,5-tetramethyl-1,3,2-dioxaborolan-2-yl)-1H-benzimidazol-2-yl]ethan-1-ol (A-18) (80 g, 230 mmol), 2,4,5-trichloropyrimidine (54.7 g, 299 mmol), Pd(PPh$_3$)$_4$ (26.5 g, 22.9 mmol), and K$_2$CO$_3$ (63.5 g, 459 mmol) in 1,4-dioxane (600 mL) and H$_2$O (250 mL) was sparged with N$_2$. The mixture was stirred at 90° C. for 3 h under N$_2$. LCMS analysis showed consumption of the starting material with formation of the desired product mass. The reaction mixture was cooled to room temperature and diluted with H$_2$O (500 mL). The two parallel reactions were combined and concentrated to remove the 1,4-dioxane. The residue was filtered and the filter cake was washed with EtOAc (2×150 mL). The mixture was separated. The organic layer was washed with brine (2 L), dried over Na$_2$SO$_4$, filtered, and concentrated. The residue was purified by flash chromatography (SiO$_2$, 1:5 EtOAc/petroleum ether→100% EtOAc). The product-containing fractions were concentrated to ~400 mL, resulting in precipitation. The solids were collected by filtration. The filter cake was washed with petroleum ether (200 mL) and the dried in vacuum to provide (1R)-1-[6-(2,5-dichloropyrimidin-4-yl)-4-fluoro-1-(propan-2-yl)-1H-benzimidazol-2-yl]ethan-1-ol (A-19) (70 g, 39% yield) as a white solid. $^1$H NMR (400 MHz, CDCl$_3$) b 8.68 (s, 1H), 7.98 (d, J=1.5 Hz, 1H), 7.59 (dd, J=1.3, 11.3 Hz, 1H), 5.19 (quin, J=7.0 Hz, 1H), 4.96 (sept, J=6.8 Hz, 1H), 3.11 (d, J=7.8 Hz, 1H), 1.75 (d, J=6.5 Hz, 3H), 1.71 (d, J=7.0 Hz, 6H); m/z (ESI+) for $C_{16}H_{15}Cl_2FN_4O$, 368.8 (M+H)+.

Step 6: Synthesis of (3R,4R)-4-[(5-chloro-4-{4-fluoro-2-[(1R)-1-hydroxyethyl]-1-(propan-2-yl)-1H-benzimidazol-6-yl}pyrimidin-2-yl)amino]-1-(methanesulfonyl)piperidin-3-ol (Example A93)

This transformation was carried out in two parallel batches. To a stirred solution of (1R)-1-[6-(2,5-dichloropyrimidin-4-yl)-4-fluoro-1-(propan-2-yl)-1H-benzimidazol-2-yl]ethan-1-ol (A-19) (50 g, 135 mmol) and (3R,4R)-4-amino-1-(methanesulfonyl)piperidin-3-ol (Int-69) in DMSO (350 mL) was added DIPEA (85.7 g, 664 mmol). The reaction mixture was stirred at 60° C. for 56 h. LCMS analysis showed consumption of the starting material with formation of the desired product mass. The two parallel reactions were combined and filtered through a pad of celite. The filtrate was poured into stirring saturate aqueous NaHCO$_3$ (2 L). The mixture was extracted with DCM (3×2 L). The combined organic layers were dried over Na$_2$SO$_4$, filtered, and concentrated. The residue was taken up in EtOAc (2 L). Sulfhydryl silica gel (Accela, 20 g, 0.7-1.4 mmol/g) was added and the mixture was stirred for 1 h at 30° C. The mixture was filtered and the filtrate was concentrated. The residue was purified by flash chromatography (SiO$_2$, 1:10 EtOAc/petroleum ether→100% EtOAc). The product was taken up in EtOH (200 mL) and H$_2$O (800 mL) and then concentrated to remove the EtOH. The aqueous solution was dried by lyopilization. The solids were dried at 50° C. for 48 h under high vacuum to provide (3R,4R)-4-[(5-chloro-4-{4-fluoro-2-[(1R)-1-hydroxyethyl]-1-(propan-2-yl)-1H-benzimidazol-6-yl}pyrimidin-2-yl)amino]-1-(methanesulfonyl)piperidin-3-ol (Example A93) (95 g, 67% yield) as a white solid. $^1$H NMR (400 MHz, 80° C., DMSO-d$_6$) δ 8.40 (s, 1H), 7.99 (d, J=1.3 Hz, 1H), 7.42 (dd, J=11.8, 1.3 Hz, 1H), 7.17 (d, J=7.7 Hz, 1H), 5.50 (d, J=6.2 Hz, 1H), 5.23 (hept, J=6.9 Hz, 1H), 5.16-5.07 (m, 1H), 4.97 (d, J=4.6 Hz, 1H), 3.88-3.77 (m, 1H), 3.73-3.62 (m, 2H), 3.58-3.52 (m, 1H), 2.94-2.86 (m, 4H), 2.76-2.68 (m, 1H), 2.17-2.08 (m, 1H), 1.69-1.54 (m, 10H); m/z (ESI+) for $C_{22}H_{28}ClFN_6O_4S$, 526.8 (M+H)+; $[α]_D^{22}$=−11.4 (c=0.1, MeOH)

Example A94 (Scheme A-15): Preparation of 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol

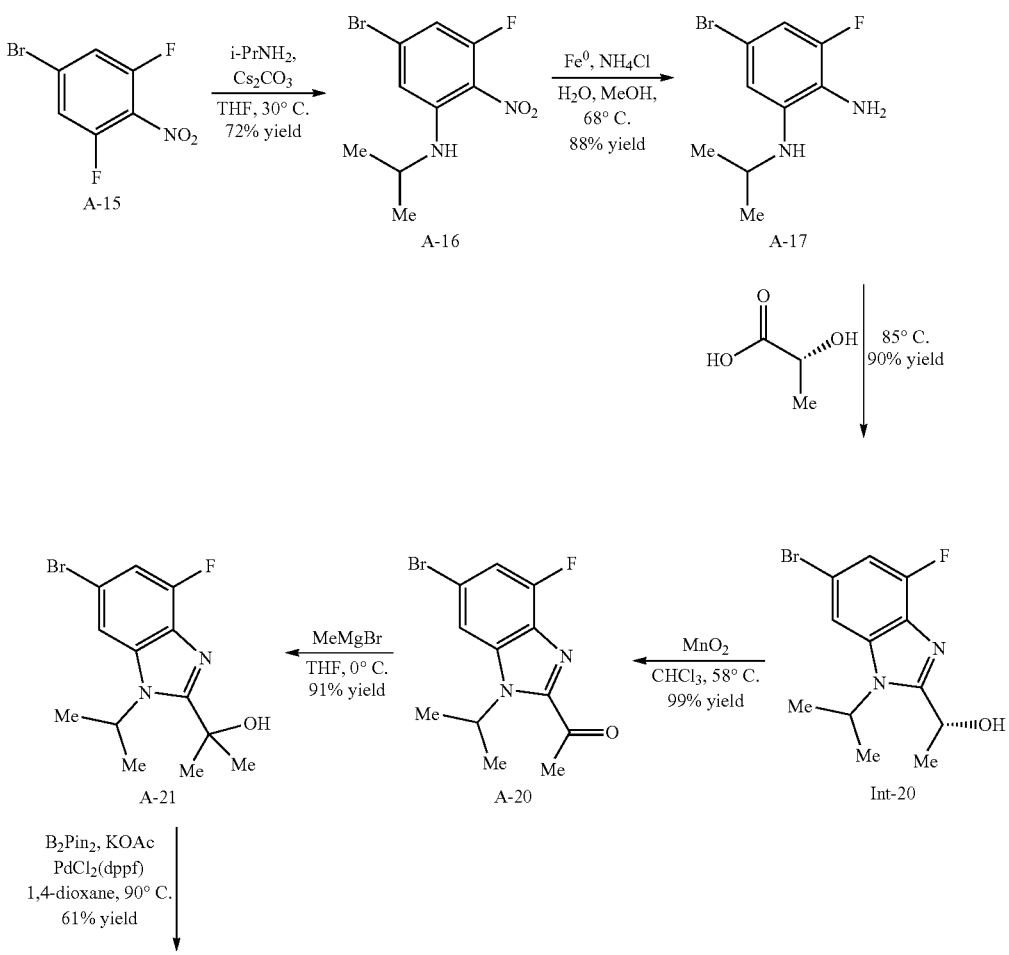

Scheme A-15

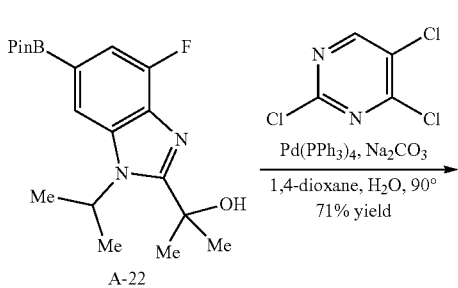
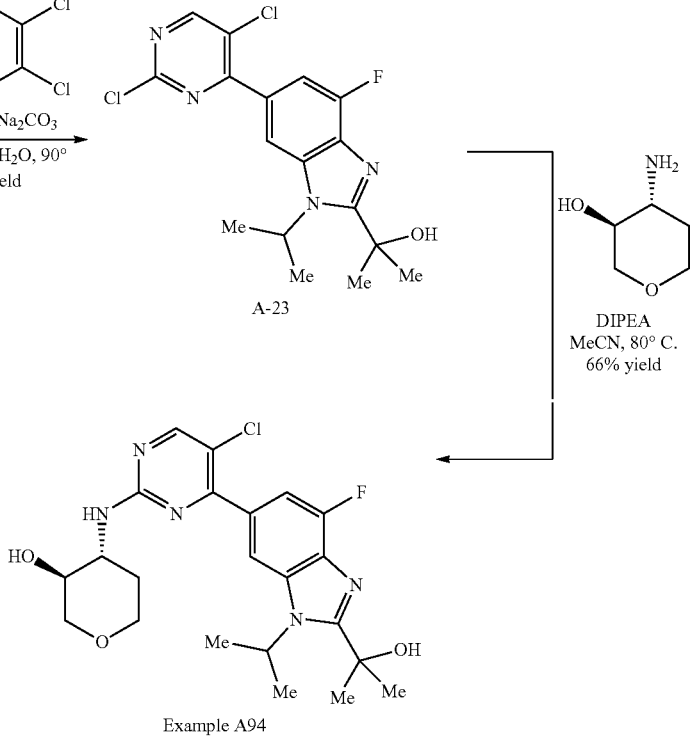

Example A94

Step 1: Synthesis of 5-bromo-3-fluoro-2-nitro-N-(propan-2-yl)aniline (A-16)

This reaction was carried out in three parallel batches. To a stirred solution of 5-bromo-1,3-difluoro-2-nitrobenzene (A-15) (166 g, 697 mmol) in THF (1.7 L) was added i-PrNH$_2$ (41.2 g, 697 mmol) and Cs$_2$CO$_3$ (455 g, 1.40 mol) at 15-30° C. Upon addition an exotherm was detected. The reaction mixture was stirred at 30° C. for 6 h. TLC analysis (100% petroleum ether, UV254, R$_f$=0.35) showed consumption of the starting material. The three reaction batches were combined. The combined mixture was filtered and the filtrate was concentrated under vacuum. The residue was purified by flash chromatography (SiO$_2$, 0-2% EtOAc/petroleum ether) to provide 5-bromo-3-fluoro-2-nitro-N-(propan-2-yl)aniline (A-16) (420 g, 72% yield) as a yellow solid. $^1$H NMR (400 MHz, DMSO-d$_6$) δ 7.09-7.00 (m, 2H), 6.90 (dd, J=11.1, 2.0 Hz, 1H), 3.94-3.84 (m, 1H), 1.20 (d, J=6.3 Hz, 6H); $^{19}$F NMR (376 MHz, DMSO-d$_6$) 5-116.9; m/z (ESI+) for (C$_9$H$_{10}$BrFN$_2$O$_2$), 276.1 (M+H)$^+$.

Step 2: Synthesis of 5-bromo-3-fluoro-N$^1$-(propan-2-yl)benzene-1,2-diamine (A-17)

This reaction was carried out in two parallel batches. To a stirred solution of 5-bromo-3-fluoro-2-nitro-N-(propan-2-yl)aniline (A-16) (210 g, 758 mmol) in MeOH (1.8 L) was added NH$_4$Cl (81.1 g, 1.52 mol) in H$_2$O (0.9 L) and Fe$^0$ powder (212 g, 3.79 mol) at 15° C. The resulting mixture was heated to 68° C. (internal temperature) and stirred at the same temperature for 8 h. TLC analysis (10% EtOAc/petroleum ether, UV254, R$_f$=0.8) showed consumption of the starting material. The two reaction batches were cooled to room temperature and combined. The two reaction mixtures were combined and filtered. The filter cake was washed with MeOH (3×500 mL). The filtrate was concentrated under vacuum to remove most of the MeOH. The resultant aqueous mixture was extracted with EtOAc (3×1 L). The combined organic layers were washed with brine (2×800 mL), dried over Na$_2$SO$_4$, filtered, and concentrated to provide 5-bromo-3-fluoro-N$^1$-(propan-2-yl)benzene-1,2-diamine (A-17) (350 g, 88% yield) as a purple solid, which was taken on without further purification. $^1$H NMR (400 MHz, DMSO-d$_6$) δ 6.55 (dd, J=10.0, 2.1 Hz, 1H), 6.38-6.34 (m, 1H), 4.93-4.41 (m, 3H), 3.55 (hept, J=6.2 Hz, 1H), 1.14 (d, J=6.3 Hz, 6H); $^{19}$F NMR (377 MHz, DMSO-d$_6$) 5-132.8; m/z (ESI+) for (C$_9$H$_{12}$BrFN$_2$), 246.6 (M+H)$^+$.

Step 3: Synthesis of (1R)-1-[6-bromo-4-fluoro-1-(propan-2-yl)-1H-benzimidazol-2-yl]ethan-1-ol (Int-20)

To a 2 L three-neck round bottom flask was added (2R)-2-hydroxypropanoic acid (951 g, 9.71 mol) at 15° C. and compound was heated to 85° C. (internal temperature). To the stirred solution at 85° C. was added 5-bromo-3-fluoro-N$^1$-(propan-2-yl)benzene-1,2-diamine (A-17) (300 g, 1.21 mol) portion-wise. The resulting mixture was stirred at 85° C. (internal temperature) for 40 h to provide a purple reaction solution. TLC analysis (1:2 EtOAc/petroleum ether, UV254, R$_f$=0.8) showed consumption of the starting material. The reaction mixture was cooled to room temperature and diluted with THF (1.5 L). The mixture was adjusted to pH~8 with saturated aqueous LiOH at 10-15° C. with ice-water bath cooling. The mixture was extracted with MTBE (3×1.5 L). The combined organic layers were washed with brine (2×800 mL), dried over Na$_2$SO$_4$ and filtered. The filtrate was concentrated under vacuum to provide (1R)-1-[6-bromo-4-fluoro-1-(propan-2-yl)-1H-benzimidazol-2-yl]ethan-1-ol (A-18) (330 g, 90% yield) as a brown solid, which was taken on to the next step without further purification. $^1$H NMR (400 MHz, DMSO-d$_6$) δ 7.80 (d, J=1.5 Hz, 1H), 7.27 (dd, J=10.1, 1.5 Hz, 1H), 5.74 (d, J=6.6 Hz, 1H), 5.17-5.00 (m, 2H), 1.63-1.49 (m, 9H); $^{19}$F NMR (376 MHz, DMSO-d$_6$) 5-126.3; m/z (ESI+) for (C$_{12}$H$_{14}$BrFN$_2$O), 302.6 (M+H)$^+$.

Step 4: Synthesis of 1-[6-bromo-4-fluoro-1-(propan-2-yl)-1H-benzimidazol-2-yl]ethan-1-one (A-20)

To a stirred solution of compound (1R)-1-[6-bromo-4-fluoro-1-(propan-2-yl)-1H-benzimidazol-2-yl]ethan-1-ol (Int-20) (365 g, 1.21 mol) in CHCl$_3$ (3 L) was added activated MnO$_2$ (738 g, 8.48 mol) at room temperature. The reaction mixture was heated to 58° C. (internal temperature) and stirred at the same temperature for 16 h. TLC analysis (1:2 EtOAc/petroleum ether, UV254, R$_f$=0.3) showed consumption of the starting material. The reaction mixture was cooled to room temperature and filtered through a pad of Celite. The filter cake was washed with EtOAc (3×500 mL) and the filtrate was concentrated under vacuum. The residue was purified by flash chromatography (SiO$_2$, 0-30% EtOAc/petroleum ether) to provide 1-[6-bromo-4-fluoro-1-(propan-2-yl)-1H-benzimidazol-2-yl]ethan-1-one (A-20) (362 g, 99% yield) as a yellow solid. $^1$H NMR (400 MHz, CDCl$_3$) δ 7.54 (d, J=1.6 Hz, 1H), 7.12 (dd, J=9.5, 1.5 Hz, 1H), 5.82 (hept, J=7.0 Hz, 1H), 2.79 (s, 3H), 1.56 (d, J=7.0 Hz, 6H); $^{19}$F NMR (377 MHz, DMSO-d$_6$) 5-124.1; m/z (ESI+) for (C$_{12}$H$_{12}$BrFN$_2$O), 300.6 (M+H)$^+$.

Step 5: Synthesis of 2-[6-bromo-4-fluoro-1-(propan-2-yl)-1H-benzimidazol-2-yl]propan-2-ol (A-21)

This reaction was carried out in two parallel batches. A solution of 1-[6-bromo-4-fluoro-1-(propan-2-yl)-1H-benzimidazol-2-yl]ethan-1-one (A-20) (165 g, 552 mmol) in THF (1.7 L) was degassed and purged with N$_2$ three times. The stirred solution was cooled to 0-5° C. (internal temperature) with ice-brine bath cooling and a solution of MeMgBr (3.0 M in Et$_2$O, 221 mL) was added drop-wise. During the addition the purple solution turned to a gray slurry. The resulting mixture was stirred at 0-5° C. with ice-brine bath cooling for 3 h. TLC analysis (20% EtOAc/petroleum ether, UV254, R$_f$=0.8) showed consumption of the starting material. The reaction mixture was slowly quenched with saturated aqueous NH$_4$Cl (400 mL) at 0-5° C. with ice-brine bath cooling and then stirred at room temperature for 1 h. The two reaction batches were combined and diluted with EtOAc (1 L). The organic layer was separated. The aqueous layer was extracted with EtOAc (2×1 L). The combined organic layers were dried over MgSO$_4$, filtered, and concentrated. The crude residue was purified by flash chromatography (SiO$_2$, 0-50% EtOAc/petroleum ether) to provide 2-[6-bromo-4-fluoro-1-(propan-2-yl)-1H-benzimidazol-2-yl]propan-2-ol (A-21) (316 g, 91% yield) as a yellow solid. $^1$H NMR (400 MHz, CDCl$_3$) δ 7.49 (d, J=1.6 Hz, 1H), 7.08 (dd, J=9.7, 1.5 Hz, 1H), 5.45 (hept, J=7.0 Hz, 1H), 2.87 (s, 1H), 1.77 (s, 6H), 1.63 (d, J=7.0 Hz, 6H); $^{19}$F NMR (377 MHz, DMSO-d$_6$) 5-126.3; m/z (ESI+) for (C$_{13}$H$_{16}$BrFN$_2$O), 314.7 (M+H)$^+$.

Step 6: Synthesis of 2-[4-fluoro-1-(propan-2-yl)-6-(4,4,5,5-tetramethyl-1,3,2-dioxaborolan-2-yl)-1H-benzimidazol-2-yl]propan-2-ol (A-22)

A 3 L three-neck round bottom flask was charged with 2-[6-bromo-4-fluoro-1-(propan-2-yl)-1H-benzimidazol-2-yl]propan-2-ol (A-21) (300 g, 952 mmol), B$_2$Pin$_2$ (290 g, 1.14 mol), Pd(dppf)Cl$_2$ (34.8 g, 47.6 mmol), KOAc (280 g, 2.86 mol), and 1,4-dioxane (2 L). The reaction mixture was degassed and purged with N$_2$ three times. The reaction mixture was heated to 90° C. (internal temperature) and stirred at this temperature for 3 h to provide an orange slurry. TLC analysis (1:2 EtOAc/petroleum ether, UV254, R$_f$=0.4) showed consumption of the starting material. The reaction mixture was cooled to room temperature and filtered. The filtrate was diluted with EtOAc (2 L) and washed with brine (2×1 L). The organic layer was dried over MgSO$_4$, filtered, and concentrated under vacuum. The residue was purified by flash chromatography (SiO$_2$, 10-50% EtOAc/petroleum ether) to provide 2-[4-fluoro-1-(propan-2-yl)-6-(4,4,5,5-tetramethyl-1,3,2-dioxaborolan-2-yl)-1H-benzimidazol-2-yl]propan-2-ol (A-22) (210 g, 61% yield) as a light yellow solid. $^1$H NMR (400 MHz, CDCl$_3$) δ 7.77 (s, 1H), 7.34 (d, J=10.8 Hz, 1H), 5.41 (hept, J=6.9 Hz, 1H), 3.10 (s, 1H), 1.79 (s, 6H), 1.69 (d, J=7.0 Hz, 6H), 1.36 (s, 12H); $^{19}$F NMR (377 MHz, DMSO-d$_6$) 5-129.5; m/z (ESI+) for (C$_{13}$H$_{16}$FN$_2$O), 362.9 (M+H)$^+$.

Step 7: Synthesis of 2-[6-(2,5-dichloropyrimidin-4-yl)-4-fluoro-1-(propan-2-yl)-1H-benzimidazol-2-yl]propan-2-ol (A-23)

This reaction was carried out in two parallel batches. To a mixture of compound 2-[4-fluoro-1-(propan-2-yl)-6-(4,4,5,5-tetramethyl-1,3,2-dioxaborolan-2-yl)-1H-benzimidazol-2-yl]propan-2-ol (A-22) (100 g, 276 mmol), and Na$_2$CO$_3$ (87.8 g, 828 mmol) in 1,4-dioxane (1 L) and H$_2$O (300 mL) was added 2,4,5-trichloropyrimidine (67.2 g, 359 mmol). The mixture was degassed and purged with N$_2$ three times. Pd(PPh$_3$)$_4$ (31.9 g, 27.6 mmol) was added and the mixture was degassed and purged with N$_2$ three times. The reaction mixture was placed into a pre-heated oil bath at 100° C. and stirred at 90° C. (internal temperature) for 24 h. LCMS showed consumption of the starting material with formation of the desired product mass. The reaction was cooled to room temperature. The two reaction mixtures were combined. The combined mixture was filtered and concentrated under vacuum to remove the 1,4-dioxane. The residue was diluted with EtOAc (1 L) and the organic layer was collected. The aqueous layer was extracted with EtOAc (3×1 L). The combined organic layers were dried over MgSO$_4$, filtered, concentrated. The crude residue was purified by flash chromatography (SiO$_2$, 0-50% EtOAc in 1:5 petroleum ether/DCM). The product-containing fractions were concentrated under vacuum to ~200 mL with concomitant precipitation of a white solid. The suspension was filtered and the filter cake was washed with petroleum ether (2×300 mL). The filter cake was collected and dried under vacuum to provide 2-[6-(2,5-dichloropyrimidin-4-yl)-4-fluoro-1-(propan-2-yl)-1H-benzimidazol-2-yl]propan-2-ol (A-23) (112 g). The filtrate was concentrated and residue was re-purified by flash chromatography (SiO$_2$, 0-50% EtOAc in 1:5 petroleum ether/DCM). The product-containing fractions were concentrated under vacuum to ~50 mL with precipitation of additional product. The suspension was filtered and the filter cake was washed with petroleum ether (2×100 mL). The filter cake was collected and dried under vacuum to provide an additional batch of 2-[6-(2,5-dichloropyrimidin-4-yl)-4-fluoro-1-(propan-2-yl)-1H-benzimidazol-2-yl]propan-2-ol (A-23) (41 g). The product batches were combined to provide 2-[6-(2,5-dichloropyrimidin-4-yl)-4-fluoro-1-(propan-2-yl)-1H-benzimidazol-2-yl]propan-2-ol (A-23) (153 g, 71% yield) as a white solid. $^1$H NMR (400 MHz, DMSO-$d_6$) δ 9.01 (s, 1H), 8.06 (d, J=1.3 Hz, 1H), 7.41 (dd, J=11.5, 1.3 Hz, 1H), 5.85-5.72 (m, 2H), 1.67 (s, 6H), 1.61 (d, J=7.0 Hz, 6H); $^{19}$F NMR (377 MHz, CDCl$_3$) δ −128.2; m/z (ESI+) for (C$_{17}$H$_{17}$Cl$_2$FN$_4$O), 383.0 (M+H)$^+$.

Step 8: Synthesis of 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol (Example A94)

A 2 L three-neck round bottom flask was charged with 2-[6-(2,5-dichloropyrimidin-4-yl)-4-fluoro-1-(propan-2-yl)-1H-benzimidazol-2-yl]propan-2-ol (A-23) (112 g, 292 mmol), 3-amino-1,5-anhydro-2,3-dideoxy-D-threo-pentitol hydrochloride (51.6 g, 336 mmol), and MeCN (1.1 L). DIPEA (132 g, 1.02 mol, 178 mL) was added at room temperature. The reaction mixture was heated to 80° C. (internal temperature) and stirred at the same temperature for 40 h to provide a brown solution. LCMS analysis showed remaining starting material. Additional 3-amino-1,5-anhydro-2,3-dideoxy-D-threo-pentitol hydrochloride (6.73 g, 43.8 mmol) was added at 80° C. (internal temperature) and the reaction was stirred at 80° C. (internal temperature) for an additional 10 h. The reaction mixture was cooled to room temperature and concentrated under vacuum. The residue was taken up in 1:1 EtOAc/H$_2$O (1.5 L). Some solids were precipitated. EtOH (100 mL) was added. The organic layer was collected and the aqueous layer was extracted with EtOAc (2×500 mL). The combined organic layers were washed with H$_2$O (2×300 mL), dried over Na$_2$SO$_4$, and filtered. To the filtrate was added sulfhydryl silica gel (Accela, 8 g, 0.7-1.4 mmol/g). The resulting mixture was stirred at room temperature for 1 h and then filtered through a pad of Celite. Treatment with sulfhydryl silica gel was repeated in identical fashion and the filtrate was concentrated to dryness. The crude residue was slurried in MeCN (500 mL) at room temperature for 16 h. The suspension was filtered and the filter cake was washed with MeCN (2×100 mL). The filter cake was slurried again with MeCN (300 mL) at room temperature for 6 h. The mixture was filtered and the filter cake was washed with MeCN (2×100 mL). The filter cake was collected and dried under vacuum and then dried in a drying oven (45° C. for 20 h, 50° C. for 64 h) to provide 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol (Example A94) (90 g, 66% yield) as a white solid. $^1$H NMR (400 MHz, 80° C., DMSO-$d_6$) δ 8.38 (s, 1H), 8.00 (s, 1H), 7.43 (d, J=11.8 Hz, 1H), 7.13 (d, J=7.5 Hz, 1H), 5.80 (hept, J=7.0 Hz, 1H), 5.56 (s, 1H), 4.71 (d, J=5.3 Hz, 1H), 3.91-3.79 (m, 3H), 3.61-3.52 (m, 1H), 3.41-3.31 (m, 1H), 3.12-3.07 (m, 1H), 2.09-2.00 (m, 1H), 1.70 (s, 6H), 1.67-1.52 (m, 7H); $^{19}$F NMR (377 MHz, CDCl$_3$) 5-127.2; m/z (ESI+) for (C$_{22}$H$_{27}$ClFN$_5$O$_3$), 464.2 (M+H)$^+$; [α]D$_{22}$=−12.6 (c=0.2, MeOH).

Alternative Preparation of 2-[6-(2,5-dichloropyrimidin-4-yl)-4-fluoro-1-(propan-2-yl)-1H-benzimidazol-2-yl]propan-2-ol (A-23) to Scheme A-16

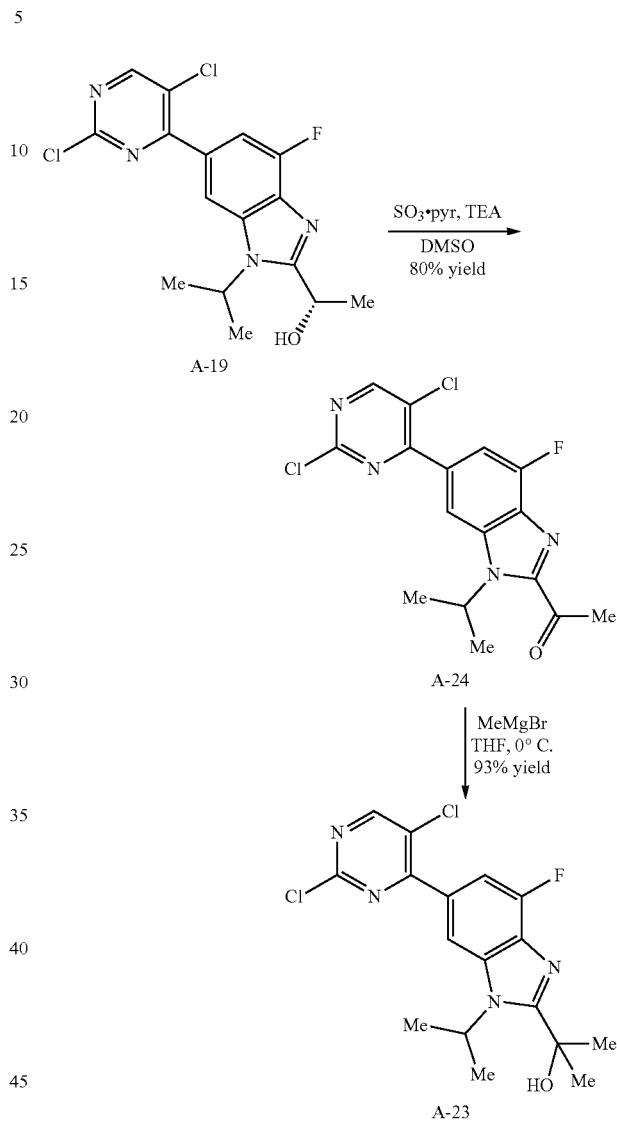

Step 1: Synthesis of 1-[6-(2,5-dichloropyrimidin-4-yl)-4-fluoro-1-(propan-2-yl)-1H-benzimidazol-2-yl]ethan-1-one (A-19)

To a solution of (1S)-1-[6-(2,5-dichloropyrimidin-4-yl)-4-fluoro-1-(propan-2-yl)-1H-benzimidazol-2-yl]ethan-1-ol (A-19) (3.86 g, 10.5 mmol) in DMSO (130 mL) was added Et$_3$N (10.6 g, 105 mmol). Sulfur trioxide pyridine complex (10 g, 62.7 mmol) was added and mixture stirred at ambient temperature. After 4 h LCMS analysis showed ~10% residual starting material. Additional sulfur trioxide pyridine complex (4.7 g) was added. After 1 h LCMS analysis showed consumption of the starting material Th mixture was partitioned between H$_2$O and EtOAc. The aqueous layer was extracted with EtOAc (3×). The combined organic layers were washed with H$_2$O, dried over Na$_2$SO$_4$, filtered, and concentrated. The residue was purified by flash chromatography (ISCO, 80 g SiO$_2$, 10-40% EtAOc/heptane) to provide 1-[6-(2,5-dichloropyrimidin-4-yl)-4-fluoro-1-(propan-2-yl)-1H-benzimidazol-2-yl]ethan-1-one (A-24) (3.1 g, 80% yield) as a white solid. $^1$H NMR (400 MHz, DMSO-$d_6$) δ 9.06 (s, 1H), 8.20 (d, J=1.3 Hz, 1H), 7.55 (dd, J=11.4, 1.3 Hz, 1H), 5.77 (hept, J=7.1 Hz, 1H), 2.79 (s, 3H), 1.61 (d, J=7.0 Hz, 6H); m/z (APCI) for ($C_{16}H_{13}Cl_2FN_4O$), 366.8 (M+H)$^+$.

Step 2: Synthesis of 2-[6-(2,5-dichloropyrimidin-4-yl)-4-fluoro-1-(propan-2-yl)-1H-benzimidazol-2-yl]propan-2-ol (A-23)

A solution of 1-[6-(2,5-dichloropyrimidin-4-yl)-4-fluoro-1-(propan-2-yl)-1H-benzimidazol-2-yl]ethan-1-one (A-24) (3.1 g, 8.7 mmol) in THF (87 mL) was cooled to 0° C. under an atmosphere of $N_2$. A solution of methylmagnesium bromide (3.0 M in $Et_2O$, 4.0 mL, 12 mmol) was added dropwise. The mixture was stirred for 30 min at 0° C. LCMS analysis indicated consumption of starting material with formation of the desired product mass. The reaction was quenched with saturated aqueous $NH_4Cl$ and partitioned between EtOAc and $H_2O$. The aqueous layer was extracted with EtOAc (2×). The combined organics were washed with brine, dried over $Na_2SO_4$, filtered, and concentrated. The residue was purified by flash chromatography (ISCO, 80 g $SiO_2$, 20-60% EtOAc/heptane) to provide 2-[6-(2,5-dichloropyrimidin-4-yl)-4-fluoro-1-(propan-2-yl)-1H-benzimidazol-2-yl]propan-2-ol (A-23) (3.11 g, 93% yield) as a white solid. $^1$H NMR (400 MHz, DMSO-$d_6$) δ 9.01 (s, 1H), 8.06 (d, J=1.3 Hz, 1H), 7.41 (dd, J=11.5, 1.3 Hz, 1H), 5.85-5.72 (m, 2H), 1.67 (s, 6H), 1.61 (d, J=7.0 Hz, 6H); m/z (APCI) for ($C_{17}H_{17}Cl_2FN_4O$), 382.8 (M+H)$^+$.

Example B1 (Scheme B): Preparation of 4-[4-fluoro-2-methyl-1-(propan-2-yl)-1H-benzimidazol-6-yl]-2-{[(3R,4R)-3-hydroxy-1-(methanesulfonyl)piperidin-4-yl]amino}pyrimidine-5-carbonitrile

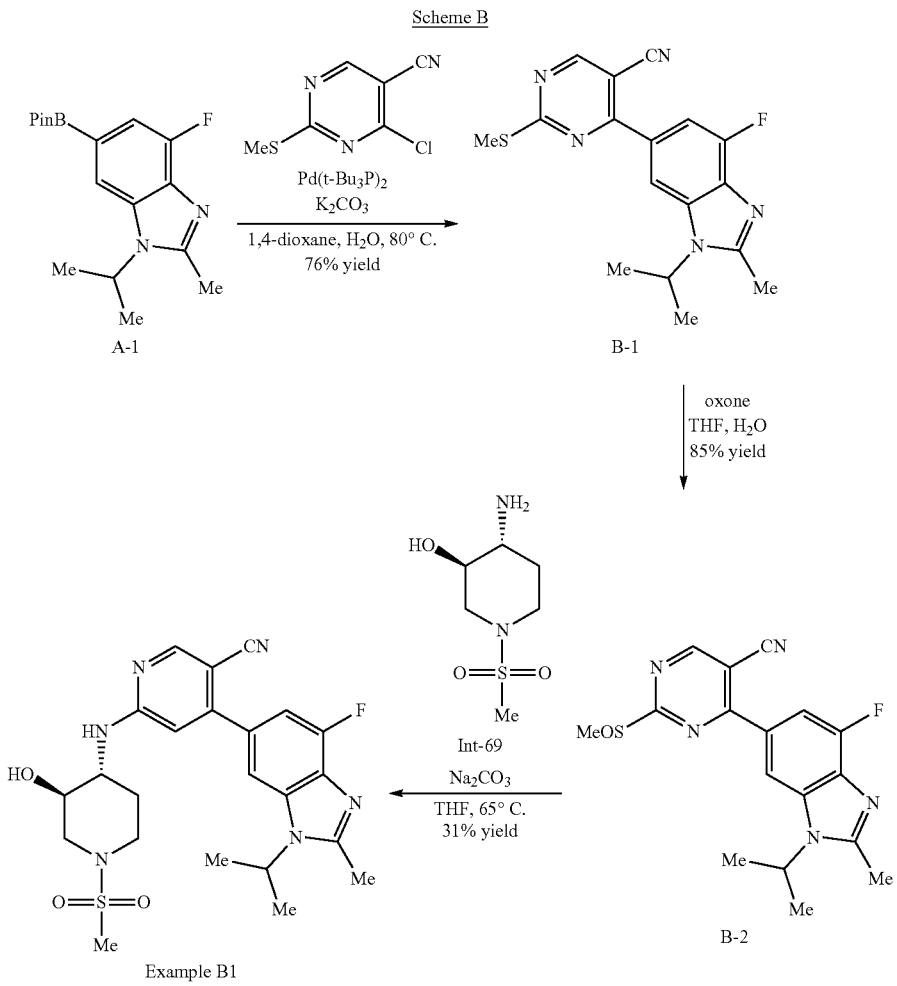

Scheme B

Example B1

Step 1: Synthesis of 4-[4-fluoro-2-methyl-1-(propan-2-yl)-1H-benzimidazol-6-yl]-2-(methylsulfanyl)pyrimidine-5-carbonitrile (B-1)

To a mixture of 4-chloro-2-(methylsulfanyl)pyrimidine-5-carbonitrile (150 mg, 0.808 mmol), 4-fluoro-2-methyl-1-(propan-2-yl)-6-(4,4,5,5-tetramethyl-1,3,2-dioxaborolan-2-yl)-1H-benzimidazole (A-1) (257 mg, 0.808 mmol), and $K_2CO_3$ (335 mg, 2.42 mmol) in 1,4-dioxane (15.0 mL) and $H_2O$ (2.1 mL) was added Pd(t-$Bu_3P)_2$ (41.3 mg, 0.0808 mmol). The reaction was sparged with $N_2$ and then stirred at 80° C. for 1 h. LCMS analysis indicated consumption of the starting material with formation of the desired product mass. The mixture was combined with a second reaction run in the identical fashion with 85.7 mg 4-fluoro-2-methyl-1-(propan-2-yl)-6-(4,4,5,5-tetramethyl-1,3,2-dioxaborolan-2-yl)-1H-benzimidazole (A-1). The mixture was diluted with EtOAc (20 mL) and washed with $H_2O$ (5 mL). The aqueous layer was extracted with EtOAc (3×10 mL). The combined organic layers were washed with brine, dried over $Na_2SO_4$, filtered, and concentrated. The residue was purified by flash chromatography (Biotage, $SiO_2$, 1:1 petroleum ether/EtOAc) to provide 4-[4-fluoro-2-methyl-1-(propan-2-yl)-1H-benzimidazol-6-yl]-2-(methylsulfanyl)pyrimidine-5-carbonitrile (B-1) (280 mg, 76% yield) as a yellow solid. $^1$H NMR (400 MHz, $CDCl_3$) δ 8.78 (s, 1H), 8.31-8.22 (m, 1H), 7.82-7.72 (m, 1H), 2.71 (s, 3H), 2.69 (s, 3H), 2.67-2.64 (m, 1H), 1.72 (d, J=6.8 Hz, 6H); m/z (ESI) for ($C_7H_{16}FN_5S$), 342.0 $(M+H)^+$.

Step 2: Synthesis of 4-[4-fluoro-2-methyl-1-(propan-2-yl)-1H-benzimidazol-6-yl]-2-(methanesulfinyl)pyrimidine-5-carbonitrile (B-2)

To a solution of 4-[4-fluoro-2-methyl-1-(propan-2-yl)-1H-benzimidazol-6-yl]-2-(methylsulfanyl)pyrimidine-5-carbonitrile (B-1) (200 mg, 0.586 mmol) in THF (9.0 mL) and $H_2O$ (4.5 mL) was added oxone (540 mg, 0.879 mmol) at 10° C. The resultant mixture was stirred at the same temperature for 1.5 h. LCMS analysis showed consumption of the starting material with formation of the desired product mass. The reaction was combined with a parallel reaction run in identical fashion with 80 mg 4-[4-fluoro-2-methyl-1-(propan-2-yl)-1H-benzimidazol-6-yl]-2-(methylsulfanyl)pyrimidine-5-carbonitrile (B-1). The combined solution was diluted with EtOAc (20 mL) and washed with brine (10 mL). The aqueous layer was extracted with EtOAc (4×10 mL). The combined organic layers were washed with brine (10 mL), dried over $Na_2SO_4$, filtered, and concentrated to provide 4-[4-fluoro-2-methyl-1-(propan-2-yl)-1H-benzimidazol-6-yl]-2-(methanesulfinyl)pyrimidine-5-carbonitrile (B-2) (250 mg, 85% yield) as an off-white solid, which was taken on without further purification. m/z (ESI) for ($C_{17}H_{16}FN_5OS$), 358.3 $(M+H)^+$.

Step 3: Synthesis of 4-[4-fluoro-2-methyl-1-(propan-2-yl)-1H-benzimidazol-6-yl]-2-{[(3R,4R)-3-hydroxy-1-(methanesulfonyl)piperidin-4-yl]amino}pyrimidine-5-carbonitrile (Example B1)

To a mixture of 4-[4-fluoro-2-methyl-1-(propan-2-yl)-1H-benzimidazol-6-yl]-2-(methanesulfinyl)pyrimidine-5-carbonitrile (B-2) (120 mg, 0.336 mmol) and (3R,4R)-4-amino-1-(methanesulfonyl)piperidin-3-ol (Int-69) in THF (15.0 mL) was added $Na_2CO_3$ (71.2 mg, 0.672 mmol). The resultant mixture was stirred at 65° C. for 12 h. LCMS analysis indicated consumption of the starting material with formation of the desired product mass. The mixture was diluted with EtOAc (30 mL) and washed with $H_2O$ (10 mL). The aqueous layer was extracted with EtOAc (2×20 mL). The combined organic layers were washed with brine (10 mL), dried over $Na_2SO_4$, filtered, and concentrated. The residue was purified by preparative TLC ($SiO_2$, 10:1 DCM/MeOH, $R_f$=0.55). The material was further purified by preparative HPLC with a YMC-Actus Triart C18 column (150×30 mm, 5 µm particle size), which was eluted with 8-48% $MeCN/H_2O$ (+0.225% formic acid) to provide 4-[4-fluoro-2-methyl-1-(propan-2-yl)-1H-benzimidazol-6-yl]-2-{[(3R,4R)-3-hydroxy-1-(methanesulfonyl)piperidin-4-yl]amino}pyrimidine-5-carbonitrile (Example B1) (50 mg, 31% yield) as a white solid. $^1$H NMR (400 MHz, DMSO-$d_6$) δ 8.82-8.74 (m, 1H), 8.43-8.32 (m, 1H), 8.21-8.11 (m, 1H), 7.59-7.48 (m, 1H), 5.35-5.28 (m, 1H), 4.88-4.76 (m, 1H), 4.05-3.90 (m, 1H), 3.70-3.59 (m, 2H), 3.56-3.47 (m, 1H), 2.91-2.81 (m, 4H), 2.71-2.59 (m, 4H), 2.10-1.95 (m, 1H), 1.65-1.51 (m, 7H); m/z (ESI) for ($C_{23}H_{27}FN_6O_3S$), 488.1 $(M+H)^+$.

The example the below table was synthesized according to the methods used for the synthesis of 4-[4-fluoro-2-methyl-1-(propan-2-yl)-1H-benzimidazol-6-yl]-2-{[(3R,4R)-3-hydroxy-1-(methanesulfonyl)piperidin-4-yl]amino}pyrimidine-5-carbonitrile (Example B1). The following example was synthesized with non-critical changes or substitutions to the exemplified procedures that someone who is skilled in the art would be able to realize.

| Example number | Structure/Name | LCMS | NMR |
|---|---|---|---|
| B2 | 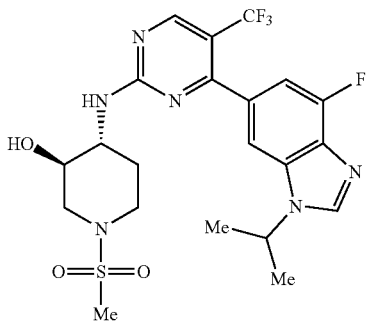 [SMILES: CC(C)n1cnc2c(F)cc(-c3nc(N[C@@H]4CCN(S(C)(=O)=O)C[C@H]4O)ncc3C(F)(F)F)cc21]<br>(3R,4R)-4-({4-[4-fluoro-1-(propan-2-yl)-1H-benzimidazol-6-yl]-5-(trifluoromethyl)pyrimidin-2-yl}amino)-1-(methanesulfonyl)piperidin-3-ol | 516.9 [M + H]+ (ESI) | $^1$H NMR (400 MHz, DMSO-$d_6$) δ 8.71-8.66 (m, 1H), 8.51 (s, 1H), 8.20-8.09 (m, 1H), 7.64 (s, 1H), 7.23-7.14 (m, 1H), 5.27 (br s, 1H), 4.79 (hept, J = 6.6 Hz, 1H), 3.99-3.80 (m, 1H), 3.67-3.56 (m, 2H), 3.54-3.42 (m, 1H), 2.94-2.77 (m, 4H), 2.70-2.58 (m, 1H), 2.08-1.97 (m, 1H), 1.61-1.49 (m, 7H) |

Example C1 (Scheme C-1): Preparation of (3R,4R)-4-({4-[5-chloro-2-methyl-1-(propan-2-yl)-1H-benzimidazol-6-yl]-5-fluoropyrimidin-2-yl}amino)-1-(methanesulfonyl)piperidin-3-ol

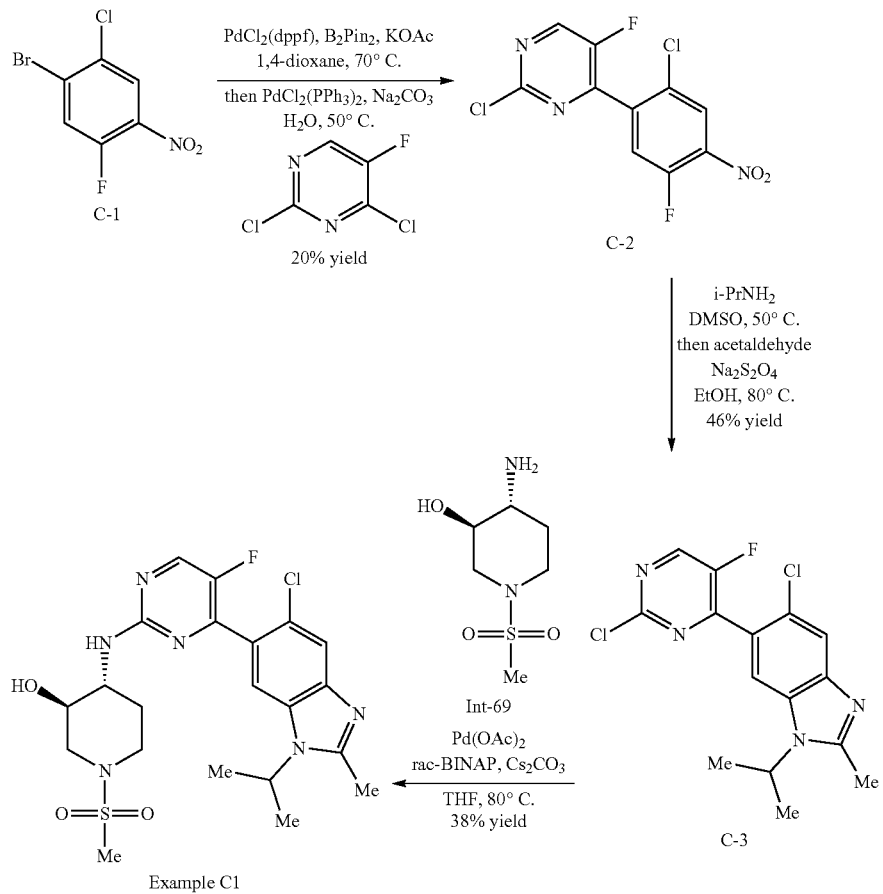

Scheme C-1

Step 1: Synthesis of 2-chloro-4-(2-chloro-5-fluoro-4-nitrophenyl)-5-fluoropyrimidine (C-2)

To a solution of 1-bromo-2-chloro-5-fluoro-4-nitrobenzene (C-1) (0.5 g, 1.97 mmol) in 1,4-dioxane (10.0 mL) were added KOAc (579 mg, 5.9 mmol) and $B_2Pin_2$ (749 mg, 2.95 mmol). The mixture was sparged with $N_2$ and then $PdCl_2(dppf)$ was added. The mixture was stirred at 70° C. with microwave irradiation for 30 min. LCMS analysis indicated consumption of the starting material with conversion to the boronate ester. To the mixture were added 2,4-dichloro-5-fluoropyrimidine, aqueous $Na_2CO_3$ (2.0 M, 2.95 mL), and $PdCl_2(dppf)$ (80 mg, 0.1 mmol). The mixture was stirred at 50° C. with microwave irradiation for 2 h. LCMS analysis indicated consumption of the boronate ester with formation of the desired product mass. The mixture was combined with a parallel reaction run in an identical fashion with 100 mg 1-bromo-2-chloro-5-fluoro-4-nitrobenzene (C-1). The combined mixture was partitioned between EtOAc and $H_2O$. The organic layer was washed with brine, dried over $MgSO_4$, filtered, and concentrated onto $SiO_2$. The crude material was purified by flash chromatography (ISCO, 40 g $SiO_2$, 0-30% EtOAc/heptanes) to provide 2-chloro-4-(2-chloro-5-fluoro-4-nitrophenyl)-5-fluoropyrimidine (C-2) (120 mg, 20% yield) as an off-white solid. $^1$H NMR (400 MHz, DMSO-$d_6$) 9.19 (d, J=1.3 Hz, 1H), 8.53 (d, J=6.7 Hz, 1H), 8.01 (d, J=11.0 Hz, 1H); m/z (ESI) for ($C_1H_3Cl_2F_2N_3O_2$), 304.7 (M+H)$^+$.

Step 2: Synthesis of 5-chloro-6-(2-chloro-5-fluoropyrimidin-4-yl)-2-methyl-1-(propan-2-yl)-1H-benzimidazole (C-3)

A mixture of 2-chloro-4-(2-chloro-5-fluoro-4-nitrophenyl)-5-fluoropyrimidine (C-2) (55 mg, 0.018 mmol) and i-PrNH$_2$ (0.016 mL, 0.018 mmol) in DMSO (1 mL) was stirred at 50° C. with microwave irradiation for 1.5 h. LCMS analysis indicated consumption of the starting material. After cooling to room temperature the mixture was diluted with EtOH (0.5 mL) and treated with acetaldehyde (39.6 mg, 0.05 mL, 0.899 mmol) and $Na_2S_2O_4$ (156 mg, 0.899 mmol). The mixture was stirred at 80° C. for 16 h overnight. LCMS analysis indicated formation of the desired product mass. The mixture was concentrated to remove the EtOH. The remaining solution in DMSO was added dropwise to saturated aqueous $NaHCO_3$. The resultant yellow solids were collected by filtration and washed with $H_2O$. The solids were taken up into DCM/MeOH and concentrated to provide 5-chloro-6-(2-chloro-5-fluoropyrimidin-4-yl)-2-methyl-1-(propan-2-yl)-1H-benzimidazole (C-3) (28 mg, 46% yield), which was taken on without further purification. ¹H NMR (400 MHz, DMSO-d₆) δ 9.05 (s, 1H), 7.97 (s, 1H), 7.79 (s, 1H), 4.79 (spt, J=6.8 Hz, 1H), 2.62 (s, 3H), 1.55 (d, J=7.0 Hz, 6H). m/z (ESI) for (C₁₀H₃Cl₂F₂N₃O₂), 304.7 (M+H)⁺.

Step 3: Synthesis of (3R,4R)-4-({4-[5-chloro-2-methyl-1-(propan-2-yl)-1H-benzimidazol-6-yl]-5-fluoropyrimidin-2-yl}amino)-1-(methanesulfonyl)piperidin-3-ol (Example C1)

To a solution of 5-chloro-6-(2-chloro-5-fluoropyrimidin-4-yl)-2-methyl-1-(propan-2-yl)-1H-benzimidazole (C-3) (28 mg, 0.083 mmol) in THF (1.0 mL) were added (3R, 4R)-4-amino-1-(methanesulfonyl)piperidin-3-ol (Int-69) (24.1 mg, 0.124 mmol) and Cs₂CO₃ (81 mg, 0.25 mmol). The mixture was sparged with N₂ and then Pd(OAc)₂ (3.71 mg, 0.0165 mmol) and rac-BINAP (10 mg, 0.0165 mmol) were added. The mixture was heated to 80° C. overnight. LCMS analysis indicated consumption of the starting material with formation of the desired product mass. The mixture was partitioned between EtOAc and H₂O. The aqueous layer was extracted with EtOAc. The combined organic layers were dried over MgSO₄, filtered, and concentrated. The residue was purified by preparative SFC with an HA-morpholine column (150×21.1 mm, 5 μm particle size, 35° C. column temperature), which was eluted with 10-50% MeOH/CO₂ with a flow rate of 80 g/min. The material was re-purified by preparative SFC with a Nacalai Cosmosil 3-hydroxyphenyl column (150×20 mm, 5 μm particle size. 35° C. column temperature), which was eluted with 12-50% MeOH/CO₂ with a flow rate of 80 g/min to provide (3R,4R)-4-({4-[5-chloro-2-methyl-1-(propan-2-yl)-1H-benzimidazol-6-yl]-5-fluoropyrimidin-2-yl}amino)-1-(methanesulfonyl)piperidin-3-ol (Example C1) (16 mg, 38% yield) as a solid. ¹H NMR (600 MHz, DMSO-d₆, 75° C.) δ 8.35-8.33 (m, 1H), 7.71 (s, 1H), 7.68 (s, 1H), 6.84 (d, J=7.3 Hz, 1H), 5.13 (d, J=4.0 Hz, 1H), 4.78-4.72 (m, 1H), 2.86-2.81 (m, 4H), 2.69-2.63 (m, 1H), 2.57 (s, 3H), 2.14-2.09 (m, 1H), 1.59-1.43 (m, 7H); four protons obscured by residual solvent peak; m/z (ESI) for (C₂₁H₂₆ClFN₆O₃S), 496.9 (M+H)⁺.

Example C2 (Scheme C-2): Preparation of 1,5-anhydro-3-({4-[2-(azetidin-3-yl)-4-fluoro-1-(propan-2-yl)-1H-benzimidazol-6-yl]-5-chloropyrimidin-2-yl}amino)-2,3-dideoxy-D-threo-pentitol Scheme C-2

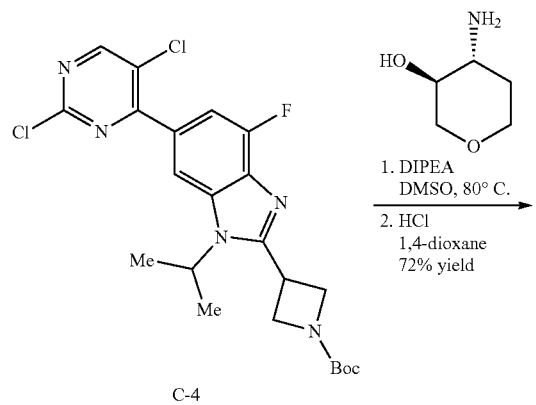

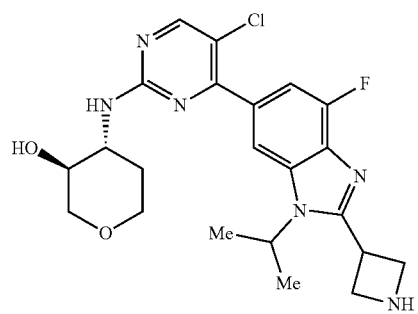

Example C2

A solution of (C-4) (as prepared in Example C1, 155.0 mg, 0.22 mmol), 3-amino-1,5-anhydro-2,3-dideoxy-D-threo-pentitol (49.8 mg, 0.324 mmol), and DIPEA (126 mg, 0.173 mmol, 0.973 mmol) in DMSO (2 mL) was heated to 80° C. for 16 h overnight. LCMS analysis showed consumption of the starting material with formation of the desired product mass. The mixture was loaded directly onto SiO₂ and purified by flash chromatography (ISCO, 12 g SiO₂, 0-100% EtOAc/heptanes). The product-containing fractions were concentrated, taken up into DCM (5 mL), and treated with a solution of HCl (4.0 N in 1,4-dioxane, 1.0 mL). After 15 min, LCMS analysis showed conversion to the desired product. The reaction was concentrated to dryness. The residue was purified by preparative SFC with a ChiralPak IC column (21×250 mm column, 10 μm particle size, 35° C. column temperature), which was eluted with 60% MeOH/CO₂ (+10 mM NH₃) with a flow rate of 82 mL/min to provide 1,5-anhydro-3-({4-[2-(azetidin-3-yl)-4-fluoro-1-(propan-2-yl)-1H-benzimidazol-6-yl]-5-chloropyrimidin-2-yl}amino)-2,3-dideoxy-D-threo-pentitol (Example C2) (72 mg, 72% yield) as a solid. ¹H NMR (400 MHz, DMSO-d₆, 80° C.) δ 8.39 (s, 1H), 7.96 (s, 1H), 7.45 (d, J=11.7 Hz, 1H), 7.13 (d, J=7.6 Hz, 1H), 4.78-4.58 (m, 2H), 4.39-4.29 (m, 1H), 4.15-3.99 (m, 2H), 3.92-3.77 (m, 5H), 3.66-3.52 (m, 2H), 3.39-3.31 (m, 1H), 2.09-1.97 (m, 1H), 1.64-1.53 (m, 7H); m/z (ESI) for (C₂₂H₂₆ClFN₆O₂), 461.1 (M+H)⁺.

Example D1 (Scheme D-1): Preparation of (3R,4R)-4-[(5-chloro-4-{4-fluoro-2-[(1S)-1-hydroxyethyl]-1-(propan-2-yl)-1H-benzimidazol-6-yl}pyridin-2-yl)amino]-1-(methanesulfonyl)piperidin-3-ol Scheme D-1

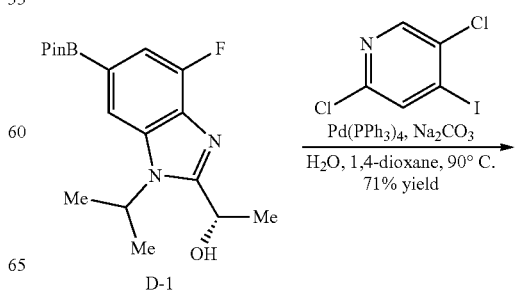

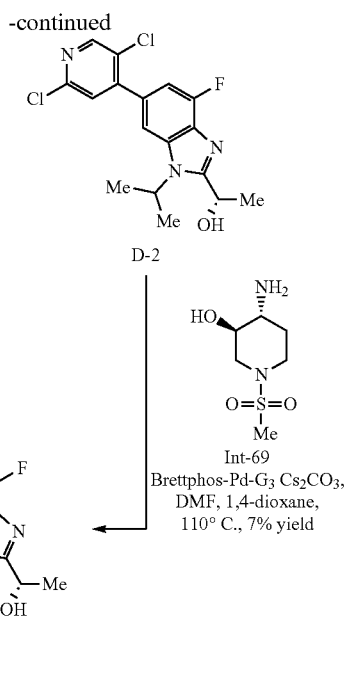

Step 1: Synthesis of (1S)-1-[6-(2,5-dichloropyridin-4-yl)-4-fluoro-1-(propan-2-yl)-1H-benzimidazol-2-yl]ethan-1-ol (D-2)

To a solution of (1S)-1-[4-fluoro-1-(propan-2-yl)-6-(4,4,5,5-tetramethyl-1,3,2-dioxaborolan-2-yl)-1H-benzimidazol-2-yl]ethan-1-ol (D-1) (Prepared as in Example A1, 650 mg, 1.87 mmol) in $H_2O$ (2.0 mL) and 1,4-dioxane (7.0 mL) were added 2,5-dichloro-4-iodopyridine (562 mg, 2.05 mmol), $Na_2CO_3$ (396 mg, 3.73 mmol), and $Pd(PPh_3)_4$ (216 mg, 0.187 mmol). The reaction mixture was stirred at 90° C. under an atmosphere of $N_2$. LCMS analysis showed consumption of the starting material with formation of the desired product mass. The reaction was concentrated to dryness. The residue was purified by flash chromatography (ISCO, 40 g $SiO_2$, 2:1 petroleum ether/EtOAc) to provide (1S)-1-[6-(2,5-dichloropyridin-4-yl)-4-fluoro-1-(propan-2-yl)-1H-benzimidazol-2-yl]ethan-1-ol (D-2) (490 mg, 71% yield) as a light yellow solid. m/z (ESI+) for ($C_{17}H_{16}Cl_2FN_3O$), 368.0 (M+H)$^+$.

Step 2: Synthesis of (3R,4R)-4-[(5-chloro-4-{4-fluoro-2-[(1S)-1-hydroxyethyl]-1-(propan-2-yl)-1H-benzimidazol-6-yl}pyridin-2-yl)amino]-1-(methanesulfonyl)piperidin-3-ol (Example D1)

A heterogeneous mixture of (1S)-1-[6-(2,5-dichloropyridin-4-yl)-4-fluoro-1-(propan-2-yl)-1H-benzimidazol-2-yl]ethan-1-ol (D-2) (390 mg, 1.06 mmol), (3R,4R)-4-amino-1-(methanesulfonyl)piperidin-3-ol (Int-69) (411 mg, 2.12 mmol), $Cs_2CO_3$ (1.04 g, 3.18 mmol), and Brettphos-Pd-G3 (96 mg, 0.106 mmol) in 1,4-dioxane (4.0 mL) and DMF (2.0 mL) was sparged with $N_2$ for 3 min and then stirred at 110° C. for 4 h. LCMS analysis showed consumption of the starting material with formation of the desired product mass. The reaction was filtered and concentrated to dryness. The residue was purified by flash chromatography (ISCO, 40 g $SiO_2$, 0-15% MeOH/EtOAc) and then re-purified by preparative HPLC with a Xtimate C18 column (250×80 mm, 10 μm particle size), which was eluted with 30-50% MeCN/ $H_2O$ (+0.05% $NH_4OH$) with a flow rate of 25 mL/min. HPLC analysis found some erosion of enatiopurity (93% ee). The material was re-purified by chiral preparative SFC with a Diacel Chiralpak AD-H column (250×30 mm, 5 m particle size), which was eluted with 45% IPA/$CO_2$ (+0.1% $NH_3$) with a flow rate of 50 mL/min to provide (3R,4R)-4-[(5-chloro-4-{4-fluoro-2-[(1S)-1-hydroxyethyl]-1-(propan-2-yl)-1H-benzimidazol-6-yl}pyridin-2-yl)amino]-1-(methanesulfonyl)piperidin-3-ol (Example D1) (40.1 mg, 7% yield) as a white solid. $^1$H NMR (400 MHz, DMSO-$d_6$+ $D_2O$) δ 7.99 (br s, 1H), 7.54 (s, 1H), 7.07 (d, J=10.8 Hz, 1H), 6.62 (s, 1H), 5.13-5.02 (m, 2H), 3.70-3.66 (m, 1H), 3.65-3.45 m, 3H), 2.85-2.80 (m, 4H), 2.70-2.62 (m, 1H), 2.05-2.00 (m, 1H), 1.59-1.4 (m, 10H); m/z (ESI+) for ($C_{23}H_{29}ClFN_5O_4S$), 525.8 (M+H)$^+$.

Example D2 (Scheme D-2): Preparation of 1,5-anhydro-3-[(5-chloro-4-{4-fluoro-2-[(1S)-1-hydroxyethyl]-1-(propan-2-yl)-1H-benzimidazol-6-yl}pyridin-2-yl)amino]-2,3-dideoxy-D-threo-pentitol Scheme D-2

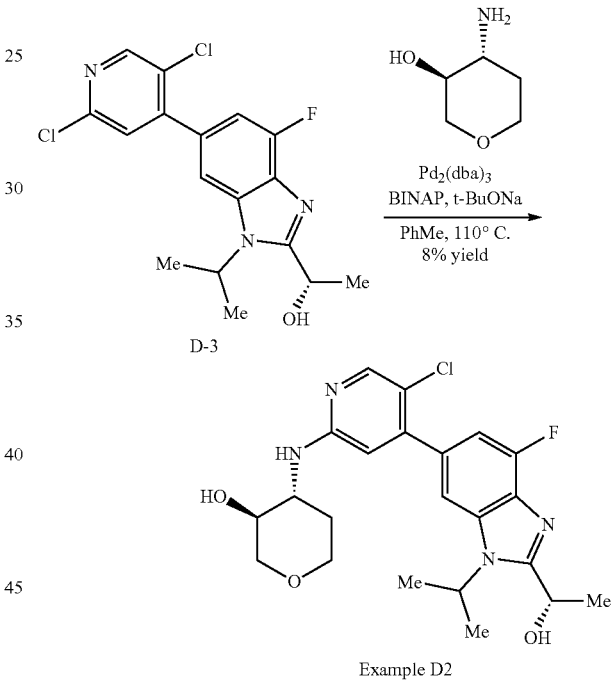

A suspension of (1S)-1-[6-(2,5-dichloropyridin-4-yl)-4-fluoro-1-(propan-2-yl)-1H-benzimidazol-2-yl]ethan-1-ol (D-3) (as prepared in Example D1, 680 mg, 1.85 mmol), 3-amino-1,5-anhydro-2,3-dideoxy-D-threo-pentitol (324 mg, 2.77 mmol), BINAP (92 mg, 0.148 mmol), t-BuONa (532 mg, 5.54 mmol), and $Pd_2(dba)_3$ (84.6 mg, 0.092 mmol) in PhMe (15.0 mL) was sparged with $N_2$ for 3 min and then stirred at 110° C. for 16 h. LCMS analysis showed consumption of the starting material with formation of the desired product mass. The reaction was concentrated to dryness. The residue was purified by flash chromatography (ISCO, 40 g $Si_2$, 0-20% MeOH/EtOAc). The material was re-purified by preparative HPLC with a Xtimate C18 column (250×80 mm, 10 μm particle size), which was eluted with 30-50% MeCN/$H_2O$ (+0.05% $NH_4OH$) with a flow rate of 25 mL/min to provide 1,5-anhydro-3-[(5-chloro-4-{4-fluoro-2-[(1S)-1-hydroxyethyl]-1-(propan-2-yl)-1H-benzimidazol-6-yl}pyridin-2-yl)amino]-2,3-dideoxy-D-threo-pentitol (Example D2) (67 mg, 8% yield) as a white solid ¹H NMR (400 MHz, DMSO-d₆) δ 8.06 (s, 1H), 7.58 (d, J=1.3 Hz, 1H), 7.07 (dd, J=11.5, 1.3 Hz, 1H), 6.80 (d, J=7.3 Hz, 1H), 6.65 (s, 1H), 5.74 (d, J=6.5 Hz, 1H), 5.24-5.01 (m, 3H), 3.84-3.71 (m, 3H), 3.08 (dd, J=9.5, 10.8 Hz, 1H), 2.06-1.98 (m, 1H), 1.64-1.55 (m, 9H), 1.44-1.33 (m, 1H); two hydrogens obscured by residual solvent peak; m/z (ESI+) for ($C_{22}H_{26}ClFN_4O_3$), 449.1 (M+H)⁺.

The example the below table was synthesized according to the methods used for the synthesis of 1,5-anhydro-3-[(5-chloro-4-{4-fluoro-2-[(1S)-1-hydroxyethyl]-1-(propan-2-yl)-1H-benzimidazol-6-yl}pyridin-2-yl)amino]-2,3-dideoxy-D-threo-pentitol (Example D2). The following example was synthesized with non-critical changes or substitutions to the exemplified procedures that someone who is skilled in the art would be able to realize.

| Example number | Structure/Name | LCMS | NMR |
|---|---|---|---|
| D3 | 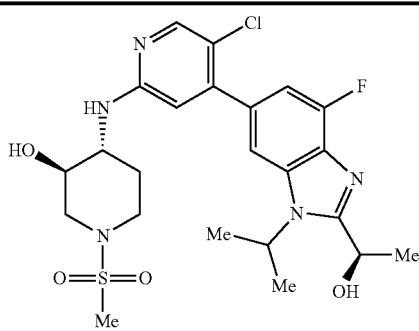<br>(3R,4R)-4-[(5-chloro-4-{4-fluoro-2-[(1R)-1-hydroxyethyl]-1-(propan-2-yl)-1H-benzimidazol-6-yl}pyridin-2-yl)amino]-1-(methanesulfonyl)piperidin-3-ol | 525.9 [M + H]+ (ESI) | ¹H NMR (400 MHz, DMSO-d₆) δ 8.07 (s, 1H), 7.59 (d, J = 1.0 Hz, 1H), 7.07 (dd, J = 11.4, 1.3 Hz, 1H), 6.83 (br d, J = 7.5 Hz, 1H), 6.64 (s, 1H), 5.74 (d, J = 6.3 Hz, 1H), 5.27 (d, J = 4.5 Hz, 1H), 5.21-5.04 (m, 2H), 3.80-3.71 (m, 1H), 3.60-3.49 (m, 2H), 3.49-3.39 (m, 1H), 2.96-2.85 (m, 4H), 2.76-2.68 (m, 1H), 2.17-2.07 (m, 1H), 1.65-1.51 (m, 9H), 1.49-1.33 (m, 1H) |

Example D4 (Scheme D-3): Preparation of (3R,4R)-4-({5-chloro-4-[2-methyl-3-(propan-2-yl)-3H-imidazo[4,5-b]pyridin-5-yl]pyridin-2-yl}amino)-1-(methanesulfonyl)piperidin-3-ol Scheme D-3

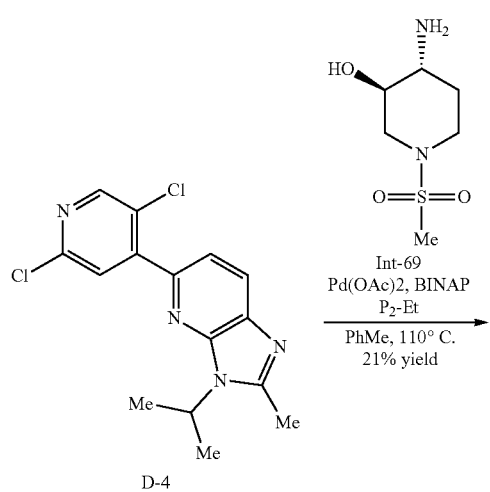

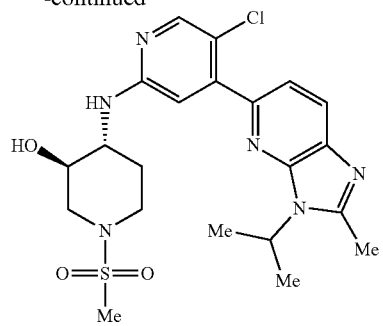

Example D4

To a solution of (D-4) (Prepared as in Example D1, 78 mg, 0.24 mmol), (3R,4R)-4-amino-1-(methanesulfonyl)piperidin-3-ol (Int-69) (41 mg, 0.27 mmol), Pd(OAc)₂ (3.4 mg, 0.015 mmol), and rac-BINAP (9.45 mg, 0.73 mmol) was added phosphazene base P₂-Et to provide a bright orange reaction solution. The mixture was sparged with N₂ and then stirred at 110° C. for 16 h overnight. LCMS analysis indicated consumption of the starting material with formation of the desired product mass. The reaction was concentrated to dryness. The residue was purified by preparative SFC with a ZymorSPHER HADP column (150×21.1 mm, 5

μm particle size, 35° C. column temperature), which was eluted with 12-50% MeOH/CO$_2$ with a flow rate of 80 g/min. The material was repurified by preparative HPLC with a Phenomenex Gemini-NX C18 column (150×21 mm, 5 μm particle size), which was eluted with 15-70% MeCN/H$_2$O (+10 nM NH$_4$OAc) with a flow rate of 40 mL/min to provide (3R,4R)-4-({5-chloro-4-[2-methyl-3-(propan-2-yl)-3H-imidazo[4,5-b]pyridin-5-yl]pyridin-2-yl}amino)-1-(methanesulfonyl)piperidin-3-ol (Example D4) (20 mg, 21% yield) as a solid. $^1$H NMR (600 MHz, DMSO-d$_6$) δ 8.08 (s, 1H), 8.00 (d, J=8.2 Hz, 1H), 7.46 (d, J=8.2 Hz, 1H), 6.88 (d, J=7.4 Hz, 1H), 6.81 (s, 1H), 5.28-5.24 (m, 1H), 4.82 (hept, J=6.7 Hz, 1H), 3.80-3.73 (m, 1H), 3.61-3.52 (m, 2H), 3.49-3.44 (m, 1H), 2.95-2.87 (m, 4H), 2.72 (dd, J=11.4, 8.7 Hz, 1H), 2.63 (s, 3H), 2.15-2.10 (m, 1H), 1.67 (dd, J=6.8, 1.6 Hz, 6H), 1.48-1.40 (m, 1H); m/z (APCI+) for (C$_{21}$H$_{27}$ClN$_6$O$_3$S), 478.9 (M+H)$^+$.

The example the below table was synthesized according to the methods used for the synthesis of (3R,4R)-4-({5-chloro-4-[2-methyl-3-(propan-2-yl)-3H-imidazo[4,5-b]pyridin-5-yl]pyridin-2-yl}amino)-1-(methanesulfonyl)piperidin-3-ol (Example D4). The following example was synthesized with non-critical changes or substitutions to the exemplified procedures that someone who is skilled in the art would be able to realize.

| Example number | Structure/Name | LCMS | NMR |
|---|---|---|---|
| D5 | 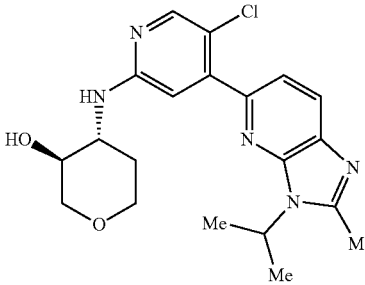<br>1,5-anhydro-3-({5-chloro-4-[2-methyl-3-(propan-2-yl)-3H-imidazo[4,5-b]pyridin-5-yl]pyridin-2-yl}amino)-2,3-dideoxy-D-threo-pentitol | 402.1 [M + H]+ (APCI) | $^1$H NMR (600 MHz, DMSO-d$_6$) δ 8.06 (s, 1H), 7.99 (d, J = 8.3 Hz, 1H), 7.45 (d, J = 8.2 Hz, 1H), 6.89-6.86 (m, 1H), 6.80 (s, 1H), 5.06 (br. s, 1H), 4.81 (hept, J = 6.4 Hz, 1H), 3.84-3.74 (m, 3H), 3.10-3.05 (m, 1H), 2.63 (s, 3H), 2.05-2.01 (m, 1H), 1.67 (dd, J = 6.8, 2.3 Hz, 6H), 1.44-1.36 (m, 1H) two protons obscured by residual solvent peak |

Example D6 (Scheme D-4): Preparation of (3R,4R)-4-{[4-(1-tert-butyl-4-fluoro-1H-benzimidazol-6-yl)-5-chloropyridin-2-yl]amino}piperidin-3-ol Scheme D-4

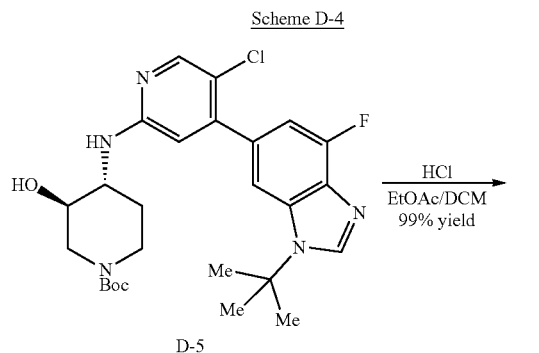

D-5

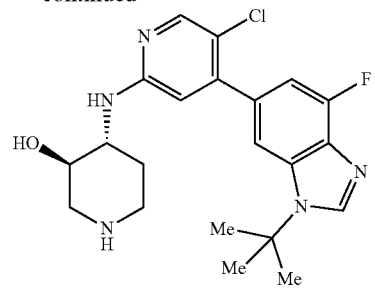

Example D6

To a solution of tert-butyl (3R,4R)-4-{[4-(1-tert-butyl-4-fluoro-1H-benzimidazol-6-yl)-5-chloropyridin-2-yl]amino}-3-hydroxypiperidine-1-carboxylate (D-5) (Prepared as in Example D1, 3.4 g, 5.9 mmol) in DCM (20.0 mL) was added a solution of HCl (1.0 M in EtOAc, 50 mL). After 18 h LCMS analysis showed consumption of the starting material with formation of the desired product mass. The reaction was concentrated to dryness. The solid was taken up in H$_2$O (50 mL) and washed with EtOAc (50 mL). The aqueous layer was lyophilized to provide (3R,4R)-4-{[4-(1-tert-butyl-4-fluoro-1H-benzimidazol-6-yl)-5-chloropyridin-2-yl]amino}piperidin-3-ol hydrochloric acid salt (Example D6) (2.7 g, 99% yield) as a yellow solid. $^1$H NMR (400 MHz, D$_2$O) δ 9.35 (s, 1H), 8.12 (d, J=0.6 Hz, 1H), 8.11 (d, J=1.2 Hz, 1H), 7.56 (dd, J=10.3, 1.2 Hz, 1H), 7.22 (s, 1H), 4.02-3.92 (m, 2H), 3.63-3.48 (m, 2H), 3.17 (td, J=12.9, 3.3 Hz, 1H), 3.05 (dd, J=12.7, 9.8 Hz, 1H), 2.42-2.34 (m, 1H), 1.98-1.79 (m, 10H); m/z (ESI+) for (C$_{21}$H$_{25}$ClFN$_5$O), 418.2 (M+H)$^+$.

Example E1 (Scheme E-1): Preparation of (3R,4R)-4-[(5-chloro-4-{4-fluoro-2-[(1S)-1-hydroxyethyl]-1-(propan-2-yl)-1H-benzimidazol-6-yl}pyridin-2-yl)amino]-1-(methanesulfonyl)piperidin-3-ol

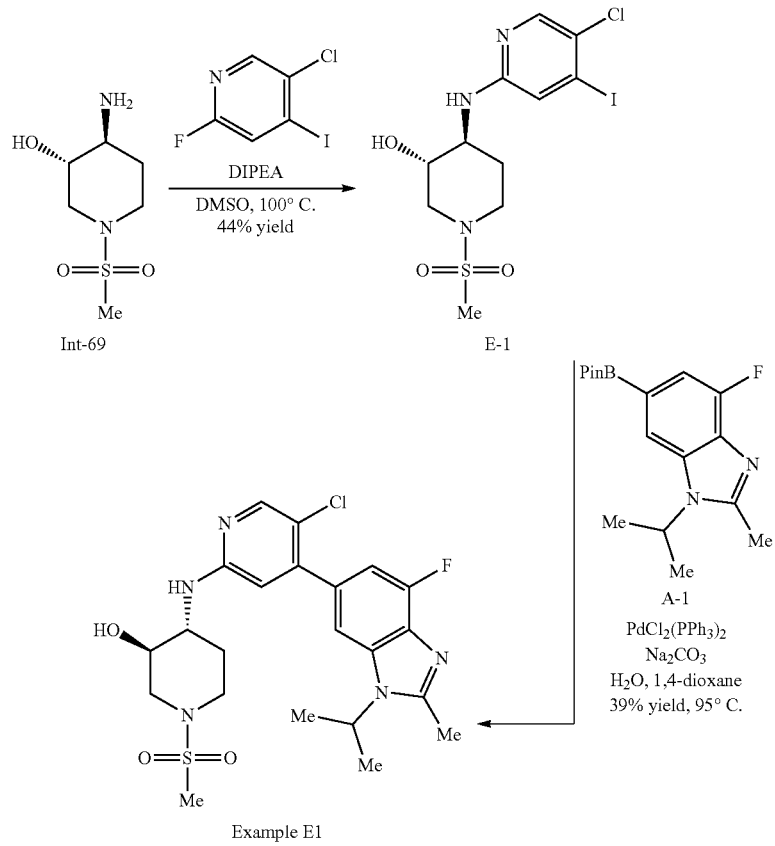

Scheme E-1

Example E1

Step 1: Synthesis of (1S)-1-[6-(2,5-dichloropyridin-4-yl)-4-fluoro-1-(propan-2-yl)-1H-benzimidazol-2-yl]ethan-1-ol (E-1)

A solution of 5-chloro-2-fluoro-4-iodopyridine (200 mg, 0.78 mmol), (3S,4S)-4-amino-1-(methanesulfonyl)piperidin-3-ol (Int-69) (181 mg, 0.93 mmol), and DIPEA (301 mg, 0.415 mL, 2.33 mmol) in DMSO (3.9 mL) was stirred at 100° C. for 16 h. LCMS analysis showed consumption of the starting material with formation of the desired product mass. The reaction was loaded directly onto SiO$_2$ and purified by flash chromatography (ISCO, 12 g SiO$_2$, 0-100% EtOAc/heptanes) to provide (3S,4S)-4-[(5-chloro-4-iodopyridin-2-yl)amino]-1-(methanesulfonyl)piperidin-3-ol (E-1) (147 mg, 44% yield) as a gum. $^1$H NMR (400 MHz, CDCl$_3$) δ 7.93 (s, 1H), 7.08 (s, 1H), 4.85-4.73 (m, 1H), 4.01-3.90 (m, 1H), 3.85-3.74 (m, 1H), 3.67-3.58 (m, 2H), 3.44 (p, J=6.7 Hz, 1H), 2.83 (s, 3H), 2.77 (dd, J=12.2, 2.8 Hz, 1H), 2.68-2.52 (m, 1H), 2.14-2.08 (m, 1H), 1.75-1.56 (m, 1H); m/z (ESI+) for (C$_{11}$H$_{15}$ClIN$_3$O$_3$S), 431.8 (M+H)$^+$.

Step 2: Synthesis of (3R,4R)-4-[(5-chloro-4-{4-fluoro-2-[(1S)-1-hydroxyethyl]-1-(propan-2-yl)-1H-benzimidazol-6-yl}pyridin-2-yl)amino]-1-(methanesulfonyl)piperidin-3-ol (Example E1)

To a solution of (3S,4S)-4-[(5-chloro-4-iodopyridin-2-yl)amino]-1-(methanesulfonyl)piperidin-3-ol (E-1) (147 mg, 0.341 mmol) in 1,4-dioxane (4.7 mL) was added 4-fluoro-2-methyl-1-(propan-2-yl)-6-(4,4,5,5-tetramethyl-1,3,2-dioxaborolan-2-yl)-1H-benzimidazole (A-1) (108 mg, 0.341 mmol), aqueous Na$_2$CO$_3$ (2.0 M, 0.51 mL), PdCl$_2$(PPh$_3$)$_2$ (12 mg, 0.017 mmol), and H$_2$O (0.4 mL). The mixture was stirred at 95° C. for 5 h. LCMS analysis showed consumption of the starting material with formation of the desired product mass. The reaction was filtered through celite and concentrated. The material was purified by preparative SFC with a DCPak SFC-B column (150×21.2 mm, 5 μm particle size, column temperature 35° C.), which was eluted with 25-35% MeOH/CO$_2$ with a flow rate of 62 mL/min to provide (3R,4R)-4-[(5-chloro-4-{4-fluoro-2-[(1S)-1-hydroxyethyl]-1-(propan-2-yl)-1H-benzimidazol-6-y}pyridin-2-yl)amino]-1-(methanesulfonyl)piperidin-3-ol (Example E1) (66 mg, 39% yield) as a white solid. $^1$H NMR (700 MHz, DMSO-d$_6$) δ 8.06 (s, 1H), 7.54 (s, 1H), 7.03 (d, J=11.2 Hz, 1H), 6.81 (d, J=7.3 Hz, 1H), 6.64 (s, 1H), 5.29 (br. s, 1H), 4.83-4.76 (m, 1H), 3.78-3.71 (m, 1H), 3.60-3.50 (m, 2H), 3.48-3.41 (m, 1H), 2.95-2.87 (m, 4H), 2.74-2.68 (m, 1H), 2.60 (s, 3H), 2.14-2.09 (m, 1H), 1.56 (d, J=6.8 Hz, 6H), 1.46-1.39 (m, 1H); m/z (APCI) for (C$_{22}$H$_{27}$ClFN$_5$O$_3$S), 495.9 (M+H)$^+$.

Example F1 (Scheme F-1): Preparation of methyl (3R,4R)-4-({5-fluoro-4-[4-fluoro-2-methyl-1-(propan-2-yl)-1H-benzimidazol-6-yl]pyrimidin-2-yl}amino)-3-hydroxypiperidine-1-carboxylate

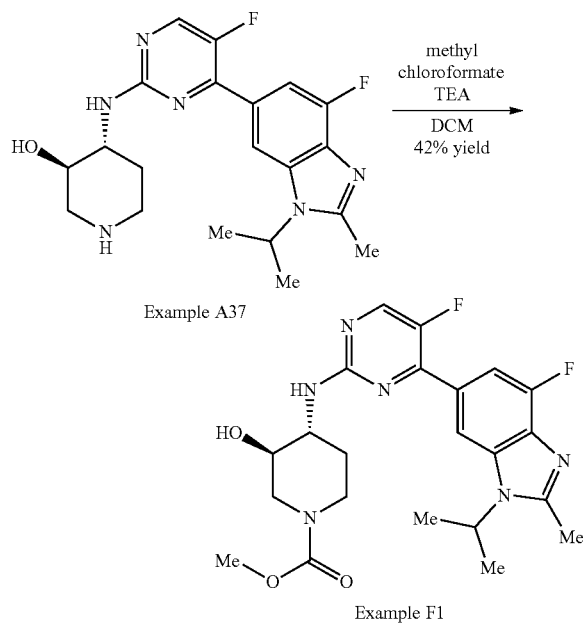

Scheme F-1

Example A37

Example F1

To a solution of (3R,4R)-4-({5-fluoro-4-[4-fluoro-2-methyl-1-(propan-2-yl)-1H-benzimidazol-6-yl]pyrimidin-2-y}amino)piperidin-3-ol (Example A37) (Prepared as in Scheme A-1, 50 mg, 0.12 mmol) and TEA (18.9 mg, 0.186 mmol) in DCM (3.0 mL) at 0° C. was added methyl chloroformate (11.7 mg, 0.124 mmol) dropwise. The reaction was stirred for 30 min at room temperature. LCMS analysis showed consumption of the starting material with formation of the desired product mass. The solution was concentrated. The residue was partitioned between H$_2$O (20 mL) and EtOAc (20 mL). The organic layer was dried over Na$_2$SO$_4$, filtered, and concentrated. The residue was combined with a second batch obtained from a parallel reaction run in identical fashion with 50 mg of (3R,4R)-4-({5-fluoro-4-[4-fluoro-2-methyl-1-(propan-2-yl)-1H-benzimidazol-6-yl]pyrimidin-2-yl}amino)piperidin-3-ol (Example A37). The mixture was purified by preparative HPLC with DuraShell column (150×25 mm, 5 μm particle size), which was eluted with 22-72% MeCN/H$_2$O (+0.05% NH$_4$OH) with a flow rate of 25 mL/min to provide methyl (3R,4R)-4-({5-fluoro-4-[4-fluoro-2-methyl-1-(propan-2-yl)-1H-benzimidazol-6-yl]pyrimidin-2-yl}amino)-3-hydroxypiperidine-1-carboxylate (Example F1) (48 mg, 42% yield) as a white solid. $^1$H NMR (400 MHz, DMSO-d$_6$) δ 8.43 (d, J=4.0 Hz, 1H), 8.13 (br s, 1H), 7.61 (d, J=12.2 Hz, 1H), 7.18 (d, J=7.7 Hz, 1H), 5.11 (d, J=4.8 Hz, 1H), 4.87-4.75 (m, 1H), 4.08-3.75 (m, 3H), 3.60 (s, 3H), 3.51-3.45 (m, 1H), 3.01-2.67 (m, 2H), 2.63 (s, 3H), 2.10-1.92 (m, 1H), 1.59 (d, J=6.8 Hz, 6H), 1.45-1.30 (m, 1H); m/z (ESI) for (C$_{22}$H$_{26}$F$_2$N$_6$O$_3$), 461.4 (M+H)$^+$.

The examples in the below table were synthesized according to the methods used for the synthesis of methyl (3R,4R)-4-({5-fluoro-4-[4-fluoro-2-methyl-1-(propan-2-yl)-1H-benzimidazol-6-yl]pyrimidin-2-yl}amino)-3-hydroxypiperidine-1-carboxylate (Example F1). The following examples were synthesized with non-critical changes or substitutions to the exemplified procedures that someone who is skilled in the art would be able to realize. If necessary, separation of the enantiomers was carried out under standard methods known in the art, such as chiral SFC or HPLC, to afford single enantiomers.

| Example number | Structure/Name | LCMS | NMR |
|---|---|---|---|
| F2 | methyl (3R,4R)-4-({5-chloro-4-[4-fluoro-1-(oxolan-3-yl)-1H-benzimidazol-6-yl]pyrimidin-2-yl}amino)-3-hydroxypiperidine-1-carboxylate<br>*second eluting stereoisomer | 491.1 [M + H]+ (ESI) | $^1$H NMR (400 MHz, DMSO-d$_6$) δ 8.47-8.39 (m, 2H), 8.08-7.90 (m, 1H), 7.57-7.36 (m, 2H), 5.41-5.30 (m, 1H), 5.09 (d, J = 4.8 Hz, 1H), 4.19-3.77 (m, 7H), 3.59 (s, 3H), 3.51-3.39 (m, 1H), 3.02-2.64 (m, 2H), 2.62-2.52 (m, 1H), 2.29-2.18 (m, 1H), 2.02-1.87 (m, 1H), 1.43-1.29 (m, 1H); [α]$_D^{20}$ = −28.8 (c = 1.0, MeOH) |

| Example number | Structure/Name | LCMS | NMR |
|---|---|---|---|
| F3 | 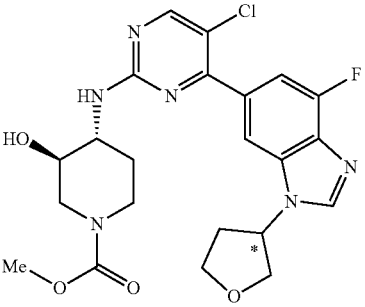  *first eluting stereoisomer  methyl (3R,4R)-4-({5-chloro-4-[4-fluoro-1-(oxolan-3-yl)-1H-benzimidazol-6-yl]pyrimidin-2-yl}amino)-3-hydroxypiperidine-1-carboxylate | 491.1 [M + H]+ (ESI) | $^1$H NMR (400 MHz, DMSO-d$_6$) δ 8.45-8.40 (m, 2H), 8.05-7.91 (m, 1H), 7.56-7.37 (m, 2H), 5.39-5.31 (m, 1H), 5.16-5.04 (m, 1H), 4.19-3.76 (m, 7H), 3.59 (s, 3H), 3.51-3.39 (m, 1H), 3.00-2.64 (m, 2H), 2.62-2.52 (m, 1H), 2.29-2.19 (m, 1H), 2.05-1.87 (m, 1H), 1.42-1.29 (m, 1H); $[α]_D^{20}$ = −4.9 (c = 1.0, MeOH) |

Example F4 (Scheme F-2): Preparation of (3R,4R)-4-({5-fluoro-4-[4-fluoro-2-methyl-1-(propan-2-yl)-1H-benzimidazol-6-yl]pyrimidin-2-yl}amino)-1-methylpiperidin-3-ol

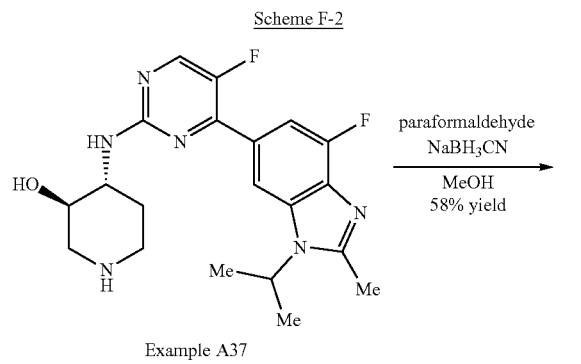

Scheme F-2

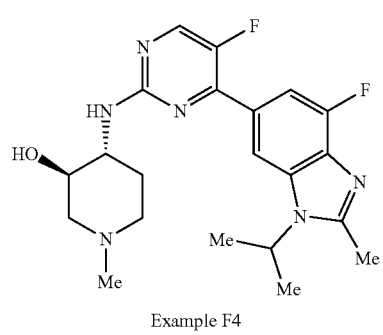

Example F4

To a solution of (3R,4R)-4-({5-fluoro-4-[4-fluoro-2-methyl-1-(propan-2-yl)-1H-benzimidazol-6-yl]pyrimidin-2-yl}amino)piperidin-3-ol (Example A37) (Prepared as in Scheme A-1, 50 mg, 0.12 mmol) in MeOH (3 mL) was added paraformaldehyde (100 mg, 1.11 mmol) and NaBH$_3$CN (100 mg, 1.59 mmol). The resultant solution was stirred at room temperature for 30 min. LCMS analysis showed consumption of starting material with formation of the desired product mass. The solution was filtered and the filtrate was combined with a parallel reaction run in an identical fashion with 50 mg (3R,4R)-4-({5-fluoro-4-[4-fluoro-2-methyl-1-(propan-2-yl)-1H-benzimidazol-6-yl]pyrimidin-2-yl}amino)-1-methylpiperidin-3-ol (Example A37) and concentrated. The residue was purified by preparative HPLC with an Agela Durashell C18 column (150×20 mm, 5 μm particle size), which was eluted with 0-38% MeCN/H$_2$O (0.225% formic acid) with a flow rate of 25 mL/min to provide (3R,4R)-4-({5-fluoro-4-[4-fluoro-2-methyl-1-(propan-2-yl)-1H-benzimidazol-6-yl]pyrimidin-2-yl}amino)-1-methylpiperidin-3-ol formic acid salt (Example F4) (60.2 mg, 58% yield) as a white solid. $^1$H NMR (400 MHz, DMSO-d$_6$) δ 8.42 (d, J=4.1 Hz, 1H), 8.21-8.13 (m, 2H), 7.61 (d, J=12.2 Hz, 1H), 7.10 (d, J=6.3 Hz, 1H), 5.22-4.57 (m, 2H), 3.65-3.52 (m, 2H), 2.99-2.88 (m, 1H), 2.81-2.72 (m, 1H), 2.63 (s, 3H), 2.24 (s, 3H), 2.08-1.85 (m, 3H), 1.64-1.42 (m, 7H); m/z (ESI) for (C$_{21}$H$_{26}$F$_2$N$_6$O), 417.1 (M+H)$^+$.

The examples in the below table were synthesized according to the methods used for the synthesis of (3R,4R)-4-({5-fluoro-4-[4-fluoro-2-methyl-1-(propan-2-yl)-1H-benzimidazol-6-yl]pyrimidin-2-yl}amino)-1-methylpiperidin-3-ol (Example F4). The following examples were synthesized with non-critical changes or substitutions to the exemplified procedures that someone who is skilled in the art would be able to realize.

| Example number | Structure/Name | LCMS | NMR |
|---|---|---|---|
| F5 | (3R,4R)-4-{[4-(1-tert-butyl-4-fluoro-1H-benzimidazol-6-yl)-5-chloropyrimidin-2-yl]amino}-1-(2-hydroxyethyl)piperidin-3-ol formic acid salt | 463.3 [M + H]+ (ESI) | $^1$H NMR (400 MHz, CD$_3$OD) δ 8.51-8.35 (m, 3H), 8.15 (s, 1H), 7.52 (d, J = 11.5 Hz, 1H), 4.06-3.90 (m, 2H), 3.82 (t, J = 5.6 Hz, 2H), 3.45-3.34 (m, 1H), 3.07-2.96 (m, 2H), 2.92-2.70 (m, 2H), 2.48-2.30 (m, 1H), 1.87-1.75 (m, 10H); one proton obscured by residual solvent peak |
| F6 | (3R,4R)-4-{[4-(1-tert-butyl-4-fluoro-1H-benzimidazol-6-yl)-5-chloropyrimidin-2-yl]amino}-1-[2-(dimethylamino)ethyl]piperidin-3-ol formic acid salt | 490.3 [M + H]+ (ESI) | $^1$H NMR (400 MHz, CD$_3$OD) δ 8.39 (s, 1H), 8.37-8.31 (m, 1H), 8.15 (s, 1H), 7.53 (d, J = 11.5 Hz, 1H), 3.87-3.77 (m, 1H), 3.75-3.64 (m, 1H), 3.13-3.05 (m, 1H), 2.94-2.79 (m, 3H), 2.65 (t, J = 6.7 Hz, 2H), 2.55 (s, 6H), 2.27-2.07 (m, 3H), 1.82 (s, 9H), 1.68-1.54 (m, 1H) |
| F7 | *second eluting stereoisomer<br><br>(3R,4R)-4-({5-chloro-4-[4-fluoro-2-(hydroxymethyl)-1-(propan-2-yl)-1H-benzimidazol-6-yl]pyrimidin-2-yl}amino)-1-(methanesulfonyl)piperidin-3-ol | 417.2 [M + H]+ (ESI) | $^1$H NMR (400 MHz, DMSO-d$_6$) δ 8.41-8.42 (m, 1H), 8.17 (s, 1 H), 7.60-7.63 (m, 1H), 7.06-7.07 (m, 1H), 4.85-4.79 (m, 2H), 3.60-3.50 (br m, 2H), 2.91-2.88 (m, 1H), 2.73-2.70 (m, 1H), 2.63 (s, 3H), 2.19 (s, 3H), 2.04-1.75 (m, 3H), 1.59-1.62 (m, 6H), 1.51-1.40 (m, 1H); [α]$_D^{20}$ = 15.4 (c = 041, CHCl$_3$) |

Example F8 (Scheme F-3): Preparation of (3R,4R)-4-({5-chloro-4-[4-fluoro-2-methyl-1-(oxetan-3-yl)-1H-benzimidazol-6-yl]pyrimidin-2-yl}amino)-1-(ethanesulfonyl)piperidin-3-ol

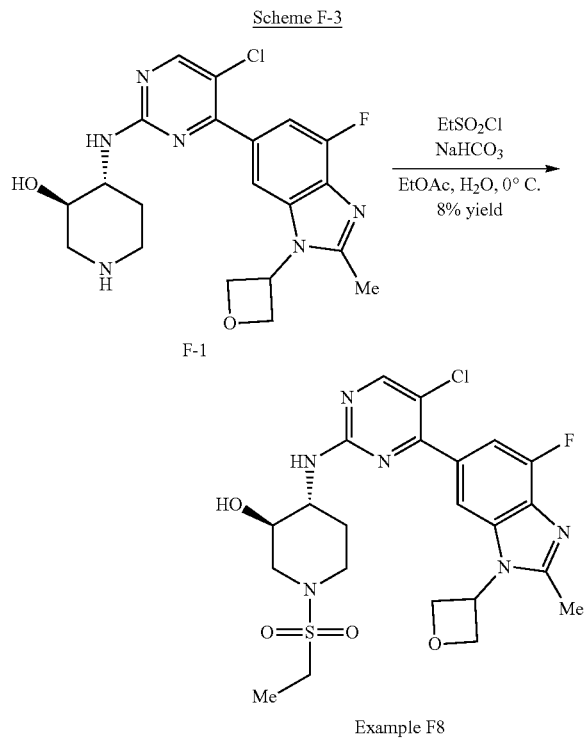

Scheme F-3

Example F8

A mixture of (3R,4R)-4-({5-chloro-4-[4-fluoro-2-methyl-1-(oxetan-3-yl)-1H-benzimidazol-6-yl]pyrimidin-2-yl}amino)piperidin-3-ol (F-1) (Prepared as in Scheme A-1, 70 mg, 0.152 mmol) and NaHCO$_3$ (204 mg, 2.43 mmol) in EtOAc (1.0 mL) and H$_2$O (1.0 mL) was cooled to 0° C. A solution of ethanesulfonyl chloride (20.8 mg, 0.162 mmol) in EtOAc (1.0 mL) was added dropwise over a period of 10 min. The reaction was stirred at 0° C. for 16 h. LMCS analysis showed consumption of the starting material with formation of the desired product mass. The reaction layers were separated. The aqueous layer was extracted with EtOAc (3×10 mL). The combined organic layers were dried over Na$_2$SO$_4$, filtered, and concentrated. The residue was purified by preparative HPLC with a DuraShell column (150×25 mm, 5 μm particle size), which was eluted with 28-48% MeCN/H$_2$O (+0.05% NH$_4$OH) with a flow rate of 25 mL/min to provide (3R,4R)-4-({5-chloro-4-[4-fluoro-2-methyl-1-(oxetan-3-yl)-1H-benzimidazol-6-yl]pyrimidin-2-yl}amino)-1-(ethanesulfonyl)piperidin-3-ol (Example F8) (7 mg, 8% yield) as a white solid. $^1$H NMR (500 MHz, CD$_3$OD) δ 8.61 (br. s, 1H), 8.36 (s, 1H), 7.70-7.55 (br. m, 1H), 5.81-5.72 (m, 1H), 5.30-5.25 (m, 2H), 5.22-5.17 (m, 2H), 3.96-3.90 (m, 1H), 3.88-3.82 (m, 1H), 3.73-3.66 (m, 2H), 3.11-3.03 (m, 2H), 3.02-2.95 (m, 1H), 2.83-2.77 (m, 1H), 2.63 (s, 3H), 2.26-2.17 (m, 1H), 1.68-1.58 (m, 1H), 1.39-1.27 (m, 3H); m/z (ESI) for (C$_{22}$H$_{26}$ClFN$_6$O$_4$S), 525.3 (M+H)$^+$.

The examples in the below table were synthesized according to the methods used for the synthesis of (3R,4R)-4-({5-chloro-4-[4-fluoro-2-methyl-1-(oxetan-3-yl)-1H-benzimidazol-6-yl]pyrimidin-2-yl}amino)-1-(ethanesulfonyl)piperidin-3-ol (Example F8). The following examples were synthesized with non-critical changes or substitutions to the exemplified procedures that someone who is skilled in the art would be able to realize. If necessary, separation of the enantiomers of was carried out under standard methods known in the art, such as chiral SFC or HPLC, to afford single enantiomers.

| Example number | Structure/Name | LCMS | NMR |
|---|---|---|---|
| F9 | (3R,4R)-4-({5-chloro-4-[4-fluoro-2-(1-hydroxyethyl)-1-(propan-2-yl)-1H-benzimidazol-6-yl]pyrimidin-2-yl}amino)-1-(difluoromethanesulfonyl)piperidin-3-ol | 563.1 [M + H]+ (ESI) | $^1$H NMR (400 MHz, CD$_3$OD) δ 8.38 (s, 1H), 8.06 (s, 1H), 7.51 (br d, J = 11.5 Hz, 1H), 6.88-6.52 (m, 1H), 5.34 (td, J = 6.9, 14.0 Hz, 1H), 5.23 (q, J = 6.8 Hz, 1H), 4.09-3.92 (m, 2H), 3.85 (br d, J = 13.7 Hz, 1H), 3.72 (dt, J = 4.7, 9.0 Hz, 1H), 3.29-3.21 (m, 1H), 3.08 (dd, J = 9.5, 12.8 Hz, 1H), 2.30-2.22 (m, 1H), 1.77-1.67 (m, 10H), 0.92 (br t, J = 6.5 Hz, 1H); [α]$_D^{22}$ = −8.3 (c = 0.1, MeOH) |

-continued

| Example number | Structure/Name | LCMS | NMR |
|---|---|---|---|
| F10 | 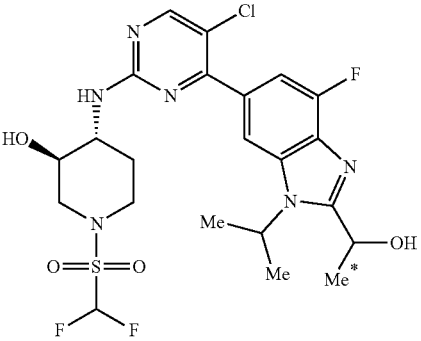 [SMILES: CC(O)c1nc2c(F)cc(-c3nc(N[C@@H]4CCN(S(=O)(=O)C(F)F)C[C@H]4O)ncc3Cl)cc2n1C(C)C]<br>(3R,4R)-4-({5-chloro-4-[4-fluoro-2-(1-hydroxyethyl)-1-(propan-2-yl)-1H-benzimidazol-6-yl]pyrimidin-2-yl}amino)-1-(difluoromethanesulfonyl)piperin-3-ol | 584.9 [M + Na]+ (ESI) | $^1$H NMR (400 MHz, CD$_3$OD) δ 8.38 (s, 1H), 8.06 (s, 1H), 7.62-7.41 (m, 1H), 6.90-6.48 (m, 1H), 5.40-5.31 (m, 1H), 5.24 (q, J = 6.7 Hz, 1H), 4.06-3.92 (m, 2H), 3.86 (br d, J = 13.2 Hz, 1H), 3.72 (td, J = 4.6, 9.0 Hz, 1H), 3.31-3.21 (m, 1H), 3.15-2.95 (m, 1H), 2.34-2.15 (m, 1H), 1.77-1.70 (m, 9H), 1.68-1.62 (m, 1H); $[α]_D^{22}$ = −25.6 (c = 0.1, MeOH) |
| F11 | 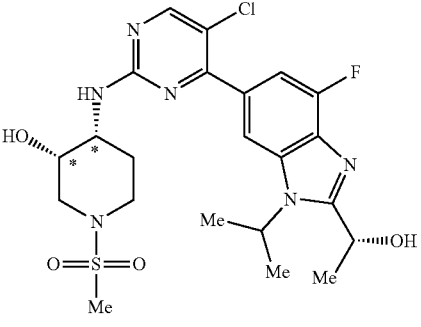 [SMILES: CC(C)n1c([C@@H](C)O)nc2c(F)cc(-c3nc(N[C@@H]4CCN(S(C)(=O)=O)C[C@@H]4O)ncc3Cl)cc21]<br>(3S,4R)-(rel)-4-[(5-chloro-4-{-fluoro-2-[(1R)-1-hydroxyethyl]-1-(propan-2-yl)-1H-benzimidazol-6-yl}pyrimidin-2-yl)amino]-1-(methanesulfonyl)piperidin-3-ol | 526.9 [M + H]+ (ESI) | $^1$H NMR (400 MHz, CD$_3$OD) δ 8.39 (s, 1H), 8.04 (s, 1H), 7.48 (d, J = 11.5 Hz, 1H), 5.40-5.29 (m, 1H), 5.23 (q, J = 6.8 Hz, 1H), 4.15-4.07 (m, 2H), 3.82-3.72 (m, 2H), 3.14 (br d, J = 11.8 Hz, 1H), 3.05 (dt, J = 3.0, 12.2 Hz, 1H), 2.95 (s, 3H), 2.12-2.00 (m, 1H), 1.90 (br d, J = 9.5 Hz, 1H), 1.75-1.70 (m, 9H) |
| F12 | 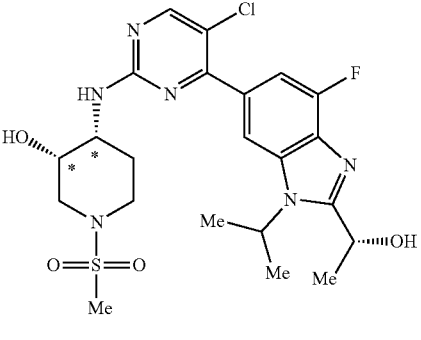 [SMILES: CC(C)n1c([C@@H](C)O)nc2c(F)cc(-c3nc(N[C@@H]4CCN(S(C)(=O)=O)C[C@@H]4O)ncc3Cl)cc21]<br>(3S,4R)-(rel)-4-[(5-chloro-4-{4-fluoro-2-[(1R)-1-hydroxyethyl]-1-(propan-2-yl)-1H-benzimidazol-6-yl}pyrimidin-2-yl)amino]-1-(methanesulfonyl)piperidin-3-ol | 526.9 [M + H]+ (ESI) | $^1$H NMR (400 MHz, CD$_3$OD) δ 8.37 (s, 1H), 8.06 (s, 1H), 7.50 (d, J = 11.5 Hz, 1H), 5.34 (m, J = 7.0, 13.9 Hz, 1H), 5.23 (m, J = 6.7 Hz, 1H), 4.00-3.91 (m, 1H), 3.87-3.81 (m, 1H), 3.78-3.66 (m, 2H), 2.95 (m, J = 2.5, 12.0 Hz, 1H), 2.90 (s, 3H), 2.76 (m, J = 9.5, 11.5 Hz, 1H), 2.29-2.20 (m, 1H), 1.75-1.65 (m, 10H) |

| Example number | Structure/Name | LCMS | NMR |
|---|---|---|---|
| F13 | 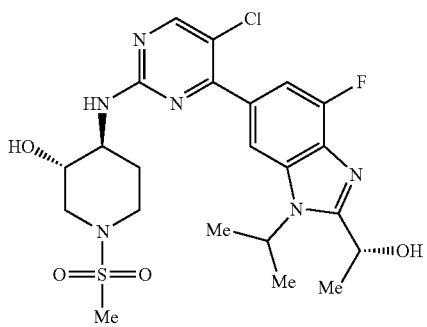 [SMILES: CC(C)n1c([C@@H](C)O)nc2c(F)cc(-c3nc(N[C@H]4CCN(S(C)(=O)=O)C[C@@H]4O)ncc3Cl)cc21]<br>(3S,4S)-4-[(5-chloro-4-{4-fluoro-2-[(1R)-1-hydroxyethyl]-1-(propan-2-yl)-1H-benzimidazol-6-yl}pyrimidin-2-yl)amino]-1-(methanesulfonyl)piperidin-3-ol | 526.9 [M + H]+ (ESI) | $^1$H NMR (400 MHz, CD$_3$OD) δ 8.37 (s, 1H), 8.06 (s, 1H), 7.50 (d, J = 11.6 Hz, 1H), 5.34 (m, J = 6.9, 13.9 Hz, 1H), 5.23 (m, J = 6.6 Hz, 1H), 4.00-3.92 (m, 1H), 3.84 (m, J = 1.7, 4.6, 11.6 Hz, 1H), 3.79-3.65 (m, 2H), 2.99-2.91 (m, 1H), 2.90 (s, 3H), 2.80-2.67 (m, 1H), 2.28-2.21 (m, 1H), 1.76-1.63 (m, 10H) |
| F14 | 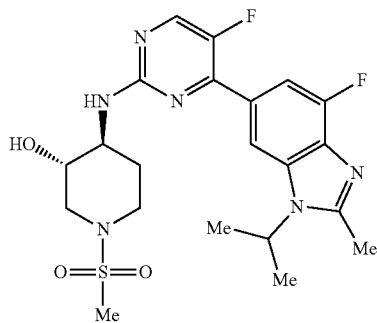 [SMILES: Cc1nc2c(F)cc(-c3nc(N[C@H]4CCN(S(C)(=O)=O)C[C@@H]4O)ncc3F)cc2n1C(C)C]<br>(3S,4S)-4-({5-fluoro-4-[4-fluoro-2-methyl-1-(propan-2-yl)-1H-benzimidazol-6-yl]pyrimidin-2-yl}amino)-1-(methanesulfonyl)piperidin-3-ol | 481.2 [M + H]+ (ESI) | $^1$H NMR (400 MHz, DMSO-d$_6$) δ 8.43 (d, J = 4.0 Hz, 1H), 8.12 (s, 1H), 7.62 (br d, J = 12.3 Hz, 1H), 7.22 (br d, J = 7.0 Hz, 1H), 5.22 (br d, J = 4.3 Hz, 1H), 4.89-4.73 (m, 1H), 3.77 (br s, 1H), 3.61 (br d, J = 10.8 Hz, 2H), 3.49 (br s, 1H), 2.91 (s, 3H), 2.89-2.82 (m, 1H), 2.71-2.64 (m, 1H), 2.63 (s, 3H), 2.09 (br s, 1H), 1.60 (d, J = 6.8 Hz, 6H), 1.52 (br s, 1H). |
| F15 | 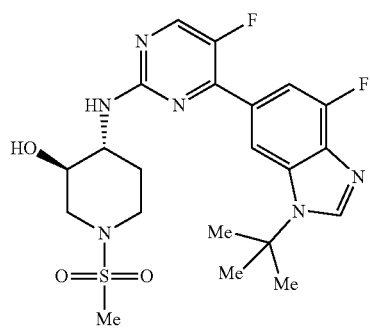 [SMILES: CC(C)(C)n1cnc2c(F)cc(-c3nc(N[C@@H]4CCN(S(C)(=O)=O)C[C@H]4O)ncc3F)cc21]<br>(3R,4R)-4-{[4-(1-tert-butyl-4-fluoro-1H-benzimidazol-6-yl)-5-fluoropyrimidin-2-yl]amino}-1-(methanesulfonyl)piperidin-3-ol | 481.1 [M + H]+ (ESI) | $^1$H NMR (700 MHz, DMSO-d$_6$) δ 8.42-8.34 (m, 2H), 8.21 (br. s., 1H), 7.65-7.54 (m, 1H), 7.15 (d, J = 7.7 Hz, 1H), 5.22-5.07 (m, 1H), 3.77-3.66 (m, 1H), 3.62-3.51 (m, 2H), 3.48-3.39 (m, 1H), 2.84 (s, 3H), 2.80 (dt, J = 2.6, 11.7 Hz, 1H), 2.61 (t, J = 10.1 Hz, 1H), 2.04 (d, J = 7.3 Hz, 1H), 1.69 (s, 9H), 1.53-1.42 (m, 1H) |

Example F16 (Scheme F-4): Preparation of 1-[(3R,4R)-4-({5-fluoro-4-[4-fluoro-2-methyl-1-(propan-2-yl)-1H-benzimidazol-6-yl]pyrimidin-2-yl}amino)-3-hydroxypiperidin-1-yl]ethan-1-one Scheme F-4

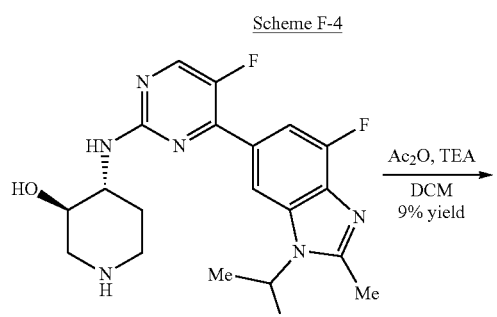

Example A37

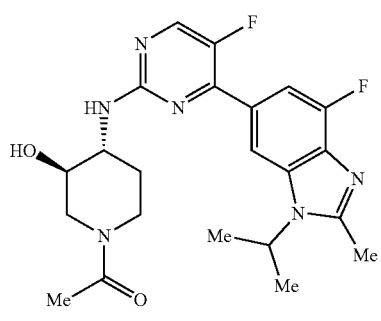

Example F16

To a stirring solution of (3R,4R)-4-({5-fluoro-4-[4-fluoro-2-methyl-1-(propan-2-yl)-1H-benzimidazol-6-yl]pyrimidin-2-yl}amino)piperidin-3-ol trifluoroacetate (Example A37) (300 mg, 0.581 mmol) and triethylamine (226 mg, 0.31 mL, 2.24 mmol) in DCM (5 mL) was added Ac₂O (152 mg, 0.14 mL, 1.49 mmol). The mixture was stirred at ambient temperature for 2 h before being diluted with water (10 mL) and extracted with DCM (3×10 mL). The combined organic phases were washed with brine (10 mL), dried over Na₂SO₄, filtered, and concentrated. The crude residue was purified by preparative HPLC with an Agela Durashell C18 column (150×25 mm, 5 μm particle size, 25° C. column temperature), which was eluted with 15-55% MeCN/H₂O (+0.05% NH₄OH) with a flow rate of 25 mL/min to provide 1-[(3R,4R)-4-({5-fluoro-4-[4-fluoro-2-methyl-1-(propan-2-yl)-1H-benzimidazol-6-yl]pyrimidin-2-yl}amino)-3-hydroxypiperidin-1-yl]ethan-1-one (Example F16) (22.0 mg, 9% yield) as a white solid. $^1$H NMR (400 MHz, DMSO-d$_6$) δ 8.43 (br s, 1H), 8.13 (br s, 1H), 7.61 (br d, J=12.0 Hz, 1H), 7.28-7.13 (m, 1H), 5.18-5.01 (m, 1H), 4.89-4.75 (m, 1H), 3.91-3.70 (m, 2H), 3.18-2.75 (m, 2H), 2.69-2.60 (m, 3H), 2.33 (br s, 1H), 2.01 (br d, J=4.3 Hz, 4H), 1.59 (br d, J=6.5 Hz, 7H), 1.36 (br d, J=14.1 Hz, 1H); m/z (ESI+) for (C$_{22}$H$_{26}$F$_2$N$_6$O$_2$), 445.4 (M+H)$^+$.

Example F17 (Scheme F-5): Preparation of 1-[(3R,4R)-4-({5-fluoro-4-[4-fluoro-2-methyl-1-(propan-2-yl)-1H-benzimidazol-6-yl]pyrimidin-2-yl}amino)-3-hydroxypiperidin-1-yl]-2-hydroxyethan-1-one Scheme F-5

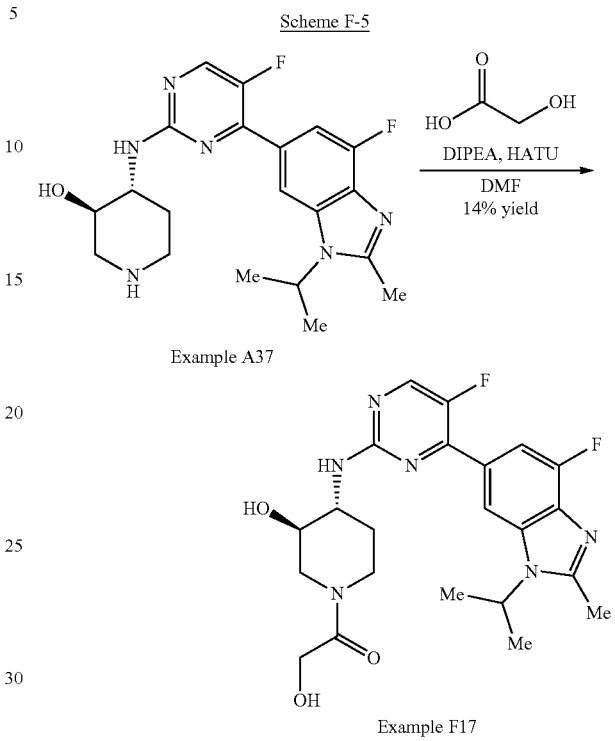

To (3R,4R)-4-({5-fluoro-4-[4-fluoro-2-methyl-1-(propan-2-yl)-1H-benzimidazol-6-yl]pyrimidin-2-yl}amino)piperidin-3-ol trifluoroacetate (Example A37) (50 mg, 0.12 mmol) and glycolic acid (9.45 mg, 0.124 mmol) in DMF (4.0 mL) were added DIPEA (48.2 mg, 0.373 mmol) and HATU (70.9 mg, 0.186 mmol). The mixture was stirred at ambient temperature for 16 h. LCMS analysis showed consumption of the starting material with formation of the desired product mass. The reaction mixture was washed with H₂O (20 mL) and saturated aqueous NaHCO₃ (20 mL). The combined aqueous layers were extracted with EtOAc (20 mL). The combined organic layers were dried over Na₂SO₄, filtered, and concentrated. The residue was purified by preparative HPLC with a DuraShell column (150×25 mm, 5 μm particle size), which was eluted with 12-52% MeCN/H₂O (+0.05% NH₄OH) with a flow rate of 25 mL/min to provide 1-[(3R,4R)-4-({5-fluoro-4-[4-fluoro-2-methyl-1-(propan-2-yl)-1H-benzimidazol-6-yl]pyrimidin-2-yl}amino)-3-hydroxypiperidin-1-yl]-2-hydroxyethan-1-one (Example F17) (8 mg, 14% yield) as a white solid. $^1$H NMR (400 MHz, DMSO-d$_6$) δ 8.44 (t, J=4.0 Hz, 1H), 8.14 (br s, 1H), 7.62 (br d, J=12.0 Hz, 1H), 7.32-7.21 (m, 1H), 5.15 (dd, J=4.8, 9.3 Hz, 1H), 4.83 (hept, J=6.9 Hz, 1H), 4.56 (t, J=5.0 Hz, 1H), 4.33 (br d, J=9.3 Hz, 1H), 4.17-4.04 (m, 2H), 4.04-3.81 (m, 2H), 3.73-3.40 (m, 2H), 3.10-2.95 (m, 1H), 2.63 (s, 3H), 2.09-1.97 (m, 1H), 1.60 (d, J=7.0 Hz, 6H), 1.48-1.33 (m, 1H); m/z (ESI+) for (C$_{22}$H$_{26}$F$_2$N$_6$O$_3$), 461.3 (M+H)$^+$.

The examples in the below table were synthesized according to the methods used for the synthesis of 1-[(3R,4R)-4-({5-fluoro-4-[4-fluoro-2-methyl-1-(propan-2-yl)-1H-benzimidazol-6-yl]pyrimidin-2-yl}amino)-3-hydroxypiperidin-1-yl]-2-hydroxyethan-1-one (Example F17). The following examples were synthesized with non-critical changes or substitutions to the exemplified procedures that someone who is skilled in the art would be able to realize.

| Example number | Structure/Name | LCMS | NMR |
|---|---|---|---|
| F18 | [(3R,4R)-4-({5-chloro-4-[4-fluoro-1-(propan-2-yl)-1H-benzimidazol-6-yl]pyrimidin-2-yl}amino)-3-hydroxypiperidin-1-yl](oxetan-3-yl)methanone | 488.9 [M + H]+ (ESI) | $^1$H NMR (400 MHz, DMSO-d$_6$) δ 8.52 (s, 1H), 8.43 (d, J = 4.8 Hz, 1H), 7.91 (br s, 1H), 7.42-7.40 (m, 2H), 5.24-5.11 (m, 1H), 4.88-4.77 (m, 1H), 4.76-4.58 (m, 4H), 4.41-3.95 (m, 4H), 3.93-3.83 (m, 1H), 3.10-2.84 (m, 1H), 2.67-2.56 (m, 1H), 1.95-1.93 (m, 1H), 1.57 (d, J = 6.8 Hz, 6H), 1.34-1.32 (m, 1H) |
| F19 | [(3R,4R)-4-({5-chloro-4-[4-fluoro-1-(propan-2-yl)-1H-benzimidazol-6-yl]pyrimidin-2-yl}amino)-3-hydroxypiperidin-1-yl](3-methyloxetan-3-yl)methanone | 502.9 [M + H]+ (ESI) | $^1$H NMR (400 MHz, DMSO-d$_6$) δ 8.54 (s, 1H), 8.44 (s, 1H), 7.91 (br s, 1H), 7.64-7.35 (m, 2H), 5.26-5.12 (m, 1H), 4.89-4.71 (m, 3H), 4.38-4.07 (m, 3H), 3.95-3.83 (m, 1H), 3.58-3.38 (m, 1H), 3.12-2.94 (m, 1H), 2.92-2.79 (m, 1H), 2.66-2.57 (m, 1H), 2.08-1.89 (m, 1H), 1.58 (s, 3H), 1.57-1.49 (m, 6H), 1.44-1.30 (m, 1H) |
| F20 | (2R)-1-[(3R,4R)-4-({5-chloro-4-[4-chloro-1-(propan-2-yl)-1H-benzimidazol-6-yl]pyrimidin-2-yl}amino)-3-hydroxypiperidin-1-yl]-2-hydroxypropan-1-one | 515.1 [M + Na]+ (ESI) | $^1$H NMR (400 MHz, DMSO-d$_6$) δ 8.58 (s, 1H), 8.48-8.36 (m, 1H), 8.04 (s, 1H), 7.67 (s, 1H), 7.55 (br s, 1H), 5.15 (br d, J = 30.2 Hz, 1H), 4.98-4.77 (m, 2H), 4.51-3.80 (m, 5H), 3.18-2.83 (m, 1H), 1.98 (s, 1H), 1.57 (d, J = 6.7 Hz, 6H), 1.49-1.26 (m, 2H), 1.18 (dd, J = 9.2, 6.5 Hz, 3H) |

| Example number | Structure/Name | LCMS | NMR |
|---|---|---|---|
| F21 | (2S)-1-[(3R,4R)-4-{[4-(1-tert-butyl-4-fluoro-1H-benzimidazol-6-yl)-5-chloropyrimidin-2-yl]amino}-3-hydroxypiperidin-1-yl]-2-hydroxypropan-1-one | 490.9 [M + H]+ (ESI) | $^1$H NMR (400 MHz, DMSO-$d_6$) δ 8.43 (s, 2H), 8.29-7.90 (m, 1H), 7.72-7.12 (m, 2H), 5.13 (br s, 1H), 4.96 (br d, J = 6.7 Hz, 1H), 4.49-4.13 (m, 2H), 4.09-3.84 (m, 2H), 3.50-3.46 (m, 1H), 3.17-2.76 (m, 2H), 2.08-1.92 (m, 1H), 1.74 (s, 9H), 1.51-1.27 (m, 1H), 1.19 (br t, J = 7.5 Hz, 3H) |
| F22 | 1-[(3R,4R)-4-{[4-(3-tert-butyl-3H-imidazo[4,5-b]pyridin-5-yl)-5-chloropyridin-2-yl]amino}-3-hydroxypiperidin-1-yl]-2-hydroxyethan-1-one | 459.0 [M + H]+ (ESI) | $^1$H NMR (500 MHz, DMSO-$d_6$) δ 8.55 (s, 1H), 8.20-8.20 (m, 1H), 8.20-8.20 (m, 1H), 8.19 (d, J = 8.2 Hz, 1H), 8.11 (d, J = 4.9 Hz, 1H), 7.54 (d, J = 8.4 Hz, 1H), 6.98-6.90 (m, 1H), 6.82 (d, J = 9.3 Hz, 1H), 5.20 (dd, J = 4.7, 11.2 Hz, 1H), 4.55 (t, J = 5.2 Hz, 1H), 4.17-4.06 (m, 2H), 3.87 (br d, J = 13.7 Hz, 1H), 3.68-3.58 (m, 1H), 3.19 (br t, J = 9.6 Hz, 1H), 3.12-3.00 (m, 1H), 2.09-2.00 (m, 1H), 1.84-1.77 (m, 9H), 1.37-1.27 (m, 1H) |

Example F23 (Scheme F-6): Preparation of 1-[(3R,4R)-4-(5-fluoro-4-[4-fluoro-2-methyl-1-(propan-2-yl)-1H-benzimidazol-6-yl]pyrimidin-2-yl)amino)-3-hydroxypiperidin-1-yl]-2-(methylamino)ethan-1-one

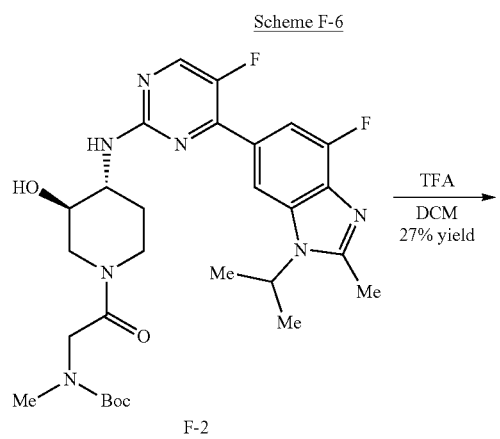

Scheme F-6

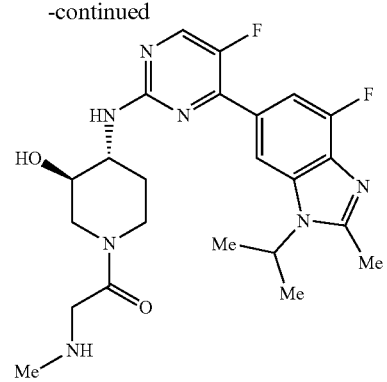

Example F23

To a solution of (F-2) (prepared as in Example F17, 160 mg, 0.279) in DCM (10.0 mL) and TFA (10.0 mL). The mixture was stirred at ambient temperature for 1 h. LCMS analysis showed consumption of the starting material with formation of the desired product mass. The reaction solution was concentrated to dryness. The residue was taken up in MeOH (5 mL) and treated with $NH_3 \cdot H_2O$ to adjust to pH~7-8. The solution was concentrated. The residue was purified by preparative HPLC with a DuraShell column (150×25 mm, 5 μm particle size), which was eluted with 22-42% MeCN/H$_2$O (+0.05% NH$_4$OH) with a flow rate of 25 mL/min to provide 1-[(3R,4R)-4-({5-fluoro-4-[4-fluoro-2-methyl-1-(propan-2-yl)-1H-benzimidazol-6-yl]pyrimidin-2-yl}amino)-3-hydroxypiperidin-1-yl]-2-(methylamino)ethan-1-one (Example F23) (35.2 mg, 27% yield) as a white solid. $^1$H NMR (400 MHz, DMSO-d$_6$) δ 8.43 (t, J=4.1 Hz, 1H), 8.13 (br s, 1H), 7.61 (br d, J=12.1 Hz, 1H), 7.31-7.11 (m, 1H), 5.10 (br d, J=4.5 Hz, 1H), 4.82 (td, J=6.8, 13.8 Hz, 1H), 4.11-3.65 (m, 3H), 3.60-3.38 (m, 2H), 3.26-2.98 (m, 3H), 2.70-2.53 (m, 4H), 2.27 (d, J=1.3 Hz, 3H), 2.02 (br s, 1H), 1.59 (d, J=6.8 Hz, 6H), 1.45-1.29 (m, 1H); m/z (ESI+) for (C$_{23}$H$_{29}$F$_2$N$_7$O$_2$), 474.5 (M+H)$^+$.

The examples in the below table were synthesized according to the methods used for the synthesis of 1-[(3R,4R)-4-({5-fluoro-4-[4-fluoro-2-methyl-1-(propan-2-yl)-1H-benzimidazol-6-yl]pyrimidin-2-yl}amino)-3-hydroxypiperidin-1-yl]-2-(methylamino)ethan-1-one (Example F23). The following examples were synthesized with non-critical changes or substitutions to the exemplified procedures that someone who is skilled in the art would be able to realize. If necessary, separation of the enantiomers was carried out under standard methods known in the art, such as chiral SFC or HPLC, to afford single enantiomers.

| Example number | Structure/Name | LCMS | NMR |
|---|---|---|---|
| F24 | 1-[(3R,4R)-4-({5-chloro-4-[4-fluoro-1-(propan-2-yl)-1H-benzimidazol-6-yl]pyrimidin-2-yl}amino)-3-hydroxpiperidin-1-yl]-2-(methylamino)ethan-1-one | 476.2 [M + H]+ (ESI) | $^1$H NMR (400 MHz, DMSO-d$_6$) δ 8.53 (s, 1H), 8.44 (d, J = 5.3 Hz, 1H), 7.90 (br s, 1H), 7.97-7.84 (m, 1H), 7.61-7.36 (m, 2H), 5.10 (br s, 1H), 4.82 (td, J = 6.7, 13.3 Hz, 1H), 4.35 (br d, J = 12.5 Hz, 1H), 4.04-3.80 (m, 2H), 3.75 (br d, J = 9.8 Hz, 1H), 3.51 (br s, 1H), 3.10-2.94 (m, 2H), 2.58 (br t, J = 11.3 Hz, 1H), 2.28 (d, J = 2.0 Hz, 3H), 1.90 (s, 1H), 1.56 (d, J = 6.7 Hz, 6H), 1.38 (br d, J = 17.2 Hz, 1H) |
| F25 | 1-[(3R,4R)-4-{[4-(1-tert-butyl-4-fluoro-1H-benzimidazol-6-yl)-5-chloropyrimidin-2-yl]amino}-3-hydroxypiperidin-1-yl]-2-(methylamino)ethan-1-one | 512.2 [M + Na]+ (ESI) | $^1$H NMR (400 MHz, D$_2$O) δ 9.43-9.31 (m, 1H), 8.43 (s, 1H), 8.31 (br s, 1H), 7.77 (br d, J = 10.8 Hz, 1H), 4.46-3.98 (m, 4H), 3.85-3.56 (m, 2H), 3.32-2.82 (m, 2H), 2.76 (d, J = 3.0 Hz, 3H), 2.15-2.14 (m, 1H), 1.84 (s, 9H), 1.60-1.59 (m, 1H) |

| Example number | Structure/Name | LCMS | NMR |
|---|---|---|---|
| F26 | [(3R,4R)-4-{[4-(1-tert-butyl-4-fluoro-1H-benzimidazol-6-yl)-5-chloropyrimidin-2-yl]amino}-3-hydroxypiperidin-1-yl](3-fluoroazetidin-3-yl)methanone | 520.0 [M + H]+ (ESI) | $^1$H NMR (500 MHz, CD$_3$OD) δ 8.42-8.17 (m, 2H), 8.04 (s, 1H), 7.42 (d, J = 11.4 Hz, 1H), 4.40-3.88 (m, 4H), 3.84-3.45 (m, 4H), 3.15-2.67 (m, 2H), 2.09 (d, J = 13.4 Hz, 1H), 1.72 (s, 9H), 1.50-1.36 (m, 1H) |
| F27 | [(3R,4R)-4-({5-chloro-4-[4-fluoro-1-(propan-2-yl)-1H-benzimidazol-6-yl]pyrimidin-2-yl}amino)-3-hydroxypiperidin-1-yl](3-fluoroazetidin-3-yl)methanone | 506.1 [M + H]+ (ESI) | $^1$H NMR (500 MHz, DMSO-d$_6$) δ 8.45 (s, 1H), 8.35 (s, 1H), 7.82 (br s, 1H), 7.55-7.04 (m, 2H), 5.13 (dd, J = 21.1, 4.8 Hz, 1H), 4.75 (p, J = 6.7 Hz, 1H), 4.27-3.74 (m, 4H), 3.70-3.35 (m, 4H), 3.09-2.62 (m, 2H), 1.96 (br s, J = 33.6 Hz, 1H), 1.49 (d, J = 6.7 Hz, 6H), 1.43-1.23 (m, 1H) |
| F28 | (1-aminocyclopropyl)[(3R,4R)-4-({5-chloro-4-[4-fluoro-1-(propan-2-yl)-1H-benzimidazol-6-yl]pyrimidin-2-yl}amino)-3-hydroxypiperidin-1-yl]methanone | 488.1 [M + H]+ (ESI) | $^1$H NMR (500 MHz, DMSO-d$_6$) δ 8.52 (s, 1H), 8.43 (s, 1H), 7.90 (br s, 1H), 7.59-7.21 (m, 2H), 5.20 (br s, 1H), 4.82 (td, J = 6.7, 13.4 Hz, 1H), 4.25 (br d, J = 10.2 Hz, 1H), 4.17-3.94 (m, 1H), 3.88 (br dd, J = 3.2, 8.1 Hz, 1H), 3.49 (br d, J = 3.4 Hz, 1H), 3.03 (br s, 1H), 2.37-2.19 (m, 2H), 1.97 (br s, 1H), 1.56 (d, J = 6.6 Hz, 6H), 1.46-1.24 (m, 1H), 0.79 (br s, 2H), 0.71-0.53 (m, 2H) |

-continued

| Example number | Structure/Name | LCMS | NMR |
|---|---|---|---|
| F29 | 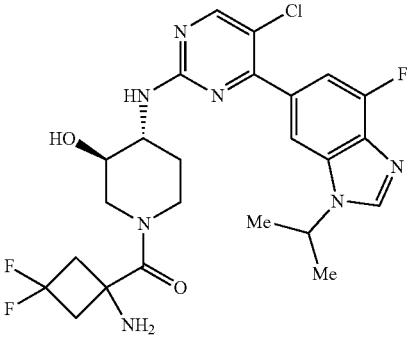 [SMILES: CC(C)n1cnc2c(F)cc(-c3nc(N[C@@H]4CCN(C(=O)C5(N)CC(F)(F)C5)C[C@H]4O)ncc3Cl)cc21]<br>(1-amino-3,3-difluorocyclobutyl)[(3R,4R)-4-({5-chloro-4-[4-fluoro-1-(propan-2-yl)-1H-benzimidazol-6-yl]pyrimidin-2-yl}amino)-3-hydroxypiperidin-1-yl]methanone | 538.0 [M + H]+ (ESI) | $^1$H NMR (400 MHz, DMSO-d$_6$) δ 8.54 (s, 1H), 8.44 (s, 1H), 7.91 (br s, 1H), 7.56-7.32 (m, 2H), 5.18 (d, J = 70.6 Hz, 1H), 4.83 (p, J = 6.8 Hz, 1H), 4.42-3.76 (m, 3H), 3.51 (d, J = 65.9 Hz, 1H), 3.25-2.92 (m, 3H), 2.64-2.55 (m, 3H), 2.48-2.42 (m, 1H), 1.99 (s, 1H), 1.57 (d, J = 6.7 Hz, 6H), 1.52-1.30 (m, 1H) |
| F30 | 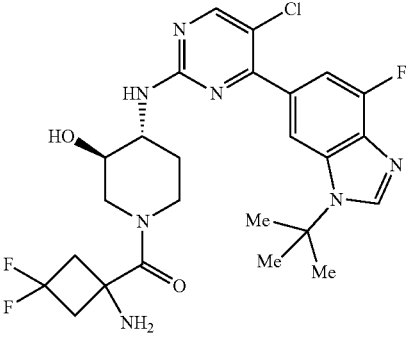 [SMILES: CC(C)(C)n1cnc2c(F)cc(-c3nc(N[C@@H]4CCN(C(=O)C5(N)CC(F)(F)C5)C[C@H]4O)ncc3Cl)cc21]<br>(1-amino-3,3-difluorocyclobutyl)[(3R,4R)-4-{[4-(1-tert-butyl-4-fluoro-1H-benzimidazol-6-yl)-5-chloropyrimidin-2-yl]amino}-3-hydroxypiperidin-1-yl]methanone | 552.2 [M + H]+ (ESI) | $^1$H NMR (500 MHz, CD$_3$OD) δ 8.27 (d, J = 5.1 Hz, 2H), 8.04 (s, 1H), 7.42 (d, J = 11.4 Hz, 1H), 4.01-3.43 (m, 4H), 3.16-3.04 (m, 3H), 2.75-2.37 (m, 3H), 2.14-2.01 (m, 1H), 1.72 (s, 9H), 1.48 (s, 1H) |
| F31 | 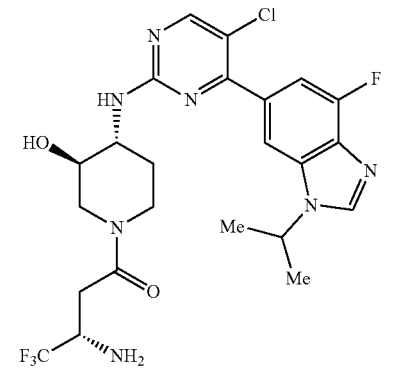 [SMILES: CC(C)n1cnc2c(F)cc(-c3nc(N[C@@H]4CCN(C(=O)C[C@H](N)C(F)(F)F)C[C@H]4O)ncc3Cl)cc21]<br>(3S)-3-amino-1-[(3R,4R)-4-({5-chloro-4-[4-fluoro-1-(propan-2-yl)-1H-benzimidazol-6-yl]pyrimidin-2-yl}amino)-3-hydroxypiperidin-1-yl]-4,4,4-trifluorobutan-1-one | 544.0 [M + H]+ (ESI) | $^1$H NMR (500 MHz, DMSO-d$_6$) δ 8.45 (s, 1H), 8.41-8.28 (m, 1H), 7.83 (br s, 1H), 7.65-7.26 (m, 2H), 5.03 (dd, J = 4.7, 12.5 Hz, 1H), 4.75 (td, J = 6.7, 13.4 Hz, 1H), 4.40-3.28 (m, 5H), 3.12-2.98 (m, 1H), 2.55-2.45 (m, 2H), 1.89 (br s, 3H), 2.02-1.79 (m, 1H), 1.50 (s, 6H), 1.36-1.21 (m, 1H) |

| Example number | Structure/Name | LCMS | NMR |
|---|---|---|---|
| F32 | 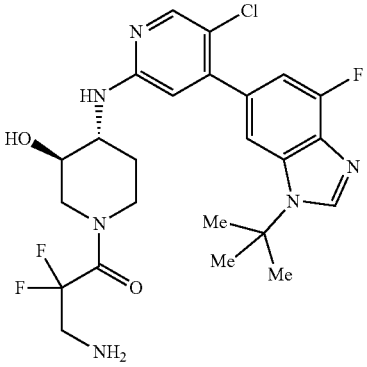 [SMILES: CC(C)(C)n1cnc2c(F)cc(-c3cc(N[C@@H]4CCN(C(=O)C(F)(F)CN)C[C@H]4O)ncc3Cl)cc21]<br>3-amino-1-[(3R,4R)-4-{[4-(1-tert-butyl-4-fluoro-1H-benzimidazol-6-yl)-5-chloropyridin-2-yl]amino}-3-hydroxypiperidin-1-yl]-2,2-difluoropropan-1-one | 525.3 [M + H]+ (ESI) | 1H NMR (400 MHz, DMSO-$d_6$) δ 8.38 (s, 1H), 8.08 (s, 1H), 7.69 (s, 1H), 7.12 (d, J = 11.4 Hz, 1H), 6.90-6.83 (m, 1H), 6.65 (s, 1H), 5.30 (br s, 1H), 4.19-4.01 (m, 2H), 3.99-3.80 (m, 2H), 3.46 (br s, 2H), 3.23-2.96 (m, 4H), 2.11 (br t, J = 12.7 Hz, 1H), 1.72 (s, 9H), 1.39-1.23 (m, 1H) |

Example F33 (Scheme F-7): Preparation of 2-[(3R,4R)-4-[4-(3-tert-butyl-3H-imidazo[4,5-b]pyridin-5-yl)-5-chloropyridin-2-yl]amino)-3-hydroxypiperidin-1-yl]-N-methylacetamide Scheme F-7

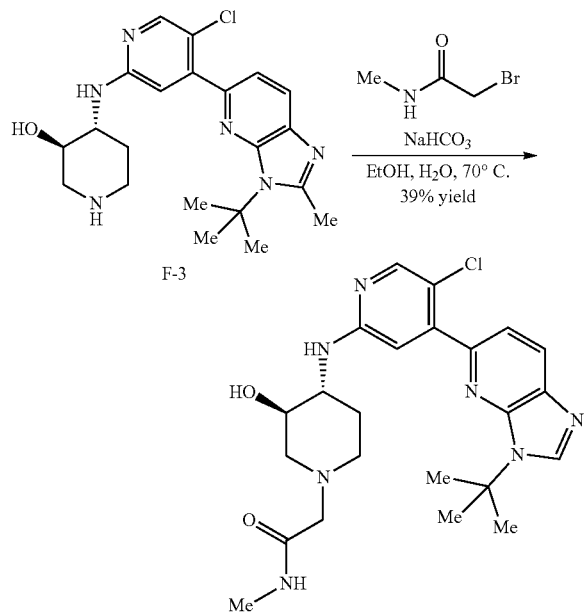

To a solution of (3R,4R)-4-{[4-(3-tert-butyl-3H-imidazo[4,5-b]pyridin-5-y)-5-chloropyridin-2-yl]amino}piperidin-3-ol (Prepared as in Example 3, 100 mg, 0.249 mmol) in EtOH (6.0 mL) was added 2-bromo-N-methylacetamide (56.7 mg, 0.374 mmol) and a solution of saturated aqueous NaHCO$_3$ (3.0 mL). The mixture was stirred at 70° C. for 16 h. TLC analysis (1:3 MeOH/EtOAc) indicated consumption of the starting material. The mixture was diluted with H$_2$O (10 mL) and extracted with EtOAc (20 mL). The organic layer was dried over Na$_2$SO$_4$, filtered, and concentrated. The residue was purified by preparative HPLC with a DuraShell column (150×25 mm, 5 μm particle size), which was eluted with 21-41% MeCN/H$_2$O (+0.05% NH$_4$OH) with a flow rate of 25 mL/min to provide 2-[(3R,4R)-4-{[4-(3-tert-butyl-3H-imidazo[4,5-b]pyridin-5-yl)-5-chloropyridin-2-yl]amino}-3-hydroxypiperidin-1-yl]-N-methylacetamide (Example F33) (45.5 mg, 39% yield) as a white solid. $^1$H NMR (500 MHz, DMSO-$d_6$) δ 8.54 (s, 1H), 8.17 (d, J=8.4 Hz, 1H), 8.07 (s, 1H), 7.72 (br d, J=4.6 Hz, 1H), 7.52 (d, J=8.4 Hz, 1H), 6.85-6.80 (m, 2H), 4.91 (d, J=5.6 Hz, 1H), 3.60-3.49 (m, 2H), 2.91 (d, J=2.0 Hz, 2H), 2.89-2.85 (m, 1H), 2.68 (br d, J=11.1 Hz, 1H), 2.62 (d, J=4.7 Hz, 3H), 2.18-2.09 (m, 1H), 2.06-1.98 (m, 2H), 1.80 (s, 9H), 1.50-1.39 (m, 1H); m/z (ESI+) for (C$_{23}$H$_{30}$ClN$_7$O$_2$), 472.2 (M+H)$^+$.

Example G1 (Scheme G-1): 1-[6-(5-chloro-2-{[(3R,4R)-3-hydroxy-1-(methanesulfonyl)piperidin-4-yl]amino}pyrimidin-4-yl)-4-fluoro-1-(propan-2-yl)-1H-benzimidazol-2-yl]ethan-1-one

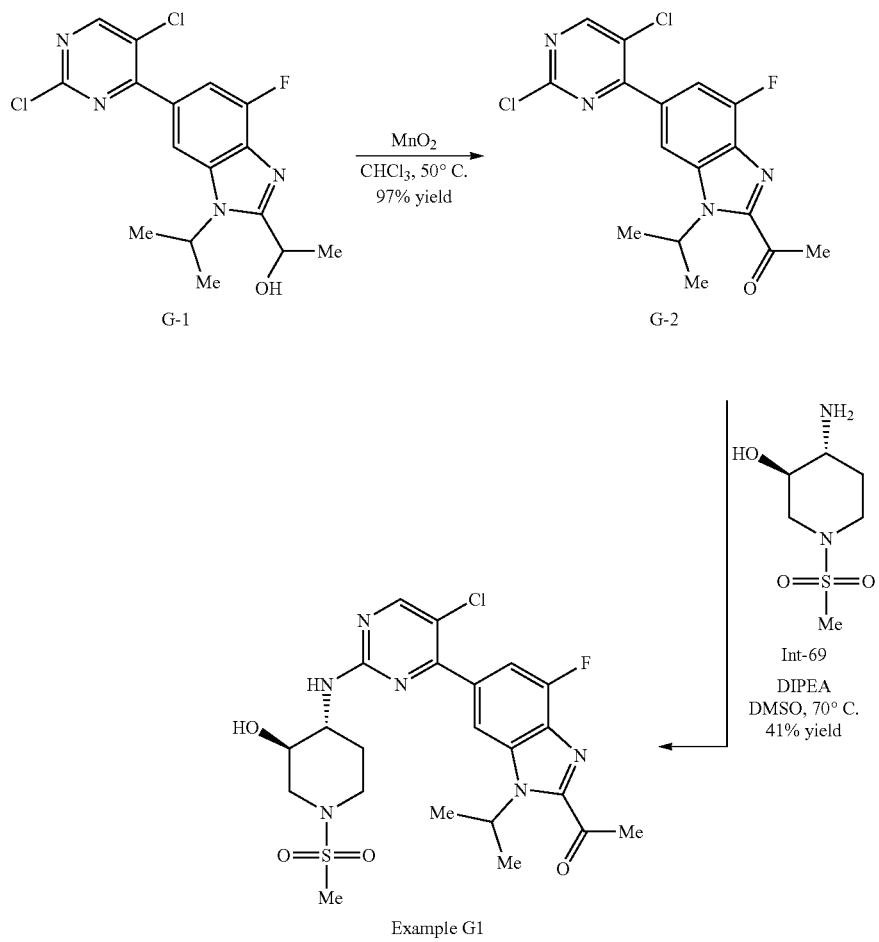

Scheme G-1

Step 1: Synthesis of 1-[6-(2,5-dichloropyrimidin-4-yl)-4-fluoro-1-(propan-2-yl)-1H-benzimidazol-2-yl]ethan-1-one (G-2)

To a solution of 1-[6-(2,5-dichloropyrimidin-4-yl)-4-fluoro-1-(propan-2-yl)-1H-benzimidazol-2-yl]ethan-1-ol (G-1) (Prepared as in Example A1, 500 mg, 1.35 mmol) in CHCl$_3$ (10 mL) was added MnO$_2$ (824 mg, 9.48 mmol). The mixture was stirred at 50° C. for 6 h. LCMS analysis showed consumption of the starting material with formation of the desired product mass. The mixture was filtered and concentrated. The residue was purified by flash chromatography (Biotage, SiO$_2$, 25% EtOAc/petroleum ether) to provide 1-[6-(2,5-dichloropyrimidin-4-yl)-4-fluoro-1-(propan-2-yl)-1H-benzimidazol-2-yl]ethan-1-one (G-2) (480 mg, 97% yield) as a white solid. $^1$H NMR (400 MHz, CDCl$_3$) δ 8.73 (s, 1H), 8.10 (d, J=1.2 Hz, 1H), 7.64 (dd, J=1.3, 10.9 Hz, 1H), 6.06-5.92 (m, 1H), 2.93 (s, 3H), 1.71 (d, J=7.1 Hz, 6H); m/z (ESI+) for (C$_{16}$H$_{13}$Cl$_2$FN$_4$O), 367.0 (M+H)$^+$.

Step 2: Synthesis of 1-[6-(5-chloro-2-{[(3R,4R)-3-hydroxy-1-(methanesulfonyl)piperidin-4-yl]amino}pyrimidin-4-yl)-4-fluoro-1-(propan-2-yl)-1H-benzimidazol-2-yl]ethan-1-one (Example G1)

To a solution of 1-[6-(2,5-dichloropyrimidin-4-yl)-4-fluoro-1-(propan-2-yl)-1H-benzimidazol-2-yl]ethan-1-one (G-2) (100 mg, 0.272 mmol) in DMSO (5.0 mL) was added DIPEA (106 mg, 0.817 mmol) and (3R,4R)-4-amino-1-(methanesulfonyl)piperidin-3-ol (Int-69). The mixture was stirred at 70° C. for 16 h. LCMS analysis showed consumption of the starting material with formation of the desired product mass. The mixture was diluted with H$_2$O (30 mL) and extracted with EtOAc (2×30 mL). The combined organic layers were dried over Na$_2$SO$_4$, filtered, and concentrated. The residue was purified by preparative TLC (SiO$_2$, 50% EtOAc/petroleum ether, R$_f$=0.4) to provide 1-[6-(5-chloro-2-{[(3R,4R)-3-hydroxy-1-(methanesulfonyl)

piperidin-4-yl]amino}pyrimidin-4-yl)-4-fluoro-1-(propan-2-yl)-1H-benzimidazol-2-yl]ethan-1-one (Example G1) (58.2 mg, 41% yield) as a white solid. $^1$H NMR (400 MHz, DMSO-d$_6$) δ 8.47 (s, 1H), 8.21-8.03 (m, 1H), 7.67-7.41 (m, 2H), 5.86-5.72 (m, 1H), 5.23 (d, J=4.6 Hz, 1H), 3.88-3.75 (m, 1H), 3.68-3.56 (m, 2H), 3.53-3.44 (m, 1H), 2.90 (s, 3H), 2.87-2.81 (m, 1H), 2.79 (s, 3H), 2.66-2.60 (m, 1H), 2.14-1.98 (m, 1H), 1.61 (d, J=7.0 Hz, 6H), 1.57-1.45 (m, 1H); m/z (ESI+) for (C$_{22}$H$_{26}$ClFN$_6$O$_4$S), 525.2 (M+H)$^+$.

Example H1 (Scheme H-1): Preparation of 1,5-anhydro-3-({5-chloro-4-[2-(chloromethyl)-4-fluoro-1-(propan-2-yl)-1H-benzimidazol-6-yl]pyrimidin-2-yl}amino)-2,3-dideoxy-D-threo-pentitol

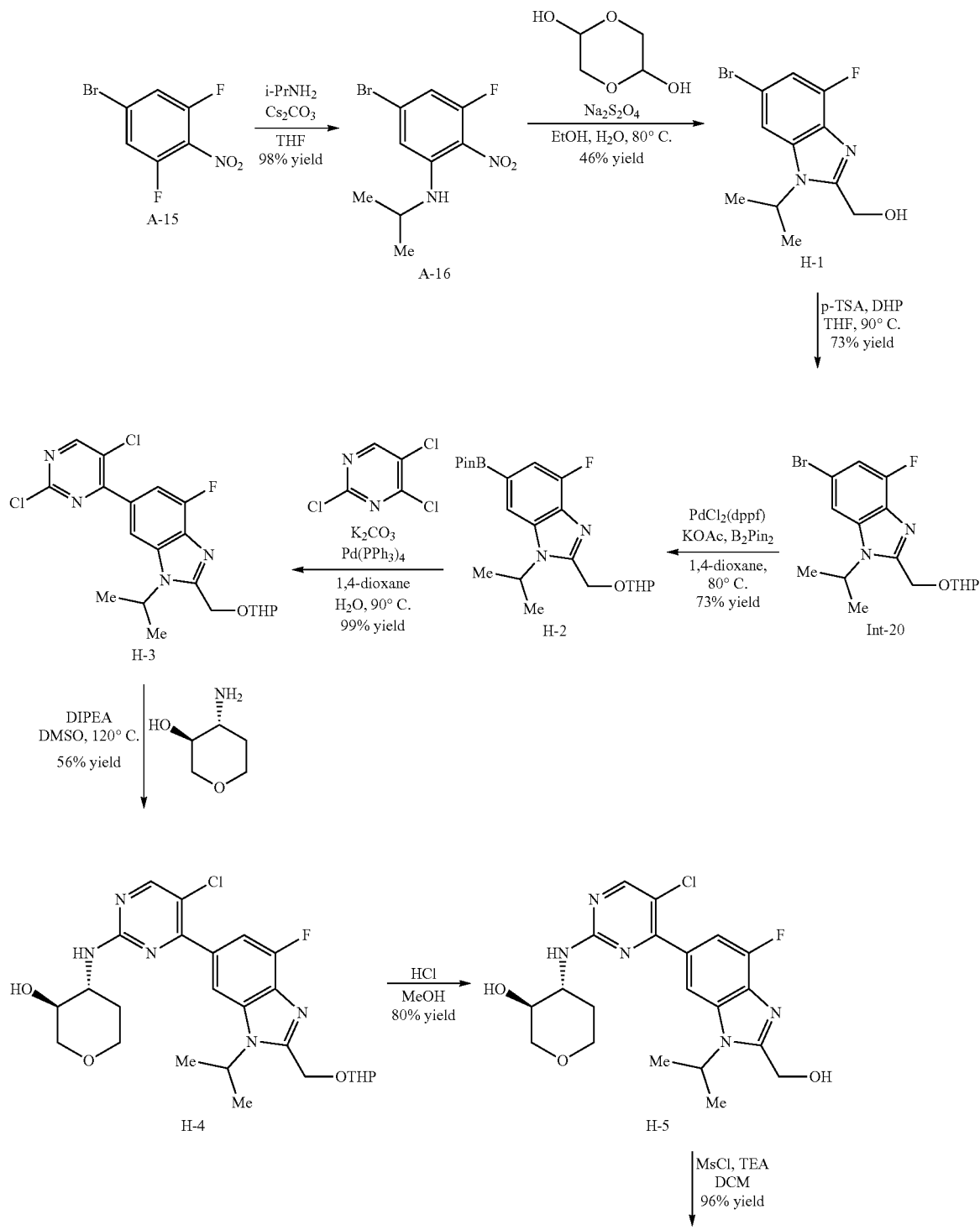

Scheme H-1

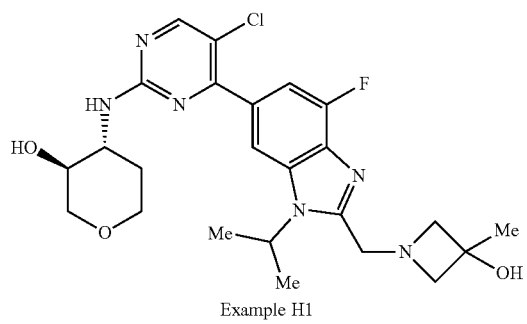

Example H1

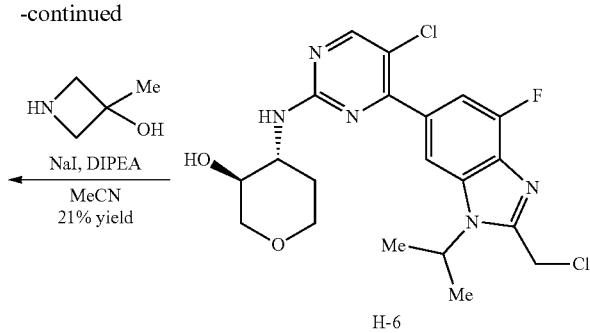

H-6

Step 1: Synthesis of 5-bromo-3-fluoro-2-nitro-N-(propan-2-yl)aniline (A-16)

To a solution of 5-bromo-1,3-difluoro-2-nitrobenzene (A-15) (35.0 g, 147 mmol) in THF (700 mL) was added i-PrNH$_2$ (8.7 g, 147 mmol) and Cs$_2$CO$_3$ (57.5 g, 176 mmol). The mixture was stirred at room temperature for 16 h. LCMS analysis showed consumption of the starting material with formation of the desired product mass. The reaction was diluted with H$_2$O (300 mL) and extracted with EtOAc (3×300 mL). The combined organic layers were washed with brine, dried over Na$_2$SO$_4$, filtered, and concentrated to provide 5-bromo-3-fluoro-2-nitro-N-(propan-2-yl)aniline (A-16) (40.0 g, 98% yield) as a red solid. $^1$H NMR (400 MHz, DMSO-d$_6$) δ 7.09-6.98 (m, 2H), 6.89 (dd, J=1.9, 11.1 Hz, 1H), 6.17 (s, 1H), 3.88 (br d, J=7.5 Hz, 1H), 1.19 (d, J=6.4 Hz, 6H); m/z (ESI+) for (C$_9$H$_{10}$BrFN$_2$O$_2$), 276.7 (M+H)$^+$.

Step 2: Synthesis of [6-bromo-4-fluoro-1-(propan-2-yl)-1H-benzimidazol-2-yl]methanol (H-1)

To a solution of 5-bromo-3-fluoro-2-nitro-N-(propan-2-yl)aniline (A-16) (40.0 g, 144 mmol) in EtOH/H$_2$O (4:1, 700 mL) was added 1,4-dioxane-2,5-diol (20.8 g, 173 mmol) and Na$_2$S2O4 (126 g, 722 mmol). The mixture was stirred at reflux for 80° C. for 16 h. LCMS analysis showed consumption of the starting material with formation of the desired product mass. The mixture was diluted with H$_2$O (100 mL) and extracted with EtOAc (3×300 mL). The combined organic layers were washed with saturated aqueous NaHCO$_3$, dried over Na$_2$SO$_4$, filtered, and concentrated. The crude residue was purified by flash chromatography (SiO$_2$, 0-100% EtOAc/petroleum ether) to provide [6-bromo-4-fluoro-1-(propan-2-yl)-1H-benzimidazol-2-yl]methanol (H-1) (19.0 g, 46% yield) as a white solid. $^1$H NMR (400 MHz, CD$_3$OD) δ 7.81 (d, J=1.5 Hz, 1H), 7.28 (dd, J=1.5, 10.0 Hz, 1H), 5.72 (t, J=5.8 Hz, 1H), 5.01-4.87 (m, 1H), 4.72 (d, J=5.5 Hz, 2H), 1.56 (d, J=6.8 Hz, 6H); m/z (ESI+) for (CH$_{12}$BrFN$_2$O), 286.8 (M+H)$^+$.

Step 3: Synthesis of 6-bromo-4-fluoro-2-{[(oxan-2-yl)oxy]methyl}-1-(propan-2-yl)-1H-benzimidazole (Int-20)

To a solution of [6-bromo-4-fluoro-1-(propan-2-yl)-1H-benzimidazol-2-yl]methanol (H-1) (19.0 g, 66.2 mmol) in THF (250 mL) was added p-TSA (1.7 g, 6.62 mmol) and DHP (22.3 g, 265 mmol). The mixture was stirred at 90° C. for 4 h. LCMS analysis showed consumption of the starting material with formation of the desired product mass. The reaction was diluted with H$_2$O (100 mL) and extracted with EtOAc (3×150 mL). The combined organic layers were dried over Na$_2$SO$_4$, filtered, and concentrated. The residue was purified by flash chromatography (SiO$_2$, 0-100% EtOAc/petroleum ether) to provide 6-bromo-4-fluoro-2-{[(oxan-2-yl)oxy]methyl}-1-(propan-2-yl)-1H-benzimidazole (Int-20) (18.0 g, 73% yield) as a pale yellow solid. $^1$H NMR (400 MHz, DMSO-d$_6$) δ 7.85 (d, J=1.5 Hz, 1H), 7.31 (dd, J=1.5, 10.1 Hz, 1H), 4.97-4.84 (m, 2H), 4.78-4.68 (m, 2H), 3.83-3.71 (m, 1H), 3.57-3.46 (m, 1H), 1.72-1.63 (m, 2H), 1.57 (d, J=6.8 Hz, 6H), 1.53-1.46 (m, 4H); m/z (ESI+) for (C$_{16}$H$_2$BrFN$_2$O$_2$), 372.6 (M+H)$^+$.

Step 4: Synthesis of 4-fluoro-2-{[(oxan-2-yl)oxy]methyl}-1-(propan-2-yl)-6-(4,4,5,5-tetramethyl-1,3,2-dioxaborolan-2-yl)-1H-benzimidazole (H-2)

To a suspension of 6-bromo-4-fluoro-2-{[(oxan-2-yl)oxy]methyl}-1-(propan-2-yl)-1H-benzimidazole (H-2) (8.0 g, 21.6 mmol), B$_2$Pin$_2$ (6.6 g, 25.9 mmol), and KOAc (6.3 g, 64.6 mmol) in 1,4-dioxane (160 mL) was added PdCl$_2$(dppf) (0.788 g, 1.08 mmol) under N$_2$. The mixture was stirred at 80° C. under N$_2$ for 16 h. LCMS analysis indicated consumption of the starting material with formation of the desired product mass. The mixture was cooled to room temperature, filtered through celite, and concentrated to dryness. The residue was taken up in H$_2$O (150 mL) and extracted with EtOAc (3×150 mL). The combined organics were washed with brine, dried over Na$_2$SO$_4$, filtered, and concentrated. The residue was purified by flash chromatography (360 g SiO$_2$, 0-100% EtOAc/petroleum ether) to provide 4-fluoro-2-{[(oxan-2-yl)oxy]methyl}-1-(propan-2-yl)-6-(4,4,5,5-tetramethyl-1,3,2-dioxaborolan-2-yl)-1H-benzimidazole (H-2) (9.4 g, 73% yield) as a yellow solution. m/z (ESI+) for (C$_{22}$H$_{32}$BFN$_2$O$_4$), 419.1 (M+H)$^+$.

Step 5: Synthesis of 6-(2,5-dichloropyrimidin-4-yl)-4-fluoro-2-{[(oxan-2-yl)oxy]methyl}-1-(propan-2-yl)-1H-benzimidazole (H-3)

A mixture of 4-fluoro-2-{[(oxan-2-yl)oxy]methyl}-1-(propan-2-yl)-6-(4,4,5,5-tetramethyl-1,3,2-dioxaborolan-2-yl)-1H-benzimidazole (H-2) (6.0 g, 14.3 mmol), 2,4,5-trichloropyrimidine (3.95 g, 21.5 mmol), and K$_2$CO$_3$ (3.96 g, 28.7 mmol) in 1,4-dioxane (90 mL) and H$_2$O (30 mL) was degassed with N$_2$ for 5 min. Pd(PPh$_3$)$_4$ (829 mg, 0.717 mmol) was added and the mixture was degassed for an additional 10 min. The reaction was stirred at 90° C. under N$_2$ for 16 h. LCMS analysis showed consumption of the starting material with formation of the desired product mass.

The reaction was cooled to room temperature, diluted with H₂O (30 mL), and extracted with EtOAc (3×100 mL). The combined organic layers were washed with brine, dried over Na₂SO₄, filtered, and concentrated. The residue was purified by flash chromatography (40 g SiO₂, 0-60% EtOAc/petroleum ether) to provide 6-(2,5-dichloropyrimidin-4-yl)-4-fluoro-2-{[(oxan-2-yl)oxy]methyl}-1-(propan-2-yl)-1H-benzimidazole (H-3) (7.4 g, 99% yield) as a white solid. m/z (ESI+) for ($C_{22}H_{32}BFN_2O_4$), 461.0 (M+H)⁺.

Step 6: Synthesis of 1,5-anhydro-3-({5-chloro-4-[4-fluoro-2-{[(oxan-2-yl)oxy]methyl}-1-(propan-2-yl)-1H-benzimidazol-6-yl]pyrimidin-2-yl}amino)-2,3-dideoxy-D-threo-pentitol (H-4)

To a solution of 6-(2,5-dichloropyrimidin-4-yl)-4-fluoro-2-{[(oxan-2-yl)oxy]methyl}-1-(propan-2-yl)-1H-benzimidazole (H-3) (2.3 g, 19.8 mmol) in DMSO (150 mL) was added DIPEA (10.6 g, 82.4 mmol) and 3-amino-1,5-anhydro-2,3-dideoxy-D-threo-pentitol (7.2 g, 16.5 mmol). The mixture was stirred at 120° C. for 16 h. LCMS analysis showed consumption of the starting material with formation of the desired product mass. The reaction solution was diluted with H₂O (200 mL) and extracted with EtOAc (3×200 mL). The combined organic layers were washed with brine, dried over Na₂SO₄, filtered, and concentrated. The residue was purified by flash chromatography (360 g SiO₂, 0-10% MeOH/DCM) to provide 1,5-anhydro-3-({5-chloro-4-[4-fluoro-2-{[(oxan-2-yl)oxy]methyl}-1-(propan-2-yl)-1H-benzimidazol-6-yl]pyrimidin-2-yl}amino)-2,3-dideoxy-D-threo-pentitol (H-4) (4.8 g, 56% yield) as a yellow solid. m/z (ESI+) for ($C_{25}H_{31}ClFN_5O_4$), 520.1 (M+H)⁺.

Step 7: Synthesis of 1,5-anhydro-3-({5-chloro-4-[4-fluoro-2-(hydroxymethyl)-1-(propan-2-yl)-1H-benzimidazol-6-yl]pyrimidin-2-yl}amino)-2,3-dideoxy-D-threo-pentitol (H-5)

To a solution of 1,5-anhydro-3-({5-chloro-4-[4-fluoro-2-{[(oxan-2-yl)oxy]methyl}-1-(propan-2-yl)-1H-benzimidazol-6-yl]pyrimidin-2-yl}amino)-2,3-dideoxy-D-threo-pentitol (H-4) (4.7 g, 9.2 mmol) in MeOH (40.0 mL) was added a solution of HCl (4 N in 1,4-dioxane, 10.0 mL) dropwise at 0° C. The solution was stirred at 20° C. for 1 h. LCMS analysis showed consumption of the starting material with formation of the desired product mass. The reaction mixture was concentrated to dryness. The residue was purified by flash chromatography (80 g SiO₂, 1:10 MeOH/DCM) to provide 1,5-anhydro-3-({5-chloro-4-[4-fluoro-2-(hydroxymethyl)-1-(propan-2-yl)-1H-benzimidazol-6-yl]pyrimidin-2-yl}amino)-2,3-dideoxy-D-threo-pentitol (H-5) (3.2 g, 80% yield) as a yellow oil. ¹H NMR (400 MHz, CD₃OD) δ 1.77-1.78 (m, 1H) 1.80 (dd, J=6.90, 2.89 Hz, 5H) 2.06-2.16 (m, 1H) 3.18-3.27 (m, 1H) 3.44-3.54 (m, 1H) 3.65 (s, 1H) 3.99 (br dd, J=11.29, 5.02 Hz, 3H) 5.07 (s, 2H) 5.21 (s, 2H) 7.92 (d, J=11.04 Hz, 1H) 8.36 (s, 1H) 8.49 (s, 1H); m/z (ESI+) for ($C_{20}H_{23}ClFN_5O_3$), 436.2 (M+H)⁺.

Step 8: Synthesis of 1,5-anhydro-3-({5-chloro-4-[2-(chloromethyl)-4-fluoro-1-(propan-2-yl)-1H-benzimidazol-6-yl]pyrimidin-2-yl}amino)-2,3-dideoxy-D-threo-pentitol (H-6)

To a solution of 1,5-anhydro-3-({5-chloro-4-[4-fluoro-2-(hydroxymethyl)-1-(propan-2-yl)-1H-benzimidazol-6-yl]pyrimidin-2-yl}amino)-2,3-dideoxy-D-threo-pentitol (H-5) (800 mg, 1.8 mmol) in DCM (10 mL) was added TEA (557 mg, 5.5 mmol). The mixture was cooled to 0° C. and treated with methanesulfonyl chloride (328 mg, 2.2 mmol) dropwise. The mixture was stirred at ambient temperature for 3 h. LCMS analysis showed consumption of the starting material. Reaction was washed with H₂O. The aqueous layer was extracted with DCM (3×10 mL). The combined organics were washed with brine, dried over Na₂SO₄, filtered, and concentrated to provide 1,5-anhydro-3-({5-chloro-4-[2-(chloromethyl)-4-fluoro-1-(propan-2-yl)-1H-benzimidazol-6-yl]pyrimidin-2-yl}amino)-2,3-dideoxy-D-threo-pentitol (H-6) (800 mg, 96% yield), which was taken on without further purification. m/z (ESI+) for ($C_{20}H_{22}Cl_2FN_5O_2$), 454.1 (M+H)⁺.

Step 9: Synthesis of 1,5-anhydro-3-[(5-chloro-4-{4-fluoro-2-[(3-hydroxy-3-methylazetidin-1-yl)methyl]-1-(propan-2-yl)-1H-benzimidazol-6-yl}pyrimidin-2-yl)amino]-2,3-dideoxy-D-threo-pentitol (Example H1)

To a solution of 1,5-anhydro-3-({5-chloro-4-[2-(chloromethyl)-4-fluoro-1-(propan-2-yl)-1H-benzimidazol-6-yl]pyrimidin-2-yl}amino)-2,3-dideoxy-D-threo-pentitol (H-6) (100 mg, 0.22 mmol) in MeCN (2.0 mL) was added 3-methylazetidin-3-ol (19.2 mg, 0.22 mmol), NaI (33.0 mg, 0.22 mmol) and DIPEA (142 mg, 1.1 mmol). The mixture was stirred under an atmosphere of N₂ at 25° C. for 3 h. LCMS analysis showed consumption of the starting material with formation of the desired product mass. The reaction solution was washed with H₂O (5 mL). The aqueous layer was extracted with DCM (3×5 mL). The combined organic layers were washed with brine (10 mL), dried over Na₂SO₄, filtered, and concentrated. The crude residue was purified by preparative HPLC with a YMC Triart column (30×150 mm, 7 μm particle size), which was eluted with 30-50% MeCN/H₂O (+0.05% NH₄OH) with a flow rate of 25 mL/min to provide 1,5-anhydro-3-[(5-chloro-4-{4-fluoro-2-[(3-hydroxy-3-methylazetidin-1-yl)methyl]-1-(propan-2-yl)-1H-benzimidazol-6-yl}pyrimidin-2-yl)amino]-2,3-dideoxy-D-threo-pentitol (Example H1) (23.5 mg, 21% yield) as a white solid. ¹H NMR (400 MHz, CD₃OD) δ 8.35 (s, 1H), 8.02 (s, 1H), 7.49 (d, J=11.4 Hz, 1H), 5.16 (app p, J=7.0 Hz, 1H), 4.03-3.87 (m, 5H), 3.61 (dt, J=4.8, 9.4 Hz, 1H), 3.48 (dt, J=2.2, 11.7 Hz, 1H), 3.30-3.27 (m, 2H), 3.24-3.19 (m, 1H), 3.18-3.14 (m, 2H), 2.19-2.08 (m, 1H), 1.68 (d, J=6.8 Hz, 6H), 1.67-1.59 (m, 1H), 1.46 (s, 3H); m/z (ESI+) for ($C_{24}H_{30}ClFN_6O_3$), 505.2 (M+H)⁺.

The examples in the below table were synthesized according to the methods used for the synthesis of 1,5-anhydro-3-({5-chloro-4-[2-(chloromethyl)-4-fluoro-1-(propan-2-yl)-1H-benzimidazol-6-yl]pyrimidin-2-yl}amino)-2,3-dideoxy-D-threo-pentitol (Example H1). The following examples were synthesized with non-critical changes or substitutions to the exemplified procedures that someone who is skilled in the art would be able to realize.

| Example number | Structure/Name | LCMS | NMR |
|---|---|---|---|
| H2 | 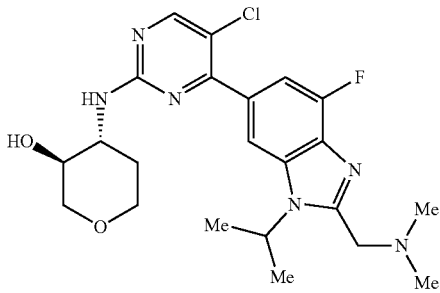 [SMILES: CC(C)n1c(CN(C)C)nc2c(F)cc(-c3nc(N[C@@H]4CCOC[C@H]4O)ncc3Cl)cc21]<br>1,5-anhydro-3-[(5-chloro-4-{2-[(dimethylamino)methyl]-4-fluoro-1-(propan-2-yl)-1H-benzimidazol-6-yl}pyrimidin-2-yl)amino]-2,3-dideoxy-D-threo-pentitol | 463.1 [M + H]+ (ESI) | $^1$H NMR (400 MHz, CD$_3$OD) δ 8.37 (s, 1H) 8.06 (s, 1H) 7.52 (d, J = 11.5 Hz, 1H) 5.25-5.18 (m, 1H) 3.88-4.06 (m, 3H) 3.80 (s, 2H) 3.63 (m, 1H) 3.36-3.54 (m, 1H) 3.16-3.29 (m, 1H) 2.31 (s, 6H) 2.03-2.20 (m, 1H) 1.69 (d, J = 7.0 Hz, 6H) 1.58-1.67 (m, 1H) |
| H3 | 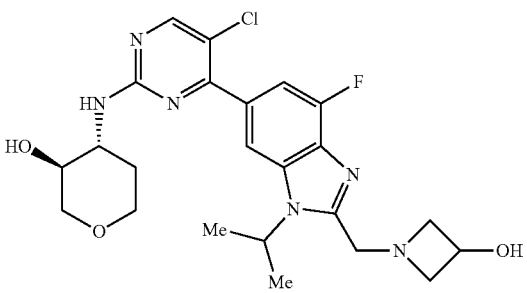 [SMILES: CC(C)n1c(CN2CC(O)C2)nc2c(F)cc(-c3nc(N[C@@H]4CCOC[C@H]4O)ncc3Cl)cc21]<br>1,5-anhydro-3-[(5-chloro-4-{4-fluoro-2-[(3-hydroxyazetidin-1-yl)methyl]-1-(propan-2-yl)-1H-benzimidazol-6-yl}pyrimidin-2-yl)amino]-2,3-dideoxy-D-threo-pentitol | 491.1 [M + H]+ (ESI) | $^1$H NMR (400 MHz, CD$_3$OD) δ 8.35 (s, 1H), 8.02 (s, 1H), 7.49 (d, J = 11.4 Hz, 1H), 5.16-5.06 (m, 1H), 4.35 (t, J = 6.2 Hz, 1H), 4.01-3.89 (m, 5H), 3.66-3.57 (m, 3H), 3.48 (dt, J = 2.1, 11.7 Hz, 1H), 3.20 (dd, J = 9.7, 11.1 Hz, 1H), 3.11-3.05 (m, 2H), 2.18-2.09 (m, 1H), 1.68 (d, J = 7.0 Hz, 6H), 1.66-1.58 (m, 1H) |
| H4 | 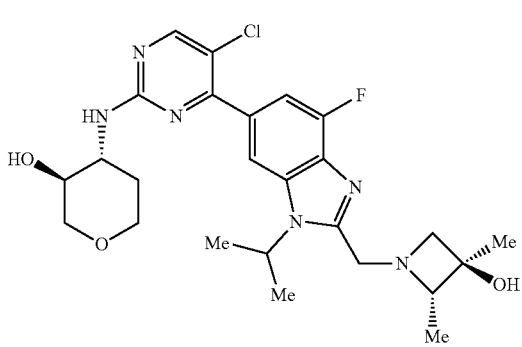 [SMILES: CC(C)n1c(CN2C[C@@](C)(O)[C@@H]2C)nc2c(F)cc(-c3nc(N[C@@H]4CCOC[C@H]4O)ncc3Cl)cc21]<br>1,5-anhydro-3-({5-chloro-4-[4-fluoro-2-{[(2S,3R)-3-hydroxy-2,3-dimethylazetidin-1-yl]methyl}-1-(propan-2-yl)-1H-benzimidazol-6-yl]pyrimidin-2-yl}amino)-2,3-dideoxy-D-threo-pentitol | 519.3 [M + H]+ (ESI) | $^1$H NMR (400 MHz, CD$_3$OD) δ 8.35 (s, 1H), 8.03 (s, 1H), 7.50 (d, J = 11.6 Hz, 1H), 5.19-5.10 (m, 1H), 4.04-3.89 (m, 5H), 3.61 (dt, J = 4.7, 9.4 Hz, 1H), 3.48 (dt, J = 2.3, 11.7 Hz, 1H), 3.25-3.17 (m, 3H), 2.97 (d, J = 6.7 Hz, 1H), 2.13 (td, J = 2.3, 13.2 Hz, 1H), 1.69 (dd, J = 6.9, 12.9 Hz, 7H), 1.28 (s, 3H), 0.88 (d, J = 6.2 Hz, 3H) |

| Example number | Structure/Name | LCMS | NMR |
|---|---|---|---|
| H5 | 1,5-anhydro-3-({5-chloro-4-[4-fluoro-2-{[(oxetan-3-yl)amino]methyl}-1-(propan-2-yl)-1H-benzimidazol-6-yl]pyrimidin-2-yl}amino)-2,3-dideoxy-D-threo-pentitol | 491.2 [M + H]+ (ESI) | $^1$H NMR (400 MHz, CD$_3$OD) δ 8.37 (s, 1H) 8.06 (s, 1H) 7.52 (d, J = 11.8 Hz, 1H) 5.08-5.16 (m, 1H) 4.80 (m, 2H) 4.46 (m, 2H) 4.11 (s, 2H) 3.90-4.08 (m, 4H) 3.63 (m, 1H) 3.50 (m, 1H) 3.19-3.26 (m, 1H) 2.13 (m, 1H) 1.72 (d, J = 6.7 Hz, 6H), 1.69-1.61 (m, 2H) |
| H6 | 1,5-anhydro-3-[(5-chloro-4-{4-fluoro-2-[(3-fluoroazetidin-1-yl)methyl]-1-(propan-2-yl)-1H-benzimidazol-6-yl}pyrimidin-2-yl)amino]-2,3-dideoxy-D-threo-pentitol | 493.2 [M + H]+ (ESI) | $^1$H NMR (400 MHz, CD$_3$OD) δ 8.35 (s, 1H), 8.03 (s, 1H), 7.49 (d, J = 11.5 Hz, 1H), 5.25-5.04 (m, 2H), 4.01 (s, 2H), 4.00-3.87 (m, 3H), 3.74-3.56 (m, 3H), 3.53-3.44 (m, 1H), 3.43-3.37 (m, 1H), 3.37-3.32 (m, 1H), 3.20 (dd, J = 9.7, 11.1 Hz, 1H), 2.18-2.09 (m, 1H), 1.68 (d, J = 6.8 Hz, 6H), 1.66-1.58 (m, 1H) |
| H7 | 1,5-anhydro-3-[(4-{2-[(azetidin-1-yl)methyl]-4-fluoro-1-(propan-2-yl)-1H-benzimidazol-6-yl}-5-chloropyrimidin-2-yl)amino]-2,3-dideoxy-D-threo-pentitol | 475.2 [M + H]+ (ESI) | $^1$H NMR (400 MHz, CD$_3$OD) δ 8.35 (s, 1H), 8.03 (s, 1H), 7.49 (d, J = 11.4 Hz, 1H), 5.15-5.07 (m, 1H), 4.01-3.89 (m, 5H), 3.61 (br d, J = 4.8 Hz, 1H), 3.52-3.44 (m, 1H), 3.35 (t, J = 7.0 Hz, 4H), 3.20 (dd, J = 9.7, 11.1 Hz, 1H), 2.16-2.08 (m, 3H), 1.69 (d, J = 7.0 Hz, 6H), 1.67-1.60 (m, 1H) |

Example H8 (Scheme H-2): 1,5-anhydro-3-({5-chloro-4-[4-fluoro-1-(propan-2-y)-2-{[(propan-2-yl)amino]methyl}-1H-benzimidazol-6-yl]pyrimidin-2-yl}amino)-2,3-dideoxy-D-threo-pentitol

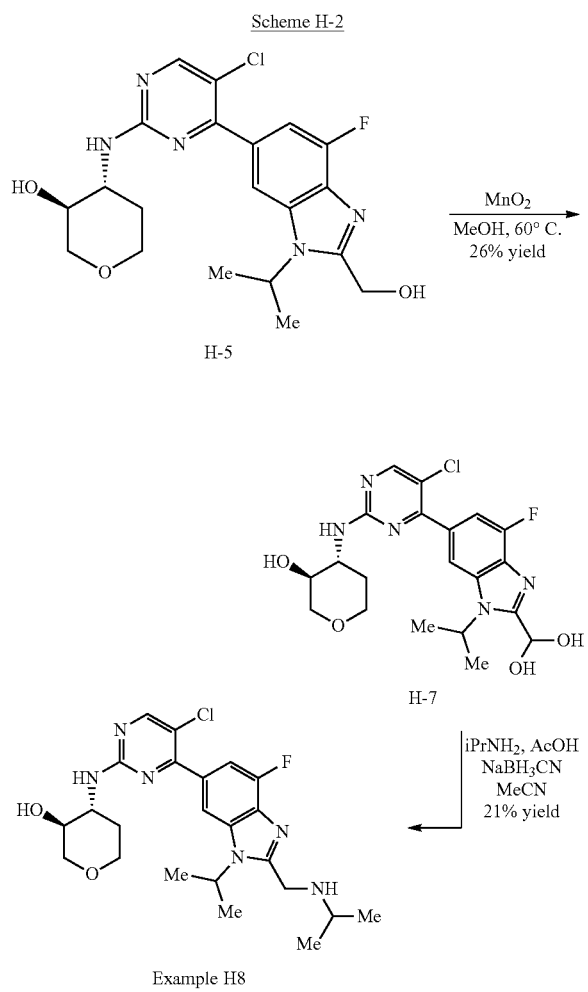

Step 1: Synthesis of 1,5-anhydro-3-({5-chloro-4-[2-(dihydroxymethyl)-4-fluoro-1-(propan-2-yl)-1H-benzimidazol-6-yl]pyrimidin-2-yl}amino)-2,3-dideoxy-D-threo-pentitol (H-7)

A mixture (3R,4R)-4-({5-chloro-4-[4-fluoro-2-(hydroxymethyl)-1-(propan-2-yl)-1H-benzimidazol-6-yl]pyrimidin-2-yl}amino)-1-(methanesulfonyl)piperidin-3-ol (H-5) (900 mg, 2.1 mmol) and MnO$_2$ (2.7 g, 31 mmol in MeOH (20.0 mL) was stirred at 60° C. for 16 h. LCMS analysis showed consumption of the starting material. The reaction was filtered and the filter cake was washed with MeOH (20 mL). The filtrate was concentrated to dryness. The residue was purified by flash chromatography (ISCO, 20 g SiO$_2$, 1:10 MeOH/DCM) to provide 1,5-anhydro-3-({5-chloro-4-[2-(dihydroxymethyl)-4-fluoro-1-(propan-2-yl)-1H-benzimidazol-6-yl]pyrimidin-2-yl}amino)-2,3-dideoxy-D-threo-pentitol (H-7) (162 mg, 26% yield) as a colorless oil. $^1$H NMR (400 MHz, CD$_3$OD) δ 1.69 (t, J=5.77 Hz, 7H) 2.00-2.23 (m, 1H) 3.18-3.26 (m, 1H) 3.50 (br d, J=2.26 Hz, 1H) 3.63 (td, J=9.29, 5.02 Hz, 1H) 3.98 (br. dd, J=11.29, 4.52 Hz, 3H) 5.44-5.53 (m, 1H) 5.88 (s, 1H) 7.53 (br d, J=11.54 Hz, 1H) 8.07 (s, 1H) 8.37 (s, 1H); m/z (ESI+) for (C$_{20}$H$_{23}$ClFN$_5$O$_4$), 452.2 (M+H)$^+$.

Step 2: Synthesis of 1,5-anhydro-3-({5-chloro-4-[4-fluoro-1-(propan-2-yl)-2-{[(propan-2-yl)amino]methyl}-1H-benzimidazol-6-yl]pyrimidin-2-yl}amino)-2,3-dideoxy-D-threo-pentitol (Example H8)

To a solution 1,5-anhydro-3-({5-chloro-4-[2-(dihydroxymethyl)-4-fluoro-1-(propan-2-yl)-1H-benzimidazol-6-yl]pyrimidin-2-yl}amino)-2,3-dideoxy-D-threo-pentitol (H-7) (50 mg, 0.11 mmol) and i-PrNH$_2$ (12.7 mg, 0.215 mmol) in MeOH (5.0 mL) was added AcOH (6.4 mg, 0.107 mmol). After stirring for 2 h at ambient temperature NaBH$_3$CN (13.5, 0.215 mmol) was added and the mixture was stirred for 16 h overnight. LCMS analysis showed consumption of the starting material with formation of the desired product mass. The reaction was poured into a solution aqueous Na$_2$CO$_3$ (1.0 M, 5 mL) and extracted with DCM (3×5 mL). The combined organic layers were washed with brine (15 mL), dried over Na$_2$SO$_4$, filtered, and concentrated. The residue was purified by preparative HPLC with an Xtimate C18 column (250×80 mm, 10 μm particle size), which was eluted with 35-55% MeCN/H$_2$O (+0.05% NH$_4$OH) with a flow rate of 25 mL/min to provide 1,5-anhydro-3-({5-chloro-4-[4-fluoro-1-(propan-2-yl)-2-{[(propan-2-yl)amino]methyl}-1H-benzimidazol-6-yl]pyrimidin-2-yl}amino)-2,3-dideoxy-D-threo-pentitol (Example H8) (10.9 mg, 21% yield) as a white solid. $^1$H NMR (400 MHz, CD$_3$OD) δ 8.37 (s, 1H) 8.05 (s, 1H) 7.51 (d, J=11.8 Hz, 1H) 5.05-5.17 (m, 1H) 4.15 (s, 2H) 3.90-4.03 (m, 3H) 3.64 (m, 1H) 3.50 (m, 1H) 3.13-3.26 (m, 1H) 2.85-2.95 (m, 1H) 2.15 (m, 1H) 1.71 (d, J=7.0 Hz, 6H) 1.66 (m, 1H) 1.16 (d, J=6.2 Hz, 6H); m/z (ESI+) for (C$_{23}$H$_{30}$ClFN$_6$O$_2$), 477.1 (M+H)$^+$.

The examples in the below table was synthesized according to the methods used for the synthesis of 1,5-anhydro-3-({5-chloro-4-[4-fluoro-1-(propan-2-yl)-2-{[(propan-2-yl)amino]methyl}-1H-benzimidazol-6-yl]pyrimidin-2-yl}amino)-2,3-dideoxy-D-threo-pentitol (Example H8). The following example was synthesized with non-critical changes or substitutions to the exemplified procedures that someone who is skilled in the art would be able to realize.

| Example number | Structure/Name | LCMS | NMR |
|---|---|---|---|
| H9 | (3R,4R)-4-({5-chloro-4-[4-fluoro-2-{[(oxetan-3-yl)amino]methyl}-1-(propan-2-yl)-1H-benzimidazol-6-yl]pyrimidin-2-yl}amino)-1-(methanesulfonyl)piperidin-3-ol | 568.1 [M + H]+ (APCI) | $^1$H NMR (700 MHz, DMSO-$d_6$) δ 8.43 (s, 1H), 8.09-7.68 (m, 1H), 7.44 (d, J = 35.3 Hz, 1H), 5.01 (p, J = 6.8 Hz, 1H), 4.59 (t, J = 6.6 Hz, 2H), 4.35-4.26 (m, 2H), 4.00 (s, 2H), 3.92 (d, J = 11.1 Hz, 1H), 3.85-3.74 (m, 2H), 3.66-3.57 (m, 6H), 2.89 (s, 3H), 1.59 (d, J = 6.8 Hz, 6H) |
| H10 | (3R,4R)-4-({5-chloro-4-[4-fluoro-1-(propan-2-yl)-2-{[(propan-2-yl)amino]methyl}-1H-benzimidazol-6-yl]pyrimidin-2-yl}amino)-1-(methanesulfonyl)piperidin-3-ol | 553.9 [M + H]+ (APCI) | $^1$H NMR (600 MHz, DMSO-$d_6$) δ 7.96 (s, 1H), 7.62-7.39 (m, 1H), 7.09-6.82 (m, 2H), 4.88-4.67 (m, 1H), 4.65-4.48 (m, 1H), 3.58 (s, 2H), 3.34 (d, J = 6.1 Hz, 1H), 3.15 (d, J = 10.1 Hz, 1H), 2.46-2.37 (m, 4H), 2.31-2.25 (m, 1H), 2.19 (t, J = 10.4 Hz, 1H), 1.63-1.55 (m, 1H), 1.41 (br. s., 3H), 1.13 (d, J = 7.0 Hz, 6H), 1.10-1.01 (m, 1H), 0.56 (d, J = 6.2 Hz, 6H) |
| H11 | 1,5-anhydro-3-[(5-chloro-4-[(cyclopropylamino)methyl]-4-fluoro-1-(propan-2-yl)-1H-benzimidazol-6-yl}pyrimidin-2-yl)amino]-2,3-dideoxy-D-threo-pentitol | 475.3 [M + H]+ (ESI) | $^1$H NMR (400 MHz, CD$_3$OD) δ 8.37 (s, 1H), 8.05 (s, 1H), 7.51 (d, J = 11.54 Hz, 1H), 5.07 (dt, J = 13.93, 6.84 Hz, 1H), 4.19 (s, 2H), 3.90-4.03 (m, 3H), 3.63 (td, J = 9.41, 4.77 Hz, 1H), 3.50 (td, J = 11.67, 2.01 Hz, 1H), 3.22 (dd, J = 11.04, 9.79 Hz, 1H), 2.26 (dt, J = 6.71, 3.29 Hz, 1H), 2.12-2.18 (m, 1H), 1.69 (d, J = 7.03 Hz, 6H), 1.60-1.68 (m, 1H), 0.45-0.51 (m, 2H), 0.31-0.36 (m, 2H) |

Biological Assays and Data
CDK4/Cyclin D1 Mobility Shift Assay

The purpose CDK4/Cyclin D1 assay is to evaluate the inhibition (% inhibition, $K_{iapp}$ and $K_i$ values) in the presence of small molecule inhibitors by using a fluorescence based microfluidic mobility shift assay. CDK4/Cyclin D1 catalyzes the production of ADP from ATP that accompanies the phosphoryl transfer to the substrate peptide 5-FAM-Dyrktide (5-FAM-RRRFRPASPLRGPPK) (SEQ ID NO:1). The mobility shift assay electrophoretically separates the fluorescently labeled peptides (substrate and phosphorylated product) following the kinase reaction. Both substrate and product are measured and the ratio of these values is used to generate % Conversion of substrate to product by the LabChip EZ Reader. Typical reaction solutions contained 2% DMSO (±inhibitor), 10 mM MgCl$_2$, 1 mM DTT, 3.5 mM ATP, 0.005% TW-20, 3 µM 5-FAM-Dyrktide, 3 nM (active sites) activated CDK4/Cyclin D1 in 40 mM HEPES buffer at pH 7.5.

Inhibitor $K_i$ determinations for activated CDK4/Cyclin D1 (2007 E1/2008+PO$_4$) were initiated with the addition of ATP (50 µL final reaction volume), following a eighteen minute pre-incubation of enzyme and inhibitor at 22° C. in the reaction mix. The reaction was stopped after 195 minutes by the addition of 50 µL of 30 mM EDTA. $K_i$ determinations were made from a plot of the fractional velocity as a function of inhibitor concentration fit to the Morrison equation with the enzyme concentration as a variable.

CDK6/Cyclin D3 Mobility Shift Assay

The purpose of the CDK6/Cyclin D3 assay is to evaluate the inhibition (% inhibition, $K_{iapp}$ and $K_i$ values) in the presence of small molecule inhibitors by using a fluorescence based microfluidic mobility shift assay. CDK6/Cyclin D3 catalyzes the production of ADP from ATP that accompanies the phosphoryl transfer to the substrate peptide 5-FAM-Dyrktide (5-FAM-RRRFRPASPLRGPPK) (SEQ ID NO:1). The mobility shift assay electrophoretically separates the fluorescently labeled peptides (substrate and phosphorylated product) following the kinase reaction. Both substrate and product are measured and the ratio of these values is used to generate % conversion of substrate to product by the LabChip EZ Reader. Typical reaction solutions contained 2% DMSO (±inhibitor), 2% glycerol, 10 mM MgCl$_2$, 1 mM DTT, 3.5 mM ATP, 0.005% Tween 20 (TW-20), 3 µM 5-FAM-Dyrktide, 4 nM (active sites) activated CDK6/Cyclin D3 in 40 mM HEPES buffer at pH 7.5.

Inhibitor $K_i$ determinations for activated CDK6/Cyclin D3 (LJIC-2009G1/2010+PO$_4$) were initiated with the addition of ATP (50 µL final reaction volume), following a eighteen minute pre-incubation of enzyme and inhibitor at 22° C. in the reaction mix. The reaction was stopped after 95 minutes by the addition of 50 µL of 30 mM EDTA. $K_i$ determinations were made from a plot of the fractional velocity as a function of inhibitor concentration fit to the Morrison equation with the enzyme concentration as a variable.

For CDK4 and CDK6 mobility shift assays, see also Morrison, J. F. (1969) Kinetics of the reversible inhibition of enzyme-catalysed reactions by tight-binding inhibitors, *Biochimica et biophysica acta* 185, 269-286; and Murphy, D. J. (2004) Determination of accurate KI values for tight-binding enzyme inhibitors: an in silico study of experimental error and assay design, *Analytical biochemistry* 327, 61-67.

Phospho-Serine 795 Rb ELISA Assays

JEKO-1 or MV4-11 cells were seeded at 15,000 or 20,000 cells per well, respectively, in 100 µL growth media and allowed to incubate at 37° C. with 5% CO$_2$ overnight. The following day, compounds were serially diluted from a 10 mM top dose for an 11-point 3-fold dilution curve in DMSO. Compounds were intermediately diluted 1:200 into growth media prior to diluting 1:5 on cells for final concentration 10 µM to 0.1 nM in 0.1% DMSO on cells. JEKO-1 and MV4-11 cells were treated were treated overnight, at 37° C. with 5% CO$_2$. Cells were lysed in 100 µL/well CST lysis buffer on ice and transferred to pre-coated and blocked anti-phospho-Ser795 Rb ELISA plates for overnight incubation at 4° C. Plates were washed to remove residual, unbound cellular proteins and total Rb detection antibody added for 90 minutes at 37° C. Following wash to remove unbound total Rb antibody, the HRP tagged antibody was allowed to bind for 30 minutes at 37° C. Following wash to remove unbound HRP antibody, Glo Substrate Reagent was added and incubated protected from light for 5 to 10 minutes. Plates were read in luminescence mode and IC$_{50}$ values calculated.

Biological Activity

Biological activity data for representative compounds of the invention are provided in Table 6. CDK4 and CDK6 in vitro Ki (nM) data are provided using calorimetric assays. CDK4 and CDK6 cell-based IC$_{50}$ (nM) data are provided for CDK4 and CDK6 using phospho-Rb S795 ELISA assays in JEKO-1 and MV4-11 cells.

| Example No. | CDK4D1 Ki (nM) | CDK4 pRB S795 ELISA JEKO-1 cells IC50 (nM) | CDK6_D3 Ki (nM) | CDK6 pRB S795 ELISA MV4-11 cells IC50 (nM) |
|---|---|---|---|---|
| A01 | 0.1 | 25.3 | 2.3 | 76.5 |
| A02 | 0.1 | 88.6 | 2.5 | 163.3 |
| A03 | 4.0 |  | 17.3 |  |
| A04 | 0.6 | 329.6 | 11.4 | 289.2 |
| A05 | 3.3 | 225.1 | 50.8 | 541.4 |
| A06 | 1.4 | 87.4 | 17.5 | 192.2 |
| A07 | 1.8 | 182.1 | 28.0 | 520.4 |
| A08 | 1.1 |  | 4.8 |  |
| A09 | 0.1 | 16.8 | 1.4 | 57.6 |
| A10 | 0.6 | 72.7 | 10.4 | 195.3 |
| A11 | 0.3 | 122.7 | 3.0 | 143.9 |
| A12 | 0.6 | 29.8 | 7.9 | 108.5 |
| A13 | 1.7 | 72.2 | 31.5 | 276.7 |
| A14 | 0.5 |  | 4.6 |  |
| A15 | 0.3 |  | 2.4 |  |
| A16 | 0.2 | 25.7 | 2.7 | 98.1 |
| A17 | 0.1 | 9.9 | 0.4 | 13.4 |
| A18 | 0.2 | 25.0 | 2.3 | 77.2 |
| A19 | 0.9 | 69.1 | 14.6 | 318.4 |
| A20 | 2.7 |  | 20.4 |  |
| A21 | 7.3 |  | 135.6 |  |
| A22 | 3.2 |  | 49.7 |  |
| A23 | 0.5 | 26.5 | 11.6 | 84.1 |
| A24 | 1.3 | 40.1 | 16.4 | 166.9 |
| A25 | 0.0 | 13.3 | 1.3 | 30.6 |
| A26 | 0.2 | 12.2 | 4.2 | 24.3 |
| A27 | 1.0 | 75.6 | 15.7 | 269.2 |
| A28 | 0.5 | 99.2 | 6.2 | 131.1 |
| A29 | 0.6 | 68.6 | 5.1 | 95.7 |
| A30 | 0.2 | 51.6 | 4.9 | 63.5 |
| A31 | 0.5 | 23.5 | 7.1 | 87.0 |
| A32 | 0.9 |  | 7.1 |  |
| A33 | 8.3 |  | 78.0 |  |
| A34 | 11.1 |  | 102.1 |  |
| A35 | 1.5 | 123.8 | 58.9 | 966.7 |
| A36 | 0.2 | 19.6 | 3.7 | 43.9 |
| A37 | 3.5 |  | 34.2 |  |
| A38 | 0.5 | 455.7 | 10.2 | 598.1 |
| A39 | 1.3 |  | 12.3 |  |
| A40 | 0.3 | 85.5 | 3.5 | 346.5 |
| A41 | 3.1 | 92.8 | 48.8 | 216.1 |
| A42 | 6.0 |  | 54.7 |  |
| A43 | 4.8 |  | 44.0 |  |
| A44 | 4.9 | 76.5 | 113.9 | 408.0 |
| A45 | 1.0 | 65.8 | 52.0 | 468.4 |
| A46 | 2.3 |  | 40.5 |  |
| A47 | 1.0 | 382.7 | 24.6 | 370.3 |
| A48 | 0.1 | 36.5 | 2.3 | 58.9 |
| A49 | 0.7 | 76.0 | 14.3 | 219.2 |
| A50 | 17.0 |  | 109.5 |  |
| A51 | 2.0 | 245.0 | 55.7 | 1528.4 |
| A52 | 2.7 | 202.1 | 60.1 | 973.1 |
| A53 | 0.6 | 67.3 | 16.7 | 208.3 |
| A54 | 2.3 | 173.1 | 37.5 | 605.3 |
| A55 | 3.2 | 197.8 | 64.9 | 283.5 |
| A56 | 1.3 |  | 9.6 |  |
| A57 | 0.4 | 49.0 | 19.1 | 269.1 |
| A58 | 0.6 | 33.1 | 17.6 | 203.0 |
| A59 | 0.6 | 47.7 | 56.7 | 521.4 |
| A60 | 1.6 | 65.2 | 33.6 | 190.3 |

| Example No. | CDK4D1 Ki (nM) | CDK4 pRB S795 ELISA JEKO-1 cells IC50 (nM) | CDK6_D3 Ki (nM) | CDK6 pRB S795 ELISA MV4-11 cells IC50 (nM) |
|---|---|---|---|---|
| A61 | 0.2 | 11.4 | 2.6 | 33.5 |
| A62 | 0.5 | 27.5 | 8.0 | 66.6 |
| A63 | 0.9 |  | 9.7 |  |
| A64 | 2.0 |  | 10.7 |  |
| A65 | 0.6 |  | 3.5 |  |
| A66 | 12.1 |  | 54.7 |  |
| A67 | 1.4 |  | 15.5 |  |
| A68 | 0.7 | 48.7 | 14.3 | 234.9 |
| A69 | 0.7 | 101.4 | 4.9 | 237.7 |
| A70 | 26.2 |  | 124.2 |  |
| A71 | 0.8 | 94.9 | 11.4 | 286.9 |
| A72 | 0.3 |  | 2.1 |  |
| A73 | 0.9 | 72.0 | 16.1 | 188.1 |
| A74 | 0.2 | 26.5 | 6.2 | 89.7 |
| A75 | 0.3 | 33.2 | 5.0 | 102.8 |
| A76 | 0.2 | 96.1 | 6.3 | 242.0 |
| A77 | 0.3 | 61.1 | 4.9 | 126.4 |
| A78 | 0.1 | 26.4 | 1.8 | 73.9 |
| A79 | 1.8 | 598.0 | 17.6 | 1138.0 |
| A80 | 0.5 | 72.9 | 14.7 | 216.7 |
| A81 |  |  |  |  |
| A82 | 3.8 |  | 24.6 |  |
| A83 | 4.1 | 394.8 | 88.5 | 1223.0 |
| A84 | 6.0 |  | 30.3 |  |
| A85 | 9.9 |  | 62.8 |  |
| A86 | 4.7 |  | 23.5 |  |
| A87 | 0.2 | 40.1 | 2.8 | 97.7 |
| A88 | 4.5 | 7318.0 | 80.4 | 10000.0 |
| A89 | 0.5 | 118.4 | 12.0 | 570.3 |
| A90 | 0.2 |  | 1.1 |  |
| A91 | 0.1 | 14.9 | 1.7 | 25.7 |
| A92 | 0.1 | 23.8 | 0.9 | 42.9 |
| A93 | 0.2 | 34.7 | 4.4 | 61.4 |
| A94 | 0.6 | 38.5 | 13.9 | 144.9 |
| B01 | 0.1 | 65.6 | 1.5 | 129.0 |
| B02 | 7.3 |  | 27.1 |  |
| C01 | 5.2 | 176.4 | 98.1 | 1379.5 |
| C02 | 4.1 | 583.7 | 89.3 | 1350.0 |
| D01 | 0.4 |  | 1.7 |  |
| D02 | 1.0 |  | 9.3 |  |
| D03 | 0.6 |  | 4.7 |  |
| D04 | 0.6 | 68.2 | 12.5 | 172.0 |
| D05 | 2.2 | 85.7 | 39.4 | 258.0 |
| D06 |  |  |  |  |
| E01 | 0.1 | 17.0 | 1.4 | 37.9 |
| F01 | 0.8 | 114.1 | 14.6 | 576.0 |
| F02 | 4.3 |  | 39.9 |  |
| F03 | 2.7 |  | 26.4 |  |
| F04 |  |  |  |  |
| F05 | 2.1 | 247.9 | 25.8 | 478.2 |
| F06 | 1.5 | 160.6 | 27.8 | 134.4 |
| F07 | 15.3 |  | 125.4 |  |
| F08 | 0.5 | 108.4 | 11.5 | 311.3 |
| F09 | 0.6 |  | 5.5 |  |
| F10 | 0.5 | 41.3 | 6.1 | 152.7 |
| F11 | 5.4 | 821.1 | 79.9 | 2402.1 |
| F12 | 50.0 |  | 109.5 |  |
| F13 | 11.6 |  | 81.1 |  |
| F14 | 3.6 |  | 30.8 |  |
| F15 | 0.0 | 34.4 | 1.0 | 39.8 |
| F16 | 1.4 | 675.3 | 26.0 | 362.7 |
| F17 | 0.5 | 83.2 | 8.3 | 126.6 |
| F18 | 0.9 | 31.7 | 10.1 |  |
| F19 | 1.5 |  | 11.8 |  |
| F20 | 2.0 | 155.1 | 24.3 | 787.5 |
| F21 | 0.4 | 59.5 | 7.7 | 246.2 |
| F22 | 0.5 | 61.3 | 9.1 | 171.1 |
| F23 | 1.0 | 691.9 | 11.0 | 1318.1 |
| F24 | 2.1 |  | 19.9 |  |
| F25 | 1.2 | 455.3 | 19.3 | 455.2 |
| F26 | 0.1 | 142.8 | 4.6 | 182.3 |
| F27 | 0.5 | 60.8 | 5.1 | 188.0 |
| F28 | 2.2 | 190.5 | 22.3 | 745.2 |
| F29 | 1.8 | 245.5 | 23.3 | 643.7 |
| F30 | 0.5 | 66.1 | 12.5 | 377.1 |
| F31 | 2.4 |  | 23.0 |  |
| F32 | 0.9 | 171.6 | 12.8 | 628.3 |
| F33 | 0.2 | 24.6 | 5.2 | 112.8 |
| G01 | 0.4 |  | 5.9 |  |
| H01 | 2.4 | 137.1 | 127.0 | 857.6 |
| H02 | 0.8 | 52.1 | 20.0 | 117.9 |
| H03 | 1.8 | 155.4 | 66.9 | 422.9 |
| H04 | 0.8 | 63.4 | 38.2 | 220.9 |
| H05 | 4.5 | 249.0 | 93.3 | 1470.2 |
| H06 | 1.1 | 79.6 | 35.6 | 343.3 |
| H07 | 1.4 | 48.3 | 43.0 | 409.1 |
| H08 | 1.2 | 35.6 | 44.5 | 305.9 |
| H09 | 0.9 | 205.1 | 18.6 | 230.3 |
| H10 | 0.5 | 14.9 | 16.4 | 51.1 |
| H11 | 0.7 | 43.4 | 22.1 | 295.1 |

All publications and patent applications cited in the specification are herein incorporated by reference in their entirety. It will be apparent to those of ordinary skill in the art that certain changes and modifications may be made thereto without departing from the spirit or scope of the appended claims.

What is claimed is:

1. A compound of Formula (IX):

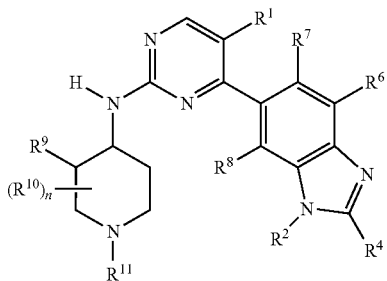

or a pharmaceutically acceptable salt thereof, wherein:
$R^1$ is H, F, Cl, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;
$R^2$ is H, $C_1$-$C_5$ alkyl, $C_1$-$C_5$ fluoroalkyl, $C_3$-$C_8$ cycloalkyl or 3-6 membered heterocyclyl, where each said $C_1$-$C_5$ alkyl and $C_1$-$C_5$ fluoroalkyl is optionally substituted by $R^{20}$ and each said $C_3$-$C_8$ cycloalkyl and 3-6 membered heterocyclyl is optionally substituted by $R^{21}$; and
$R^4$ is H, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally substituted by $R^{20}$; or
$R^6$ is H, F, Cl, CN, $CH_3$, $CH_2F$, $CHF_2$ or $CF_3$;
$R^7$ and $R^8$ are independently H, F, Cl, CN, $C_1$-$C_2$ alkyl, $C_1$-$C_2$ fluoroalkyl, $C_1$-$C_2$ alkoxy or $C_1$-$C_2$ fluoroalkoxy, where each said $C_1$-$C_2$ alkyl, $C_1$-$C_2$ fluoroalkyl, $C_1$-$C_2$ alkoxy and $C_1$-$C_2$ fluoroalkoxy is optionally substituted by $R^{20}$;
$R^9$ is H, OH, $NH_2$, $NHCH_3$ or $N(CH_3)_2$;
each $R^{10}$ is independently F, CN, $C_1$-$C_2$ alkyl or $C_1$-$C_2$ fluoroalkyl, where each said $C_1$-$C_2$ alkyl and $C_1$-$C_2$ fluoroalkyl is optionally substituted by $R^{20}$;
$R^{11}$ is H, $C_1$-$C_4$ alkyl, $C_1$-$C_4$ fluoroalkyl, $SO_2R^{14}$, $SO_2NR^{15}R^{16}$, $COR^{17}$, $COOR^{17}$ or $CONR^{18}R^{19}$;
$R^{14}$ is $C_1$-$C_4$ alkyl or $C_1$-$C_4$ fluoroalkyl;
each $R^{15}$ and $R^{16}$ is independently H or $CH_3$;
$R^{17}$ is $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$;
each $R^{18}$ and $R^{19}$ is independently H, $C_1$-$C_4$ alkyl or $C_1$-$C_4$ fluoroalkyl, where each said $C_1$-$C_4$ alkyl and $C_1$-$C_4$ fluoroalkyl is optionally substituted by $R^{20}$;
each $R^{20}$ is independently OH, $C_1$-$C_2$ alkoxy, $C_1$-$C_2$ fluoroalkoxy, CN or $NR^{22}R^{23}$;
each $R^{21}$ is independently F, OH, CN, $NR^{22}R^{23}$, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl, $C_1$-$C_4$ fluoroalkyl, $C_1$-$C_4$ alkoxy and $C_1$-$C_4$ fluoroalkoxy is optionally further substituted by OH, $NH_2$, $NHCH_3$ or $N(CH_3)_2$;
each $R^{22}$ and $R^{23}$ is independently H, $C_1$-$C_2$ alkyl or $C_1$-$C_2$ fluoroalkyl; or
$R^{22}$ and $R^{23}$ may be taken together with the nitrogen atom to which they are attached to form an azetidinyl ring, which is optionally substituted by F or OH; and
n is 0, 1, 2, 3 or 4.

2. (3R,4R)-4-[(5-chloro-4-{4-fluoro-2-[(1R)-1-hydroxyethyl]-1-(propan-2-yl)-1H-benzimidazol-6-yl}pyrimidin-2-yl)amino]-1-(methanesulfonyl)piperidin-3-ol, or a pharmaceutically acceptable salt thereof.

3. A pharmaceutical composition comprising the compound of claim 1, or a pharmaceutically acceptable salt thereof, and a pharmaceutically acceptable carrier or excipient.

4. A pharmaceutical composition comprising the compound of claim 2, or a pharmaceutically acceptable salt thereof, and a pharmaceutically acceptable carrier or excipient.

5. A method for the treatment of cancer in a subject in need thereof, comprising administering to the subject a therapeutically effective amount of the compound of claim 1, or a pharmaceutically acceptable salt thereof.

6. A method for the treatment of cancer in a subject in need thereof, comprising administering to the subject a therapeutically effective amount of the compound of claim 2, or a pharmaceutically acceptable salt thereof.

7. A method for the treatment of cancer in a subject in need thereof, comprising administering to the subject a therapeutically effective amount of 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol, or a pharmaceutically acceptable salt thereof, wherein the cancer is selected from the group consisting of breast cancer, ovarian cancer, bladder cancer, uterine cancer, prostate cancer, lung cancer, esophageal cancer, head and neck cancer, colorectal cancer, kidney cancer, liver cancer, pancreatic cancer, stomach cancer and thyroid cancer.

8. The method of claim 7, wherein the cancer is breast cancer.

9. The method of claim 8, wherein the breast cancer is hormone receptor (HR)-positive, human epidermal growth factor 2 (HER2)-negative breast cancer.

10. The method of claim 9, wherein the breast cancer is HR-positive, HER2-negative advanced or metastatic breast cancer.

11. The method of claim 10, further comprising administering to the subject an additional anti-cancer agent.

12. The method of claim 11, wherein the additional anti-cancer agent is an endocrine agent selected from the group consisting of an aromatase inhibitor, a selective estrogen receptor downregulator (SERD), and a selective estrogen receptor modulator (SERM).

13. The method of claim 12, wherein the endocrine agent is letrozole or fulvestrant.

14. The method of claim 10, wherein the 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol, or a pharmaceutically acceptable salt thereof, is administered as a first line therapy.

15. The method of claim 14, further comprising administering to the subject an additional anti-cancer agent, wherein the additional anti-cancer agent is letrozole.

16. The method of claim 10, wherein the 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol, or a pharmaceutically acceptable salt thereof, is administered as a second or later line therapy.

17. The method of claim 16, further comprising administering to the subject an additional anti-cancer agent, wherein the additional anti-cancer agent is fulvestrant.

18. The method of claim 7, wherein the cancer is lung cancer.

19. The method of claim 18, wherein the lung cancer is non-small cell lung cancer (NSCLC).

20. The method of claim 7, wherein the cancer is colorectal cancer.

21. The method of claim 7, wherein the cancer is prostate cancer.

* * * * *